United States Patent
Xu et al.

(10) Patent No.: US 12,275,727 B2
(45) Date of Patent: Apr. 15, 2025

(54) COMPOUND CONTAINING STRUCTURE OF A FIVE-MEMBERED HETEROAROMATIC RING, PHARMACEUTICAL COMPOSITIONS THEREOF AND APPLICATIONS THEREOF

(71) Applicant: 280 Bio, Inc., South San Francisco, CA (US)

(72) Inventors: Zusheng Xu, Shanghai (CN); Yangtong Lou, Shanghai (CN); Tiegang Xie, Shanghai (CN); Linlin Xu, Shanghai (CN); Li Chen, Shanghai (CN); Yanhang Liu, Shanghai (CN); Qingrui Sun, Shanghai (CN)

(73) Assignee: 280 BIO, INC., South San Francisco, CA (US)

( * ) Notice: Subject to any disclaimer, the term of this patent is extended or adjusted under 35 U.S.C. 154(b) by 0 days.

(21) Appl. No.: 18/178,668

(22) Filed: Mar. 6, 2023

(65) Prior Publication Data

US 2023/0278998 A1    Sep. 7, 2023

(30) Foreign Application Priority Data

Mar. 4, 2022  (CN) .......... 202210214607.4
Jul. 15, 2022 (CN) .......... 202210831127.2
Oct. 20, 2022 (CN) .......... 202211288698.2

(51) Int. Cl.
| | | |
|---|---|---|
| C07D 417/14 | (2006.01) |
| C07D 417/04 | (2006.01) |
| C07D 471/04 | (2006.01) |
| C07D 487/08 | (2006.01) |

(52) U.S. Cl.
CPC ......... *C07D 417/14* (2013.01); *C07D 417/04* (2013.01); *C07D 471/04* (2013.01); *C07D 487/08* (2013.01)

(58) Field of Classification Search
CPC .. C07D 417/14; C07D 417/04; C07D 471/04; C07D 487/04; C07D 487/08; C07D 498/04; C07D 519/00; Y02P 20/55
See application file for complete search history.

(56) References Cited

U.S. PATENT DOCUMENTS

| | | |
|---|---|---|
| 6,858,638 B2 | 2/2005 | Damour et al. |
| 7,473,701 B2 | 1/2009 | Damour et al. |
| 10,508,086 B2 | 12/2019 | McGonagle et al. |

FOREIGN PATENT DOCUMENTS

| | | | |
|---|---|---|---|
| WO | 2008156757 A1 | 12/2008 | |
| WO | 2016092326 A1 | 6/2016 | |
| WO | 2016097749 A1 | 6/2016 | |
| WO | WO2021055744 A1 * | 3/2021 | .............. A61P 35/00 |

OTHER PUBLICATIONS

Dong et al., (ChemMedChem 2018, 13, 1490-1507, Recent Advances in the Development of Indazole-based Anticancer Agents). (Year: 2018).*
E. Lohou et al. Bioorg. Med. Chem. 20 (2012) 5296-5304, New hypotheses for the binding mode of 4- and 7-substituted indazoles in the active site of neuronal nitric oxide synthase (Year: 2012).*
K. G. Liu et al. (Bioorg. Med. Chem. 19 (2011) 650-662, Identification of 3-sulfonylindazole derivatives as potent and selective 5-HT6 antagonists) (Year: 2011).*
Hulikal, Deuterium Labeled Compounds in Drug Discovery Process, Abstract, 2010.*
Pimlott, PubMed Abstract (Nucl Med Commun., 26(3):183-8), 2005.*
Cecil Textbook of Medicine, 20th Ed., vol. 1 (Year: 1997).*
Wu et al. Small-molecule inhibitors, immune checkpoint inhibitors, and more: FDA-approved novel therapeutic drugs for solid tumors from 1991 to 2021, J. Hematol Oncol., 15, 143 (Year: 2022).*

\* cited by examiner

*Primary Examiner* — Jeffrey H Murray
*Assistant Examiner* — Daniel John Burkett
(74) *Attorney, Agent, or Firm* — Panitch Schwarze Belisario & Nadel LLP

(57) ABSTRACT

Disclosed is a five-membered heteroaromatic ring structure containing compound, pharmaceutical compositions thereof and applications thereof. The present disclosure provides a five-membered heteroaromatic ring structure containing compound of formula I, pharmaceutical compositions thereof and applications thereof and the five-membered heteroaromatic ring structure containing compound is expected to treat and/or prevent various PARG-related diseases.

I

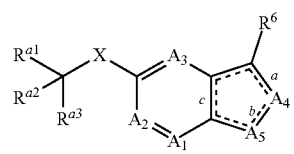

13 Claims, No Drawings

COMPOUND CONTAINING STRUCTURE OF A FIVE-MEMBERED HETEROAROMATIC RING, PHARMACEUTICAL COMPOSITIONS THEREOF AND APPLICATIONS THEREOF

TECHNICAL FIELD

The disclosure relates to a five-membered heteroaromatic ring structure containing compound, pharmaceutical compositions thereof and applications thereof.

BACKGROUND

Cancer cells tend to divide and proliferate uncontrollably, resulting in a higher incidence of DNA damage and defective DNA repair, and are more dependent on DNA damage repair mechanisms than normal cells.

Polyadenosine diphosphate ribose polymerase (PARP), polyadenosine diphosphate ribose hydrolase (PARG) and other proteins play an important role in DNA repair and have become important targets in the development of anti-cancer drugs. PARP can bind to single-strand break sites of DNA, which promotes the production of polyadenosine diphosphate ribose (PAR) chains, thus triggering the repair process. PARG is to degrade PAR on PARP and facilitate the completion of the entire repair cycle. Inhibition of either PARP or PARG affects the entire repair process.

Currently, the research and development of PARP inhibitors has been highly successful, with several drugs approved for marketing, and has demonstrated the feasibility of using DNA repair proteins as targets. At the same time, there is some problem still exist in PARP inhibitors such as not effective to all patients, drug resistance. The research on PARG inhibitors is still in the exploratory stage, and no compounds have entered clinical studies yet. There is a lot of room for research in this target direction, which is expected to fill the unmet clinical needs.

CONTENT OF THE PRESENT DISCLOSURE

The present disclosure to be solved by the present disclosure is the lack of effective drugs serving as PARG inhibitors for clinical treatment in the prior art. Therefore, the present disclosure provides a five-membered heteroaromatic ring structure containing compound, pharmaceutical compositions thereof and applications thereof, and the five-membered heteroaromatic ring structure containing compound is expected to treat and/or prevent various PARG-related diseases.

The present disclosure solves the above problem by the following technical schemes.

The present disclosure provides a compound containing structure of a five-membered heteroaromatic ring represented by formula I, a pharmaceutically acceptable salt thereof, a stereoisomer thereof, an isomer thereof or an isotopic compound thereof:

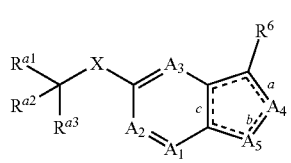

I

Wherein, "$\rlap{=}{-}$" represents a single bond or a double bond;

Both rings of

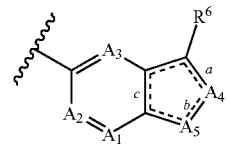

are aromatic;

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, $OR^{a-1}$, —C(=O)$R^{a-2}$, —NR$^{a-31}$R$^{a-32}$, —C(=O)OR$^{a-4}$, —C(=O)NR$^{a-51}$R$^{a-52}$, or, $C_{1-6}$ alkyl substituted with one or more $R^{a1-1}$, $R^{a1-1}$ is halogen, hydroxyl or —OC$_{1-6}$ alkyl;

or, $R^{a2}$ and $R^{a3}$, together with the carbon atom to which they are attached form $C_{3-7}$ cycloalkane, $C_{3-7}$ cycloalkane substituted with one or more $R^{a2-1}$, "3- to 8-membered heterocycloalkyl containing 1 to 3 hetroatoms independently selected from O, S and N", "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, oxo, hydroxyl, $C_{1-6}$ alkyl, or $C_{1-6}$ alkyl substituted with one or more halogen, —OC$_{1-6}$ alkyl, and —OC$_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogens;

X is *—NH—S(O)$_y$— or *—S(O)$_y$—NH—, wherein, y is 1 or 2, * represents that the end marked with * is connected with

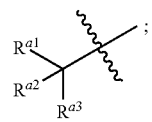

$A_1$ is N or $CR^1$;

$R^1$ is hydrogen, cyano, $C_{2-6}$ alkenyl, $C_{2-6}$ alkynyl, $C_{1-6}$ alkyl, $C_{1-6}$ alkyl substituted with one or more $R^{1-1}$, halogen, hydroxyl, —OC$_{1-6}$ alkyl, —OC$_{1-6}$ alkyl substituted with one or more $R^{1-2}$, —C(=O)$R^{1a}$, —NR$^{1b1}$R$^{1b2}$, —C(=O)OR$^{1c}$, —C(=O)NR$^{1d1}$R$^{1d2}$, $C_{3-10}$ cycloalkyl, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-2}$, $R^{1-3}$, $R^{1-4}$, $R^{1-5}$, $R^{1-6}$, $R^{1-7}$, $R^{1-8}$ and $R^{1-9}$ are independently azide, halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, $-OC_{1-6}$ alkyl, $-OC_{1-6}$ alkyl substituted with one or more $R^{1-1-2}$, $C(=O)R^{11a}$, $-NR^{11b1}R^{11b2}$, $-C(=O)OR^{11c}$, $-C(=O)NR^{11d1}R^{11d2}$, $-S(O)_2NR^{11e1}$, $R^{11e2}$, $-S(O)_2 R^{11f}$, $C_{3-10}$ cycloalkyl, $C_{3-10}$ cycloalkyl substituted with one or more $R^{1-1-3}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, $-C(=O)R^{11g}$, hydroxyl, oxo, $C_{1-6}$ alkyl, or, $C_{1-6}$ alkyl substituted with one or more $R^{1-1-1-1}$; provided that when multiple substituents are present, the substituents are the same or different;

$R^{1-1-1-1}$ is halogen, hydroxyl, $-OC_{1-6}$ alkyl or $-NR^aR^b$, $R^a$ and $R^b$ are independently hydrogen or $C_{1-6}$ alkyl;

$R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$ and Rut are independently hydrogen, $C_{1-6}$ alkyl, $C_{1-6}$ alkyl substituted with one or more $R^{1-2-1}$, $-OC_{1-6}$ alkyl, $-OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$ or, $-C(=O)R^{11h}$;

$R^{11h}$ is $C_{1-6}$ alky; provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, hydroxyl, $-NR^{12c}R^{12d}$, oxo, $C_{1-6}$ alkyl, $C_{1-6}$ alkyl substituted with one or more $R^{1-2-1-1}$; $R^{12c}$ and $R^{12d}$ are independently hydrogen or $C_{1-6}$ alkyl; provided that when multiple substituents are present, the substituents are the same or different;

$R^{1-2-1-1}$ is independently halogen, hydroxyl, $-OC_{1-6}$ alkyl or $-NR^cR^d$, $R^c$ and $R^d$ are independently hydrogen or $C_{1-6}$ alkyl;

or, when the number of $R^{1-3}$, $R^{1-4}$, $R^{1-5}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-5}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3- to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aromatic ring, $C_{6-20}$ aromatic ring substituted with one or more $R^{1-3-3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1-3-4}$, $C_{5-7}$ cyclic olefin, $C_{5-7}$ cyclic olefin substituted with one or more $R^{1-3-5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1-3-6}$; provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, $-OC_{1-6}$ alkyl, or, $-OC_{1-6}$ alkyl substituted with one or more halogen; provided that when multiple substituents are present, the substituents are the same or different;

or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$, $R^{12c}$ and $R^{12d}$ together with the nitrogen atom to which they are attached independently form, or "3- to 8-membered heterocycle containing 1 to 3 heteroatoms, wherein, one heteroatom is N, the other one or two heteroatoms independently selected from O, S and N" substituted with one or more $R^{1-4-1}$;

$R^{1-4-1}$ is independently oxo, hydroxyl, halogen, $C_{1-6}$ alkyl, $C_{1-6}$ alkyl substituted with one or more halogen, $-OC_{1-6}$ alkyl, or, $-OC_{1-6}$ alkyl substituted with one or more halogen; provided that when multiple substituents are present, the substituents are the same or different;

$A_2$ and $A_3$ are independently are N or $CR^2$, $R^2$ is hydrogen or halogen;

When a, b and c are a single bond, $A_4$ is $NR^{4a}$, $A_5$ is N or $CR^{5b}$;

when b is a single bond, both a and c are a double bond, $A_4$ is N or $CR^{4d}$, $A_5$ is O, S or $NR^{5d}$;

$R^6$ is independently "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$;

$R^{6-1}$ is halogen, hydroxyl, —CN, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, or, —$O_{1-6}$ alkyl substituted with one or more halogen; provided that when multiple substituents are present, the substituents are the same or different;

$R^{4a}$ and $R^{4d}$ are independently hydrogen, halogen, $C_{1-6}$ alkyl, $C_{1-6}$ alkyl substituted with one or more halogen, or, $C_{1-6}$ alkyl substituted with one or more $R^{4-1}$; $R^{4-1}$ is hydroxyl or —$OC_{1-6}$ alkyl; provided that when multiple substituents are present, the substituents are the same or different;

$R^{5a}$ and $R^{5d}$ are independently

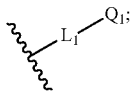

$L_1$ is a bond, $C_{1-6}$ alkylene or —C(=O)—;

$Q_1$ is hydrogen, halogen, cyano, $C_{2-6}$ alkenyl, $C_{2-6}$ alkynyl, hydroxyl, —C(=O)$R^{52a}$, —$NR^{52b1}R^{52b2}$, —C(=O)$OR^{52c}$, —C(=O)$NR^{52d1}R^{52d2}$, $C_{1-6}$ alkyl substituted with one or more halogen, $C_{1-6}$ alkyl substituted with one or more hydroxyl, —$OC_{1-6}$ alkyl, —$OC_{1-6}$ alkyl substituted with one or more $R^{5-1-1}$, $C_{6-20}$ aryl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, $C_{3-12}$ cycloalkyl, $C_{3-12}$ cycloalkyl substituted with one or more $R^{5-1-4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-1-5}$, $C_{5-7}$ cycloalkenyl, $C_{5-7}$ cycloalkenyl substituted with one or more $R^{5-1-6}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{5-1-7}$; provided that when multiple substituents are present, the substituents are the same or different;

or, $R^1$ and $R^{5d}$, together with the atoms to which they are attached independently form "5- to 12-membered heterocyclic olefin containing 1 to 3 heteroatoms independently selected from O, S and N";

$R^{5-1-1}$, $R^{5-1-2}$, $R^{5-1-3}$, $R^{5-1-4}$, $R^{5-1-5}$, $R^{5-1-6}$ and $R^{5-1-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(=O)$R^{51a}$, —$NR^{51b1}R^{51b2}$, —C(=O)$OR^{51c}$, or, —C(=O)$NR^{51d1}R^{51d2}$; provided that when multiple substituents are present, the substituents are the same or different;

$R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b2}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$;

$R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different.

In some embodiments, in the compound containing structure of a five-membered heteroaromatic ring represented by formula I, a pharmaceutically acceptable salt thereof, a stereoisomer thereof, an isomer thereof or an isotopic compound thereof, the compound containing structure of a five-membered heteroaromatic ring represented by formula I has the following structure:

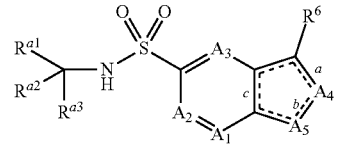

II

Wherein, "═" represents a single bond or a double bond;

Both rings of

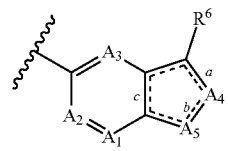

are aromatic;

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, —$OR^{a-1}$, —C(=O)$R^{a-2}$, —$NR^{a-31}R^{a-32}$, —C(=O)$OR^{a-4}$, —C(=O)$NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

or, $R^{a2}$ and $R^{a3}$, together with the carbon atom to which they are attached form $C_{3-7}$ cycloalkane, $C_{3-7}$ cycloalkane substituted with one or more $R^{a2-1}$, "3- to 8-membered heterocycloalkyl containing 1 to 3 hetroatoms independently selected from O, S and N", "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, oxo, hydroxyl, $C_{1-6}$ alkyl, or $C_{1-6}$ alkyl substituted with one or more halogen, —$OC_{1-6}$ alkyl, and —$OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogens;

$A_1$ is N or $CR^1$;

$R^1$ is hydrogen, cyano, $C_{2-6}$ alkenyl, $C_{2-6}$ alkynyl, $C_{1-6}$ alkyl, $C_{1-6}$ alkyl substituted with one or more $R^{1-1}$, halogen, hydroxyl, —$OC_{1-6}$ alkyl, —$OC_{1-6}$ alkyl substituted with one or more $R^{1-2}$, —$C(=O)R^{1a}$, —$NR^{1b1}R^{1b2}$, —$C(=O)OR^{1c}$, —$C(=O)NR^{1d1}R^{1d2}$, $C_{3-10}$ cycloalkyl, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-2}$, $R^{1-3}$, $R^{1-4}$, $R^{1-5}$, $R^{1-6}$, $R^{1-7}$, $R^{1-8}$ and $R^{1-9}$ are independently azide, halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, —$C(=O)R^{11a}$, —$NR^{11b1}R^{11b2}$, —$C(=O)OR^{11c}$, —$C(=O)NR^{11d1}R^{11d2}$, —$S(O)_2NR^{11e1}$, $R^{11e2}$, —$S(O)_2R^{11f}$, $C_{3-10}$ cycloalkyl, $C_{3-10}$ cycloalkyl substituted with one or more $R^{1-1-3}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, —$C(=O)R^{11g}$, hydroxyl, oxo, $C_{1-6}$ alkyl, or, $C_{1-6}$ alkyl substituted with one or more $R^{1-1-1-1}$; provided that when multiple substituents are present, the substituents are the same or different;

$R^{1-1-1-1}$ is halogen, hydroxyl, —$OC_{1-6}$ alkyl or —$NR^aR^b$, $R^a$ and $R^b$ are independently hydrogen or $C_{1-6}$ alkyl;

$R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$ and $R^{11g}$ are independently hydrogen, $C_{1-6}$ alkyl, $C_{1-6}$ alkyl substituted with one or more $R^{1-2-1}$, —$OC_{1-6}$ alkyl, —$OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$ or, —$C(=O)R^{11h}$; $R^{11h}$ is $C_{1-6}$ alky; provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, hydroxyl, —$NR^{12c}R^{12d}$, oxo, $C_{1-6}$ alkyl, $C_{1-6}$ alkyl substituted with one or more $R^{1-2-1-1}$; $R^{12c}$ and $R^{12d}$ are independently hydrogen or $C_{1-6}$ alkyl; provided that when multiple substituents are present, the substituents are the same or different;

$R^{1-2-1-1}$ is independently halogen, hydroxyl, —$OC_{1-6}$ alkyl or —$NR^cR^d$, $R^c$ and $R^d$ are independently hydrogen or $C_{1-6}$ alkyl;

or, when the number of $R^{1-3}$, $R^{1-4}$, $R^{1-5}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-5}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3- to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aromatic ring, $C_{6-20}$ aromatic ring substituted with one or more $R^{1-3-3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1-3-4}$, $C_{5-7}$ cyclic olefin, $C_{5-7}$ cyclic olefin substituted with one or more $R^{1-3-5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1\text{-}3\text{-}6}$; provided that when multiple substituents are present, the substituents are the same or different;

$R^{1\text{-}3\text{-}1}$, $R^{1\text{-}3\text{-}2}$, $R^{1\text{-}3\text{-}3}$, $R^{1\text{-}3\text{-}4}$, $R^{1\text{-}3\text{-}5}$ and $R^{1\text{-}3\text{-}6}$ are independently oxo, hydroxyl, halogen, $C_{1\text{-}6}$ alkyl, $C_{1\text{-}6}$ alkyl substituted with one or more halogen, —$OC_{1\text{-}6}$ alkyl, or, —$OC_{1\text{-}6}$ alkyl substituted with one or more halogen; provided that when multiple substituents are present, the substituents are the same or different;

or, $R^{a\text{-}31}$ and $R^{a\text{-}32}$, $R^{a\text{-}51}$ and $R^{a\text{-}52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$, $R^{12c}$ and $R^{12d}$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1\text{-}4\text{-}1}$;

$R^{1\text{-}4\text{-}1}$ is independently oxo, hydroxyl, halogen, $C_{1\text{-}6}$ alkyl, $C_{1\text{-}6}$ alkyl substituted with one or more halogen, —$OC_{1\text{-}6}$ alkyl, or, —$OC_{1\text{-}6}$ alkyl substituted with one or more halogen; provided that when multiple substituents are present, the substituents are the same or different;

$A_2$ and $A_3$ are independently are N or $CR^2$, $R^2$ is hydrogen or halogen;

When a, b and c are a single bond, $A_4$ is $NR^{4a}$, $A_5$ is N or $CR^{5b}$;

when b is a single bond, both a and c are a double bond, $A_4$ is N or $CR^{4d}$, $A_5$ is O, S or $NR^{5d}$;

$R^6$ is independently "5-membered heteroaryl containing 1 to 4 heteroatoms independently selected from O, S and N", or, "5-membered heteroaryl containing 1 to 4 heteroatoms independently selected from O, S and N" substituted with one or more $R^{6\text{-}1}$;

$R^{6\text{-}1}$ is halogen, hydroxyl, —CN, $C_{1\text{-}6}$ alkyl, $C_{1\text{-}6}$ alkyl substituted with one or more halogen, $C_{1\text{-}6}$ alkyl substituted with one or more —$OC_{1\text{-}6}$ alkyl, —$OC_{1\text{-}6}$ alkyl, or, —$O_{1\text{-}6}$ alkyl substituted with one or more halogen; provided that when multiple substituents are present, the substituents are the same or different;

$R^{4a}$ and $R^{4d}$ are independently hydrogen, halogen, $C_{1\text{-}6}$ alkyl, $C_{1\text{-}6}$ alkyl substituted with one or more halogen, or, $C_{1\text{-}6}$ alkyl substituted with one or more $R^4\text{-}1$; $R^{4\text{-}1}$ is hydroxyl or —$OC_{1\text{-}6}$ alkyl; provided that when multiple substituents are present, the substituents are the same or different;

$R^{5a}$ and $R^{5d}$ are independently

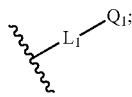

$L_1$ is a bond, $C_{1\text{-}6}$ alkylene or —C(=O)—;

$Q_1$ is hydrogen, halogen, cyano, $C_{2\text{-}6}$ alkenyl, $C_{2\text{-}6}$ alkynyl, hydroxyl, —C(=O)$R^{52a}$, —$NR^{52b1}R^{52b2}$, —C(=O)$OR^{52c}$, —C(=O)$NR^{52d1}R^{52d2}$, $C_{1\text{-}6}$ alkyl substituted with one or more halogen, $C_{1\text{-}6}$ alkyl substituted with one or more hydroxyl, —$OC_{1\text{-}6}$ alkyl, —$OC_{1\text{-}6}$ alkyl substituted with one or more $R^{5\text{-}1\text{-}1}$, $C_{6\text{-}20}$ aryl, $C_{6\text{-}20}$ aryl substituted with one or more $R^{5\text{-}1\text{-}2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5\text{-}1\text{-}3}$, $C_{3\text{-}12}$ cycloalkyl, $C_{3\text{-}12}$ cycloalkyl substituted with one or more $R^{5\text{-}1\text{-}4}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5\text{-}1\text{-}5}$, $C_{5\text{-}7}$ cycloalkenyl, $C_{5\text{-}7}$ cycloalkenyl substituted with one or more $R^{5\text{-}1\text{-}6}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{5\text{-}1\text{-}7}$; provided that when multiple substituents are present, the substituents are the same or different;

or, $R^1$ and $R^{5d}$, together with the atoms to which they are attached independently form "5- to 12-membered heterocyclic olefin containing 1 to 3 heteroatoms independently selected from O, S and N";

$R^{5\text{-}1\text{-}1}$, $R^{5\text{-}1\text{-}2}$, $R^{5\text{-}1\text{-}3}$, $R^{5\text{-}1\text{-}4}$, $R^{5\text{-}1\text{-}5}$, $R^{5\text{-}1\text{-}6}$ and $R^{5\text{-}1\text{-}7}$ are independently halogen, hydroxyl, oxo, cyano, $C_{1\text{-}6}$ alkyl, $C_{1\text{-}6}$ alkyl substituted with one or more halogen, $C_{2\text{-}6}$ alkenyl, $C_{2\text{-}6}$ alkynyl, —$OC_{1\text{-}6}$ alkyl, —$OC_{1\text{-}6}$ alkyl substituted with one or more halogen, —C(=O)$R^{51a}$, —$NR^{51b1}R^{51b2}$, —C(=O)$OR^{51c}$, or, —C(=O)$NR^{51d1}R^{51d2}$; provided that when multiple substituents are present, the substituents are the same or different;

$R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1\text{-}6}$ alkyl, or, $C_{1\text{-}6}$ alkyl substituted with one or more halogen;

or, $R^{52b1}$ and $R^{52b2}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1\text{-}5\text{-}1}$;

$R^{1\text{-}5\text{-}1}$ is oxo, hydroxyl, halogen, $C_{1\text{-}6}$ alkyl, $C_{1\text{-}6}$ alkyl substituted with one or more halogen, —$OC_{1\text{-}6}$ alkyl, —$OC_{1\text{-}6}$ alkyl substituted with one or more halogen; provided that when multiple substituents are present, the substituents are the same or different.

In some embodiments, in compound containing structure of a five-membered heteroaromatic ring represented by formula I, a pharmaceutically acceptable salt thereof, a stereoisomer thereof, an isomer thereof or an isotopic compound thereof, some groups are defined as follows, and the unmentioned groups are as defined in any embodiment of the present disclosure (this paragraph is hereinafter referred to as "in some embodiments"), in the compound containing structure of a five-membered heteroaromatic ring represented by formula I, $R^{a1}$ is cyano, $C_{1\text{-}6}$ alkyl, or, $C_{1\text{-}6}$ alkyl substituted with one or more $R^{a1\text{-}1}$, $R^{a1\text{-}1}$ is halogen;

$R^{a2}$ and $R^{a3}$ are independently $C_{1\text{-}6}$ alkyl, or, $R^{a2}$ and $R^{a3}$, together with the carbon atom to which they are attached form $C_{3\text{-}7}$ cycloalkane;

X is *—NH—S(O)$_y$—, wherein, y is 1 or 2, * represents that the end marked with * is connected with

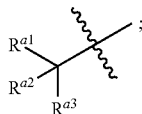

$A_1$ is N or $CR^1$;

$R^1$ is hydrogen, $C_{1-6}$ alkyl substituted with one or more $R^{1-1}$, halogen, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-3}$, $R^{1-4}$, $R^{1-5}$, $R^{1-7}$, $R^{1-8}$ and $R^{1-9}$ are independently azide, halogen, hydroxyl, $C_{1-6}$ alkyl, $C_{1-6}$ alkyl substituted with one or more $R^{1-1-1}$, $C_{6-20}$ aryl, $-C(=O)R^{11a}$, $-NR^{11b1}R^{11b2}$, $C(=O)NR^{11d1}R^{11d2}$, $-S(O)_2R^{11f}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, or, "5- to 12-membered heteroaryl containing 1 to 4 heteroatoms independently selected from O, S and N"; provided that when multiple substituents are present, the substituents are the same or different;

$R^{1-1-1}$ and $R^{1-1-4}$ are independently $-C(=O)R^{11g}$, oxo, hydroxyl, or, $C_{1-6}$ alkyl substituted with one or more $R^{1-1-1-1}$; provided that when multiple substituents are present, the substituents are the same or different;

$R^{1-1-1-1}$ is independently hydroxyl;

$R^{11a}$, $R^{11b1}$, $R^{11b2}$, $R^{11c}$, $R^{11d1}$, $R^{11d2}$, $R^{11f}$ and $R^{11g}$ are independently hydrogen, $C_{1-6}$ alkyl, $C_{1-6}$ alkyl substituted with one or more $R^{1-2-1}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N" substituted with one or more $R^{1-4}$, $C_{6-20}$ aryl, "5- to 12-membered heteroaryl containing 1 to 4 heteroatoms independently selected from O, S and N", or $-C(=O)R^{11h}$; $R^{11h}$ is $C_{1-6}$ alky; provided that when multiple substituents are present, the substituents are the same or different;

$R^{1-2-1}$, $R^{1-2-3}$ and $R^{1-2-4}$ are independently halogen, hydroxyl, $-NR^{12c}R^{12d}$, or $C_{1-6}$ alkyl; $R^{12c}$ and $R^{12d}$ are independently hydrogen or $C_{1-6}$ alkyl; provided that when multiple substituents are present, the substituents are the same or different;

or, when the number of $R^{1-4}$ and $R^{1-8}$ is more than one, two optional $R^{1-4}$, two optional $R^{1-8}$, together with the atoms to which they are attached, independently form "3- to 8-membered heterocycle containing 1 to 3 heteroatoms independently selected from O, S and N", or "5- to 12-membered heteroaromatic ring containing 1 to 4 heteroatoms independently selected from O, S and N";

or, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with one or more $R^{1-4-1}$;

$R^{1-4-1}$ is independently oxo, or halogen;

$A_2$ and $A_3$ are independently are N or $CR^2$, $R^2$ is hydrogen or halogen;

When a, b and c are a single bond, $A_4$ is $NR^{4a}$, $A_5$ is N;

when b is a single bond, both a and c are a double bond, $A_4$ is N or $CR^{4d}$, $A_5$ is S or $NR^{5d}$;

$R^{4a}$ and $R^{4d}$ are independently hydrogen, halogen, $C_{1-6}$ alkyl, or, $C_{1-6}$ alkyl substituted with one or more $R^{4-1}$; $R^{4-1}$ is halogen, hydroxyl or $-OC_{1-6}$ alkyl;

$R^{5d}$ is

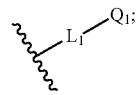

$L_1$ is a bond or $C_{1-6}$ alkylene;

$Q_1$ is hydrogen, cyano, hydroxyl, $C_{1-6}$ alkyl substituted with one or more halogen, $C_{1-6}$ alkyl substituted with one or more hydroxyl, $-OC_{1-6}$ alkyl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl; provided that when multiple substituents are present, the substituents are the same or different;

or, $R^1$ and $R^{5d}$, together with the atoms to which they are attached form "5- to 12-membered heterocyclic olefin containing 1 to 3 heteroatoms independently selected from O, S and N";

$R^{5-1-2}$ and $R^{5-1-3}$ are independently halogen or $C_{1-6}$ alkyl;

$R^6$ is "5-membered heteroaryl containing 1 to 4 heteroatoms independently selected from O, S and N" substituted with one or more $R^{6-1}$;

$R^{6-1}$ is $C_{1-6}$ alkyl, $C_{1-6}$ alkyl substituted with one or more halogen or $C_{1-6}$ alkyl substituted with one or more $-OC_{1-6}$ alkyl.

In some embodiments, in the compound containing structure of a five-membered heteroaromatic ring represented by formula I, $R^{a1}$ is cyano, $C_{1-6}$ alkyl, or, $C_{1-6}$ alkyl substituted with one or more $R^{a1-1}$, $R^{a1-1}$ is halogen;

$R^{a2}$ and $R^{a3}$ are independently $C_{1-6}$ alkyl, or, $R^{a2}$ and $R^{a3}$, together with the carbon atom to which they are attached form $C_{3-7}$ cycloalkane;

X is *—NH—S(O)$_y$—, wherein, y is 1 or 2, * represents that the end marked with * is connected with

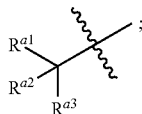

$A_1$ is N or $CR^1$;

$R^1$ is hydrogen, $C_{1-6}$ alkyl substituted with one or more $R^{1-1}$, halogen, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-3}$, $R^{1-4}$, $R^{1-5}$, $R^{1-7}$, $R^{1-8}$ and $R^{1-9}$ are independently azide, halogen, hydroxyl, $C_{1-6}$ alkyl, $C_{1-6}$ alkyl substituted with one or more $R^{1-1-1}$, $C_{6-20}$ aryl, $-C(=O)R^{11a}$, $-NR^{11b1}R^{11b2}$, $-C(=O)NR^{11d1}R^{11d2}$, $-S(O)_2R^{11f}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, or, "5- to 12-membered heteroaryl containing 1 to 4 heteroatoms independently selected from O, S and N"; provided that when multiple substituents are present, the substituents are the same or different;

$R^{1-1-1}$ and $R^{1-1-4}$ are independently $-C(=O)R^{11g}$, oxo, hydroxyl, or, $C_{1-6}$ alkyl substituted with one or more $R^{1-1-1-1}$; provided that when multiple substituents are present, the substituents are the same or different;

$R^{1-1-1-1}$ is independently hydroxyl;

$R^{11a}$, $R^{11b1}$, $R^{11b2}$, $R^{11d1}$, $R^{11d2}$, $R^{11f}$ and $R^{11g}$ are independently hydrogen, $C_{1-6}$ alkyl, $C_{1-6}$ alkyl substituted with one or more $R^{1-2-1}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N" substituted with one or more $R^{1-2-4}$, $C_{6-20}$ aryl, "5- to 12-membered heteroaryl containing 1 to 4 heteroatoms independently selected from O, S and N", or $-C(=O)R^{11h}$. $R^{11h}$ is $C_{1-6}$ alky; provided that when multiple substituents are present, the substituents are the same or different;

$R^{1-2-1}$, $R^{1-2-3}$ and $R^{1-2-4}$ are independently halogen, hydroxyl, $-NR^{12c}R^{12d}$, or $C_{1-6}$ alkyl; $R^{12c}$ and $R^{12d}$ are independently hydrogen or $C_{1-6}$ alkyl; provided that when multiple substituents are present, the substituents are the same or different;

or, when the number of $R^{1-4}$ and $R^{1-8}$ is more than one, two optional $R^{1-4}$, two optional $R^{1-8}$, together with the atoms to which they are attached, independently form "3- to 8-membered heterocycle containing 1 to 3 heteroatoms independently selected from O, S and N", or "5- to 12-membered heteroaromatic ring containing 1 to 4 heteroatoms independently selected from O, S and N";

or, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with one or more $R^{1-4-1}$;

$R^{1-4-1}$ is independently oxo, or halogen;

$A_2$ and $A_3$ are independently are N or $CR^2$, $R^2$ is hydrogen or halogen;

When a, b and c are a single bond, $A_4$ is $NR^{4a}$, $A_5$ is N;

when b is a single bond, both a and c are a double bond, $A_4$ is N or $CR^{4d}$, $A_5$ is S or $NR^{5d}$;

$R^{4a}$ and $R^{4d}$ are independently hydrogen, halogen, $C_{1-6}$ alkyl, or, $C_{1-6}$ alkyl substituted with one or more $R^{4-1}$;

$R^{4-1}$ is halogen, hydroxyl or $-OC_{1-6}$ alkyl;

$R^{5d}$ is

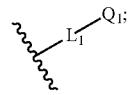

$L_1$ is a bond or $C_{1-6}$ alkylene;

$Q_1$ is hydrogen, cyano, hydroxyl, $C_{1-6}$ alkyl substituted with one or more halogen, $C_{1-6}$ alkyl substituted with one or more hydroxyl, $-OC_{1-6}$ alkyl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl; provided that when multiple substituents are present, the substituents are the same or different;

or, $R^1$ and $R^{5d}$, together with the atoms to which they are attached form "5- to 12-membered heterocyclic olefin containing 1 to 3 heteroatoms independently selected from O, S and N";

$R^{5-1-2}$ and $R^{5-1-3}$ are independently halogen or $C_{1-6}$ alkyl;

$R^6$ is "5-membered heteroaryl containing 1 to 4 heteroatoms independently selected from O, S and N" substituted with one or more $R^{6-1}$;

$R^{6-1}$ is $C_{1-6}$ alkyl, $C_{1-6}$ alkyl substituted with one or more halogen or $C_{1-6}$ alkyl substituted with one or more $-OC_{1-6}$ alkyl; provided that when multiple substituents are present, the substituents are the same or different.

In some embodiments, in compound containing structure of a five-membered heteroaromatic ring represented by formula I, a pharmaceutically acceptable salt thereof, a stereoisomer thereof, an isomer thereof or an isotopic compound thereof, some groups are defined as follows, and the unmentioned groups are as defined in any embodiment of the present disclosure.

In some embodiments, $R^{a1}$, $R^{a2}$ and $R^{a3}$ are independently $C_{1-6}$ alkyl.

In some embodiments, $R^{a1}$ is cyano, $C_{1-6}$ alkyl, or, $C_{1-6}$ alkyl substituted with one or more $R^{a1-1}$, $R^{a1-1}$ is halogen.

In some embodiments, $R^{a2}$ and $R^{a3}$, are independently $C_{1-6}$ alkyl, or, together with the carbon atom to which they are attached form $C_{3-7}$ cycloalkane, $R^{a1}$ is cyano, $C_{1-6}$ alkyl, or, $C_{1-6}$ alkyl substituted with one or more $R^{a1-1}$, $R^{a1-1}$ is halogen.

In some embodiments, X is *—NH—S(O)$_y$—, wherein, y is 1 or 2, * represents that the end marked with * is connected with

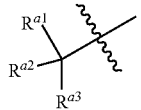

In some embodiments, $A_1$ is N.

In some embodiments, $A_1$ is $CR^1$.

In some embodiments, $R^1$ is hydrogen, $C_{1-6}$ alkyl substituted with one or more $R^{1-1}$ halogen, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different.

In some embodiments, $R^{1-1}$ is independently halogen, or, "4- to 10-membered heterocycloalkyl containing 1 to 3 heteroatoms independently selected from O, S and N" substituted with one or more $R^{1-1-4}$.

In some embodiments, in $R^{1-1}$, $R^{1-1-4}$ is independently —C(=O)$R^{11g}$ or $C_{1-6}$ alkyl substituted with one or more $R^{1-1-1-1}$; $R^{11g}$ is $C_{1-6}$ alkyl; $R^{1-1-1-1}$ is independently hydroxyl.

In some embodiments, $R^{1-3}$ is independently —C(=O)NR$^{11d1}$R$^{11d2}$, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N".

In some embodiments, $R^{1-4}$ is independently azide, hydroxyl, $C_{1-6}$ alkyl, $C_{1-6}$ alkyl substituted with one or more $R^{1-1-1}$, $C_{6-20}$ aryl, —C(=O)$R^{11a}$, —C(=O)NR$^{11d1}$R$^{11d2}$, —S(O)$_2$R$^{11f}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, or, "5- to 12-membered heteroaryl containing 1 to 4 heteroatoms independently selected from O, S and N"; provided that when multiple substituents are present, the substituents are the same or different; when the number of $R^{1-4}$ is more than one, two optional $R^{1-4}$, together with the atoms to which they are attached, independently form "3- to 8-membered heterocycle containing 1 to 3 heteroatoms independently selected from O, S and N"; when the number of $R^{1-4}$ is more than one, two optional $R^{1-4}$, together with the atoms to which they are attached, independently form "5- to 12-membered heteroaromatic ring containing 1 to 4 heteroatoms independently selected from O, S and N".

In some embodiments, in $R^{1-4}$, $R^{1-1-1}$ is hydroxyl.

In some embodiments, in $R^{1-4}$, $R^{11a}$ is $C_{1-6}$ alkyl, $C_{3-10}$ cycloalkyl, $C_{1-6}$ alkyl substituted with one or more $R^{1-2-1}$, $C_{3-10}$ cycloalkyl substituted with one or more $R^{1-2-3}$, $C_{6-20}$ aryl, or "5- to 12-membered heteroaryl containing 1 to 4 heteroatoms independently selected from O, S and N"; $R^{1-2-1}$ is independently halogen, hydroxyl or —NR$^{12c}$R$^{12d}$; $R^{12c}$ and $R^{12d}$ are independently hydrogen; $R^{1-2-3}$ is independently $C_{1-6}$ alkyl.

In some embodiments, in $R^{1-4}$, $R^{11d1}$ and $R^{11d2}$ are independently $C_{1-6}$ alkyl, $C_{1-6}$ alkyl substituted with one or more $R^{1-2-1}$, $R^{1-2-1}$ is independently —NR$^{12c}$R$^{12d}$; $R^{12c}$ and $R^{12d}$ are independently $C_{1-6}$ alkyl; or, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with one or more $R^{1-4-1}$; $R^{1-4-1}$ is independently halogen.

In some embodiments, in $R^{1-4}$, $R^{11f}$ is $C_{1-6}$ alkyl.

In some embodiments, in $R^{1-4}$, $R^{1-1-4}$ is oxo.

In some embodiments, $R^{1-5}$ is independently —C(=O)NR$^{11d1}$R$^{11d2}$, $R^{11d1}$ and $R^{11d2}$ are independently $C_{1-6}$ alkyl, or $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N".

In some embodiments, $R^{1-7}$ is independently —C(=O)NR$^{11d1}$R$^{11d2}$, or, when the number of $R^{1-7}$ is more than one, two optional $R^{1-7}$, together with the atoms to which they are attached, independently form "3- to 8-membered heterocyclic containing 1 to 3 heteroatoms independently selected from O, S and N".

In some embodiments, in $R^{1-7}$, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N".

In some embodiments, $R^{1-8}$ is independently —C(=O)R$^{11a}$, —S(O)$_2$R$^{11f}$, —C(=O)NR$^{11d1}$R$^{11d2}$, or, when the number of $R^{1-8}$ is more than one, two optional $R^{1-8}$, together with the atoms to which they are attached, independently form "3- to 8-membered heterocyclic alkene containing 1 to 3 heteroatoms independently selected from O, S and N".

In some embodiments, in $R^{1-8}$, $R^{11a}$ is $C_{1-6}$ alkyl, $C_{3-10}$ cycloalkyl, $C_{1-6}$ alkyl substituted with one or more $R^{1-2-1}$; $R^{1-2-1}$ is independently hydroxyl or —NR$^{12c}$R$^{12d}$; $R^{12c}$ and $R^{12d}$ are independently hydrogen.

In some embodiments, in $R^{1-8}$, $R^{11f}$ is $C_{1-6}$ alkyl.

In some embodiments, in $R^{1-8}$, $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N".

In some embodiments, $R^{1-9}$ is —NR$^{11b1}$R$^{11b2}$, $R^{11b1}$ and $R^{11b2}$ are independently hydrogen or —C(=O)R$^{11h}$; $R^{11h}$ is $C_{1-6}$ alkyl.

In some embodiments, in $R^{1-9}$, $R^{11b1}$ is hydrogen, $R^{11b2}$ is —C(=O)$R^{11h}$; $R^{11h}$ is $C_{1-6}$ alkyl.

In some embodiments, When a and b are a single bond, $A_4$ is $NR^{4a}$, $A_5$ is N.

In some embodiments, when b is a single bond, a is a double bond, $A_4$ is N or $CR^{4d}$, $A_5$ is S or $NR^{5d}$; $R^{4d}$ is hydrogen or halogen.

In some embodiments, when b is a single bond, a is a double bond, $A_4$ is N, $A_5$ is $NR^{5d}$.

In some embodiments, $R^{4a}$ is $C_{1-6}$ alkyl substituted with one or more $R^4$-1; $R^{4-1}$ is hydroxyl or —$OC_{1-6}$ alkyl.

In some embodiments, $L_1$ is a bond or $C_{1-6}$ alkylene; $Q_1$ is hydrogen, cyano, hydroxyl, $C_{1-6}$ alkyl substituted with one or more halogen, $C_{1-6}$ alkyl substituted with one or more hydroxyl, —$OC_{1-6}$ alkyl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl.

In some embodiments, $L_1$ is a bond; $Q_1$ is hydrogen, $C_{3-12}$ cycloalkyl, or $C_{1-6}$ alkyl substituted with one or more halogen.

In some embodiments, $L_1$ is $C_{1-6}$ alkylene, $Q_1$ is hydrogen, cyano, hydroxyl, $C_{1-6}$ alkyl substituted with one or more hydroxyl, —$OC_{1-6}$ alkyl, $C_{6-20}$ aryl substituted with one or more $R^{5-1-2}$ "5- to 12-membered heteroaryl containing 1 to 4 heteroatoms independently selected from O, S and N", or "5- to 12-membered heteroaryl containing 1 to 4 heteroatoms independently selected from O, S and N" substituted with one or more $R^{5-1-3}$.

In some embodiments, $R^{5-1-2}$ is independently halogen.

In some embodiments, $R^{5-1-3}$ is independently $C_{1-6}$ alkyl.

In some embodiments, $A_1$ is N or $CR^1$, $R^1$ is hydrogen, halogen, or $C_{1-6}$ alkyl substituted with one or more $R^{1-1}$; provided that when multiple substituents are present, the substituents are the same or different; $R^{1-1}$ is halogen;

$A_5$ is $NR^{5d}$, $R^{5d}$ is

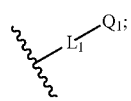

$L_1$ is a bond or $C_{1-6}$ alkylene;

$Q_1$ is $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl.

In some embodiments, in the compound containing structure of a five-membered heteroaromatic ring represented by formula I, $A_1$ is $CR^1$, $A_5$ is $NR^{5d}$ or S; $R^1$ is $C_{1-6}$ alkyl substituted with one or more $R^{1-1}$, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$;

$R^{5d}$ is

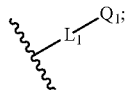

$L_1$ is a bond or $C_{1-6}$ alkylene; $Q_1$ is hydrogen, cyano, hydroxyl, $C_{1-6}$ alkyl substituted with one or more halogen, $C_{1-6}$ alkyl substituted with one or more hydroxyl, —$OC_{1-6}$ alkyl, "5- to 12-membered heteroaryl containing 1 to 4 heteroatoms independently selected from O, S and N" substituted with one or more $R^{5-1-3}$, or $C_{3-12}$ cycloalkyl.

In some embodiments, when the definition of $R^{a1}$, $R^{a2}$, $R^{a3}$, $R^{a-1}$, $R^{a2-1}$, $R^{a2-2}$, $R^{a-1}$, $R^{a-2}$, $R^{a-31}$, $R^{a-32}$, $R^{a-4}$, $R^{a-51}$, $R^{a-52}$, $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{1-1-1-1}$, $R^{1-2-1}$, $R^{1-2-2}$, $R^{1-2-3}$, $R^{1-2-4}$, $R^{1-2-5}$, $R^{1-2-6}$, $R^{1-2-7}$, $R^{1-2-8}$, $R^{1-2-1-1}$, $R^{1-3-1}$, $R^{1-3-2}$, $R^{1-3-3}$, $R^{1-3-4}$, $R^{1-3-5}$, $R^{1-3-6}$, $R^{1-4-1}$, $A_2$, $A_3$, $R^{6-1}$, $R^{4a}$, $R^{4d}$, $Q_1$, $R^{5-1-1}$, $R^{5-1-2}$, $R^{5-1-3}$, $R^{5-1-4}$, $R^{5-1-5}$, $R^{5-1-6}$, $R^{5-1-7}$, $R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$, $R^{51d2}$ and $R^{1-5-1}$ refers to halogen, the halogen is fluorine, chlorine, bromine or iodine.

In some embodiments, when the definition of $R^{a1}$, $R^{a2}$, $R^{a3}$, $R^{a1-1}$, $R^{a2-1}$, $R^{a2-2}$, $R^{a-1}$, $R^{a-2}$, $R^{a-31}$, $R^{a-32}$, $R^{a-4}$, $R^{a-51}$, $R^{a-52}$, $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{1-1-1-1}$, $R^{1a}$, $R^{1b1}$, $R^{1b2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$, $R^{11g}$, $R^{1-2-1}$, $R^{1-2-2}$, $R^{1-2-3}$, $R^{1-2-4}$, $R^{1-2-5}$, $R^{1-2-6}$, $R^{1-2-7}$, $R^{1-2-8}$, $R^{1-2-1-1}$, $R^{1-3-1}$, $R^{1-3-2}$, $R^{1-3-3}$, $R^{1-3-4}$, $R^{1-3-5}$, $R^{1-3-6}$, $R^{1-4-1}$, $R^{6-1}$, $R^{4a}$, $R^{4d}$, $Q_1$, $R^{5-1-1}$, $R^{5-1-2}$, $R^{5-1-3}$, $R^{5-1-4}$, $R^{5-1-5}$, $R^{5-1-6}$, $R^{5-1-7}$, $R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$, $R^{51d2}$ and $R^{1-5-1}$ refers to $C_{1-6}$ alkyl, the $C_{1-6}$ alkyl is $C_{1-4}$ alkyl, for example, methyl, ethyl, n-propyl, isopropyl, n-butyl, sec-butyl, isobutyl or tert-butyl.

In some embodiments, when the definition of $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$, and $R^{11g}$ refers to $C_{3-10}$ cycloalkyl, the $C_{3-10}$ cycloalkyl is $C_{3-6}$ cycloalkyl, for example, cyclohexyl, cyclopentyl, cyclobutyl or cyclopropyl.

In some embodiments, when the definition of $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$, $R^{11g}$ and $Q_1$ refers to $C_{6-20}$ aryl, the $C_{6-20}$ aryl is $C_{6-10}$ aryl, for example, phenyl or naphthyl, for another example, phenyl.

In some embodiments, when $R^{a1}$ is $C_{1-6}$ alkyl substituted with one or more halogen, the $C_{1-6}$ alkyl substituted with one or more halogen is $C_{1-2}$ alkyl substituted with one halogen, for example, —$CH_2F$.

In some embodiments, when $R^{a2}$ and $R^{a3}$, together with the carbon atom to which they are attached form $C_{3-7}$ cycloalkane, the $C_{3-7}$ cycloalkane is $C_{3-6}$ cycloalkane, for example, cyclopropane, cyclobutane or cyclopentane.

In some embodiments, when $R^1$ is $C_{1-6}$ alkyl substituted with one or more $R^{1-1}$, the more is two or three.

In some embodiments, when $R^1$ is $C_{1-6}$ alkyl substituted with one or more $R^{1-1}$ and $R^{1-1}$ is halogen, the $R^1$ is $C_{1-2}$ alkyl substituted with two or three halogen, for example, $-CF_3$.

In some embodiments, when $R^{1-1}$ is independently "4- to 10-membered heterocycloalkyl containing 1 to 3 heteroatoms independently selected from O, S and N" substituted with one or more $R^{1-1-4}$, the "4- to 10-membered heterocycloalkyl containing 1 to 3 heteroatoms independently selected from O, S and N" substituted with one or more $R^{1-1-4}$ is monocyclic or bridged cycloalkyl. When the "4- to 10-membered heterocycloalkyl containing 1 to 3 heteroatoms independently selected from O, S and N" is monocyclic, the "4- to 10-membered heterocycloalkyl containing 1 to 3 heteroatoms independently selected from O, S and N" is "5- to 6-membered heterocycloalkyl containing 1 to 2 heteroatoms being N", for example,

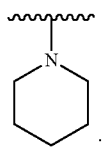

When the "4- to 10-membered heterocycloalkyl containing 1 to 3 heteroatoms independently selected from O, S and N" is bridged cycloalkyl, the "4- to 10-membered heterocycloalkyl containing 1 to 3 heteroatoms independently selected from O, S and N" is "8- to 10-membered heterocycloalkyl containing 1 to 2 heteroatoms being N", for example,

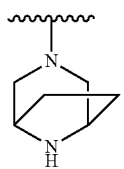

In some embodiments, when $R^1$ is "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-4}$, the "4- to 12-membered heterocycloalkyl containing 1 to 3 heteroatoms independently selected from O, S and N" and the "4- to 12-membered heterocycloalkyl containing 1 to 3 heteroatoms independently selected from O, S and N" in the "4- to 12-membered heterocycloalkyl containing 1 to 3 heteroatoms independently selected from O, S and N" substituted with one or more $R^{1-4}$ is monocyclic heteroalkyl, spirocyclic heteroalkyl, fused heteroalkyl or bridged cycloalkyl. The monocyclic heteroalkyl can be "4- to 6-membered heterocycloalkyl containing 1 to 2 heteroatoms independently selected from O and N", for example,

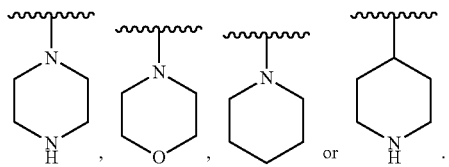

The spirocyclic heteroalkyl can be "8- to 11-membered heterocycloalkyl containing 1 to 2 heteroatoms independently selected from O and N", for example,

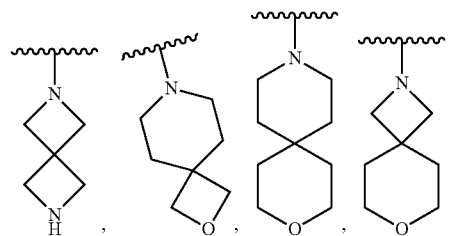

The fused heteroalkyl can be "8- to 11-membered heterocycloalkyl containing 1 to 2 heteroatoms independently selected from O and N", for example,

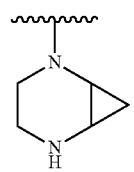

The bridged cycloalkyl can be "8- to 11-membered heterocycloalkyl containing 1 to 2 heteroatoms independently selected from O and N", for example,

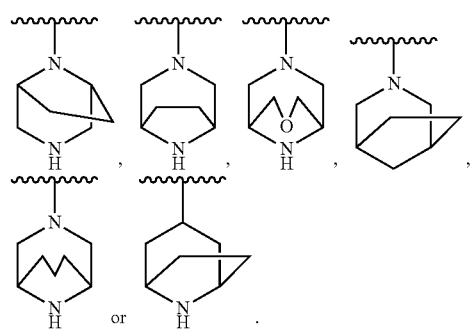

In some embodiments, when $R^1$ is "4- to 12-membered heterocycloalkyl containing 1 to 3 heteroatoms independently selected from O, S and N" substituted with one or more $R^{1-4}$, the "4- to 12-membered heterocycloalkyl containing 1 to 3 heteroatoms independently selected from O, S and N" substituted with one or more $R^{1-4}$ is "6-membered heterocycloalkyl containing 1 to 3 heteroatoms independently selected from O, S and N" substituted with one or more $R^{1-4}$, preferably, "6-membered heterocycloalkyl containing 2 heteroatoms independently selected from O and N" substituted with one or more $R^{1-4}$ (for example,

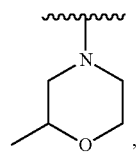 [SMILES: *N1CCOC(C)C1]

for another example,

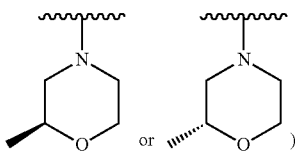

or )

or "6-membered heterocycloalkyl containing 1 heteroatom being N" substituted with one or more $R^{1-4}$ (for example N

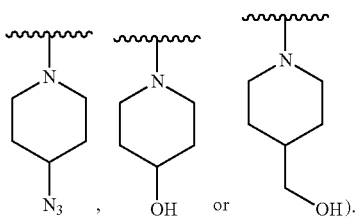

In some embodiments, in $R^{1-3}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "3- to 6-membered heterocyclic alkane containing 1 heteroatom being N (for example,

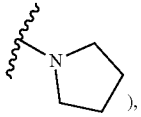

), or, 3- to 6-membered heterocyclic alkane containing 2 heteroatoms being N and O".

In some embodiments, when $R^{1-4}$ is "4- to 10-membered heterocycloalkyl containing 1 to 3 heteroatoms independently selected from O, S and N" substituted with one or more $R^{1-1-4}$, the "4- to 10-membered heterocycloalkyl containing 1 to 3 heteroatoms independently selected from O, S and N" substituted with one or more $R^{1-1-4}$ is "4- to 6-membered heterocycloalkyl containing 1 heteroatom being N".

In some embodiments, in $R^{1-5}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "3- to 6-membered heterocyclic alkane containing 1 heteroatom being N, or, 3- to 6-membered heterocyclic alkane containing 2 heteroatoms being N and O".

In some embodiments, when $R^1$ is "5- to 12-membered heteroaryl containing 1 to 4 heteroatoms independently selected from O, S and N", or "5- to 12-membered heteroaryl containing 1 to 4 heteroatoms independently selected from O, S and N" substituted with $R^{1-6}$, the "5- to 12-membered heteroaryl containing 1 to 4 heteroatoms independently selected from O, S and N" and "5- to 12-membered heteroaryl containing 1 to 4 heteroatoms independently selected from O, S and N" in the "5- to 12-membered heteroaryl containing 1 to 4 heteroatoms independently selected from O, S and N" substituted with $R^{1-6}$ are "5- to 9-membered heteroaryl containing 1 to 3 heteroatoms independently selected from O, S and N", for example,

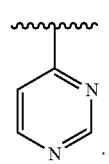

In some embodiments, when the number of $R^{1-4}$ is more than 1, two optional $R^{1-4}$, together with the atoms to which they are attached, independently form "5- to 12-membered heteroaromatic ring containing 1 to 4 heteroatoms independently selected from O, S and N", the two optional $R^{1-4}$ are on the adjacent atoms.

In some embodiments, when two optional $R^{1-4}$ are on the adjacent atoms, together with the atoms to which they are attached, independently form "5- to 12-membered heteroaromatic ring containing 1 to 4 heteroatoms independently selected from O, S and N", the "5- to 12-membered heteroaromatic ring containing 1 to 4 heteroatoms independently selected from O, S and N" is "5- to 6-membered heteroaromatic ring containing 1 to 2 heteroatoms independently selected from O, S and N", for example,

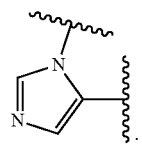

The "5- to 12-membered heteroaromatic ring containing 1 to 4 heteroatoms independently selected from O, S and N" substituted with one or more $R^{1-4}$ is

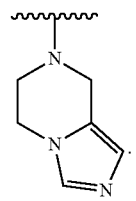

In some embodiments, in $R^{1-4}$, when $R^{11a}$ is $C_{1-6}$ alkyl substituted with one or more $R^{1-2-1}$, the more is two or three.

In some embodiments, in $R^{1-4}$, when $R^{11a}$ is $C_{1-6}$ alkyl substituted with one or more $R^{1-2-1}$, $R^{1-2-1}$ is halogen, the $R^{11a}$ is $C_{1-2}$ alkyl substituted with one or more halogen, for example, trifluoromethyl or trifluoroethyl.

In some embodiments, in $R^{1-4}$, when $R^{11a}$ is "5- to 12-membered heteroaryl containing 1 to 4 heteroatoms independently selected from O, S and N", the "5- to 12-membered heteroaryl containing 1 to 4 heteroatoms independently selected from O, S and N" is "5- to 6-membered heteroaryl containing 1 to 2 heteroatoms independently selected from O, S and N", for example, pyridinyl.

In some embodiments, in $R^{1-4}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with $R^{1-1-4}$, the "3- to 8-membered heterocyclic alkane containing 1 to 3 heteroatoms, wherein, one heteroatom is N, the other one or two heteroatoms independently selected from O, S and N" is "4- to 6-membered heterocyclic alkane containing 1 heteroatom being N". For example, the $-C(=O)NR^{11d1}R^{11d2}$ is

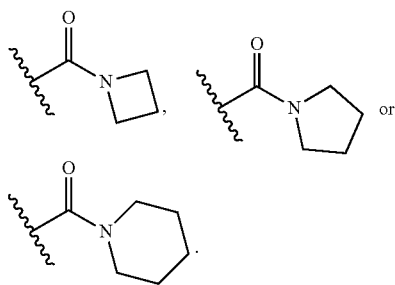

In some embodiments, in $R^{1-7}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "4- to 6-membered heterocyclic alkane containing 1 heteroatom being N".

In some embodiments, when $R^1$ is "5- to 7-membered heterocycloalkenyl containing 1 to 3 heteroatoms independently selected from O, S and N" substituted with one or more $R^{1-8}$, or "5- to 7-membered heterocycloalkenyl containing 1 to 3 heteroatoms independently selected from O, S and N" substituted with one or more $R^{1-8}$, the "5- to 7-membered heterocycloalkenyl containing 1 to 3 heteroatoms independently selected from O, S and N" is monocyclic or bridged heterocycloalkenyl.

In some embodiments, when $R^1$ is $C_{2-6}$ alkynyl substituted with one or more $R^{1-9}$, the $C_{2-6}$ alkynyl is $C_{2-3}$ alkynyl, for example, ethynyl, propynyl or propargyl.

In some embodiments, when $Q_1$ is $C_{1-6}$ alkyl substituted with one or more halogen, the $Q_1$ is $C_{1-2}$ alkyl substituted with 2 to 3 halogen, preferably $C_{1-2}$ alkyl substituted with 2 to 3 fluorine, for example, $-CF_3$ or $-CH_2CF_3$.

In some embodiments, when $Q_1$ is $C_{1-6}$ alkyl substituted with one or more hydroxyl, the $Q_1$ is $C_{1-2}$ alkyl substituted with 1 to 3 hydroxyl.

In some embodiments, when $Q_1$ is "5- to 12-membered heteroaryl containing 1 to 4 heteroatoms independently selected from O, S and N", or "5- to 12-membered heteroaryl containing 1 to 4 heteroatoms independently selected from O, S and N" substituted with one or more $R^{5-1-3}$ the "5- to 12-membered heteroaryl containing 1 to 4 heteroatoms independently selected from O, S and N" is "5- to 9-membered heteroaryl containing 1 to 2 heteroatoms independently selected from S and N".

In some embodiments, when $Q_1$ is $C_{3-12}$ cycloalkyl, the $C_{3-12}$ cycloalkyl is $C_{3-6}$ cycloalkyl, for example, Cyclopropyl, cyclobutyl, cyclopentyl or cyclohexyl.

In some embodiments, when $R^1$ and $R^{5d}$, together with the atoms to which they are attached form "5- to 12-membered heterocyclic olefin containing 1 to 3 heteroatoms independently selected from O, S and N"; the "5- to 12-membered heterocyclic olefin containing 1 to 3 heteroatoms independently selected from O, S and N" is "5- to 7-membered heterocyclic olefin containing 1 to 2 heteroatoms independently selected from O and N", for example, "5- to 7-membered heterocyclic olefin containing 2 heteroatoms being N", for example,

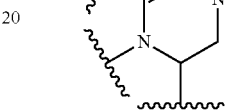

In some embodiments, when $L_1$ is $C_{1-6}$ alkylene, the $C_{1-6}$ alkylene is $-CH_2-$, $-CH_2CH_2-$, $-CH_2CH_2CH_2-$, $-CH(CH_3)CH_2-$, $-CH_2CH_2CH_2CH_2-$, $-CH(CH_3)CH_2CH_2-$, $-CH_2CH(CH_3)CH_2-$ or $-C(CH_3)_2CH_2-$.

In some embodiments,

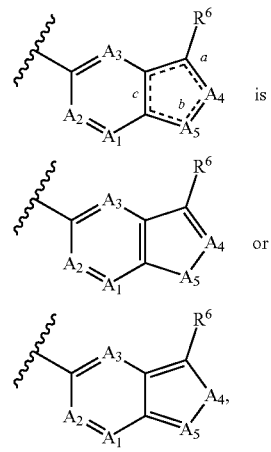

preferably

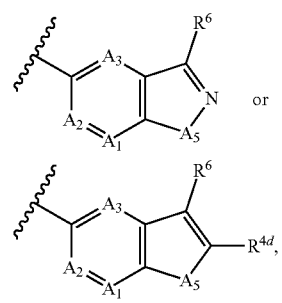

for example,
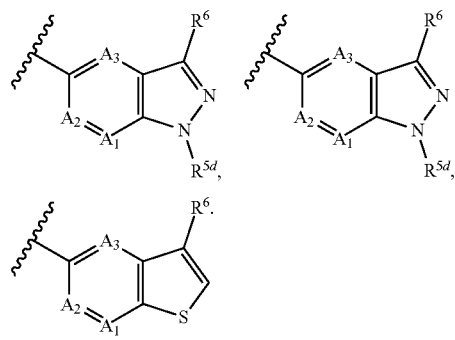
In some embodiments, $A_2$ is CH or CF.
In some embodiments, $A_3$ is N, CH or CF.
In some embodiments, $A_1$ is $CR^1$; $R^1$ is hydrogen, —F, —$CF_3$,
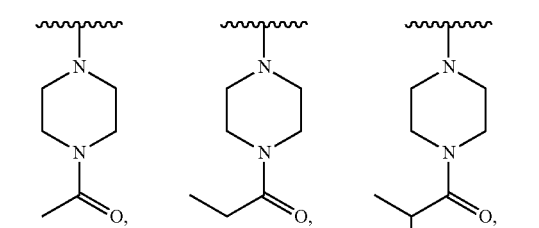
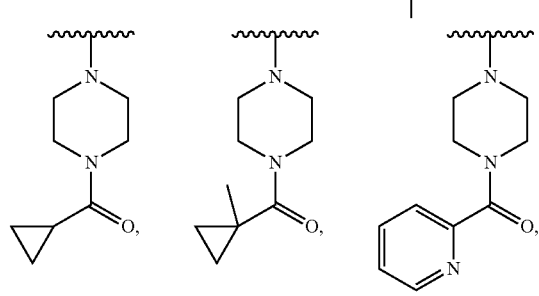
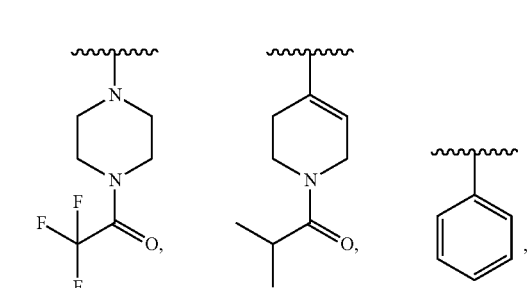
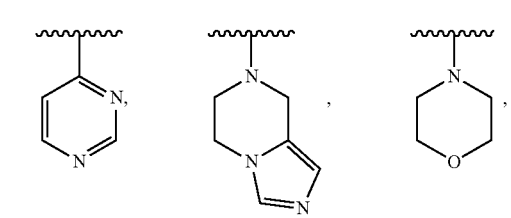
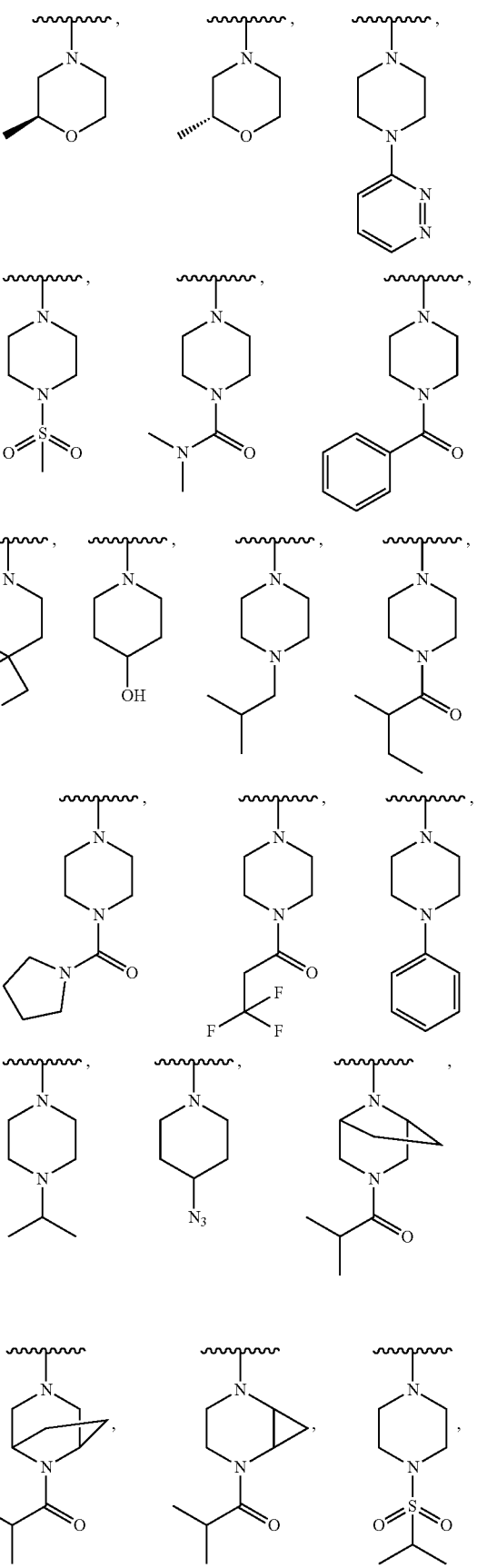

-continued
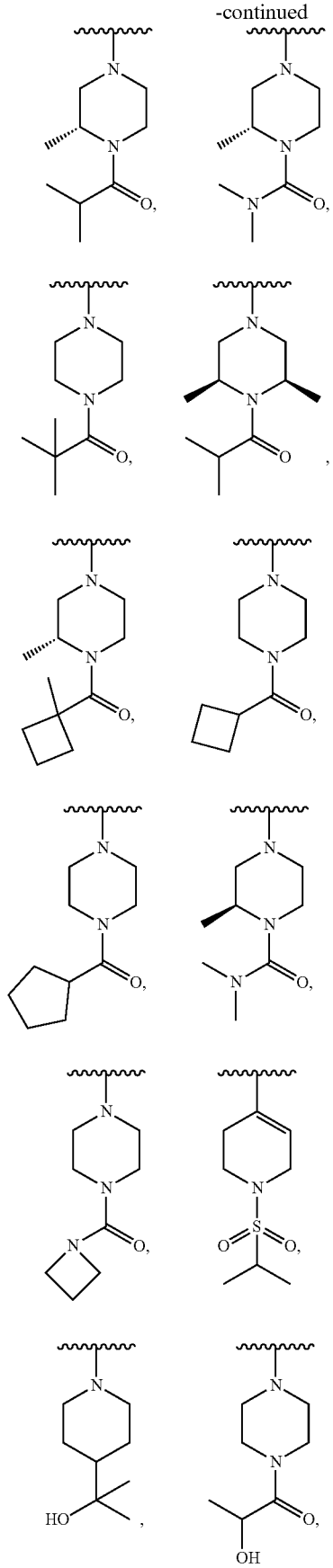
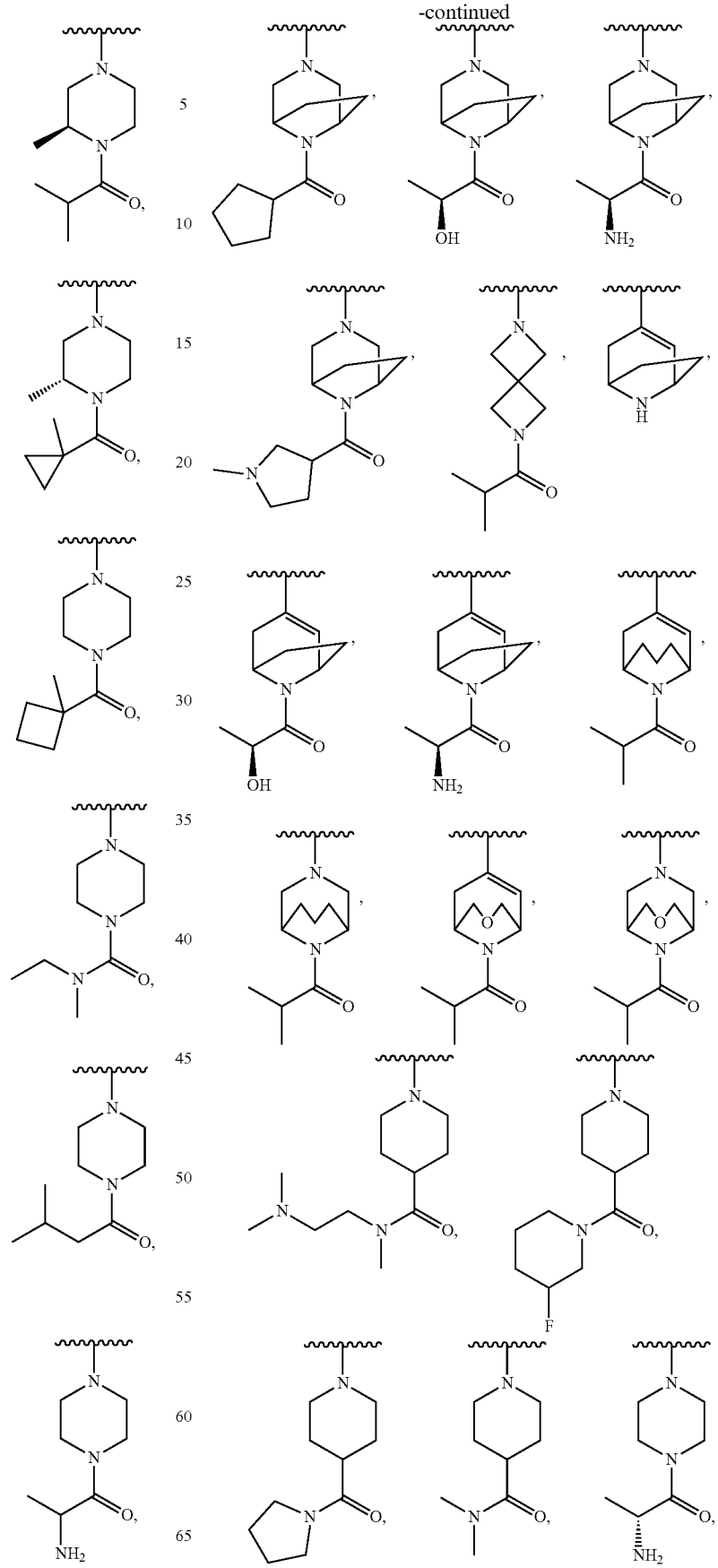

-continued
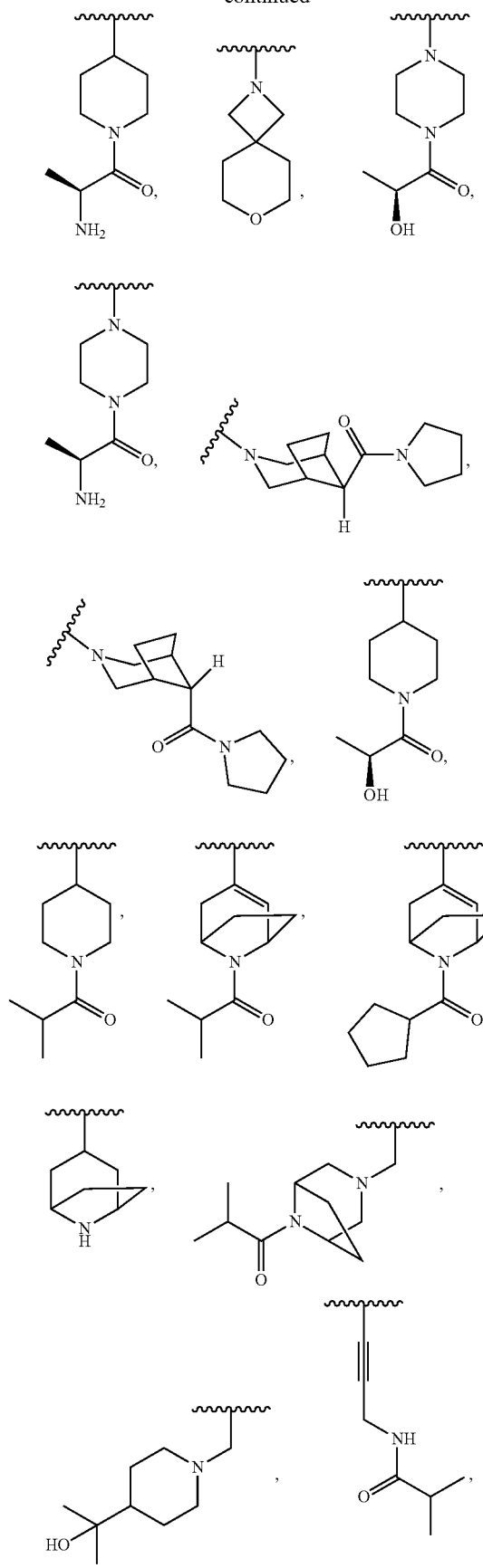
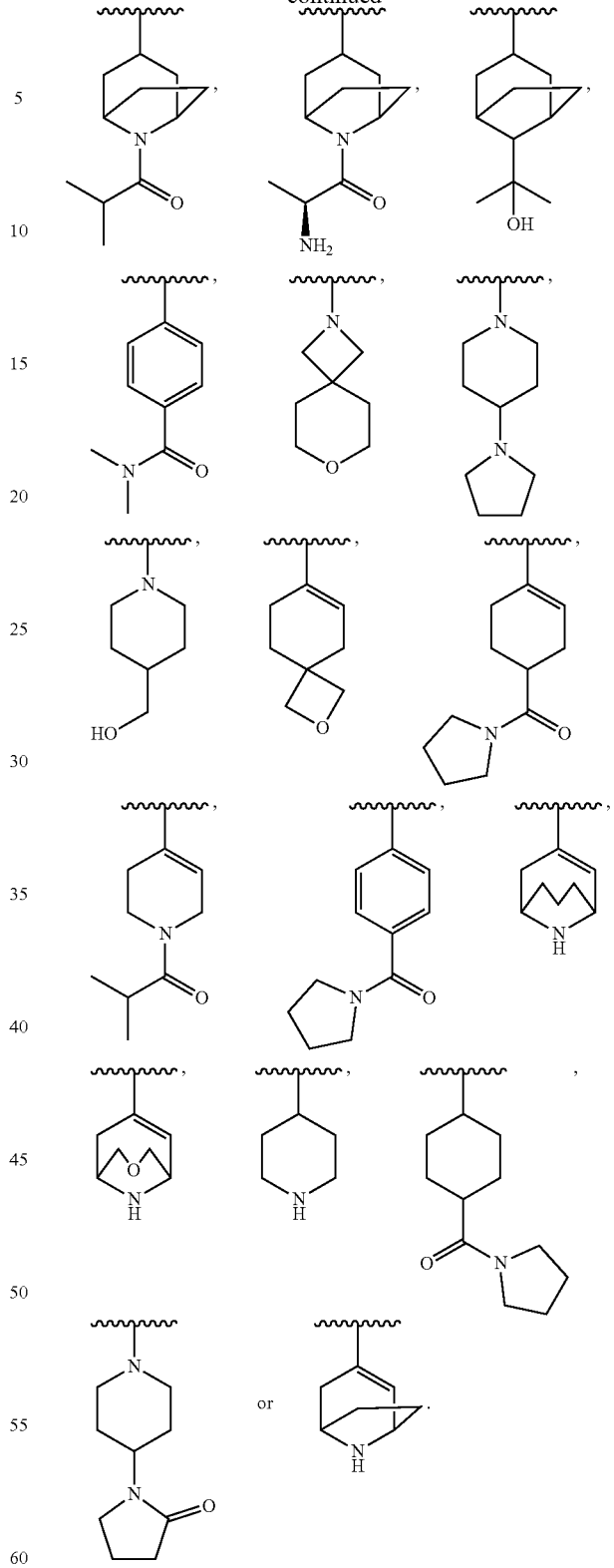
In some embodiments, $A_1$ is $CR^1$, $A_2$ is CH, $A_3$ is CH or CF.
In some embodiments, $A_1$ is N, $A_2$ is CH, $A_3$ is CH.
In some embodiments, $A_4$ is N or $CR^{4d}$.
In some embodiments, $R^{4d}$ is hydrogen or chloride.

In some embodiments, when a and b are a single bond, $A_4$ is $NR^{4a}$, $A_5$ is N.

In some embodiments, $A_5$ is S or $NR^{5d}$; $R^{5d}$ is H, —$CH_3$,

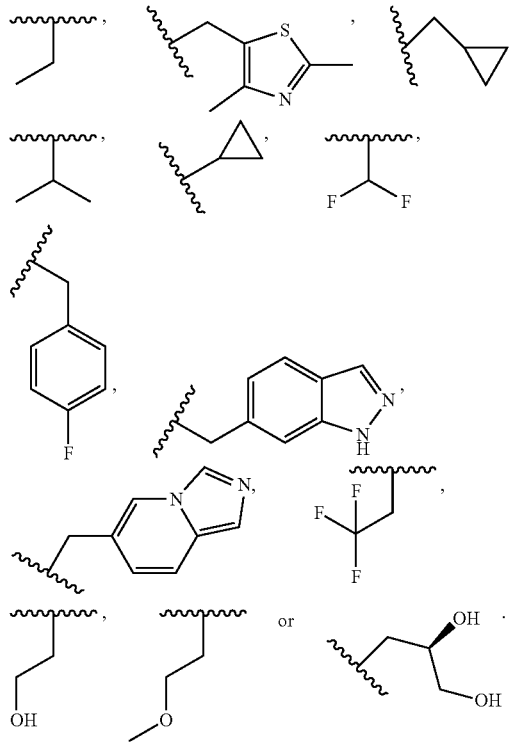

In some embodiments, $R^6$ is

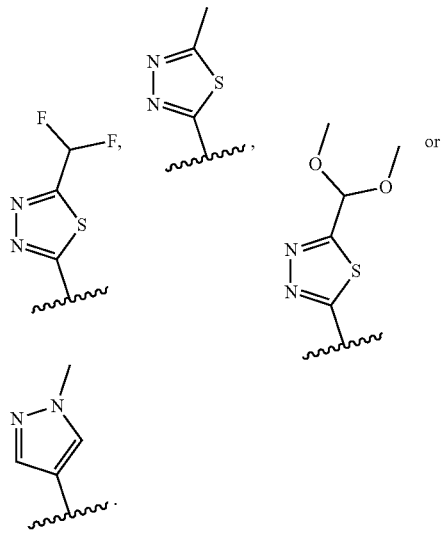

In some embodiments, the compound containing structure of a five-membered heteroaromatic ring represented by formula I as described above, a pharmaceutically acceptable salt thereof, a stereoisomer thereof, an isomer thereof or an isotopic compound thereof, wherein, compound containing structure of a five-membered heteroaromatic ring represented by formula I is defined as solution 1, solution 2 or solution 3;

solution 1: A compound containing structure of a five-membered heteroaromatic ring represented by formula IV, a pharmaceutically acceptable salt thereof, a stereoisomer thereof, an isomer thereof or an isotopic compound thereof,

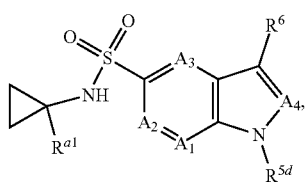

IV

Wherein, $R^{a1}$ is hydrogen, halogen, cyano, $C_{1-6}$ alkyl, $C_{2-6}$ alkenyl, $C_{2-6}$ alkynyl, —$OR^{a-1}$, —$C(=O)R^{a-2}$, —$NR^{a-31}R^{a-32}$, —$C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

$A_1$ is N or $CR^1$;

$R^1$ is hydrogen, $C_{1-6}$ alkyl substituted with one or more $R^{1-1}$, halogen, $C_{3-10}$ cycloalkyl, $C_{3-10}$ cycloalkyl substituted with one or more $R^{1-3}$, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N" or "5- to 7-membered heterocycloalkenyl containing 1 to 3 heteroatoms independently selected from O, S and N" substituted with one or more $R^{1-8}$; provided that when multiple substituents are present, the substituents are the same or different;

$R^{1-1}$, $R^{1-3}$, $R^{1-4}$, $R^{1-5}$, $R^{1-6}$, $R^{1-7}$ and $R^{1-8}$ are independently halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, —$C(=O)R^{11a}$, —$NR^{11b1}R^{11b2}$, —$C(=O)OR^{11c}$, —$C(=O)NR^{11d1}R^{11d2}$, —$S(O)_2NR^{11e1}R^{11e2}$, —$S(O)_2R^{11f}$, $C_{3-10}$ cycloalkyl, $C_{3-10}$ cycloalkyl substituted with one or more $R^{1-1-3}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-1-8}$; provided that when multiple substituents are present, the substituents are the same or different;

$R^{1\text{-}1\text{-}1}$, $R^{1\text{-}1\text{-}2}$, $R^{1\text{-}1\text{-}3}$, $R^{1\text{-}1\text{-}4}$, $R^{1\text{-}1\text{-}5}$, $R^{1\text{-}1\text{-}6}$, $R^{1\text{-}1\text{-}7}$ and $R^{1\text{-}1\text{-}8}$ are independently halogen, hydroxyl, oxo, $C_{1\text{-}6}$ alkyl, or, $C_{1\text{-}6}$ alkyl substituted with one or more $R^{1\text{-}1\text{-}1\text{-}1}$; provided that when multiple substituents are present, the substituents are the same or different;

$R^{1\text{-}1\text{-}1\text{-}1}$ is halogen, hydroxyl, $-OC_{1\text{-}6}$ alkyl or $-NR^aR^b$, $R^a$ and $R^b$ are independently hydrogen or $C_{1\text{-}6}$ alkyl;

$R^{1a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen, $C_{1\text{-}6}$ alkyl, $C_{1\text{-}6}$ alkyl substituted with one or more $R^{1\text{-}2\text{-}1}$, $-OC_{1\text{-}6}$ alkyl, $-OC_{1\text{-}6}$ alkyl substituted with one or more $R^{1\text{-}2\text{-}2}$, $C_{3\text{-}10}$ cycloalkyl, $C_{3\text{-}10}$ cycloalkyl substituted with one or more $R^{1\text{-}2\text{-}3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1\text{-}2\text{-}4}$, $C_{6\text{-}20}$ aryl, $C_{6\text{-}20}$ aryl substituted with one or more $R^{1\text{-}2\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1\text{-}2\text{-}6}$, $C_{5\text{-}7}$ cycloalkenyl, $C_{5\text{-}7}$ cycloalkenyl substituted with one or more $R^{1\text{-}2\text{-}7}$, "5- to 7-membered heterocycloalkenyl containing 1 to 3 heteroatoms independently selected from O, S and N", or "5- to 7-membered heterocycloalkenyl containing 1 to 3 heteroatoms independently selected from O, S and N" substituted with one or more $R^{1\text{-}2\text{-}8}$; provided that when multiple substituents are present, the substituents are the same or different;

$R^{1\text{-}2\text{-}1}$, $R^{1\text{-}2\text{-}2}$, $R^{1\text{-}2\text{-}3}$, $R^{1\text{-}2\text{-}4}$, $R^{1\text{-}2\text{-}5}$, $R^{1\text{-}2\text{-}6}$, $R^{1\text{-}2\text{-}7}$ and $R^{1\text{-}2\text{-}8}$ are independently halogen, oxo, $C_{1\text{-}6}$ alkyl, $C_{1\text{-}6}$ alkyl substituted with one or more $R^{1\text{-}2\text{-}1\text{-}1}$; provided that when multiple substituents are present, the substituents are the same or different;

$R^{1\text{-}2\text{-}1\text{-}1}$ is independently halogen, hydroxyl, $-OC_{1\text{-}6}$ alkyl or $-NR^cR^d$, $R^c$ and $R^d$ are independently hydrogen or $C_{1\text{-}6}$ alkyl;

Or, when the number of $R^{1\text{-}3}$, $R^{1\text{-}4}$, $R^{1\text{-}5}$, $R^{1\text{-}6}$, $R^{1\text{-}7}$, $R^{1\text{-}8}$, $R^{1\text{-}1\text{-}3}$, $R^{1\text{-}1\text{-}4}$, $R^{1\text{-}1\text{-}5}$, $R^{1\text{-}1\text{-}6}$, $R^{1\text{-}1\text{-}7}$, $R^{1\text{-}1\text{-}8}$, $R^{1\text{-}2\text{-}3}$, $R^{1\text{-}2\text{-}4}$, $R^{1\text{-}2\text{-}5}$, $R^{1\text{-}2\text{-}6}$, $R^{1\text{-}2\text{-}7}$ or $R^{1\text{-}2\text{-}8}$ is more than one, two optional $R^{1\text{-}3}$, two optional $R^{1\text{-}4}$, two optional $R^{1\text{-}5}$, two optional $R^{1\text{-}6}$, two optional $R^{1\text{-}7}$, two optional $R^{1\text{-}8}$, two optional $R^{1\text{-}1\text{-}3}$, two optional $R^{1\text{-}1\text{-}4}$, two optional $R^{1\text{-}1\text{-}5}$, two optional $R^{1\text{-}1\text{-}6}$, two optional $R^{1\text{-}1\text{-}7}$, two optional $R^{1\text{-}1\text{-}8}$, two optional $R^{1\text{-}2\text{-}3}$, two optional $R^{1\text{-}2\text{-}4}$, two optional $R^{1\text{-}2\text{-}5}$, two optional $R^{1\text{-}2\text{-}6}$, two optional $R^{1\text{-}2\text{-}7}$ or two optional $R^{1\text{-}2\text{-}8}$, together with the atoms to which they are attached, independently form 3- to 8-membered carbon ring, "3- to 8-membered carbon ring" substituted with one or more $R^{1\text{-}3\text{-}1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1\text{-}3\text{-}2}$, $C_{6\text{-}20}$ aromatic ring, $C_{6\text{-}20}$ aromatic ring substituted with one or more $R^{1\text{-}3\text{-}3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1\text{-}3\text{-}4}$, $C_{5\text{-}7}$ cyclic olefin, $C_{5\text{-}7}$ cyclic olefin substituted with one or more $R^{1\text{-}3\text{-}5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1\text{-}3\text{-}6}$; provided that when multiple substituents are present, the substituents are the same or different;

$R^{1\text{-}3\text{-}1}$, $R^{1\text{-}3\text{-}2}$, $R^{1\text{-}3\text{-}3}$, $R^{1\text{-}3\text{-}4}$, $R^{1\text{-}3\text{-}5}$ and $R^{1\text{-}3\text{-}6}$ are independently oxo, hydroxyl, halogen, $C_{1\text{-}6}$ alkyl, $C_{1\text{-}6}$ alkyl substituted with one or more halogen, $-OC_{1\text{-}6}$ alkyl, or, $-OC_{1\text{-}6}$ alkyl substituted with one or more halogen;

or, $R^{a\text{-}31}$ and $R^{a\text{-}32}$, $R^{a\text{-}51}$ and $R^{a\text{-}52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1\text{-}4\text{-}1}$;

$R^{1\text{-}4\text{-}1}$ is independently oxo, hydroxyl, halogen, $C_{1\text{-}6}$ alkyl, $C_{1\text{-}6}$ alkyl substituted with one or more halogen, $-OC_{1\text{-}6}$ alkyl, or, $-OC_{1\text{-}6}$ alkyl substituted with one or more halogen;

$A_2$ and $A_3$ are independently are N or $CR^2$, $R^2$ is hydrogen or halogen;

$A_4$ is N or $R^{4d}$;

$R^{4d}$ is hydrogen, halogen, $C_{1\text{-}6}$ alkyl, $C_{1\text{-}6}$ alkyl substituted with one or more halogen;

$R^{5d}$ are independently

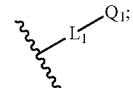

$L_1$ is a bond or $C_{1\text{-}6}$ alkylene;

$Q_1$ is hydrogen, halogen, cyano, $C_{2\text{-}6}$ alkenyl, $C_{2\text{-}6}$ alkynyl, hydroxyl, $-C(=O)R^{52a}$, $-NR^{52b1}R^{52b2}$, $-C(=O)OR^{52c}$, $-C(=O)NR^{52d1}R^{52d2}$, $C_{1\text{-}6}$ alkyl substituted with one or more halogen, $-OC_{1\text{-}6}$ alkyl, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5\text{-}1\text{-}3}$, $C_{3\text{-}12}$ cycloalkyl, $C_{3\text{-}12}$ cycloalkyl substituted with one or more $R^{5\text{-}1\text{-}4}$, "4- to 12-membered heterocycloalkyl containing 1 to 3 heteroatoms independently selected from O, S and N" or "4- to 12-membered heterocycloalkyl containing 1 to 3 heteroatoms independently selected from O, S and N" substituted with one or more $R^{5\text{-}1\text{-}5}$; provided that when multiple substituents are present, the substituents are the same or different;

$R^{5\text{-}1\text{-}3}$, $R^{5\text{-}1\text{-}4}$ and $R^{5\text{-}1\text{-}5}$ are independently halogen, hydroxyl, oxo, cyano, $C_{1\text{-}6}$ alkyl, $C_{1\text{-}6}$ alkyl substituted with one or more halogen, $-OC_{1\text{-}6}$ alkyl, $-OC_{1\text{-}6}$ alkyl substituted with one or more halogen, $-C(=O)R^{51a}$, $-NR^{51b1}R^{51b2}$, $-C(=O)OR^{51c}$, or $-C(=O)NR^{51d1}R^{51d2}$; provided that when multiple substituents are present, the substituents are the same or different;

$R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1\text{-}6}$ alkyl, or, $C_{1\text{-}6}$ alkyl substituted with one or more halogen;

or, $R^{52b1}$ and $R^{52b2}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$;

$R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different;

$R^6$ is independently "5-membered heteroaryl containing 1 to 4 heteroatoms independently selected from O, S and N", or "5-membered heteroaryl containing 1 to 4 heteroatoms independently selected from O, S and N" substituted with one or more $R^{6-1}$;

$R^{6-1}$ is $C_{1-6}$ alkyl, or $C_{1-6}$ alkyl substituted with one or more halogen.

Solution 2: A compound containing structure of a five-membered heteroaromatic ring represented by formula IV', a pharmaceutically acceptable salt thereof, a stereoisomer thereof, an isomer thereof or an isotopic compound thereof,

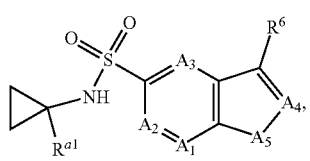

IV'

$R^{a1}$ is hydrogen, halogen, cyano, $C_{1-6}$ alkyl, $C_{2-6}$ alkenyl, $C_{2-6}$ alkynyl, —$OR^{a-1}$, —$C(=O)R^{a-2}$, —$NR^{a-31}R^{a-32}$, —$C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

$A_1$ is N or $CR^1$;

$R^1$ is hydrogen, $C_{1-6}$ alkyl, $C_{1-6}$ alkyl substituted with one or more $R^{1-1}$, halogen, $C_{3-10}$ cycloalkyl, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", or "5- to 7-membered heterocycloalkenyl containing 1 to 3 heteroatoms independently selected from O, S and N" substituted with one or more $R^{1-8}$; provided that when multiple substituents are present, the substituents are the same or different;

$R^{1-1}$, $R^{1-3}$, $R^{1-4}$, $R^{1-5}$, $R^{1-6}$, $R^{1-7}$ and $R^{1-8}$ are independently azide, halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, —$C(=O)R^{11a}$, —$NR^{11b1}R^{11b2}$, —$C(=O)OR^{11c}$, —$C(=O)NR^{11d1}R^{11d2}$, —$S(O)_2NR^{11e1}R^{11e2}$, —$S(O)_2R^{11f}$, $C_{3-10}$ cycloalkyl, $C_{3-10}$ cycloalkyl substituted with one or more $R^{1-1-3}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from 0, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, hydroxyl, oxo, $C_{1-6}$ alkyl, or, $C_{1-6}$ alkyl substituted with one or more $R^{1-1-1-1}$; provided that when multiple substituents are present, the substituents are the same or different;

$R^{1-1-1-1}$ is halogen, hydroxyl, —$OC_{1-6}$ alkyl or —$NR^aR^b$, $R^a$ and $R^b$ are independently hydrogen or $C_{1-6}$ alkyl;

$R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen, $C_{1-6}$ alkyl, $C_{1-6}$ alkyl substituted with one or more $R^{1-2-1}$, —$OC_{1-6}$ alkyl, —$OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", or, "5- to 7-membered heterocycloalkenyl containing 1 to 3 heteroatoms independently selected from O, S and N" substituted with one or more $R^{1-2-8}$; provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, hydroxyl, —$NR^{12c}R^{12d}$, oxo, $C_{1-6}$ alkyl, $C_{1-6}$ alkyl substituted with one or more $R^{1-2-1-1}$; $R^{12c}$ and $R^{12d}$ are independently hydrogen or $C_{1-6}$ alkyl; provided that when multiple substituents are present, the substituents are the same or different;

$R^{1-2-1-1}$ is independently halogen, hydroxyl, —$OC_{1-6}$ alkyl or —$NR^cR^d$, $R^c$ and $R^d$ are independently hydrogen or $C_{1-6}$ alkyl;

or, when the number of $R^{1-3}$, $R^{1-4}$, $R^{1-5}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-5}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3- to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aromatic ring, $C_{6-20}$ aromatic ring substituted with one or more $R^{1-3-3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1-3-4}$, $C_{5-7}$ cyclic olefin, $C_{5-7}$ cyclic olefin substituted with one or more $R^{1-3-5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1-3-6}$; provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen; or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-4-1}$; $R^{1-4-1}$ is independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen;

$A_2$ and $A_3$ are independently are N or $CR^2$, $R^2$ is hydrogen or halogen;

$A_4$ is N or $CR^{4d}$;

$R^{4d}$ is hydrogen, halogen, $C_{1-6}$ alkyl or $C_{1-6}$ alkyl substituted with one or more halogen;

$A_5$ is S or $NR^{5d}$;

$R^{5d}$ is independently

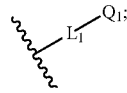

$L_1$ is a bond or $C_{1-6}$ alkylene;

$Q_1$ is hydrogen, halogen, cyano, $C_{2-6}$ alkenyl, $C_{2-6}$ alkynyl, hydroxyl, —$C(=O)R^{2a}$, —$NR^{52b1}R^{52b2}$, —$C(=O)OR^{52c}$, —$C(=O)NR^{52d1}R^{52d2}$, $C_{1-6}$ alkyl substituted with one or more halogen, —$OC_{1-6}$ alkyl, $C_{6-20}$ aryl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, $C_{3-12}$ cycloalkyl, $C_{3-12}$ cycloalkyl substituted with one or more $R^{5-1-4}$, "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{5-1-5}$; provided that when multiple substituents are present, the substituents are the same or different;

$R^{5-1-2}$, $R^{5-1-3}$, $R^{5-1-4}$ and $R^{5-1-5}$ are independently halogen, hydroxyl, oxo, cyano, $C_{1-6}$ alkyl, $C_{1-6}$ alkyl substituted with one or more halogen, —$OC_{1-6}$ alkyl, —$OC_{1-6}$ alkyl substituted with one or more halogen, —$C(=O)R^{51a}$, —$NR^{51b1}R^{51b2}$, —$C(=O)OR^{51c}$, or, —$C(=O)NR^{51d1}R^{51d2}$; provided that when multiple substituents are present, the substituents are the same or different;

$R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b2}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$;

$R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different;

$R^6$ is independently "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$;

$R^{6-1}$ is $C_{1-6}$ alkyl, or, $C_{1-6}$ alkyl substituted with one or more halogen.

Solution 3: A compound containing structure of a five-membered heteroaromatic ring represented by formula IV'', a pharmaceutically acceptable salt thereof, a stereoisomer thereof, an isomer thereof or an isotopic compound thereof,

IV''

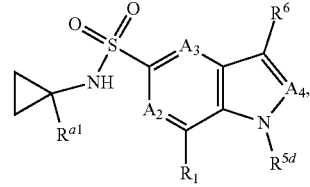

$R^{a1}$ is hydrogen, halogen, cyano, $C_{1-6}$ alkyl, $C_{2-6}$ alkenyl, $C_{2-6}$ alkynyl, —$OR^{a-1}$, —$C(=O)R^{a-2}$, —$NR^{a-31}R^{a-32}$, $C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

$R^1$ is $C_{3-10}$ cycloalkyl, $C_{3-10}$ cycloalkyl substituted with one or more $R^{1-3}$, 4- to 12-membered heterocycloalkyl containing 1 to 3 heteroatoms independently selected from O, S and N, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$; Provided that when multiple substituents are present, the substituents are the same or different;

$R^{1-3}$, $R^{1-4}$, $R^{1-5}$, $R^{1-6}$, $R^{1-7}$ and $R^{1-8}$ are independently halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, $C(=O)R^{11a}$, —$NR^{11b1}R^{11b2}$, —$C(=O)OR^{11c}$, —$C(=O)NR^{11d1}R^{11d2}$, —$S(O)_2NR^{11e1}$, $R^{11e2}$ $C_{3-10}$ cycloalkyl, $C_{3-10}$ cycloalkyl substituted with one or more $R^{1-1-3}$, 4- to 10-membered heterocycloalkyl containing 1 to 3 heteroatoms independently selected from O, S and N, "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-1-8}$; provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, oxo, $C_{1-6}$ alkyl, or, $C_{1-6}$ alkyl substituted with one or more $R^{1-1-1-1}$; Provided that when multiple substituents are present, the substituents are the same or different;

$R^{1-1-1-1}$ is independently halogen, hydroxyl, $C_{1-6}$ alkyO— or —$NR^aR^b$, $R^a$ and $R^b$ are independently hydrogen or $C_{1-6}$ alkyl;

$R^{11a}$, $R^{11b1}$, $R^{11b2}$, $R^{11c}$, $R^{11d1}$, $R^{11d2}$, $R^{11e1}$ and $R^{11e2}$ are independently hydrogen, $C_{1-6}$ alkyl, $C_{1-6}$ alkyl substituted with one or more $R^{1-2-1}$, —$OC_{1-6}$ alkyl, —$OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$; provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, oxo, $C_{1-6}$ alkyl, $C_{1-6}$ alkyl substituted with one or more $R^{1-2-1-1}$; provided that when multiple substituents are present, the substituents are the same or different;

$R^{1-2-1-1}$ is halogen, hydroxyl, —$OC_{1-6}$ alkyl or —$NR^cR^d$, $R^c$ and $R^d$ are independently hydrogen or $C_{1-6}$ alkyl;

or, when the number of $R^{1-3}$, $R^{1-4}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-8}$ or $R^{1-2-8}$ is more than one, two optional $R^{1-3}$, two optional $R^{1-4}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3- to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aryl, $C_{6-20}$ aryl substituted with one or more $R^{1-3-3}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-3-4}$, $C_{5-7}$ cycloalkenyl, $C_{5-7}$ cycloalkenyl substituted with one or more $R^{1-3-5}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-3-6}$; provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen;

or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-4-1}$; $R^{1-4-1}$ is oxo, hydroxyl, halogen, $C_{1-6}$ alkyl, $C_{1-6}$ alkyl substituted with one or more halogen, $C_{1-6}$ alkyl-O—, or, $C_{1-6}$ alkyl-O— substituted with one or more halogen;

$A_2$ and $A_3$ are independently N or $CR^2$, $R^2$ is hydrogen or halogen;

$A_4$ is N or $CR^{4d}$;

$R^{4d}$ is hydrogen, halogen, $C_{1-6}$ alkyl, or, $C_{1-6}$ alkyl substituted with one or more halogen;

$R^{5d}$ is

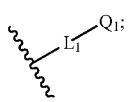

$L_1$ is a bond or $C_{1-6}$ alkylene;

$Q_1$ is hydrogen, halogen, cyano, $C_{2-6}$ alkenyl, $C_{2-6}$ alkynyl, hydroxyl, —C(=O)$R^{52a}$, —N$R^{52b1}R^{52b2}$, —C(=O)O$R^{52c}$, —C(=O)N$R^{52d1}R^{52d2}$, $C_{1-6}$ alkyl substituted with one or more halogen, —$O_{1-6}$ alkyl, $C_{3-12}$ cycloalkyl, $C_{3-12}$ cycloalkyl substituted with one or more $R^{5-1-4}$, "4- to 12-membered heterocycloalkyl containing 1 to 3 heteroatoms independently selected from O, S and N", or, "4- to 12-membered heterocycloalkyl containing 1 to 3 heteroatoms independently selected from O, S and N" substituted with one or more $R^{5-1-5}$; provided that when multiple substituents are present, the substituents are the same or different;

$R^{5-1-4}$ and $R^{5-1-5}$ are independently halogen, hydroxyl, oxo, cyano, $C_{1-6}$ alkyl, $C_{1-6}$ alkyl substituted with one or more halogen, —O$C_{1-6}$ alkyl, —O$C_{1-6}$ alkyl substituted with one or more halogen, —C(=O)$R^{51a}$, —N$R^{51b1}R^{51b2}$, —C(=O)O$R^{51c}$, or, —C(=O)N$R^{51d1}R^{51d2}$; Provided that when multiple substituents are present, the substituents are the same or different;

$R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b2}$, $R^{52d1}$ and $R^{52d2}$, $R^{51b}1$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$;

$R^{1-5-1}$ is oxo, hydroxyl, halogen, $C_{1-6}$ alkyl, $C_{1-6}$ alkyl substituted with one or more halogen, —O$C_{1-6}$ alkyl, —O$C_{1-6}$ alkyl substituted with one or more halogen; provided that when multiple substituents are present, the substituents are the same or different;

$R^6$ is "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$;

$R^{6-1}$ is $C_{1-6}$ alkyl, or $C_{1-6}$ alkyl substituted with one or more halogen.

In some embodiments, the compound containing structure of a five-membered heteroaromatic ring represented by formula I as described above is any one of the following structures:

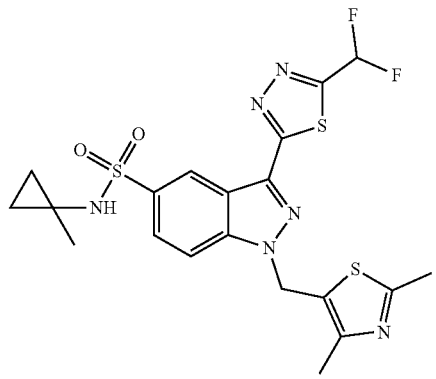

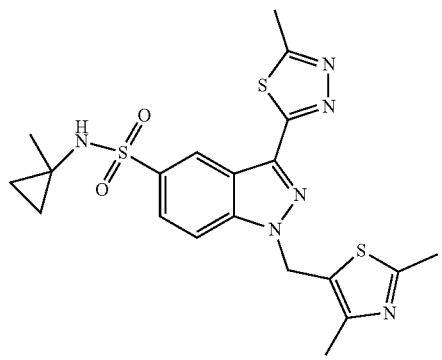

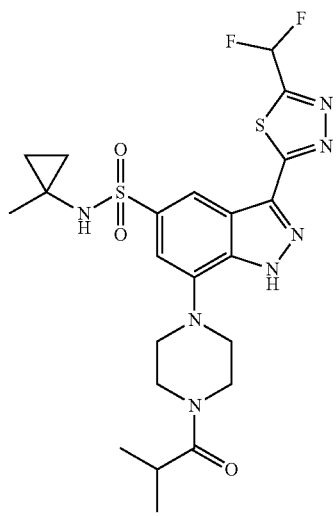

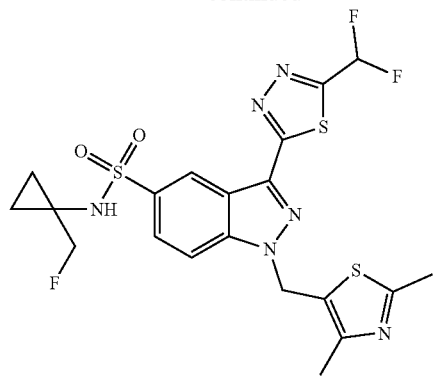
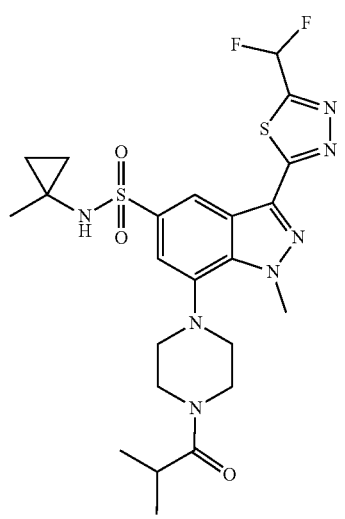
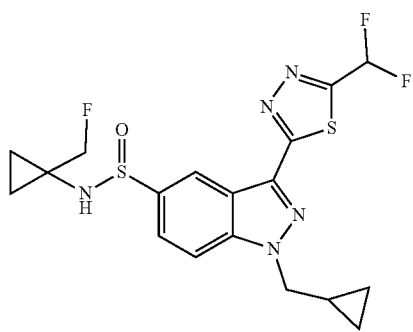
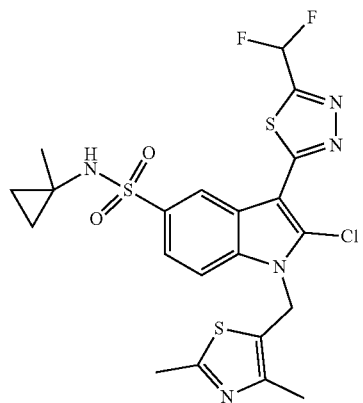
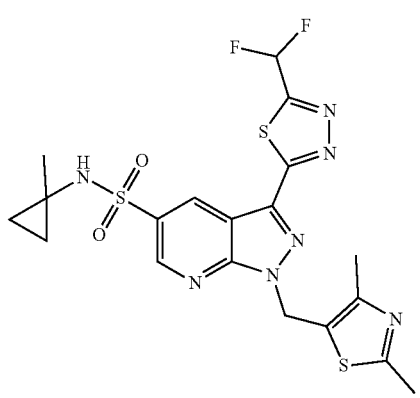
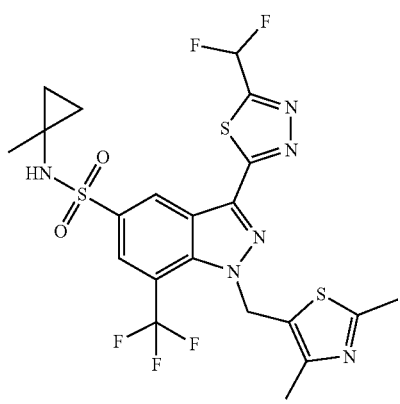
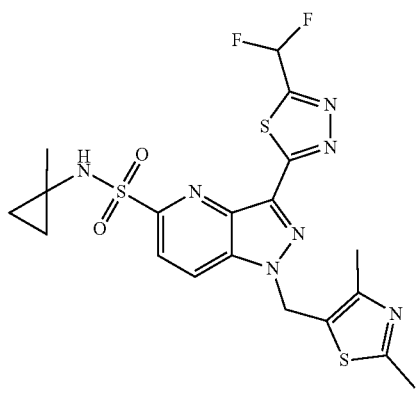

-continued
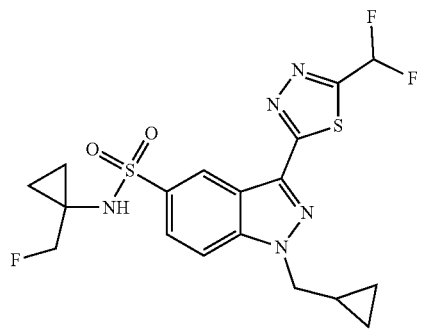
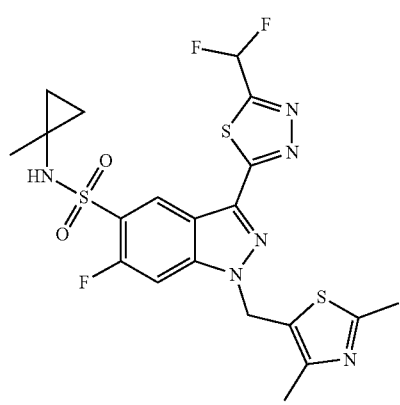
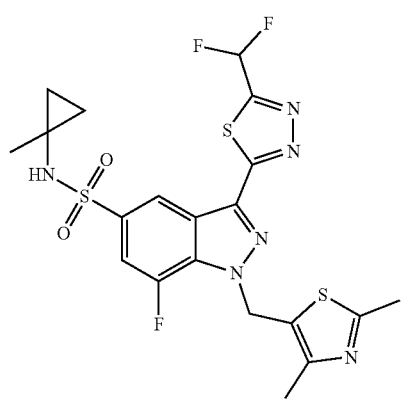
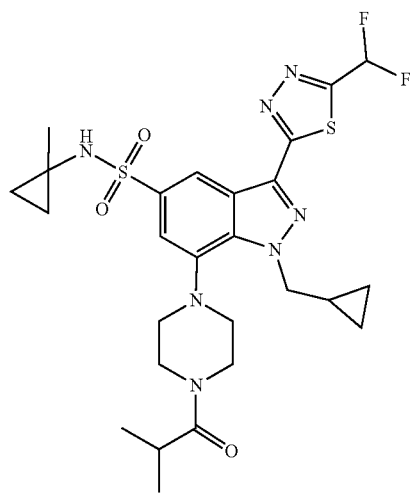
-continued
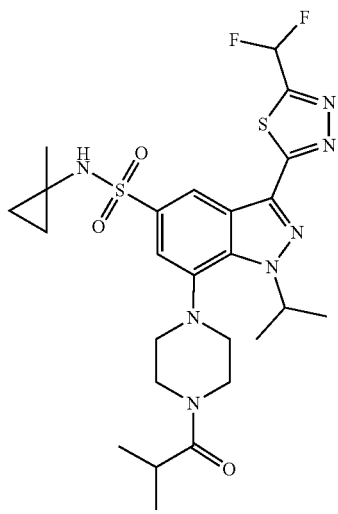
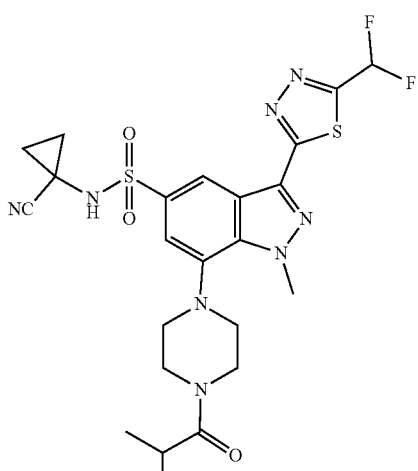
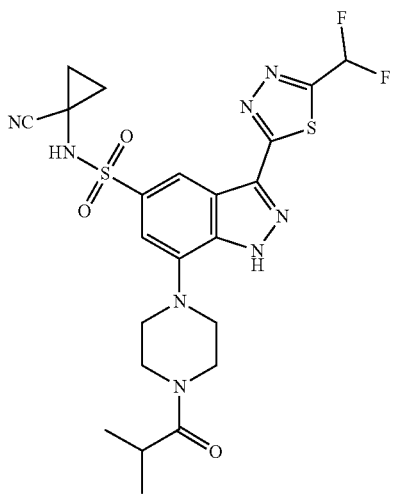

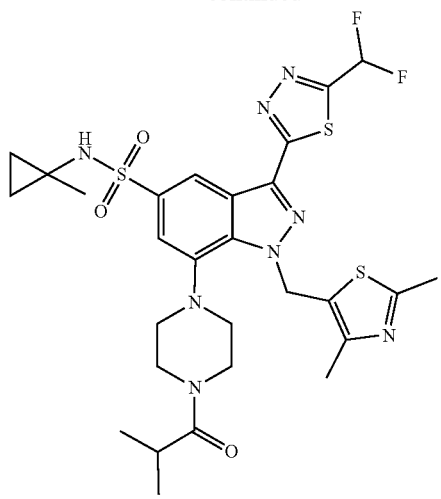
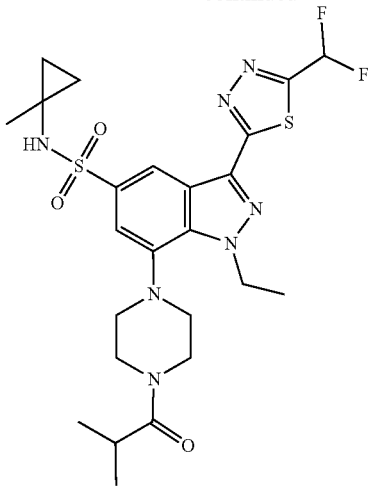
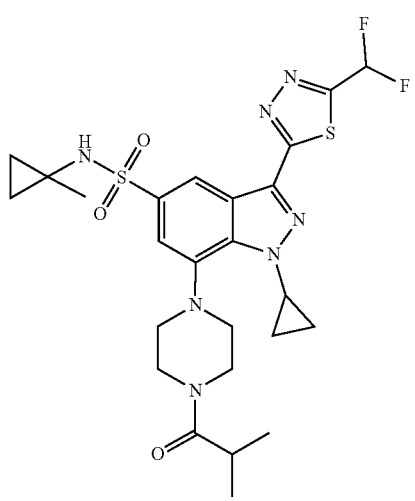

49
-continued
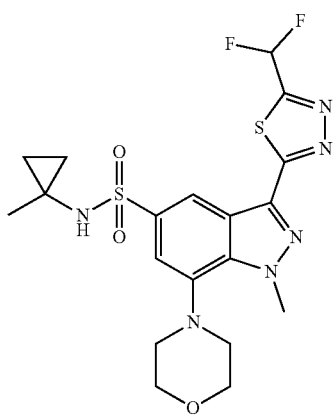
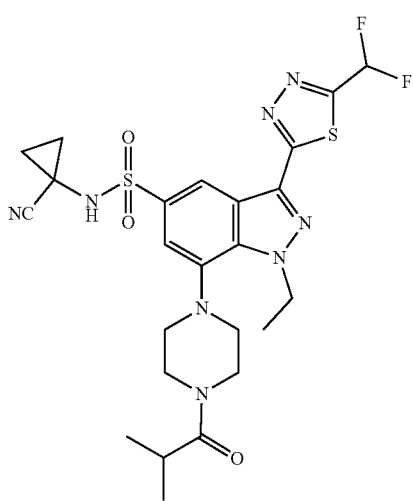
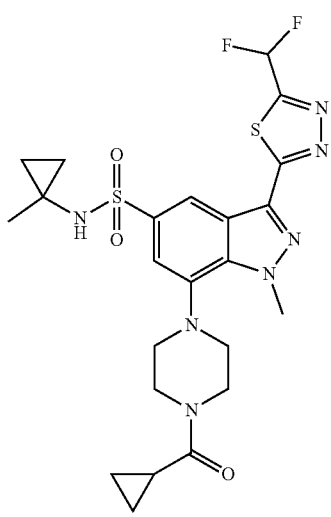
50
-continued
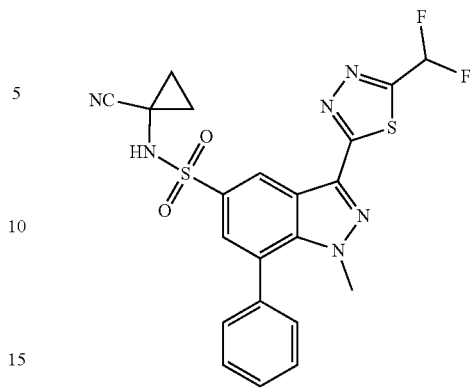
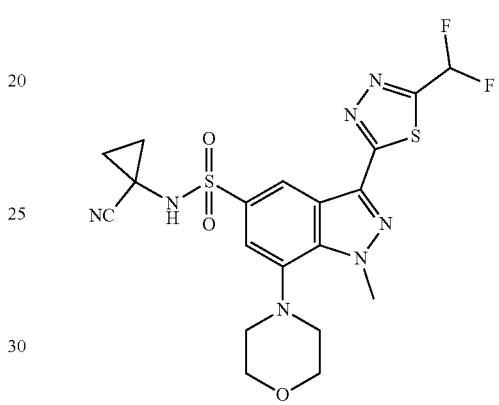
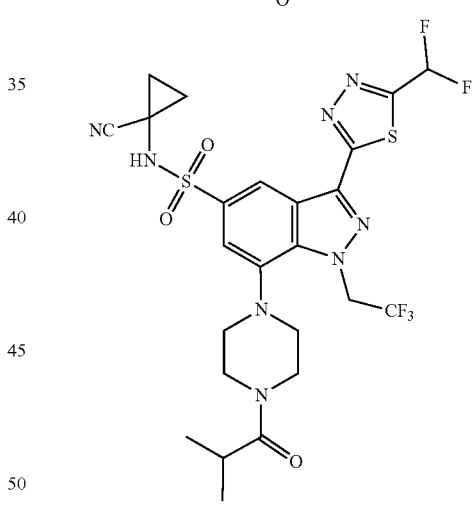

51
-continued
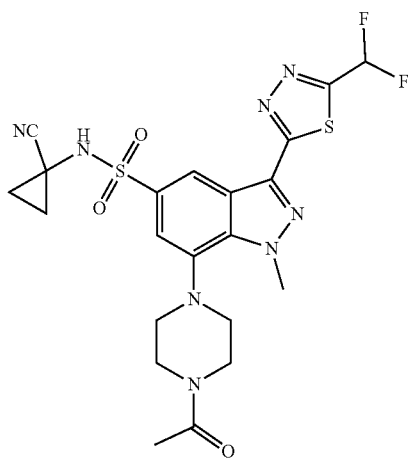
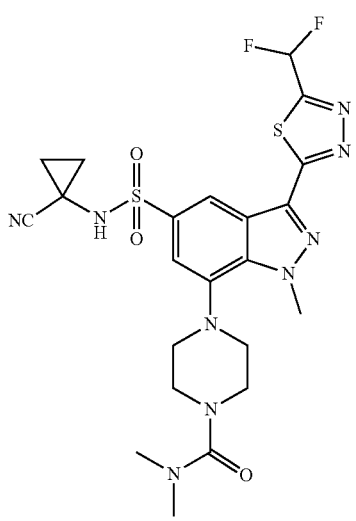
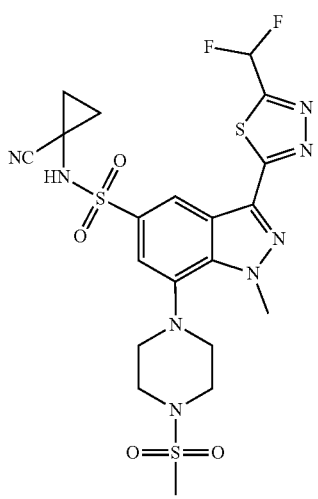
52
-continued
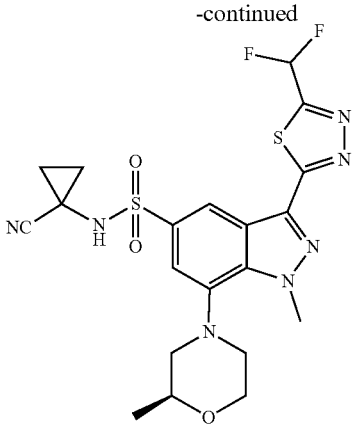
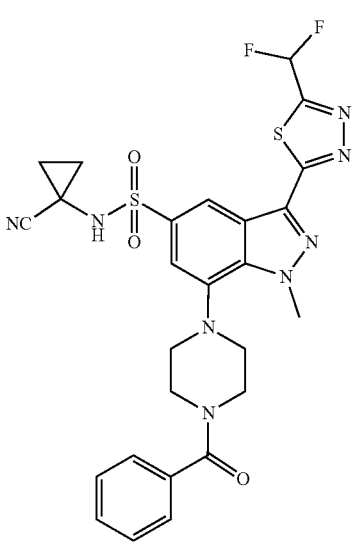
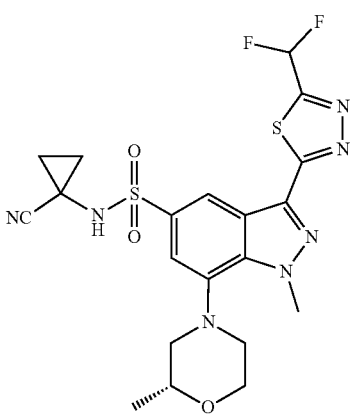

53
-continued
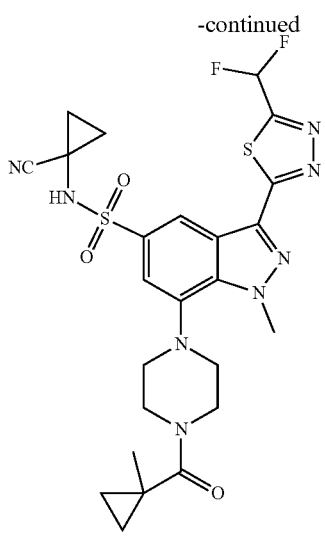
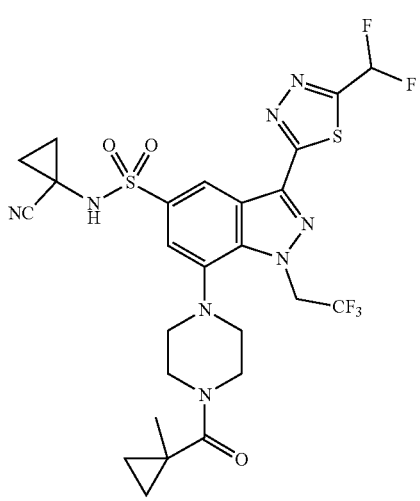
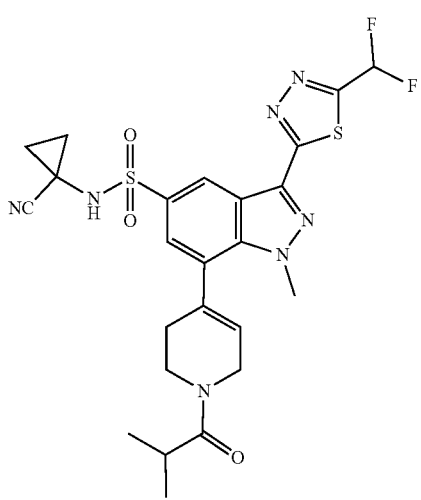
54
-continued
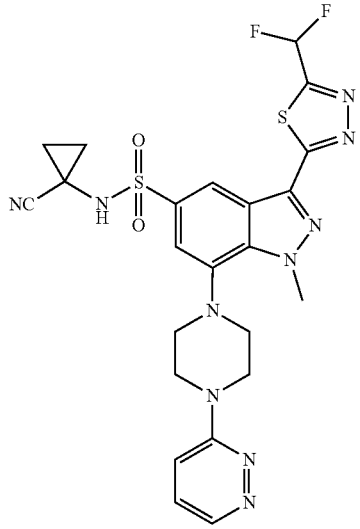
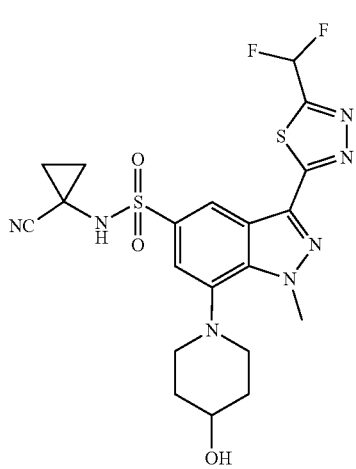
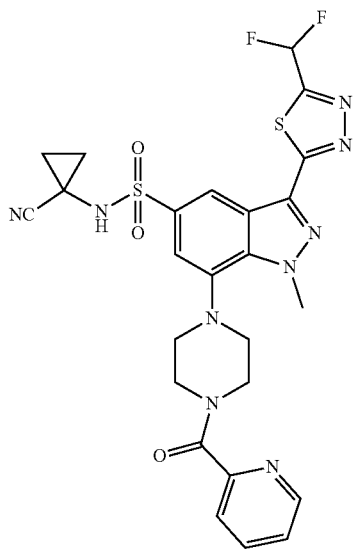

55
-continued
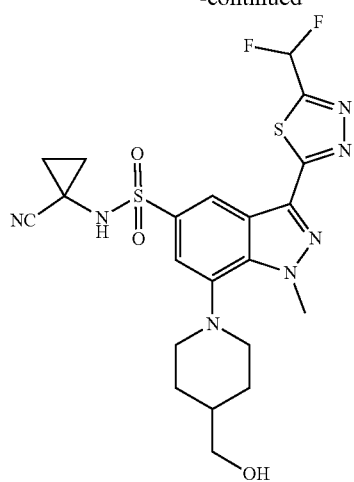
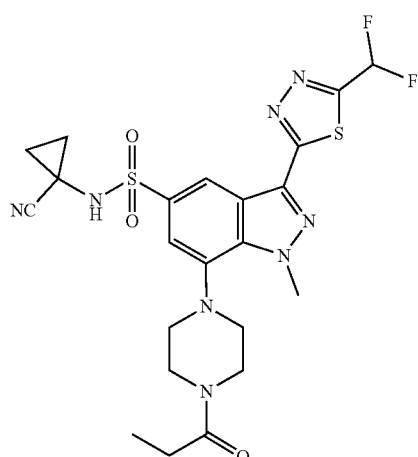
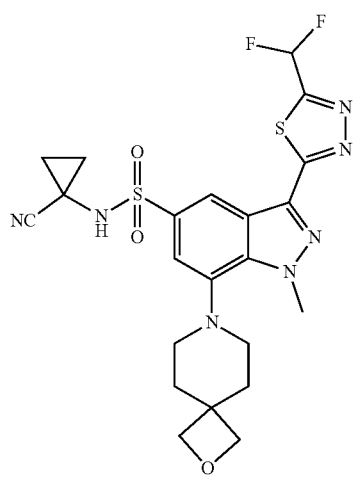
56
-continued
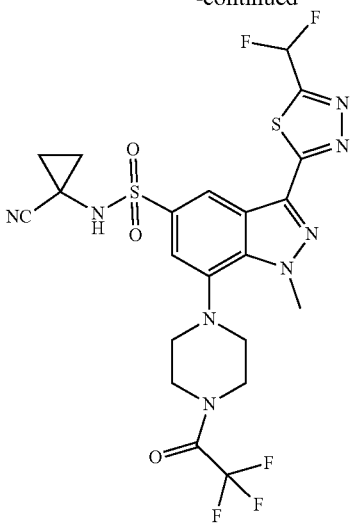
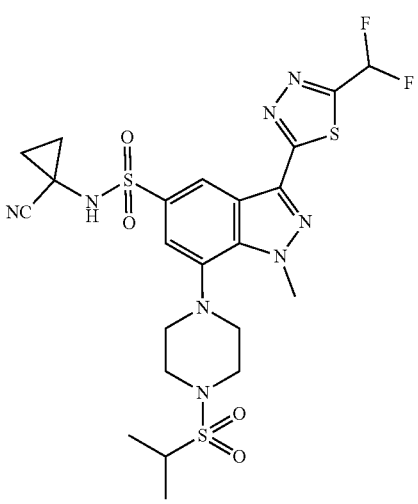
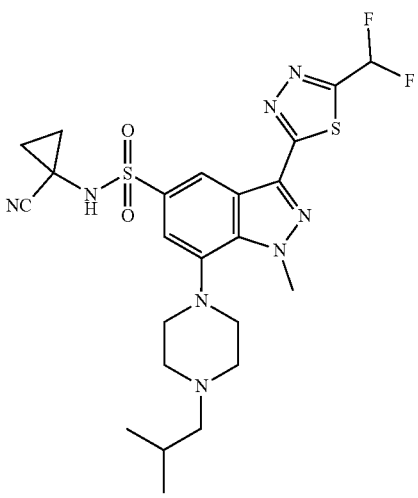

57
-continued
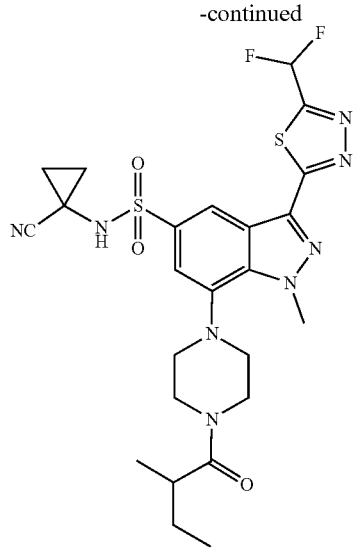
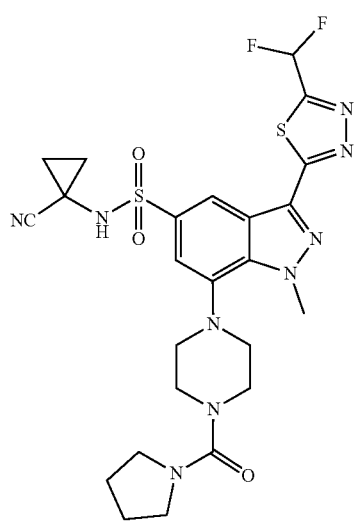
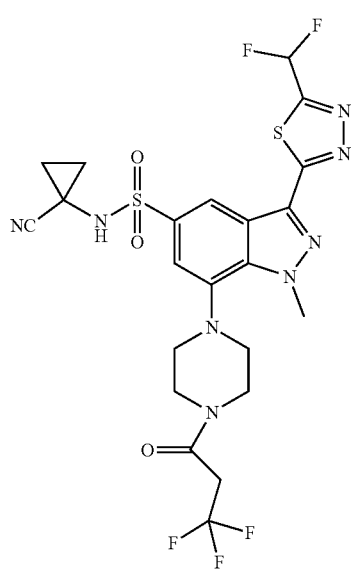
58
-continued
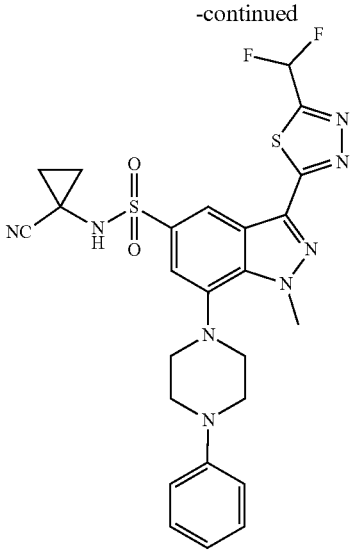
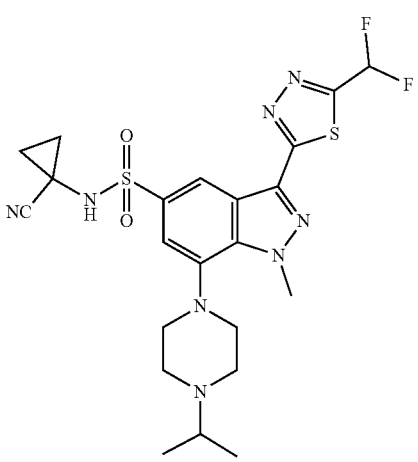
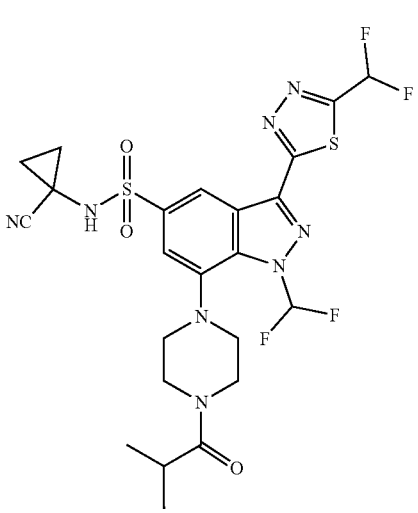

59
-continued
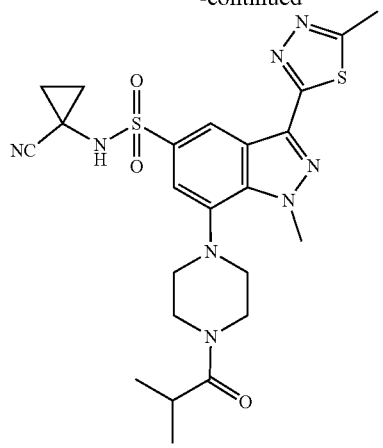
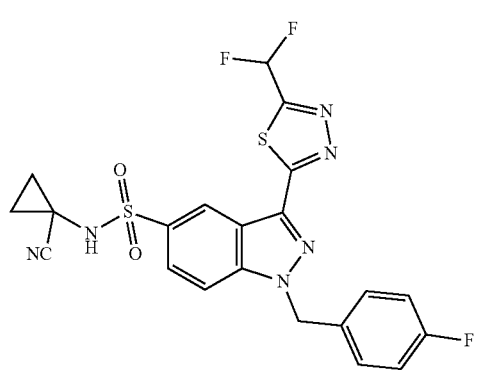
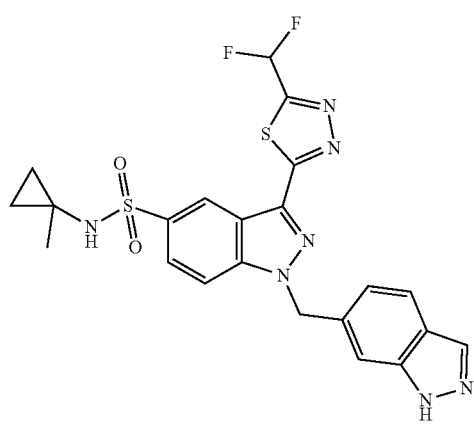
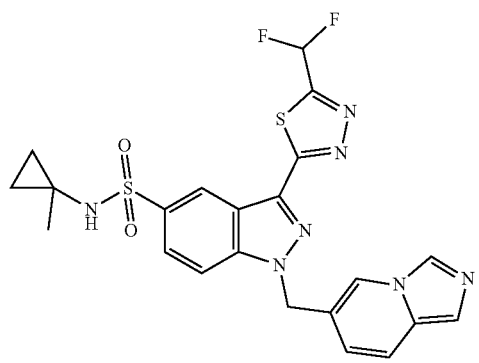
60
-continued
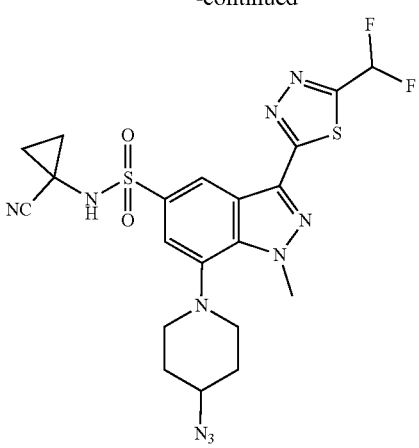
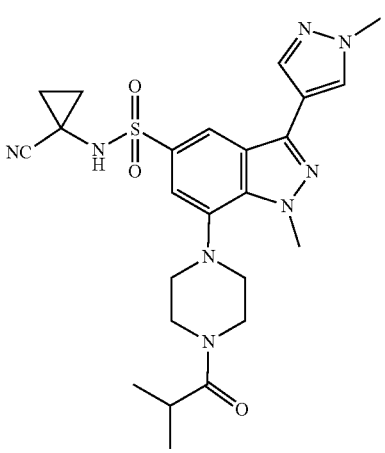
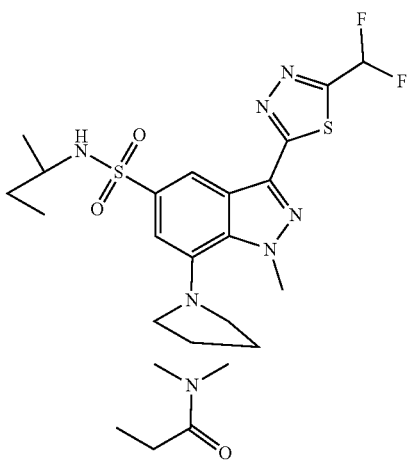

61
-continued
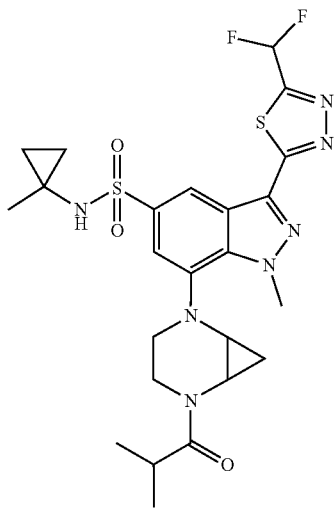
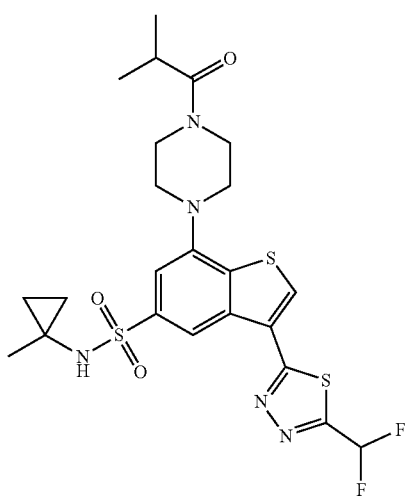
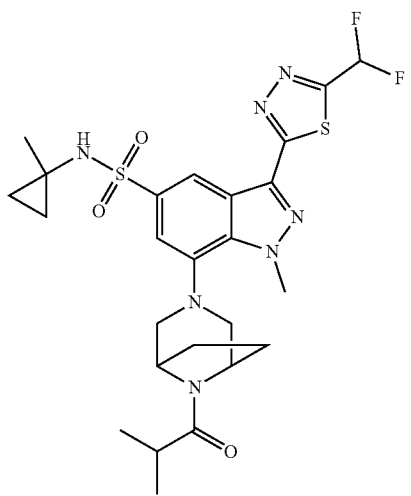
62
-continued
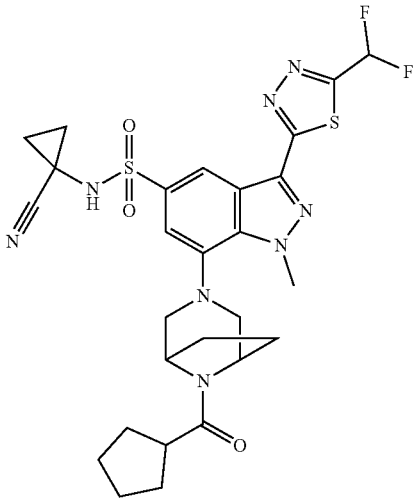
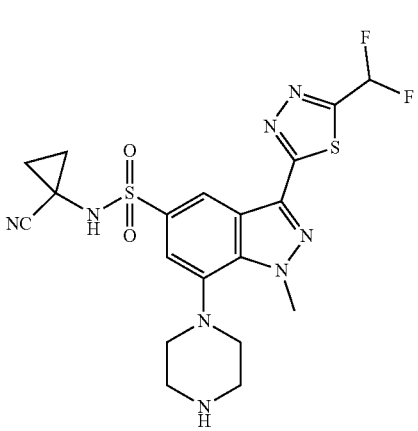
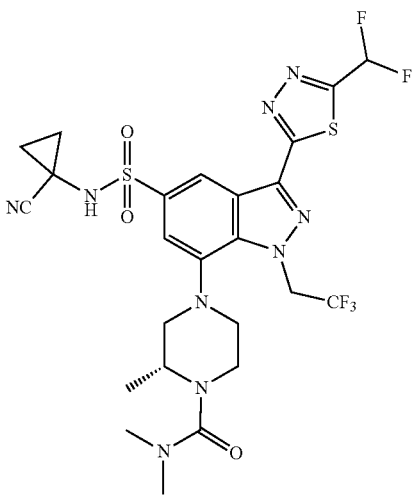

63
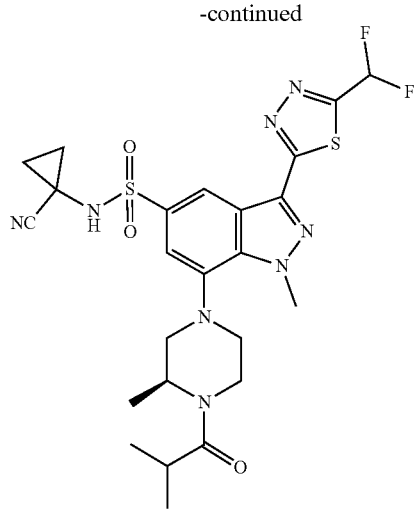
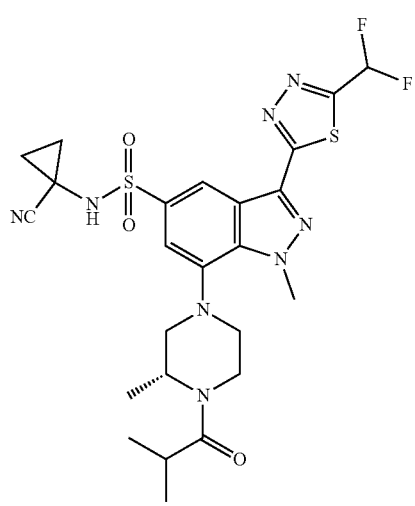
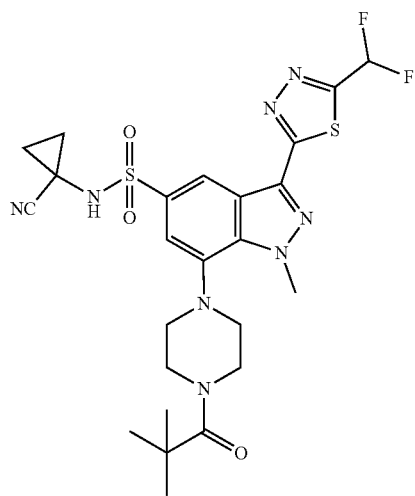
64
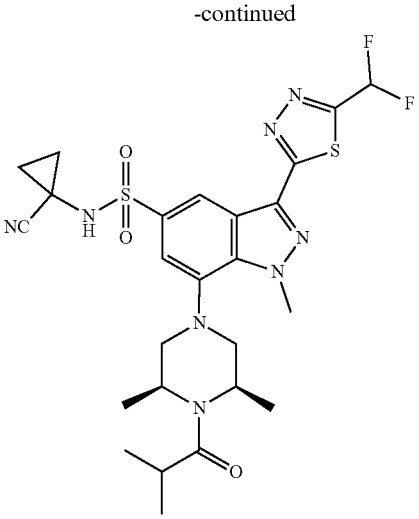
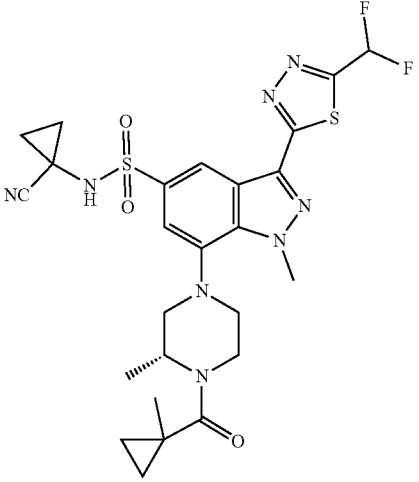

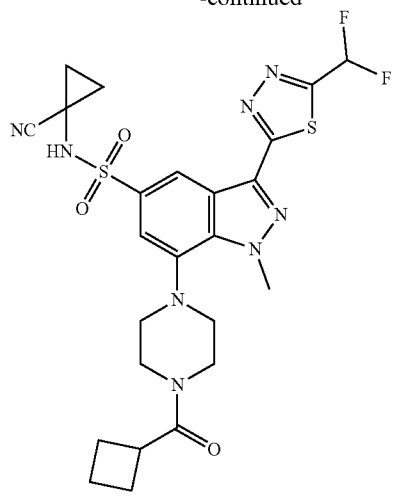
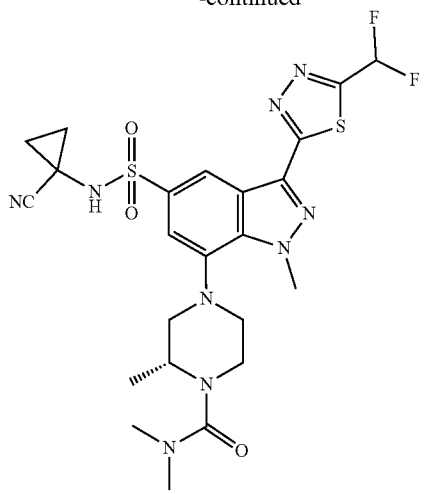
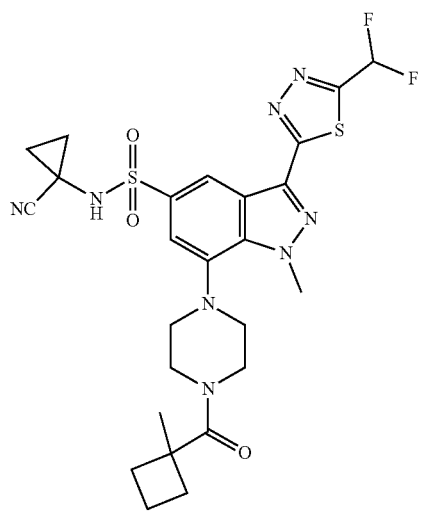
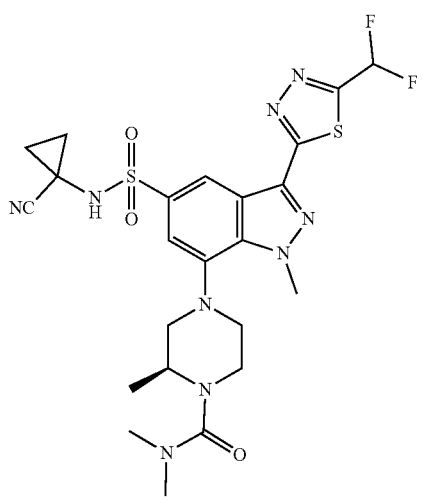
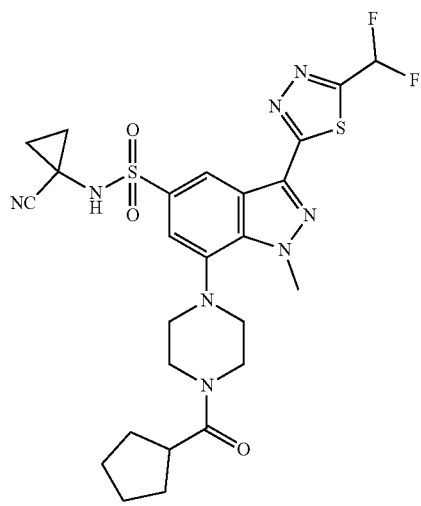
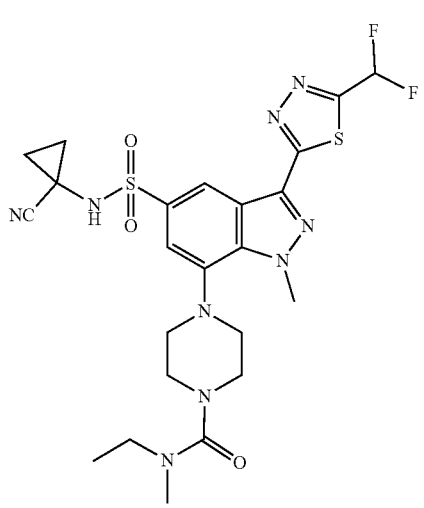

67
-continued
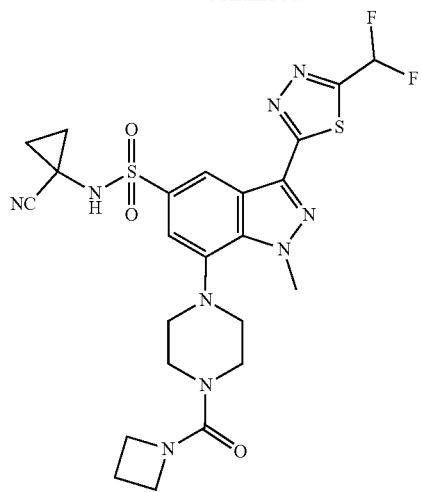
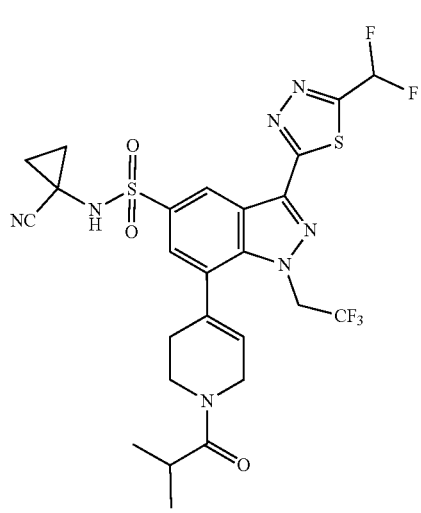
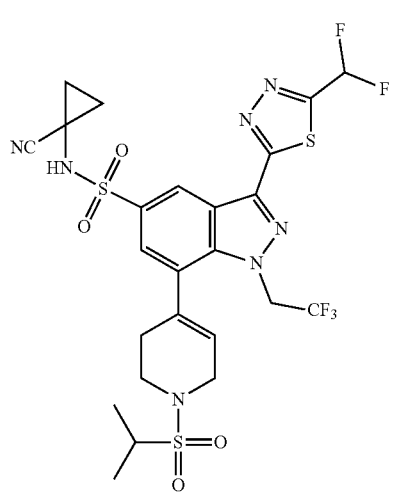
68
-continued
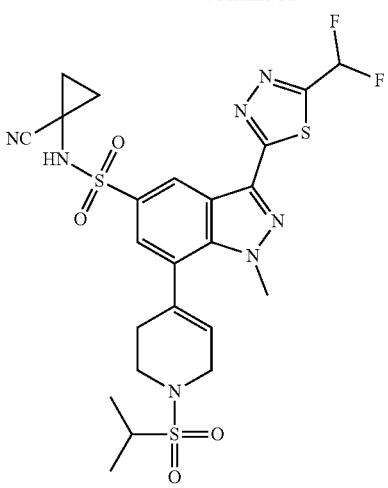
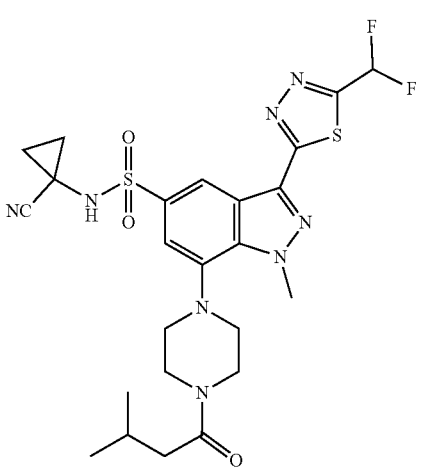
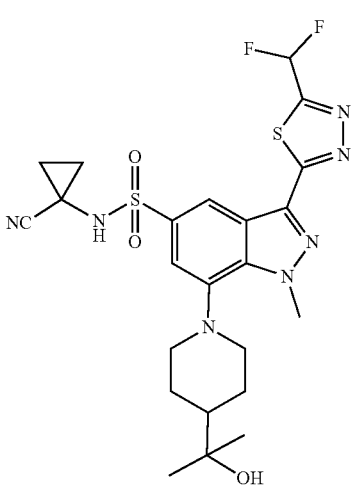

69
-continued
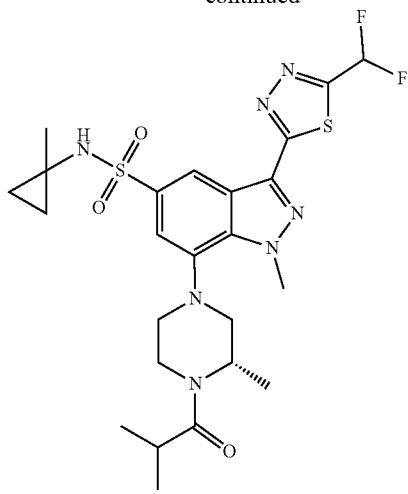
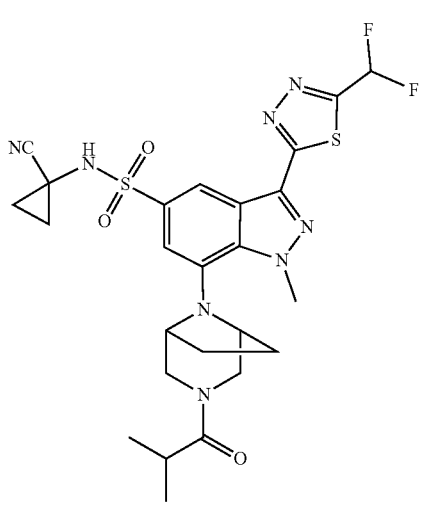
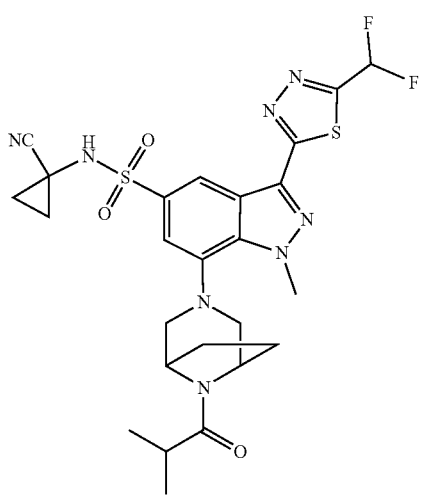
70
-continued
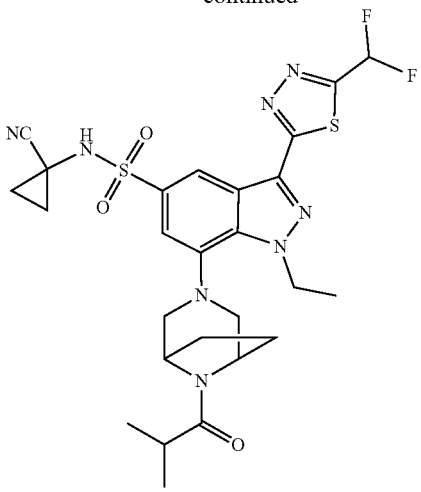
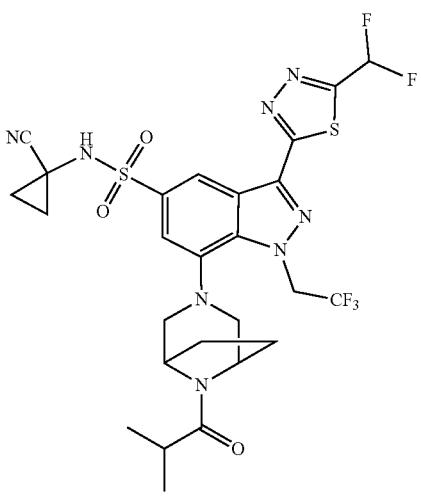
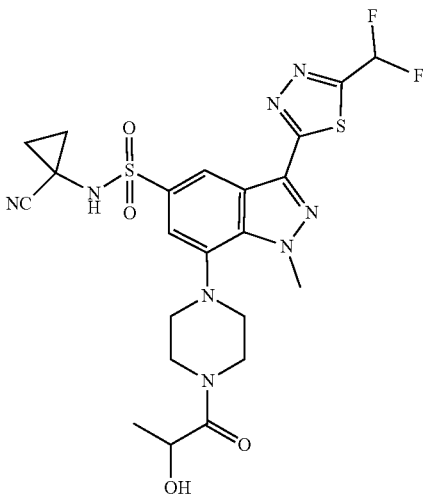

71
-continued
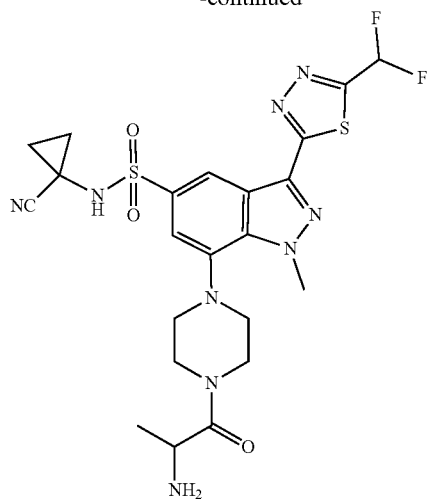
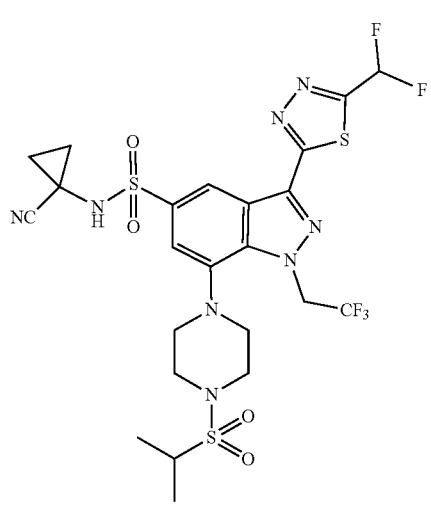
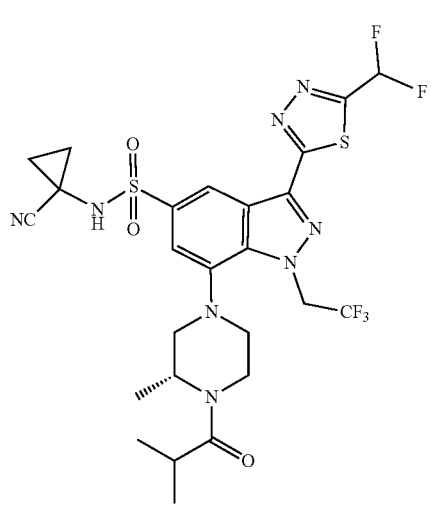
72
-continued
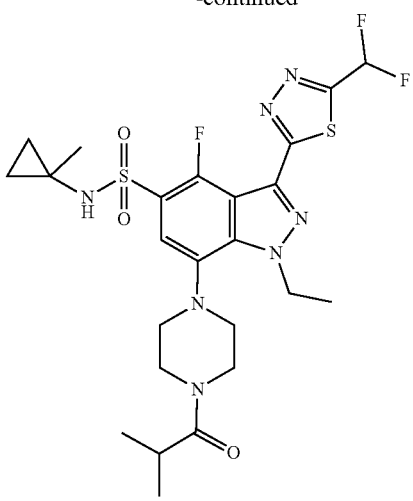
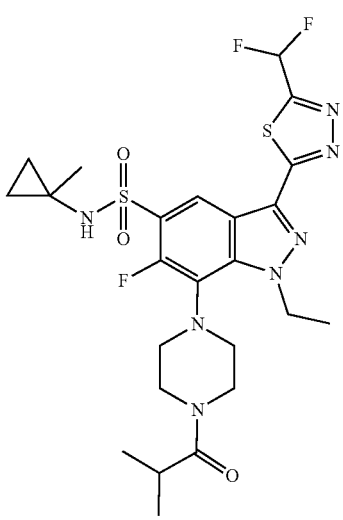
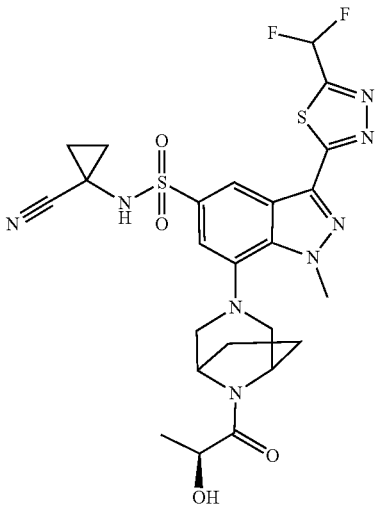

73
-continued
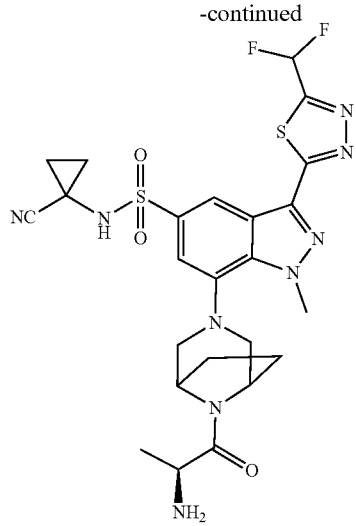
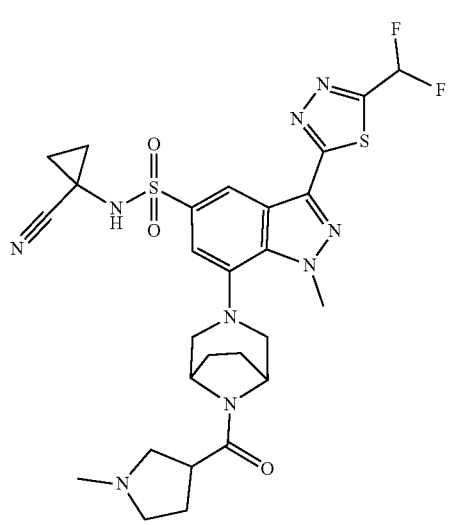
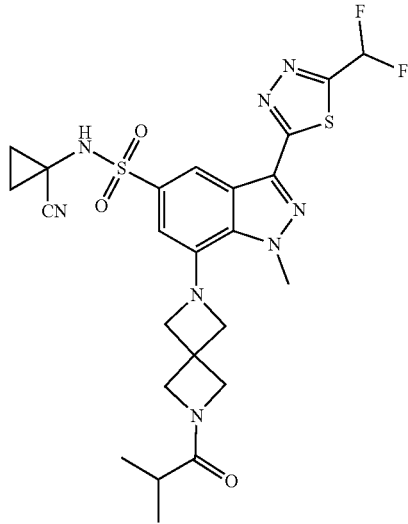
74
-continued
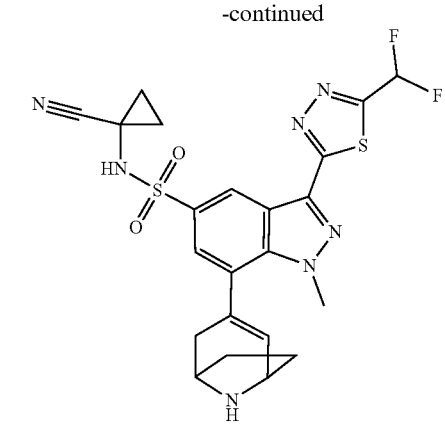
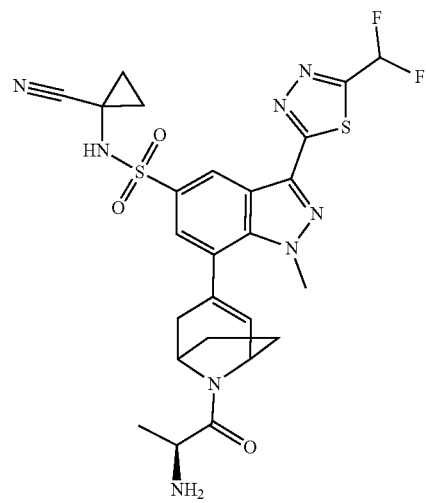
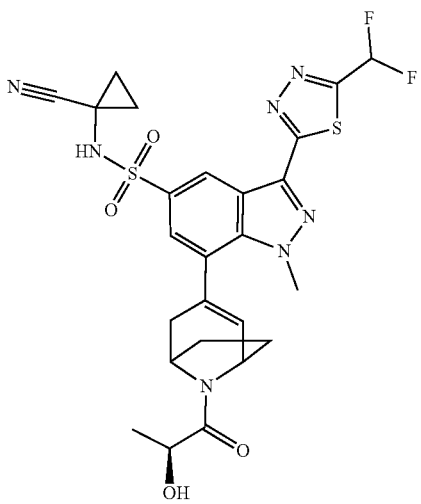

75
-continued
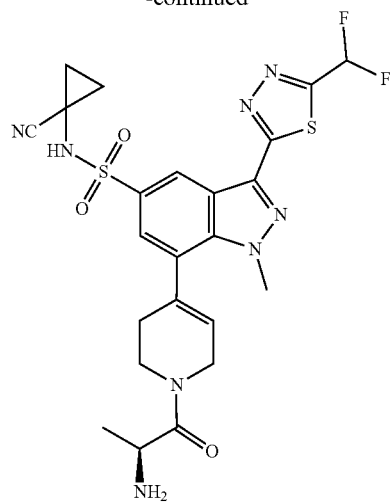
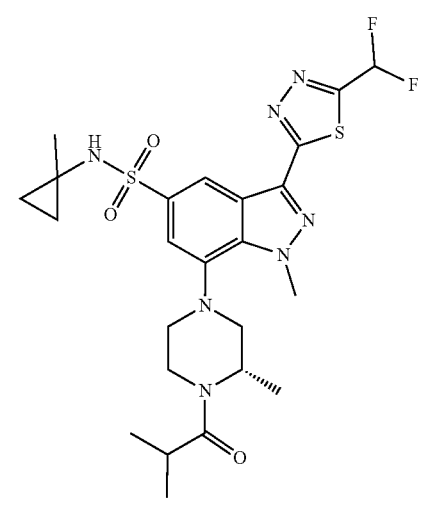
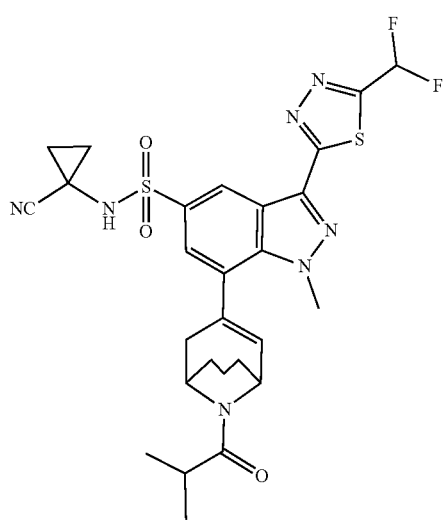
76
-continued
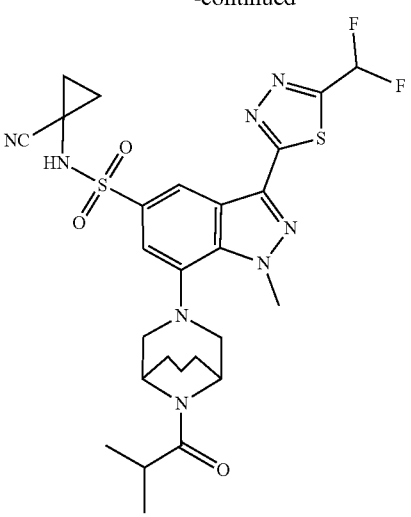
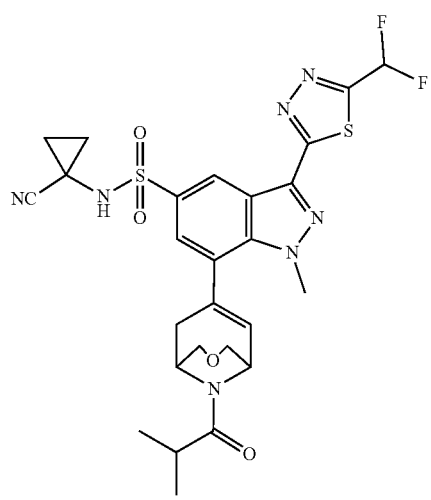
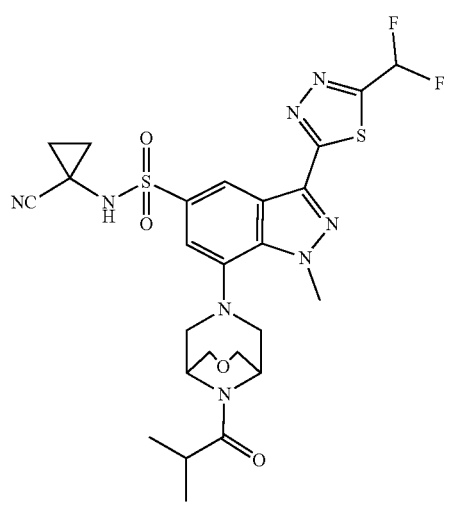

77
-continued
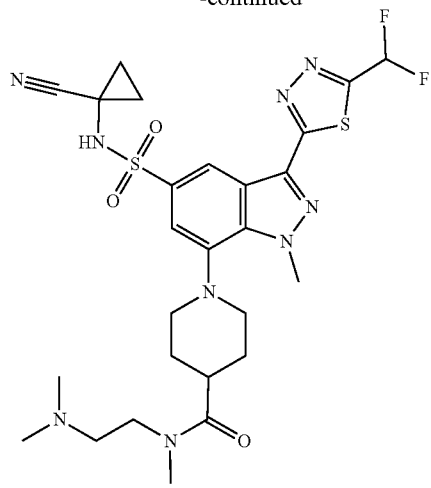
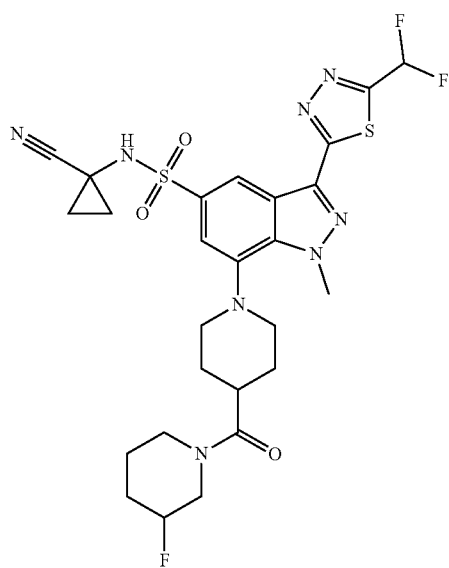
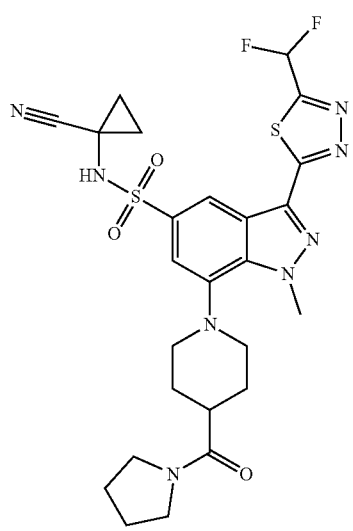
78
-continued
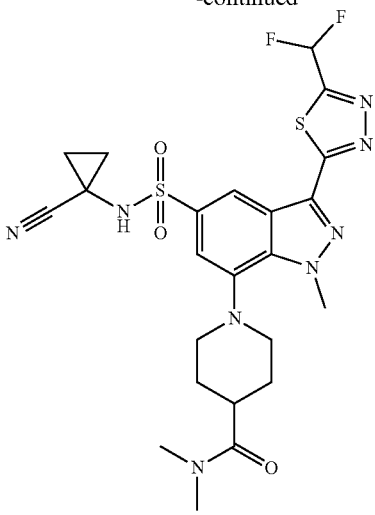
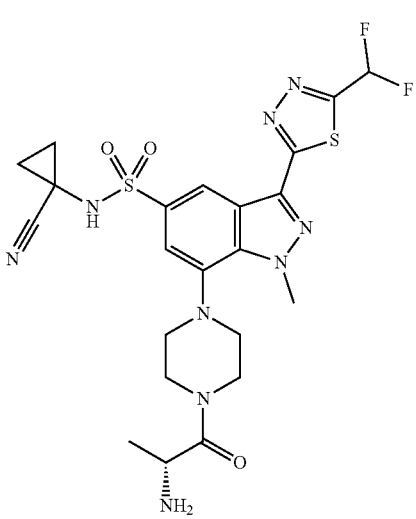
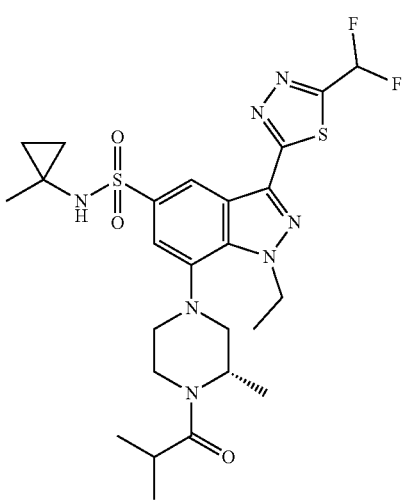

79
-continued
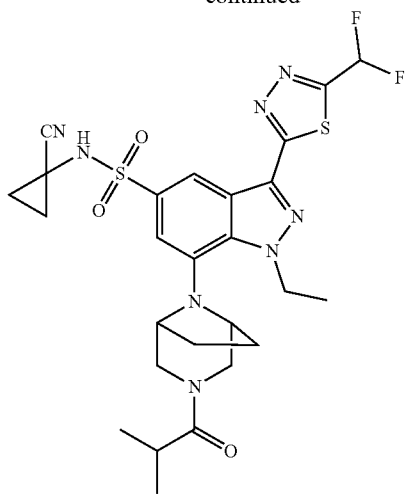
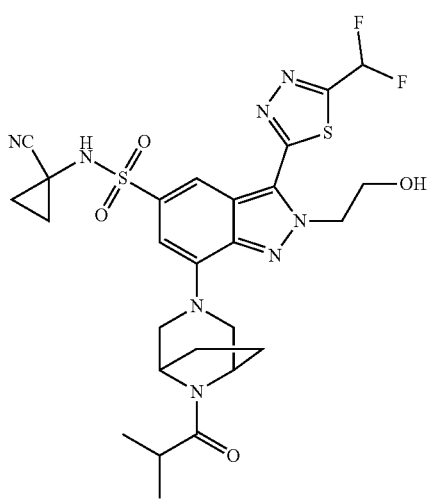
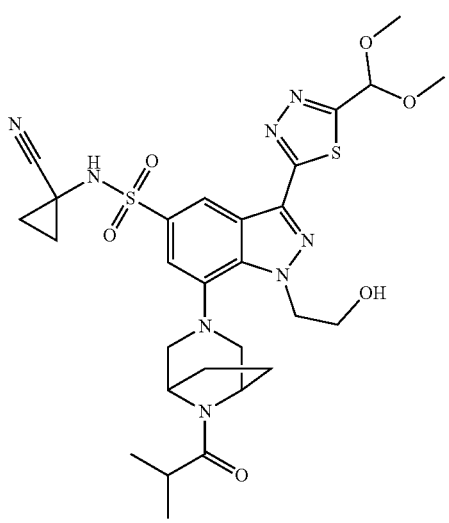
80
-continued
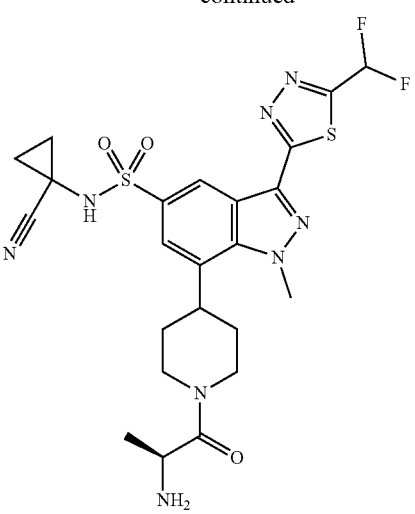
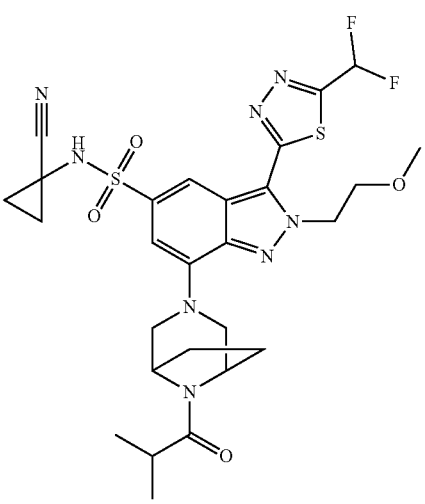
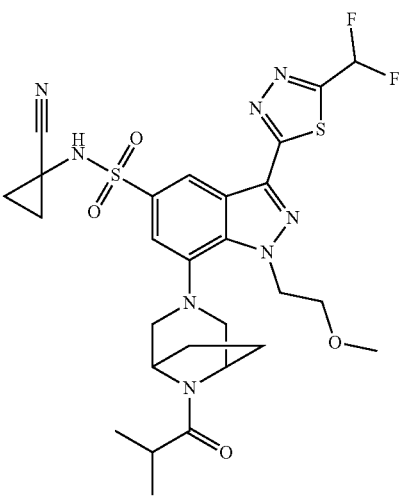

81
-continued
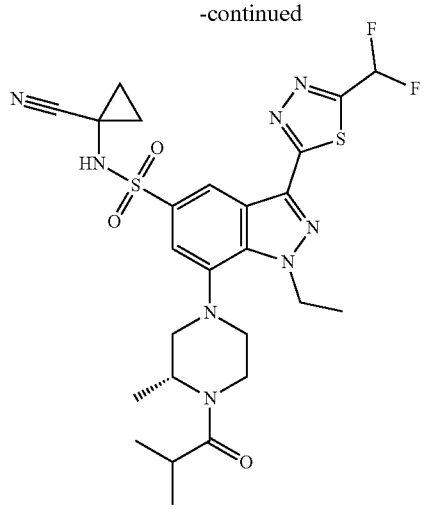
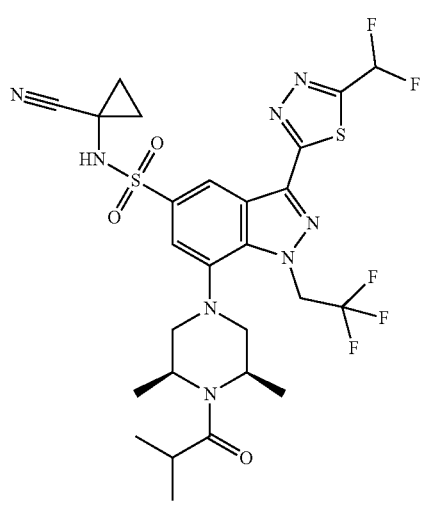
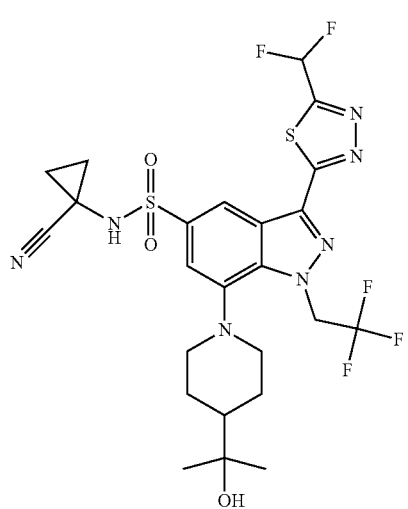
82
-continued
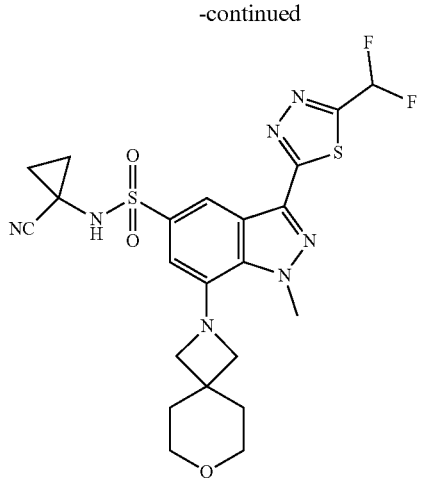
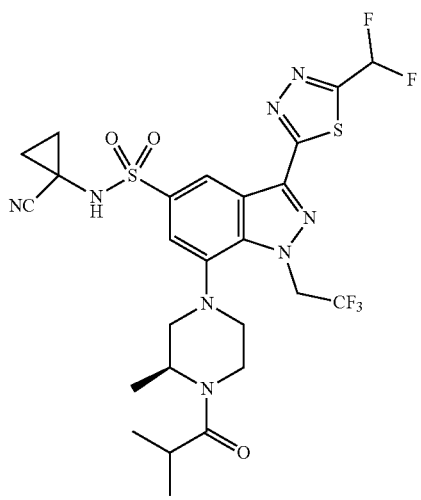
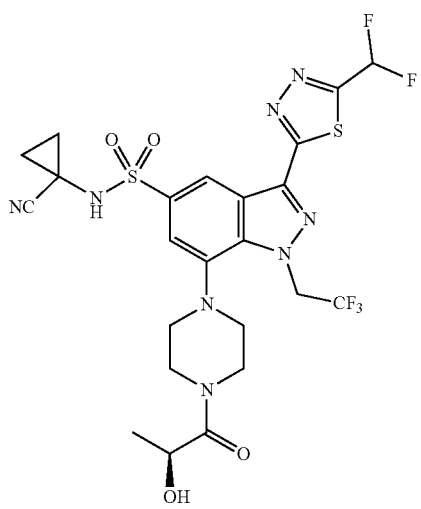

83
-continued
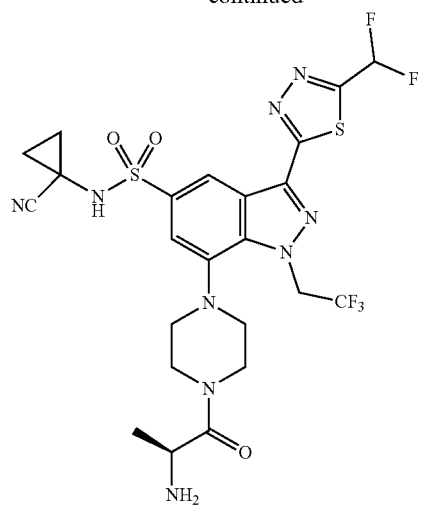
84
-continued
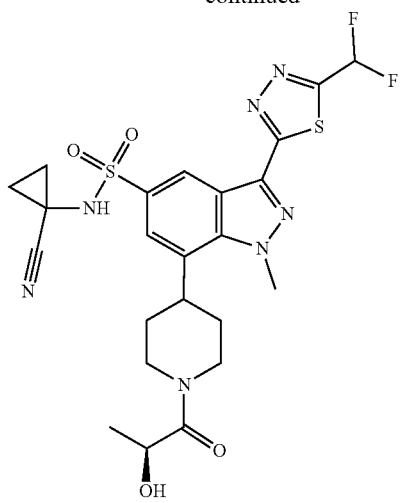
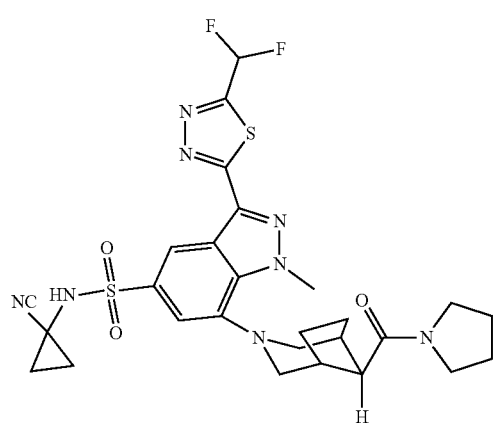
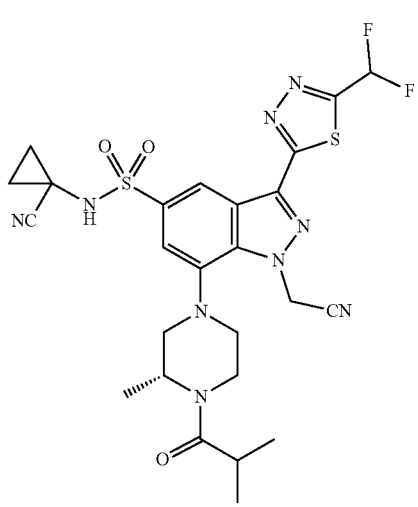
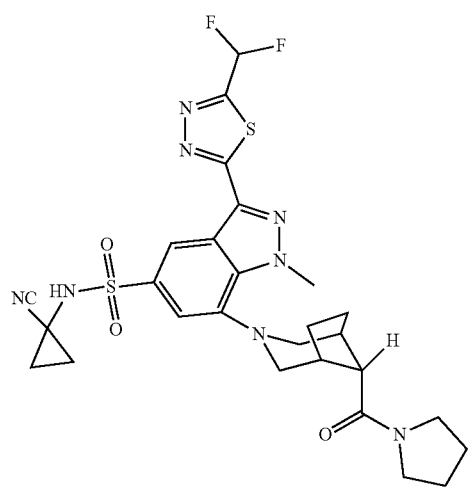

85
-continued
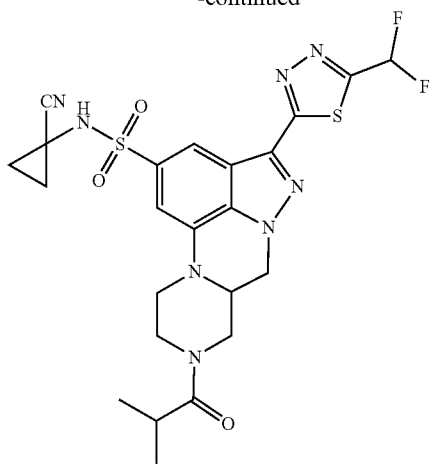
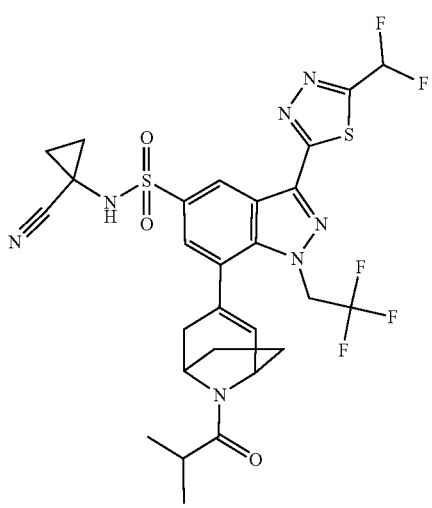
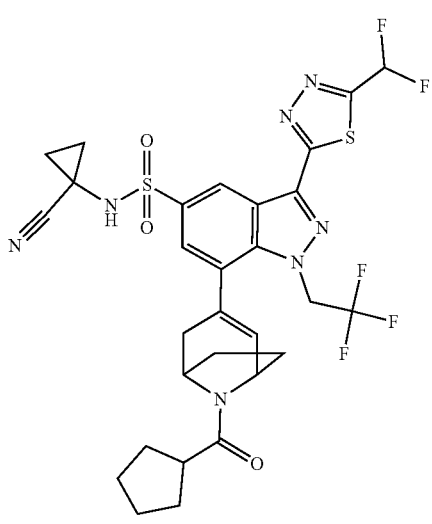
86
-continued
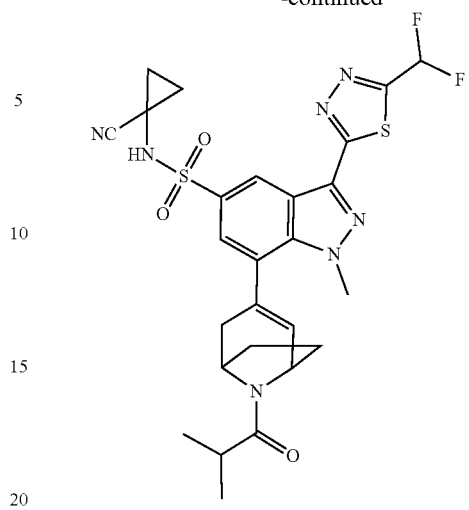
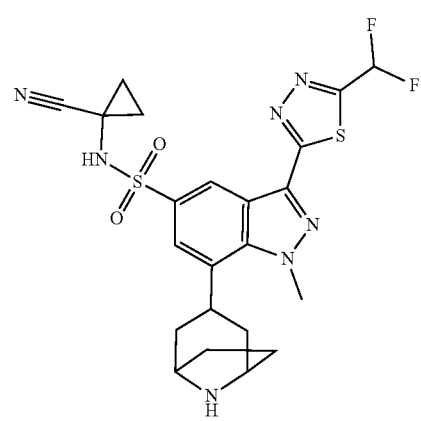
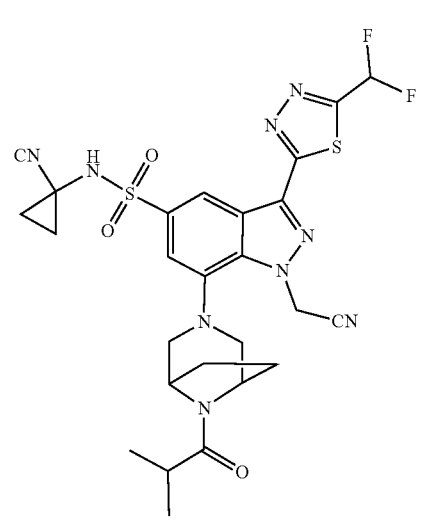

87
-continued
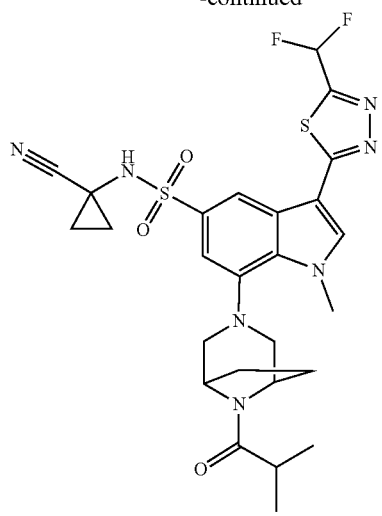
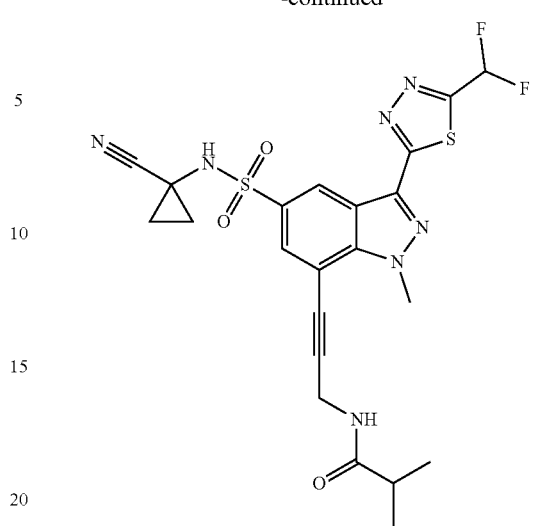
88
-continued
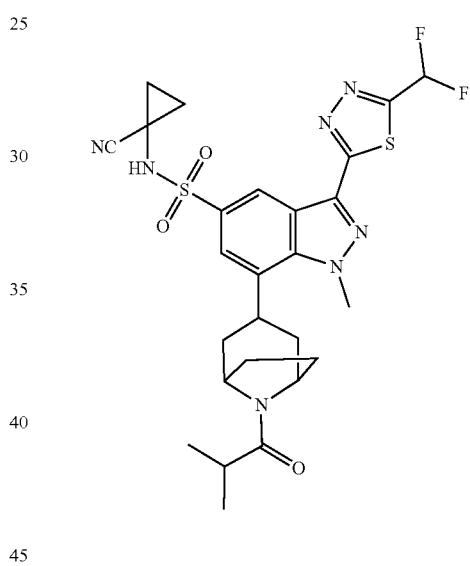
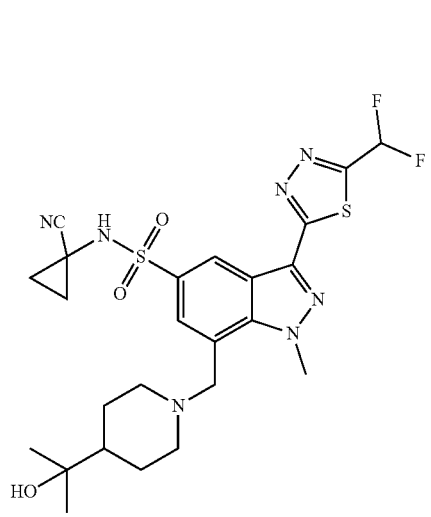
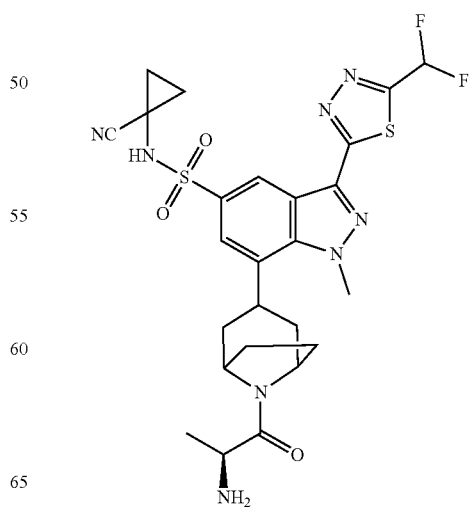

89
-continued
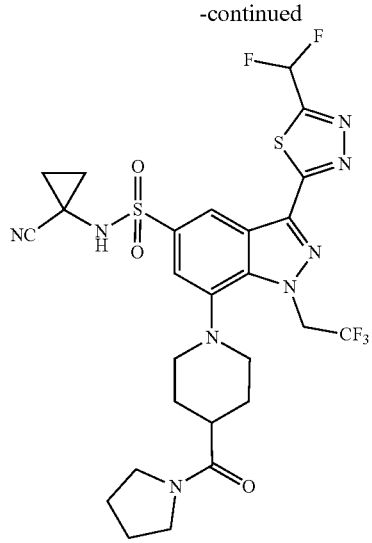
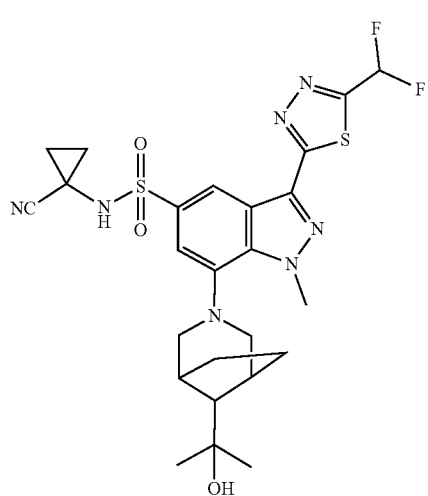
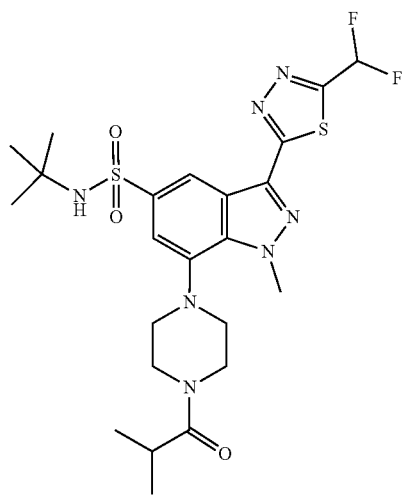
90
-continued
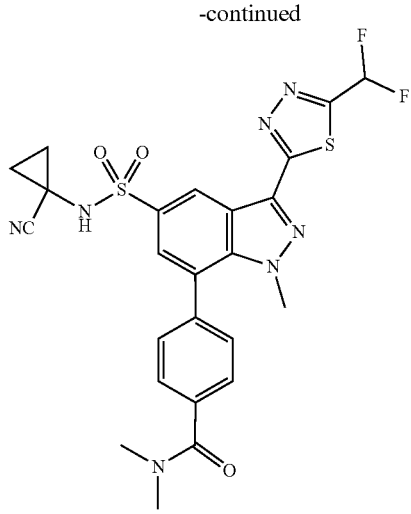
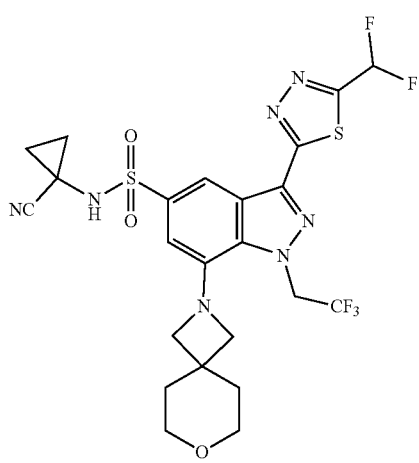
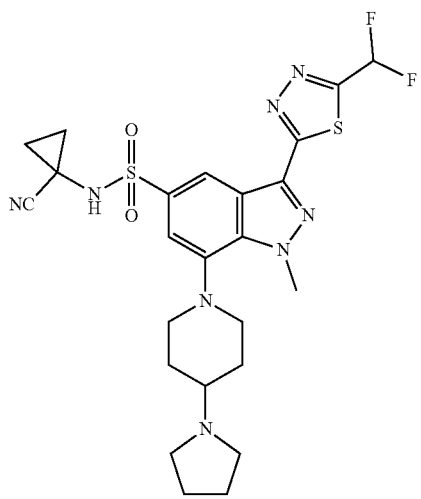

91
-continued
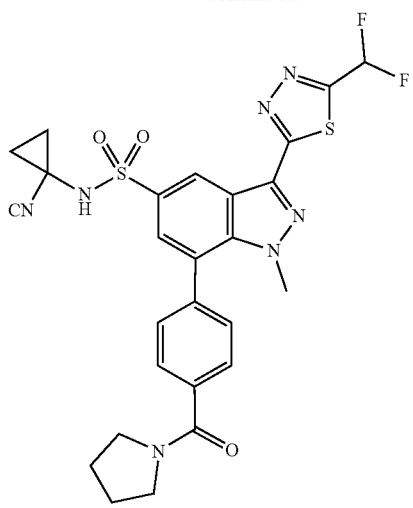
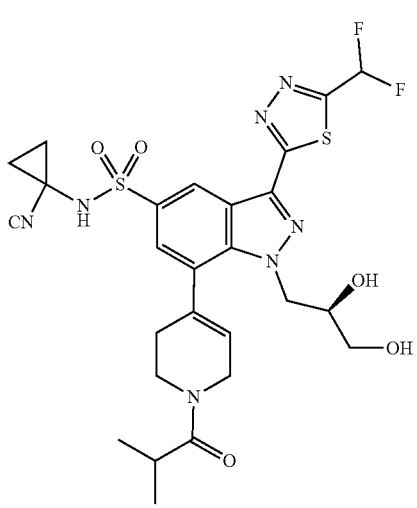
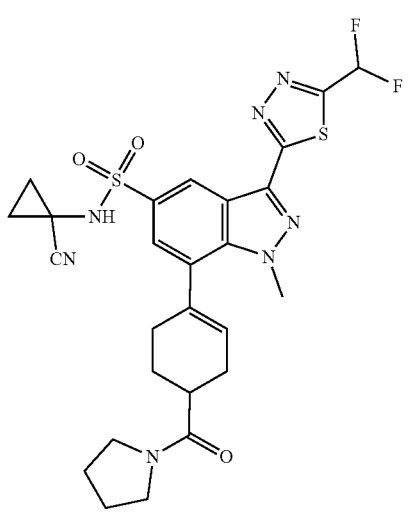
92
-continued
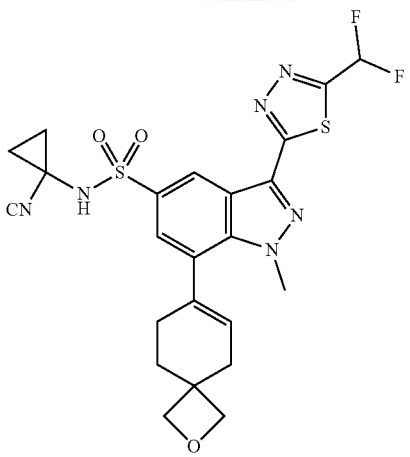
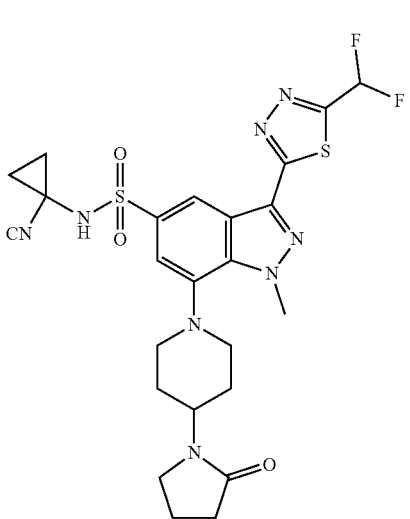
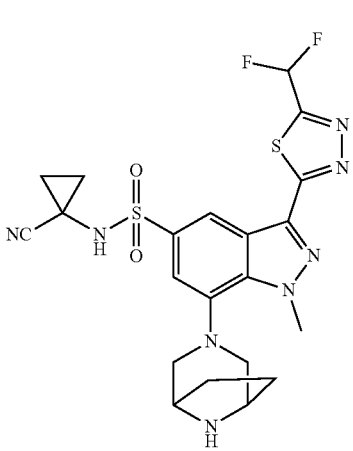

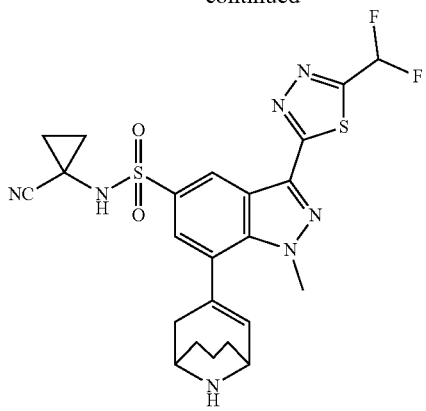
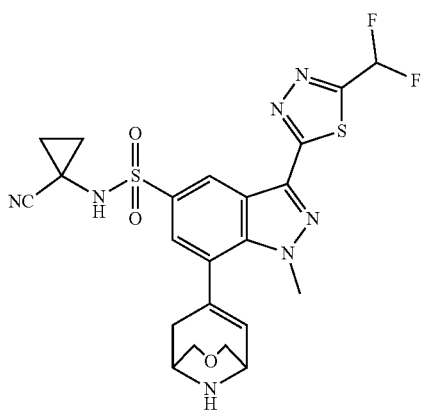
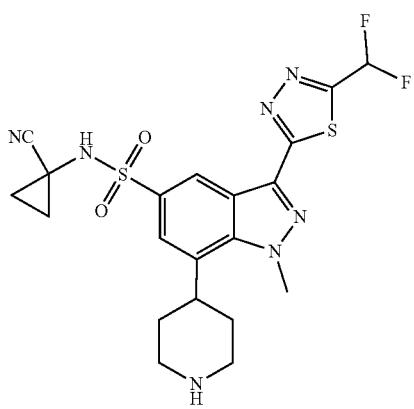
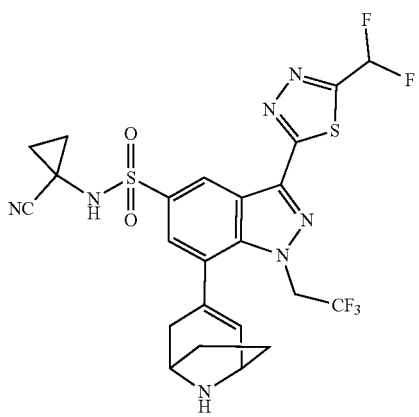
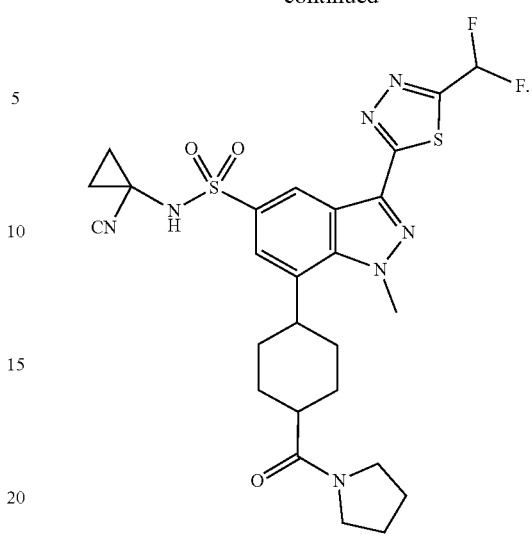
The present disclosure also provides a method for preparing the compound containing structure of a five-membered heteroaromatic ring represented by formula I as described above, wherein the method has any one of the following routes:
Route I
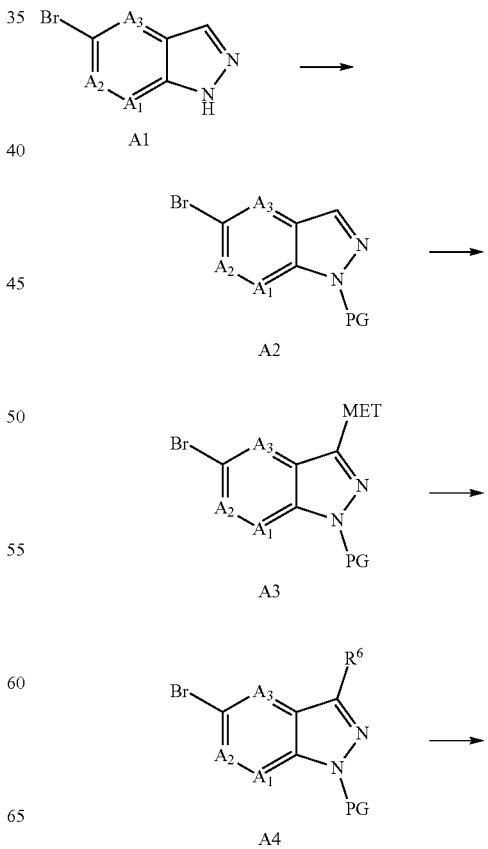

95
-continued

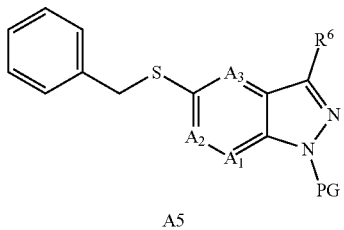
A5

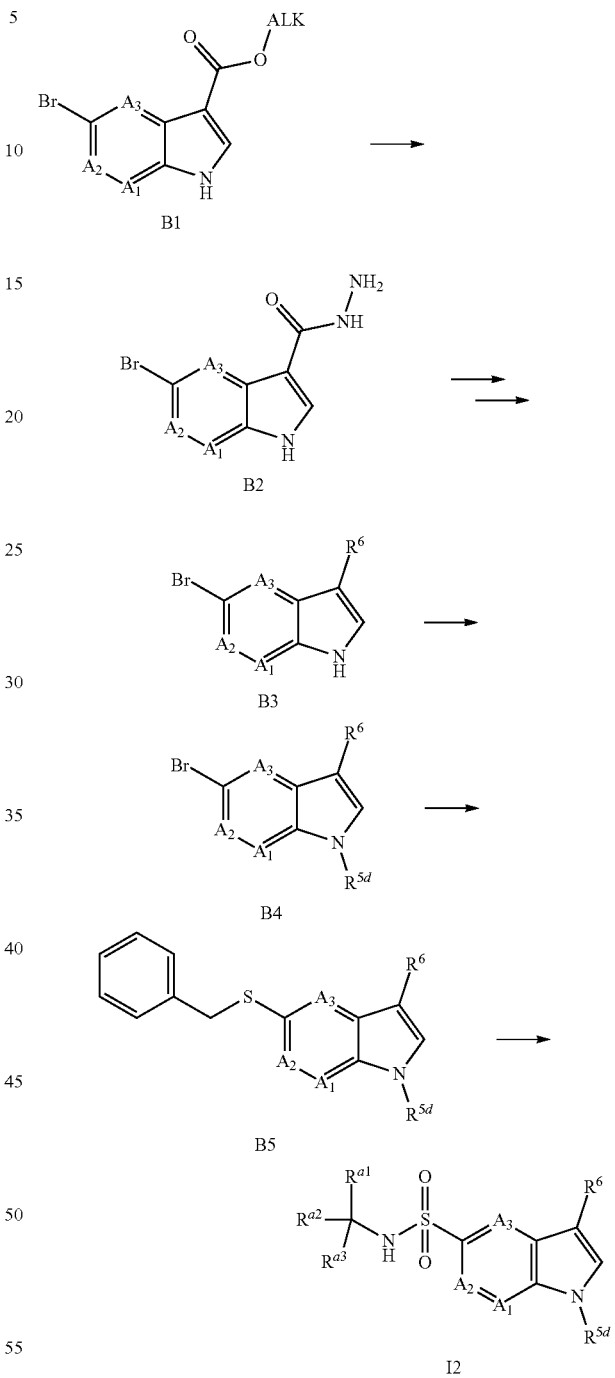

96
Route II wherein, $R^{a1}$, $R^{a2}$, $R^{a3}$, $R^{5d}$, $R^6$, $A_1$, $A_2$, $A_3$ are defined as above; MET is a metallic group, for example,

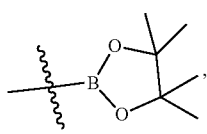 [SMILES: *B1OC(C)(C)C(C)(C)O1]

BF$_3$K or B(OH)$_2$; PG is a protecting group, such as Boc or THP; the route I comprises the following steps: compound A1 was introduced protecting group to obtain compound A2, A2 was converted to A3 containing MET, then was converted to A4 by coupling reaction, A4 was converted to benzylthio compound A5, A5 is deprotected to give compound A6, which is converted to compound A7 by nucleophilic substitution or other reactions, and A7 is further converted to obtain compound I1;

Wherein, $R^{a1}$, $R^{a2}$, $R^{a3}$, $R^{5d}$, $R^6$, $A_1$, $A_2$ and $A_3$ are defined as above; ALK is $C_{1-6}$ alkyl, for example, methyl or ethyl; The route II comprises the following steps: ester compound B1 was converted to compound B2 in the presence of hydrazine compounds, B2 is converted to compound B3 by introducing acyl groups and ring formation, B3 is converted to compound B4 by reactions such as nucleophilic substitution, B4 is converted to benzylthio compound B5, and B5 is further converted to compound I2;

Route III

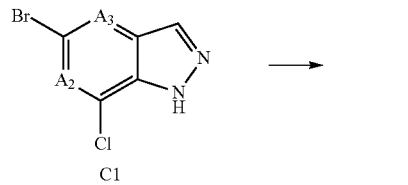
C1

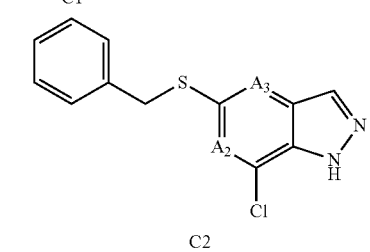
C2

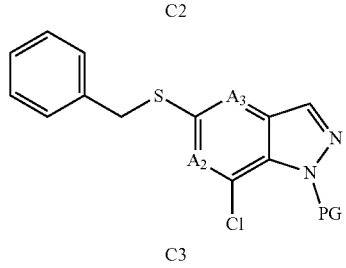
C3

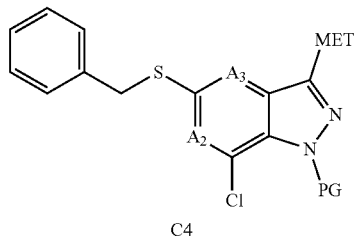
C4

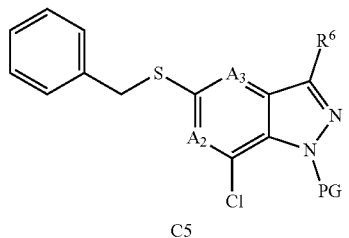
C5

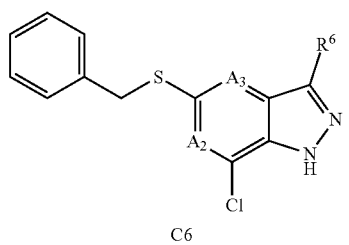
C6

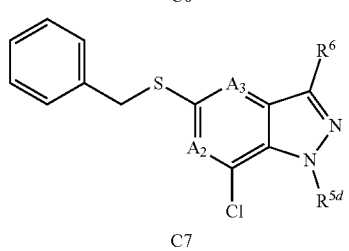
C7

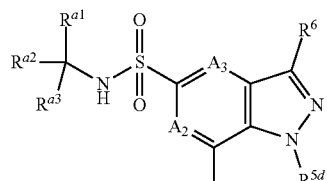
C8

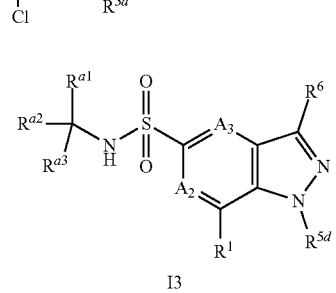
I3 wherein, $R^{a1}$, $R^{a2}$, $R^{a3}$, $R^d$, $R^6$, $A_2$ and $A_3$ are defined as above; MET is a metal group, for example,

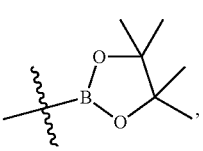 [SMILES: *B1OC(C)(C)C(C)(C)O1]

$BF_3K$, $B(OH)_2$; PG is a protecting group such as Boc or THP; The route III comprises the following steps: compound C1 was converted to benzylthio compound C2, C2 was introduced a protecting group to obtain compound C3, C3 was converted to metallic compound C4, C4 was converted to compound C5 by coupling reaction, C5 was deprotected to give compound C6, C6 was converted to compound C7 by nucleophilic substitution or other reactions, C7 is further transformed to compound C8, and C8 transformed to compound I3 by nucleophilic substitution, coupling or other reactions;

Route IV

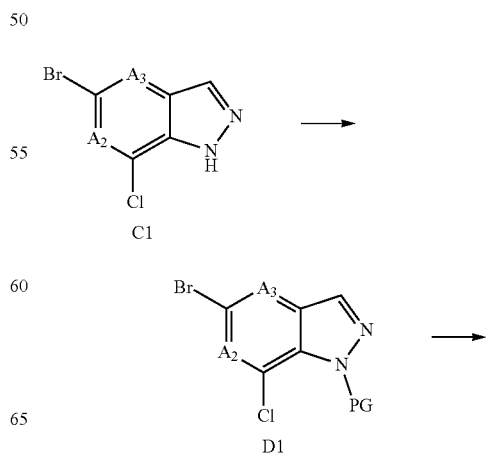

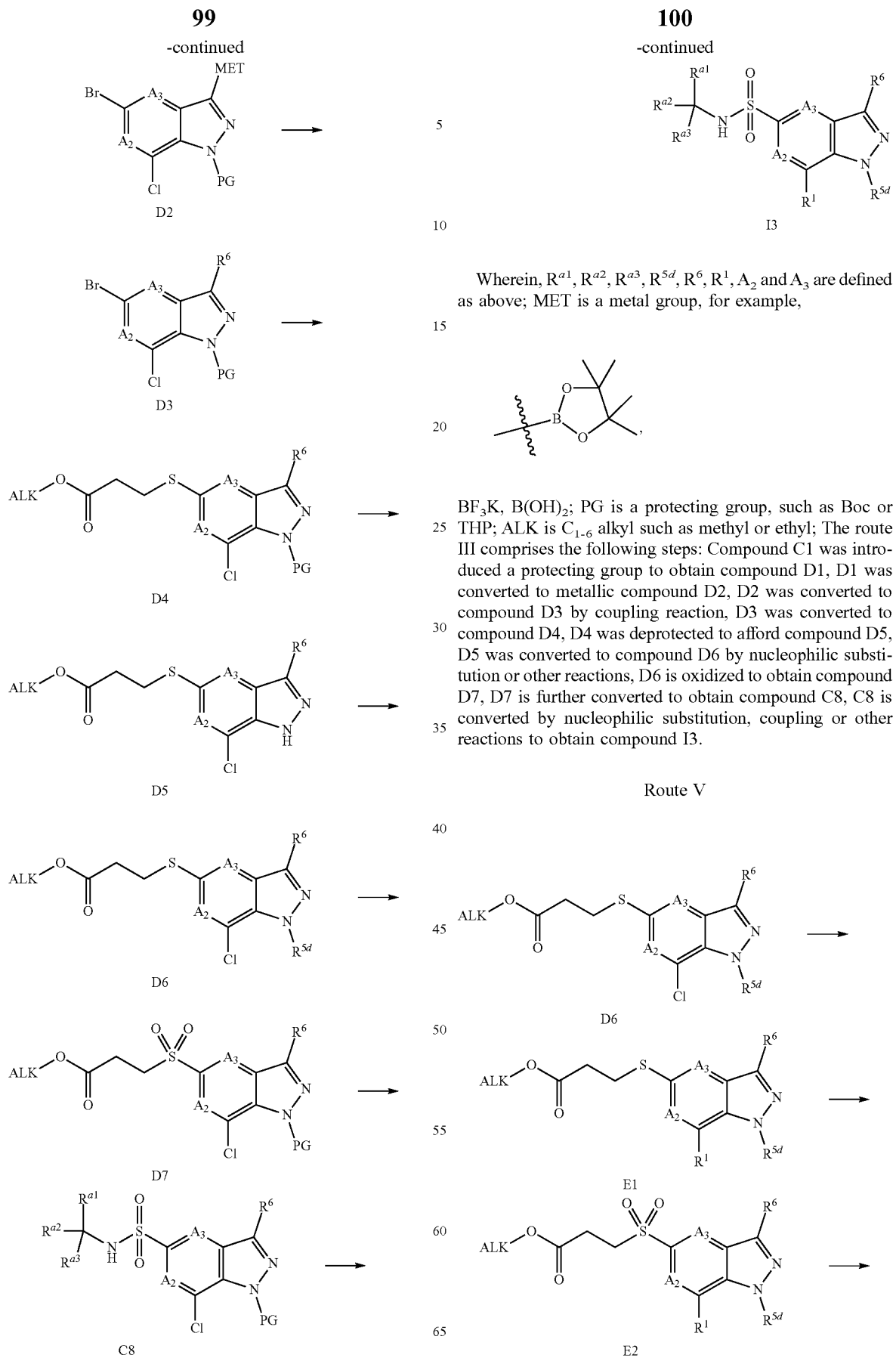

Wherein, $R^{a1}$, $R^{a2}$, $R^{a3}$, $R^{5d}$, $R^6$, $R^1$, $A_2$ and $A_3$ are defined as above; MET is a metal group, for example, $BF_3K$, $B(OH)_2$; PG is a protecting group, such as Boc or THP; ALK is $C_{1-6}$ alkyl such as methyl or ethyl; The route III comprises the following steps: Compound C1 was introduced a protecting group to obtain compound D1, D1 was converted to metallic compound D2, D2 was converted to compound D3 by coupling reaction, D3 was converted to compound D4, D4 was deprotected to afford compound D5, D5 was converted to compound D6 by nucleophilic substitution or other reactions, D6 is oxidized to obtain compound D7, D7 is further converted to obtain compound C8, C8 is converted by nucleophilic substitution, coupling or other reactions to obtain compound I3.

Route V

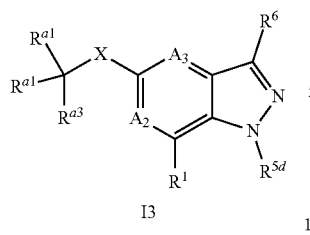

I3 wherein, $R^{a1}$, $R^{a2}$, $R^{a3}$, X, $R^{5d}$, $R^6$, $R^1$, $A_2$ and $A_3$ are defined as above; ALK is $C_{1-6}$ alkyl such as methyl or ethyl; The route V is described as follows: compound D6 was converted to compound E1 by nucleophilic substitution, coupling or other reactions, E1 was oxidized to give compound E2, which was further converted to give compound I3.

Route VI

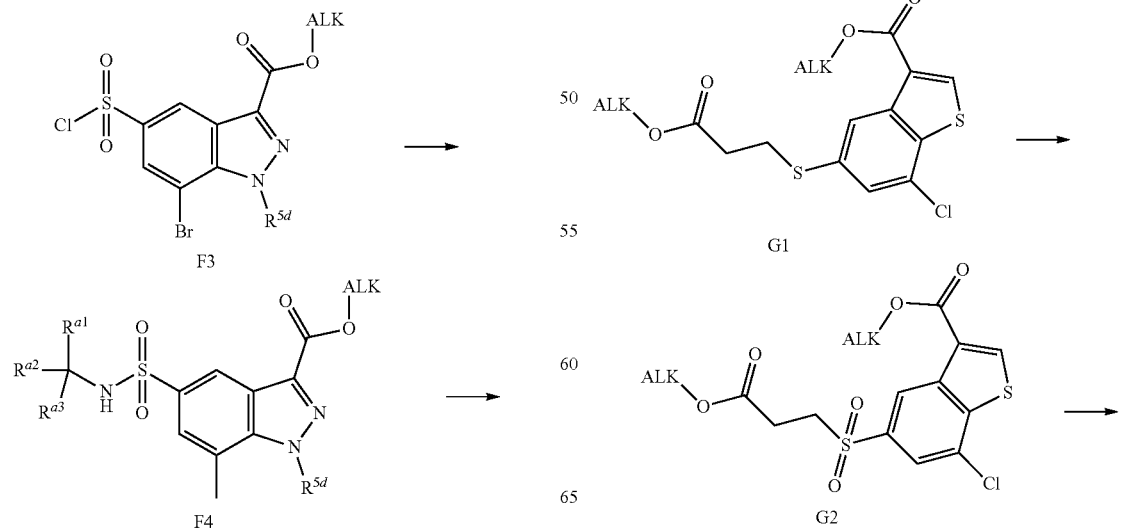

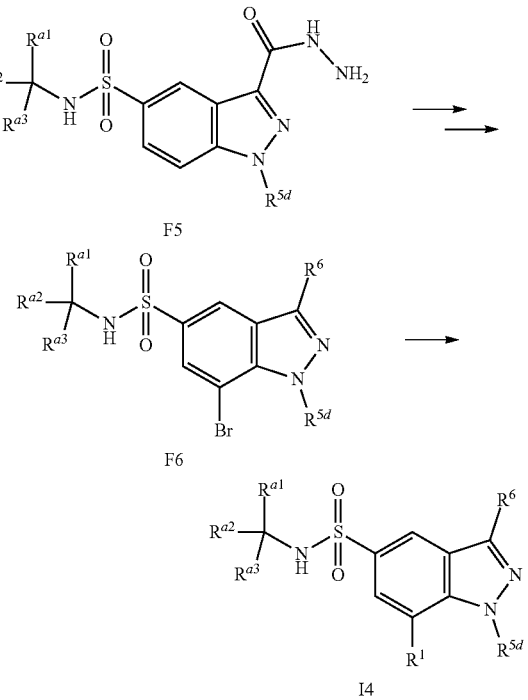

wherein, $R^{a1}$, $R^{a2}$, $R^{a3}$, $R^{5d}$, $R^6$ and $R^1$ are defined as above; ALK is $C_{1-6}$ alkyl such as methyl or ethyl; The route VI comprises the following steps: chlorosulfonation of compound F1 to give compound F2, F2 was converted to compound F3 by bromination reaction, F3 was further converted to compound F4, F4 was converted to compound F5 in the presence of hydrazine compounds, F5 was converted to compound F6 by the introduction of acyl groups and ring formation, F6 is converted to compound I4 by nucleophilic substitution, coupling or other reactions.

Route VII

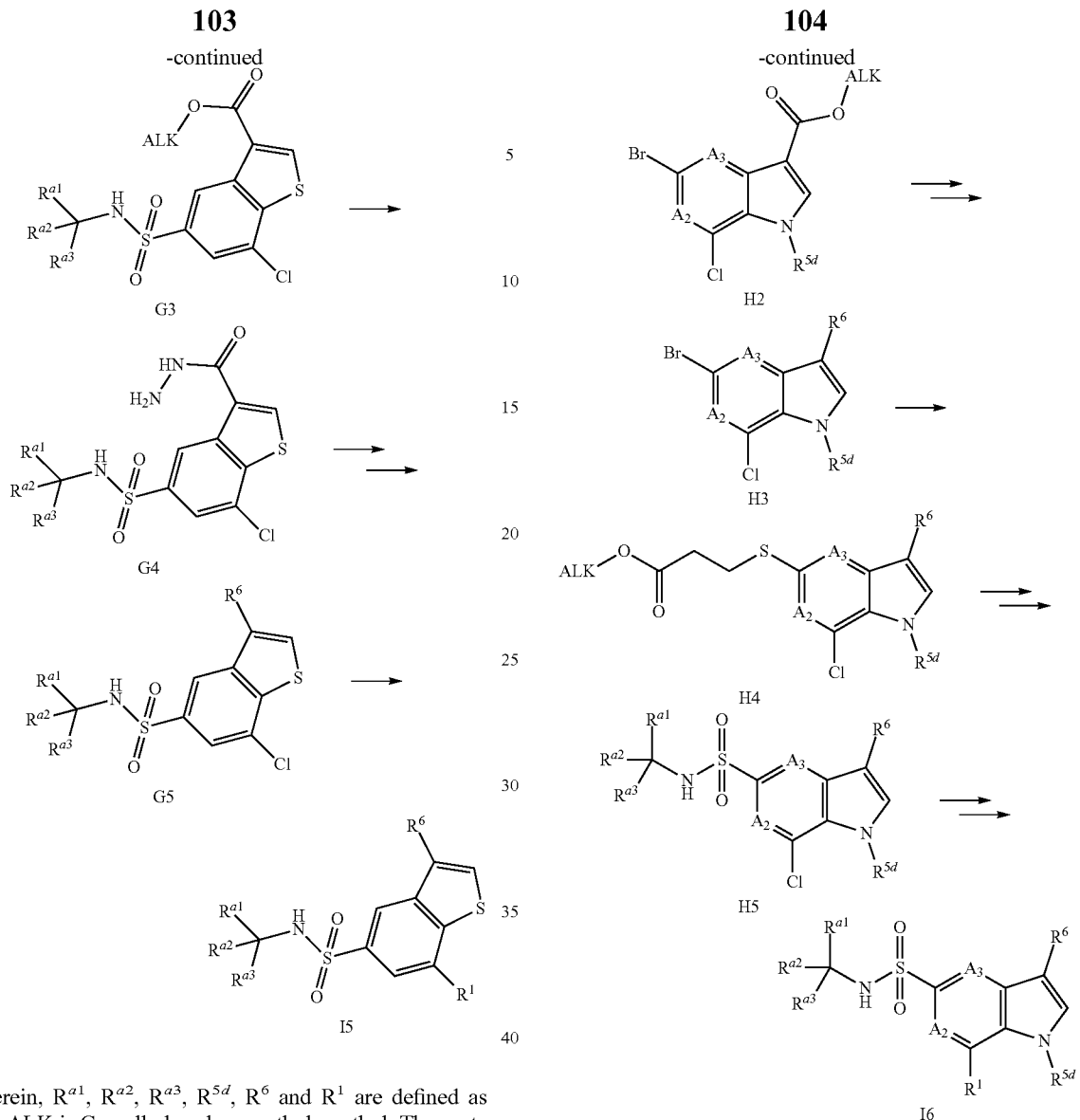

wherein, $R^{a1}$, $R^{a2}$, $R^{a3}$, $R^{5d}$, $R^6$ and $R^1$ are defined as above; ALK is $C_{1-6}$ alkyl such as methyl or ethyl; The route VII comprises the following steps: Oxidation of compound G1 to give compound G2, which was further converted give compound G3, G3 was converted to compound G4 in the presence of hydrazine compounds, G4 was converted to compound G5 by the introduction of acyl groups and ring formation, and c G5 was converted to compound I5 by nucleophilic substitution or coupling reaction.

Route VIII

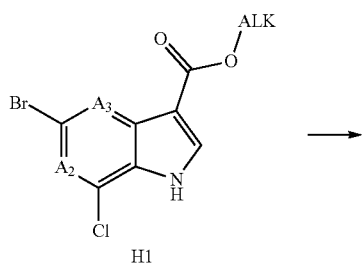

Wherein, $R^{a1}$, $R^{a2}$, $R^{a3}$, $R^{5d}$, $R^6$, $R^1$, $A_2$ and $A_3$ are defined as above; ALK is $C_{1-6}$ alkyl such as methyl or ethyl; The route VIII comprises the following steps: the ester compound H1 was converted to compound H2 by reactions such as nucleophilic substitution, H2 reacted with hydrazine compounds, then introduced acyl groups, and formed a ring to give compound H3, H3 was converted to H4, H4 was converted to compound H5 by reactions such as oxidation and substitution, and H5 is further converted to give compound I6.

Route IX

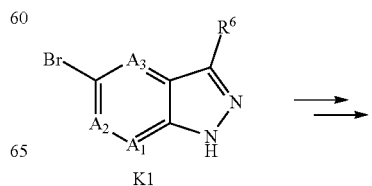

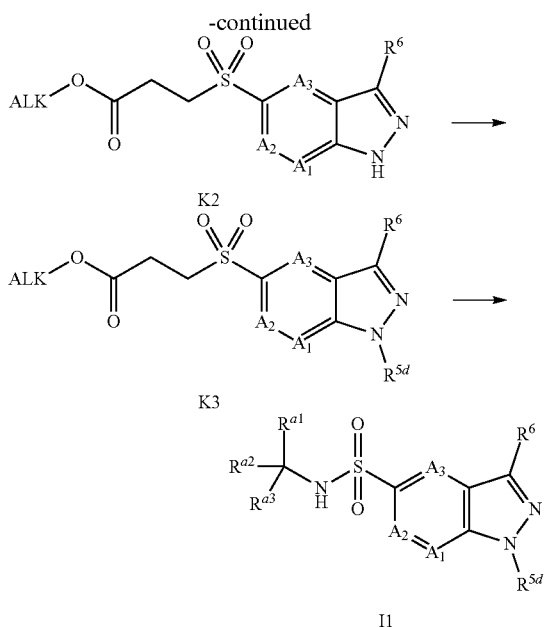

Wherein, $R^{a1}$, $R^{a2}$, $R^{a3}$, $R^{5d}$, $R^6$, $A_1$, $A_2$ and $A_3$ are defined as above; ALK is $C_{1-6}$ alkyl such as methyl or ethyl; The route IX comprises the following steps: compound K1 was converted to compound K2 by coupling and oxidation reactions, K2 was converted to compound K3 by nucleophilic substitution or other reactions, and K3 was further converted to obtain compound I1.

The present disclosure also provides a pharmaceutical composition comprising a substance A and a pharmaceutically acceptable excipient, wherein the substance A is a therapeutically effective amount of the compound containing structure of a five-membered heteroaromatic ring of formula I, the pharmaceutically acceptable salt thereof, the stereoisomer thereof, the tautomer thereof or the isotopically labeled compound thereof as described above.

The present disclosure also provides a method for inhibiting PARG in a subject in need thereof, comprising: administering a therapeutically effective amount of a substance A to the subject, wherein the substance A is the compound containing structure of a five-membered heteroaromatic ring of formula I, the pharmaceutically acceptable salt thereof, the stereoisomer thereof, the tautomer thereof or the isotopically labeled compound thereof as described above.

The present disclosure also provides a method for treating or preventing an PARG related disease in a subject in need thereof, comprising: administering an effective amount of a substance A, wherein the substance A is the compound containing structure of a five-membered heteroaromatic ring of formula I, the pharmaceutically acceptable salt thereof, the stereoisomer thereof, the tautomer thereof or the isotopically labeled compound thereof as described above.

In the method for treating or preventing an PARG related disease in a subject in need thereof, wherein the PARG related disease is cancer, the cancer is selected from the group consisting of colon cancer, appendicle cancer, pancreatic cancer, MYH-related polyposis, hematologic cancer, breast cancer, endometrial cancer, gallbladder cancer, bile duct cancer, prostate cancer, lung cancer, brain cancer, ovarian cancer, cervical cancer, testicular cancer, kidney cancer, head or neck cancer, bone cancer, skin cancer, rectal cancer, liver cancer, esophageal cancer, stomach cancer, thyroid cancer, bladder cancer, lymphoma, leukemia and melanoma.

The term "pharmaceutically acceptable salt" refers to a salt prepared from compounds of the present disclosure with relatively non-toxic, pharmaceutically acceptable acids or bases. When compounds of the present disclosure contain relatively acidic functional groups, base addition salts can be obtained by contacting the neutral form of such compounds with a sufficient amount of pharmaceutically acceptable bases, either in pure solution or a suitable inert solvent. The pharmaceutically acceptable base addition salts include but are not limited to: lithium salt, sodium salt, potassium salt, calcium salt, aluminum salt, magnesium salt, zinc salt, bismuth salt, ammonium salt and diethanolamine salt. When compounds of the present disclosure contain relatively basic functional groups, acid addition salts can be obtained by contacting the neutral form of such compounds with a sufficient amount of pharmaceutically acceptable acids, either in pure solution or a suitable inert solvent. The pharmaceutically acceptable acids include inorganic acids, and the inorganic acids include but are not limited to: hydrochloric acid, hydrobromic acid, hydroiodic acid, nitric acid, carbonic acid, phosphoric acid, phosphorous acid and sulfuric acid. The pharmaceutically acceptable acids include organic acids, and the organic acids include but are not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, hydrogen tartrate, ascorbic acid, gentisic acid, fumaric acid, gluconic acid, saccharic acid, formic acid, ethanesulfonic acid, pamoic acid (i.e., 4,4'-methylene-bis(3-hydroxy-2-naphthoic acid)) and amino acid (such as glutamic acid and arginine). When compounds of the present disclosure contain relatively acidic functional groups and relatively basic functional groups, such compounds can be converted into base addition salts or acid addition salts. For details, reference can be made to Berge et al., "Pharmaceutical Salts", Journal of Pharmaceutical Science 66: 1-19 (1977), or Handbook of Pharmaceutical Salts: Properties, Selection, and Use (P. Heinrich Stahl and Camille G. Wermuth, ed., Wiley-VCH, 2002).

In the present disclosure, when multiple substituents are present, the substituents are the same or different.

The term "stereoisomer" refers to an isomer in which the atoms or atomic groups in a molecule have the same interconnection order but different spatial arrangements, such as cis-trans isomers, optical isomers or atropisomers. These stereoisomers can be separated, purified and enriched by means of asymmetric synthesis methods or chiral separation methods (including but not limited to thin layer chromatography, rotation chromatography, column chromatography, gas chromatography and high-pressure liquid chromatography) or can also be obtained by means of chiral resolution via forming bonds (chemical bonding, etc.) or forming salts (physical bonding) with other chiral compounds, etc.

The term "tautomer" refers to a functional group isomer resulting from the rapid movement of an atom in two positions in a molecule. For example, acetone and 1-propene-2-ol can be converted into each other by the rapid movement of hydrogen atoms on oxygen and α-carbon.

The term "isotopic compound" refers to a compound in which one or more atoms are substituted with one or more atoms having a specific atomic mass or mass number. Examples of isotopes that can be incorporated into compounds of the present disclosure include, but are not limited to, isotopes of hydrogen, carbon, nitrogen, oxygen, fluorine, sulfur and chlorine (e.g., 2H, 3H, 13C, 14C, 15N, 18O, 17O, 18F, 35S and 36Cl). The isotopic compounds of the present disclosure can generally be prepared by substituting non-isotopically-labeled reagents with isotopically-labeled reagents according to the methods described herein.

The term "halogen" refers to fluorine, chlorine, bromine or iodine.

The term "alkyl" refers to a linear or branched alkyl group having a specified number of carbon atoms. Examples of alkyl include methyl, ethyl, n-propyl, isopropyl, n-butyl, tert-butyl, isobutyl, sec-butyl, n-pentyl, n-hexyl, n-heptyl, n-octyl, and the like.

The term "alkylene" refers to a linking group between two other species, which may be linear or branched. Examples include, but are not limited to, —$CH_2$—, —$CH_2CH_2$—, —$CH_2CH_2CH_2CH(CH_3)$— and —$CH_2CH(CH_2CH_3)CH_2$—.

The terms "cycloalkyl" and "carbocyclic ring" refer to a saturated cyclic group consisting only of carbon atoms having a specified number of carbon atoms (e.g., $C_3$-$C_6$), which is a monocyclic, bridged or spiro ring. The cycloalkyl includes, but is not limited to, cyclopropyl, cyclobutyl, cyclopentyl, and cyclohexyl.

The term "aryl" refers to an aromatic group consisting of carbon atoms, each ring having aromaticity. For example, phenyl or naphthyl.

The term "heteroaryl" refers to a cyclic group having a specified number of ring atoms (e.g., 5-12 members), a specified number of heteroatoms (e.g., 1, 2, or 3) and specified heteroatom species (one or more of N, O and S), which is monocyclic or polycyclic, and has at least one aromatic ring (according to the Hückel's rule). Heteroaryls are linked to other fragments of the molecule through aromatic or non-aromatic rings. Heteroaryls include, but are not limited to, furyl, pyrrolyl, thienyl, pyrazolyl, imidazolyl, oxazolyl, thiazolyl, pyridinyl, pyrimidinyl, and indolyl.

The terms "heterocyclyl", "heterocycle" or "heterocycloalkyl" refer to a cyclic group having a specified number of ring atoms (e.g., 3-8 members), a specified number of heteroatoms (e.g., 1, 2, or 3) and specified heteroatom species (one or more of N, O and S), which is monocyclic, bridged, or spiro, and where each ring is saturated. Heterocycloalkyls include, but are not limited to, azetidinyl, tetrahydropyrrolyl, tetrahydrofuryl, morpholinyl, piperidinyl, and the like.

The term "hydroxyl" refers to a —OH group.

The term "cyano" refers to a —CN group.

The term "oxo" refers to a =O group.

Substituted "$C_{x1}$-$C_{y1}$" groups with specified numbers of carbon atoms (x1 and y1 are integers), for example, "$C_{x1}$-$C_{y1}$" alkyl, "$C_{x1}$-$C_{y1}$" cycloalkyl, "$C_{x1}$-$C_{y1}$" cycloalkenyl, "$C_{x1}$-$C_{y1}$" alkoxyl, "$C_{x1}$-$C_{y1}$" alkenyl, "$C_{x1}$-$C_{y1}$" alkynyl, "$C_{x1}$-$C_{y1}$" aryl, "$C_{x1}$-$C_{y1}$" heteroaryl, or "$C_{x1}$-$C_{y1}$" heterocyclyl, all represent numbers of carbon atoms excluding substituents, e.g., a $C_1$-$C_6$ alkyl represents a $C_1$-C6 alkyl excluding substituents.

The above preferred conditions may be combined arbitrarily to obtain preferred embodiments of the present disclosure without departing from the general knowledge in the art.

The reagents and starting materials used in the present disclosure are commercially available.

The positive/progressive effects of the present disclosure are as follows: the present disclosure provides a five-membered heteroaromatic ring structure containing compound, pharmaceutical compositions thereof and applications thereof, and the five-membered heteroaromatic ring structure containing compound is expected to treat and/or prevent various PARG-related diseases.

DETAILED DESCRIPTION OF THE PREFERRED EMBODIMENT

The present disclosure is further illustrated by the following examples, but the present disclosure is not limited thereto. Experimental methods with specific conditions are not indicated in the following examples, but can be chosen according to conventional methods and conditions or commodity instructions.

In the present disclosure, the room temperature refers to the ambient temperature, which is 10° C. to 35° C. Overnight refers to 8-15 hours. Reflux refers to the reflux temperature of the solvent under normal pressure.

The following is a list of abbreviations used in the examples:

DCM dichloromethane

DMF N,N-dimethylforamide

EA ethyl acetate

DMSO dimethyl sulfoxide

MTBE methyl tert-butyl ether

DMAP 4-dimethylaminopyridine

DIPEA diisopropylethylamine $Pd_2(dba)_3$ tris(dibenzylideneacetone)dipalladium m-CPBA m-chloroperoxybenzoic acid Xantphos 9,9-dimethyl-4,5-bis(diphenylphosphino)xanthene RuPhos 2-dicyclohexylphosphino-2',6'-diisopropoxy-1,1'-biphenyl DMF-DMA N,N-dimethylformamide dimethyl Acetal THE tetrahydrofuran THP tetrahydropyran TFA trifluoroacetic acid Ms methanesulfonyl Tf trifluoromethylsulfonyl CDI carbonyl diimidazole EDCI 1-Ethyl-3-(3-dimethylaminopropyl)carbodiimide hydrochloride HOBT 1-Hydroxybenzotriazole PMBCl 4-methoxybenzyl chloride DBDMH 1,3-dibromo-5,5-dimethylimidazolidine-2,4-dione SEMCl 2-(trimethylsilyl)ethoxymethyl chloride DHP 3,4-2H-dihydropyran RuPhos Pd G3 (2-dicyclohexylphosphino-2',6'-diisopropoxy-1,1'-biphenyl)[2-(2'-amino-1,1'-biphenyl)]palladium(II) methanesulfonate NMM N-methylmorpholine

[Ir(COD)OMe]$_2$ (1,5-cyclooctadiene)(methoxy)iridium (I) dimer

SelectFluor II 1-fluoro-4-methyl-1,4-diazabicyclo[2.2.2]octane tetrafluoroborate

Synthetic Route of Intermediate 1-f

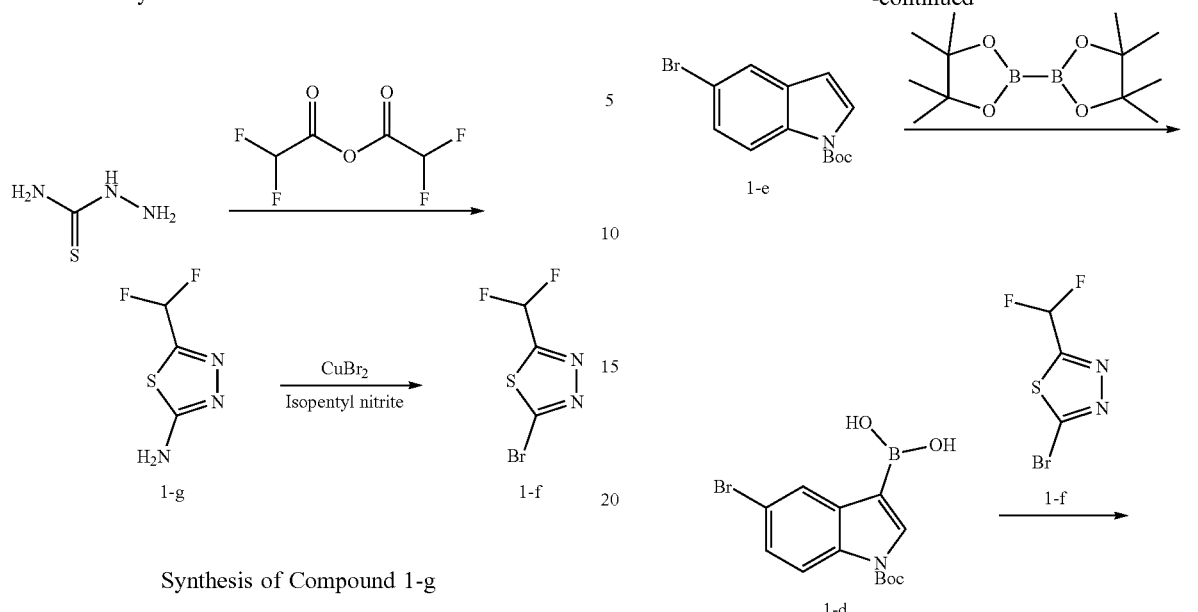

Synthesis of Compound 1-g

Thiosemicarbazide (3 g, 32.9 mmol) was added into difluoroacetic anhydride (8.6 g, 49.4 mol) in four batches in an ice-water bath. After addition, the ice-water bath was withdrawn and the reaction was stirred at 85° C. for 36 h. The reaction was cooled to room temperature and the pH was adjusted to 7-8 with saturated sodium bicarbonate solution in an ice-water bath, then some solids precipitated and was filtered, and the solids were washed with water (5 mL) and added acetonitrile (10 mL), and the product was concentrated to dryness at reduced pressure. The filtrate was extracted 8 times with DCM:MeOH=10:1 (100 mL) and the organic phase was dried over sodium sulfate, filtered and the filtrate was concentrated at reduced pressure to obtain the crude product, which was purified by column chromatography (SiO$_2$, DCM:MeOH=10:1) to obtain the product. The compound 1-g (1.6 g, 32%) was obtained as a solid. LC-MS (ESI): m/z 152.1 (M+H)$^+$; $^1$H NMR (400 MHz, DMSO-d$_6$): δ 7.77 (s, 2H), 7.24 (t, J=56.0 Hz, 1H).

Synthesis of Compound 1-f

Copper bromide (620.1 mg, 2.78 mmol) was added to a solution of compound 1-g (400 mg, 2.65 mmol) in anhydrous acetonitrile (20 mL). Isopentyl nitrite (1.183 g, 5.3 mmol) in acetonitrile (1 mL) was added dropwise to the above mixture at 0° C. After addition, the reaction was stirred at room temperature for 20 min and then at 63° C. for 12 h. The reaction was cooled to room temperature, filtered through celite, and the filtrate was concentrated under pressure to obtain the concentrate, which was purified by column chromatography (SiO$_2$, petroleum ether: ethyl acetate=10:1) to give compound 1-f (370 mg, 65%) as a yellow liquid. $^1$H NMR (400 MHz, DMSO-d$_6$): δ 7.59 (t, J=52.0 Hz, 1H).

Example 1 Synthesis of Compound 1

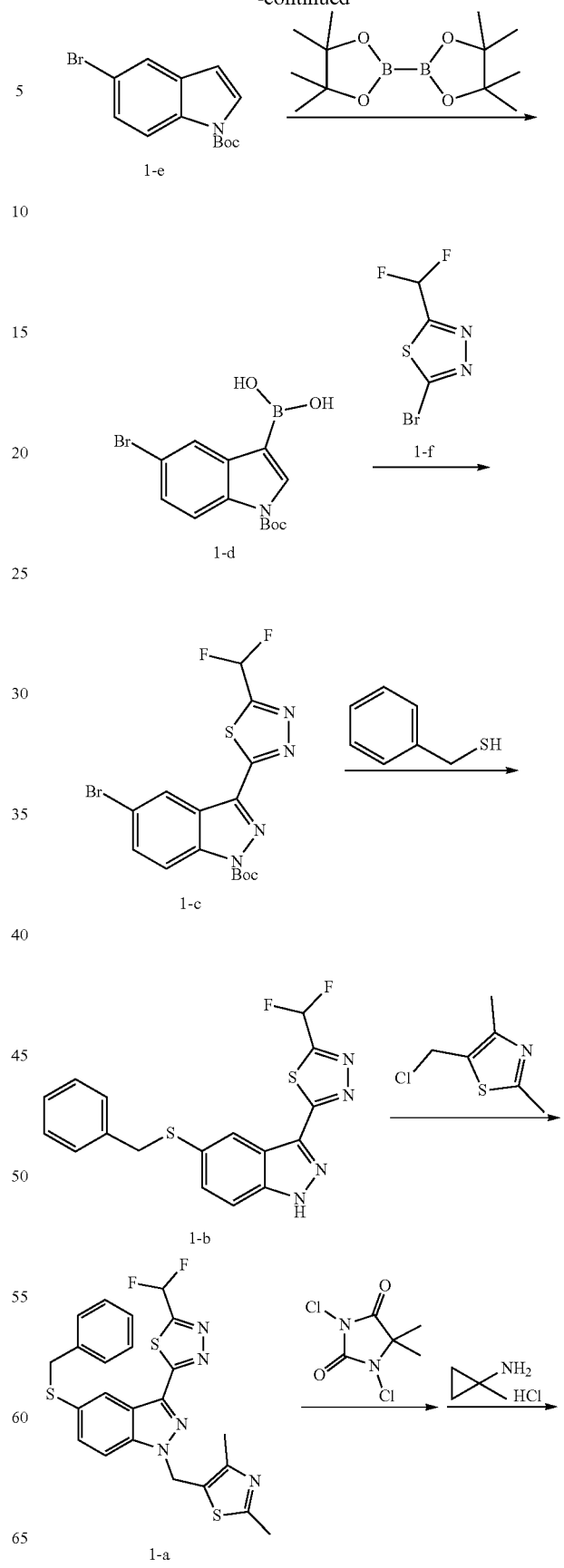

-continued

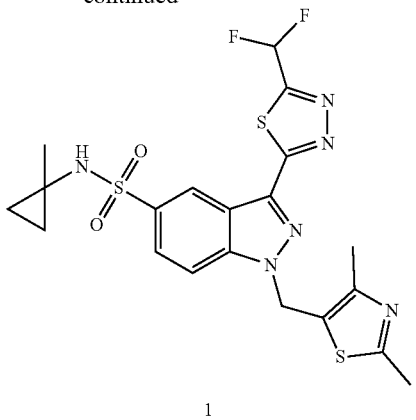

1

Synthesis of Compound 1-e 5-bromoindazole (1.5 g, 7.61 mmol), acetonitrile (20 mL), di-tert-butyl dicarbonate (2.50 g, 11.40 mmol), triethylamine (770 mg, 7.61 mmol) and DMAP (93 mg, 7.60 mmol) were mixed in an ice-water bath in a reaction vial. The mixture was stirred at room temperature for 3 hours, then was concentrated and the residue was purified by column chromatography (mobile phase: petroleum ether/ethyl acetate 100/0 to 80/20) to give compound 1-e (2.0 g, 88%). LC-MS (ESI): m/z 297.0 (M+H)$^+$.

Synthesis of Compounds 1-d

[Ir(COD)OMe]$_2$ (153 mg, 0.23 mmol), 4,4'-di-tert-butyl-2,2'-bipyridine (125 mg, 0.47 mmol), bis(pinacolato)diboron (829 mg, 3.26 mmol) and anhydrous methyl tert-butyl ether (10 mL) were mixed in a reaction flask under the protection of argon. The resulting mixture was stirred at room temperature for 5 min, and was added 1-e (1.85 g, 6.22 mmol) and anhydrous methyl tert-butyl ether solution (10 mL). After addition, the reaction was stirred at 25° C. for 1 h under the protection of argon, then at 80° C. for 1 h under argon protection. The reaction mixture was concentrated to give compound 1-d (2.9 g of crude product). LC-MS (ESI): m/z 341.1 (M+H)$^+$.

Synthesis of Compounds 1-c 1-d (1.9 g crude, 4.00 mmol), 1-f (540 mg, 2.52 mmol), palladium acetate (32 mg, 0.13 mmol), XantPhos (73 mg, 0.13 mmol), toluene (20 mL) and pure water (10 mL) were mixture in a reaction flask. Cesium carbonate (2.46 g, 7.56 mmol) was added to the above mixture while cooling in an ice-water bath, and the reaction was stirred at room temperature for 20 hours. The reaction mixture was diluted with ethyl acetate, washed with water and brine, dried over anhydrous Na$_2$SO$_4$, filtered, concentrated and the residue was purified by column chromatography (mobile phase: petroleum ether, dichloromethane (4:1)/ethyl acetate 100/0 to 80/20) to give compounds 1-c (550 mg, 50%). LC-MS (ESI): m/z 431.0 (M+H)$^+$.

Synthesis of Compounds 1-b 1-c (525 mg, 1.22 mmol), benzyl mercaptan (460 mg, 3.65 mmol), tris(dibenzylideneacetone)dipalladium (112 mg, 0.12 mmol), XantPhos (140 mg, 0.24 mmol), DIPEA (630 mg, 4.87 mmol) and 1,4-dioxane (20 mL) were combined in a reaction vial. After addition, the reaction was stirred at 110° C. for 20 hours. The reaction mixture was concentrated and the residue was purified by column chromatography (mobile phase: petroleum ether, dichloromethane (4:1)/ethyl acetate 100/0 to 70/30) to give compound 1-b (340 mg, 74%). LC-MS (ESI): m/z 375.0 (M+H)$^+$.

Synthesis of Compounds 1-a

To a reaction flask were added 1-b (190 mg, 0.51 mmol), 5-(chloromethyl)-2,4-dimethyl-1,3-thiazole (164 mg, 1.01 mmol) and DMF (5 mL), respectively. Cesium carbonate (496 mg, 1.52 mmol) was added while cooling in an ice-water bath. After addition, the reaction was stirred at room temperature for 2 hours. The reaction mixture was diluted with ethyl acetate, washed with water and brine, dried over anhydrous Na$_2$SO$_4$, filtered, concentrated and the residue was purified by column chromatography (mobile phase: petroleum ether, dichloromethane (4:1)/ethyl acetate 100/0 to 70/30) to give compound 1-a (200 mg, 78%). LC-MS (ESI): m/z 500.0 (M+H)$^+$; $^1$H NMR (400 MHz, CDCl$_3$): δ 8.24 (1H, d, J=1.6 Hz), 7.90 (1H, d, J=9.0 Hz), 7.67 (1H, t, J=53.2 Hz), 7.61 (1H, dd, J=8.8, 1.7 Hz), 7.40-7.33 (2H, m), 7.27 (2H, dd, J=8.2, 6.5 Hz), 7.23-7.18 (1H, m), 5.94 (2H, s), 4.31 (2H, s), 2.50 (3H, s), 2.46 (3H, s).

Synthesis of Compound 1

1-a (30 mg, 0.06 mmol), acetonitrile (2 mL), acetic acid (50 mg) and water (50 mg) were combined in a reaction flask, and the resulting mixture was added 1,3-dichloro-5,5-dimethylimidazolidine-2,4-dione (18 mg, 0.09 mmol) in an ice-salt bath (about −18° C.). The reaction was stirred at −18 to −10° C. for 1.5 h, then was added additional dichlorohydantoin (12 mg, 0.06 mmol) in an ice-salt bath (about −18 to −10° C.). The reaction was continued stirring at −18 to −10° C. for 1 h, then was added additional dichlorhydantoin (12 mg, 0.06 mmol) was added under the ice salt bath. The reaction was stirred at −18 to −10° C. for 1 h. The mixture was evaporated, diluted with ethyl acetate, washed with water, brine, dried over anhydrous Na$_2$SO$_4$, filtered and the filtrate was evaporated to obtain the crude intermediate. The crude intermediate was mixed with 1-methylcyclopropylamine hydrochloride (13 mg, 0.12 mmol), was added anhydrous dichloromethane (3 mL) and DIPEA (30 mg, 0.23 mmol) in an ice-water bath, and the resulting mixture was stirred at 25° C. for 2 h. The reaction mixture was concentrated to dryness and the residue was purified by column chromatography (mobile phase: dichloromethane/methanol=100/0 to 90/10, dichloromethane/(dichloromethane/methanol/7M ammonia-methanol))=100/0 to 20/80) to give the crude product, and separated on C8 column chromatography (mobile phase: 10 mM aqueous ammonium bicarbonate solution/acetonitrile=95/5 to 5/95) to give compound 1 (6 mg, 19%) as a white solid. LC-MS (ESI): m/z 511.0 (M+H)$^+$.

Example 2 Synthesis of Compound 2

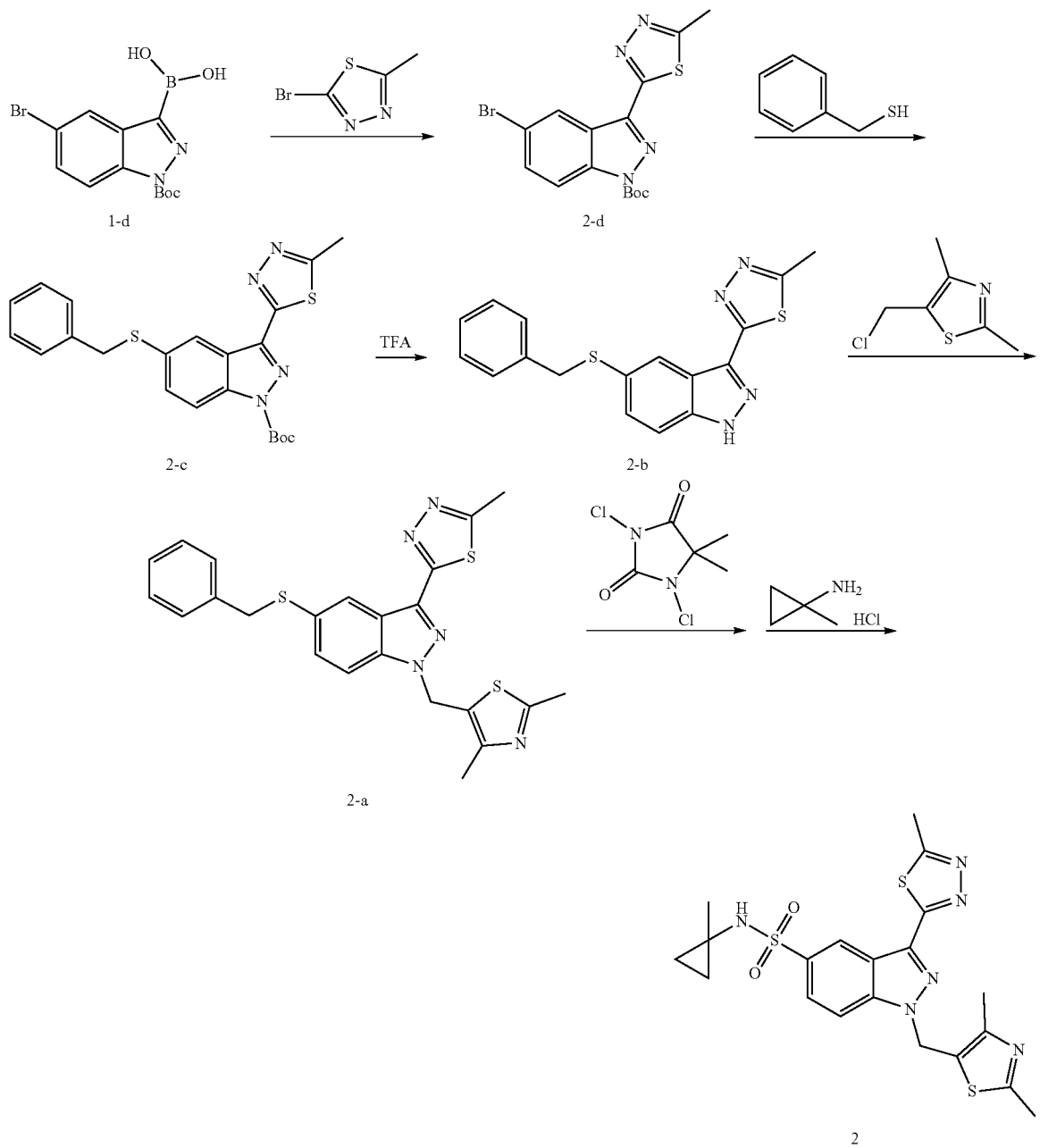

Synthesis of Compound 2-d

At room temperature, 5-bromo-2-methyl-1,3,4-thiadiazole (100 mg, 0.56 mmoL) was dissolved in toluene (10 mL), and the resulting mixture was added water (5 mL), 1-d (381 mg, approximately 0.67 mmol according to purity), palladium acetate (25 mg, 0.11 mmoL), Xantphos (129 mg, 0.22 mmoL) and N-methylmorpholine (0.12 mL, 1.12 mmoL). After addition, the reaction mixture was stirred for 16 h at room temperature under nitrogen atmosphereprotection. The reaction mixture was added water (20 mL) and extracted with ethyl acetate (50 mL*2). The organic phase was dried over anhydrous sodium sulfate, filtered, and the filtrate was concentrated at reduced pressure and the crude product was purified by a flash column chromatography (PE/EA=1:2) to give compound 2-d (108 mg, 48%) as a white solid. LC-MS (ESI): m/z=395.0 [M+1]$^+$.

Synthesis of Compound 2-c

Compound 2-d (108 mg, 0.27 mmoL) was dissolved in 1,4-dioxane (10 mL) at room temperature, and the resulting mixture was added Pd$_2$(dba)$_3$ (25 mg, 0.027 mmoL), XantPhos (32 mg, 0.055 mmoL), DIPEA (135 μL, 0.82 mmoL) and benzyl mercaptan (35 μL, 0.30 mmoL), and the reaction mixture was stirred at 110° C. under nitrogen atmosphere for 16 hours. The reaction mixture was cooled to room temperature, concentrated at reduced pressure and the residue was purified by a flash column chromatography (PE/EA=1:1) to give compound 2-c (115 mg) as a yellow oil and the obtained product was used directly in the next reaction step. LC-MS (ESI): m/z=439.1 [M+1]$^+$.

Synthesis of Compound 2-b

TFA (3 mL) was added to a solution of 2-c (115 mg) dissolved in DCM (9 mL) at 0° C., and the reaction mixture was warmed to room temperature and stirred for 3 hr. Concentrate at reduced pressure, the residue was added ethyl acetate (50 mL), washed with saturated sodium bicarbonate (50 mL), and the aqueous phase was extracted with ethyl acetate (50 mL*2). The organic phases were combined, dried over anhydrous sodium sulfate, filtered, and the filtrate was concentrated at reduced pressure, and the crude product was purified by a flash column chromatography (DCM/MeOH=10:1) to give compound 2-b (40 mg, two-step yield 44%) as a yellow solid. LC-MS (ESI): m/z=339.0 [M+1]$^+$.

Synthesis of Compound 2-a 2-b (58 mg, 0.17 mmoL) was dissolved in DMF (5 mL) at room temperature, and the resulting mixture was added cesium carbonate (111 mg, 0.34 mmoL) and stirred at room temperature for 10 min. The mixture was added 5-(chloromethyl)-2,4-dimethyl-1,3-thiazole (41 mg, 0.25 mmoL) and then stirred at room temperature for 2 hours. The reaction mixture was added water (20 mL), extracted with ethyl acetate (50 mL*2) and the organic phase was washed with brine (100 mL*3), dried over anhydrous sodium sulfate, filtered, and the filtrate was concentrated at reduced pressure and the crude product which was purified by a flash column chromatography (PE/EA=1:1 to EA) to give compound 2-a (45 mg, 57%) as a yellow solid. LC-MS (ESI): m/z=464.1 [M+1]$^+$.

Synthesis of Compound 2

Acetic acid (22 μL, 0.39 mmoL), water (18 μL, 1.0 mmoL), and 1,3-dichloro-5,5-dimethylimidazolidine-2,4-dione (38 mg, 0.19 mmoL) were added sequentially to a solution of 2-a (45 mg, 0.097 mmoL) dissolved in acetonitrile (5 mL) at 0° C. The mixture was stirred at 0° C. for 2 h. The reaction mixture was concentrated at reduced pressure and dried in vacuum for 30 min to obtain the intermediate (crude product). The above intermediate was dissolved in 5 mL of DCM at 0° C., then was added 1-methylcyclopropylamine hydrochloride (31 mg, 0.29 mmoL) and triethylamine (108 μL, 0.78 mmoL) sequentially, and the reaction mixture was warmed to room temperature and stirred for 16 hours. The reaction mixture was concentrated at reduced pressure and the crude product was purified by a flash column chromatography (DCM/MeOH=20:1) and preparative TLC (DCM/MeOH=20:1) to afford compound 2 (22 mg, 48%) as a white solid. LC-MS (ESI): m/z=475.0 [M+1]$^+$; $^1$H NMR (CDCl$_3$, 400 MHz): δ 9.11 (1H, s), 7.97 (1H, d, J=8.4 Hz), 7.51 (1H, d, J=8.8 Hz), 7.37-7.27 (1H, m), 5.70 (2H, s), 2.87 (3H, s), 2.62 (3H, s), 2.56 (3H, s), 1.22 (3H, s), 0.81-0.78 (2H, m), 0.49-0.46 (2H, m).

Example 3 Synthetic Route of Compound 3

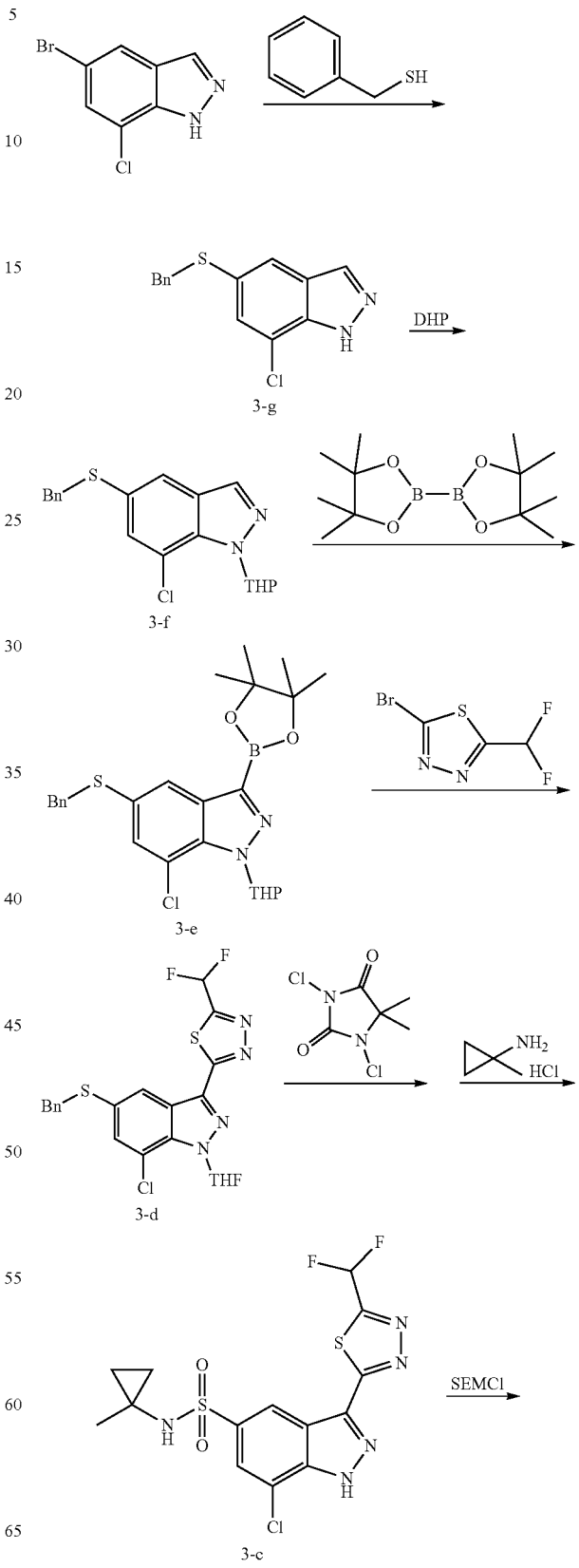

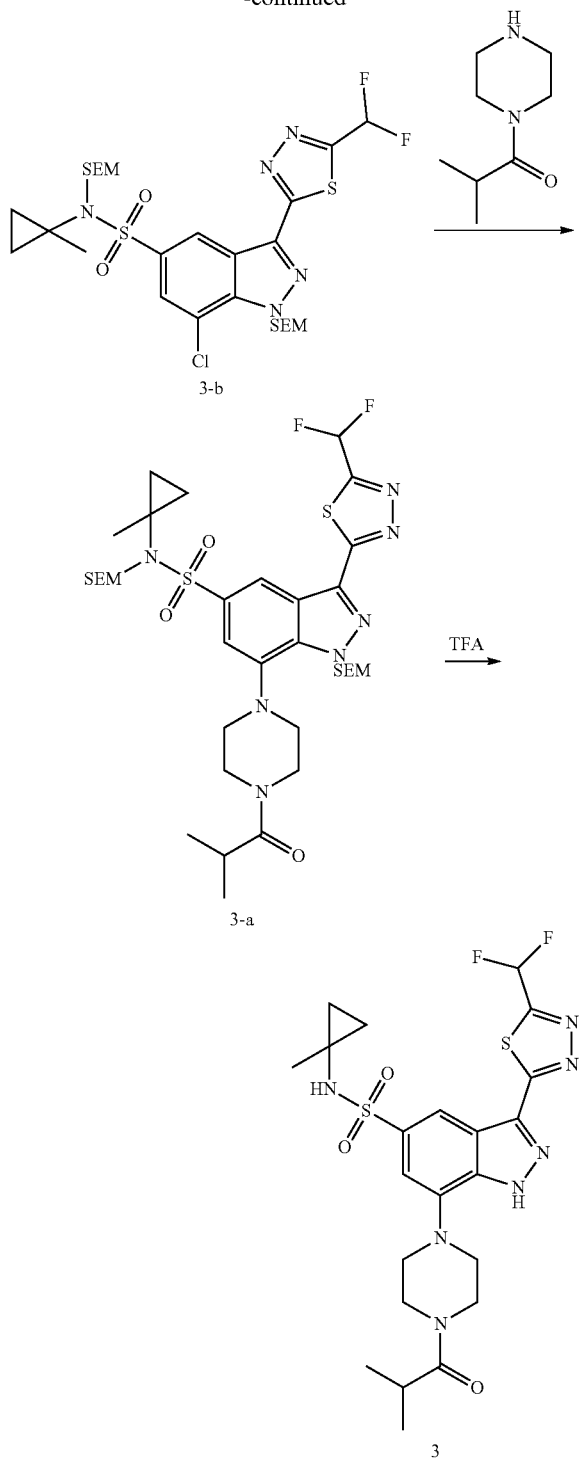

Synthesis of Compound 3-g

A three-necked flask was charged with 5-bromo-7-chloroindazole (2.0 g, 8.64 mmol), Xantphos (0.50 g, 0.85 mmol), 1,4-dioxane (60 mL), DIPEA (4.5 mL, 25.06 mmol) and benzyl mercaptan (3 mL, 24.79 mmol). Degassed and purged with nitrogen twice, the above mixture was added Pd$_2$(dba)$_3$ (0.40 g, 0.42 mmol). Degassed and purged with nitrogen for 3 times, the reaction was refluxed at 100° C. for 5 hours. The reaction was cooled to room temperature, concentrated to dryness, and the residue was purified by column chromatography (mobile phase: petroleum ether/ethyl acetate, 100/0 to 80/20) to give compound 3-g (2.3 g, 97%) as a light brown viscous liquid.

Synthesis of Compound 3-f

To a reaction flask, 3-g (2.3 g, 8.37 mmol), 3,4-dihydro-2H-pyran (30 mL), and trifluoroacetic acid (0.12 mL, 1.57 mmol) were added respectively. After addition, the reaction mixture was stirred at 90° C. for 3 hours. The reaction mixture was diluted with dichloromethane, washed with saturated sodium bicarbonate solution and brine, dried over anhydrous sodium sulfate, filtered and the filtrate was evaporated and the residue was purified by column chromatography (mobile phase: petroleum ether/ethyl acetate, 100/0 to 80/20) to give compound 3-f (2.10 g, 70%) as a brownish red viscous liquid. LC-MS (ESI): m/z 359.1 (M+H)$^+$.

Synthesis of Compound 3-e

Methoxy(cyclooctadiene)chloroiridium dimer (0.175 g, 0.27 mmol), 4,4'-di-tert-butyl-2,2'-dipyridine (0.144 g, 0.54 mmol), biboronic acid pinacol ester (1.38 g, 5.43 mmol) and methyl tert-butyl ether (6 mL) were combined in a microwave tube and the resulting mixture was stirred at room temperature for 5 min after degassed and purged with nitrogen twice. Then the mixture was added a solution of 3-f (0.65 g, 1.81 mmol) in methyl tert-butyl ether (6 mL) and stirred at 80° C. for 3.5 hours after degassed and purged with nitrogen for 3 times. The reaction mixture was evaporated to dryness to afford compound 3-e (870 mg, 99%) as a brown-red viscous liquid.

Synthesis of Compound 3-d 3-e (870 mg, 1.79 mmol), 2-bromo-5-(difluoromethyl)-1,3,4-thiadiazole (374 mg, 1.74 mmol), palladium acetate (44 mg, 0.20 mmol), Xantphos (224 mg, 0.39 mmol), toluene (20 mL) and water (10 mL) were combined in a reaction flask. Degassed and purged with nitrogen twice, the resulting mixture was added N-methylmorpholine (0.64 mL, 5.80 mmol). The reaction mixture was stirred at 25° C. for 18 hours. The reaction mixture was diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 80/20) to give compound 3-d (200 mg, 23%) as a light brown solid. LC-MS (ESI): m/z 493.2 (M+H)$^+$.

Synthesis of Compound 3-c

A reaction vial charged with 3-d (180 mg, 0.37 mmol), acetonitrile (3 mL), acetic acid (0.014 mL, 0.25 mmol) and water (0.015 mL, 0.832 mmol) was added 1,3-dichloro-5,5-dimethylimidazolidine-2,4-dione (144 mg, 0.73 mmol) in an ice-water bath. The reaction mixture was stirred in an ice-water bath for 1.5 hours. The reaction mixture was concentrated to dryness at room temperature and dried by an oil pump for 10 min. The crude intermediate was added 1-methylcyclopropylamine hydrochloride (79 mg, 0.73 mmol) and dichloromethane (5 mL), and the resulting mixture was added triethylamine (0.25 mL, 1.8 mmol) in an ice-water bath. The reaction mixture was stirred at room temperature for 1 hour. The reaction mixture was evaporated and the residue was purified by column chromatography (mobile phase: (petroleum ether/dichloromethane 4:1)/ethyl acetate, 100/0 to 70/30) to give compound 3-c (70 mg, 46%) as a light brown solid. LC-MS (ESI): m/z 420.2 (M+H)⁺.

Synthesis of Compound 3-b

Sodium hydrogen (27 mg, 0.67 mmol) was added to a solution of 3-c (70 mg, 0.17 mmol) in DMF (2.5 mL) in a reaction flask in an ice-water bath. The reaction mixture was stirred for 5 min in an ice-water bath, was added SEMCl (83 mg, 0.50 mmol) and continued stirring for 1 hr. The reaction was quenched with saturated ammonium chloride, diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 90/10) to give compound 3-b (40 mg, 35%) as a light brown solid.

Synthesis of Compound 3-a

Microwave tube was charged with 3-b (30 mg, 0.044 mmol), 2-methyl-1-(piperazin-1-yl) propyl-1-one (28 mg, 0.18 mmol), RuPhos (4.1 mg, 0.009 mmol), RuPhos Pd G3 (3.7 mg, 0.004 mmol), cesium carbonate (43 mg, 0.13 mmol) and 1,4-dioxane (3 mL). Degassed and purged with nitrogen for 3 times, the reaction was heated at 100° C. for 2 hours. Cooled to room temperature, the mixture was removed 1,4-dioxane, diluted with ethyl acetate, washed with water, brine, dried over anhydrous sodium sulfate, filtered and the filtrate was evaporated to give compound 3-a (35 mg, 99%) as a brown solid. LC-MS (ESI): m/z 822.4 (M+Na)⁺.

Synthesis of Compound 3

A reaction flask was charged with 3-a (35 mg, 0.044 mmol), dichloromethane (2 mL) and anisole (0.2 mL). Trifluoroacetic acid (0.5 mL) was added dropwise to the above mixture at room temperature. The reaction mixture was stirred at room temperature for 5 hours. The solvent was concentrated at room temperature, diluted by adding ethyl acetate, washed with saturated sodium bicarbonate, brine, dried over anhydrous sodium sulfate, filtered and the filtrate was evaporated and the residue was purified by column chromatography (mobile phase: dichloromethane/(dichloromethane/methanol/amyl alcohol (7M)=20:1:1), 100/0 to 75/25) to give compound 3 (3.1 mg, 13%) as an off-white solid. LC-MS (ESI): m/z 540.2 (M+H)⁺; ¹H NMR (DMSO-d₆, 400 MHz): δ 14.54 (1H, s), 8.49 (1H, d, J=1.3 Hz), 8.11 (1H, s), 7.70 (1H, t, J=53.2 Hz), 7.29 (1H, s), 3.85-3.73 (4H, m), 3.24-3.08 (4H, m), 2.98 (1H, hept, J=6.7 Hz), 1.05 (6H, d, J=6.7 Hz), 1.02 (3H, s), 0.62 (2H, t, J=5.3 Hz), 0.38-0.34 (2H, m).

Example 4 Synthetic Route of Compound 4

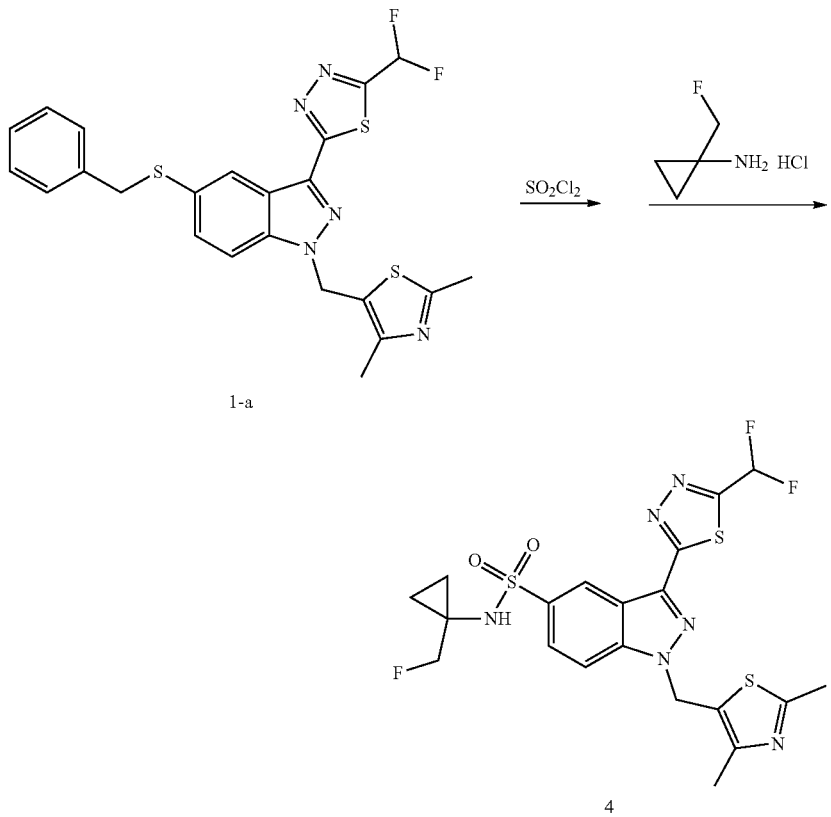

Synthesis of Compound 4

Acetic acid (26 mg, 0.43 mmol) and water (8 mg, 0.43 mmol) were added to a solution of compound 1-a (43 mg, 0.086 mmol) in dichloromethane (5 mL). Sulfonyl chloride (58 mg, 0.43 mmol) in dichloromethane (0.1 mL) was added to the above mixture at 0° C. After addition, the reaction mixture was stirred at 0° C. for 1 h. Saturated NaCl solution (20 mL) was added to the reaction mixture, and the mixture was stirred for 20 s. The organic phase was separated and concentrated at reduced pressure to obtain the crude product. Acetonitrile (10 mL) was added to the crude product, and the crude product was obtained by evaporation at reduced pressure. The crude product was dissolved in N,N-dimethylformamide (5 mL), to which 1-fluoromethylenecyclopropanamine hydrochloride (22 mg, 0.17 mmol), 4-dimethylaminopyridine (11 mg, 0.086 mmol) and diisopropylethylamine (67 mg, 0.52 mmol) were added respectively. After addition, the reaction mixture was stirred at 50° C. under nitrogen atmosphere for 1 h. The reaction mixture was added water (50 mL), extracted with ethyl acetate (100 mL), the organic phase was washed with brine (50 mL), dried over sodium sulfate, filtered to remove the desiccant, and concentrated at reduced pressure to obtain the crude product, which was purified by preparative HPLC (basic conditions) to obtain compound 4 (13 mg, 28%). LC-MS (ESI): m/z 529.0 (M+H)$^+$; $^1$H NMR (400 MHz, DMSO-d$_6$): δ 8.82 (s, 1H), 8.60 (s, 1H), 8.19 (d, J=12.0 Hz, 1H), 7.96 (d, J=8.0 Hz, 1H), 7.70 (t, J=52.0 Hz, 1H), 6.03 (s, 1H), 4.25 (s, 1H), 4.13 (s, 1H), 2.50 (s, 3H), 2.48 (s, 3H), 0.74-0.65 (m, 4H).

Example 5 Synthetic Route of Compound 5

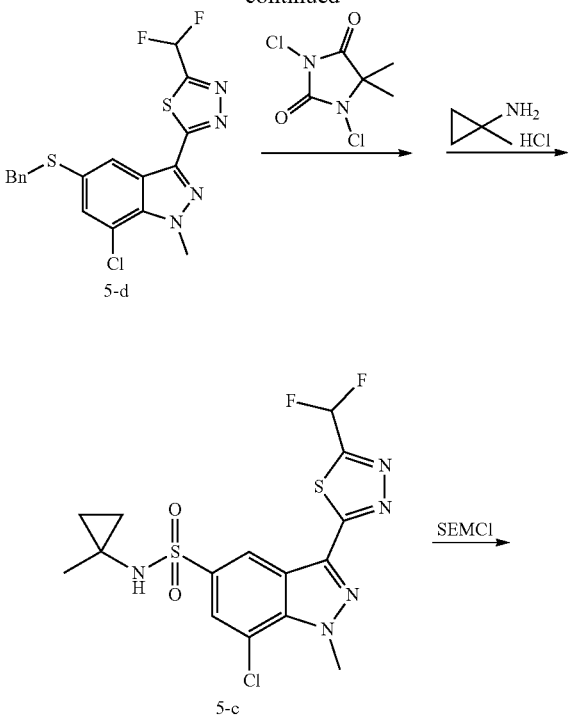
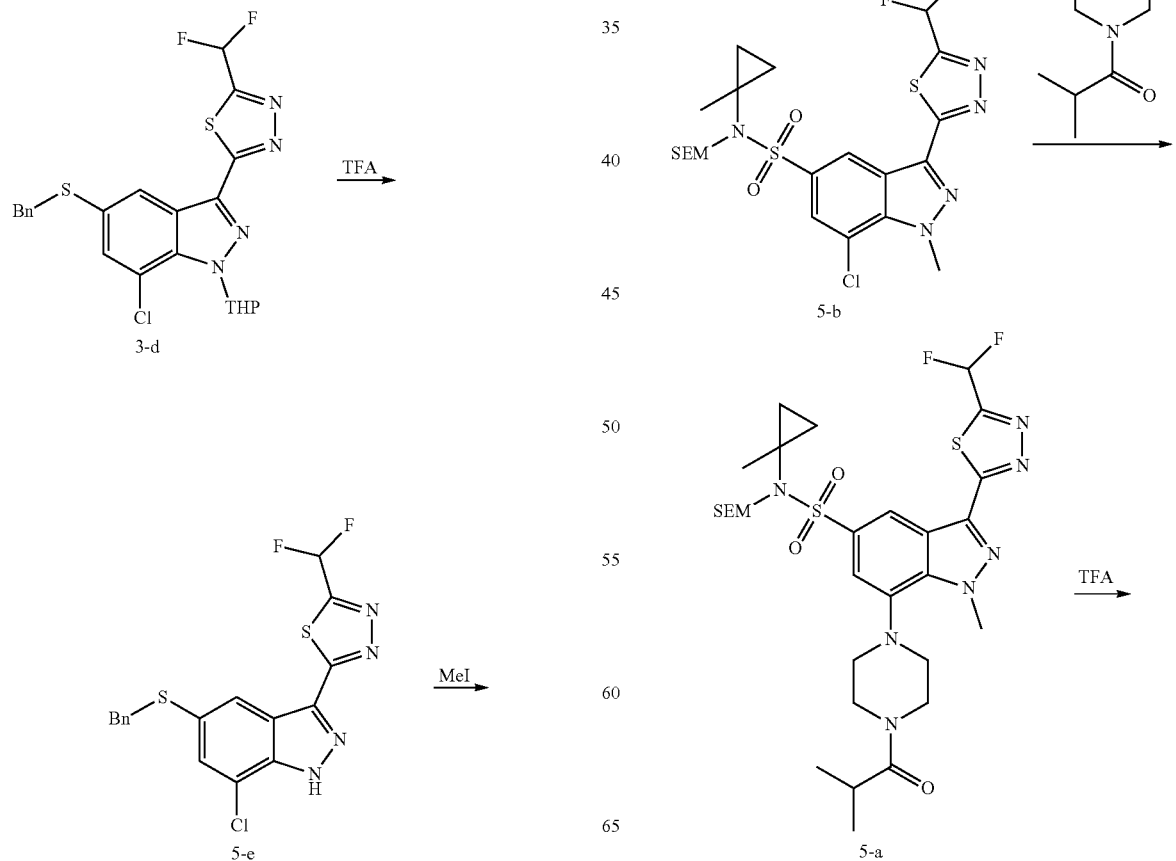

-continued

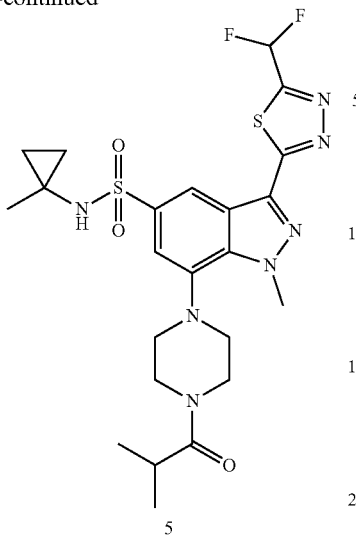

5

Synthesis of Compound 5-e

Trifluoroacetic acid (1.5 mL) was added dropwise to a solution of 3-d (160 mg, 0.32 mmol) in dichloromethane (4 mL) in a reaction flask at room temperature. After addition, the reaction mixture was stirred at room temperature for 2 hours. The reaction mixture was concentrated, diluted with ethyl acetate, washed with saturated sodium bicarbonate, brine, dried over anhydrous sodium sulfate, filtered and the filtrate was evaporated to give compound 5-e (132 mg, 99%) as a white solid. LC-MS (ESI): m/z 409.0 (M+H)$^+$.

Synthesis of Compound 5-d

A reaction flask was charged with 5-e (132 mg, 0.32 mmol), DMF (3 mL) and cesium carbonate (480 mg, 1.47 mmol). Iodomethane (0.069 mL, 0.84 mmol) was added dropwise to the above mixture under stirring at room temperature. After addition, the reaction mixture was stirred at room temperature for 3 hours. The reaction mixture was added a small amount of methanol and ethyl acetate to and evaporated at room temperature in a water bath for 5 min. The residue was diluted with ethyl acetate, washed with water, brine, dried over anhydrous sodium sulfate, evaporated and the residue was purified by column chromatography (mobile phase: petroleum ether/ethyl acetate 100/0 to 50/50) to obtain compound 5-d (100 mg, 73%) as a solid.

Synthesis of Compound 5-c

A reaction vial charged with 5-d (100 mg, 0.24 mmol), acetonitrile (4 mL), acetic acid (0.014 mL, 0.25 mmol) and water (0.015 mL, 0.83 mmol) was added 1,3-dichloro-5,5-dimethylimidazolidine-2,4-dione (93 mg, 0.47 mmol) in an ice-water bath. The reaction mixture was stirred in an ice-water bath for 1.5 hours. The reaction mixture was concentrated to dryness at low temperature and dried by an oil pump for 10 min. To the crude intermediate was added 1-methylcyclopropylamine hydrochloride (51 mg, 0.47 mmol), dichloromethane (5 mL), and added triethylamine (0.18 mL, 1.29 mmol) in an ice-water bath. The reaction mixture was stirred at room temperature for 1 hour. The reaction mixture was evaporated and the residue was purified by column chromatography (mobile phase: (petroleum ether/dichloromethane 4:1)/ethyl acetate, 100/0 to 70/30) to give compound 5-c (102 mg, 99%) as a light brown solid. LC-MS (ESI): m/z 434.0 (M+H)$^+$.

Synthesis of Compound 5-b

Sodium hydrogen (28 mg, 0.70 mmol) was added to a solution of 5-c (102 mg, 0.24 mmol) in DMF (2.8 mL) in a reaction flask in an ice-water bath. After addition, the reaction mixture was stirred in an ice-water bath for 5 min, then was added SEMCl (60 mg, 0.36 mmol) and continued stirring for 1 h. The reaction mixture was quenched with saturated ammonium chloride, diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 80/20) to give compound 5-b (120 mg, 90%) as a white solid. LC-MS (ESI): m/z 581.2 (M+NH$_4$)$^+$.

Synthesis of Compound 5-a

A microwave tube was charged with 5-b (51 mg, 0.090 mmol), 2-methyl-1-(piperazin-1-yl)propyl-1-one (42 mg, 0.27 mmol), RuPhos (7.5 mg, 0.016 mmol), RuPhos Pd G3 (7.5 mg, 0.009 mmol), cesium carbonate (88 mg, 0.27 mmol) and 1,4-dioxane (3.5 mL). The reaction mixture was degassed and purged with nitrogen for 3 times. It was stirred at 80° C. for 7 hours. The reaction mixture was cooled to room temperature, removed 1,4-dioxane, diluted with ethyl acetate, washed with water, brine, dried over anhydrous sodium sulfate, filtered and the filtrate was evaporated and the residue was purified by column chromatography (mobile phase: dichloromethane/methanol, 100/0 to 98/2) to give compound 5-a (55 mg, 89%) as a light brown solid. LC-MS (ESI): m/z 701.3 (M+NH$_4$)$^+$.

Synthesis of Compound 5

Trifluoroacetic acid (0.7 mL) was added dropwise to a solution of 5-a (55 mg, 0.080 mmol), and anisole (0.3 mL) in dichloromethane (2.8 mL) in a reaction flask at room temperature. After addition, the reaction mixture was stirred at room temperature for 5 hours. The reaction mixture was concentrated to dryness at low temperature, and the residue was diluted with ethyl acetate, washed with saturated sodium bicarbonate, brine, dried over anhydrous sodium sulfate, filtered and the filtrate was evaporated, and the residue was purified by column chromatography (mobile phase: dichloromethane/(dichloromethane/methanol/ammonium-methanol=20:1:1), 100/0 to 75/25), and the obtained sample was purified by column chromatography again (mobile phase: 10 mM ammonium bicarbonate/acetonitrile, 95/5 to 48/52) to afford compound 5 (13.8 mg, 31%) as a white solid. LC-MS (ESI): m/z 554.2 (M+H)$^+$; $^1$H NMR (DMSO-d$_6$, 400 MHz): δ 8.59 (1H, d, J=1.5 Hz), 7.63 (1H, t, J=53.1 Hz), 7.56 (1H, d, J=1.5 Hz), 4.55 (1H, bs), 4.50 (3H, s), 4.10 (1H, bs), 3.55-3.40 (2H, m), 3.30-2.65 (4H, m), 2.97 (1H, hept, J=6.6 Hz), 1.06 (6H, d, J=6.6 Hz), 1.02 (3H, s), 0.62 (2H, q, J=4.5 Hz), 0.40-0.35 (2H, m).

Example 6 Synthetic Route of Compound 6

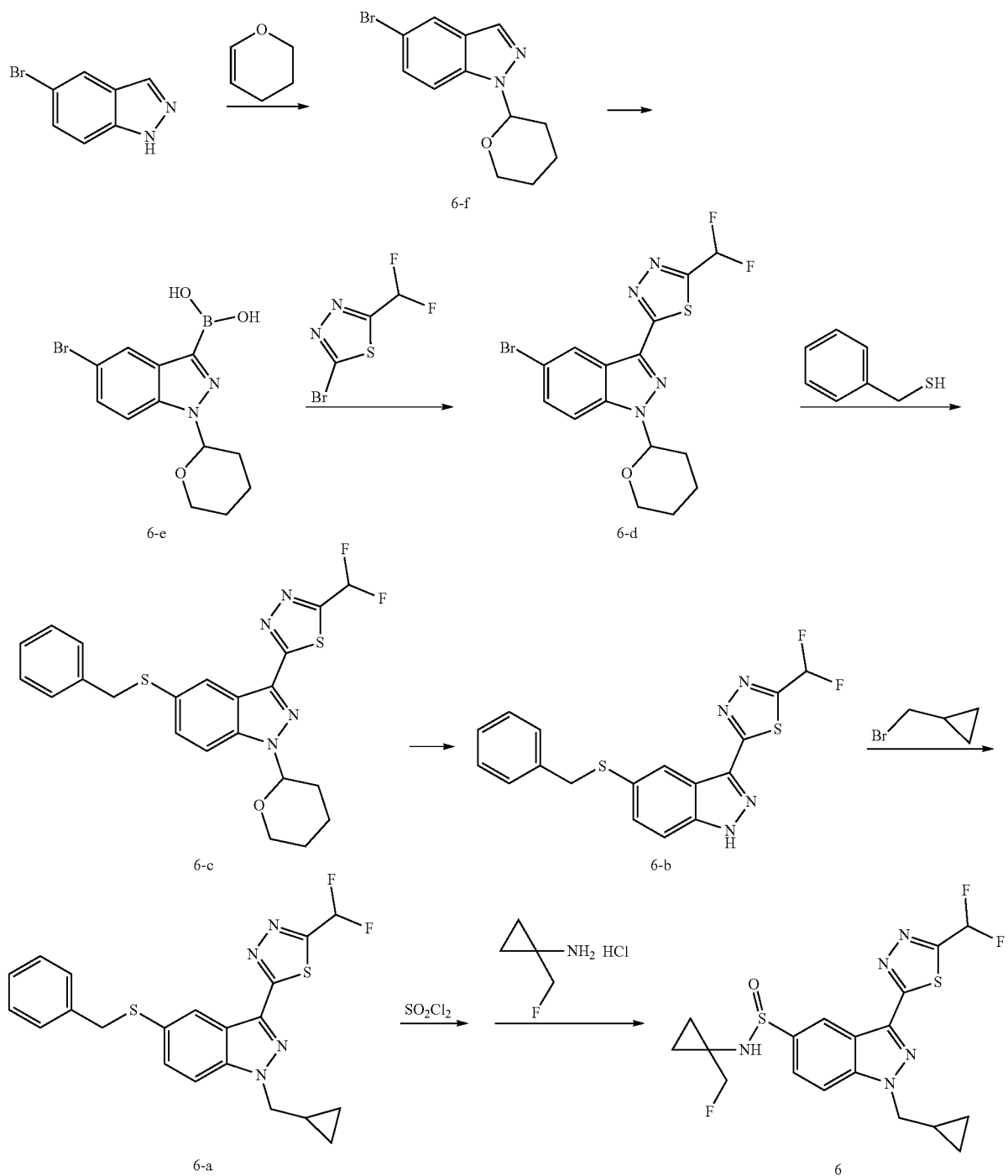

Synthesis of Compound 6-f p-toluenesulfonic acid monohydrate (0.17 g, 0.89 mmol) and 3,4-dihydropyran (0.85 g, 10.15 mmol) were added to a solution of compound 5-bromoindazole (2 g, 10.15 mmol) in dichloromethane (20 mL), and the resulting mixture was stirred at room temperature for 12 h. The reaction mixture was added saturated sodium bicarbonate solution (10 mL), water (50 mL), extracted with dichloromethane (100 mL), brine (50 mL), dried over sodium sulfate, filtered to remove desiccant and concentrated at reduced pressure to obtain the crude product, which was purified by column chromatography (mobile phase, PE/EA 3/1) to give compound 6-f (1.20 g, 42%).

Synthesis of Compound 6-e

Bis(pinacol borate) (361.29 mg, 1.42 mmol), 2,2'-bi(4-tert-butylpyridine) (38.19 mg, 0.14 mmol), and methoxy (cyclooctadiene)iridium dimer (47.15 mg, 0.07 mmol) were mixed in a microwave tube, and the resulting mixture was added methyl tert-butyl ether (4 mL) under nitrogen atmosphereprotection and then stirred at room temperature for 10 minutes. 6-f (200 mg, 0.71 mmol) dissolved in methyl tert-butyl ether (4 mL) was added to the above mixture under nitrogen atmosphere, then stirred for 3 hours at 85° C. under the seal after nitrogen injection for 60 seconds. The reaction mixture was cooled to room temperature and the crude 6-e (650 mg, crude) was obtained by evaporation at reduced pressure. LC-MS (ESI): m/z 325.0 (M+H)+.

Synthesis of Compounds 6-d

Compound 2-bromo-5-difluoromethyl-1,3,4-thiadiazole (229.27 mg, 1.07 mmol), palladium acetate (15.96 mg, 0.07 mmol), 4,5-bis(diphenylphosphino)-9,9-dimethylxanthene (82.26 mg, 0.14 mmol), 6-e (231 mg, 0.71 mmol), toluene (10 mL) and water (5 mL) were combined in a reaction flask, then was added cesium carbonate (463.21 mg, 1.42 mmol), and then the resulting mixture was degassed and purged with nitrogen three times and stirred at 26° C. in an oil bath for 16 hours. To the reaction mixture was added water (100 mL), and the aqueous phase was extracted with ethyl acetate (100 mL), the organic phase was washed with brine (50 mL), dried over sodium sulfate, filtered to remove desiccant, and concentrated at reduced pressure to obtain the crude product, which was purified by column chromatography (mobile phase, PE/EA=10/1) to give compound 6-d (154 mg, 47%). LC-MS (ESI): m/z 415.0 (M+H)+.

Synthesis of Compound 6-c

Compound 6-d (179 mg, 0.43 mmol), benzyl mercaptan (160.61 mg, 1.29 mmol), tris(dibenzylideneacetone)dipalladium (39.47 mg, 0.04 mmol), 4,5-bis(diphenylphosphino)-9,9-dimethylxanthene (49.88 mg, 0.09 mmol) and diisopropylethylamine (222.86 mg, 1.72 mmol) were added to 1.4-dioxane (20 mL), and the resulting mixture was degassed and purged with nitrogen three times and then stirred at 120° C. in an oil bath for 12 h. The crude product was obtained after concentrated and purified by column chromatography (mobile phase, PE/EA 10/1) to give compound 6-c (189 mg, 96%). LC-MS (ESI): m/z 459.2 (M+H)+.

Synthesis of Compound 6-b

Trifluoroacetic acid (4 mL) was added to a solution of compound 6-c (189 mg, 0.41 mmol) in dichloromethane (15 mL) and the reaction mixture was stirred at room temperature for 12 h. The reaction mixture was adjusted to pH 8 with saturated sodium bicarbonate solution, extracted with dichloromethane (100 mL), washed with brine (50 mL), dried over sodium sulfate, filtered to remove the desiccant, and evaporated at reduced pressure to get the crude product, which was purified by column chromatography (mobile phase, DCM/EA 10/1) to give compound 6-b (115 mg, 75%). LC-MS (ESI): m/z 375.0 (M+H)+.

Synthesis of Compound 6-a

Compound 6-b (115 mg, 0.31 mmol) was dissolved in N,N-dimethylformamide (6 mL), to which was added cesium carbonate (300.21 mg, 0.92 mmol) and bromomethylcyclopropane (62.19 mg, 0.46 mmol), and the reaction mixture was stirred at 50° C. in an oil bath for 1 h. To the above mixture was added water (50 mL), and the aqueous phase was extracted twice with ethyl acetate (100 mL), washed with brine (100 mL), dried over sodium sulfate, filtered to remove the desiccant, and evaporated at reduced pressure to obtain the crude product, which was purified by column chromatography (mobile phase, PE/EA 10/1) to give compound 6-a (120 mg, 91%). LC-MS (ESI): m/z 429.0 (M+H)+.

Synthesis of Compound 6

Acetic acid (24.52 mg, 0.41 mmol) and water (7.36 mg, 0.41 mmol) were added to a solution of compound 6-a (35 mg, 0.08 mmol) in dichloromethane (5 mL), and the resulting mixture was added sulfonyl chloride (55.12 mg, 0.41 mmol) in dichloromethane (0.1 mL) dropwise at 0° C. After addition, the reaction mixture was stirred at 0° C. for 1 h. Brine (20 mL) was added to the reaction mixture and the mixture was stirred for 10 s. The organic phase was separated and dried over sodium sulfate, the desiccant was filtered off, and the crude product was obtained by evaporation at reduced pressure to afford the crude product. The crude product was dissolved in N,N-dimethylformamide (5 mL), and was added 1-fluoromethylenecyclopropanamine hydrochloride (14.61 mg, 0.12 mol), dimethylaminopyridine (9.98 mg, 0.08 mmol) and diisopropylethylamine (52.99 mg, 0.41 mmol), and the reaction was stirred at 50° C. in an oil bath for 1 hour. To the reaction mixture was added water (50 mL), and the aqueous phase was extracted with ethyl acetate (100 mL), the organic phase was washed with brine (50 mL), dried over sodium sulfate, filtered to remove desiccant and evaporated at reduced pressure to give the crude product, which was purified by column chromatography (mobile phase, PE/EA=10/1) to give compound 6 (10 mg, 25%). LC-MS (ESI): m/z 442.0 (M+H)+; $^1$H NMR (400 MHz, DMSO-$d_6$): δ 8.69 (s, 1H), 8.08 (d, J=12.0 Hz, 1H), 7.84-7.56 (m, 2H), 7.35 (s, 1H), 4.56-4.42 (m, 2H), 4.41-4.31 (m, 1H), 1.41-1.33 (m, 1H), 1.13-1.05 (m, 1H), 0.96-0.89 (m, 1H), 0.88-0.81 (m, 2H), 0.60-0.44 (m, 4H).

Example 7 Synthetic Route of Compound 7

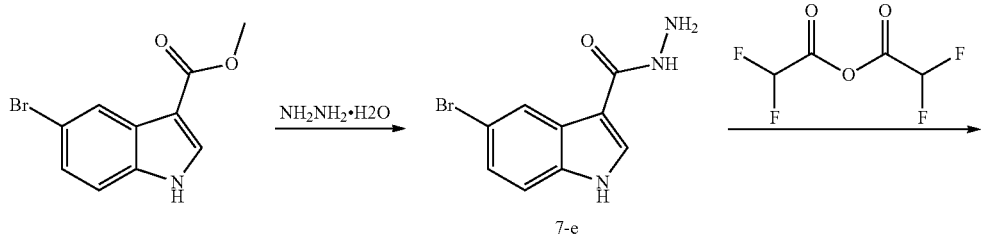

7-e

-continued

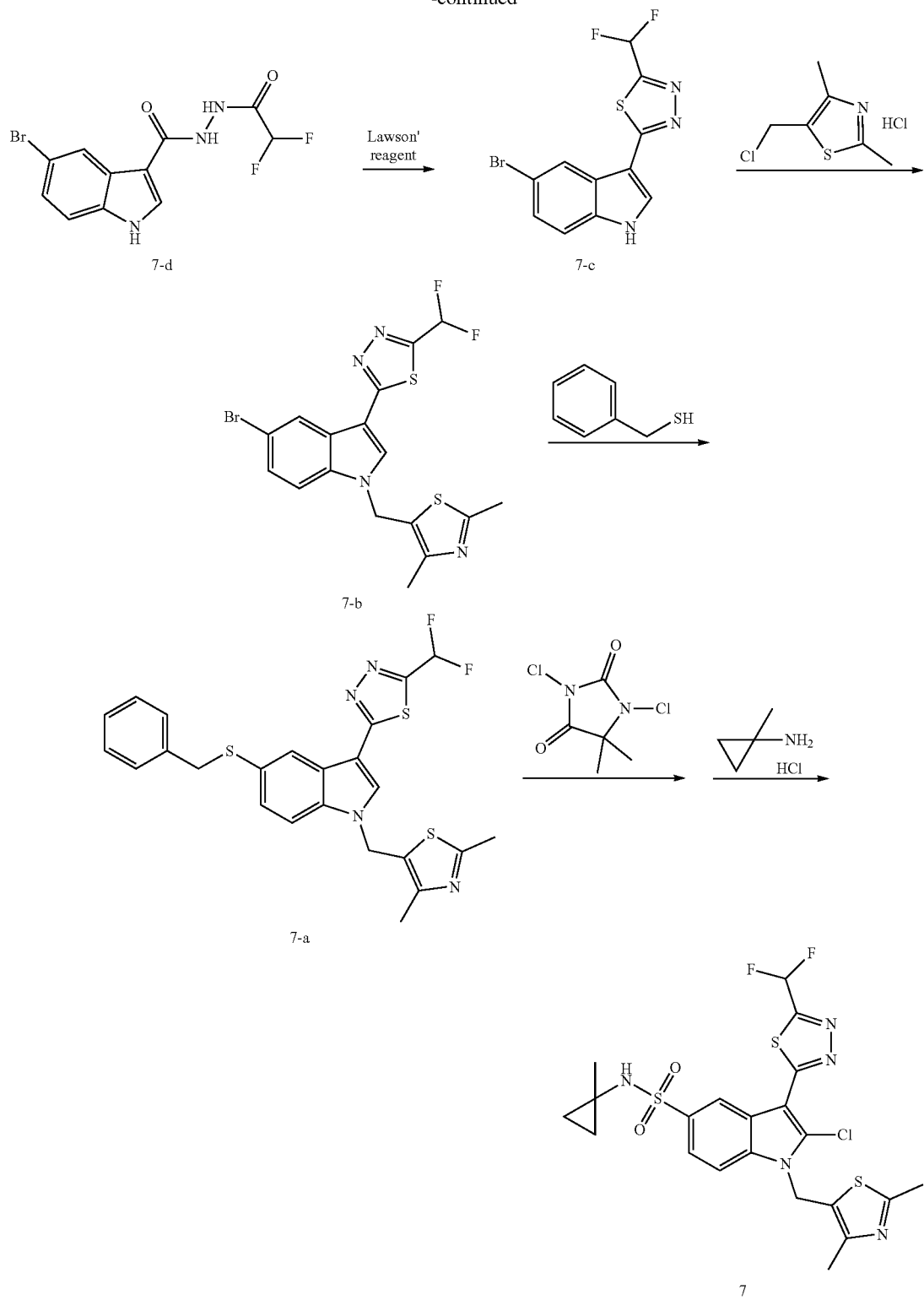

Synthesis of Compound 7-e

Hydrazine hydrate (1.9 mL, 33 mmoL) was added to a solution of methyl 5-bromo-1H-indole-3-carboxylate (1.0 g, 3.94 mmoL) in ethanol (20 mL) at room temperature, then the mixture was stirred at 80° C. under nitrogen atmosphere for 16 hours. The reaction mixture was cooled to room temperature, filtered, and the solid was collected and washed with ethanol (10 mL), and the solid was dried in vacuum for 2 h. The crude compound 7-e (468 mg) was obtained as a light yellow solid and was used directly in the next reaction step without purification. LC-MS (ESI): m/z=253.9 [M+1]+.

Synthesis of Compounds 7-d

Compound 7-e (368 mg, 1.45 mmoL) was dissolved in THF (10 mL) at room temperature, and was added DCM (10 mL) and TEA (604 μL, 4.35 mmoL). Difluoroacetic anhydride (216 μL, 1.74 mmoL) was added dropwise to the above mixture at 0° C. and the reaction mixture was warmed to room temperature and stirred for 16 hours. The reaction mixture was concentrated at reduced pressure and the crude product was purified by a flash column chromatography (DCM/MeOH=10:1) to give compound 7-d (120 mg, 25%) as a white solid. LC-MS (ESI): m/z=332.0[M+1]+.

Synthesis of Compounds 7-c

Lawesson's reagent (219 mg, 0.54 mmoL) was added to a solution of compound 7-d (120 mg, 0.36 mmoL) in 1,4-dioxane (15 mL) at room temperature, and the reaction mixture was stirred at 80° C. under nitrogen atmosphere for 3 h. The reaction mixture was cooled to room temperature, concentrated at reduced pressure, and the crude product was purified by separation on a flash column chromatography (PE/EA=1:1) to give compound 7-c (105 mg, 88%) as a white solid. LC-MS (ESI): m/z=329.9[M+1]+.

Synthesis of Compound 7-b

Compound 7-c (105 mg, 0.32 mmoL) was dissolved in 5 mL of DMF at 0° C., was added 5-chloromethyl-2,4-dimethyl-1,3-thiazole hydrochloride (95 mg, 0.48 mmoL) and cesium carbonate (311 mg, 0.95 mmoL) and the mixture was stirred at room temperature for 16 h under nitrogen atmosphereprotection. The reaction mixture was quenched by adding water (10 mL), extracted with ethyl acetate (80 mL*2), the organic phase was washed with brine (100 mL*3), dried over anhydrous sodium sulfate, filtered and the filtrate was concentrated at reduced pressure, and the crude product was purified by a flash column chromatography (PE/EA=1:2) to give compound 7-b (103 mg, 71%) as a white solid. LC-MS (ESI): m/z=454.9[M+1]+.

Synthesis of Compound 7-a

Pd$_2$(dba)$_3$ (21 mg, 0.023 mmoL), Xantphos (26 mg, 0.045 mmoL), DIPEA (112 μL, 0.68 mmoL) and benzyl mercaptan (29 μL, 0.25 mmoL) were added to a solution of compound 7-b (103 mg, 0.23 mmoL) in anhydrous 1,4-dioxane (10 mL) at room temperature, and the reaction mixture was stirred at 105° C. for 16 h under nitrogen atmosphereprotection. The reaction mixture was cooled to room temperature, concentrated at reduced pressure and the crude product was purified by a flash column chromatography (PE/EA=1:1 to EA) to give compound 7-a (103 mg, 91%) as a light yellow solid. LC-MS (ESI): m/z=499.2[M+1]+.

Synthesis of Compound 7

Acetic acid (23 uL, 0.40 mmoL), water (9.0 μL, 0.50 mmoL) and 1,3-dichloro-5,5-dimethylimidazolidine-2,4-dione (40 mg, 0.2 mmoL) were added to a solution of compound 7-a (50 mg, 0.10 mmoL) in anhydrous acetonitrile (5 mL) at 0° C. After addition, the reaction mixture was stirred at 0° C. under nitrogen atmosphere for 2 h. The reaction mixture was concentrated at reduced pressure at room temperature. The reaction mixture was concentrated at reduced pressure at 0° C. for 2 h. The intermediate was dried in vacuum for 30 min, then dissolved in dichloromethane (10 mL), cooled to 0° C., was added 1-methyl-cyclopropylamine hydrochloride (32 mg, 0.30 mmoL) and triethylamine (360 μL, 2.59 mmoL), and the reaction mixture was warmed to room temperature and stirred for 16 h. The reaction mixture was concentrated at reduced pressure to give the crude product, which was purified by Prep-HPLC (basic method) to give compound 7 (6 mg, 11%) as a white solid. LC-MS (ESI): m/z=543.8[M+1]+; $^1$H NMR (CDCl$_3$, 400 MHz): δ9.20 (1H, d, J=1.6 Hz), 7.93 (1H, dd, J$_1$=1.6 Hz, J$_2$=8.4 Hz), 7.46 (1H, d, J=8.8 Hz), 7.12 (1H, t, J=53.6 Hz), 5.58 (2H, s), 4.96 (1H, s), 2.56 (6H, s), 1.21 (3H, s), 0.89-0.79 (2H, m), 0.51-0.45 (2H, m).

Example 8 Synthetic Route of Compound 8

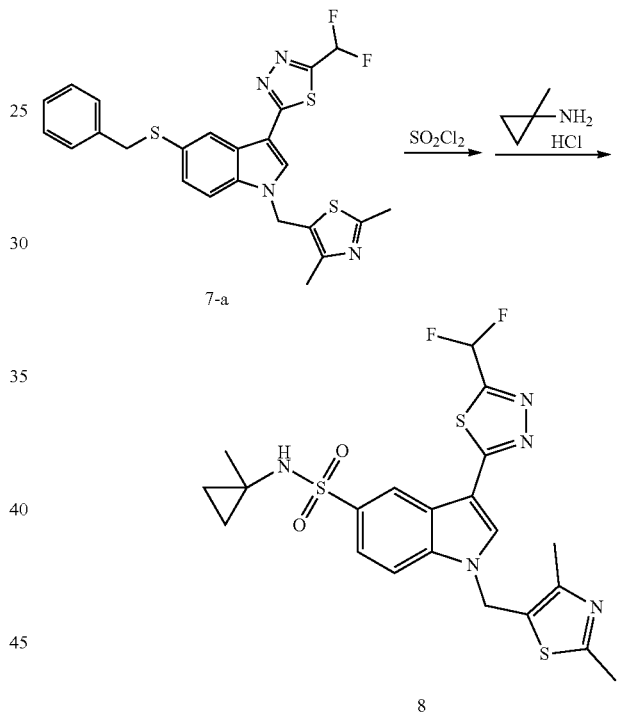

Synthesis of Compound 8

Acetic acid (23 μL, 0.40 mmoL), water (7.4 uL, 0.41 mmoL) and sulfuryl chloride (33 μL, 0.41 mmoL) were added to a solution of compound 7-a (50 mg, 0.10 mmoL) in dichloromethane (5 mL) under nitrogen atmosphere at 0° C., and the reaction mixture was stirred at 0° C. under nitrogen atmosphere for 1 h. The reaction mixture was then concentrated at reduced pressure at room temperature for 30 min. The resulting intermediate was dried in vacuum for 30 min, then was dissolved in DMF (3 mL), cooled to 0° C., was added 1-methyl-cyclopropylamine hydrochloride (32 mg, 0.30 mmoL), DMAP (25 mg, 0.2 mmoL) and DIPEA (66 μL, 0.40 mmoL), and the reaction mixture was warmed to room temperature and stirred for 30 min. The reaction was quenched by adding water (10 mL), and the aqueous phase was extracted with ethyl acetate (50 mL*2), the organic phase was washed with brine (100 mL*3), dried over anhydrous sodium sulfate, filtered and the filtrate was concentrated at reduced pressure to give the crude product, which was purified by a flash column chromatography (DCM/MeOH=10:1) to give compound 8 (50 mg, 98%) as a white solid. LC-MS (ESI): m/z=510.0 [M+1]+; 1H NMR (DMSO-d6, 400 MHz): δ 8.77 (1H, s), 8.64 (1H, s), 8.05 (1H, s), 7.86 (1H, d, J=9.2 Hz), 7.80-7.70 (1H, m), 7.64 (1H, t, J=52.8 Hz), 5.74 (2H, s), 3.33 (3H, s), 2.46 (3H, s), 1.03 (3H, s), 0.65-0.55 (2H, m), 0.37-0.30 (2H, m).
Example 9 Synthesis of Compound 9
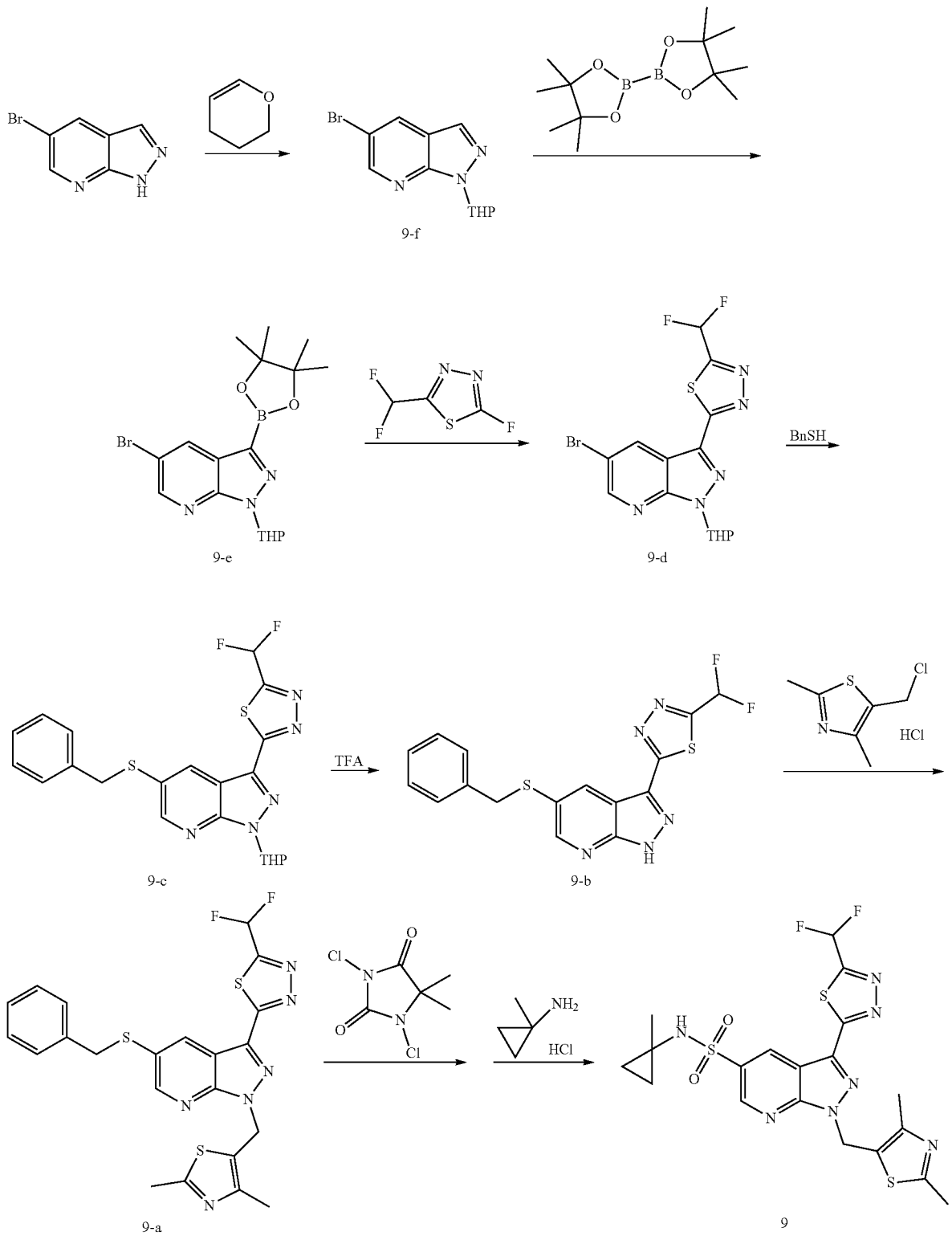

Synthesis of Compound 9-f

To a solution of compound 5-bromo-1H-pyrazolo[3,4-b]pyridine (0.5 g, 2.53 mmol) in dichloromethane (10 mL) was added 3,4-dihydro-2H-pyran (0.69 mL, 8.08 mmol) and p-toluenesulfonic acid monohydrate (48 mg, 0.25 mmol). After addition, the reaction mixture were stirred at room temperature overnight. After completion, the reaction mixture was diluted with dichloromethane, washed with saturated sodium bicarbonate, brine, dried over anhydrous sodium sulfate, filtered and the filtrate was concentrated to obtain the crude product. Purified by a flash column chromatography (mobile phase: ethyl acetate/petroleum ether 0% to 50%), compound 9-f (0.5 g, 70%) was obtained as a colorless oil. LC-MS (ESI): m/z=282.0 [M+H]$^+$.

Synthesis of Compound 9-e

A microwave tube charged with methoxy(cyclooctadiene)chloroiridium dimer (139 mg, 0.21 mmol), 4,4'-di-tert-butyl-2,2'-dipyridine (114 mg, 0.43 mmol), biboronic acid pinacol ester (675 mg, 2.66 mmol) and methyl tert-butyl ether (6 mL) was degassed and purged with nitrogen twice and then stirred for 5 min at room temperature. A solution of 9-f (0.3 g, 1.06 mmol) in methyl tert-butyl ether (6 mL) was added and stirred for 3.5 h at 85° C. after degassed and purged with nitrogen for 3 times. The reaction mixture was evaporated dry to give compound 9-e (430 mg, 99%) as a brownish red viscous liquid.

Synthesis of Compound 9-d

A reaction flask charged with 9-e (430 mg, 1.04 mmol), 2-bromo-5-(difluoromethyl)-1,3,4-thiadiazole (446 mg, 2.08 mmol), palladium acetate (23 mg, 0.10 mmol), Xantphos (120 mg, 0.21 mmol), toluene (20 mL) and water (10 mL) was degassed and purged with nitrogen twice, and was added cesium carbonate (1.01 g, 3.10 mmol). The reaction mixture was stirred at 25° C. for 18 hours. The reaction mixture was diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 80/20) to give compound 9-d (120 mg, 28%) as an earthy solid. LC-MS (ESI): m/z=416.0 [M+H]$^+$.

Synthesis of Compound 9-c

A three-necked vial charged with 9-d (120 mg, 0.29 mmol), Xantphos (34 mg, 0.058 mmol), 1,4-dioxane (10 mL), DIPEA (0.15 mL, 0.87 mmol) and benzyl mercaptan (0.051 mL, 0.43 mmol) was degassed and purged with nitrogen twice and was added Pd$_2$(dba)$_3$ (27 mg, 0.029 mmol), degassed and purged with nitrogen for 3 times. The reaction mixture was refluxed at 100° C. for 5 hours. The reaction mixture was cooled to room temperature, evaporated, and purified by column chromatography (mobile phase: petroleum ether/ethyl acetate, 100/0 to 80/20) to give compound 9-c (110 mg, 83%) as a light brown viscous liquid. LC-MS (ESI): m/z=460.1 [M+H]$^+$.

Synthesis of Compound 9-b

TFA (5 mL) was added to a solution of 9-c (110 mg, 0.24 mmol) in dichloromethane (10 mL) at room temperature. After addition, the reaction was stirred at room temperature overnight. After completion, the solvent was removed by rotary evaporation at room temperature, diluted by adding ethyl acetate, washed with saturated sodium bicarbonate, washed with brine, dried over anhydrous sodium sulfate, filtered and the filtrate was evaporated. The crude product was purified by a flash column chromatography (mobile phase: ethyl acetate/petroleum ether 0% to 100%) to give compound 9-b (80 mg, 89%) as an earthy yellow solid. LC-MS (ESI): m/z=376.0 [M+H]$^+$.

Synthesis of Compound 9-a

Cesium carbonate (139 mg, 0.43 mmol) and 5-(chloromethyl)-2,4-dimethyl-1,3-thiazole hydrochloride (63 mg, 0.32 mmol) were added to a DMF (5 mL) solution of 9-b (1 g, 2.83 mmol) at room temperature. After addition, the reaction was stirred at room temperature overnight. After completion, the reaction was diluted by adding ethyl acetate, washed with water, brine, dried over anhydrous sodium sulfate, filtered and the filtrate was evaporated. After purification by a flash column chromatography (mobile phase: ethyl acetate/petroleum ether 0% to 100%), compound 9-a (70 mg, 66%) was obtained as an amber oil. LC-MS (ESI): m/z=501.2 [M+H]$^+$.

Synthesis of Compound 9

To a solution of 9-a (70 mg, 0.14 mmol) in acetonitrile (5 mL) was added acetic acid (34 mg, 0.56 mmol) and H$_2$O (10 mg, 0.57 mmol). The mixture was cooled to −15° C. and was added dichlorhydantoin (55 mg, 0.28 mmol) in an ice-water bath. After addition, the reaction mixture was stirred at low temperature for 1 hour. The reaction mixture was concentrated to dryness at room temperature and dried by an oil pump for 10 min. 1-methylcyclopropylamine hydrochloride (30 mg, 0.28 mmol) and dichloromethane (5 mL) were added to the crude intermediate, and added triethylamine (0.078 mL, 0.56 mol) in an ice-water bath. The reaction mixture was stirred at room temperature for 1 hour. The reaction mixture was evaporated and the crude product was obtained. Purification by Prep-HPLC afforded 9 (5 mg, 7%) as a white solid. LC-MS (ESI): m/z=512.1 [M+H]$^+$; $^1$H NMR (DMSO-d$_6$, 400 MHz): δ 9.11 (1H, d, J=2.0 Hz), 9.09 (1H, d, J=2.0 Hz), 8.23 (1H, bs), 7.71 (1H, t, J=52.8 Hz), 5.99 (2H, s), 2.52 (3H, s), 2.48 (3H, s), 1.09 (3H, s), 0.60-0.64 (2H, m), 0.42-0.46 (2H, m).

Example 10 Synthetic Route of Compound 10

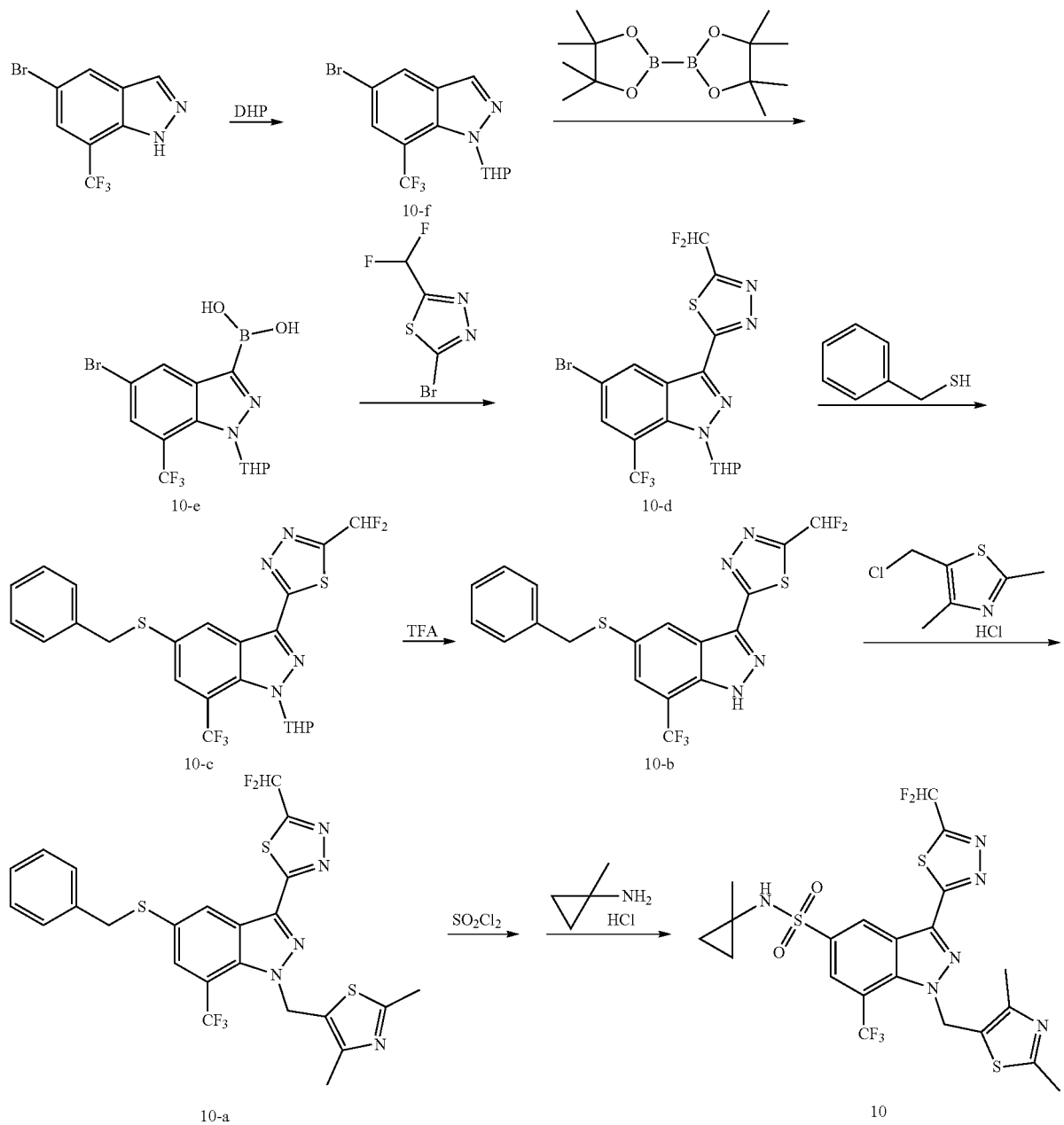

Synthesis of Compound 10-f

5-Bromo-7-(trifluoromethyl)-1H-indazole (500 mg, 1.89 mmoL) suspended in 3,4-dihydro-2H-pyran (DHP) (5 mL) at room temperature was added trifluoroacetic acid (20 μL, 0.26 mmoL), and the mixture was stirred at 95° C. under nitrogen atmosphere for 3 h. Cooled to room temperature, the reaction mixture was added DCM (100 mL). The mixture was washed sequentially with saturated sodium bicarbonate (100 mL) and brine (100 mL), and the organic phase was dried over anhydrous sodium sulfate, filtered and the filtrate was concentrated at reduced pressure to obtain the crude product, which was purified by a flash column chromatography (PE/EA=2:1) to give compound 10-f (577 mg, 88%) as a yellow oil. LC-MS (ESI): m/z=349.0 [M+1]$^+$.

Synthesis of Compound 10-e

Methoxy(cyclooctadiene)chloroiridium dimer (29 mg, 0.043 mmoL) and 4,4'-di-tert-butyl-2,2'-dipyridine (23 mg, 0.086) were added to a solution of biboronic acid pinacol ester (164 mg, 0.65 mmoL) in MTBE (3 mL) under nitrogen atmosphere at room temperature and the and the mixture was stirred at room temperature for 10 min under nitrogen atmosphere. Then a solution of compound 10-f (151 mg, 0.43 mmoL) in MTBE (3 mL) was added and the reaction mixture was stirred at 85° C. for 16 hours under nitrogen atmosphere. The reaction mixture was concentrated at reduced pressure to give the crude compound 10-e (265 mg) as a brown oil. The crude product was used directly in the next step.

Synthesis of Compound 10-d

A solution of compound 5-bromo-2-(difluoromethyl)-1,3,4-thiadiazole (100 mg, 0.47 mmoL) in toluene (10 mL) was added water (5 mL), compound 10-e (265 mg, estimated about 0.56 mmoL), palladium acetate (21 mg, 0.093 mmoL), Xantphos (108 mg. 0.19 mmoL) and NMM (0.15 mL, 1.40 mmoL) sequentially, and the reaction mixture was stirred at 50° C. under nitrogen atmosphere for 18 h. Cooled to room temperature, the reaction mixture was added water (20 mL), extracted with ethyl acetate (50 mL*2), the organic phase was dried over anhydrous sodium sulfate, filtered, and the filtrate was concentrated at reduced pressure, and the crude product was purified by a flash column chromatography (PE/EA=1:1) to give compound 10-d (150 mg, 67%) as a white solid. LC-MS (ESI): m/z=483.0 [M+1]$^+$.

Synthesis of Compound 10-c

Compound 10-d (150 mg, 0.31 mmoL) was dissolved in 10 mL of anhydrous 1,4-dioxane at room temperature and the resulting mixture was added Pd$_2$(dba)$_3$ (28 mg, 0.031 mmoL), Xantphos (36 mg, 0.062 mmoL), DIPEA (154 µL, 0.93 mmoL) and benzyl mercaptan (40 uL, 0.34 mmoL). The above mixture was stirred at 110° C. for 16 h under nitrogen atmosphere. The reaction mixture was cooled to room temperature, concentrated at reduced pressure and the crude product was purified by a flash column chromatography (PE/EA=3:1) to give the crude compound 10-c (186 mg) as a light yellow oil. LC-MS (ESI): m/z=527.1[M+1]$^+$.

Synthesis of Compound 10-b

TFA (6 mL) was added to a solution of compound 10-c (186 mg, 0.35 mmoL) in DCM (10 mL) at 0° C., and the reaction mixture was warmed to room temperature and stirred for 5 hours. The reaction mixture was concentrated at reduced pressure, and the crude product was suspended in saturated sodium bicarbonate solution (50 mL) and extracted with DCM (50 mL*2). The organic phase was dried over anhydrous sodium sulfate, filtered and the filtrate was concentrated at reduced pressure, and the crude product was purified by a flash column chromatography (PE/EA=2:1) to give compound 10-b (118 mg, 75%) as a light yellow solid. LC-MS (ESI): m/z=443.0[M+1]$^+$.

Synthesis of Compound 10-a

5-Chloromethyl-2,4-dimethyl-1,3-thiazole hydrochloride (79 mg, 0.40 mmoL) and cesium carbonate (261 mg, 0.80 mmoL) were added to a solution of compound 10-b (118 mg, 0.27 mmoL) in DMF (5 mL) at 0° C., and the mixture was stirred at room temperature for 16 h under nitrogen atmosphere. The reaction was quenched by adding water (20 mL), extracted with ethyl acetate (80 mL*2), the organic phase was washed with brine (100 mL*3), dried over anhydrous sodium sulfate, filtered, and the filtrate was concentrated at reduced pressure, and the crude product was purified by a flash column chromatography (PE/EA=1:1) to give compound 10-a (110 mg, 73%) as a white solid. LC-MS (ESI): m/z=568.2[M+1]$^+$.

Synthesis of Compound 10

Acetic acid (20 µL, 0.35 mmoL), water (6.5 µL, 0.36 mmoL) and sulfuryl chloride (29 µL, 0.36 mmoL) were added to a solution of compound 10-a (50 mg, 0.088 mmoL) in dichloromethane (5 mL) at 0° C. under nitrogen atmosphere. After addition, the reaction mixture was stirred at 0° C. under nitrogen atmosphere for 1 h. The reaction mixture was concentrated at reduced pressure at room temperature and the intermediate obtained was dried in vacuum for 30 min, then was added DMF (3 mL), cooled to 0° C., was added 1-methyl-cyclopropylamine hydrochloride (28 mg, 0.26 mmoL), DMAP (22 mg, 0.18 mmoL) and DIPEA (73 µL, 0.44 mmoL), the reaction mixture was warmed to room temperature and stirred for 30 min. The reaction was quenched by adding water (10 mL), extracted with ethyl acetate (50 mL*2) and the organic phase was washed with brine (100 mL*3), dried over anhydrous sodium sulfate, filtered and the filtrate was concentrated at reduced pressure to give the crude product, which was purified by a flash column chromatography (DCM/MeOH=20:1) and Prep-HPLC (basic method) to give compound 10 (30 mg, 59%) as a white solid. LC-MS (ESI): m/z=579.1 [M+1]$^+$; $^1$H NMR (DMSO-d$_6$, 400 MHz): δ9.18 (1H, s), 8.50 (1H, brs), 8.35 (1H, s), 7.70 (1H, t, J=53.2 Hz), 5.91 (2H, s), 2.51 (3H, s), 2.43 (3H, s), 1.05 (3H, s), 0.65-0.55 (2H, m), 0.50-0.40 (2H, m).

Example 11 Synthetic Route of Compound 11

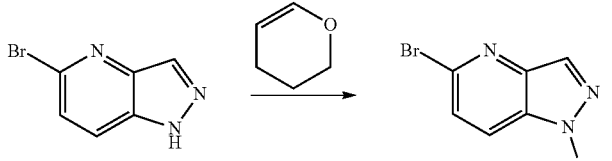

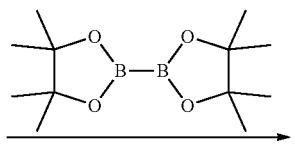

11-f

-continued

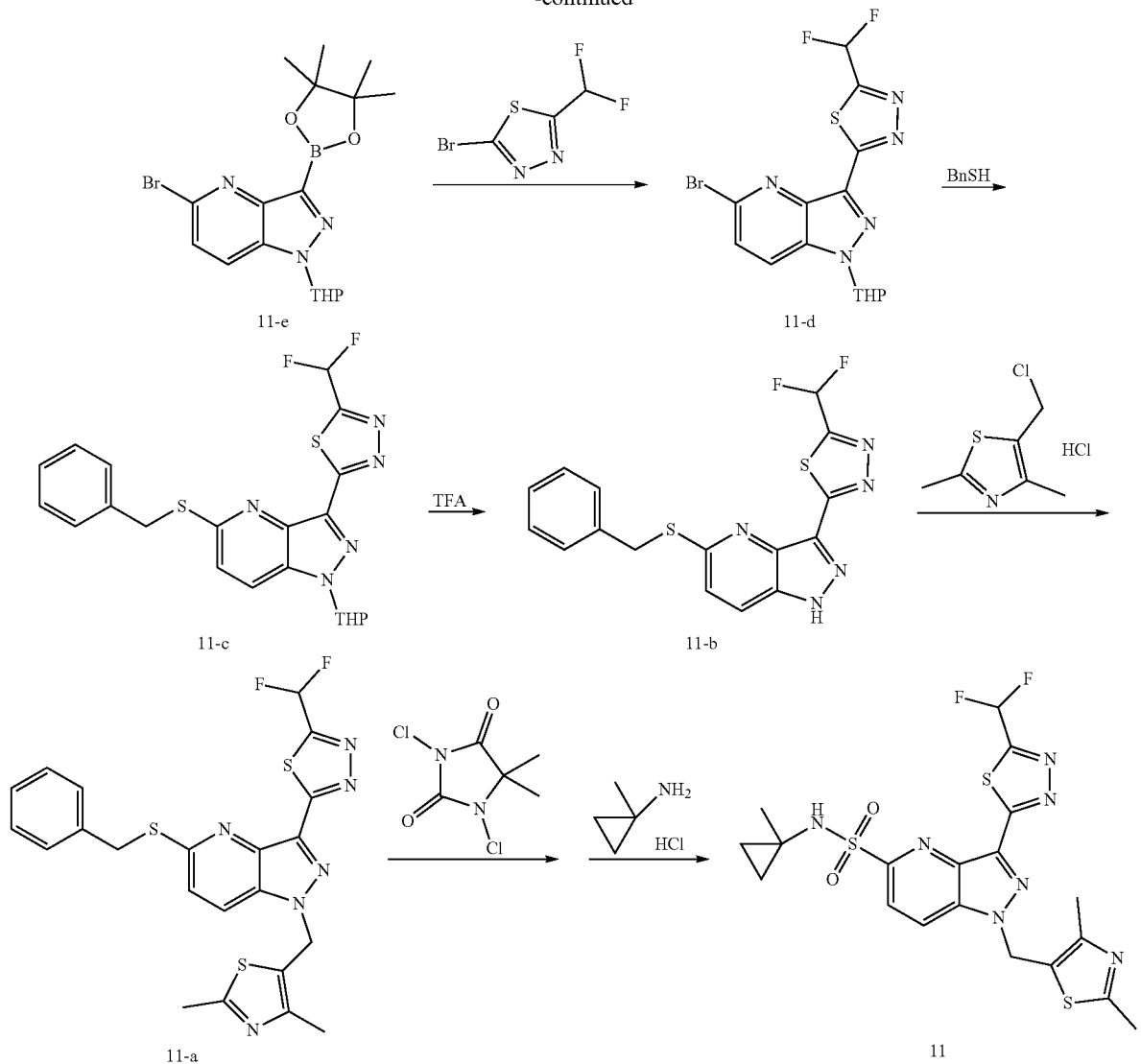

Synthesis of Compound 11-f

To a solution of compound 5-bromo-1H-pyrazolo[4,3-b]pyridine (0.5 g, 2.53 mmol) in dichloromethane (10 mL) was added 3,4-dihydro-2H-pyran (0.69 mL, 8.08 mmol) and p-toluenesulfonic acid monohydrate (48 mg, 0.25 mmol). After addition, the reaction was stirred at room temperature overnight. Upon completion, the reaction mixture was diluted with dichloromethane, washed with saturated sodium bicarbonate, brine, dried over anhydrous sodium sulfate, filtered and the filtrate was concentrated to obtain the crude product. The crude product was purified by a flash column chromatography (mobile phase: ethyl acetate/petroleum ether 0% to 50%) to afford compound 11-f (0.5 g, 70%) as a colorless oil. LC-MS (ESI): m/z=282.0 [M+H]$^+$.

Synthesis of Compound 11-e

Methoxy(cyclooctadiene)chloroiridium dimer (93 mg, 0.14 mmol), 4,4'-di-tert-butyl-2,2'-dipyridine (76 mg, 0.28 mmol), biboronic acid pinacol ester (765 mg, 3.01 mmol) and methyl tert-butyl ether (6 mL) were combined in a microwave tube. After degassed and purged with nitrogen twice, the reaction mixture was stirred at room temperature for 5 min, then was added a solution of 11-f (0.5 g, 1.77 mmol) in methyl tert-butyl ether (6 mL) and the mixture was stirred at 85° C. for 3.5 h after degassed and purged with nitrogen for 3 times. The reaction mixture was concentrated to dryness to obtain compound 11-e (720 mg, 99%) as a brown-red viscous liquid.

Synthesis of Compound 11-d

A reaction flask charged with 11-e (720 mg, 1.76 mmol), 2-bromo-5-(difluoromethyl)-1,3,4-thiadiazole (680 mg, 3.16 mmol), palladium acetate (36 mg, 0.16 mmol), Xantphos (183 mg, 0.32 mmol), toluene (20 mL) and water (10 mL) was degassed and purged with nitrogen twice, and was added cesium carbonate (1.03 g, 3.16 mmol). The reaction mixture was stirred at 25° C. for 18 hours. The reaction mixture was diluted with ethyl acetate, washed with water, brine, dried over anhydrous sodium sulfate, filtered and the filtrate was evaporated and the residue was purified by column chromatography (mobile phase: petroleum ether/ ethyl acetate, 100/0 to 80/20) to give compound 11-d (120 mg, 18%) as an earthy solid. LC-MS (ESI): m/z=416.0 [M+H]$^+$.

Synthesis of Compound 11-c

A three-necked vial charged with 11-d (120 mg, 0.29 mmol), Xantphos (34 mg, 0.058 mmol), 1,4-dioxane (10 mL), DIPEA (0.15 mL, 0.87 mmol) and benzyl mercaptan (0.051 mL, 0.43 mmol) was degassed and purged with nitrogen twice and was added Pd$_2$(dba)$_3$ (27 mg, 0.029 mmol). After degassed and purged with nitrogen for 3 times, the reaction mixture was refluxed at 100° C. for 6 hours. The reaction mixture was cooled to room temperature, concentrated to dryness, and the residue was purified by column chromatography (mobile phase: petroleum ether/ethyl acetate, 100/0 to 80/20) to give compound 11-c (100 mg, 75%) as an earthy solid. LC-MS (ESI): m/z=460.5 [M+H]$^+$.

Synthesis of Compound 11-b

TFA (5 mL) was added to a solution of 11-c (100 mg, 0.22 mmol) in dichloromethane (10 mL) at room temperature. After addition, the reaction was stirred at room temperature overnight. Upon completion, the solvent was removed by rotary evaporation at room temperature, and the residue was diluted by adding ethyl acetate, washed with saturated sodium bicarbonate, brine, dried over anhydrous sodium sulfate, filtered and the filtrate was concentrated to dryness. The crude product was purified by a flash column chromatography (mobile phase: ethyl acetate/petroleum ether 0% to 100%) to give compound 11-b (60 mg, 73%) as an earthy yellow solid. LC-MS (ESI): m/z=376.0 [M+H]$^+$.

Synthesis of Compound 11-a

Cesium carbonate (104 mg, 0.32 mmol) and 5-(chloromethyl)-2,4-dimethyl-1,3-thiazole hydrochloride (48 mg, 0.24 mmol) were added to a solution of 11-b (60 mg, 0.16 mmol) in DMF (5 mL) at room temperature. After addition, the reaction was stirred at room temperature overnight. Upon completion, the reaction mixture was diluted by adding ethyl acetate, washed with water and brine, dried over anhydrous sodium sulfate, filtered and the filtrate was concentrated to dryness. The residue was purified by a flash column chromatography (mobile phase: ethyl acetate/petroleum ether 0% to 100%) to give compound 11-a (40 mg, 50%) as amber oil. LC-MS (ESI): m/z=501.2 [M+H]$^+$.

Synthesis of Compound 11

Acetic acid (19 mg, 0.32 mmol) and H$_2$O (6 mg, 0.33 mmol) were added to a solution of 11-a (19 mg, 0.08 mmol) in DCM (10 mL). The mixture was cooled to 0° C. and was added sulfonyl chloride (44 mg, 0.33 mmol) dropwise carefully. After addition, the reaction was stirred at 0° C. for 1 hr. Upon completion, the reaction mixture was concentrated at reduced pressure at room temperature and dried by an oil pump for 10 min to obtain the crude sulfonyl chloride compound. This crude product was dissolved in DMF (5 mL), then was added 1-methylcyclopropanamine hydrochloride (13 mg, 0.12 mmol), N,N-diisopropylethylamine (0.042 mL, 0.24 mmol) and DMAP (10 mg, 0.08 mmol) at 0° C. The reaction mixture was stirred at room temperature for half an hour. When finished, the reaction mixture was diluted with ethyl acetate and water. The organic phase was separated and the aqueous phase was extracted with ethyl acetate. The organic phases were combined, washed with water and brine, dried over anhydrous Na$_2$SO$_4$, filtered and concentrated to obtain the crude product, which was purified by Prep-HPLC to give 11 (12 mg, 29%) as a white solid. LC-MS (ESI): m/z=511.9 [M+H]$^+$; $^1$H NMR (DMSO-d$_6$, 400 MHz): δ 8.72 (1H, d, J=9.2 Hz), 8.57 (1H, bs), 8.18 (1H, d, J=9.2 Hz), 7.72 (1H, t, J=53.2 Hz), 6.09 (2H, s), 2.52 (3H, s), 2.47 (3H, s), 1.14 (3H, s), 0.68-0.76 (2H, m), 0.38-0.45 (2H, m).

Example 12 Synthetic Route of Compound 12

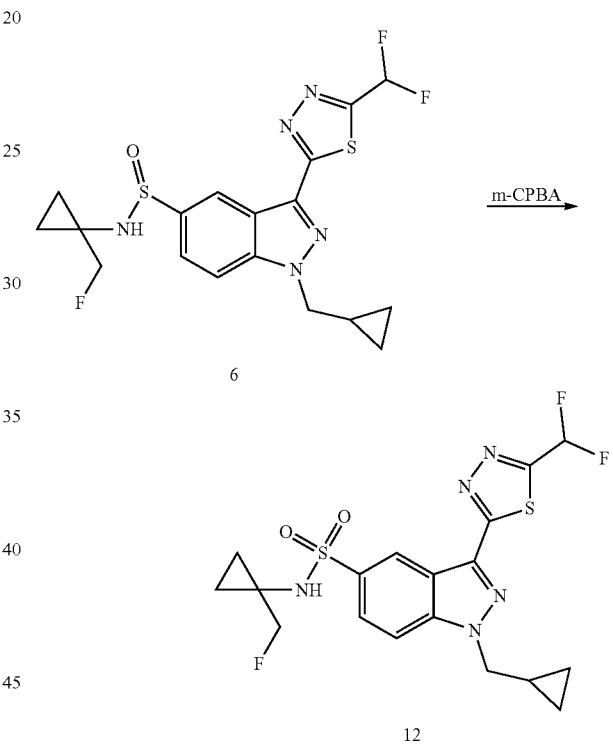

Synthesis of Compound 12 m-chloroperoxybenzoic acid (21 mg, 0.11 mmol) was added to a solution of compound 6 (31 mg, 0.07 mmol) in dichloromethane (6 mL) at 0° C. After addition, the reaction mixture was stirred at room temperature for 2 hours, then was added saturated NaHCO$_3$ (10 mL), diluted with DCM (50 mL). The resulting mixture was washed with brine, dried over Na$_2$SO$_4$, filtered and the filtrate was concentrated to dryness. The crude product was purified by column chromatography (mobile phase, PE/EA 3/1 to 1/1) and then purified by prep-HPLC (ammonium bicarbonate condition) to obtain 12 (6 mg, 19%). LC-MS (ESI): m/z 458.1 (M+H)$^+$; $^1$H NMR (400 MHz, DMSO-d$_6$): δ 8.83 (s, 1H), 8.60 (s, 1H), 8.17 (d, J=12.0H, 1H), 7.95-7.85 (m, 1H), 7.70 (t, J=56.0 Hz, 1H), 4.53 (d, J=4.0 Hz, 2H), 4.20 (d, J=48.0 Hz, 2H), 1.46-1.33 (m, 1H), 0.78-0.62 (m, 1H), 0.60-0.45 (m, 4H).

145

Example 13 Synthetic Route of Compound 13

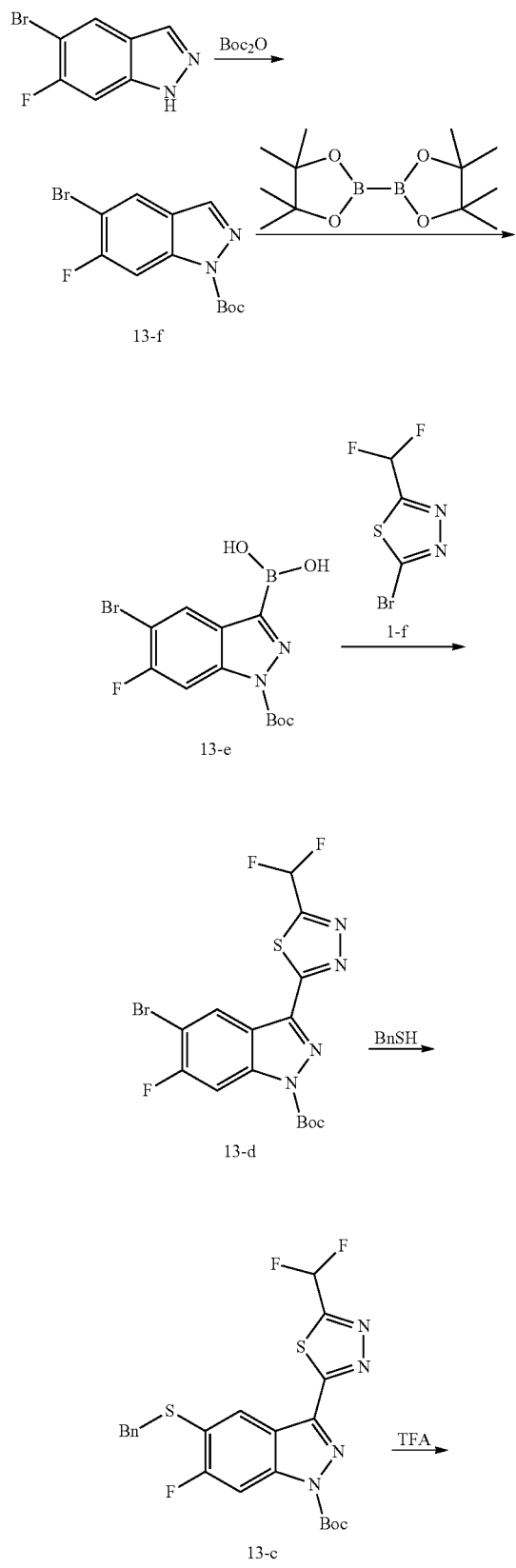

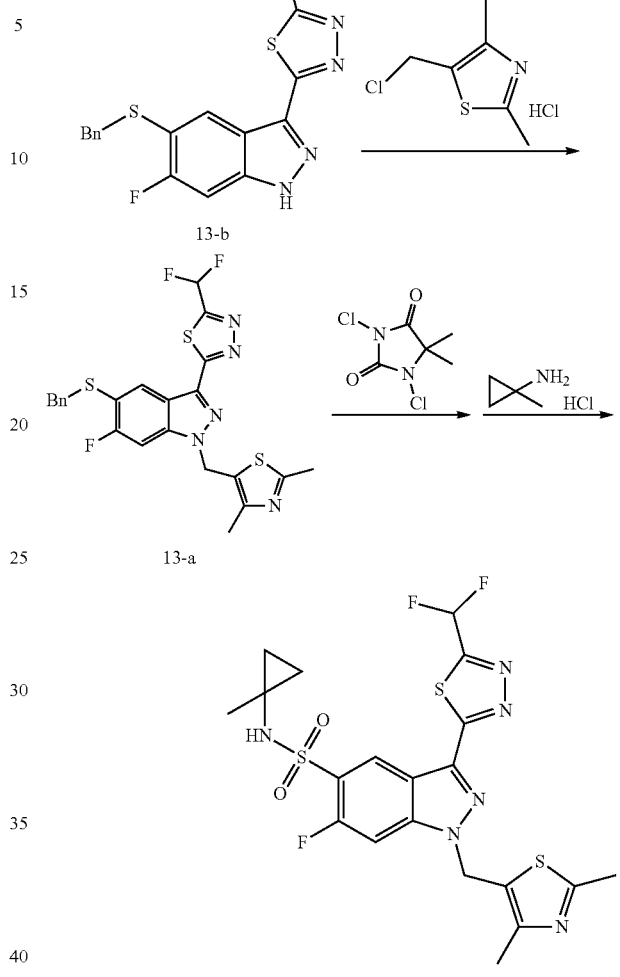

146

Synthesis of Compound 13-f 5-bromo-6-fluoroindazole (300 mg, 1.40 mmol), DMAP (20 mg, 0.16 mmol) and dichloromethane (15 mL) were combined in a reaction flask, and the mixture was added di-tert-butyl dicarbonate (470 mg, 2.15 mmol). The reaction mixture was stirred at room temperature for 2 hours. Removed the solvent, diluted with ethyl acetate, washed with water and brine, dried over anhydrous sodium sulfate, filtered and the filtrate was concentrated to dryness to obtain 13-f (439 mg, 99%) as a brownish-red liquid which was left to solidify. LC-MS (ESI): m/z 315.0 (M+H)$^+$.

Synthesis of Compound 13-e

Methoxy(cyclooctadiene)iridium dimer (45 mg, 0.069 mmol), 4,4'-di-tert-butyl-2,2'-dipyridine (37 mg, 0.14 mmol), biboronic acid pinacol ester (354 mg, 1.39 mmol) and methyl tert-butyl ether (4 mL) were combined in a microwave tube under protection of argon. After degassed and purged with nitrogen, the reaction was stirred at room temperature for 5 min. After addition of a solution of 13-f (439 mg, 1.39 mmol) in methyl tert-butyl ether (4 mL), the reaction was stirred at 80° C. for 2 h after degassed and purged with nitrogen. The reaction mixture was concentrated to dryness to give compound 13-e (499 mg, 99%) as a brownish red solid. LC-MS (ESI): m/z 359.0 (M+H)+.

Synthesis of Compound 13-d 13-e (499 mg, 1.39 mmol), 1-f (452 mg, 2.10 mmol), palladium acetate (27 mg, 0.12 mmol), XANT PHOS (152 mg, 0.26 mmol), toluene (10 mL) and water (5 mL) were combined in a reaction flask, and the resulting mixture was added cesium carbonate (860 mg, 2.64 mmol) after degassed and purged with nitrogen twice, then was stirred at 20° C. for 18 hours. After additional cesium carbonate (420 mg, 1.29 mmol) was added, the reaction was stirred at 20° C. for 4 hours. The reaction mixture was diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 88/12) to give compound 13-d (200 mg, 32%) as a light yellow solid. LC-MS (ESI): m/z 449.1 (M+H)+.

Synthesis of Compound 13-c

A reaction flask charged with 13-d (200 mg, 0.45 mmol), Pd$_2$(dba)$_3$ (20 mg, 0.022 mmol), XANT PHOS (25 mg, 0.043 mmol), 1,4-dioxane (10 mL), DIPEA (180 mg, 1.39 mmol) and benzyl mercaptan (180 mg, 1.45 mmol) was degassed and purged with nitrogen for 3 times. The reaction mixture was refluxed at 100° C. for 2 hours. Cooled to room temperature, the reaction mixture was evaporated to give compound 13-c (219 mg, 99%) as a dark green viscous liquid. LC-MS (ESI): m/z 493.1 (M+H)+.

Synthesis of Compound 13-b

A reaction vial charged with 13-c (219 mg, 0.44 mmol), dichloromethane (3 mL) and anisole (0.3 mL) was added trifluoroacetic acid (0.7 mL) dropwise at room temperature. The reaction was stirred at room temperature for 3 hours. The solvent was removed at room temperature and the residue was purified by column chromatography (mobile phase: (petroleum ether:dichloromethane=4:1)/ethyl acetate, 100/0 to 90/10) to give 13-b (115 mg, 66%) as a white solid. LC-MS (ESI): m/z 393.1 (M+H)+.

Synthesis of Compound 13-a

A reaction flask charged with 13-b (80 mg, 0.20 mmol), 5-(chloromethyl)-2,4-dimethyl-1,3-thiazole hydrochloride (80 mg, 0.40 mmol), tetrahydrofuran (3 mL) and DMF (1 mL) was degassed and purged with nitrogen twice, then was added sodium hydrogen (40 mg, 1.00 mmol) in an ice-water bath. The reaction mixture was stirred for 20 minutes in an ice-water bath and then 2 hours at room temperature. Take a quick sample of the reaction with a capillary tube to monitor the reaction. The color of the reaction deepened. The reaction mixture was stirred at room temperature for 2 hours. The color turned deep red. Quenched with dry ice, the reaction mixture was diluted with ethyl acetate and added saturated aqueous ammonium chloride. The organic phase was separated and concentrated to dryness and the residue was purified by column chromatography (mobile phase: dichloromethane/ethyl acetate, 100/0 to 90/10) to give 13-a (30 mg, 28%) as a colorless solid. LC-MS (ESI): m/z 518.1 (M+H)+.

Synthesis of Compound 13

1,3-Dichloro-5,5-dimethylimidazolidine-2,4-dione (36 mg, 0.18 mmol) was added to a reaction vial charged with 13-a (38 mg, 0.073 mmol), acetonitrile (2 mL), acetic acid (0.005 mL, 0.083 mmol) and water (0.005 mL, 0.28 mmol) in an ice-water bath. The reaction mixture was stirred in an ice-water bath for 1 hour. The reaction mixture was concentrated to dryness at room temperature and the residue was dried by an oil pump for 10 min. The crude product was combined with 1-methylcyclopropylamine hydrochloride (32 mg, 0.30 mmol) and dichloromethane (2.5 mL), and the resulting mixture was added triethylamine (0.11 mL, 0.79 mmol) in an ice-water bath. The reaction mixture was stirred at room temperature for 2 hours. The reaction mixture was concentrated to dryness at low temperature and the residue was purified by column chromatography (mobile phase: dichloromethane/ethyl acetate, 100/0 to 69/31) to give 13 (10 mg, 27%) as a white solid. LC-MS (ESI): m/z 529.0 (M+H)+; $^1$H NMR (DMSO-d$_6$, 400 MHz) δ 8.82 (1H, d, J=6.8 Hz), 8.54 (1H, s), 8.21 (1H, d, J=10.4 Hz), 7.70 (1H, t, J=53.0 Hz), 5.97 (2H, s), 2.52 (3H, s), 2.47 (3H, s), 1.13 (3H, s), 0.68-0.62 (2H, m), 0.46-0.39 (2H, m).

Example 14 Synthetic Route of Compound 14

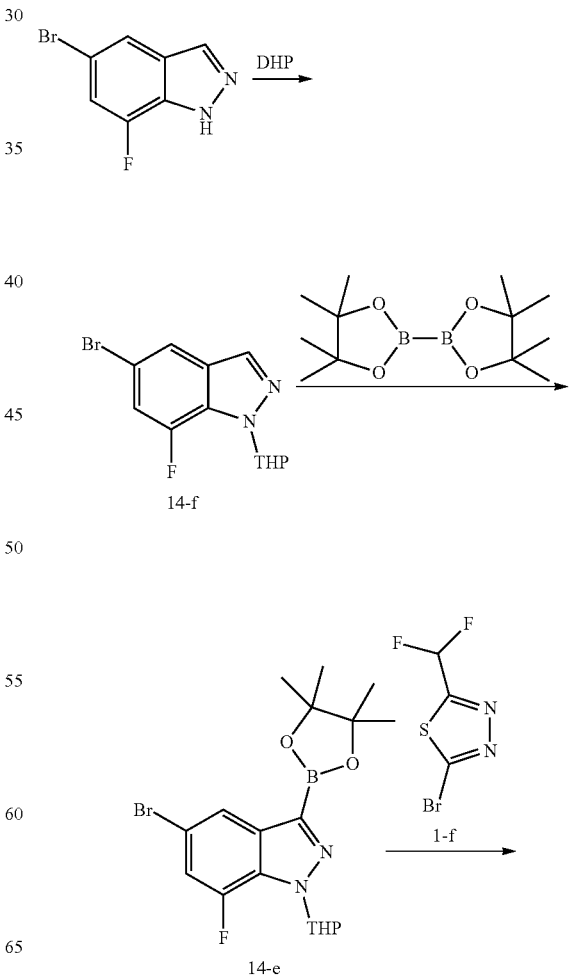

-continued

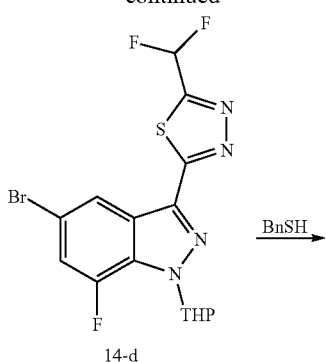

14-d

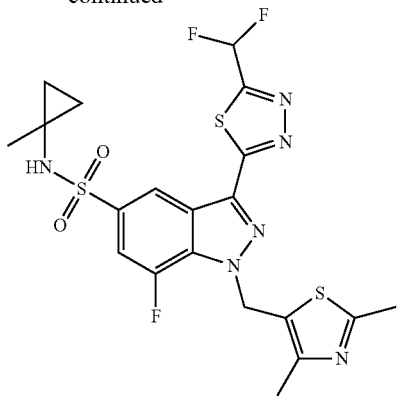

14

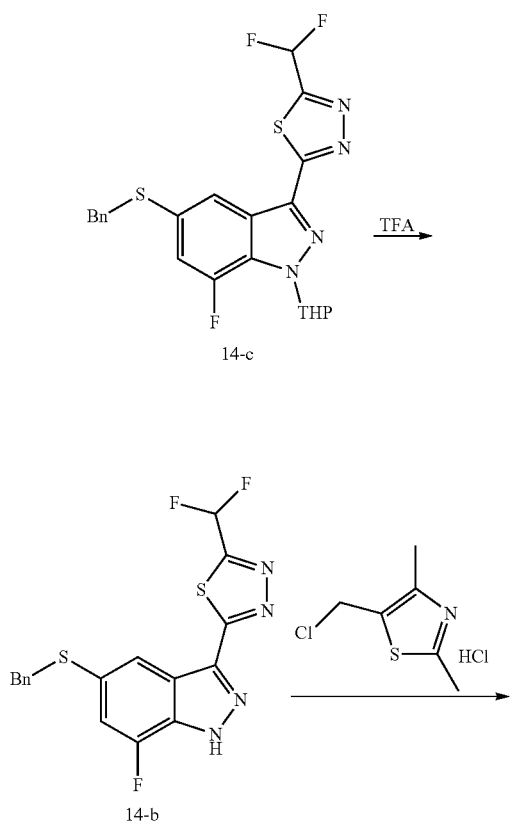

14-c 14-b

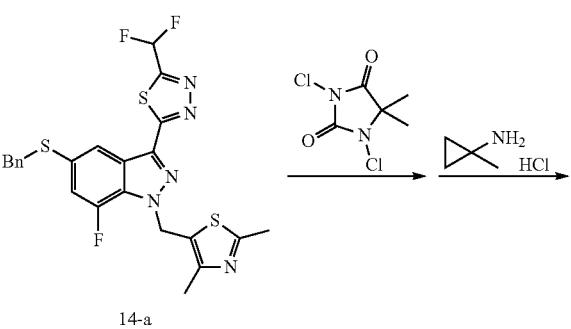

14-a

Synthesis of Compound 14-f

Trifluoroacetic acid (0.012 mL, 0.16 mmol) was added to a reaction vial charged with 5-bromo-7-fluoroindazole (645 mg, 3.00 mmol) and 3,4-dihydro-2H-pyran (6.4 mL) while stirring. The reaction mixture was stirred at 90° C. for 2 h, diluted with dichloromethane, washed with saturated sodium bicarbonate solution, brine, dried over anhydrous sodium sulfate, filtered and the filtrate was evaporated and the residue was purified by column chromatography (mobile phase: petroleum ether/ethyl acetate, 100/0 to 88/12) to give compound 14-f (680 mg, 76%) as a colorless viscous liquid. LC-MS (ESI): m/z 299.0 M+H)+.

Synthesis of Compound 14-e

Methoxy(cyclooctadiene)chloroiridium dimer (57 mg, 0.087 mmol), 4,4'-di-tert-butyl-2,2'-dipyridine (57 mg, 0.21 mmol), biboronic acid pinacol ester (308 mg, 1.21 mmol) and methyl tert-butyl ether (4 mL) were combined in a microwave tube, and the resulting mixture was stirred for 5 min at room temperature after degassed and purged with nitrogen twice. Then was added a solution of 14-f (350 mg, 1.17 mmol) in methyl tert-butyl ether (4 mL), and stirred at 80° C. for 2 hours after degassed and purged with nitrogen twice. The reaction mixture was concentrated to dryness to obtain compound 14-e (497 mg, 99%) as a brownish red viscous liquid.

Synthesis of Compound 14-d

A reaction flask, charged with 14-e (497 mg, 1.17 mmol), 1-f (377 mg, 1.75 mmol), palladium acetate (26 mg, 0.12 mmol), XANT PHOS (123 mg, 0.21 mmol), toluene (10 mL) and water (5 mL) was degassed and purged with nitrogen twice, then was added cesium carbonate (760 mg, 2.33 mmol). The reaction mixture was stirred at room temperature for 18 h, then was diluted with ethyl acetate, washed with water, brine, dried over anhydrous sodium sulfate, filtered and the filtrate was evaporated and the residue was purified by column chromatography (mobile phase: petroleum ether/ethyl acetate, 100/0 to 88/12) to give compound 14-d (370 mg, 73%) as a white solid. LC-MS (ESI): m/z 433.1 (M+H)+.

Synthesis of Compound 14-c

A reaction flask charged with 14-d (370 mg, 0.85 mmol), XANT PHOS (49 mg, 0.085 mmol), Pd₂(dba)₃ (39 mg, 0.043 mmol), 1,4-dioxane (10 mL), DIPEA (330 mg, 2.55 mmol) and benzyl mercaptan (320 mg, 2.58 mmol) was degassed and purged with nitrogen for 3 times, then was refluxed at 100° C. for 3 hours. The reaction mixture was cooled to room temperature and evaporated to dryness and the residue was purified by column chromatography (mobile phase: petroleum ether/ethyl acetate, 100/0 to 88/12) to give compound 14-c (280 mg, 68%) as a yellow solid. LC-MS (ESI): m/z 477.1 (M+H)$^+$.

Synthesis of Compound 14-b

Trifluoroacetic acid (0.6 mL) was added dropwise to a solution of 14-c (280 mg, 0.59 mmol) in dichloromethane (3 mL) in a reaction vial, and the reaction mixture was stirred at room temperature for 3 hours. Then the reaction mixture was added HCl/1,4-dioxane (0.7 mL) and stirred at room temperature for 2 hours. The solvent was removed by rotary evaporation at room temperature. The residue was diluted with ethyl acetate, washed with saturated sodium bicarbonate, dried over anhydrous sodium sulfate, filtered, and the filtrate was evaporated to dryness. The residue was combined with dichloromethane (3 mL) in a reaction flask and was added HCl/methanol (1 mL) dropwise in an ice-water bath. The reaction mixture was stirred at room temperature for 1 hour. then was added trifluoroacetic acid (0.6 mL) dropwise and stirred at room temperature for 1 hour. The solvent was removed by rotary evaporation at room temperature, and the residue with diluted with ethyl acetate, washed with saturated sodium bicarbonate, dried over anhydrous sodium sulfate, filtered and the filtrate was evaporated and the residue was purified by column chromatography (mobile phase: (petroleum ether:dichloromethane=4:1)/ ethyl acetate, 100/0 to 85/15) to give 14-b (90 mg, 39%) as a white solid. LC-MS (ESI): m/z 393.0 (M+H)$^+$.

Synthesis of Compound 14-a

A reaction vial charged with 14-b (85 mg, 0.22 mmol), 5-(chloromethyl)-2,4-dimethyl-1,3-thiazole hydrochloride (65 mg, 0.33 mmol), cesium carbonate (260 mg, 0.80 mmol) and DMF (2.5 mL) was stirred at room temperature for 1 h. The reaction was detected by rapid sampling with a capillary tube. The reaction mixture continued stirring at room temperature for 1.5 h. The color turned to light brown. The reaction mixture was diluted with ethyl acetate, washed with saturated aqueous ammonium chloride, water, and brine sequentially, dried over anhydrous sodium sulfate, and the organic phase was evaporated and the residue was purified by column chromatography (mobile phase: dichloromethane/ethyl acetate, 100/0 to 90/10) to give 14-a (90 mg, 80%) as a solid. LC-MS (ESI): m/z 518.1 (M+H)$^+$.

Synthesis of Compound 14

1,3-Dichloro-5,5-dimethylimidazolidine-2,4-dione (137 mg, 0.70 mmol) was added in three batches (at 1 h intervals) to a reaction vial charged with 14-a (90 mg, 0.17 mmol), acetonitrile (3 mL), acetic acid (0.014 mL, 0.25 mmol) and water (0.015 mL, 0.83 mmol) in an ice-water bath. The reaction mixture was stirred in an ice-water bath for 3 hours. The reaction mixture was evaporated to dryness at low temperature and dried by an oil pump for 10 min to obtain the crude product. 1-methylcyclopropylamine hydrochloride (75 mg, 0.70 mmol), dichloromethane (4 mL) and triethylamine (0.234 mL, 1.68 mmol) were combined in a second reaction vial and the mixture was stirred at room temperature for 5 minutes and then added to the crude reaction vial in an ice-water bath. The reaction mixture was stirred at room temperature for 2 hours. The reaction mixture was concentrated to dryness at room temperature and the residue was purified by a column chromatography (mobile phase: dichloromethane/ethyl acetate, 100/0 to 69/31) to give compound 14 (58.0 mg, 63%) as a light brown solid. LC-MS (ESI): m/z 529.0 (M+H)$^+$; $^1$H NMR (DMSO-d$_6$, 400 MHz): δ 8.67 (1H, d, J=1.2 Hz), 8.34 (1H, s), 7.77 (1H, dd, J=11.2, 1.2 Hz), 7.71 (1H, t, J=53.0 Hz), 6.00 (2H, s), 2.52 (3H, s), 2.45 (3H, s), 1.08 (3H, s), 0.66-0.58 (2H, m), 0.45-0.39 (2H, m).

Example 15 Synthetic Route of Compound 15

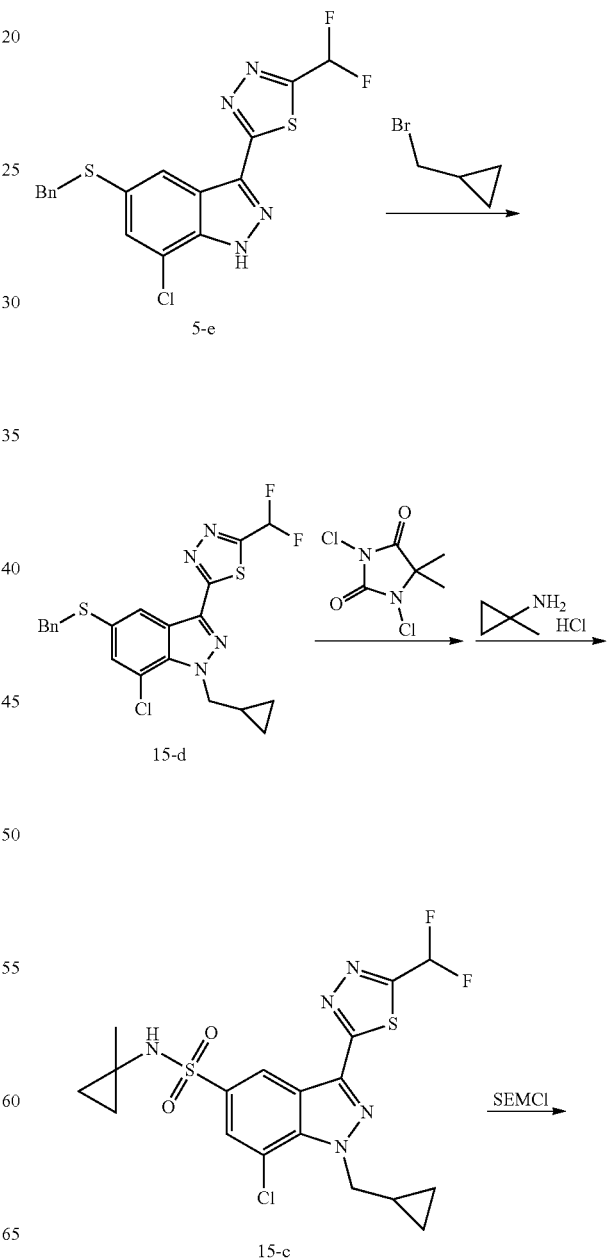

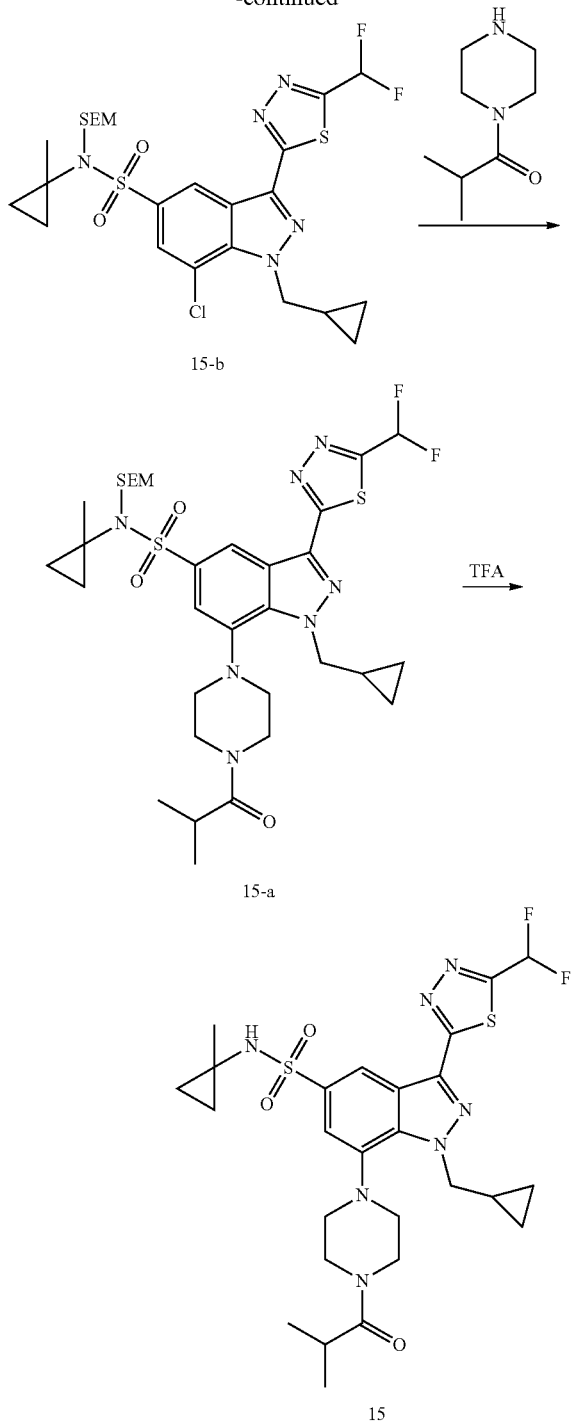

the crude product, which was purified by column chromatography (mobile phase, PB/EA=10/1) to obtain compounds 15-d (110 mg, 97%). LC-MS (ESI): m/z 463.2 (M+H)$^+$.

Synthesis of Compound 15-c

Acetic acid (98 mg, 1.63 mmol) and water (29 mg, 1.61 mmol) were added to a solution of compound 15-d (155 mg 0.33 mmol) in acetonitrile (10 m). Then cooled to 0° C., the above mixture was added dichlorohydantoin in three batches. The reaction mixture was stirred at 0° C. for 1 h. The reaction mixture was rotary evaporated at room temperature at reduced pressure to obtain the crude product. Meanwhile, diisopropylethylamine (50 µL) was added to a solution of 1-methylcyclopropylamine hydrochloride (70 mg, 0.65 mmol) in dichoromethane (2 m), and the resulting mixture was stirred at room temperature for 20 min, and then was added into a solution of the crude product in dichloromethane (10 mL), and then the above mixture was added diisopropylethylamine (211 mg, 1.65 mmol), and the reaction mixture was stirred at room temperature for 12 h. The reaction mixture was rotary evaporated at reduced pressure to give the crude product, which was purified by column chromatography (mobile phase, PB/BA=3/1) to give compound 15-c (93 mg, 59%). LC-MS (BSI): m/z 474.2 (M+H)$^+$.

Synthesis of Compound 15-b

Compound 15-c (93 mg, 0.20 mmol) was dissolved in tetrahydrofuran (6 mL), degassed and purged with nitrogen, and the mixture was cooled to 0° C., was added sodium hydrogen (24 mg, 0.60 mmol) under nitrogen atmosphere. The reaction mixture was stirred at 0° C. for 30 min and then was added 2-(trimethylsilyl)ethoxymethyl chloride (49 mg, 0.29 mmol). After addition, the mixture was stirred at 0° C. for 3 h. After that, the reaction mixture was added dry ice (5 g) in batches at 0° C. and stirred for 20 min. The reaction mixture was concentrated to dryness at reduced pressure to give the crude product, which was purified by column chromatography (mobile phase, PE/EA=10/1) to give compound 15-b (108 mg, 91%). LC-MS (ESI): m/z 604.3 (M+H)$^+$.

Synthesis of Compound 15-a

Compound 15-b (108 mg, 0.18 mmol), 2-methyl-1-(piperazin-1-yl)propan-1-one (56 mg, 0.36 mmol), 2-dicyclohexylphosphino-2',6'-diisopropoxy-1,1'-biphenyl (17 mg, 0.04 mmol), methanesulfonic acid, (2-dicyclohexylphosphino-2',6'-diisopropoxy-1,1'-biphenyl), (2-amino-1,1'-biphenyl-2-yl)palladium(II) (15 mg, 0.03 mmol), and cesium carbonate (174 mg, 0.53 mmol) were added to a microwave tube charged with 1,4-dioxane (6 mL), the resulting mixture was stirred at 80° C. for 12 h in a sealed tube after degassed and purged with nitrogen three times. The reaction mixture was cooled to room temperature and evaporated at reduced pressure to give the crude product, which was purified by column chromatography (mobile phase, PE/EA=3/1 to 1/1) to give compound 15-a (67 mg, 52%). LC-MS (ESI): m/z 724.5 (M+H)$^+$.

Synthesis of Compound 15

Trifluoroacetic acid (3 mL) was added to a solution of compound 15-a (67 mg, 0.09 mmol) in dichloromethane (7 mL), and the reaction was stirred for 2 h at room tempera- Synthesis of Compound 15-d Bromomethylcyclopropane (66 g, 0.49 mmol) and cesium carbonate (239 mg, 0.73 mmol) were added to a solution of compound 5-c (1000 mg, 0.24 mol) in N, N-dimethylfomamide (10 mL) and the mixture was stirred at 40° C. for 12 hours. Then the reaction mixture was added water (50 mL), extracted with ethyl acetate (100 mL) twice, washed with brine (100 mL), dried over sodium sulfate, filtered desiccant, and the filtrate was evaporated at reduced pressure to obtain ture. The reaction mixture was adjusted to pH 8 with saturated sodium bicarbonate solution, added water (30 mL), extracted with ethyl acetate (100 mL), washed with brine (50 mL), dried over sodium sulfate, filtered to remove desiccant, and evaporated at reduced pressure to obtain the crude product, which was purified by preparative HPLC (basic conditions) to obtain compound 15 (15 mg, 27%). LC-MS (ESI): m/z 594.2 (M+H)$^+$; $^1$HNMR ((400 MHz, DMSO-d$_6$): δ 8.64 (s, 1H), 8.14 (s, 1H), 7.85-7.56 (m, 2H), 4.74-4.65 (m, 2H), 4.6-4.5 (m, 1H), 4.19-4.08 (m, 1H), 3.45-3.34 (m, 1H), 3.30-3.20 (m, 2H), 3.02-2.80 (m, 3H), 2.77-2.64 (m, 1H), 1.47-1.34 (m, 1H), 1.14-0.97 (m, 7H), 0.68-0.32 (m, 7H).

Example 16 Synthetic Route of Compound 16

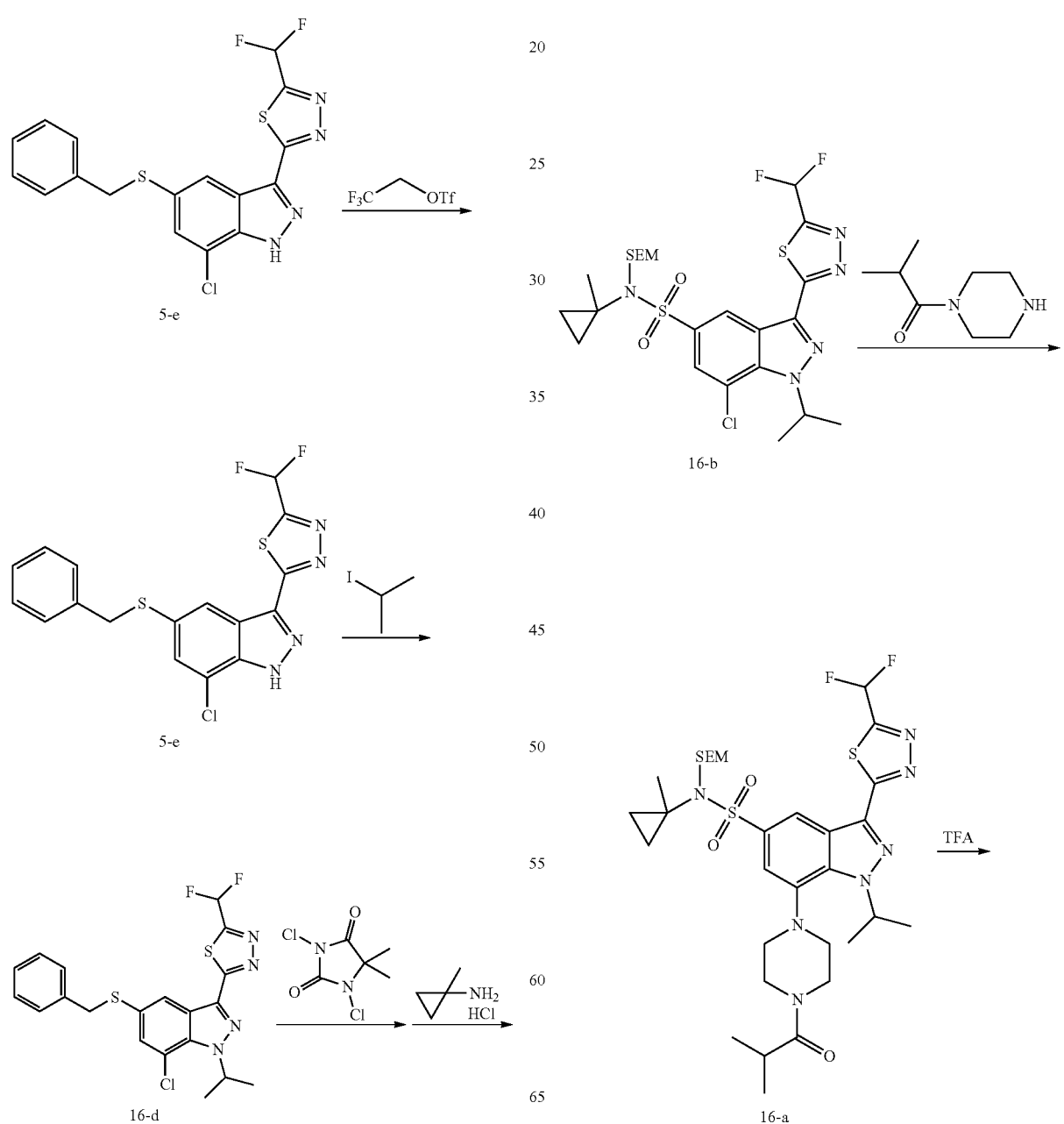

-continued

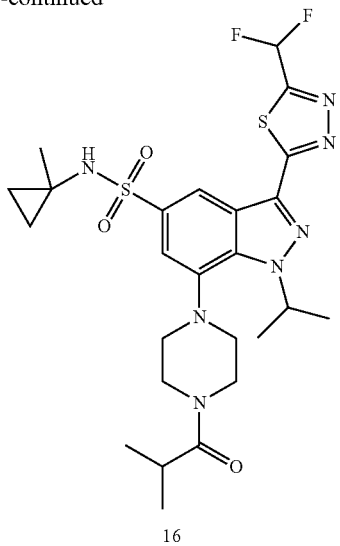

16

Synthesis of Compound 16-d

Cesium carbonate (191 mg, 0.59 mmol) and 2-iodopropane (0.073 mL, 0.73 mmol) were added to a solution of 5-e (200 mg, 0.49 mmol) in DMF (5 mL) at room temperature. After addition, the reaction was stirred at room temperature overnight. After the reaction was finished, the reaction was diluted by adding ethyl acetate, washed with water, brine, dried over anhydrous sodium sulfate, filtered and the filtrate was evaporated. The residue was purified by a flash column chromatography (mobile phase: ethyl acetate/petroleum ether 0% to 50%) to obtain compound 16-d (175 mg, 79%). LC-MS (ESI): m/z=451.1 [M+H]$^+$.

Synthesis of Compound 16-c

To a solution of acetonitrile (5 mL) of 16-d (175 mg, 0.39 mmol) was added acetic acid (0.089 mL, 1.55 mmol) and H$_2$O (0.029 mL, 1.59 mmol), and 1,3-dichloro-5,5-dimethylimidazolidine-2,4-dione (153 mg, 0.78 mmol) was carefully added to the above mixture at 0° C. After addition, the reaction was stirred at 0° C. for 1 hr. Upon completion, the reaction was concentrated at reduced pressure at room temperature and dried by an oil pump for 30 min to obtain the crude sulfonyl chloride compound. This crude product was dissolved in DCM (10 mL), and was added 1-methylcyclopropanamine hydrochloride (63 mg, 0.58 mmol) and triethylamine (0.27 mL, 1.94 mmol) at 0° C. The reaction mixture was warmed to room temperature and stirred for half an hour. When finished, the reaction was diluted with dichloromethane and water. The organic phase was separated and the aqueous phase was extracted with dichloromethane. The organic phases were combined, washed with water, brine, dried over anhydrous Na$_2$SO$_4$, filtered and the filtrate was evaporated to give the crude product, which was purified by a flash column chromatography (mobile phase: ethyl acetate/petroleum ether 0% to 100%) to give 16-c (80 mg, 45%). LC-MS (ESI): m/z=462.1 [M+H]$^+$.

Synthesis of Compound 16-b

Sodium hydrogen (60% in oil, 21 mg, 0.52 mmol) was added to a reaction vial charged with 16-c (80 mg, 0.17 mmol) and THF (10 mL) in an ice-water bath. The reaction mixture was stirred in an ice-water bath for 10 min, then was added SEMCl (43 mg, 0.26 mmol) and was continued stirring for 1 hr. The reaction was carefully quenched with dry-ice powder, continued stirring for 30 min, diluted with ethyl acetate, washed with water, brine, dried over anhydrous sodium sulfate, filtered and the filtrate was evaporated and the residue was purified over column (mobile phase: ethyl acetate/petroleum ether 0% to 100%) to give compound 16-b (60 mg, 59%). LC-MS (ESI): m/z=592.1 [M+H]$^+$.

Synthesis of Compound 16-a

A microwave tube charged with 16-b (40 mg, 0.068 mmol), 2-methyl-1-(piperazin-1-yl)propyl-1-one (21 mg, 0.14 mmol), Xantphos (7.82 mg, 0.014 mmol), Pd$_2$dba$_3$ (6.89 mg, 0.007 mmol), cesium carbonate (66 mg, 0.20 mmol) and 1,4-dioxane (3 mL) was degassed and purged with nitrogen for 3 times. The reaction mixture was heated at 90° C. for 6 hours. When finished, the reaction was cooled to room temperature, removed 1,4-dioxane, and the residue was diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether 0% to 100%) to give compound 16-a (20 mg, 42%). LC-MS (ESI): m/z 729.3 (M+NH$_4$)$^+$.

Synthesis of Compound 16

Trifluoroacetic acid (1 mL) was added dropwise to a reaction flask charged with 16-a (20 mg, 0.028 mmol) and dichloromethane (5 mL) at room temperature. The reaction was stirred at room temperature for 5 h. The solvent was removed by concentration at room temperature. Diluted by adding ethyl acetate, washed with saturated sodium bicarbonate, brine, dried over anhydrous sodium sulfate, filtered and the filtrate was evaporated to obtain the crude product. The residue was purified by Prep-HPLC to afford compound 16 (2.5 mg, 15%). LC-MS (ESI): m/z 582.2 (M+H)$^+$.

Example 17 Synthetic Route of Compound 17

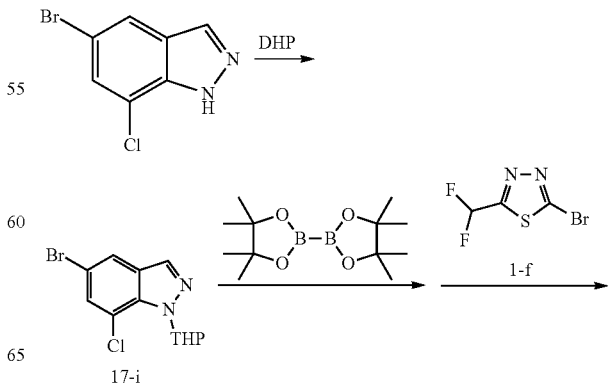

159
-continued
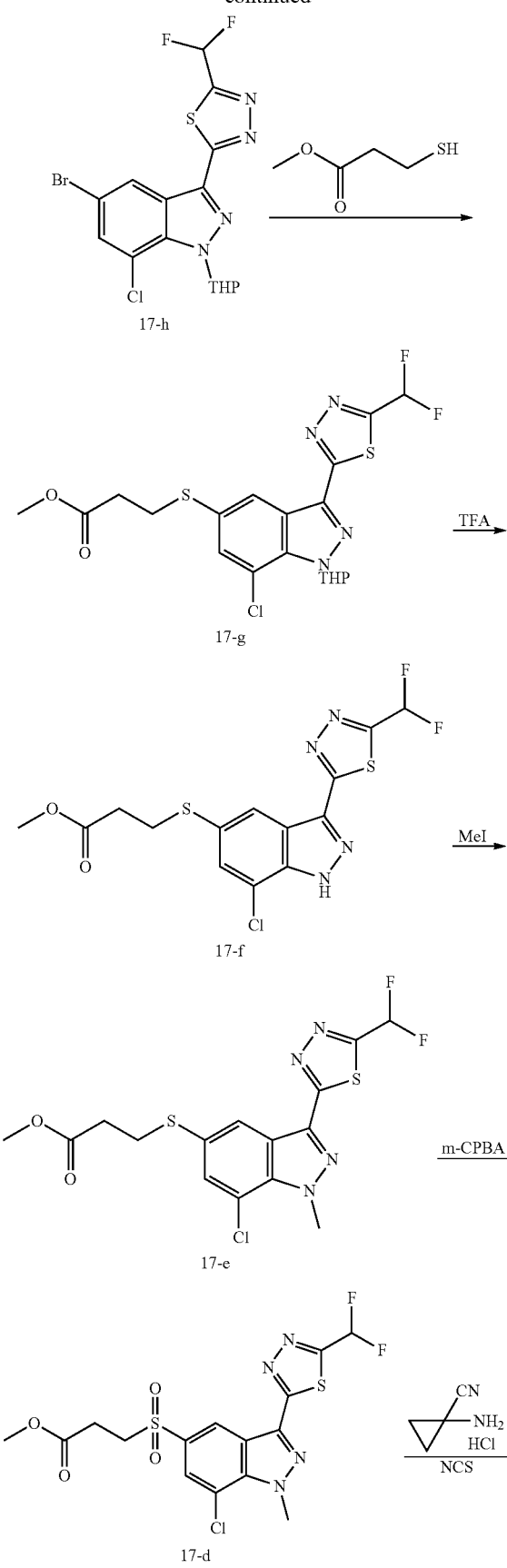
160
-continued
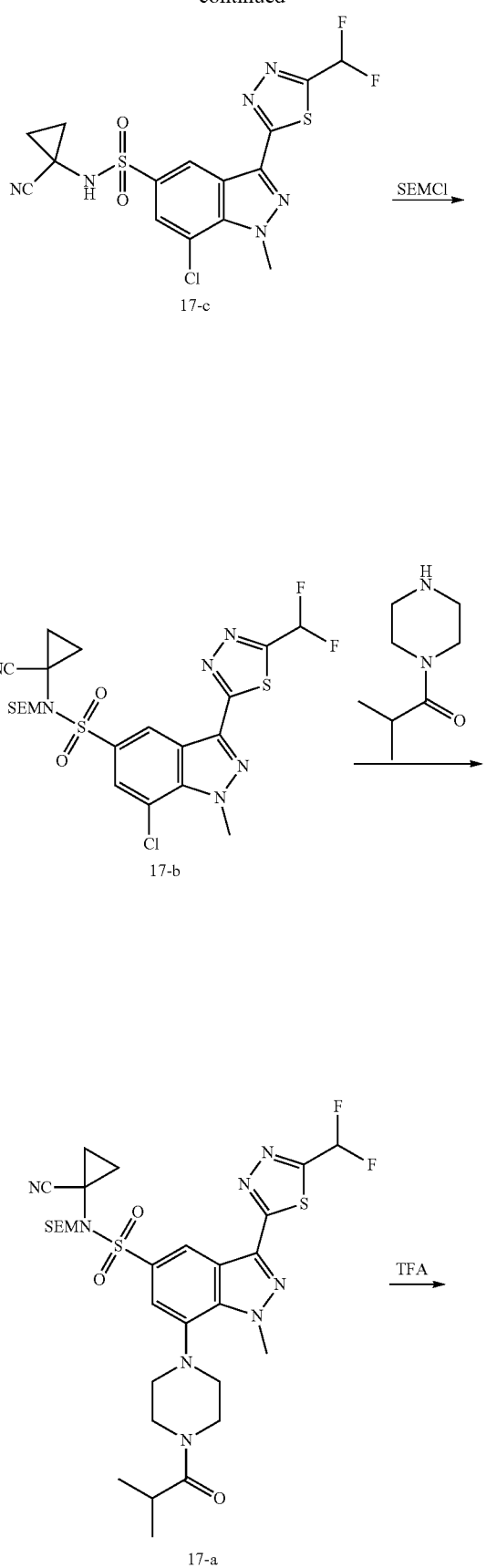

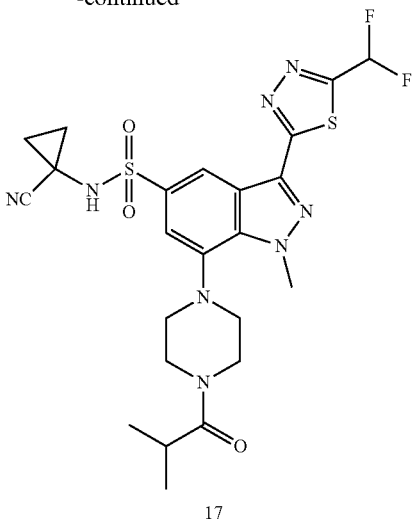

17

Synthesis of Compound 17-i

To a solution of compound 5-bromo-7-chloro-1H-indazole (5 g, 21.6 mmol) in 3,4-dihydro-21H-pyran (74 mL, 864.01 mmol) was added trifluoroacetic acid (0.17 mL, 2.16 mmol). After addition, the reaction was stirred at 90° C. for three hours. When finished, the reaction mixture was diluted with ethyl acetate, washed with saturated sodium bicarbonate, brine, dried over anhydrous sodium sulfate, filtered and the filtrate was concentrated to obtain the crude product, which was purified by a flash column chromatography (mobile phase: ethyl acetate/petroleum ether 0% to 10%) to give compound 17-i (5.7 g, 84%). LC-MS (ESI): m/z=315.0 [M+H]$^+$.

Synthesis of Compound 17-h

A sealed tube charged with biboronic acid pinacol ester (1.21 g, 4.75 mmol), 4,4'-di-tert-butyl-2,2'-dipyridine (208 mg, 0.32 mmol), and methyl tert-butyl ether (10 mL) was added methoxy(cyclooctadiene)chloroiridium dimer (170 mg, 0.63 mmol) under nitrogen atmosphere. The resulting mixture was stirred at room temperature for 10 min after degassed and purged with nitrogen. Then was added a solution of 17-i (1.0 g, 3.17 mmol) in methyl tert-butyl ether (10 mL) and stirred at 85° C. for 3.5 h after degassed and purged with nitrogen three times. The reaction mixture was concentrated to obtain the crude borate ester.

The resulting crude borate ester was dissolved in toluene (20 mL) and water (10 mL), and the resulting mixture was added 1-f (886 mg, 4.12 mmol), palladium acetate (71 mg, 0.32 mmol), Xantphos (367 mg, 0.63 mmol), and N-methylmorpholine (1.05 mL, 9.51 mmol). After degassed and purged with nitrogen twice, the reaction mixture was stirred at 40° C. for 18 h. Upon completion, the reaction mixture was diluted with ethyl acetate, washed with water, brine, dried over anhydrous sodium sulfate, filtered, concentrated and purified by column chromatography (mobile phase: ethyl acetate/petroleum ether 0% to 50%) to give compound 17-h (1.0 g, 70%). LC-MS (ESI): m/z=449.0 (M+H)$^+$.

Synthesis of Compound 17-g

A reaction flask charged with 17-h (200 mg, 0.44 mmol), XANT PHOS (16 mg, 0.028 mmol), Pd$_2$(dba)$_3$ (11 mg, 0.01 mmol), 1,4-dioxane (4 mL), DIPEA (180 mg, 1.39 mmol) and methyl 3-mercaptopropionate (57 mg, 0.47 mmol) was degassed and purged with nitrogen for 3 times. The reaction was refluxed at 85° C. for 2 hours. Cooled to room temperature, the reaction mixture was evaporated, and the residue was diluted with ethyl acetate, washed with water, brine, dried over anhydrous sodium sulfate, filtered and the filtrate was evaporated to give compound 17-g (217 mg, 100%). LC-MS (ESI): m/z 489.0 (M+H)$^+$.

Synthesis of Compound 17-f

Trifluoroacetic acid (1.5 mL) was added dropwise to a reaction vial charged with 17-g (217 mg, 0.44 mmol) and dichloromethane (4.5 mL) in an ice-water bath. The reaction was stirred at room temperature for 2 hours. Rotary evaporated to remove the solvent, the residue was diluted with ethyl acetate, wash with saturated sodium bicarbonate, brine, dried over anhydrous sodium sulfate, filter and evaporate to obtain 17-f (179 mg, 100%). LC-MS (ESI): m/z 405.0 (M+H)$^+$.

Synthesis of Compound 17-e

Iodomethane (0.042 mL, 0.68 mmol) was added dropwise to a reaction flask charged with 17-f (171 mg, 0.42 mmol), DMF (4.2 mL) and cesium carbonate (360 mg, 1.10 mmol) in an ice-water bath. The reaction mixture was stirred at room temperature for 2 hours, then was added a small amount of methanol and ethyl acetate. Rotary evaporated at room temperature for 5 min, the reaction mixture was diluted by adding ethyl acetate, washed with water, brine, dried over anhydrous sodium sulfate and evaporated to dryness and the residue was purified by column chromatography (mobile phase: dichloromethane/methanol 100/0 to 96/4) to give 17-e (140 mg, 79%). LC-MS (ESI): m/z 419.0 (M+H)$^+$.

Synthesis of Compound 17-d m-CPBA (136 mg, 0.79 mmol) was added to a reaction flask charged with 17-e (110 mg, 0.26 mmol) and DCM (12 mL) in an ice-water bath. The reaction mixture was stirred in an ice-water for 1 hour. Diluted with ethyl acetate, the reaction mixture was washed with aqueous sodium bicarbonate, water and brine, dried over anhydrous sodium sulfate, filtered and the filtrate was evaporated and the residue was purified by column chromatography (mobile phase: (petroleum ether/dichloromethane 4:1)/ethyl acetate, 100/0 to 50/50, dichloromethane/methanol, 100/0 to 96/4) to obtain compound 17-d (110 mg, 93%). LC-MS (ESI): m/z 451.0 (M+H)$^+$.

Synthesis of Compound 17-c

Sodium methanol (40 mg, 0.74 mmol) was added to a reaction flask charged with 17-d (110 mg, 0.24 mmol) and methanol (3 mL) in an ice-water bath. The reaction mixture was stirred in an ice-water bath for 30 min and then was added dichloromethane (2 mL) and continued stirring at room temperature for 30 min, and TLC showed the reaction was complete. 1-amino-1-cyclopropanecarbonitrile hydrochloride (116 mg, 0.98 mmol) was added to the above reaction mixture in an ice-water bath and stirred until the solid was dissolved complete. The solvent was removed by rotary evaporation at room temperature and the residue was dried by an oil pump for 15 min. The residue was combined with a small amount of dried 3 A molecular sieve and DMF (3 mL). The resulting mixture was added triethylamine (0.034 mL, 0.25 mmol) and NCS (98 mg, 0.73 mmol) in an ice-water bath. The reaction mixture was stirred in an ice-water bath for 2 hours. The reaction mixture was diluted with ethyl acetate, washed once with diluted sodium bisulfite solution, once with water, and the washing solution was reverse extracted once with ethyl acetate. The organic phases were combined, washed with brine, dried over anhydrous sodium sulfate, filtered and the filtrate was evaporated to give 17-c (108 mg, 100%). LC-MS (ESI): m/z 444.9 (M+H)+.

Synthesis of Compound 17-b

SEMCl (81 mg, 0.49 mmol) was added dropwise into a reaction vial charged with 17-c (108 mg, 0.24 mmol) and triethylamine (0.14 mL, 0.97 mmol) in an ice-water bath. The reaction mixture was stirred at room temperature for 1 hour, then was added methanol (0.25 mL) dropwise in an ice-water bath. The reaction mixture was stirred at room temperature for 10 min. the solvent was removed by rotary evaporation at room temperature. The crude product was purified by column chromatography (mobile phase: petroleum ether, dichloromethane 4:1)/ethyl acetate, 100/0 to 60/40) to give 17-b (115 mg, 82%). LC-MS (ESI): m/z 575.0 (M+H)+.

Synthesis of Compound 17-a

A microwave tube charged with 17-b (90 mg, 0.16 mmol), 2-methyl-1-(piperazin-1-yl)propan-1-one (98 mg, 0.63 mmol), RuPhos (7 mg, 0.015 mmol), RuPhos Pd G3 (7 mg, 0.008 mmol), cesium carbonate (158 mg, 0.48 mmol) and 1,4-dioxane (2.5 mL) was degassed and purged with nitrogen for 3 times. The reaction mixture was heated at 75-80° C. for 2 hours, then switched to a large microwave tube and added 2-methyl-1-(piperazin-1-yl)propan-1-one (86 mg, 0.54 mmol), RuPhos (28 mg, 0.060 mmol), RuPhos Pd G3 (27 mg, 0.032 mmol), cesium carbonate (102 mg, 0.31 mmol) and 1,4-dioxane (6 mL). The reaction mixture was heated at 85° C. for 1.5 h under argon protection. Cool to room temperature, the reaction mixture was removed 1,4-dioxane by rotary evaporation, diluted with ethyl acetate, washed with water, brine, dried over anhydrous sodium sulfate, filtered, evaporate and purify over column (mobile phase: (petroleum ether/dichloromethane 4:1)/ethyl acetate, 100/0 to 60/40, dichloromethane/methanol, 100/0 to 95/5) to give compound 17-a (90 mg, 83%). LC-MS (ESI): m/z 695.3 (M+H)+.

Synthesis of Compound 17

Trifluoroacetic acid (1 mL) was added dropwise to a reaction flask charged with 17-a (90 mg, 0.13 mmol) and dichloromethane (3 mL) in an ice-water bath. The reaction mixture was stirred at room temperature for 2.5 hours. The solvent was removed at room temperature, and the residue was diluted with ethyl acetate, washed with saturated sodium bicarbonate solution, dried over anhydrous sodium sulfate, filtered and the filtrate was evaporated to get the residue, which was purified column chromatography (mobile phase: 10 mM ammonium bicarbonate water, acetonitrile) to give 17 (15.5 mg, 21%). LC-MS(ESI): m/z 565.2 (M+H)+; 1H NMR (DMSO-d6, 400 MHz) δ 9.19 (1H, s), 8.65 (1H, d, J=1.6 Hz), 7.77 (1H, t, J=53.2 Hz), 7.57 (1H, d, J=1.6 Hz), 4.51 (4H, s), 4.11 (1H, s), 3.51-3.48 (2H, m), 3.11-2.69 (5H, m), 1.49-1.41 (2H, m), 1.36-1.29 (2H, m), 1.06 (6H, d, J=6.4 Hz).

Example 18 Synthetic Route of Compound 18

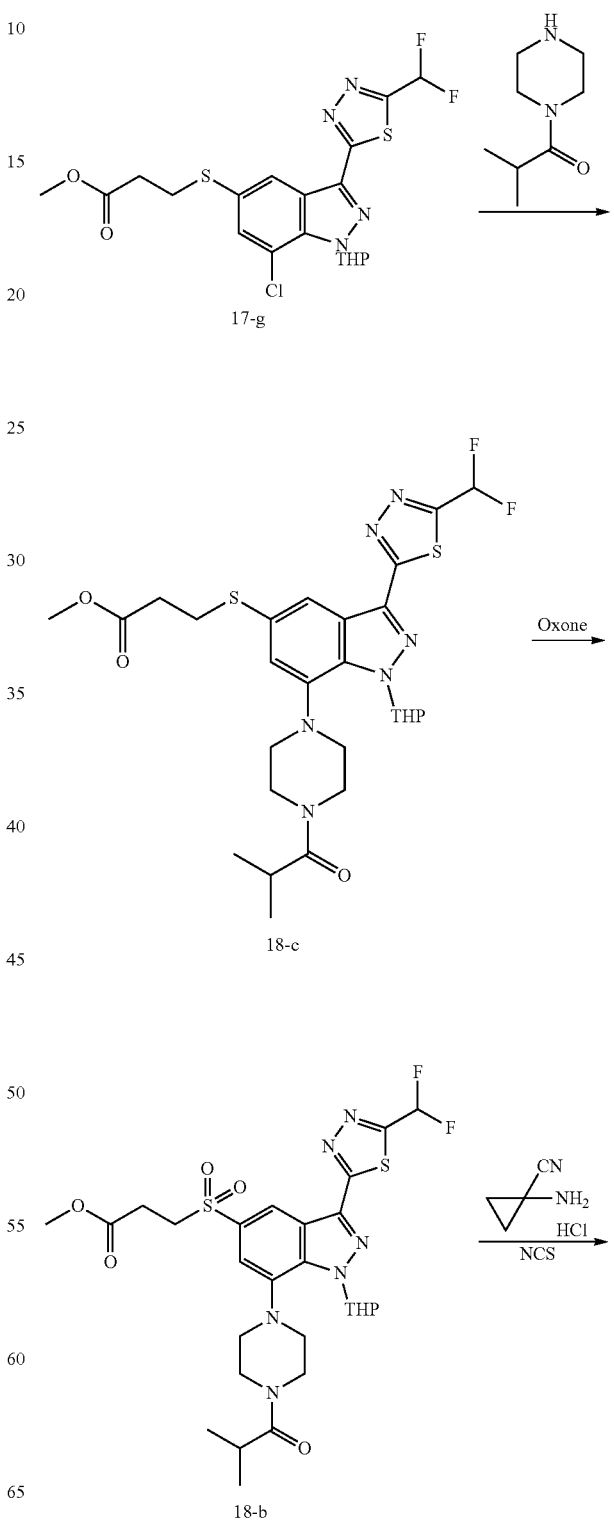

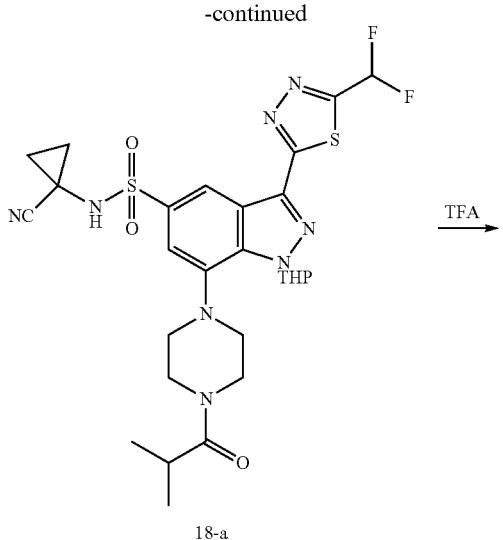

18-a

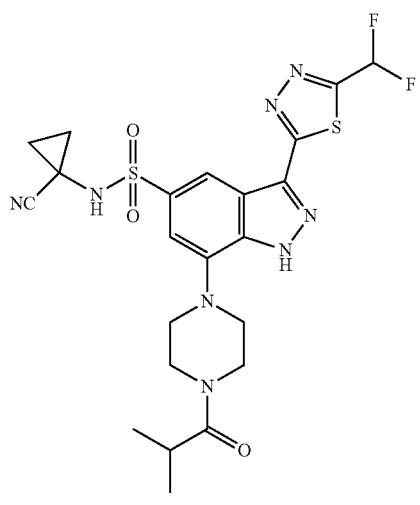

18

Synthesis of Compound 18-c

A microwave tube charged with 17-g (120 mg, 0.24 mmol), 2-methyl-1-(piperazin-1-yl)propan-1-one (153 mg, 0.98 mmol), RuPhos (23 mg, 0.049 mmol), RuPhos Pd G3 (21 mg, 0.025 mmol), cesium carbonate (245 mg, 0.75 mmol) and 1,4-dioxane (8 mL) was degassed and purged with argon gas 3 times. The reaction was heated at 80° C. for 5 hours under argon protection. Cooled to room temperature, the reaction mixture was removed dioxane by rotary evaporation, diluted with ethyl acetate, washed with water, brine, dried over anhydrous sodium sulfate, filtered and the filtrate was evaporated and the residue was purified by column chromatography (mobile phase: (petroleum ether/dichloromethane 4:1)/ethyl acetate, 100/0 to 0/100) to give compound 18-c (100 mg, 67%). LC-MS (ESI): m/z 609.3 (M+H)$^+$.

Synthesis of Compound 18-b

A solution of oxone (302 mg, 0.49 mmol) in water (8 mL) was added dropwise to a reaction vial charged with 18-c (100 mg, 0.16 mmol) and acetonitrile (5 mL) in an ice-water bath. The reaction mixture was stirred in an ice-water bath for 2 hours, then was added additional Oxone (40 mg, 0.065 mmol). After stirred in an ice-water bath for 1 hour, the reaction mixture was added ethyl acetate to dilute it and a small amount of sodium bisulfite solid. The mixture was stirred in an ice-water bath for 5 min. The aqueous phase was extracted once with ethyl acetate, and the organic phases were combined, washed with water, brine, dried over anhydrous sodium sulfate, filtered and the filtrate was evaporated to give compound 18-b (97 mg, 92%). LC-MS (ESI): m/z 663.2 (M+Na)$^+$.

Synthesis of Compound 18-a

Sodium methanol (28 mg, 0.52 mmol) was added to a reaction flask charged with 18-b (97 mg, 0.15 mmol) and methanol (5 mL) in an ice-water bath. The reaction mixture was stirred in an ice-water bath for 30 min and then at room temperature for 30 min. TLC showed the reaction was complete. The reaction mixture was added 1-amino-1-cyclopropanecarbonitrile hydrochloride (90 mg, 0.76 mmol) in an ice-water bath and stirred until the solid dissolved. The solvent was removed by rotary evaporation at room temperature and dried by an oil pump for 15 min. The residue was combined with a small amount of dry 3 A molecular sieve and DMF (3 mL), then was added triethylamine (0.022 mL, 0.16 mmol) and NCS (61 mg, 0.46 mmol) in an ice-water bath. The reaction mixture was stirred in an ice-water bath for 1 hour. The reaction mixture was diluted with ethyl acetate, washed once with diluted sodium bisulfite solution, washed once with water, and the washing solution was reverse extracted once with ethyl acetate. The organic phases were combined, washed with brine, dried over anhydrous sodium sulfate, filtered and the filtrate was evaporated to give 18-a (90 mg, 94%). LC-MS (ESI): m/z 635.3 (M+H)$^+$.

Synthesis of Compound 18

A reaction vial was charged with 18-a (90 mg, 0.14 mmol) and dichloromethane (3 mL). Trifluoroacetic acid (1 mL) was added dropwise while cooling in an ice-water bath. The reaction mixture was protected by nitrogen in an ice-water bath for 1 hour. Removed the solvent at room temperature, dilute with ethyl acetate, wash with water, wash with brine, dried over anhydrous sodium sulfate, filter and concentrated to dryness. The crude product was purified by column chromatography (mobile phase: dichloromethane/methanol, 100/0 to 96/4) to give 18 (24.4 mg, 31%) on column purification (C8 column, mobile phase: 10 mM ammonium bicarbonate water/acetonitrile). LC-MS(ESI): m/z 551.2 (M+H)$^+$; $^1$H NMR (DMSO-d$_6$, 400 MHz) δ 9.07 (1H, bs), 8.53 (1H, d, J=1.6 Hz), 7.69 (1H, t, J=53.2 Hz), 7.26 (1H, s), 3.84-3.74 (4H, m), 3.28-3.16 (4H, m), 3.05-2.90 (1H, m), 1.44-1.37 (2H, m), 1.33-1.28 (2H, m), 1.05 (6H, d, J=6.7 Hz).

Example 19 Synthetic Route of Compound 19

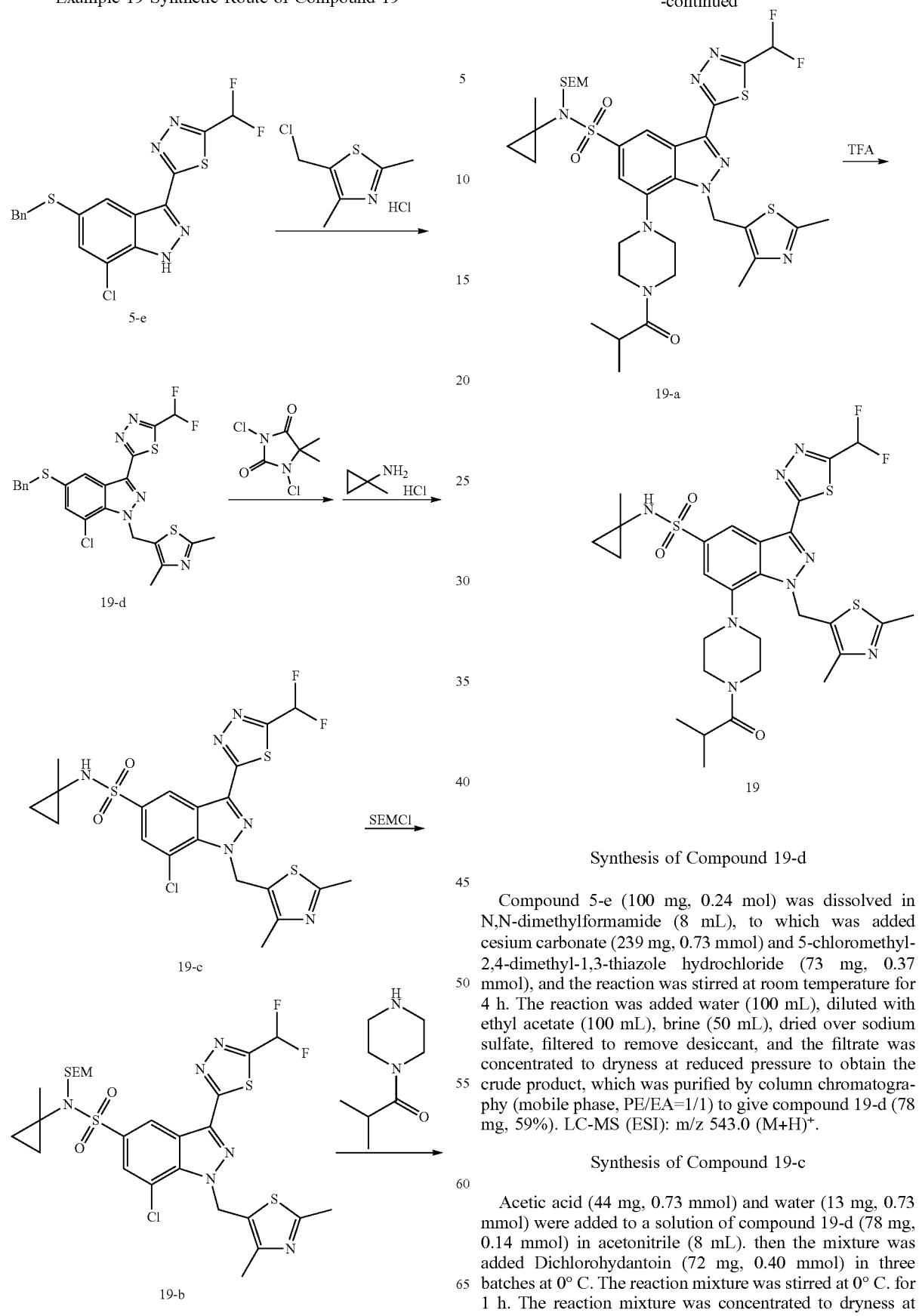

Synthesis of Compound 19-d

Compound 5-e (100 mg, 0.24 mol) was dissolved in N,N-dimethylformamide (8 mL), to which was added cesium carbonate (239 mg, 0.73 mmol) and 5-chloromethyl-2,4-dimethyl-1,3-thiazole hydrochloride (73 mg, 0.37 mmol), and the reaction was stirred at room temperature for 4 h. The reaction was added water (100 mL), diluted with ethyl acetate (100 mL), brine (50 mL), dried over sodium sulfate, filtered to remove desiccant, and the filtrate was concentrated to dryness at reduced pressure to obtain the crude product, which was purified by column chromatography (mobile phase, PE/EA=1/1) to give compound 19-d (78 mg, 59%). LC-MS (ESI): m/z 543.0 (M+H)$^+$.

Synthesis of Compound 19-c

Acetic acid (44 mg, 0.73 mmol) and water (13 mg, 0.73 mmol) were added to a solution of compound 19-d (78 mg, 0.14 mmol) in acetonitrile (8 mL). then the mixture was added Dichlorohydantoin (72 mg, 0.40 mmol) in three batches at 0° C. The reaction mixture was stirred at 0° C. for 1 h. The reaction mixture was concentrated to dryness at reduced pressure at room temperature to obtain the crude product, which was combined with 1-methylcyclopropylamine hydrochloride (31 mg, 0.29 mmol) in dichloromethane (8 mL) and was added diisopropylethylamine (94 mg, 0.73 mmol), then stirred under nitrogen atmosphere at room temperature for 2 h. The reaction mixture was then concentrated to dryness at reduced pressure to obtain the crude product, which was purified by column chromatography (mobile phase, PE/EA=1/1) to give compound 19-c (40 mg, 50%). LC-MS (ESI): m/z 545.0 (M+H)⁺.

Synthesis of Compound 19-b

A solution of compound 19-c (40 mg, 0.07 mmol) in tetrahydrofuran (5 mL) was degassed and purged with nitrogen, then was added sodium hydrogen (15 mg, 0.37 mmol) and 2-(trimethylsilyl)ethoxymethyl chloride (18 mg, 0.11 mmol) sequentially under nitrogen atmosphere at 0° C. After addition, the mixture was stirred at 0° C. for 30 min, and then was added dry ice (5 g) in batches at 0° C. and stirred for 10 min. The reaction mixture was concentrated at reduced pressure to obtain the crude product, which was purified by column chromatography (mobile phase, PE/EA=3/1) to give compound 19-b (40 mg, 80%). LC-MS (ESI): m/z 675.3 (M+H)⁺.

Synthesis of Compound 19-a

Compound 19-b (40 mg, 0.06 mmol), 2-dicyclohexylphosphino-2',6'-diisopropoxy-1,1'-biphenyl (8 mg, 0.02 mmol), (2-dicyclohexylphosphino-2',6'-diisopropoxy-1,1'-biphenylyl)(2-amino-1,1'-biphenyl-2-yl)palladium(II) methanesulfonate (7 mg, 0.01 mmol), cesium carbonate (19 mg, 0.06 mmol), 2-methyl-1-(piperazin-1-yl)prop-1-one (14 mg, 0.09 mmol) were added to 1,4-dioxane (3 mL), replaced with nitrogen for 2 min and then the tube was sealed and heated at 85° C. and stirred for 10 h. The reaction mixture was cooled to room temperature and the crude product was purified by column chromatography (mobile phase, PE/EA=1/1 to DCM/EA=1/1) to give compound 19-a (10 mg, 21%). LC-MS (ESI): m/z 795.7 (M+H)⁺.

Synthesis of Compound 19

Compound 19-a (45 mg, 0.06 mmol) was dissolved in dichloromethane (7 mL), to which trifluoroacetic acid (2.5 mL) was added and the reaction was stirred for 2 h at room temperature. The reaction mixture was removed dichloromethane by rotary evaporation and the pH was adjusted to 8 with saturated sodium bicarbonate solution, water (30 mL) was added, extracted with ethyl acetate (100 mL), and the crude product was obtained by rotary evaporation at reduced pressure. The crude product was purified by TLC (unfolding agent, DCM/MeOH 10/1) and then purified by preparative HPLC (basic conditions) to obtain compound 19 (8 mg, 21%) MS (ESI): m/z 665.3 (M+H)⁺.

Example 20 Synthesis of Compound 20

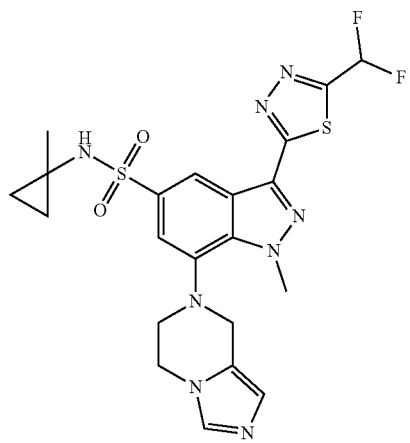

Referring to the synthesis of compound 5, compound 20 was synthesized using 5-b as the starting reactant and 5,6,7,8-tetrahydroimidazo-1,5-pyrazine instead of 2-methyl-1-(piperazin-1-yl)prop-1-one. LC-MS (ESI): m/z 521.1 (M+H)⁺.

Example 21 Synthetic Route of Compound 21

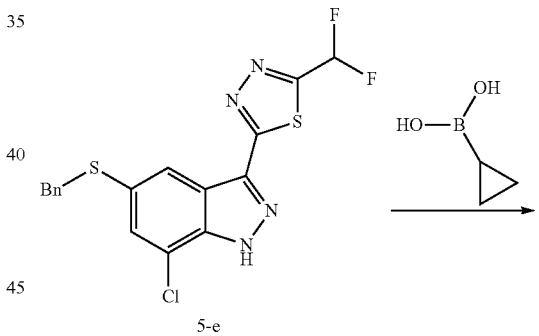

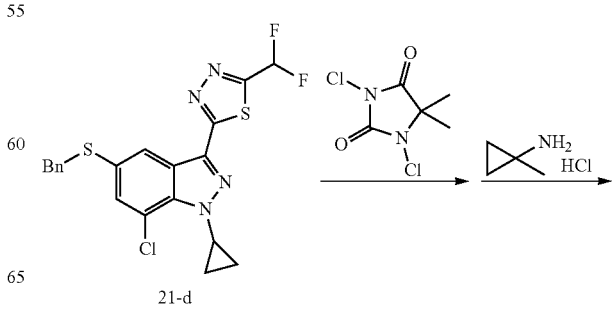

171
-continued

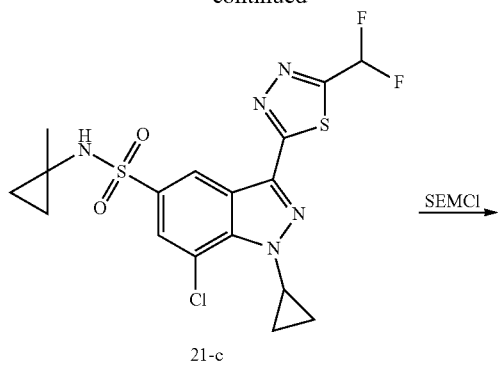

21-c

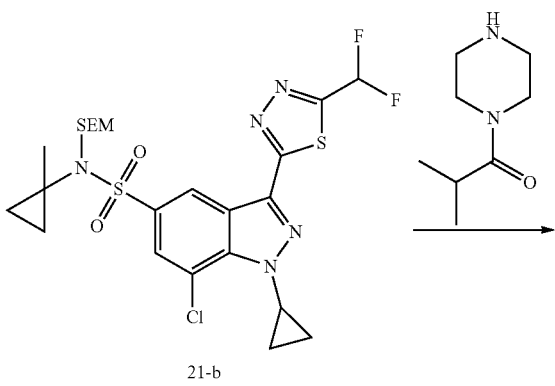

21-b

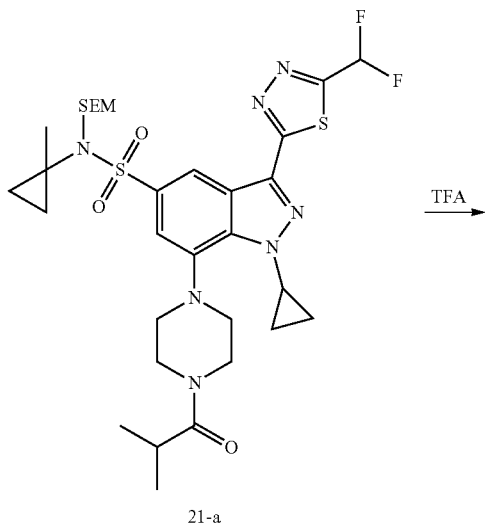

21-a

172
-continued

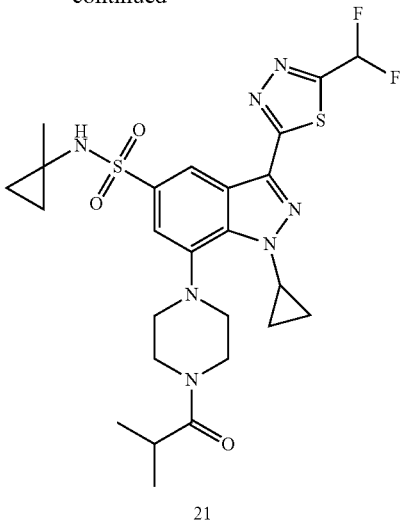

21

Synthesis of Compound 21-d

Compound 5-c (250 mg, 0.61 mmol), cyclopropylboronic acid (131 mg, 1.53 mmol), copper acetate (122 mg, 0.61 mmol), 2,2'-bipyridine (96 mg, 0.61 mmol), sodium carbonate (130 mg, 1.22 mmol) were dissolved in 1,2-dichloroethane (15 mL). After stirring for 2 hours at 70° C. in air, the reaction mixture was cooled to room temperature, filtered through celite, and the filtrate was concentrated at reduced pressure to obtain the residue, which was added saturated ammonium chloride solution (10 mL), water (100 mL), extracted with ethyl acetate (150 mL), washed with brine (100 mL), dried over sodium sulfate, filtered to remove the desiccant, concentrated at reduced pressure to give the crude product, which was purified by column chromatography (mobile phase, PE/EA=3/1) to obtain compound 21-d (200 mg, 73%). LC-MS (ESI): m/z 449.0 $(M+H)^+$.

Synthesis of Compound 21-c

Compound 21-d (230 mg, 0.51 mmol) was dissolved in acetonitrile (20 mL), to which was added acetic acid (92 mg, 1.54 mmol) and water (28 mg, 1.54 mmol). Then cooled down to 0° C., the reaction mixture was added 1,3-dichloro-5,5-dimethylimidazolidine-2,4-dione (202 mg, 1.03 mmol) in three batches and stirred at 0° C. for 1 h, then concentrated by rotary evaporation at room temperature to give the crude product, which was combined with 1-methylcyclopropylamine hydrochloride (110 mg, 1.03 mmol) and dichloromethane (20 mL) and the resulting mixture was added diisopropylethylamine (529 mg, 4.10 mmol), and the reaction mixture was stirred at room temperature under nitrogen atmosphere for 2 h. The crude product was purified by column chromatography (mobile phase, DCM/EA 10/1) to obtain compound 21-c (180 mg, 76%). LC-MS (ESI): m/z 460.0 $(M+H)^+$.

Synthesis of Compound 21-b

Sodium hydrogen (63 mg, 1.57 mmol) and 2-(trimethylsilyl)ethoxymethyl chloride (131 mg, 0.78 mmol) were added to a solution of compound 21-c (180 mg, 0.39 mmol) in N,N-dimethylformamide (6 mL) and tetrahydrofuran (6 mL) at 0° C. under nitrogen atmosphere. After addition, the reaction mixture was stirred at 0° C. for 30 min, then was added dry ice (5 g) in batches at 0° C. and stirred for 10 min. The mixture was concentrated to dryness at reduced pressure to obtain the crude product, which was purified by column chromatography (mobile phase, PE/EA=3/1) to give compound 21-b (220 mg, 95%). LC-MS (ESI): m/z 590.1 (M+H)⁺.

Synthesis of Compound 21-a

Compound 21-b (100 mg, 0.17 mmol), 2-dicyclohexylphosphino-2',6'-diisopropoxy-1,1'-biphenyl (32 mg, 0.07 mmol), (2-dicyclohexylphosphino-2',6'-diisopropoxy-1,1'-biphenylyl)(2-amino-1,1'-biphenyl-2-yl)palladium(II) methanesulfonate (29 mg, 0.03 mmol), cesium carbonate (166 mg, 0.51 mmol) was added to 1,4-dioxane (10 mL) followed by the addition of 2-methyl-1-(piperazin-1-yl)prop-1-one (53 mg, 0.34 mmol). The mixture was degassed and purged with nitrogen for 10 times and then stirred at 78° C. in a sealed tube for 2 hours. The reaction mixture was cooled to room temperature and the crude product was purified by column chromatography (mobile phase, PE/EA=3/1 to DCM/EA=10/1) to give compound 21-a (75 mg, 62%). LC-MS (ESI): m/z 710.3 (M+H)⁺.

Synthesis of Compound 21

Compound 21-a (90 mg, 0.13 mmol) was dissolved in dichloromethane (4 mL) and was added trifluoroacetic acid (2 mL) at 0° C. The reaction was stirred at room temperature for 2 h. The reaction mixture was removed dichloromethane by rotary evaporation and the pH was adjusted to 8 with saturated sodium bicarbonate solution, extracted with ethyl acetate (100 mL), and the crude product was obtained by rotary evaporation at reduced pressure, and the crude product was purified by TLC (unfolding agent, DCM/MeOH 10/1) to obtain the crude product and then purified by HPLC (basic conditions) to obtain compound 21 (23 mg, 31%). LC-MS (ESI): m/z 580.2 (M+H)⁺; ¹H NMR (400 MHz, DMSO-d₆): δ 8.57 (s, 1H), 8.16 (s, 1H), 7.69 (t, J=56.0 Hz, 1H), 7.55 (s, 1H), 4.85-4.76 (m, 1H), 4.65-4.40 (m, 1H), 4.19-3.94 (m, 1H), 3.56-3.46 (m, 2H), 3.02-2.93 (m, 2H), 2.87-2.64 (m, 2H), 1.45-1.38 (m, 2H), 1.28-1.21 (m, 3H), 1.08-1.02 (m, 9H), 0.65-0.61 (m, 2H), 0.41-0.36 (m, 2H).

Example 22 Synthetic Route of Compound 22

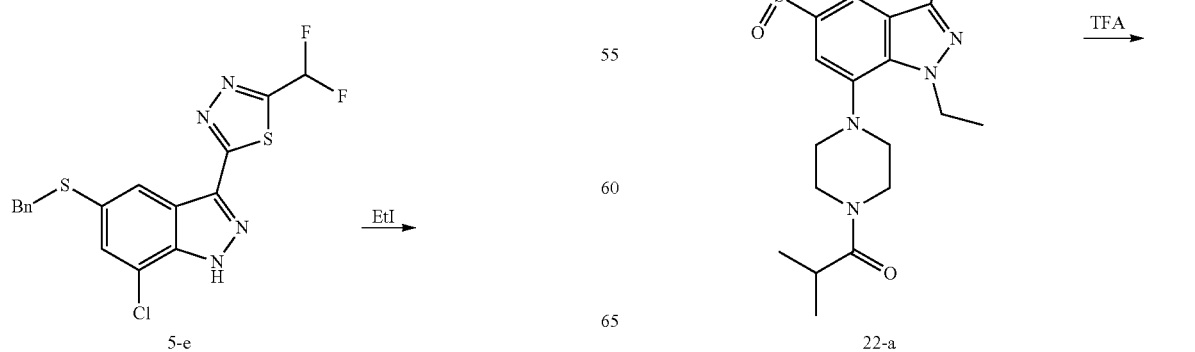

-continued

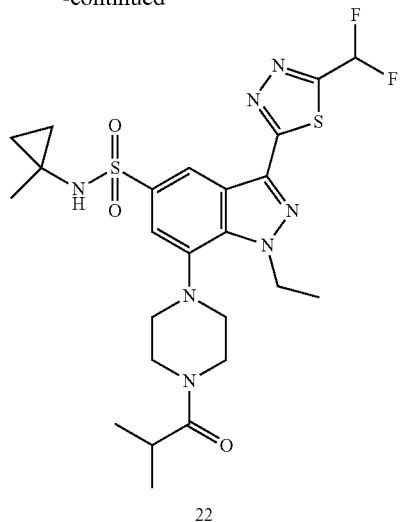

22

Synthesis of Compound 22-d

Compound 5-e (141 mg, 0.34 mmol) was dissolved in N,N-dimethylformamide (4 mL), to which was added iodoethane (0.055 mL, 0.69 mmol) and $Cs_2CO_3$ (338 mg, 1.04 mmol). The reaction was stirred at 40° C. overnight, then was added water (30 mL), extracted with ethyl acetate (50 mL×3), washed with brine (60 mL×6), dried over sodium sulfate, filtered to remove the desiccant, and the filtrate was concentrated at reduced pressure to obtain the crude product, which was purified by column chromatography (mobile phase, PE/EA=20/1) to give compound 22-d (85 mg, 56%). LC-MS (ESI): m/z=437.1 $(M+H)^+$.

Synthesis of Compound 22-c

Acetic acid (0.056 mL, 0.97 mmol) and water (0.018 mL, 0.97 mmol) were added to a solution of compound 22-d (85 mg, 0.20 mmol) in acetonitrile (5 mL) at 0° C., and the resulting mixture was added 1,3-dichloro-5,5-dimethylimidazolidine-2,4-dione (77 mg, 0.40 mmol) in three batches, then stirred at 0° C. for 1 h. The reaction mixture was concentrated at room temperature at reduced pressure to obtain the residue, which was dissolved in DCM (5 mL) and cooled to 0° C., was added slowly a solution of 1-methylcyclopropylamine hydrochloride (43 mg, 0.40 mmol) and diisopropylethylamine (50 μL) dissolved in dichloromethane (1 mL), and finally was added diisopropylethylamine (0.14 mL, 0.76 mmol) and the reaction mixture was stirred at room temperature overnight. The reaction mixture was concentrated at reduced pressure to give the crude product, which was purified by column chromatography (mobile phase, PE/EA=3/1) to give compound 22-c (54 mg, 62%). LC-MS (ESI): m/z=448.0 $(M+H)^+$.

Synthesis of Compound 22-b

A reaction vial charged with 22-c (162 mg, 0.36 mmol) and DMF (4.5 mL) was added cesium carbonate (295 mg, 0.90 mmol) in an ice-water bath. The reaction mixture was stirred in an ice-water bath for 5 min, and then was added SEMCl (79 mg, 0.47 mmol). The reaction mixture was stirred at room temperature for 1 hour, then was added cesium carbonate (118 mg, 0.36 mmol) and SEMCl (39 mg, 0.24 mmol). The reaction mixture was stirred at room temperature for 1 hour, then was diluted with ethyl acetate, washed with water, brine, dried over anhydrous sodium sulfate, filtered and the filtrate was evaporated to give compound 22-b (180 mg, 86%). LC-MS (ESI): m/z 595.0 $(M+NH_4)^+$.

Synthesis of Compound 22-a

To a microwave tube charged with RuPhos (19 mg, 0.041 mmol), RuPhos Pd G3 (17 mg, 0.020 mmol), and cesium carbonate (135 mg, 0.41 mmol) was added a solution of 22-b (80 mg, 0.14 mmol) in 1,4-dioxane (4 mL) solution by syringe. Degassed and purged with nitrogen twice, the resulting mixture was added a solution of 2-methyl-1-(piperazin-1-yl)propan-1-one (64 mg, 0.41 mmol) in 1,4-dioxane (4 mL) by syringe. Degassed and purged with nitrogen twice, the reaction was heated at 70-75° C. for 4 hours. Cooled to room temperature. To another microwave tube charged with RuPhos (19 mg, 0.041 mmol), RuPhos Pd G3 (17 mg, 0.020 mmol), and cesium carbonate (135 mg, 0.41 mmol) was added a solution of 22-b (80 mg, 0.14 mmol) in 1,4-dioxane (4 mL) by syringe. Degassed and purged with nitrogen twice, the resulting mixture was added a solution of 2-methyl-1-(piperazin-1-yl) propan-1-one (64 mg, 0.41 mmol) in 1,4-dioxane (4 mL) by syringe. Degassed and purged with nitrogen twice, the reaction was heated at 60° C. for 4 hours. Cooled to room temperature, combined with the first reaction mixture, removed the solvent, diluted with ethyl acetate, washed with water, brine, dried over anhydrous sodium sulfate, filtered and the filtrate was evaporated and the residue was purified by column chromatography (silica, mobile phase (petroleum ether/dichloromethane (4:1))/ethyl acetate 0%-70%) to give 22-a (64 mg, 33%). LC-MS (ESI): m/z 715.4 $(M+NH_4)^+$.

Synthesis of Compound 22

A reaction vial charged with 22-a (64 mg, 0.092 mmol) was added dichloromethane (1.5 mL) and trifluoroacetic acid (0.5 mL) in an ice-water bath. The reaction mixture was stirred in an ice-water bath for 10 minutes and then at room temperature for 2 hours. Removed the solvent by rotary evaporation, diluted with ethyl acetate, washed once with saturated sodium bicarbonate solution and once with brine, dried over anhydrous sodium sulfate, filtered and the filtrate was evaporated and the crude product was purified by column chromatography (C8 column, mobile phase: 10 mM aqueous ammonium bicarbonate solution, acetonitrile) to give 22 (20 mg, 38%). LC-MS(ESI): m/z 568.2 $(M+H)^+$. $^1H$ NMR (DMSO-$d_6$, 400 MHz): δ 8.62 (1H, d, J=1.6 Hz), 8.15 (1H, s), 7.86-7.55 (2H, m), 4.95-4.79 (2H, m), 4.55 (1H, d, J=12.8 Hz), 4.14 (1H, d, J=13.2 Hz), 3.52-3.41 (1H, m), 3.33-3.25 (2H, m), 3.04-2.91 (2H, m), 2.91-2.81 (1H, m), 2.79-2.67 (1H, m), 1.53 (3H, t, J=7.2 Hz), 1.11-1.03 (6H, m), 1.03 (3H, s), 0.66-0.60 (2H, m), 0.45-0.35 (2H, m).

Example 23 Synthetic Route of Compound 23

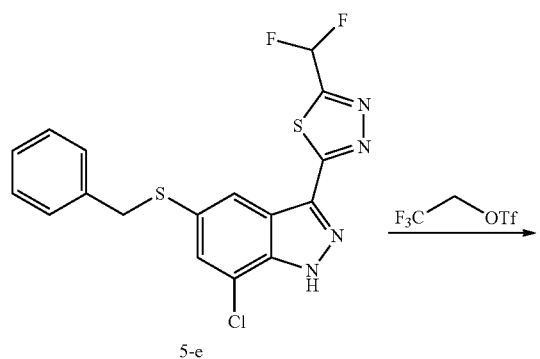

5-e

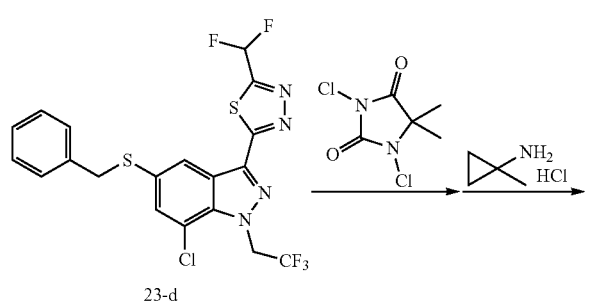

23-d

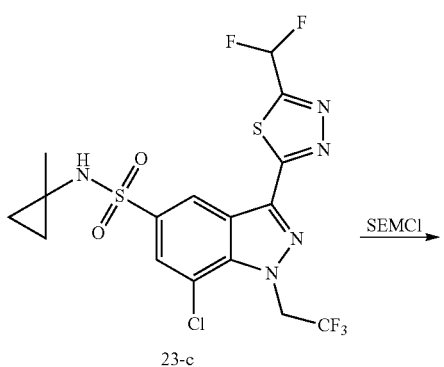

23-c

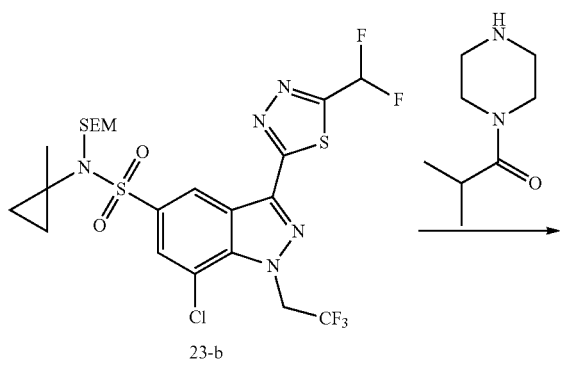

23-b

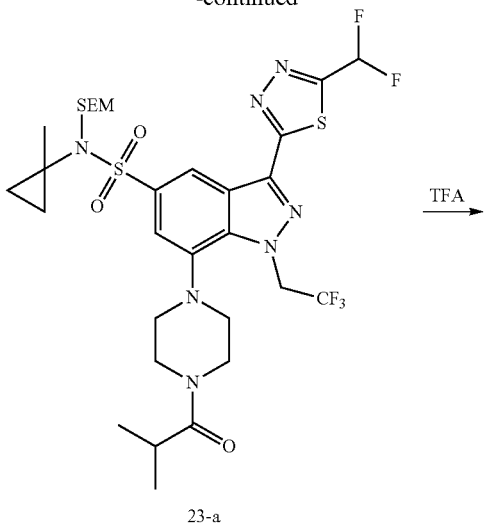

23-a

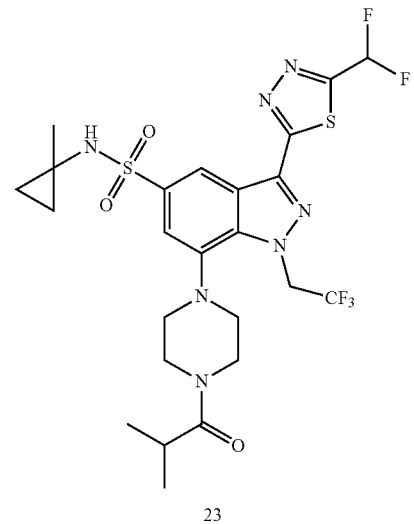

23

Synthesis of Compound 23-d

Potassium carbonate (101 mg, 0.73 mmol) and 2,2,2-trifluoroethyl trifluoromethanesulfonate (0.14 m, 0.98 mmol) were added to a solution of 5-e (200 mg, 0.49 mmol) in DMF (5 mL) at room temperature. After addition, the reaction were stirred at room temperature for 2 hours. After completion, the reaction was diluted by adding ethyl acetate, washed with water, brine, dried over anhydrous sodium sulfate, filtered and the filtrate was evaporated to dryness. The compound 23-d (200 mg, 83%) was obtained by a flash column chromatography (mobile phase: ethyl acetate/petroleum ether 0% to 50%). LC-MS (ESI): m/z=491.0 [M+H]+.

Synthesis of Compound 23-c

To a solution of acetonitrile (5 m) of 23-d (200 mg, 0.41 mmol) was added acetic acid (0.093 mL, 1.63 mmol) and $H_2$ (0.030 mL, 1.67 mmol). The mixture was carefully added 1,3-dichloro-5,5-dimethylimidazolidine-2,4-dione (161 mg, 0.82 mmol) at 0° C. After addition, the reaction was stirred at 0° C. for 1 hr. After completion, the reaction was concentrated at reduced pressure at room temperature and dried by an oil pump for 30 min to obtain the crude sulfonyl chloride compound. This crude product was dissolved in DCM (10 mL), was added 1-methylcyclopropylamine hydrochloride (66 mg, 0.61 mmol) and triethylamine (0.28 mL, 2.04 mmol) at 0° C. The reaction mixture was warmed to room temperature and stirred for half an hour. After completion, the reaction was diluted with dichloromethane and water. The organic phase was separated and the aqueous phase was extracted with dichloromethane. The organic phases were combined, washed with water, brine, dried over anhydrous Na₂SO₄, filtered and the filtrate was evaporated to give the crude product, which was purified by a flash column chromatography (mobile phase: ethyl acetate/petroleum ether 0% to 100%) to give 23-c (150 mg, 73%). LC-MS (ESI): m/z=502.0 [M+H]⁺.

Synthesis of Compound 23-b

Sodium hydrogen (48 mg, 1.20 mmol) and 2-(trimethylsilyl)ethoxymethyl chloride (100 mg, 0.60 mmol) were added to a solution of compound 23-c (150 mg, 0.3 mmol) in N,N-dimethylformamide (5 mL) and tetrahydrofuran (5 mL) at 0° C. under nitrogen atmosphere. After addition, the reaction mixture was stirred at 0° C. for 30 min, then was added 5 g of dry ice in batches at 0° C. and stirred for 10 min, and the mixture was concentrated at reduced pressure to obtain the crude product, which was purified by column chromatography (mobile phase, PE/EA=10/1) to obtain compound 23-b (148 mg, 78%).

Synthesis of Compound 23-a

2-Methyl-1-(piperazin-1-yl)prop-1-one (55 mg, 0.35 mmol) was added to a solution of compound 23-b (112 mg, 0.18 mmol), 2-dicyclohexylphosphino-2',6'-diisopropoxy-1,1'-biphenyl (33 mg, 0.07 mmol), (2-dicyclohexylphosphino-2',6'-diisopropoxy-1,1'-biphenylyl)(2-amino-1,1'-biphenyl-2-yl)palladium(II) methanesulfonate (30 mg, 0.04 mmol), cesium carbonate (173 mg, 0.53 mmol) in 1,4-dioxane (12 mL), then degassed and purged with nitrogen for 10 times and then the reaction was stirred at 67° C. in a sealed tube for 8 hours. The reaction mixture was cooled to room temperature and concentrated at reduced pressure to give the crude product, which was purified by column chromatography (mobile phase, PE/EA=3/1 to 1/1) to give compound 23-a (31 mg, 24%). LC-MS (ESI): m/z 752.1 (M+H)⁺.

Synthesis of Compound 23

Trifluoroacetic acid (1 mL) was added to a solution of compound 23-a (40 mg, 0.05 mmol) in dichloromethane (3 mL) at 0° C. The reaction was stirred for 2 h at room temperature. The reaction mixture was removed dichloromethane by rotary evaporation, adjusted to pH 8 with saturated sodium bicarbonate solution, extracted with ethyl acetate (100 mL), washed with brine (50 mL), dried over sodium sulfate, filtered out desiccant, and the filtrate was concentrated to obtain the crude product, which was purified by preparative HPLC (basic conditions) to give compound 23 (15 mg, 45%). LC-MS (ESI): m/z 622.1 (M+H)⁺; ¹HNMR (400 MHz, DMSO-d₆): δ 8.72 (s, 1H), 8.18 (s, 1H), 7.91 (s, 1H), 7.72 (t, J=56.0 Hz, 1H), 5.87-5.76 (m, 2H), 4.57 (d, J=12.0 Hz, 1H), 4.16 (d, J=12.0 Hz, 1H), 3.45-3.35 (m, 1H), 3.17 (d, J=8.0 Hz, 2H), 2.99-2.75 (m, 4H), 1.10-0.99 (m, 9H), 0.69-0.60 (m, 2H), 0.42-0.37 (m, 2H).

Example 24 Synthetic Route of Compound 24

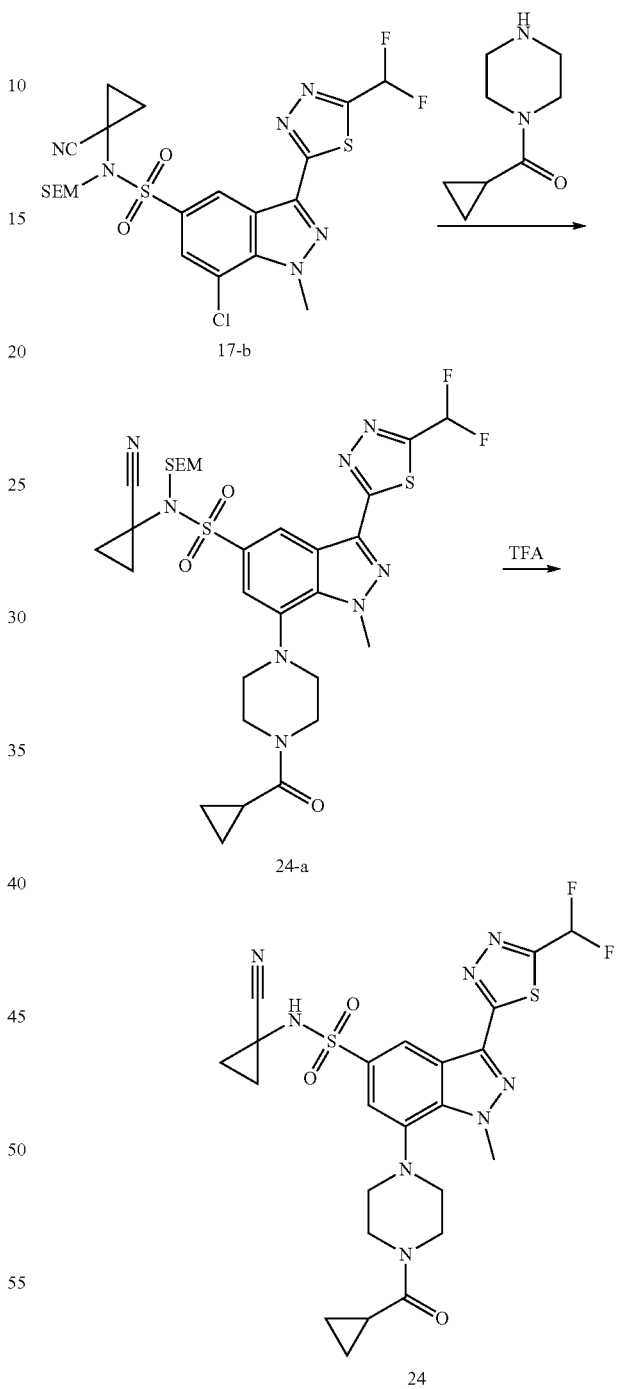

Synthesis of Compound 24-a

Compound 17-b (100 mg, 0.17 mmol), 2-dicyclohexylphosphino-2',6'-diisopropoxy-1,1'-biphenyl (32 mg, 0.07 mmol), (2-dicyclohexylphosphino-2',6'-diisopropoxy-1,1'-biphenyl)(2-amino-1,1'-biphenyl-2-yl)palladium(II) (29 mg, 0.04 mmol), methanesulfonic acid (2-dicyclohexylphosphino-2',6'-diisopropoxy-1,1-biphenyl) (2-Amino-1,1'-biphenyl-2-yl), 0.04 mmol), cesium carbonate (170 mg, 0.52 mmol) were mixed with 1,4-dioxane (10 mL) and the resulting mixture was stirred at room temperature for 5 min before adding cyclopropyl(piperazin-1-yl)methyl ketone (54 mg, 0.35 mmol). After degassed and purged with nitrogen for 12 times, the reaction was stirred at 62° C. in a sealed tube for 12 hours. Cooled to room temperature, the reaction mixture was filtered through celite, and the filtrate was concentrated at reduced pressure to obtain the crude product, which was purified by column chromatography (mobile phase, PE/EA=3/1 to DCM/EA 3/1) to give compound 24-a (105 mg, 87%). LC-MS (ESI): m/z 1385.6 (2M+H)$^+$.

Synthesis of Compound 24

Trifluoroacetic acid (1.5 mL) was added to a solution of compound 24-a (145 mg, 0.21 mmol) in dichloromethane (4.5 mL) at 0° C. The reaction was stirred for 2 h at room temperature, then removed dichloromethane by concentration and the pH was adjusted to 7-8 with saturated sodium bicarbonate solution, extracted with ethyl acetate (100 mL), washed with brine (100 mL), dried over sodium sulfate, filtered out desiccant, and the filtrate was concentrated at reduced pressure to obtain the crude product, which was purified by HPLC (basic conditions) to give compound 24 (35 mg, 30%). LC-MS (ESI): m/z 563.1 (M+H)$^+$; $^1$H NMR (400 MHz, DMSO-$d_6$): δ 9.18 (s, 1H), 8.65 (s, 1H), 7.71 (t, J=52.0 Hz, 1H), 7.58 (s, 1H), 4.52 (s, 3H), 4.45-4.35 (m, 1H), 3.62-3.47 (m, 2H), 3.09-2.68 (m, 3H), 2.58-2.50 (m, 2H), 1.46-1.22 (m, 5H), 0.80-0.74 (m, 4H).

Example 25 Synthetic Route of Compound 25

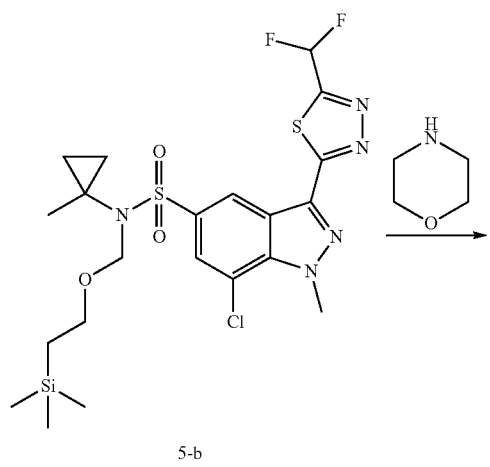

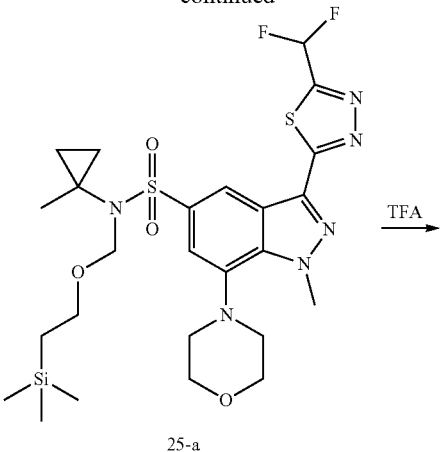

Synthesis of Compound 25-a

A microwave tube charged with 5-b (30 mg, 0.053 mmol), morpholine (14 mg, 0.088 mmol), Xantphos (6.13 mg, 0.011 mmol), Pd$_2$dba$_3$ (4.85 mg, 0.005 mmol), cesium carbonate (52 mg, 0.16 mmol) and 1,4-dioxane (3 mL) was degassed and purged with nitrogen for 3 times. The reaction mixture was heated at 85° C. overnight. After completion, the reaction was cooled to room temperature, removed 1,4-dioxane by rotary evaporation, diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether 0% to 100%) to give compound 25-a (25 mg, 76%). LC-MS (ESI): m/z 1251.6 (2M+Na)$^+$.

Synthesis of Compound 25

A reaction flask charged with 25-a (25 mg, 0.041 mmol) and dichloromethane (5 mL) was added trifluoroacetic acid (1 mL) dropwise at room temperature. The reaction mixture was stirred at room temperature for 5 h. The solvent was removed by concentration at room temperature. The residue was added ethyl acetate to dilute, washed by saturated sodium bicarbonate, brine, dried over anhydrous sodium sulfate, filtered and the filtrate was evaporated to obtain the crude product, which was purified by Prep-HPLC to give compound 25 (8 mg, 41%). LC-MS (ESI): m/z 485.0

(M+H)+; 1H NMR (DMSO-d6, 400 MHz): δ 8.58 (1H, d, J=1.6 Hz), 7.70 (1H, t, J=52.8 Hz), 7.55 (1H, d, J=1.2 Hz), 4.49 (3H, s), 3.75-4.11 (4H, m), 2.80-3.29 (4H, m), 1.03 (3H, s), 0.58-0.66 (2H, m), 0.34-0.41 (2H, m).
Example 26 Synthetic Route of Compound 26
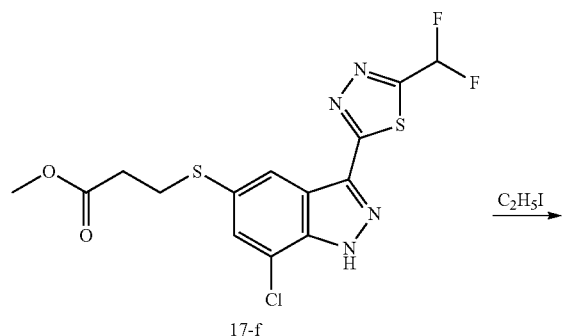
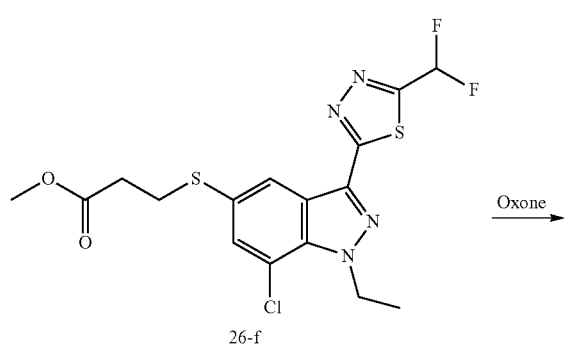
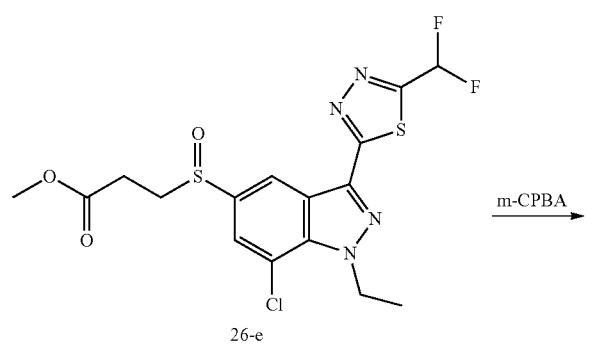
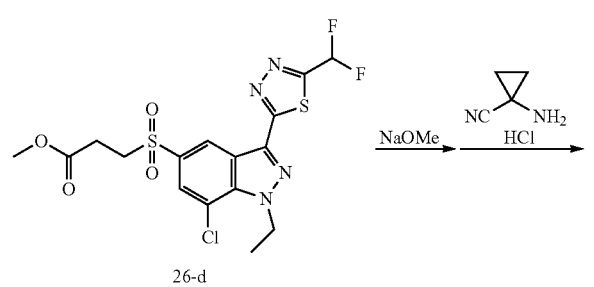
-continued
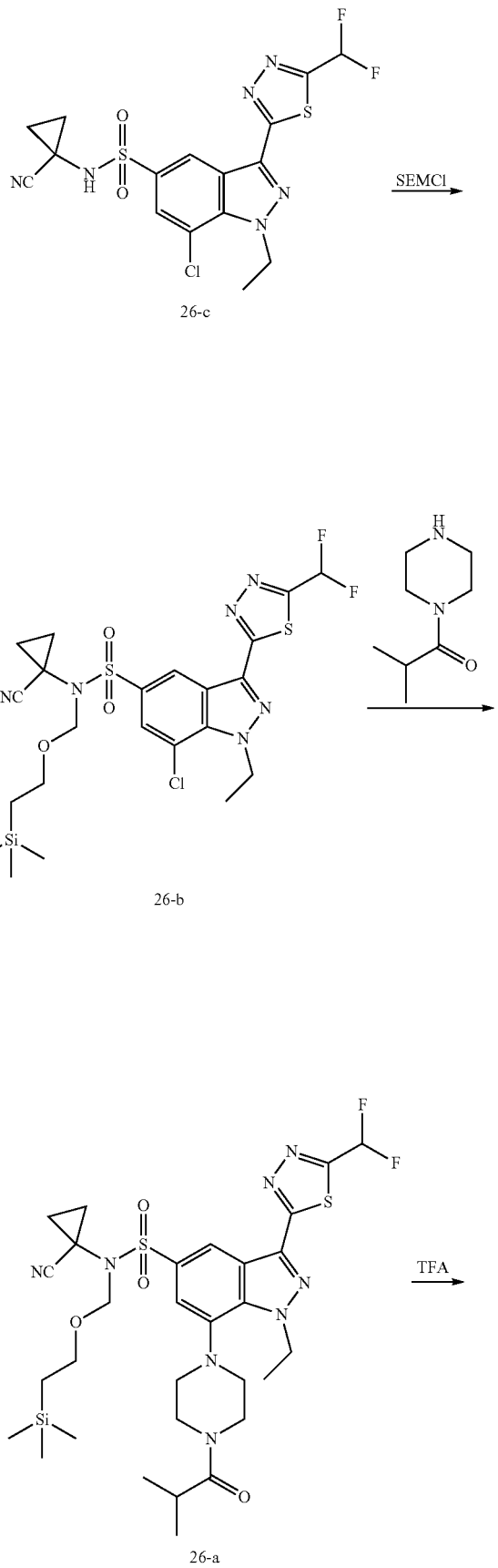

-continued

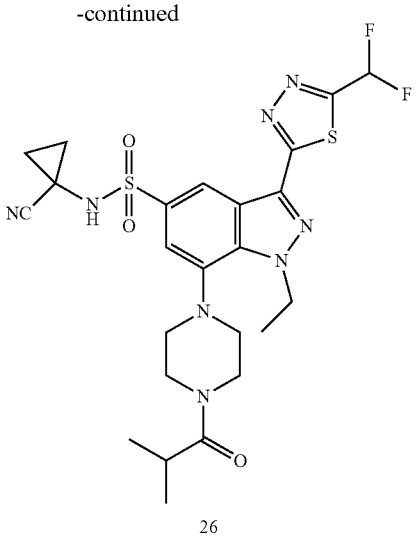

26

Synthesis of Compound 26-f

Cesium carbonate (385 mg, 1.18 mmol) was added to a reaction flask charged with 17-f (160 mg, 0.40 mmol) and DMF (3 mL) in an ice-water bath, then was added ethyl iodide (120 mg, 0.77 mmol) dropwise after stirred for 5 min. The reaction mixture was stirred at room temperature for 2 hours. The organic phase was washed with brine, dried over anhydrous sodium sulfate, filtered and the filtrate was evaporated to give 26-f (171 mg, 100%). LC-MS (ESI): m/z 432.9 (M+H)$^+$.

Synthesis of Compound 26-e

A solution of Oxone (729 mg, 1.19 mmol) in water (7 mL) was added dropwise to a reaction vial charged with 26-f (171 mg, 0.40 mmol) and acetonitrile (7 mL) in an ice-water bath. The reaction mixture was stirred in an ice-water bath for 1 hour. The solution was extracted twice with ethyl acetate, washed with brine, dried over anhydrous sodium sulfate, filtered and the filtrate was evaporated to obtain 26-e (177 mg, 99%).

Synthesis of Compound 26-d

To a solution of 26-e (200 mg, 0.45 mmol) in dichloromethane (10 mL) in an ice-water bath was added m-CPBA (231 mg, 1.34 mmol). After addition, kept at 0° C., the reaction was and stirred for 1 hour. After completion, 26-d (150 mg, 72%) was obtained by rotary evaporation at room temperature. LC-MS (ESI): m/z=929.0 [2M+H]$^+$.

Synthesis of Compound 26-c

Sodium methanol (52 mg, 0.97 mmol) was added to a reaction vial charged with 26-d (150 mg, 0.32 mmol), methanol (10 mL) and dichloromethane (10 mL) at 0° C. in an ice-water bath, and the reaction mixture was stirred in the ice-water bath for 1 h, then was added 1-amino-1-cyclopropanecarbonitrile hydrochloride (153 mg, 1.29 mmol), concentrate at room temperature to remove the solvent, and dried in vacuum for 20 minutes. The residue was combined with DMF (8 mL) and a small amount of 3 A molecular sieve, was added triethylamine (0.09 mL, 0.65 mmol) and 1-amino-1-cyclopropanecarbonitrile hydrochloride (38 mg, 0.32 mmol) after stirring for 3 min in an ice-water bath. Then was added NCS (86 mg, 0.65 mmol) in an ice-water bath. The reaction mixture was stirred in an ice-water bath for 1 hour. The reaction was diluted with ethyl acetate, washed with sodium bisulfite solution, water, and brine, dried over anhydrous sodium sulfate, filtered and the filtrate was evaporated to give 26-c (100 mg, 68%). LC-MS (ESI): m/z=459.0 [M+H]$^+$.

Synthesis of Compound 26-b

Triethylamine (0.12 mL, 0.87 mmol) and SEMCl (0.077 mL, 0.44 mmol) were added to a reaction vial charged with 26-c (100 mg, 0.22 mmol) and DCM (10 mL) in an ice-water bath and the mixture was stirred at room temperature for 1 hr. The reaction was quenched with methanol (0.25 mL) in an ice-water bath and continued stirring for 10 min. After completion, the reaction was removed the solvent by concentration at low temperature and the crude product was purified by column chromatography (mobile phase: ethyl acetate/petroleum ether, 0% to 100%) to give compound 26-b (110 mg, 86%). LC-MS (ESI): m/z=589.0 [M+H]$^+$.

Synthesis of Compound 26-a

A microwave tube charged with 26-b (110 mg, 0.19 mmol), 2-methyl-1-(piperazin-1-yl)propan-1-one (58 mg, 0.37 mmol), Ruphos (35 mg, 0.075 mmol), Ruphos Pd G3 (31 mg, 0.037 mmol), cesium carbonate (183 mg, 0.56 mmol) and 1,4-dioxane (8 mL) with degassed and purged with nitrogen for 3 times. The reaction was heated at 60° C. overnight. After completion, the reaction was cooled to room temperature, removed the 1,4-dioxane by rotary evaporation, diluted with ethyl acetate, washed with water, brine, dried over anhydrous sodium sulfate, filtered and the filtrate was evaporated to obtain the crude product, which was purified by a flash column chromatography (mobile phase: ethyl acetate/(petroleum ether/dichloromethane 4:1), 0% to 100%) to give compound 26-a (110 mg, 83%). LC-MS (ESI): m/z 1417.4 [2M+H]$^+$.

Synthesis of Compound 26

A reaction vial charged with 26-a (110 mg, 0.16 mmol) and dichloromethane (5 mL) was added trifluoroacetic acid (1 mL) dropwise at room temperature. The reaction mixture was stirred at room temperature for 4 h. The solvent was removed by concentration at room temperature. Diluted by adding dichloromethane, washed by saturated sodium bicarbonate, brine, dried over anhydrous sodium sulfate, filtered and the filtrate was evaporated to dryness to obtain the crude product, which was purified by Prep-HPLC to give compound 26 (10 mg, 11%). LC-MS (ESI): m/z 579.1 [M+H]$^+$.

Example 27 Synthetic Route of Compound 27

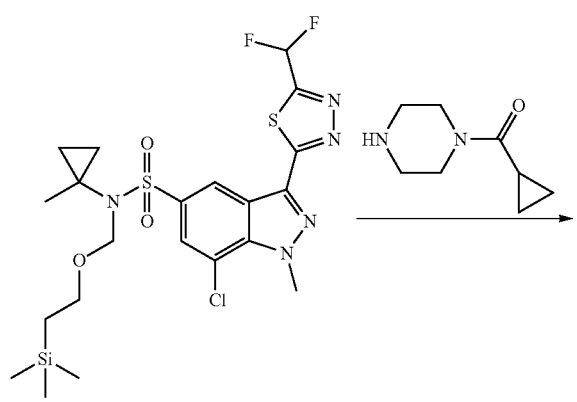

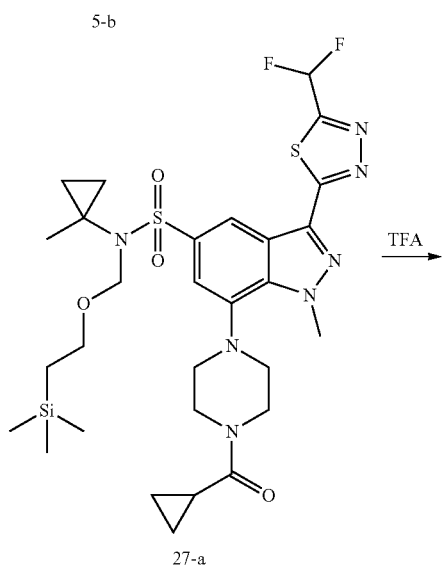

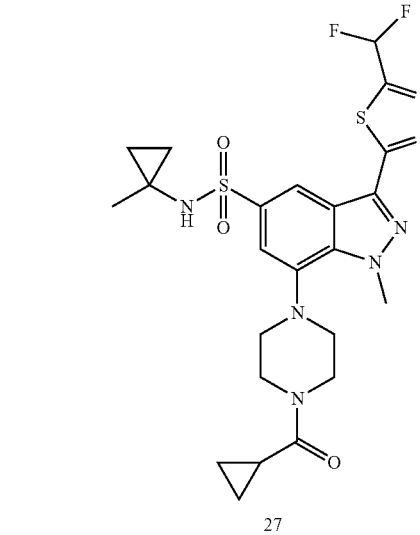

Synthesis of Compound 27-a

A microwave tube charged with 5-b (80 mg, 0.14 mmol), cyclopropyl-piperazin-1-yl-methyl ketone (44 mg, 0.28 mmol), Xantphos (16 mg, 0.028 mmol), Pd₂dba₃ (13 mg, 0.014 mmol), cesium carbonate (139 mg, 0.44 mmol) and 1,4-dioxane (3 mL) was degassed and purged with nitrogen for 3 times. The reaction mixture was heated at 85° C. overnight. After completion, the reaction was cooled to room temperature, removed 1,4-dioxane by rotary evaporation, diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether 0% to 100%) to give compound 27-a (70 mg, 72%). LC-MS (ESI): m/z 704.0 $[M+Na]^+$.

Synthesis of Compound 27

Trifluoroacetic acid (1 mL) was added dropwise to a reaction flask charged with 27-a (70 mg, 0.10 mmol) and dichloromethane (5 mL) at room temperature. The reaction mixture was stirred at room temperature for 4 h. The solvent was removed by concentration at room temperature. Diluted with dichloromethane, washed with saturated sodium bicarbonate, brine, dried over anhydrous sodium sulfate, filtered and the filtration was evaporated to obtain the crude product, which was purified by a flash column chromatography (mobile phase: methanol/dichloromethane 0% to 10%) to give compound 27 (15 mg, 26%). LC-MS (ESI): m/z 552.1 $[M+H]^+$; $^1H$ NMR (DMSO-$d_6$, 400 MHz): δ 8.59 (1H, s), 8.14 (1H, s), 7.70 (1H, t, J=53.2 Hz), 7.57 (1H, s), 4.51 (3H, s), 4.15-4.58 (2H, m), 3.40-3.80 (2H, m), 2.60-3.23 (4H, m), 2.02-2.13 (1H, m), 1.03 (3H, s), 0.71-0.91 (4H, m), 0.58-0.68 (2H, m), 0.34-0.45 (2H, m).

Example 28 Synthetic Route of Compound 28

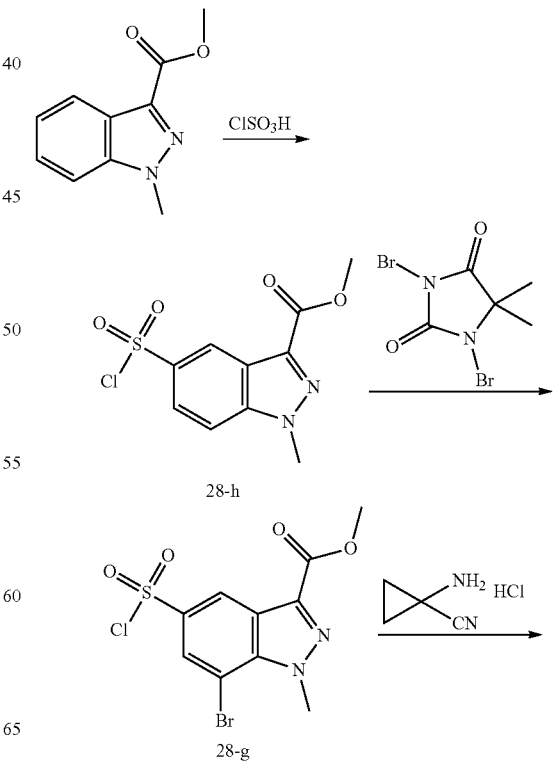

-continued

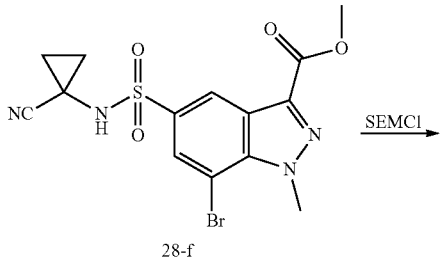

28-f

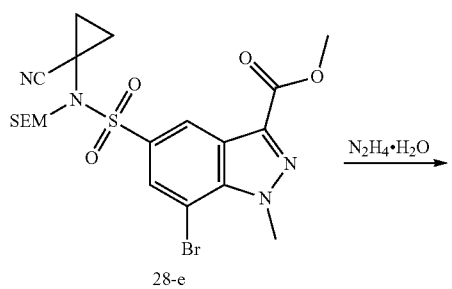

28-e

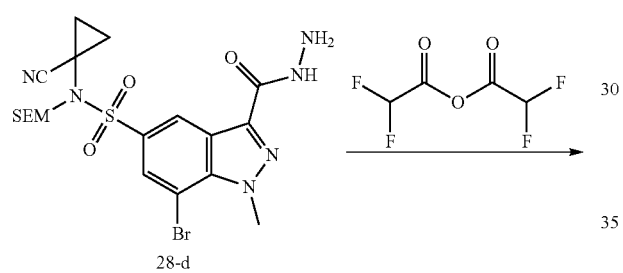

28-d

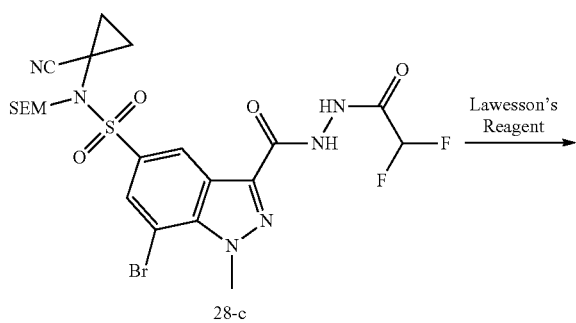

28-c

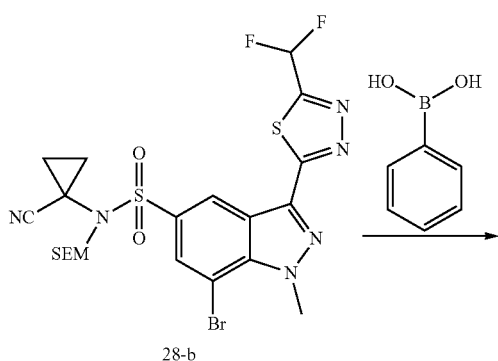

28-b

-continued

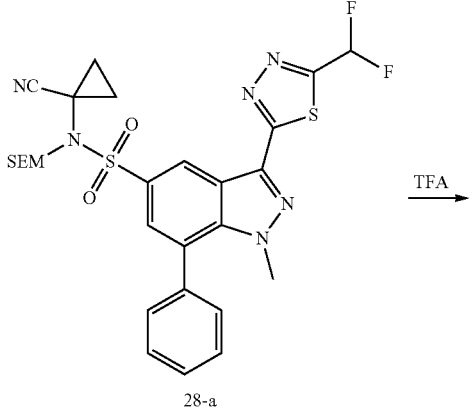

28-a

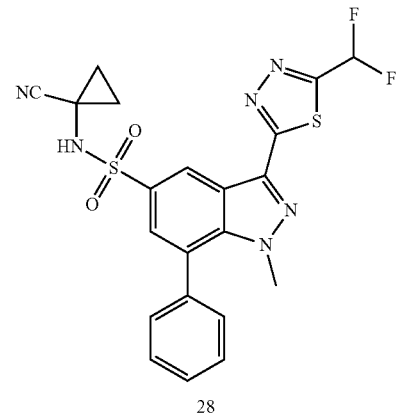

28

Synthesis of Compound 28-h

A reaction flask charged with chlorosulfonic acid (30 mL) was added 1-methyl-3-methoxycarbonylindazole (10 g, 52.58 mmol) in batches over 10 min in an ice-water bath. The reaction was stirred first at room temperature for 5 min, then at 65° C. for 18 hours (an exhaust absorption device was attached). Cooled to room temperature, the reaction mixture was added dropwise to ice (300 g), extracted with ethyl acetate, washed with water, brine, dried over anhydrous sodium sulfate, filter and evaporate to obtain 28-h (13.5 g, 89%).

Synthesis of Compound 28-g

A reaction flask charged with 28-h (13.5 g, 46.76 mmol) and dichloromethane (135 mL) was added dibromohydantoin (13.37 g, 46.76 mmol) in an ice-water bath. The suspension was added trifluoromethanesulfonic acid (5 mL) dropwise, first stirred in an ice-water bath for 10 minutes and then stirred at room temperature for 1.5 hours. The suspension was added trifluoromethanesulfonic acid (5 mL) dropwise and dichloromethane (60 mL). The reaction mixture was stirred at room temperature for 1.5 hours. The reaction mixture was added ice-water, extracted twice with ethyl acetate, washed twice with water, brine, dried over anhydrous sodium sulfate, filtered and the filtrate was evaporated and the residue was purified by column chromatography (mobile phase: petroleum ether/ethyl acetate 100:0-60:40) to obtain the product 28-g (10.1 g, 59%).

Synthesis of Compound 28-f

A reaction vial charged with 1-amino-1-cyclopropanecarbonitrile hydrochloride (7.05 g, 59.46 mmol), pyridine (35 mL) and a small amount of 3 A molecular sieve was stirred for 5 min in an ice-water bath, then was added a solution of 28-g (10.1 g, 27.48 mmol) in dichloromethane (70 mL) containing dried molecular sieve dropwise over 5 min in the ice-water bath. Stirred in an ice-water bath for 10 min and then at room temperature for 2 h, the reaction was removed solvent, was added ice-water and sodium bisulfate solids to pH=6-7, added petroleum ether, filtered, the filter cake was washed with aqueous sodium bisulfate, brine and petroleum ether. The aqueous phase was extracted with ethyl acetate, and the organic phase was washed with water, evaporated to dryness, pulsed with ethyl acetate and petroleum ether, the solids were combined and dried in vacuum to give 28-f (11.3 g, 100%). LC-MS (ESI): m/z 412.9 (M+H)+.

Synthesis of Compound 28-e

A reaction flask charged with 28-f (11.3 g, 27.34 mmol) and dichloromethane (150 mL) was added triethylamine (12.5 mL, 89.93 mmol) in an ice-water bath and stirred for 10 min, then was added SEMCl (8.0 mL, 45.20 mmol) dropwise in an ice-water bath and stirred for 10 min. Stirred in a water bath at room temperature for 1.5 hours, the reaction mixture was removed solvent by rotary evaporation at room temperature, was added water and ethyl acetate, stirred thoroughly and filtered, the filtrate was partitioned, the aqueous phase was extracted once with ethyl acetate, the organic phase were combined, washed with water, brine and evaporated to obtain 28-e (14.8 g, 100%). LC-MS (ESI): m/z 560.1 (M+NH$_4$)+.

Synthesis of Compound 28-d

A reaction flask charged with 28-e (14.8 g, 27.23 mmol), anhydrous ethanol (150 mL) and hydrazine hydrate (10 mL, 206.15 mmol) was stirred at 52° C. for 7 hours. Cooled to room temperature, the reaction mixture was removed solvent by rotary evaporation at room temperature, was added ice-water, extracted with ethyl acetate twice, washed with water, brine, dried over anhydrous sodium sulfate, filtered and the filtrate was evaporated to give 28-d (14.5 g, 98%). LC-MS (ESI): m/z 1084.8 (2M+H)+.

Synthesis of Compound 28-c

A reaction flask charged with 28-d (14.5 g, 26.68 mmol) and dichloromethane (150 mL) was added triethylamine (5.19 mL, 37.35 mmol) dropwise in an ice-water bath. Stirred in an ice-water bath for 5 min, the above mixture was added difluoroacetic anhydride (3.25 mL, 28.01 mmol) dropwise in an ice-water bath. the reaction mixture was stirred in an ice-water bath for 1 hour, then was added methanol (2.5 mL), stirred from ice-water bath to room temperature for 20 min. removed the solvent at room temperature, the reaction mixture was added water and ethyl acetate, partitioned, the aqueous phase was extracted once, the organic phases were combined, wash with water, brine, dried over anhydrous sodium sulfate, filtered, evaporate and the residue was purified by column chromatography (mobile phase: petroleum ether/ethyl acetate, 100/0 to 60/40) to give 28-c (13.2 g, 80%). LC-MS (ESI): m/z 638.0 (M+NH$_4$)+.

Synthesis of Compound 28-b

A reaction flask charged with 28-c (11.3 g, 18.18 mmol), Lawesson's reagent (17.75 g, 43.89 mmol) and THF (200 mL) was stirred directly at 80° C. under argon atmosphere for 10 hours. Cool to room temperature, the reaction was removed the solvent. The crude product was diluted with ethyl acetate/petroleum ether mixture, washed with aqueous sodium bicarbonate for 3 times, washed with brine, dried over anhydrous sodium sulfate, filtered and the filtrate was evaporated to obtain the crude product which was added ammonia-methanol/methanol/dichloromethane (1:1:20) solution (200 mL) and stirred at room temperature for 2 hours. The reaction mixture was concentrated to dryness, then was purified by column chromatography (mobile phase: petroleum ether/ethyl acetate, 100/0 to 70/30) to give 28-b (5.8 g, 51%). LC-MS (ESI): m/z 619.0 (M+H)+.

Synthesis of Compound 28-a

Compound 28-b (30 mg, 0.048 mmol), phenylboronic acid (18 mg, 0.15 mmol), tetrakis(triphenylphosphine)palladium (6 mg, 0.0050 mmol), Cs$_2$CO$_3$ (31 mg, 0.096 mmol) were added into the mixed solvent 1,4-dioxane (5 mL) and water (1 mL) at room temperature, and the reaction mixture was stirred at 100° C. overnight under nitrogen atmosphere. Cooled to room temperature, the reaction mixture was added brine (50 mL), extracted with ethyl acetate (50 mL×3), the organic phases were washed with brine (60 mL×3), dried over anhydrous sodium sulfate, filtered, and concentrated at reduced pressure to obtain the crude product. The crude product was purified by a flash column chromatography (PE/EA=10:1) to give compound 28-a (20 mg, 67%). LC-MS (ESI): m/z=617.1[M+1]+.

Synthesis of Compound 28

Compound 28-a (20 mg, 0.032 mmol) was dissolved in dichloromethane (4 mL), to which trifluoroacetic acid (1 mL) was added and the reaction was stirred at room temperature for 2 h. The reaction mixture was adjusted to pH=8 with saturated sodium bicarbonate solution, was added water (30 mL), extracted with ethyl acetate (50 mL×3), washed with brine (60 mL×3), dried over sodium sulfate, filtered out the desiccant, and concentrated at reduced pressure to give the crude product, which was purified by Prep-TLC (DCM:MeOH=20:1) to give compound 28 (5 mg, 32%). LC-MS (ESI): m/z=487.0 [M+1]+.

Example 29 Synthetic Route of Compound 29

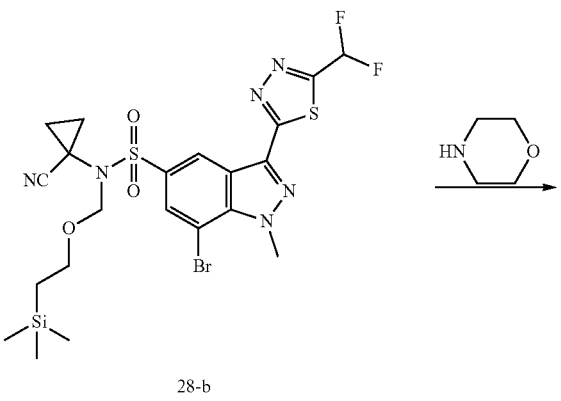

28-b

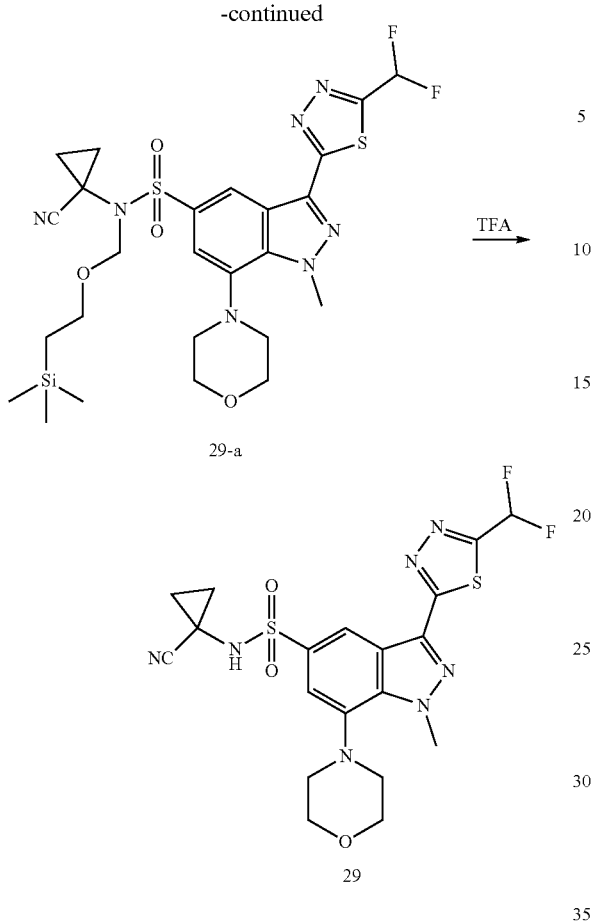

29-a

29

Synthesis of Compound 29

Synthesis of Compound 29-a

A microwave tube charged with 28-b (90 mg, 0.15 mmol), morpholine (25 mg, 0.29 mmol), Ruphos (27 mg, 0.058 mmol), Ruphos Pd G3 (24 mg, 0.029 mmol), cesium carbonate (142 mg, 0.44 mmol) and 1,4-dioxane (8 mL) with degassed and purged with nitrogen for 3 times. The reaction mixture was heated at 60° C. overnight. After completion, the reaction was cooled to room temperature, removed the 1,4-dioxane, diluted with ethyl acetate, washed with water, brine, dried over anhydrous sodium sulfate, filtered and the filtrate was evaporated to obtain the crude product, which was purified by a flash column chromatography (mobile phase: ethyl acetate/(petroleum ether/dichloromethane 4:1), 0% to 100%) to give compound 29-a (70 mg, 77%). LC-MS (ESI): m/z 1251.2 [2M+H]$^+$.

Synthesis of Compound 29

A reaction flask charged with 29-a (70 mg, 0.11 mmol) and dichloromethane (5 mL) was added trifluoroacetic acid (1 mL) dropwise at room temperature. The reaction mixture was stirred at room temperature for 4 h. The reaction mixture was removed solvent by concentration at room temperature, diluted by adding dichloromethane dilution, washed with saturated sodium bicarbonate, brine, dried over anhydrous sodium sulfate, filtered, and the filtrate was concentrated to obtain the crude product, which was purified by a flash column chromatography (mobile phase: ethyl acetate/(petroleum ether/dichloromethane 4:1), 0% to 100%), compound 29 (20 mg, 36%) was obtained. LC-MS (ESI): m/z 496.0 [M+H]$^+$; $^1$H NMR (DMSO-$d_6$, 400 MHz): δ 9.22 (1H, s), 8.64 (1H, s), 7.01 (1H, t, J=53.2 Hz), 7.56 (1H, s), 4.50 (3H, s), 3.70-3.99 (4H, m), 2.85-3.26 (4H, m), 1.39-1.49 (2H, m), 1.25-1.36 (2H, m).

Example 30 Synthetic Route of Compound 30

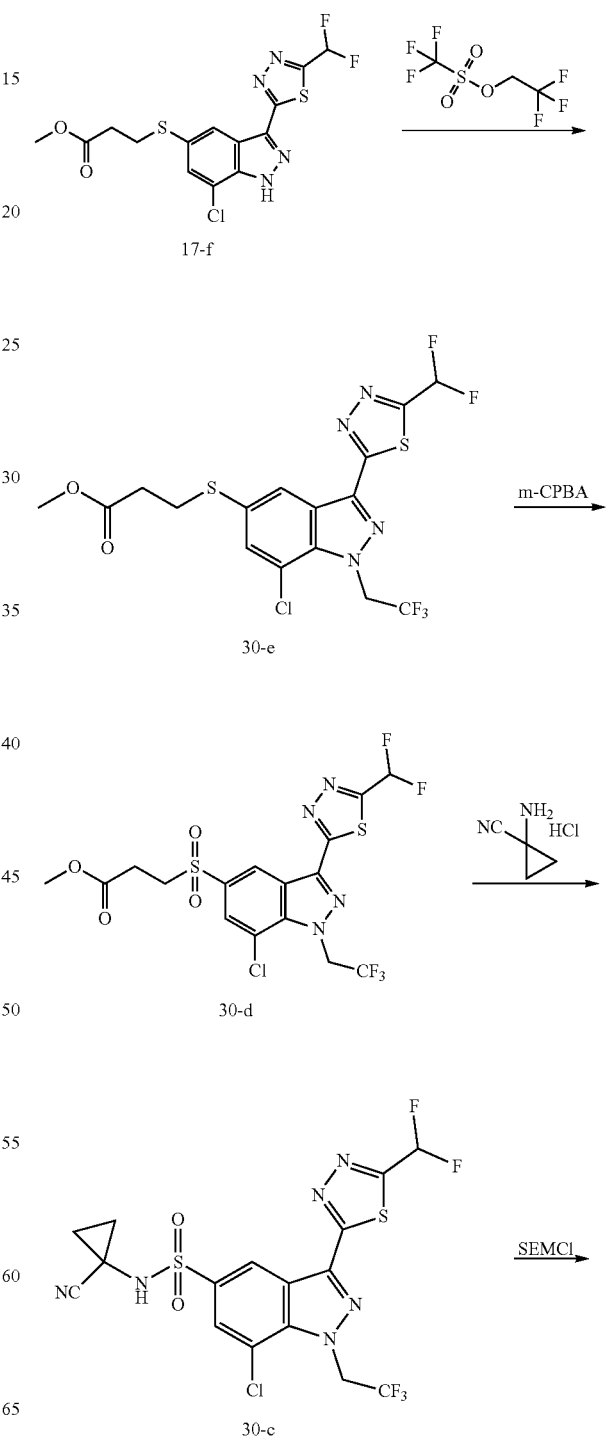

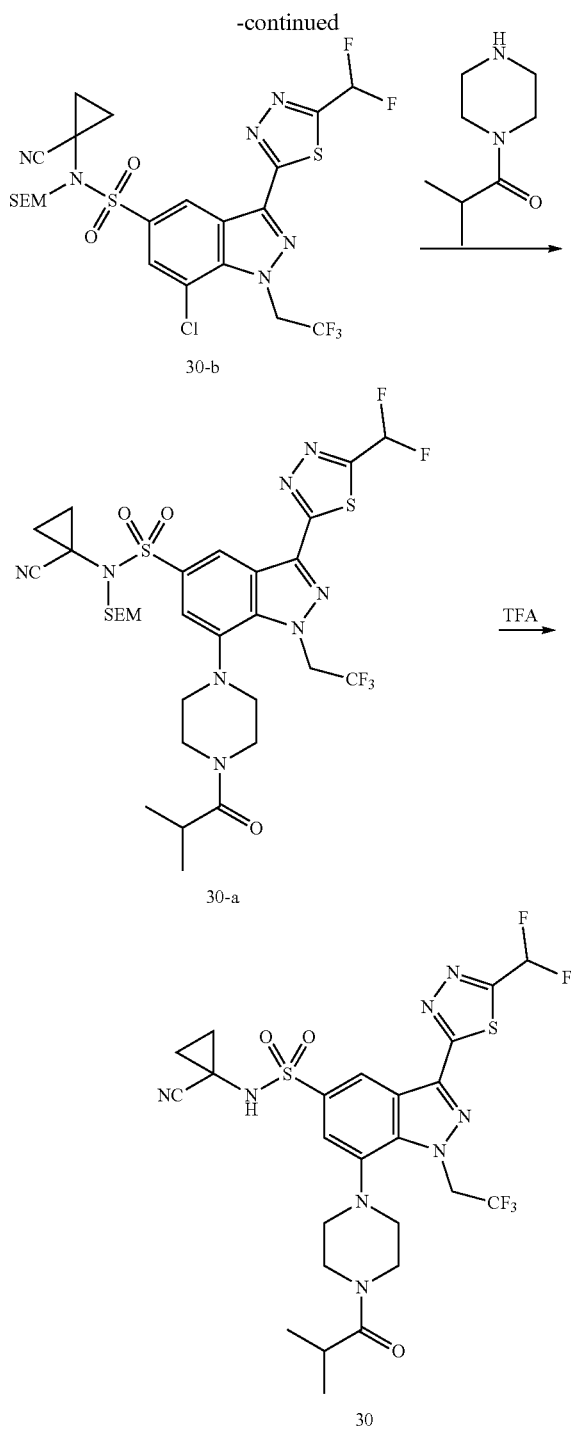

Synthesis of Compound 30-e

Compound 17-f (880 mg, 2.17 mmol), potassium carbonate (601 mg, 4.35 mmol) was added into N,N-dimethylformamide (20 mL), to which 2,2,2-trifluoroethyl trifluoromethanesulfonate (757 mg, 3.26 mmol) was added dropwise, and the reaction was stirred at room temperature for 2 h. The reaction mixture was added water (100 mL), extracted with ethyl acetate (100 mL), washed with water (100 mL) and brine (100 mL), dried over sodium sulfate, filtered out the desiccant and concentrated at reduced pressure to give the crude product, which was purified by column chromatography (mobile phase, PE/EA=10/1) to give compound 30-e (263 mg, 25%). LC-MS (ESI): m/z 486.8 (M+H)$^+$.

Synthesis of Compound 30-d

Compound 30-e (163 mg, 0.34 mmol) was dissolved in dichloromethane (10 mL) and m-chloroperoxybenzoic acid (204 mg, 1.00 mmol) was added to the above mixture in batches at 0° C. The reaction mixture was stirred for 1 h at 0° C., was added saturated sodium bicarbonate solution (50 mL) and water (50 mL) and extracted with dichloromethane (100 mL). The crude product was purified by column chromatography (mobile phase, PE/EA=3/1 to PE:DCM (4:1)/EA 3/1) to give compound 30-d (153 mg, 88%) which was used directly in the next reaction step. LC-MS (ESI): m/z 518.8 (M+H)$^+$.

Synthesis of Compound 30-c

Compound 30-d (153 mg, 0.30 mmol) was dissolved in dichloromethane (4 mL) and methanol (4 mL), to which sodium methanol (48 mg, 0.89 mmol) was added at 0° C. The reaction mixture was stirred at 0° C. for 1 h, then was added 1-amino-cyclopropanecarbonitrile hydrochloride (140 mg, 1.18 mmol) and stirred at room temperature for 10 minutes. The reaction mixture was concentrated to obtain the crude product, which was dissolved in N,N-dimethylformamide (15 mL), to which triethylamine (33 mg, 0.32 mmol) and N-chlorosuccinimide (118 mg, 0.89 mmol) were added at 0° C., and the reaction was stirred at room temperature for 2 h. Water (100 mL) was added to the reaction mixture extracted with ethyl acetate (200 mL), washed with water (50 mL), brine, dried over sodium sulfate, filtered out the desiccant, concentrated under pressure to obtain crude product 30-c (190 mg) which was used directly in the next reaction step. LC-MS (ESI): m/z 512.6 (M+H)$^+$.

Synthesis of Compound 30-b

Compound 30-c (190 mg, 0.37 mmol) was dissolved in dichloromethane (20 mL), to which triethylamine (112 mg, 1.11 mmol) was added and 2-(trimethylsilyl)ethoxymethyl chloride (124 mg, 0.74 mmol) was added dropwise. After addition, the reaction mixture was stirred at room temperature for 2 h. The reaction mixture was added methanol (0.5 mL) and stirred for 10 min. The mixture was concentrated at reduced pressure to obtain the crude product, which was purified by column chromatography (mobile phase, PE/EA=3/1) to give compound 30-b (110 mg, 46%). LC-MS (ESI): m/z 642.9 (M+H)$^+$.

Synthesis of Compound 30-a

Compound 30-b (43 mg, 0.07 mmol), 2-dicyclohexylphosphino-2',6'-diisopropoxy-1,1'-biphenyl (12 mg, 0.03 mmol), (2-dicyclohexylphosphino-2',6'-diisopropoxy-1,1'-biphenylyl)(2-amino-1,1'-biphenyl-2-yl)palladium(II) methanesulfonate (11 mg, 0.01 mmol), cesium carbonate (65 mg, 0.20 mmol) were added to 1,4-dioxane (5 mL) and stirred for 10 min at room temperature before adding 2-methyl-1-(piperazin-1-yl)propan-1-one (21 mg, 0.13 mmol), degassed and purged with nitrogen for 10 times and then the reaction mixture was stirred at 72° C. for 16 hours. The reaction mixture was cooled to room temperature, filtered through celite, and the filtrate was concentrated at reduced pressure to obtain the crude product, which was purified by column chromatography (mobile phase, PE/EA=3/1 to 1/1) to give compound 30-a (10 mg, 20%). LC-MS (ESI): m/z 763.1 (M+H)$^+$.

Synthesis of Compound 30

Compound 30-a (53 mg, 0.07 mmol) was dissolved in dichloromethane (3 mL) and trifluoroacetic acid (1 mL) was added to it at 0° C. The reaction was stirred for 2 h at room temperature. The reaction mixture was removed dichloromethane by concentration and the pH was adjusted to 7-8 with saturated sodium bicarbonate solution, extracted with ethyl acetate (100 mL), washed with brine (100 mL), dried over sodium sulfate, filtered out the desiccant, and concentrated at reduced pressure to obtain the crude product, which was purified by HPLC (basic conditions) to give compound 30 (9 mg, 20%). LC-MS (ESI): m/z 633.1 (M+H)$^+$.

Example 31 Synthetic Route of Compound 31 phine)palladium (9 mg, 0.0080 mmol), and LiCl (0.1 mg, 0.0020 mmol) were added to the solvent toluene (5 mL) at room temperature and the reaction mixture was stirred at 110° C. under nitrogen atmosphere overnight. Cooled to room temperature, the reaction mixture was concentrated at reduced pressure to obtain the crude product. The crude product was purified by a flash column chromatography (PE/EA=10:1) to give compound 31-a (25 mg, 50%). LC-MS (ESI): m/z=619.2[M+H]$^+$.

Synthesis of Compound 31

Compound 31-a (25 mg, 0.040 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, added water (30 mL), extracted with ethyl acetate (50 mL×3), washed with brine (60 mL×3), dried over sodium sulfate,

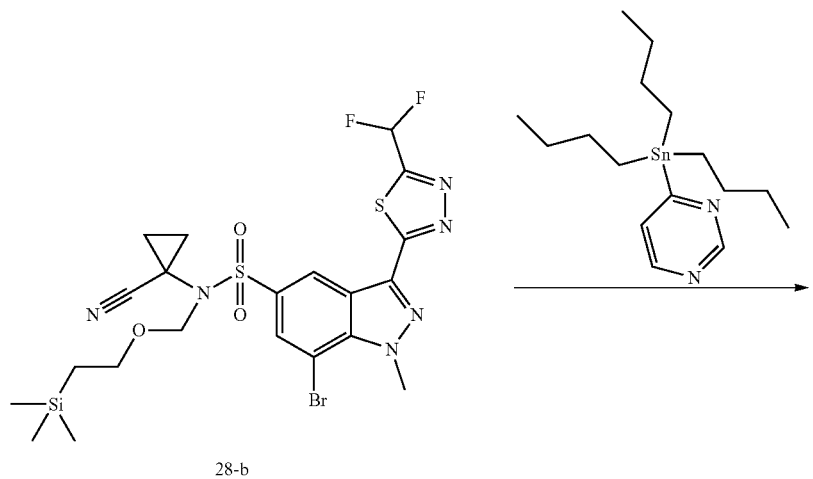

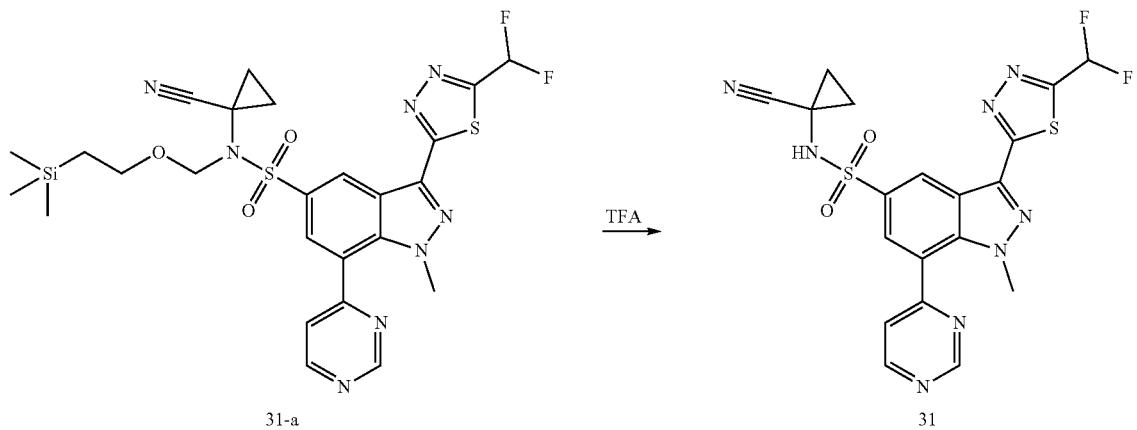

Synthesis of Compound 31-a

Compound 28-b (50 mg, 0.081 mmol), 4-(tri-n-butylstannyl)pyrimidine (45 mg, 0.12 mmol), tetrakis(triphenylphosfiltered out the desiccant and concentrated at reduced pressure to give the crude product, which was purified by Pre-TLC (DCM:MeOH=20:1) to give compound 31 (5 mg, 25%). LC-MS (ESI): m/z=489.0 [M+1]$^+$.

Example 32 Synthetic Route of Compound 32

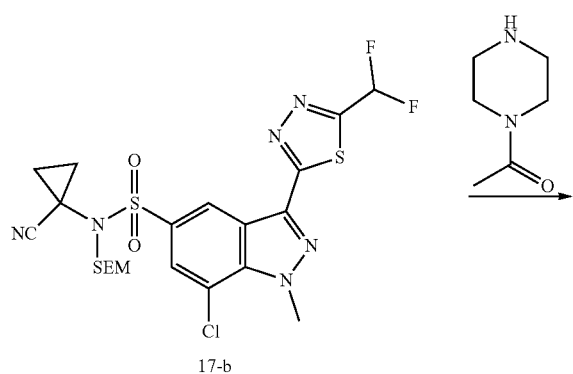

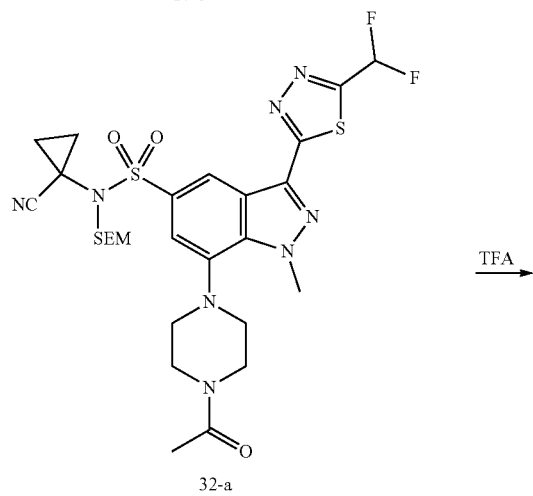

Synthesis of Compound 32-a

Compound 17-b (145 mg, 0.25 mmol), 2-dicyclohexylphosphino-2',6'-diisopropoxy-1,1'-biphenyl (47 mg, 0.10 mmol), (2-dicyclohexylphosphino-2',6'-diisopropoxy-1,1'-biphenyl)(2-amino-1,1'-biphenyl-2-yl)palladium(II) (42 mg, 0.05 mmol), methanesulfonic acid (2-dicyclohexylphosphino-2',6'-diisopropoxy-1,1'-biphenyl) (2-Amino-1,1'-biphenyl-2-yl), 0.05 mmol), cesium carbonate (246 mg, 0.76 mmol) were added to 1,4-dioxane (13 mL) and stirred for 5 min at room temperature before adding 1-acetyl piperazine (32 mg, 0.25 mmol), degassed and purged with nitrogen for 12 times and then the mixture was stirred at 62° C. in a sealed tube for 12 hours. The reaction mixture was cooled to room temperature, filtered through celite, and the filtrate was concentrated at reduced pressure to obtain the crude product, which was purified by column chromatography (mobile phase, PE/EA=10/1 to 1/1) to give compound 32-a (100 mg, 59%). LC-MS (ESI): m/z 667.0 (M+H)$^+$.

Synthesis of Compound 32

Compound 32-a (100 mg, 0.15 mmol) was dissolved in dichloromethane (4 mL) and trifluoroacetic acid (1.5 mL) was added to it at 0° C. The reaction was stirred for 2 h at room temperature. The reaction mixture was removed dichloromethane by rotary evaporation, and the pH was adjusted to 7-8 with saturated sodium bicarbonate solution, extracted with ethyl acetate (100 mL), washed with brine (100 mL), and the crude product was obtained by rotary evaporation at reduced pressure, and the crude product was purified by HPLC (basic conditions) to obtain compound 32 (32 mg, 40%). LC-MS (ESI): m/z 537.1 (M+H)$^+$; $^1$H NMR ((400 MHz, DMSO-d$_6$): δ 9.19 (s, 1H), 8.65 (s, 1H), 7.71 (t, J=52.0 Hz, 1H), 7.56 (s, 1H), 4.51 (s, 3H), 4.48-4.36 (m, 1H), 4.02-3.90 (m, 1H), 3.56-3.38 (m, 2H), 3.16-2.58 (m, 4H), 2.09 (s, 3H), 1.46-1.29 (m, 4H).

Example 33 Synthetic Route of Compound 33

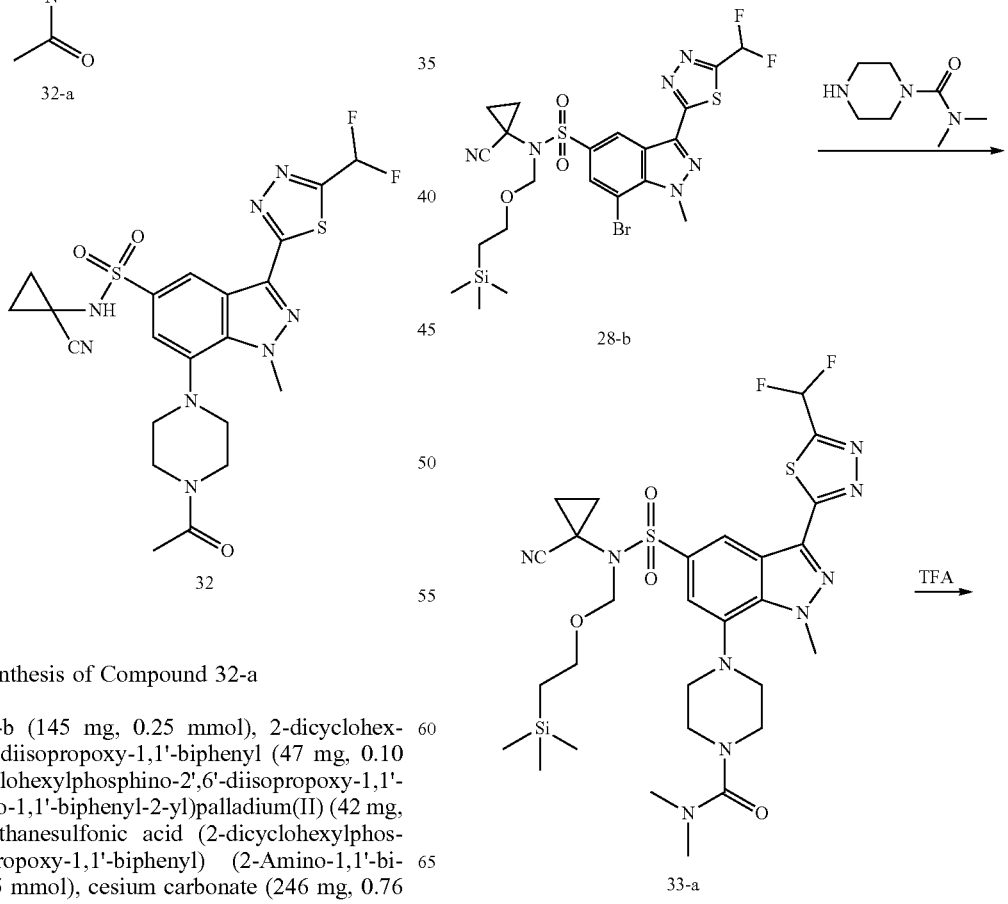

201
-continued

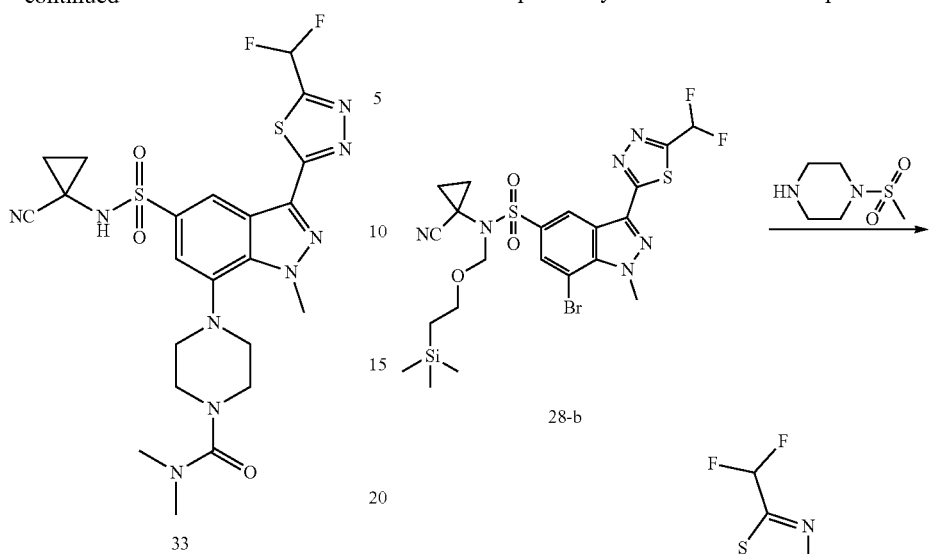

33

Synthesis of Compound 33-a

A microwave tube charged with 28-b (80 mg, 0.13 mmol), N,N-dimethyl piperazine-1-carboxamide (41 mg, 0.26 mmol), Ruphos (24 mg, 0.052 mmol), Ruphos Pd G3 (22 mg, 0.026 mmol), cesium carbonate (126 mg, 0.39 mmol) and 1,4-dioxane (8 mL) was degassed and purged with nitrogen for 3 times. The reaction mixture was heated at 60° C. overnight. After completion, the reaction was cooled to room temperature, removed the 1,4-dioxane, diluted with ethyl acetate, washed with water, brine, dried over anhydrous sodium sulfate, filtered and the filtrate was evaporated to obtain the crude product, which was purified by a flash column chromatography (mobile phase: ethyl acetate/(petroleum ether/dichloromethane 4:1), 0% to 100%) to give compound 33-a (70 mg, 77%). ESI): m/z 696.2 [M+H]⁺.

Synthesis of Compound 33

A reaction flask charged with 33-a (70 mg, 0.10 mmol), dichloromethane (5 mL) was added trifluoroacetic acid (1 mL) dropwise at room temperature. The reaction mixture was stirred at room temperature for 4 h. The solvent was removed by concentration at room temperature. Diluted by adding dichloromethane, washed by saturated sodium bicarbonate, brine, dried over anhydrous sodium sulfate, filtered, and the filtrate was evaporated to dryness to obtain the crude product, which was purified by Prep-TLC (PE:EA=1:2), compound 33 (20 mg, 35%) to give compound 33 (20. g, 35%). LC-MS (ESI): m/z 566.1 [M+H]⁺.

202

Example 34 Synthetic Route of Compound 34

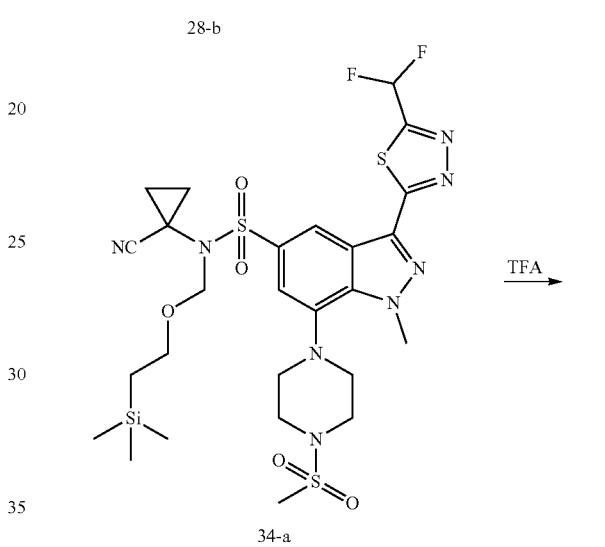

28-b

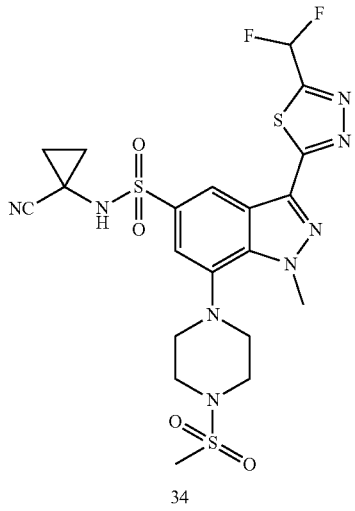

34

Synthesis of Compound 34-a

The microwave tube charged with 28-b (30 mg, 0.048 mmol), 1-methanesulfonylpiperazine (16 mg, 0.096 mmol), Ruphos (9 mg, 0.019 mmol), Ruphos Pd G3 (8 mg, 0.010 mmol), cesium carbonate (47 mg, 0.15 mmol) and 1,4-dioxane (3 mL) was degassed and purged with nitrogen for 3 times. The reaction mixture was heated at 60° C. overnight. After completion, the reaction was cooled to room temperature, removed the 1,4-dioxane, diluted with ethyl acetate, washed with water, brine, dried over anhydrous sodium sulfate, filtered and the filtrate was evaporated to obtain the crude product, which was purified by a flash column chromatography (mobile phase: ethyl acetate/(petroleum ether/dichloromethane 4:1), 0% to 100%) to give compound 34-a (25 mg, 73%). LC-MS (ESI): m/z 703.1 [M+H]⁺.

Synthesis of Compound 34

A reaction flask charged with 34-a (25 mg, 0.036 mmol), dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtration was evaporated to dryness to obtain the crude product, which was purified by Prep-TLC (PE:EA=1:2) to give compound 34 (10 mg, 49%). LC-MS (ESI): m/z 573.0 [M+H]⁺.

Example 35 Synthetic Route of Compound 35

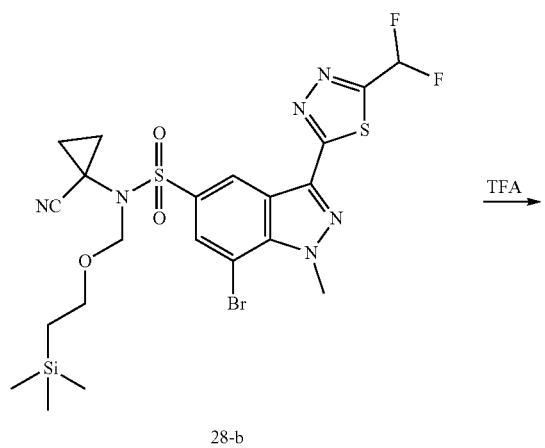

28-b

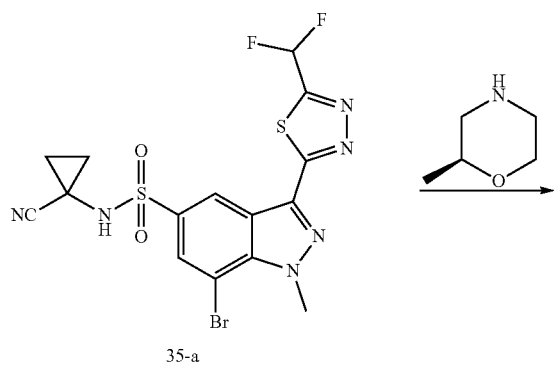

35-a

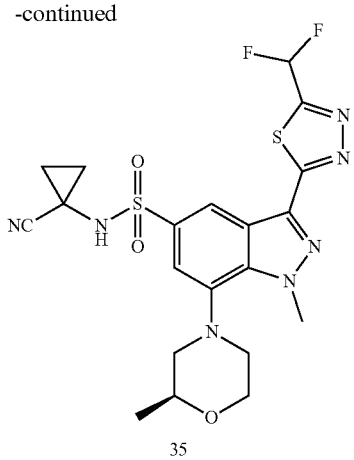

35

Synthesis of Compound 35-a

A reaction flask charged with 28-b (80 mg, 0.13 mmol) and dichloromethane (5 mL) was added Trifluoroacetic acid (1 mL) dropwise at room temperature. The reaction mixture was stirred at room temperature for 4 h. The solvent was removed by concentration at room temperature. The residue was diluted by adding dichloromethane, washed with saturated sodium bicarbonate, brine, dried over anhydrous sodium sulfate, filtered and the filtration was evaporation to obtain the crude product, which was purified by a flash column chromatography (mobile phase: ethyl acetate/(petroleum ether/dichloromethane 4:1), 0% to 100%) to give compound 35-a (50 mg, 79%). LC-MS (ESI): m/z 488.9 [M+H]⁺.

Synthesis of Compound 35

A microwave tube charged with 35-a (30 mg, 0.061 mmol), (S)-2-methylmorpholine (12 mg, 0.12 mmol), Ruphos (12 mg, 0.025 mmol), Ruphos Pd G3 (10 mg, 0.012 mmol), cesium carbonate (60 mg, 0.18 mmol) and 1,4-dioxane (3 mL) was degassed and purged with nitrogen for 3 times. The reaction mixture was heated at 60° C. overnight. On the next day, the reaction mixture was warmed up to 90° C. and stirred for 4 hours. After cooled to room temperature, the reaction was removed 1,4-dioxane by concentration at reduced pressure, diluted with ethyl acetate, washed with water, brine, dried over anhydrous sodium sulfate, filtered and the filtrate was evaporated to obtain the crude product, which was subjected to Prep-TLC (PE:EA=1: 1) to give compound 35 (8 mg, 26%). LC-MS (ESI): m/z 510.1 [M+H]⁺.

Example 36 Synthetic Route of Compound 36

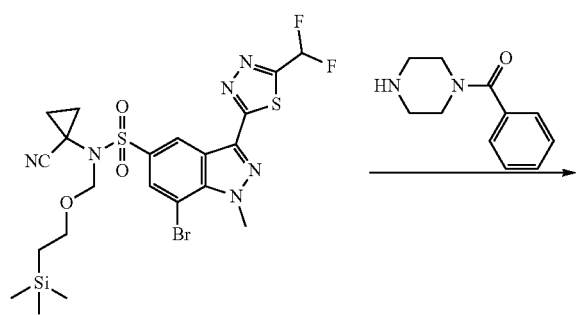

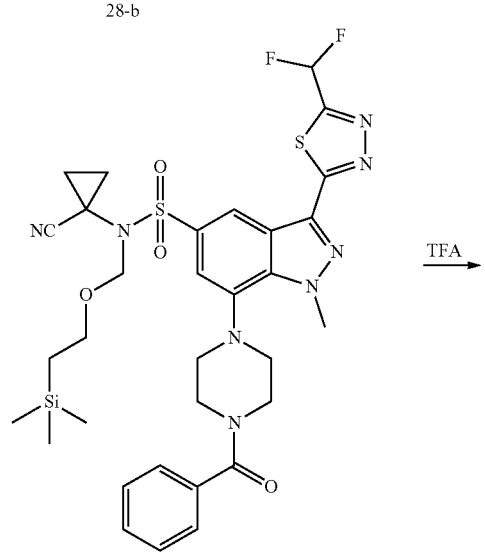

Synthesis of Compound 36-a

A microwave tube charged with 28-b (30 mg, 0.048 mmol), 1-benzoylpiperazine (18 mg, 0.096 mmol), Ruphos (9 mg, 0.019 mmol), Ruphos Pd G3 (8 mg, 0.010 mmol), cesium carbonate (47 mg, 0.15 mmol) and 1,4-dioxane (3 mL) was degassed and purged with nitrogen for 3 times. The reaction mixture was heated at 60° C. overnight. After cooled to room temperature, the reaction was removed the 1,4-dioxane, diluted with ethyl acetate, washed with water, brine, dried over anhydrous sodium sulfate, filtered and the filtrate was evaporated to obtain the crude product, which was purified by a flash column chromatography (mobile phase: ethyl acetate/(petroleum ether/dichloromethane 4:1), 0% to 100%) to give compound 36-a (25 mg, 71%). ESI): m/z 729.1 [M+H]$^+$.

Synthesis of Compound 36

A reaction flask charged with 36-a (25 mg, 0.034 mmol), dichloromethane (5 mL) was added trifluoroacetic acid (1 mL) dropwise at room temperature. The reaction mixture was stirred at room temperature for 4 h. The solvent was removed by concentration at room temperature. The residue was diluted by adding dichloromethane, washed with saturated sodium bicarbonate, brine, dried over anhydrous sodium sulfate, filtered, and the filtration was evaporated to dryness to obtain the crude product, which was by Prep-TLC (PE:EA=1:2) to give compound 36 (15 mg, 73%). LC-MS (ESI): m/z 599.1 [M+H]$^+$.

Example 37 Synthetic Route of Compound 37

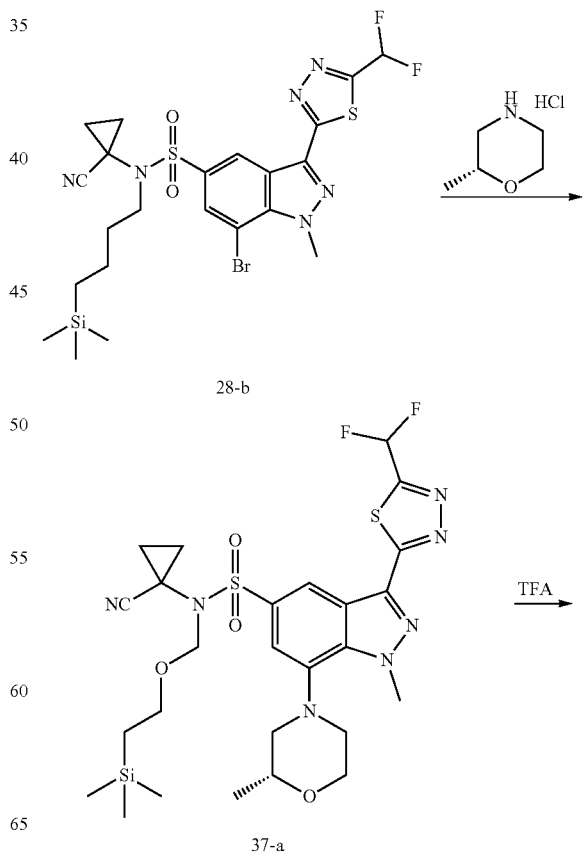

207
-continued

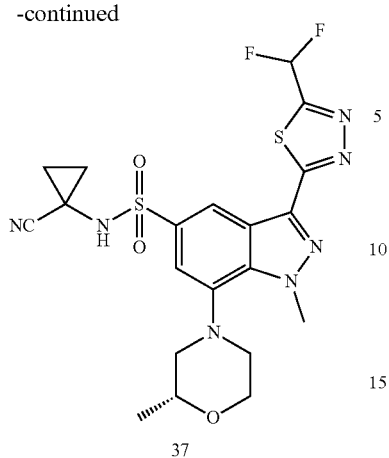

37

Synthesis of Compound 37-a

A microwave tube charged with 28-b (50 mg, 0.081 mmol), (R)-2-methylmorpholine hydrochloride (22 mg, 0.16 mmol), Ruphos (15 mg, 0.032 mmol), Ruphos Pd G3 (14 mg, 0.016 mmol), cesium carbonate (132 mg, 0.40 mmol) and 1,4-dioxane (8 mL) was degassed and purged with nitrogen for 3 times. The reaction mixture was heated at 60° C. overnight. After completion, the reaction was cooled to room temperature, removed the 1,4-dioxane, diluted with ethyl acetate, washed with water, brine, dried over anhydrous sodium sulfate, filtered and the filtration was evaporated to obtain the crude product, which was purified by a flash column chromatography (mobile phase: ethyl acetate/petroleum ether, 0% to 100%) to give compound 37-a (40 mg, 77%). LC-MS (ESI): m/z 640.1 [M+H]$^+$.

Synthesis of Compound 37

A reaction flask charged with 37-a (40 mg, 0.063 mmol) and dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtration was evaporated to dryness to obtain the crude product, which was subjected to Prep-TLC (PE:EA=1:1) to give compound 37 (15 mg, 47%). LC-MS (ESI): m/z 510.0 [M+H]$^+$.

Example 38 Synthetic Route of Compound 38

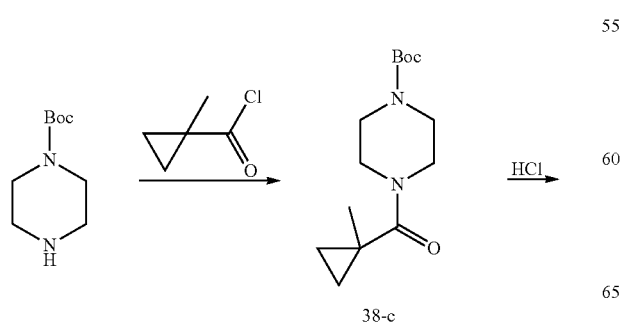

38-c

208
-continued

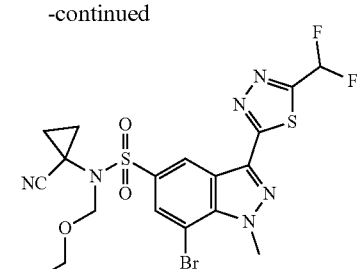

38-b 28-b →

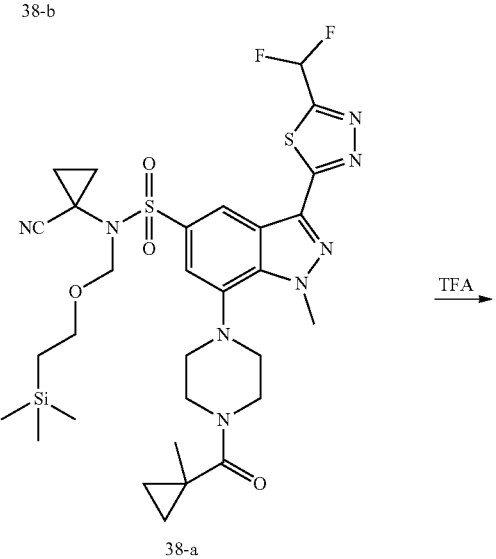

38-a

TFA →

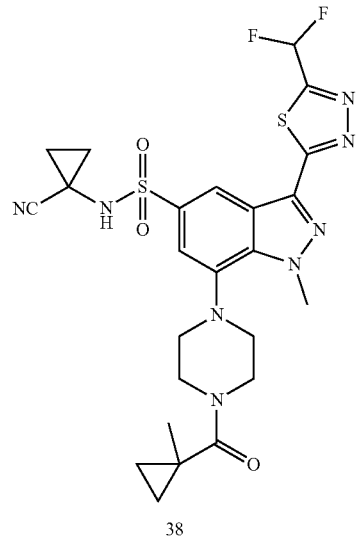

38

Synthesis of Compound 38-c

A reaction vial charged with N-Boc-piperazine (500 mg, 2.68 mmol), dichloromethane (5 mL) and triethylamine (1.12 mL, 8.05 mmol) was added 1-methyl-cyclopropanecarbonyl chloride (477 mg, 4.02 mmol) dropwise in an ice-water bath and stirred at room temperature overnight. The next day, the reaction was quenched with water, extracted with dichloromethane, washed with brine, dried over anhydrous sodium sulfate, concentrated to dryness and the residue was purified on a silica column (mobile phase: methanol/dichloromethane: 0% to 10%) to give compound 38-c (700 mg, 97%). LC-MS (ESI): m/z=269.1 [M+H]$^+$.

Synthesis of Compound 38-b

A reaction flask charged with 38-c (700 mg, 2.61 mmol) and 1,4-dioxane (10 mL) was added HCl/1,4-dioxane (4 M, 4.66 mL, 18.63 mmol) dropwise in an ice-water bath, and the reaction mixture was stirred at room temperature overnight. The next day, the reaction mixture was filtered and the resulting white filter cake was washed with a small amount of 1,4-dioxane and dried in vacuum to give compound 38-b (400 mg, 75%). LC-MS (ESI): m/z 169.0 [M+H]$^+$.

Synthesis of Compound 38-a

A microwave tube charged with 28-b (45 mg, 0.073 mmol), 38-b (30 mg, 0.15 mmol), Ruphos (14 mg, 0.029 mmol), Ruphos Pd G3 (12 mg, 0.015 mmol), cesium carbonate (118 mg, 0.36 mmol) and 1,4-dioxane (8 mL) was degassed and purged with nitrogen for 3 times. The reaction mixture was heated at 60° C. overnight. After completion, the reaction was cooled to room temperature, removed the 1,4-dioxane by concentration at reduced pressure, diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 38-a (40 mg, 78%). LC-MS (ESI): m/z 707.1 [M+H]$^+$.

Synthesis of Compound 38

A reaction flask charged with 38-a (40 mg, 0.057 mmol), dichloromethane (5 mL). was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered and the filtrate was evaporated to obtain the crude product, which was purified by Prep-HPLC to give compound 38 (15 mg, 46%). LC-MS (ESI): m/z 577.0 [M+H]$^+$; $^1$H NMR (DMSO-d$_6$, 400 MHz): δ 9.12 (1H, bs), 8.65 (1H, d, J=1.6 Hz), 7.70 (1H, t, J=53.2 Hz), 7.58 (1H, d, J=1.6 Hz), 4.52 (3H, s), 4.18-4.49 (2H, m), 3.04-3.43 (4H, m), 2.70-3.02 (2H, m), 1.38-1.51 (2H, m), 1.30-1.35 (2H, m), 1.29 (3H, s), 0.83-0.89 (2H, m), 0.55-0.62 (2H, m).

Example 39 Synthesis of Compound 39

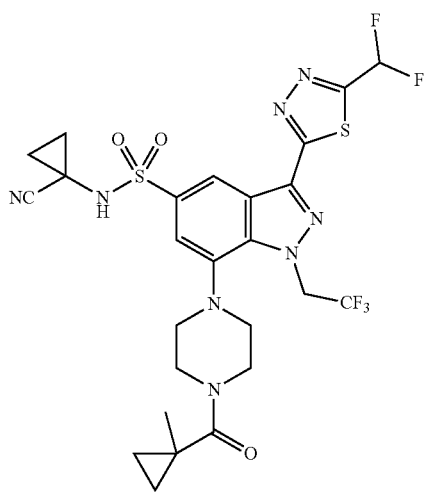

39

Referring to the synthesis of compound 30, compound 39 was synthesized by replacing (1-methylcyclopropyl)(piperazin-1-yl)methanone with 38-b, and using 30-b as the starting reactant. LC-MS (ESI): m/z 645.0 (M+H)$^+$.

Example 40 Synthetic Route of Compound 40

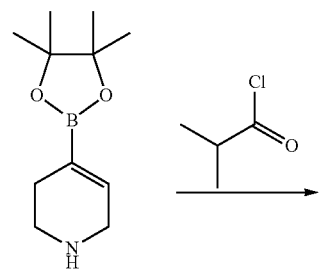

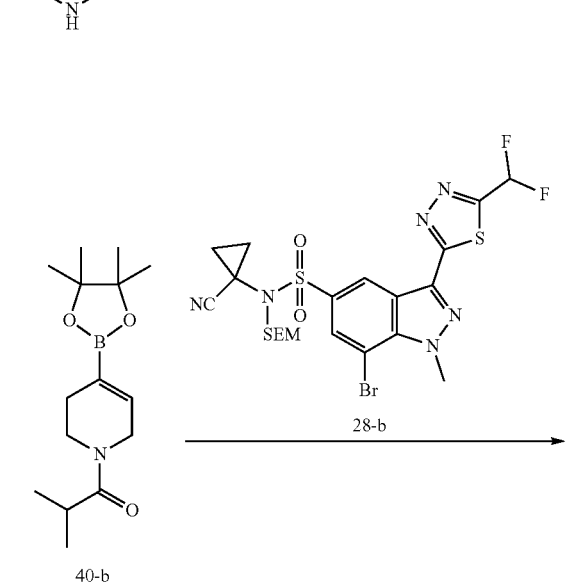

40-b

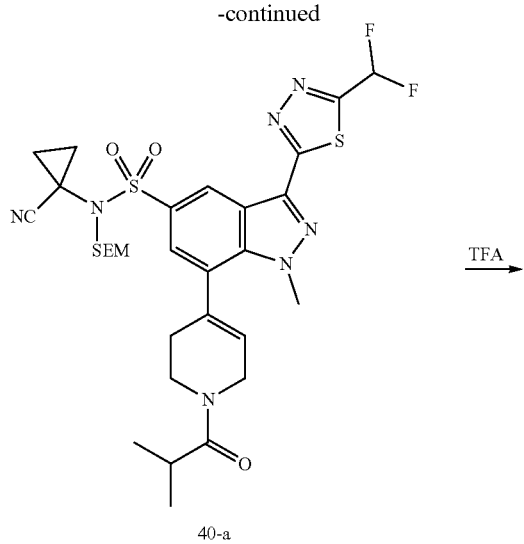

40-a

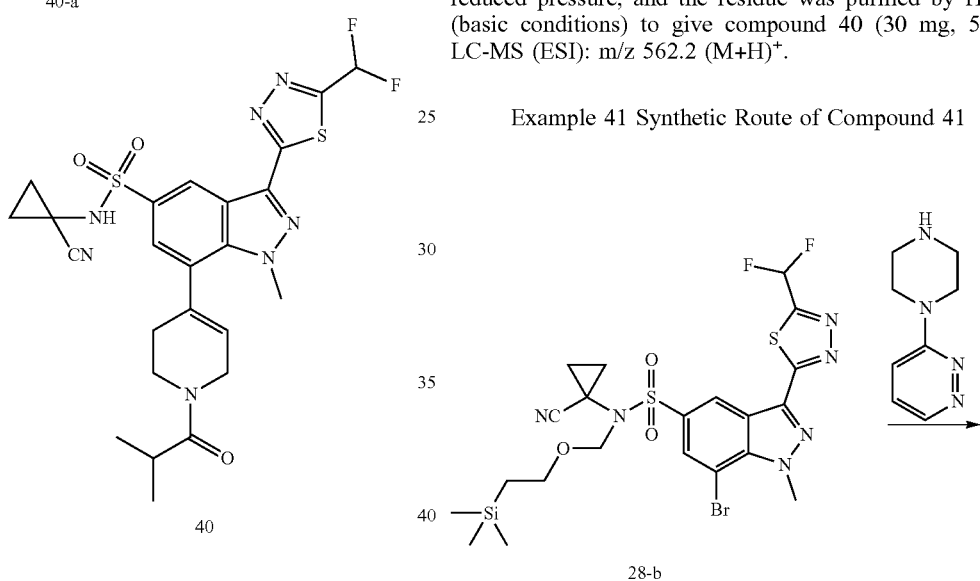

40

Synthesis of Compound 40-b

The compound 1,2,3,6-tetrahydropyridine-4-boronic acid pinacol ester (100 mg, 0.48 mmol) was dissolved in dichloromethane (5 mL), to which diisopropylethylamine (185 mg, 1.43 mmol) was added, and then the system was cooled to 0° C., was added isobutyryl chloride (61 mg, 0.57 mmol) dropwise, after addition, and the reaction was stirred at room temperature for 2 hours. Saturated sodium bicarbonate solution (10 mL) was added to the reaction mixture, extracted twice with dichloromethane (50 mL), dried over sodium sulfate, filtered out the desiccant, and concentrated at reduced pressure to obtain the crude product, which was purified by column chromatography (mobile phase, PE/EA=1/1 to 1/5) to give compound 40-b (75 mg, 56%). M+H)⁺.

Synthesis of Compound 40-a

Compounds 28-b (55 mg, 0.09 mmol), 40-b (37 mg, 0.13 mmol), [1,1'-bis(diphenylphosphino)ferrocene]palladium dichloride (13 mg, 0.02 mmol), potassium carbonate (37 mg, 0.27 mmol) were combined with 1,4-dioxane (5 mL) and water (0.5 mL). The reaction mixture was degassed and purged with nitrogen for 10 times and then the mixture was heated at 100° C. in a sealed tube for 6 hours. The reaction mixture was cooled to room temperature, concentrated at reduced pressure and the residue was purified by column chromatography (mobile phase, PE/EA=3/1 to 1/1) to give compound 40-a (60 mg, 98%). LC-MS (ESI): m/z 692.1 (M+H)⁺.

Synthesis of Compound 40

Compound 40-a (70 mg, 0.10 mmol) was dissolved in dichloromethane (4.5 mL) and trifluoroacetic acid (1.5 mL) was added to the above at 0° C. The reaction was stirred for 2 h at room temperature. The reaction mixture was removed dichloromethane by rotary evaporation and the pH was adjusted to 7-8 with saturated sodium bicarbonate, extracted with ethyl acetate (100 mL), washed with brine (100 mL), and the crude product was obtained by rotary evaporation at reduced pressure, and the residue was purified by HPLC (basic conditions) to give compound 40 (30 mg, 53%). LC-MS (ESI): m/z 562.2 (M+H)⁺.

Example 41 Synthetic Route of Compound 41

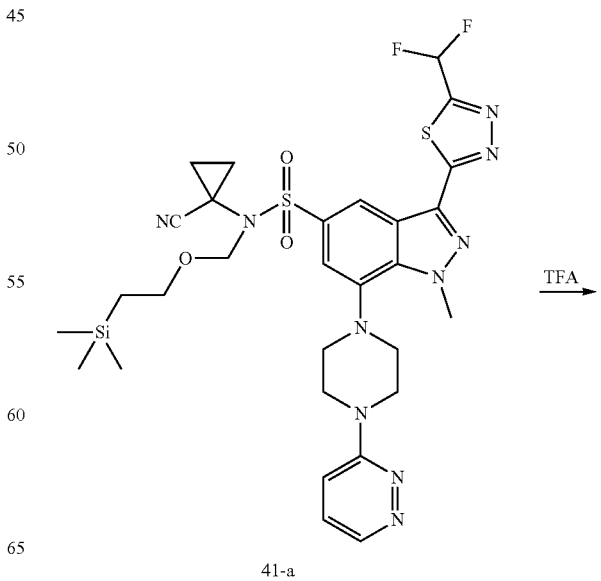

41-a

213
-continued

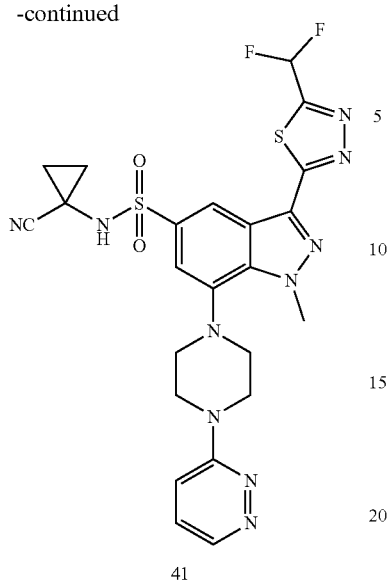

41

214
Example 42 Synthetic Route of Compound 42

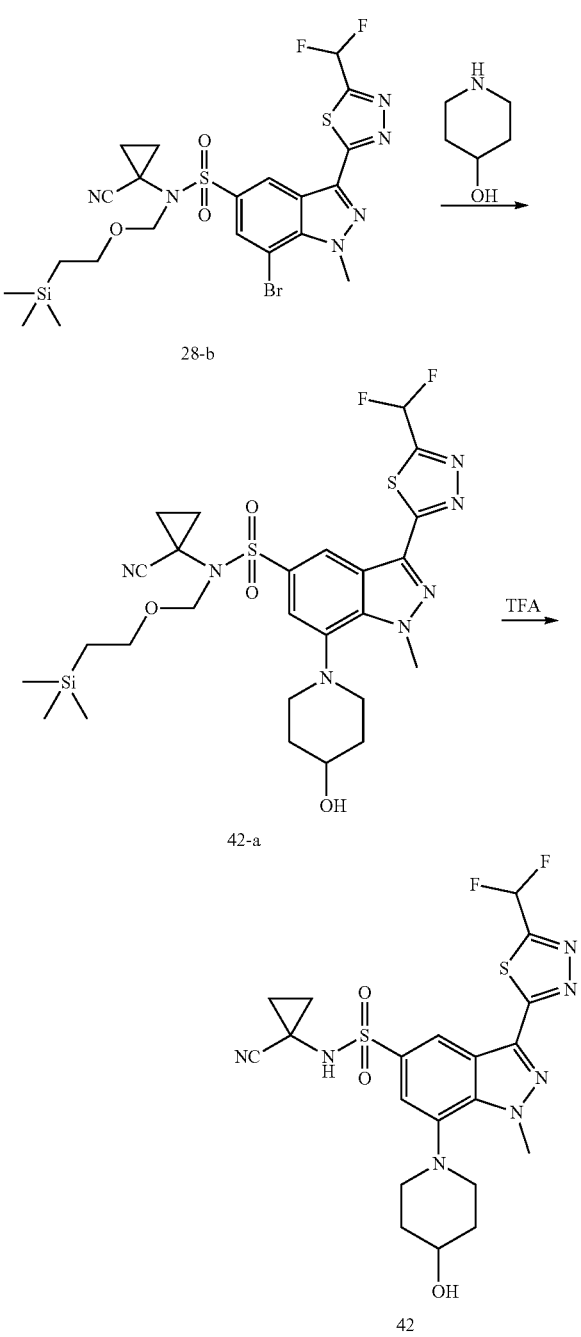

Synthesis of Compound 41-a

A sealed tube (25 mL) charged with 28-b (100 mg, 0.16 mmol), 1-(6-pyridazinyl)piperazine (53 mg, 0.32 mmol), RuPhos Pd G3 (27 mg, 0.032 mmol), RuPhos (30 mg, 0.065 mmol), $Cs_2CO_3$ (105 mg, 0.32 mmol), 1,4-dioxane (6 mL) was stirred overnight at 90° C. under nitrogen atmosphere. Cooled to room temperature, the reaction mixture was added brine (60 mL), extracted with ethyl acetate (50 mL×3), the organic phase was washed with brine (40 mL×3), the organic phase was dried over anhydrous sodium sulfate, filtered, and concentrated at reduced pressure to obtain the crude product. The crude product was purified by a flash column chromatography (PE/EA=3:1) to give compound 41-a (65 mg, 57%). LC-MS (ESI):m/z=703.1[M+H]$^+$.

Synthesis of Compound 41

Compound 41-a (65 mg, 0.092 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, added water (30 mL), extracted with ethyl acetate (50 mL×3), washed with brine (60 mL×3), dried over sodium sulfate, filtered out the desiccant and concentrated at reduced pressure to obtain the crude product, which was purified by Prep-TLC (DCM/MeOH=20/1) to give compound 41 (9 mg, 17%). LC-MS (ESI): m/z=573.0 [M+H]$^+$.

Synthesis of Compound 42-a

A sealed tube (25 mL) charged with Compound 28-b (50 mg, 0.081 mmol), 4-hydroxypiperidine (16 mg, 0.16 mmol), RuPhos Pd G3 (14 mg, 0.016 mmol), RuPhos (15 mg, 0.032 mmol), $Cs_2CO_3$ (79 mg, 0.24 mmol) and 1,4-dioxane (5 mL) was stirred at 90° C. under nitrogen atmosphere overnight. Cooled to room temperature, the reaction was added (60 mL), extracted with ethyl acetate (50 mL×3), the organic phases were washed with brine (60 mL×3), dried over anhydrous sodium sulfate, filtered, and concentrated at reduced pressure to obtain the crude product. The crude product was purified by a flash column chromatography (PE/EA=3:1) to give compound 42-a (13 mg, 25%). LC-MS (ESI):m/z=640.2[M+H]⁺.

Synthesis of Compound 42

Compound 42-a (13 mg, 0.020 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, added water (30 mL), extracted with ethyl acetate (50 mL×3), washed with brine (60 mL×3), dried over anhydrous sodium sulfate, filtered out the desiccant, and concentrated at reduced pressure to obtain the crude product, which was purified by Pre-HPLC (TFA method) to give compound 42 (2 mg, 19%). LC-MS (ESI): m/z=510.1 [M+H]⁺.

Example 43 Synthetic Route of Compound 43

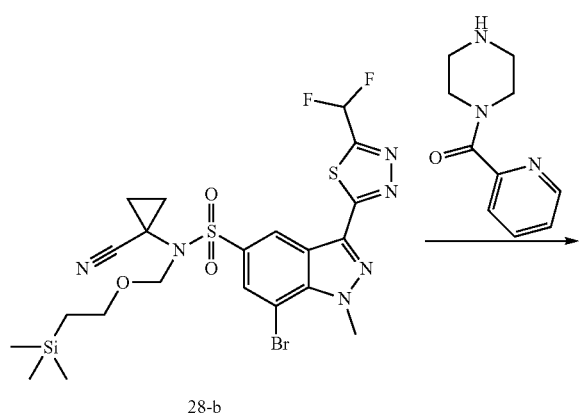

28-b

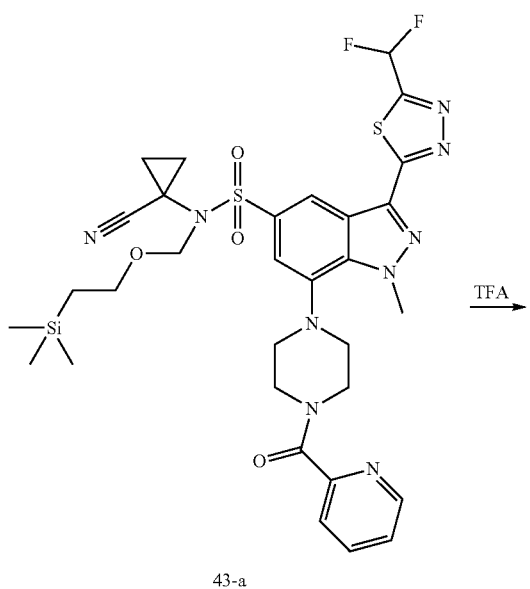

43-a

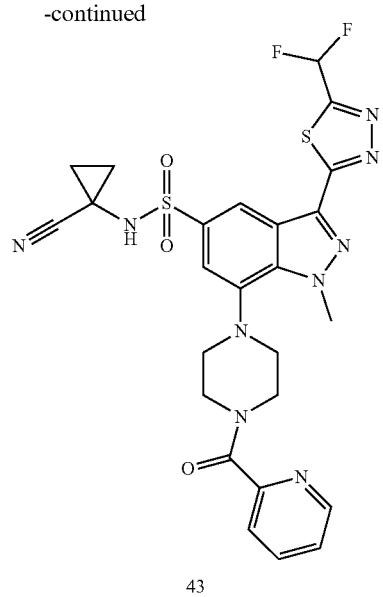

43

Synthesis of Compound 43-a

A sealed tube (25 mL) charged with 28-b (50 mg, 0.081 mmol), N-(2-pyridinecarbonyl)piperazine (31 mg, 0.16 mmol), RuPhos Pd G3 (13.50 mg, 0.016 mmol), RuPhos (15 mg, 0.032 mmol), Cs₂CO₃ (79 mg, 0.24 mmol) and 1,4-dioxane (5 mL) was stirred at 90° C. overnight under nitrogen atmosphere. Cooled to room temperature, the reaction mixture was brine (60 mL) was added to, extracted with ethyl acetate (50 mL×3), the organic phase was washed with brine (40 mL×3), dried over anhydrous sodium sulfate, filtered, and concentrated at reduced pressure to obtain the crude product, which was purified by a flash column chromatography (PE/EA=3:1) to give compound 43-a (40 mg, 68%). 1C-MS (ESI): m/z=730.1 [M+H]⁺.

Synthesis of Compound 43

Compound 43-a (40 mg, 0.055 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, added water (30 mL), extracted with ethyl acetate (50 mL×3), washed with brine (60 mL×3), dried over sodium sulfate, filtered out desiccant, and concentrated at reduced pressure to obtain the crude product, which was purified by Pre-HPLC (TFA method) to give compound 43 (2 mg, 6.1%). LC-MS (ESI): m/z=600.2 [M+H]⁺.

Example 44 Synthetic Route of Compound 44

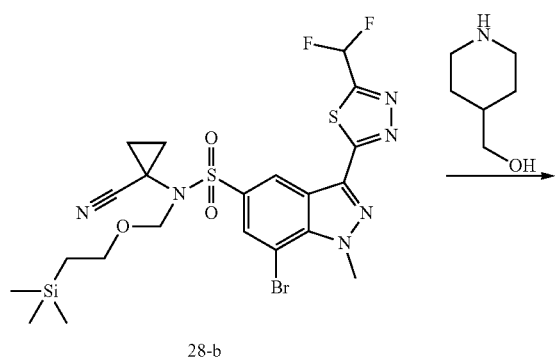

28-b

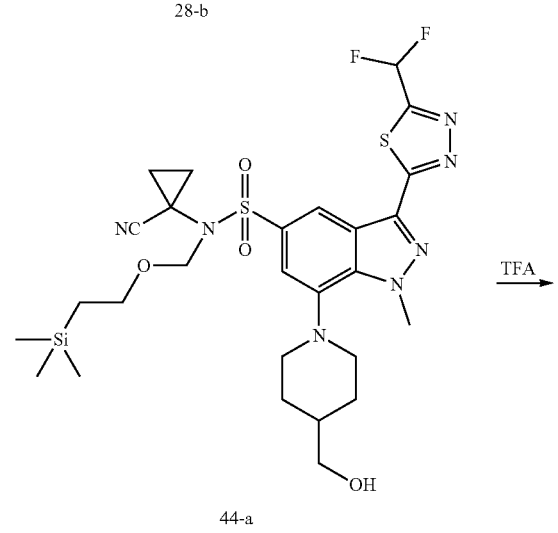

44-a

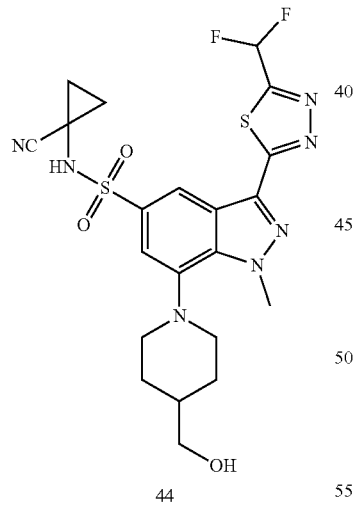

44

Synthesis of Compound 44-a

A sealed tube (25 mL) charged with 28-b (100 mg, 0.16 mmol), 4-hydroxymethylpiperidine (37 mg, 0.32 mmol), RuPhos Pd G3 (27 mg, 0.032 mmol), RuPhos (30 mg, 0.065 mmol), Cs2CO3 (105 mg, 0.32 mmol) and 1,4-dioxane (6 mL) was stirred at 90° C. under nitrogen atmosphere overnight. Cooled to room temperature, the reaction was added brine (60 mL), extracted with ethyl acetate (50 mL×3), the organic phase were washed with brine (40 mL×3), dried over anhydrous sodium sulfate, filtered, and concentrated at reduced pressure to obtain the crude product, which was purified by a flash column chromatography (PE/EA=3:1) to give compound 44-a (85 mg, 81%). LC-MS (ESI): m/z=654.1 [M+H]$^+$.

Synthesis of Compound 44

Compound 44-a (85 mg, 0.13 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, added water (30 mL), extracted with ethyl acetate (50 mL×3), washed with brine (60 mL×3), dried over sodium sulfate, filtered over desiccant and concentrated at reduced pressure to give the crude product, which was purified by Prep-HPLC (NH4HCO3 method) to give compound 44 (2 mg, 2.9%). LC-MS (ESI): m/z=524.0 [M+H]$^+$.

Example 45 Synthetic Route of Compound 45

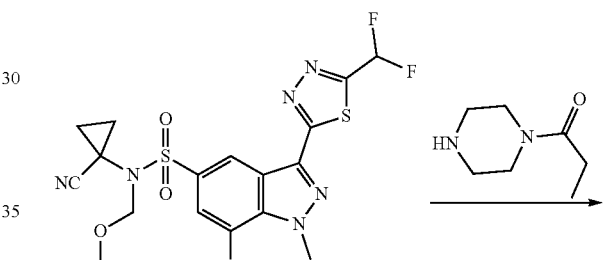

28-b

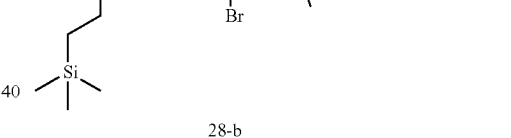

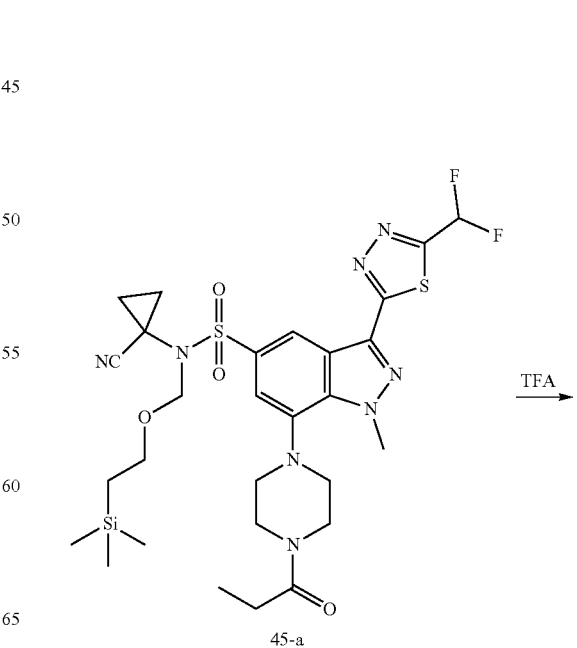

45-a

219
-continued

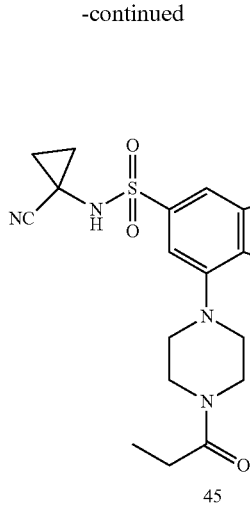

45

Synthesis of Compound 45-a

A microwave tube charged with 28-b (50 mg, 0.081 mmol), 1-(piperazin-1-yl)propan-1-one (23 mg, 0.16 mmol), Ruphos (15 mg, 0.032 mmol), Ruphos Pd G3 (14 mg, 0.016 mmol), cesium carbonate (79 mg, 0.24 mmol) and 1,4-dioxane (8 mL) was degassed and purged with nitrogen 3 times, then heated at 60° C. overnight. After the reaction was cooled to room temperature, the 1,4-dioxane was removed by concentration at reduced pressure, diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 45-a (40 mg, 73%). z 681.1 $[M+H]^+$.

Synthesis of Compound 45

A reaction flask charged with 45-a (40 mg, 0.059 mmol), dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to dryness to obtain the crude product, which was purified by Prep-TLC (PE:EA=1:2) to obtain Compound 45 (20 mg, 62%). LC-MS (ESI): m/z 551.1 $[M+H]^+$.

220

Example 46 Synthetic Route of Compound 46

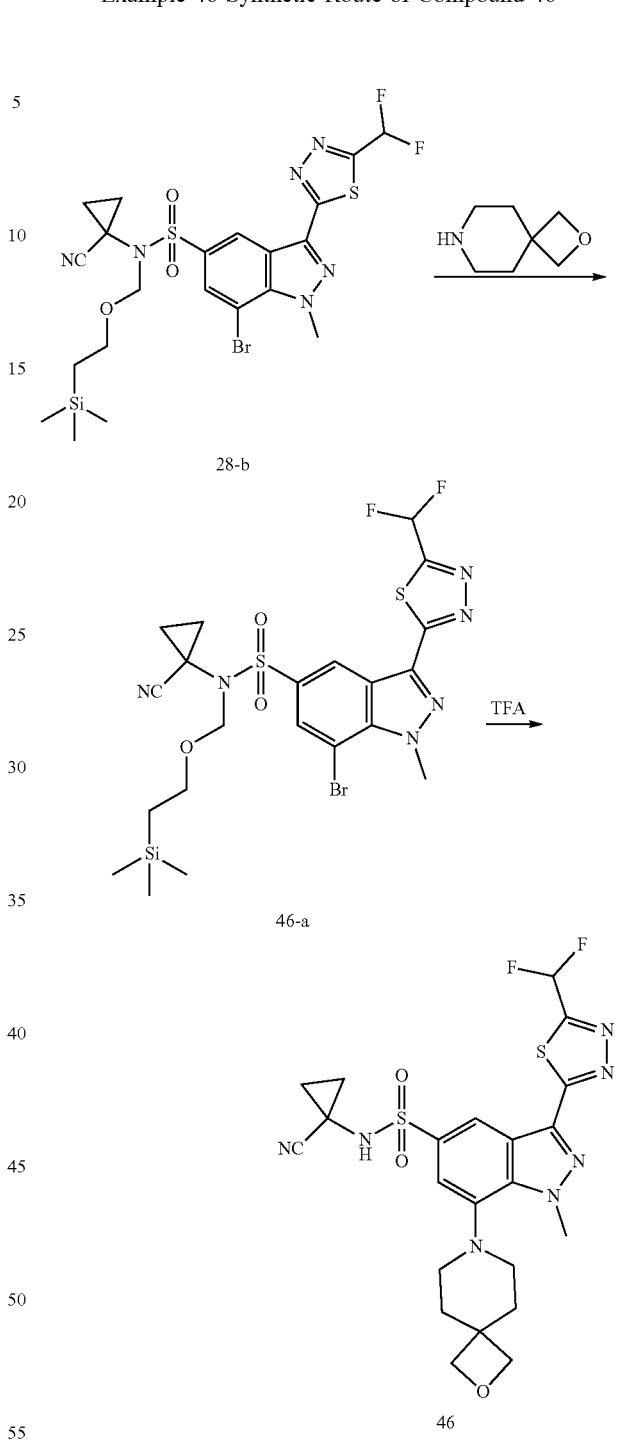

Synthesis of Compound 46

A microwave tube charged with 28-b (50 mg, 0.081 mmol), 2-oxazole-7-azaspiro[3.5]nonane (21 mg, 0.16 mmol), Ruphos (15 mg, 0.032 mmol), Ruphos Pd G3 (14 mg, 0.016 mmol), cesium carbonate (79 mg, 0.24 mmol) and 1,4-dioxane (8 mL) was degassed and purged with nitrogen for 3 times, then heated at 60° C. overnight. After the reaction was cooled to room temperature, removed the 1,4-dioxane by concentration at reduced pressure, the residue was diluted with ethyl acetate, washed with water, brine, dried over anhydrous sodium sulfate, filtered, and the filtrate was evaporated to dryness to obtain the crude product, which was purified by a flash column chromatography (mobile phase: ethyl acetate/petroleum ether, 0% to 100%) to give compound 46-a (40 mg, 74%). LC-MS (ESI): m/z 666.1 [M+H]⁺.

Synthesis of Compound 46

A reaction flask charged with 46-a (40 mg, 0.060 mmol) and dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to dryness to obtain the crude product, which was purified by Prep-TLC (PE:EA=1:2) to give compound 46 (15 mg, 47%). LC-MS (ESI): m/z 536.0 [M+H]⁺.

Example 47 Synthetic Route of Compound 47

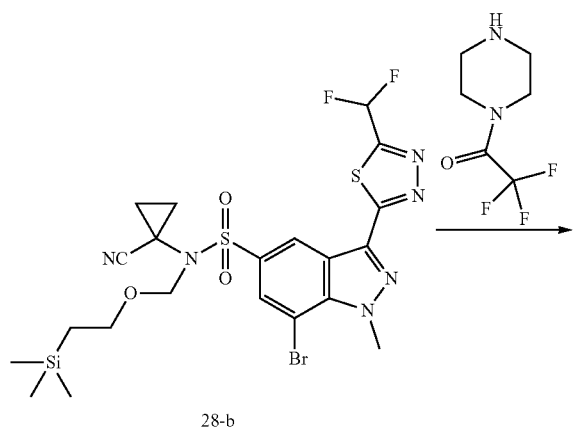

28-b

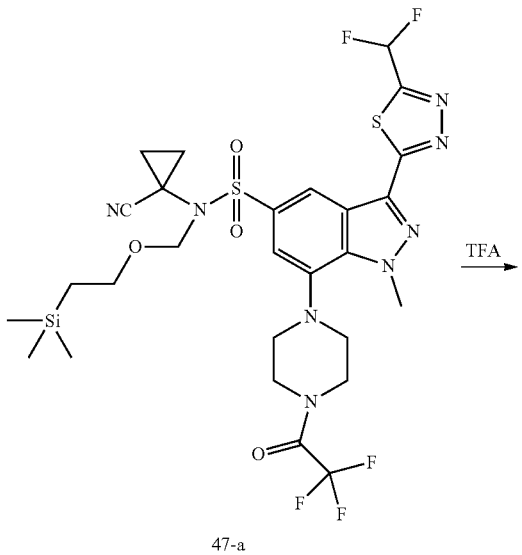

47-a

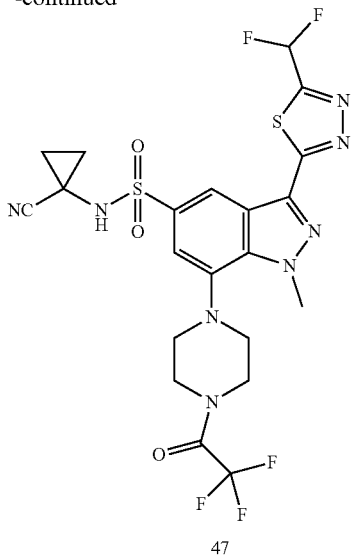

47

Synthesis of Compound 47-a

A sealed tube (25 mL) charged with 28-b (100 mg, 0.16 mmol), 2,2,2-trifluoro-1-(piperazin-1-yl)ethanone (59 mg, 0.32 mmol), RuPhos Pd G3 (27 mg, 0.032 mmol), RuPhos (30 mg, 0.065 mmol), Cs₂CO₃ (105 mg, 0.32 mmol) and 1,4-dioxane (6 mL) was stirred at 90° C. overnight under nitrogen atmosphere. Cooled to room temperature, brine (60 mL) was added to the reaction mixture, extracted with ethyl acetate (50 mL×3), the organic phase was washed with brine (40 mL×3), the organic phase was dried over anhydrous sodium sulfate, filtered, and the filtrate was evaporated to dryness to obtain the crude product, which was purified by a flash column chromatography (PE/EA=3:1) to give compound 47-a (77 mg, 66%). LC-MS (ESI):m/z=721.1[M+H]⁺.

Synthesis of Compound 47

Compound 47-a (77 mg, 0.11 mmol) was dissolved in dichloromethane (4 mL), to which trifluoroacetic acid (1 mL) was added and the reaction mixture was stirred for 2 h at room temperature. The reaction mixture was adjusted to pH 8 with saturated sodium bicarbonate solution, was added water (30 mL), extracted with ethyl acetate (50 mL×3), washed with brine (60 mL×3), dried over sodium sulfate, filtered out desiccant, and concentrated at reduced pressure to obtain the crude product, which was purified by Prep-TLC (DCM/MeOH=20/1) to give compound 47 (35 mg, 55%). LC-MS (ESI): m/z=591.0 [M+H]⁺; ¹H NMR (400 MHz, DMSO-d₆): δ 9.20 (1H, s), 8.67 (1H, d, J=1.2 Hz), 7.70 (1H, d, J=53.2 Hz), 7.61 (1H, d, J=1.2 Hz), 4.52 (3H, s), 4.49-4.29 (1H, m), 4.08-3.63 (2H, m), 3.62-3.35 (3H, m), 3.20-2.72 (2H, m), 1.46-1.39 (2H, m), 1.35-1.27 (2H, m).

Example 48 Synthesis of Compound 48

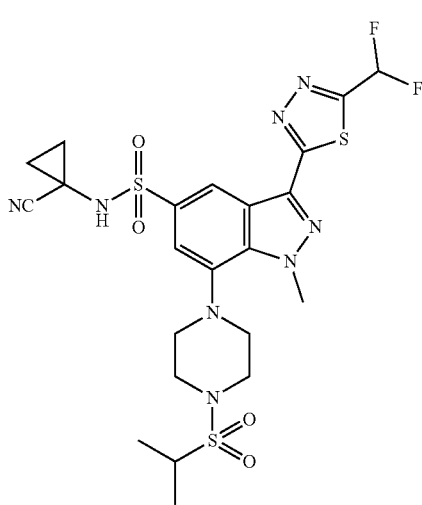

The title compound was synthesized according to synthesis of compound 29, using 28-b as the starting reactant, and 1-(isopropylsulfonyl)piperazine instead of morpholine.

Example 49 Synthesis of Compound 49

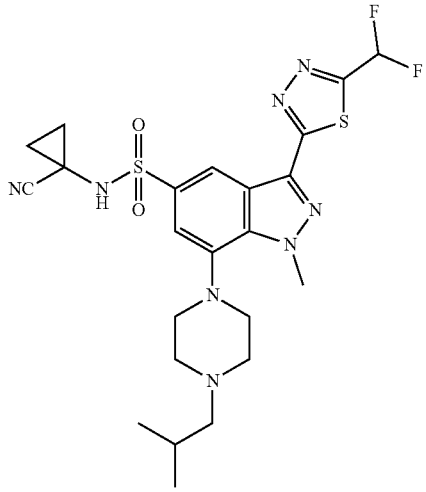

The title compound was synthesized according to synthesis of compound 29, using 28-b as the starting reactant, substituting N-isobutylpiperazine for morpholine. LC-MS (ESI): m/z 551.1 [M+H]$^+$; $^1$H NMR (DMSO-d$_6$, 400 MHz): δ 9.18 (1H, s), 8.62 (1H, s), 7.70 (1H, t, J=53.2 Hz), 7.56 (1H, s), 4.48 (3H, s), 2.72-3.30 (6H, m), 2.23-2.45 (2H, m), 2.17 (2H, d, J=7.2 Hz), 1.77-1.89 (1H, m), 1.39-1.49 (2H, m), 1.29-1.35 (2H, m), 0.96 (6H, d, J=6.4 Hz).

Example 50 Synthetic Route of Compound 50

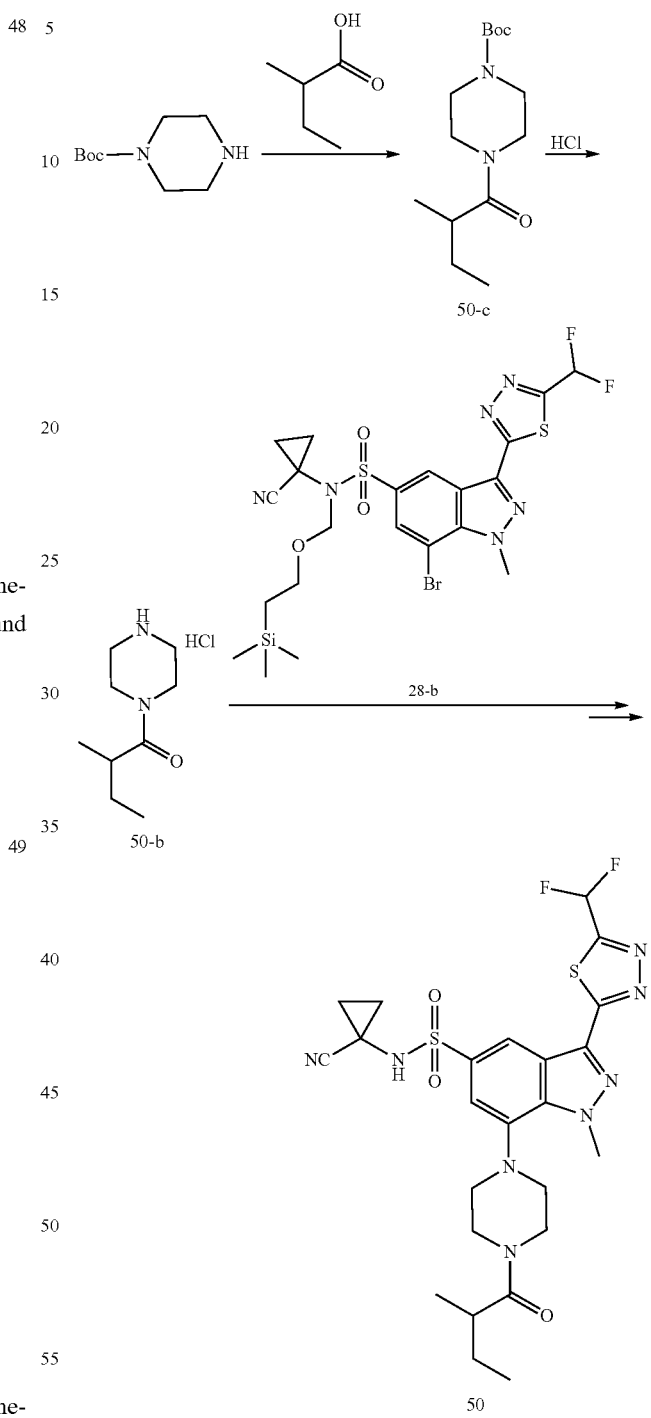

Synthesis of Compound 50-c

To a reaction vial charged with N-Boc-piperazine (500 mg, 2.68 mmol), dichloromethane (10 mL), DMAP (618 mg, 3.22 mmol) and EDCI (618 mg, 3.22 mmol) was added 2-methylbutyric acid (0.35 mL, 3.22 mmol) and the resulting mixture was stirred at room temperature overnight. The next day, the reaction was quenched with water, extracted with dichloromethane, washed with brine, dried over anhydrous sodium sulfate, concentrated to dryness and the residue was purified by column chromatography (mobile phase: ethyl acetate/petroleum ether: 0% to 50%) to give compound 50-c (700 mg, 96%). LC-MS (ESI): m/z=271.2 [M+H]$^+$.

Synthesis of Compound 50-b

A reaction flask charged with 50-c (700 mg, 2.59 mmol) and 1,4-dioxane (10 mL) was added Hydrochloric acid 1,4-dioxane solution (4 M, 3.24 mL, 12.96 mmol) dropwise in an ice-water bath and the reaction mixture was stirred at room temperature overnight. The next day, the reaction mixture was filtered and the resulting white filter cake was washed with a small amount of 1,4-dioxane and dried in vacuum to give compound 50-b (400 mg, 75%). LC-MS (ESI): m/z 171.2 [M+H]$^+$.

Synthesis of Compound 50

Referring to the synthesis of compound 29, compound 50 was synthesized using 28-b as the starting reactant and 50-b instead of morpholine. LC-MS (ESI): m/z 579.1 [M+H]$^+$.

Example 51 Synthetic Route of Compound 51

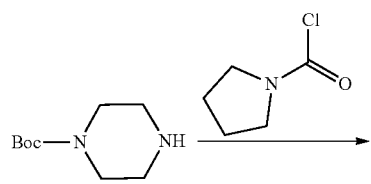

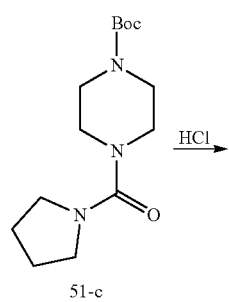

51-c

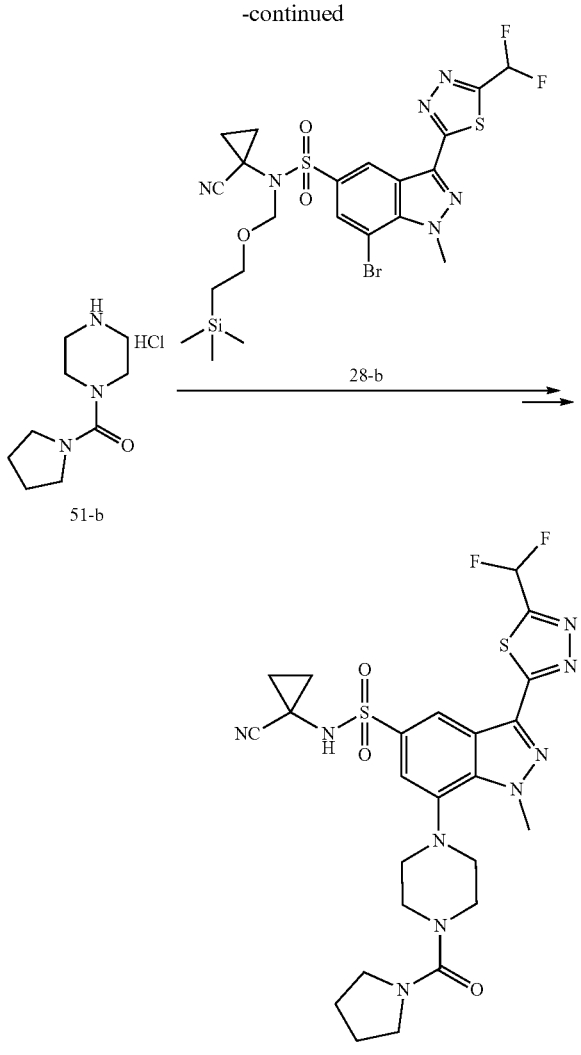

Synthesis of Compound 51-c 1-pyrrolidinecarbonyl chloride (0.59 mL, 5.37 mmol) was added dropwise to a reaction vial charged with N-Boc-piperazine (500 mg, 2.68 mmol), dichloromethane (5 mL) and triethylamine (1.12 mL, 8.05 mmol) in an ice-water bath and stirred at room temperature overnight. The next day, the reaction was quenched with water, extracted with dichloromethane, washed with brine, dried over anhydrous sodium sulfate, concentrated to dryness and the residue was purified by column chromatography (mobile phase: methanol/dichloromethane: 0% to 10%) to give compound 51-c (700 mg, 92%). LC-MS (ESI): m/z=284.2 [M+H]$^+$.

Synthesis of Compound 51-b

HCl/1,4-dioxane (4 M, 3.09 mL, 12.35 mmol) was added dropwise to a reaction flask charged with 51-c (700 mg, 2.47 mmol) and 1,4-dioxane (10 mL) in an ice-water bath, and the reaction mixture was stirred at room temperature overnight. The next day, the reaction mixture was filtered and the resulting white filter cake was washed with a small amount of 1,4-dioxane and dried in vacuum to give compound 51-b (400 mg, 74%). LC-MS (ESI): m/z 184.2 [M+H]$^+$.

Synthesis of Compound 51

Referring to the synthesis of compound 29, compound 51 was synthesized using 28-b as the starting reactant and 51-b instead of morpholine. LC-MS (ESI): m/z 592.1 [M+H]$^+$.

Example 52 Synthesis of Compound 52

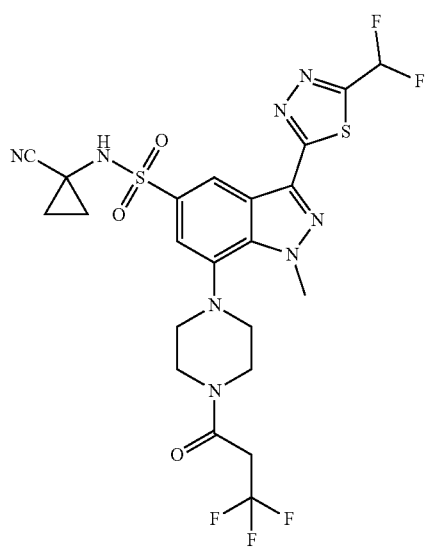

Referring to the synthesis of compound 29, compound 52 was synthesized using 28-b as the starting reactant and 3,3,3-trifluoro-1-(piperazin-1-yl)propan-1-one instead of morpholine. LC-MS (ESI): m/z=605.1[M+H]$^+$.

Example 53 Synthesis of Compound 53

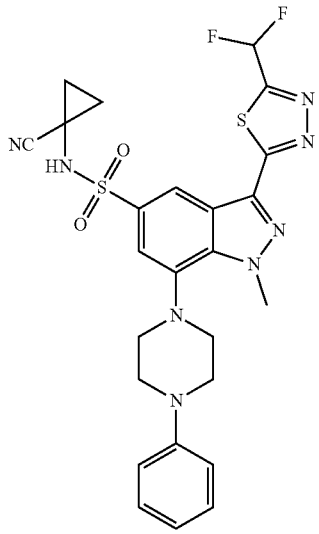

Referring to the synthesis of compound 29, compound 53 was synthesized using N-phenylpiperazine instead of morpholine with 28-b as the starting reactant. LC-MS(ESI):m/z=571.0[M+H]$^+$.

Example 54 Synthesis of Compound 54

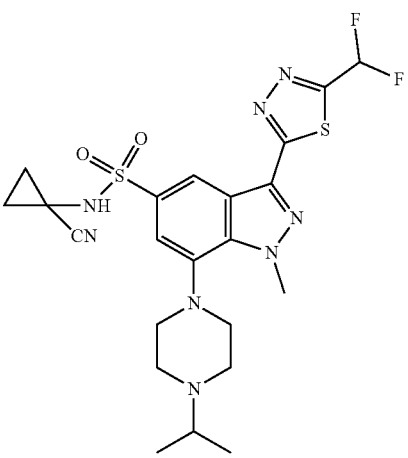

Referring to the synthesis of compound 17, compound 54 was synthesized by substituting 2-methyl-1-(piperazin-1-yl) propan-1-one with 1-isopropylpiperazine using 17-b as the starting reactant. LC-MS (ESI): m/z 537.1 (M+H)$^+$.

Example 55 Synthetic Route of Compound 55
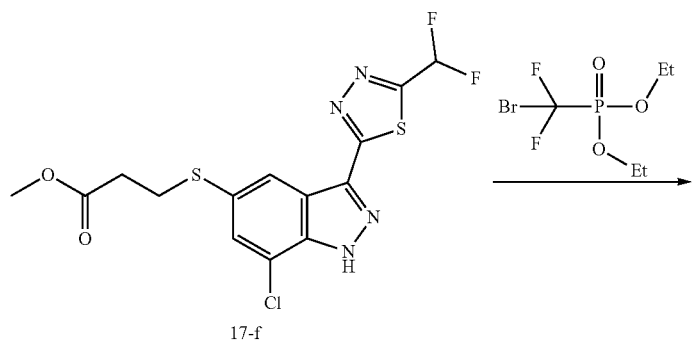
17-f
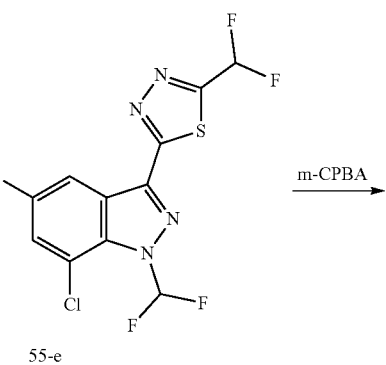
55-e
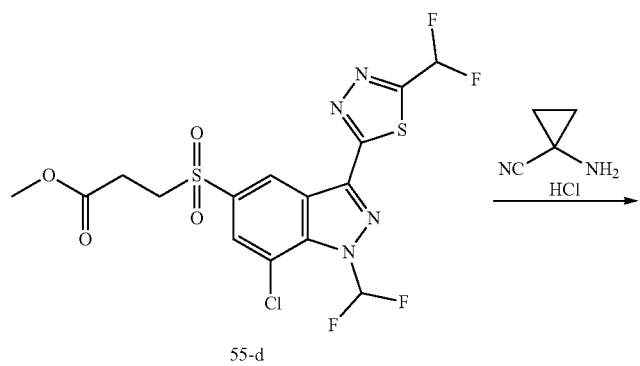
55-d
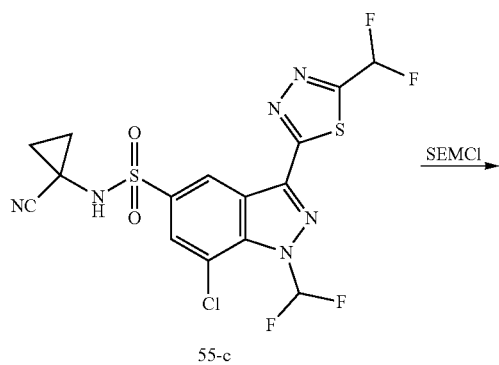
55-c -continued

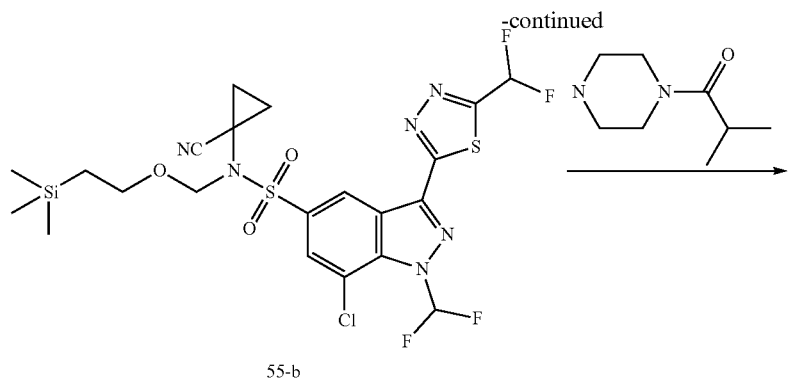

55-b

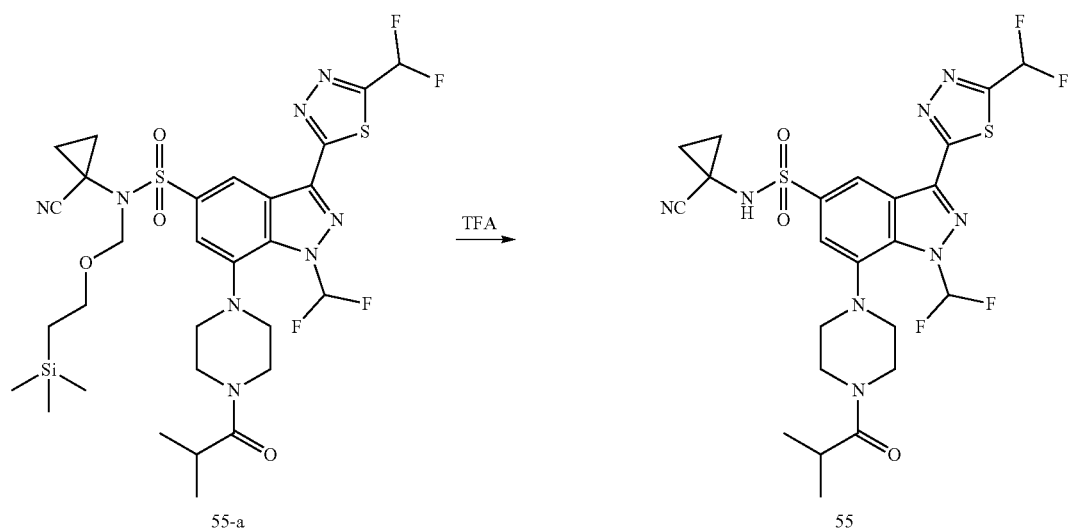 [SMILES: CC(C)C(=O)N1CCN(c2cc(S(=O)(=O)N(COCC[Si](C)(C)C)C3(C#N)CC3)cc3c(-c4nnc(C(F)F)s4)nn(C(F)F)c23)CC1 ; CC(C)C(=O)N1CCN(c2cc(S(=O)(=O)NC3(C#N)CC3)cc3c(-c4nnc(C(F)F)s4)nn(C(F)F)c23)CC1]

55-a

55

Synthesis of Compound 55-e

Potassium fluoride (115 mg, 1.98 mmol) and diethyl bromofluoromethylphosphonate (0.35 mL, 1.98 mmol) were added to a solution of 17-f (400 mg, 0.99 mmol) in acetonitrile (10 mL) at room temperature. After addition, the reaction was warmed up to 35° C. and stirred at this temperature overnight. After completion, the reaction was diluted by adding ethyl acetate, washed with water, brine, dried over anhydrous sodium sulfate, filtered, and the filtrate was evaporated to dryness to obtain the crude product, which was purified by a flash column chromatography (mobile phase: ethyl acetate/petroleum ether 0% to 50%) to give compound 55-e (120 mg, 27%). LC-MS (ESI): m/z=454.9 [M+H]$^+$.

Synthesis of Compound 55-d

To a solution of 55-e (120 mg, 0.26 mmol) in dichloromethane (10 mL) in an ice-water bath was added m-CPBA (137 mg, 0.79 mmol). After addition, the reaction was kept at 0° C. and stirred for 1 hour. After completion, the reaction was removed solvent by rotary evaporation at room temperature, diluted by adding ethyl acetate, washed with saturated sodium bicarbonate, brine, dried over anhydrous sodium sulfate, filtered, and the filtrate was evaporated to dryness to obtain the crude product, which was purified by a flash column chromatography (mobile phase: ethyl acetate/petroleum ether, 0% to 100%) to give compound 55-d (100 mg, 78%). LC-MS (ESI): m/z=487.0 [M+H]$^+$.

Synthesis of Compound 55-c

Sodium methanol (33 mg, 0.62 mmol) was added to a reaction flask charged with 55-d (100 mg, 0.21 mmol), methanol (10 mL) and dichloromethane (10 mL) at 0° C. in an ice-water bath, and the reaction mixture was kept in an ice-water bath for 1 h, then was added 1-amino-1-cyclopropanecarbonitrile hydrochloride (97 mg, 0.82 mmol), concentrated at room temperature to remove the solvent, and dried in vacuum for 20 minutes. The residue was combined with DMF (8 mL) and a small amount of 3 A molecular sieve. The resulting mixture was added triethylamine (0.06 mL, 0.41 mmol) and 1-amino-1-cyclopropanecarbonitrile hydrochloride (24 mg, 0.21 mmol) after stirred for 3 min in an ice-water bath, then was added NCS (55 mg, 0.41 mmol) in an ice-water bath. The reaction mixture was stirred for 1 h in an ice-water bath. The reaction was diluted with ethyl acetate, washed with sodium bisulfite solution, washed with water, brine, dried over anhydrous sodium sulfate, filtered, and the filtrate was evaporated to dryness to obtain 55-c (80 mg, 81%). LC-MS (ESI): m/z=480.9 [M+H]$^+$.

Synthesis of Compound 55-b

Triethylamine (0.093 mL, 0.67 mmol) and SEMCl (0.059 mL, 0.33 mmol) were added to a reaction vial charged with 55-c (80 mg, 0.17 mmol) and DCM (10 mL) in an ice-water bath. After addition, the reaction was warmed to room temperature and stirred for 1 h. The reaction was quenched with methanol (0.25 mL) in an ice-water bath and continued stirring was for 10 min. After completion, the solvent was removed by concentration at low temperature to give the crude product, which was purified by column chromatography (mobile phase: ethyl acetate/petroleum ether, 0% to 100%) to give compound 55-b (85 mg, 84%). LC-MS (ESI): m/z=611.0 [M+H]$^+$.

Synthesis of Compound 55-a

A microwave tube charged with 55-b (60 mg, 0.098 mmol), 2-methyl-1-(piperazin-1-yl)propan-1-one (31 mg, 0.20 mmol), Ruphos (18 mg, 0.039 mmol), Ruphos Pd G3 (16 mg, 0.020 mmol), cesium carbonate (96 mg, 0.30 mmol) and 1,4-dioxane (8 mL) was degassed and purged with nitrogen for 3 times, then heated at 60° C. overnight. After completion, the reaction was cooled to room temperature, removed the 1,4-dioxane by concentrated, diluted with ethyl acetate, washed with water, brine, dried over anhydrous sodium sulfate, filtered, and the filtrate was evaporated to dryness to obtain the crude product, which was purified by a flash column chromatography (mobile phase: ethyl acetate/petroleum ether, 0% to 100%) to give compound 55-a (40 mg, 56%). LC-MS (ESI): m/z 731.1 [M+H]$^+$.

Synthesis of Compound 55

A reaction flask charged with 55-a (40 mg, 0.055 mmol) and dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to dryness to obtain the crude product, which was purified by was purified by Prep-HPLC to afford the compound 55 (10 mg, 30%). LC-MS (ESI): m/z 601.0 [M+H]$^+$; $^1$H NMR (DMSO-$d_6$, 400 MHz): δ 9.08 (1H, bs), 8.60 (1H, t, J=57.2 Hz), 7.92 (1H, s), 7.79 (1H, t, J=52.8 Hz), 6.96 (1H, s), 3.35-3.88 (8H, m), 2.91-3.03 (1H, m), 1.39-1.49 (2H, m), 1.27-1.35 (2H, m), 1.05 (6H, d, J=6.4 Hz).

Example 56 Synthetic Route of Compound 56

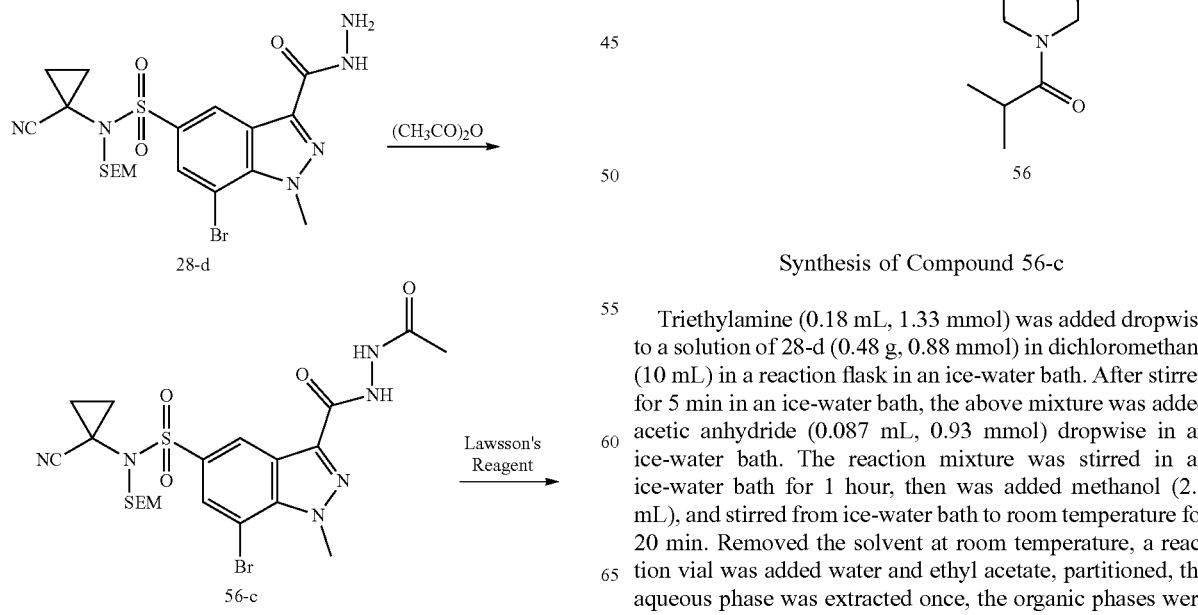

Synthesis of Compound 56-c

Triethylamine (0.18 mL, 1.33 mmol) was added dropwise to a solution of 28-d (0.48 g, 0.88 mmol) in dichloromethane (10 mL) in a reaction flask in an ice-water bath. After stirred for 5 min in an ice-water bath, the above mixture was added acetic anhydride (0.087 mL, 0.93 mmol) dropwise in an ice-water bath. The reaction mixture was stirred in an ice-water bath for 1 hour, then was added methanol (2.5 mL), and stirred from ice-water bath to room temperature for 20 min. Removed the solvent at room temperature, a reaction vial was added water and ethyl acetate, partitioned, the aqueous phase was extracted once, the organic phases were combined, washed with water, brine, dried over anhydrous sodium sulfate, filtered, and the filtrate was evaporated to dryness to obtain the crude product, which was purified by column chromatography (mobile phase: petroleum ether/ethyl acetate, 100/0 to 60/40) to give 56-c (0.45 g, 87%). LC-MS (ESI): m/z 585.0 [M+H]$^+$.

Synthesis of Compound 56-b

A reaction flask charged with 56-c (0.45 g, 0.77 mmol), Lawesson's reagent (0.78 g, 1.92 mmol) and THF (20 mL) was stirred at 80° C. for 10 hours under nitrogen atmosphere. Cooled to room temperature and removed the solvent by rotary evaporation. The crude product was diluted with ethyl acetate/petroleum ether mixture, washed with aqueous sodium bicarbonate 3 times, brine, dried over anhydrous sodium sulfate, filtered, and the filtrate was evaporated to dryness to obtain the crude product, which was added ammonia-methanol/methanol/dichloromethane (1:1:20) solution (20 mL) and stirred at room temperature for 2 hours. Evaporated to dryness and the residue was purified by column chromatography (mobile phase: petroleum ether/ethyl acetate, 100/0 to 70/30) to give 56-b (0.2 g, 45%). LC-MS (ESI): m/z 583.0 [M+H]$^+$.

Synthesis of Compound 56-a

A microwave tube charged with 56-b (80 mg, 0.14 mmol), 2-methyl-1-(piperazin-1-yl)propan-1-one (43 mg, 0.27 mmol), Ruphos (26 mg, 0.055 mmol), Ruphos Pd G3 (23 mg, 0.027 mmol), cesium carbonate (134 mg, 0.41 mmol) and 1,4-dioxane (8 mL) was degassed and purged with nitrogen for 3 times, then heated at 60° C. overnight. After completion, the reaction was cooled to room temperature, removed 1,4-dioxane by concentration at reduced pressure, diluted with ethyl acetate, washed with water, brine, dried over anhydrous sodium sulfate, filtered, and the filtrate was evaporated to dryness to obtain the crude product, which was purified by a flash column chromatography (mobile phase: ethyl acetate/petroleum ether, 0% to 100%) to give compound 56-a (60 mg, 66%). LC-MS (ESI): m/z 659.4 [M+H]$^+$.

Synthesis of Compound 56

Trifluoroacetic acid (1 mL) was added dropwise to a solution of 56-a (60 mg, 0.091 mmol) in dichloromethane (5 mL) in a reaction flask at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to dryness to obtain the crude product, which was purified by Prep-TLC (PE:EA=1:2) to give compound 56 (25 mg, 52%). LC-MS (ESI): m/z 529.2 [M+H]$^+$.

Example 57 Synthetic Route of Compound 57

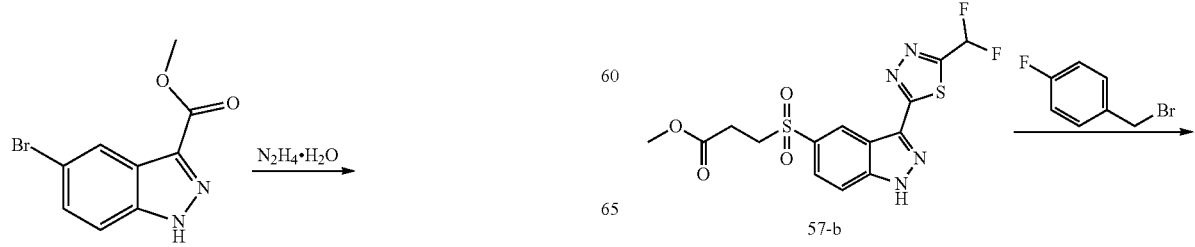

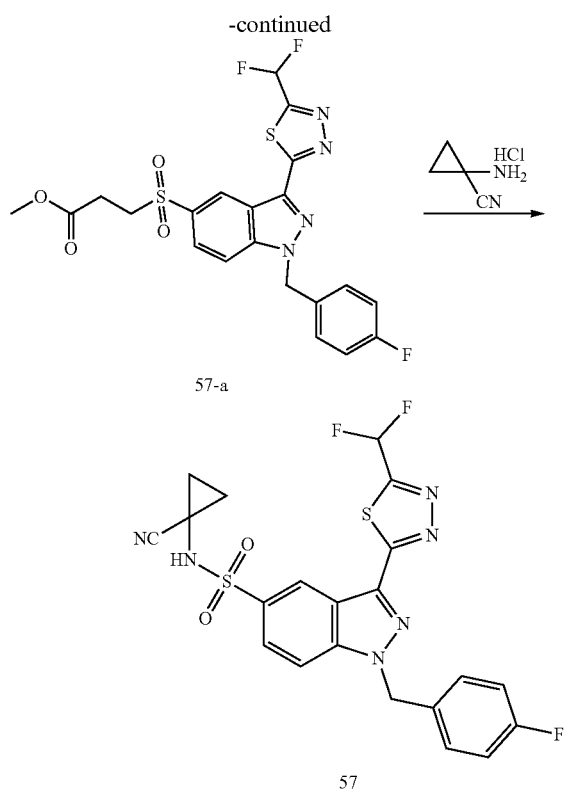

Synthesis of Compound 57-f

A reaction flask charged with methyl 5 bromo-1H-indazole-3-carboxylate (2.55 g, 9.997 mmol), D (12.5 mL) and ethanol (12.5 mL) was added Hydrazine hydrate (2.5 mL, 51.538 mmol) dropwise at room temperature. The reaction mixture was stirred at 55° C. for 6 hours. The ethanol was removed by rotary evaporation, poured into ice-water, filtered and dried to give 57-f (2.40 g, 94%). LC-MS (ESI): m/z 255.0 (M+H)+.

Synthesis of Compound 57-e

A reaction flask charged with 57-f (2.40 g, 9.41 mmol), dichloromethane (20 mL) and DMF (10 me) with added triethylamine (1.962 mL, 14.114 mmol) in an ice-water bath, and difluoroacetic anhydride (1.97 g, 11.291 mmol) dropwise (6 times, every 5 min) in an ice-water bath. The reaction mixture was stirred in an ice-water bath for 30 min after the dropwise addition. Removed dichloromethane by rotary evaporation. The residual suspension was added to ice-water, filtered and dried to give 57-e (2.9 g, 93%). LC-MS (ESI): m/z 332.9 (M+H)+.

Synthesis of Compound 57-d

A reaction flask charged with 57-e (2.9 g, 8.706 mmol), Lawesson's reagent (4.6 g, 11.373 mmol) and tetrahydrofuran (40 mL) was reflux for 3 h under nitrogen atmosphere. Cooled to room temperature, the reaction was removed solvent by rotary evaporation. The residue was diluted with ethyl acetate, dichloromethane and petroleum ether, washed twice with saturated sodium bicarbonate, once with brine, dried over anhydrous sodium sulfate, filtered, and the filtrate was evaporated to dryness to obtain the crude product, which was purified by column chromatography (mobile phase: petroleum ether/ethyl acetate, 100/0 to 80/20, mixed with ethyl acetate, product solubility was poor and trailing) to afford compound 57-d (2.5 g, 87%). LC-MS(ESI): m/z 330.8 (M+H)+.

Synthesis of Compound 57-c

A reaction flask was sequentially charged with 57-d (500 mg, 1.510 mmol), $Pd_2(dba)_3$ (69.13 mg, 0.075 mmol), XANT PHOS (87.37 mg, 0.151 mmol), 1,4-dioxane (6 mL), DIPEA (586 mg, 4.534 mmol) and 3-mercaptopropionic acid methyl ester (362.90 mg, 3.020 mmol). After degassed and purged with nitrogen for 3 times, the reaction mixture was heated at 110° C. and stirred for 3 h. A large amount of solid was precipitated. Cooled to room temperature, the solvent was removed by rotary evaporation, diluted with ethyl acetate, washed twice with water, and the suspension was concentrated to dryness to give 57-c (559 mg, 100%). LC-MS (ESI): m/z 371.0 (M+H)+.

Synthesis of Compound 57-b

A reaction flask charged with 57-c (559 mg, 1.51 mmol) and dichloromethane (20 mL) was added m-CPBA (651 mg, 3.773 mmol) in an ice-water bath. The reaction mixture was stirred in an ice-water bath for 1 h. Supplemented with m-CPBA (469 mg, 2.72 mmol). The reaction mixture was stirred in an ice-water bath for 1 hour. The solvent was concentrated at room temperature, diluted with ethyl acetate, washed 5 times with 5% aqueous sodium bicarbonate, evaporated and the residue was purified on a silica column (mobile phase: petroleum ether/ethyl acetate, 100/0 to 80/20) to give compound 57-b (450 mg, 74%). LC-MS (ESI): m/z 403.0 (M+H)+.

Synthesis of Compound 57-a

Potassium carbonate (69 mg, 0.50 mmol) and 4-fluorobenzylbromide (71 mg, 0.37 mmol) were added to a solution of 57-b (100 mg, 0.25 mmol) in DMF (5 mL) at room temperature. After addition, the reaction was stirred at room temperature for 6 h. After completion, the reaction was diluted by adding ethyl acetate, washed with water, brine, dried over anhydrous sodium sulfate, filtered and the filtrate was evaporated. The residue was purified by a flash column chromatography (mobile phase: ethyl acetate/petroleum ether 0% to 100%) to afford compound 57-a (100 mg, 79%). LC-MS (ESI): m/z=511.1 [M+H]+.

Synthesis of Compound 57

A reaction flask charged with 57-a (100 mg, 0.20 mmol), methanol (10 mL) and dichloromethane (10 mL) was added sodium methanol (32 mg, 0.59 mmol) at 0° C. in an ice-water bath. The reaction mixture was kept in an ice-water bath for 1 hr, was added 1-amino-1-cyclopropanecarbonitrile hydrochloride (93 mg, 0.78 mmol), concentrate at room temperature to remove the solvent, and then dried in vacuum for 20 minutes. The residue was combined with DMF (8 mL) and a small amount of 3 A molecular sieve. After stirred in an ice-water bath for 3 min, the resulting mixture was added triethylamine (0.054 mL, 0.39 mmol) and 1-amino-1-cyclopropanecarbonitrile hydrochloride (23 mg, 0.20 mmol), then was added NCS (52 mg, 0.39 mmol) in an ice-water bath. The reaction mixture was stirred for 1 h in an ice-water bath. The reaction mixture was diluted with ethyl acetate, washed with sodium bisulfite solution, water, brine, dried over anhydrous sodium sulfate, filtered and the filtrate was evaporated. The residue was purified by a flash column chromatography (mobile phase: ethyl acetate/petroleum ether 0% to 100%) to give compound 57 (50 mg, 51%). LC-MS (ESI): m/z 505.0 (M+H)⁺; ¹H NMR (DMSO-d₆, 400 MHz): δ 9.26 (1H, s), 8.93 (1H, d, J=1.2 Hz), 8.24 (1H, d, J=8.8 Hz), 7.98 (1H, dd, J=8.8, 1.6 Hz), 7.71 (1H, t, J=53.2 Hz), 7.34-7.44 (2H, m), 7.12-7.21 (2H, m), 5.91 (2H, s), 1.38-1.46 (2H, m), 1.24-1.32 (2H, m).

Example 58 Synthetic Route of Compound 58

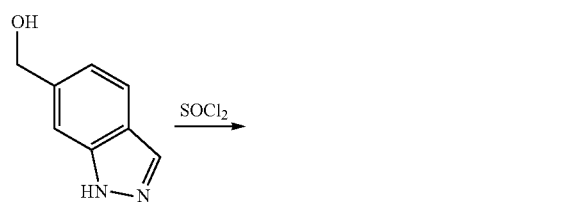

Synthesis of Compound 58-b

Sulfoxide chloride (1.45 mL, 20.45 mmol) was added carefully dropwise to a solution of 1H-indazole-6-methanol (300 mg, 2.02 mmol) in dichloromethane (10 mL) in a reaction flask in an ice-water bath. After addition, the reaction was raised to 40° C. and stirred for 6 hours. After completion, the reaction mixture was removed the solvent by concentration at reduced pressure, then diluted by adding ethyl acetate, washed with saturated aqueous sodium bicarbonate, washed with brine, dried over anhydrous sodium sulfate, filtered, and evaporated. The residue was purified by a flash column chromatography (mobile phase: ethyl acetate/petroleum ether 0% to 100%) to give compound 58-b (300 mg, 89%). LC-MS (ESI): m/z=167.1 [M+H]⁺.

Synthesis of Compound 58-a

Potassium carbonate (34 mg, 0.25 mmol) and 58-b (31 mg, 0.19 mmol) were added to a solution of 57-b (50 mg, 0.12 mmol) in DMF (5 mL) at room temperature. After addition, the reaction were stirred at room temperature for 6 h. After completion, the reaction was diluted by adding ethyl acetate, washed with water, brine, dried over anhydrous sodium sulfate, filtered and the filtrate was evaporated. The compound 58-a (40 mg, 60%) was purified by a flash column chromatography (mobile phase: methanol/dichloromethane 0% to 10%). LC-MS (ESI): m/z=533.1 [M+H]⁺.

Synthesis of Compound 58

A reaction vial charged with 58-a (40 mg, 0.075 mmol), methanol (10 mL) and dichloromethane (10 mL). was added sodium methanol (12 mg, 0.23 mmol) at 0° C., and the reaction mixture was kept in an ice-water bath for 1 hr, then was added 1-methylcyclopropylamine hydrochloride (32 mg, 0.30 mmol), concentrate at room temperature to remove the solvent, and then dried in vacuum for 20 minutes. The residue was combined with DMF (8 mL) and a small amount of 3 A molecular sieve. After stirred in an ice-water bath for 3 min, the resulting mixture was added triethylamine (0.02 mL, 0.15 mmol) and 1-methylcyclopropylamine hydrochloride (8 mg, 0.075 mmol). Then was added NCS (20 mg, 0.15 mmol) in the ice-water bath. The reaction mixture was stirred in an ice-water bath for 1 hour. The product was diluted with ethyl acetate, washed with sodium bisulfite solution, water, brine, dried over anhydrous sodium sulfate, filtered and the filtrate was evaporated. The residue was purified by Prep-HPLC to give 58 (15 mg, 39%). LC-MS (ESI): m/z=516.0 [M+H]⁺.

Example 59 Synthesis of Compound 59

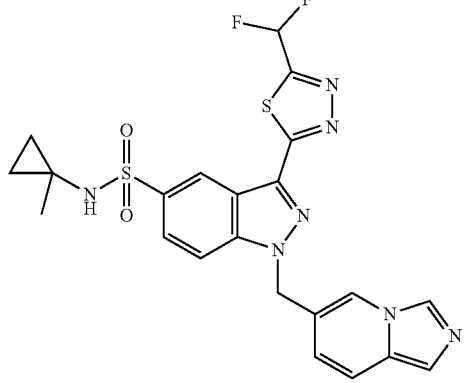

59

Referring to the synthesis of compound 58, compound 59 was synthesized by substituting 58-b with 6-(chloromethyl)imidazo[1,5-a]pyridine using 57-b as the starting reactant. LC-MS (ESI): m/z=516.0 [M+H]⁺.

Example 60 Synthetic Route of Compound 60

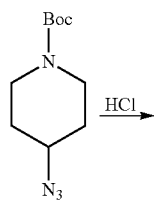

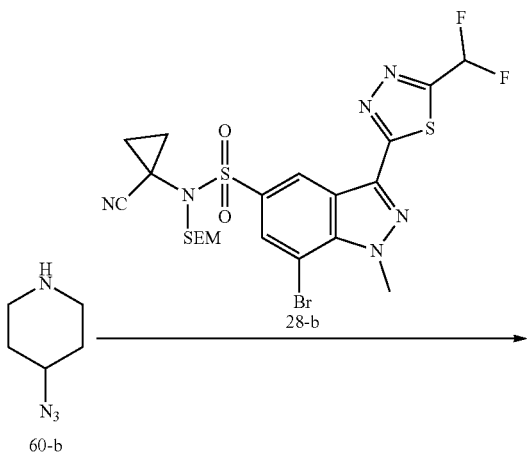

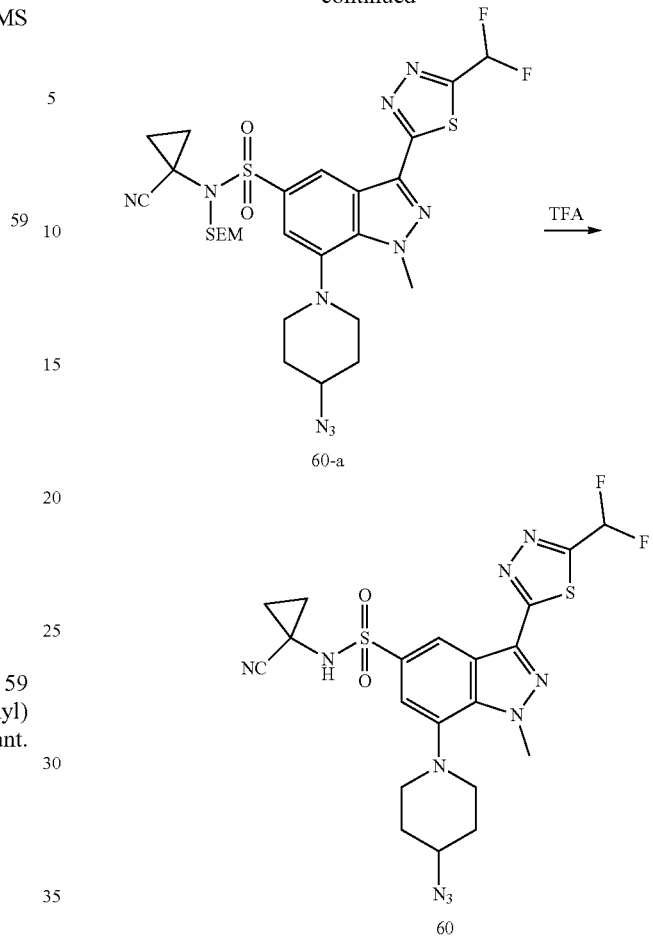

Synthesis of Compound 60-b

HCl/1,4-dioxane (6 mL) was added dropwise to a solution of compound 4-azidopiperidine-1-carboxylic acid tert-butyl ester (300 mg, 1.33 mmol) in 1,4-dioxane (0.5 mL) in an ice-water bath, and the reaction mixture was stirred at room temperature for 12 h. The reaction mixture was concentrated at reduced pressure, and methanol (8 mL) and potassium carbonate (600 mg) were added to the residue, and the mixture was stirred at room temperature for 1 h. The mixture was filtered through celite, and the filter cake was washed with dichloromethane (50 mL). The filtrate was combined and concentrated at reduced pressure. The residue was purified by column chromatography (mobile phase, DCM/7M ammonia-methanol 10/1) to give compound 60-b (75 mg, 45%). LC-MS (ESI): m/z 127.2 (M+H)⁺.

Synthesis of Compound 60-a

Compound 28-b (100 mg, 0.16 mmol), 2-dicyclohexylphosphino-2',6'-diisopropoxy-1,1'-biphenyl (30 mg, 0.07 mmol), (2-dicyclohexylphosphino-2',6'-diisopropoxy-1,1'-biphenylyl)(2-amino-1,1'-biphenyl-2-yl)palladium(II) methanesulfonate (27 mg, 0.03 mmol), cesium carbonate (158 mg, 0.48 mmol) was added to 1,4-dioxane (10 mL) followed by 60-b (71 mg, 0.57 mmol), and the reaction mixture was degassed and purged with nitrogen for 10 times and then was stirred at 64° C. in a sealed tube for 15 hours.

The reaction mixture was cooled to room temperature, filtered through celite, and the filtrate was concentrated at reduced pressure to obtain the crude product, which was purified by column chromatography (mobile phase, PE/EA=3/1) to give compound 60-a (70 mg, 65%). LC-MS (ESI): m/z 665.2 (M+H)$^+$.

Synthesis of Compound 60

Compound 60-a (70 mg, 0.11 mmol) was dissolved in dichloromethane (3 mL) and trifluoroacetic acid (1 mL) was added to the above solution at 0° C. The reaction was stirred at room temperature for 2 h. The reaction mixture was removed dichloromethane by rotary evaporation, and the pH was adjusted to 7-8 with saturated sodium bicarbonate solution, extracted with ethyl acetate (100 mL), and the crude product was obtained by rotary evaporation at reduced pressure, and the crude product was purified by preparative HPLC (basic conditions) to give compound 60 (8 mg, 14%). LC-MS (ESI): m/z 535.1 (M+H)$^+$.

Example 61 Synthetic Route of Compound 61

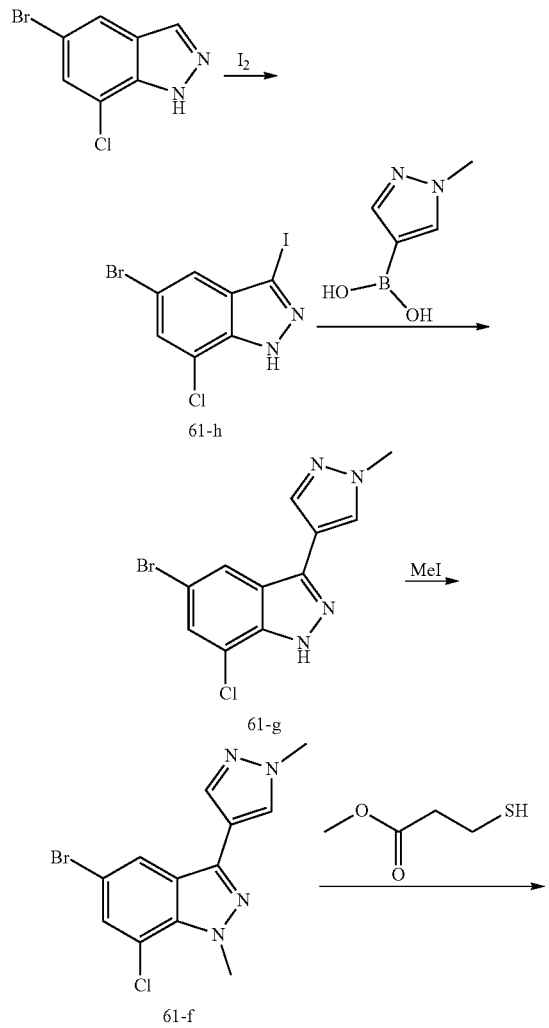

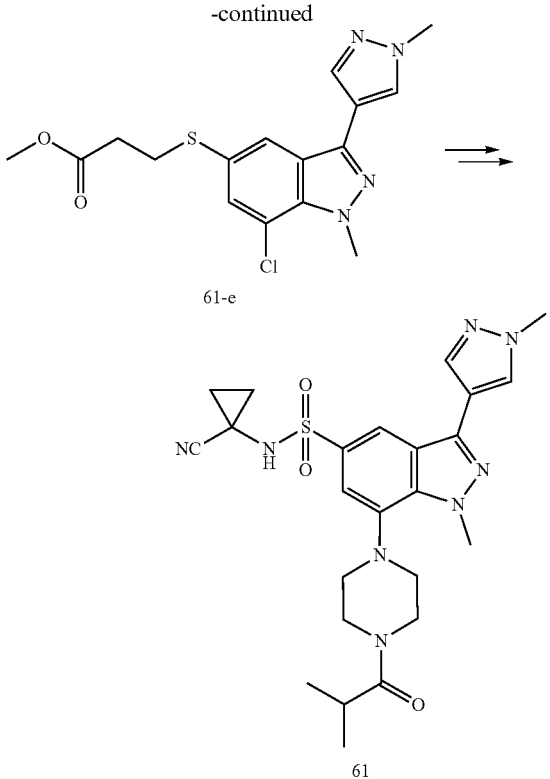

Synthesis of Compound 61-h

The compound 5-bromo-7-chloro-1H-indazole (400 mg, 1.73 mmol) was dissolved in N,N-dimethylformamide (6 mL), to which potassium hydroxide (194 mg, 3.46 mmol) was added, and a solution of iodine (1150 mg, 4.53 mmol) dissolved in N,N-dimethylformamide (1 mL) was added dropwise to the above at 0° C. After addition, the reaction mixture was stirred for 3 h at room temperature, and was added saturated sodium bisulfite solution dropwise until the brownish red color of the reaction mixture faded, to which was added water (100 mL), extracted with ethyl acetate (100 mL), washed with brine (100 mL), dried over sodium sulfate, filtered out the desiccant, and concentrated at reduced pressure to obtain the crude product, which was purified by column chromatography (mobile phase, PE/EA=3/1) to obtain Compound 61-h (592 mg, 96%).

Synthesis of Compound 61-g

Compound 61-h (492 mg, 1.38 mmol), 1-methyl-1H-pyrazole-4-boronic acid (260 mg, 2.06 mol), and potassium phosphate (731 mg, 3.44 mmol) were added to 1,4-dioxane (40 mL) and water (10 mL) and stirred under nitrogen for 5 min, to which was added 1,1'-bis(diphenylphosphino) ferrocene palladium dichloride (50 mg, 0.07 mmol). After degassed and purged with nitrogen for three times, the reaction mixture was stirred at 77° C. for 3 h under nitrogen atmosphere, was added water (200 mL) and extracted with ethyl acetate (200 mL). The organic phases were washed with brine (100 mL), dried over sodium sulfate, filtered out desiccant and concentrated at reduced pressure to obtain the crude product. The crude product was purified by column chromatography (mobile phase, PE/EA=1/1 to EA) to give compound 61-g (300 mg, 70%). LC-MS (ESI): m/z 310.9 (M+H)⁺.

Synthesis of Compound 61-f

Compound 61-g (300 mg, 0.96 mmol) was dissolved in N,N-dimethylformamide (15 mL), to which cesium carbonate (627 mg, 1.93 mmol) and iodomethane (205 mg, 1.44 mmol) were added. The reaction mixture was stirred at room temperature for 1.5 h, added water (200 mL) and extracted with ethyl acetate (200 mL). The organic phases were washed with brine (100 mL), dried over sodium sulfate, filtered out desiccant and concentrated at reduced pressure to give the crude product, which was purified by column chromatography (mobile phase, PE/EA=1/1) to give compound 61-f (235 mg, 75%). LC-MS (ESI): m/z 324.9 (M+H)⁺.

Synthesis of Compound 61-e

Methyl 3-mercaptopropionate (104 mg, 0.87 mmol) was added to a solution of compound 61-f (235 mg, 0.72 mmol), tris(dibenzylideneacetone)dipalladium (66 mg, 0.07 mmol), 4,5-bis(diphenylphosphino)-9,9-dimethyloxanthene (84 mg, 0.14 mmol), diisopropylethylamine (280 mg, 2.17 mmol) in 1.4-dioxane (20 mL). After degassed and purged with nitrogen for 3 times, the reaction mixture was stirred at 80° C. for 3 hours. The reaction mixture was concentrated to give the crude product, which was purified by column chromatography (mobile phase, PE/EA=1/1) to give compound 61-e (255 mg, 97%). LC-MS (ESI): m/z 365.5 (M+H)⁺.

Synthesis of Compound 61

Referring to the synthesis of compound 17, compound 61 was synthesized using 61-e instead of 17-e. LC-M (ESI): m/z 511.2 (M+H)⁺; ¹H NMR (400 MHz, DMSO-d₆): δ 8.95 (s, 1H), 8.35 (s, 1H), 8.12 (s, 1H), 7.93 (s, 1H), 7.43 (d, J=4.0 Hz, 1H), 4.65-4.38 (m, 1H), 4.37 (s, 3H), 4.20-4.04 (m, 1H), 3.96 (s, 3H), 3.63-3.37 (m, 2H), 3.30-3.15 (m, 1H), 3.02-2.91 (m, 2H), 2.86-2.58 (m, 2H), 1.43-1.37 (m, 2H), 1.32-1.26 (m, 2H), 1.05 (d, J=8.0 Hz, 6H).

Example 62 Synthetic Route of Compound 62

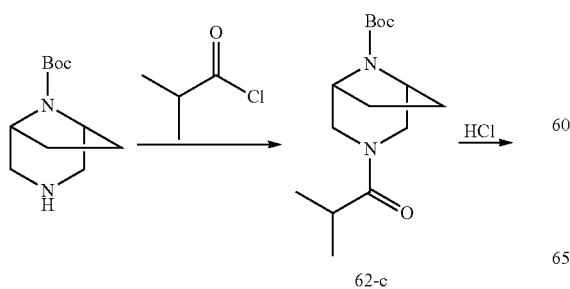

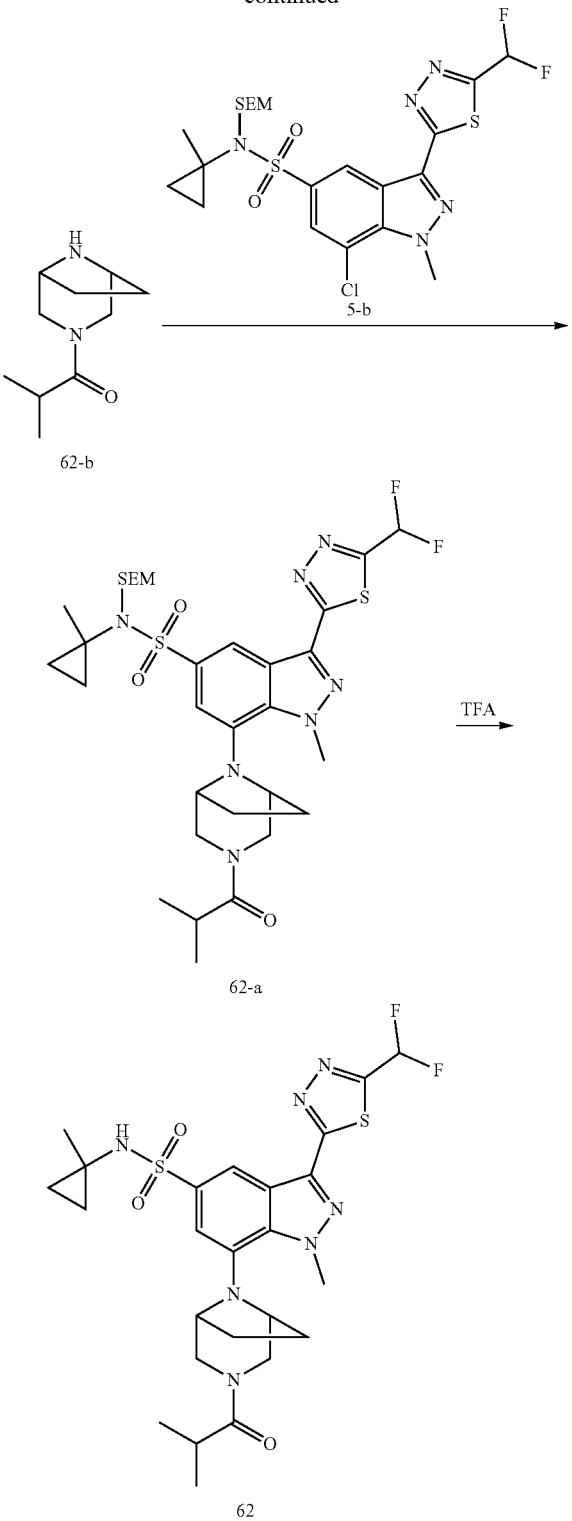

Synthesis of Compound 62-c

Compound 3,8-diazabicyclo[3.2.1]octane-8-carboxylic acid tert-butyl ester (300 mg, 1.41 mmol) was dissolved in dichloromethane (15 mL), to which triethylamine (315 mg, 3.11 mmol) was added, and isobutyryl chloride (181 mg, 1.70 mmol) was added dropwise at 0° C. After stirring at room temperature overnight, the reaction mixture was concentrated at reduced pressure to obtain the crude product, to which water (100 mL) was added and extracted with ethyl acetate (100 mL). The organic phase was washed with brine (100 mL), dried over sodium sulfate, filtered out the desiccant and concentrated at reduced pressure to give the crude product, which was purified by column chromatography (mobile phase, PE/EA=1/1) to give compound 62-c (365 mg, 91%). LC-MS (ESI): m/z 283.2 (M+H)+.

Synthesis of Compound 62-b

Compound 62-c (365 mg, 1.29 mmol) was dissolved in 1,4-dioxane (2 mL), to which 4 M HCl/1,4-dioxane (12 mL) was added, and the reaction was stirred at room temperature for 2 h. The reaction mixture was concentrated at reduced pressure to obtain the crude product, which was added methanol (10 mL) and potassium carbonate (600 mg), and the mixture was stirred at room temperature for 20 min, then filtered through celite, and the filter cake was washed with dichloromethane (50 mL), and the filtrate was filtered through celite, concentrated to give the crude product, which was dried in vacuum by an oil pump to obtain compound 62-b (200 mg, 85%). LC-MS (ESI): m/z 183.1 (M+H)+.

Synthesis of Compound 62-a

Compound 5-b (100 mg, 0.18 mmol), 2-dicyclohexylphosphino-2',6'-diisopropoxy-1,1'-biphenyl (33 mg, 0.07 mmol), (2-dicyclohexylphosphino-2',6'-diisopropoxy-1,1'-biphenylyl)(2-amino-1,1'-biphenyl-2-yl)palladium(II)methanesulfonate (30 mg, 0.04 mmol), cesium carbonate (173 mg, 0.53 mmol) were added to 1,4-dioxane (10 mL). The mixture was stirred at room temperature for 5 min and then was added 62-b (65 mg, 0.36 mmol), purged with nitrogen for 3 min and then stirred at 68° C. in a sealed tube for 15 hours. The reaction mixture was cooled to room temperature, filtered through celite, and the filtrate was concentrated at reduced pressure to obtain the crude product, which was purified by column chromatography (mobile phase, PE/EA=1/1) to give compound 62-a (60 mg, 48%). LC-MS (ESI): 710.7 m/z (M+H)+.

Synthesis of Compound 62

Compound 62-a (60 mg, 0.09 mmol) was dissolved in dichloromethane (6 mL) and trifluoroacetic acid (2 mL) was added to the above mixture at 0° C. The reaction mixture was stirred for 2 h at room temperature. The reaction mixture was removed dichloromethane by rotary evaporation, and the pH was adjusted to 7-8 with saturated sodium bicarbonate solution and extracted with ethyl acetate (100 mL). The organic phase was washed with brine (100 mL), dried over sodium sulfate, filtered out the desiccant and concentrated at reduced pressure to obtain the crude product, which was purified by preparative HPLC (basic conditions) to give compound 62 (8 mg, 16%). LC-MS (ESI): m/z 580.2 (M+H)+; $^1$H NMR (400 MHz, DMSO-$d_6$): δ 8.51 (s, 1H), 8.23 (s, 1H), 7.68 (t, J=52.0 Hz, 1H), 7.29 (s, 1H), 4.54 (s, 3H), 4.28-4.23 (m, 1H), 4.12-4.00 (m, 2H), 3.92-3.87 (m, 1H), 3.67-3.62 (m, 1H), 3.14-3.08 (m, 1H), 2.97-2.88 (m, 1H), 1.97-1.90 (m, 2H), 1.82-1.72 (m, 1H), 1.67-1.58 (m, 1H), 1.12-1.00 (m, 9H), 0.64-0.59 (m, 2H), 0.39-0.35 (m, 2H).

Example 63 Synthetic Route of Compound 63

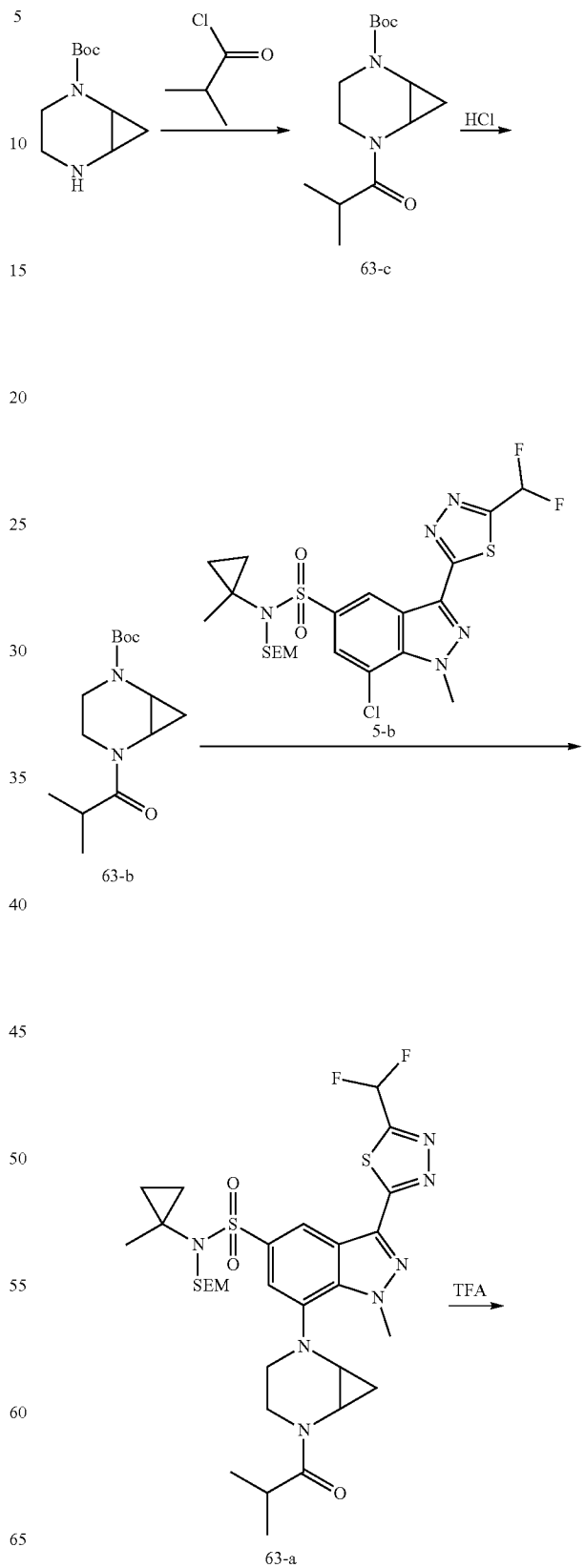

249

-continued

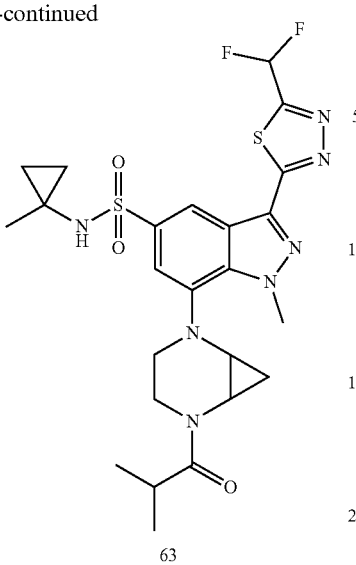

63

Synthesis of Compound 63-c

To a reaction vial charged with tert-butyl 2,5-diazabicyclo[4.1.0]heptane-2-carboxylate (250 mg, 1.26 mmol), dichloromethane (10 mL) and triethylamine (0.53 mL, 3.78 mmol) was added isobutyryl chloride (0.20 mL, 1.89 mmol) dropwise in an ice-water bath and stirred at room temperature overnight. The next day, the reaction was quenched with water, extracted with dichloromethane, washed with brine, dried over anhydrous sodium sulfate, concentrated to dryness and the residue was purified by column chromatography (mobile phase: methanol/dichloromethane: 0% to 10%) to give compound 63-c (300 mg, 89%). LC-MS (ESI): m/z=269.2 $[M+H]^+$.

Synthesis of Compound 63-b

To a reaction flask charged with 63-c (300 mg, 1.12 mmol) and 1,4-dioxane (10 mL) was added HCl/1,4-dioxane solution (4 M, 1.40 mL, 5.60 mmol) dropwise in an ice-water bath and the reaction mixture was stirred at room temperature for 2 hours. After completion, the reaction was removed solvent by concentration at reduced pressure, and the crude product was dissolved in methanol, neutralized by adding sodium bicarbonate powder and stirred for half an hour. Filtered, and the filtrated was concentrated and dried in vacuum to give compound 63-b (150 mg, 80%). LC-MS (ESI): m/z 169.2 $[M+H]^+$.

Synthesis of Compound 63-a

A microwave tube charged with 5-b (100 mg, 0.18 mmol), 63-b (60 mg, 0.36 mmol), Xantphos (21 mg, 0.036 mmol), $Pd_2dba_3$ (16 mg, 0.018 mmol), cesium carbonate (173 mg, 0.53 mmol) and 1,4-dioxane (8 mL) was degassed and purged with nitrogen for 3 times. The reaction mixture was heated at 85° C. overnight. Upon completion, the reaction was cooled to room temperature, removed 1,4-dioxane by concentration at reduced pressure, diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 63-a (40 mg, 32%). LC-MS (ESI): m/z 713.3 $[M+NH_4]^+$.

Synthesis of Compound 63

A reaction flask charged with 63-a (40 mg, 0.057 mmol), dichloromethane (5 mL) was added trifluoroacetic acid (1 mL) dropwise at room temperature. The reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to dryness to obtain the crude product, which was purified by Prep-HPLC to afford compound 63 (10 mg, 31%). LC-MS (ESI): m/z 566.0 $[M+H]^+$.

Example 64 Synthetic Route of Compound 64

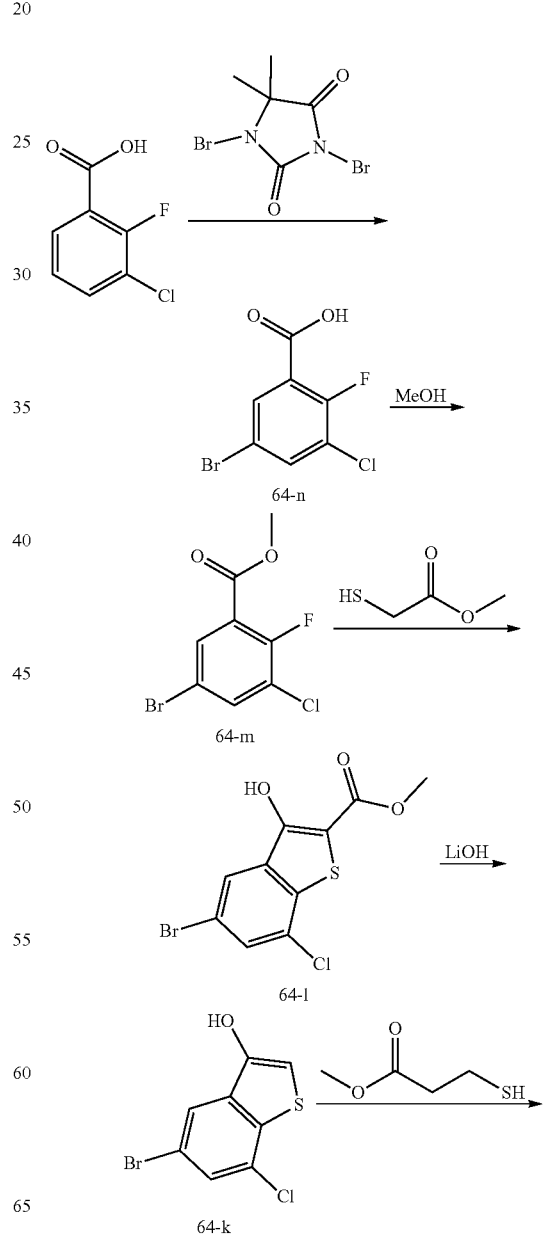

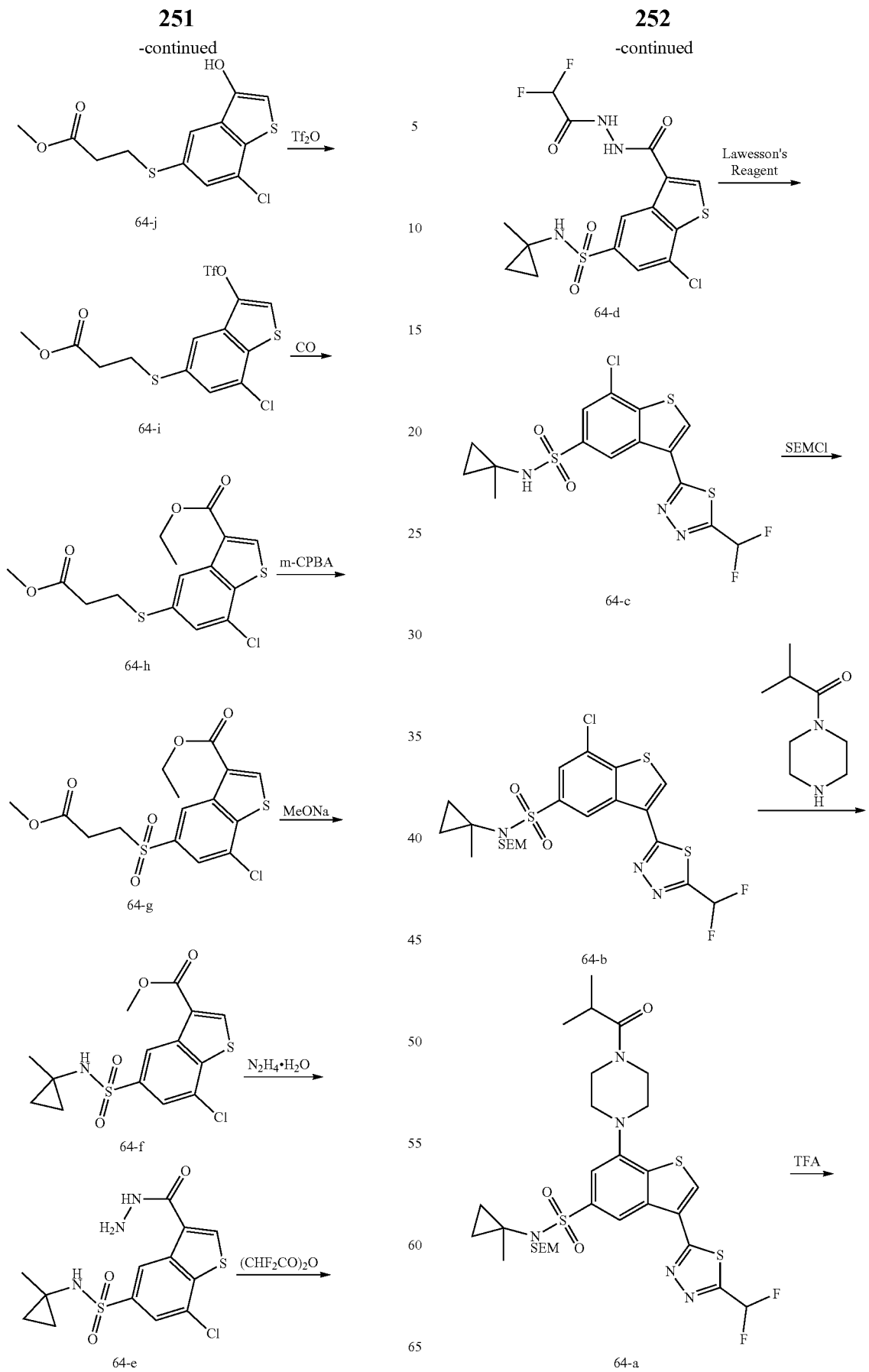

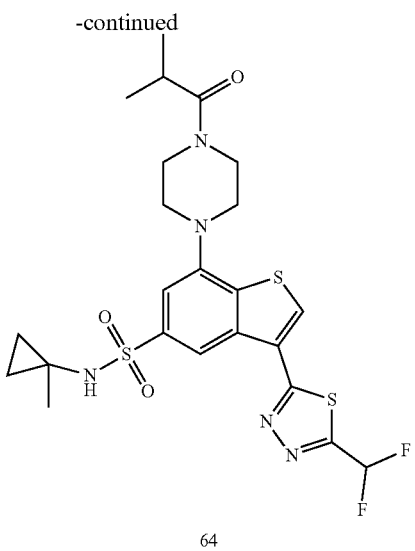

64

Synthesis of Compound 64-n

To a reaction flask charged with 3-chloro-2-fluoro-benzoic acid (6.99 g, 40.04 mmol), dibromohydantoin (9.16 g, 32.04 mmol) and dichloromethane (80 mL) was added trifluoromethanesulfonic acid (5 mL) in an ice-water bath. The reaction was stirred from ice-water bath to room temperature water for 3 hours, then was poured into ice-water, was added ethyl acetate (80 mL), partitioned, and the aqueous phase was extracted once with dichloromethane. The organic phases were washed twice with water, and the organic phases were combined, washed once with aqueous sodium bisulfite, once with water, brine, dried over anhydrous sodium sulfate, filtered and the filtrate was evaporated to give 64-n (8.6 g, 85%). LC-MS (ESI): m/z 250.9 (M−H)⁻.

Synthesis of Compound 64-m

A reaction flask charged with 64-n (8.6 g, 33.93 mmol) and methanol (70 mL) was added thionyl chloride (6.5 mL) dropwise while stirring in an ice-water bath. The reaction mixture was stirred at 80° C. for 4 hours. Removed the solvent and dried by an oil pump for 1 h to obtain 64-m (9.0 g, 99%).

Synthesis of Compound 64-l

A reaction flask charged with 64-m (9.0 g, 33.65 mmol), anhydrous DMF (45 mL) and methyl mercaptoacetate (3.61 mL, 40.38 mmol) was added Lithium hydroxide (2.82 g, 117.77 mmol) in an ice-water bath under nitrogen atmosphere. The reaction mixture was stirred at room temperature for 2 h and then poured into ice-water containing acetic acid (9 mL) and stirred for 2 min, filtered, and the filter cake was air-dried at room temperature to obtain 64-l (10 g, 92%). LC-MS (ESI): m/z 321.0 (M+H)⁺.

Synthesis of Compound 64-k

A reaction flask charged with 64-l (6 g, 18.66 mmol), DMSO (40 mL) and lithium hydroxide monohydrate (3.15 g, 75.07 mmol) was stirred at 80° C. for 2 h. Lithium hydroxide monohydrate (0.95 g, 22.64 mmol) was added to the above mixture. The reaction mixture was stirred at 100° C. for 15 hours. After cooled to room temperature, the reaction mixture was added acetic acid (4.5 mL) dropwise (be careful of gas release), stirred at room temperature for 1 h and then was added acetic acid (1.5 mL) dropwise and continued stirring for 1 h at room temperature. The reaction mixture was poured into ice water (gas release), extracted twice with ethyl acetate, washed with brine, dried over anhydrous sodium sulfate, filtered and the filtrate was evaporated to obtain 64-k (4.0 g, 81%). LC-MS (ESI): m/z 260.8 (M−H)⁻.

Synthesis of Compound 64-j

A reaction flask charged with 64-k (4.25 g, 16.13 mmol), Pd₂(dba)₃ (0.74 g, 0.81 mmol), Xantphos (0.93 g, 1.61 mmol), 1,4-dioxane (60 mL), DIPEA (8.6 mL, 48.57 mmol) and methyl 3-mercaptopropionate (1.89 mL, 16.93 mmol) was degassed and purged with nitrogen for 3 times, then stirred at 90° C. for 6 hours. After cooled to room temperature, the reaction mixture was removed the solvent and the crude product was purified by column chromatography (mobile phase: petroleum ether/ethyl acetate, 100/0 to 75/25) to give compound 64-j (3.5 g, 72%). LC-MS (ESI): m/z 301.0 (M−H)⁻.

Synthesis of Compound 64-i

A reaction flask charged with 64-j (3.5 g, 11.56 mmol), dichloromethane (25 mL) and triethylamine (4.82 mL, 34.68 mmol) was added trifluoromethanesulfonic anhydride (4.89 g, 17.34 mmol) dropwise in an ice-salt bath. The reaction mixture was stirred for 1 hour in an ice-salt bath (ice basically melted away), then was added aqueous sodium bicarbonate solution and stirred for 5 min, partitioned, concentrated to dryness and the residue was purified by column chromatography (mobile phase: petroleum ether/ethyl acetate, 100/0 to 90/10) to give compound 64-i (3.2 g, 64%).

Synthesis of Compound 64-h

To a reaction flask charged with 64-i (3.0 g, 6.90 mmol), anhydrous DMF (15 mL), anhydrous ethanol (7.5 mL) (dried over molecular sieve) and triethylamine (2.8 mL, 20.14 mmol) was added Palladium acetate (0.090 g, 0.40 mmol) and 1,3-bis(diphenylphosphine)propane (0.38 g, 0.92 mmol). After degassed and purged with carbon monoxide for 3 times, the reaction mixture was stirred for 3 h under carbon monoxide atmosphere at 70-78° C. Then, the reaction mixture was stirred at 75° C. under carbon monoxide atmosphere for 5 hours. After cooled to room temperature, the reaction mixture was removed part of the solvent, added ice-water, extracted with mixture of ethyl acetate and petroleum ether once. The organic phases were washed with water, brine, dried over anhydrous sodium sulfate, filtered and the filtrate was evaporated, the residue was subjected to a silica column (mobile phase: petroleum ether/ethyl acetate, 100/0 to 90/10) to give compound 64-h (1.05 g, 42%). LC-MS (ESI): m/z 359.0 (M+H)⁺.

Synthesis of Compound 64-g

A reaction flask charged with 64-h (1.05 g, 2.93 mmol) and dichloromethane (20 mL) was added m-CPBA (1.26 g, 7.30 mmol) in an ice-water bath. The reaction mixture was stirred in an ice-bath for 1.5 hours. The reaction mixture was washed once with saturated sodium bicarbonate solution, dried over anhydrous sodium sulfate, filtered and the filtrate was evaporated and the residue was purified by column chromatography (mobile phase: petroleum ether/ethyl acetate, 100/0 to 78/32) to give compound 64-g (1.1 g, 96%). LC-MS (ESI): m/z 391.1 (M+H)+.

Synthesis of Compound 64-f

A reaction flask charged with 64-g (1.15 g, 2.94 mmol), methanol (15 mL) and dichloromethane (15 mL) was added sodium methanol (0.48 g, 8.83 mmol) in an ice-water bath. The reaction mixture was stirred in an ice-water bath for 1 hour, then placed in an ice-water bath and was added 1-methylcyclopropylamine hydrochloride (1.27 g, 11.77 mmol). Removed the solvent at room temperature and dried for with an oil pump 30 min. The residue was combined with a small amount of 3 A molecular sieve, 1-methylcyclopropylamine hydrochloride (0.32 g, 2.97 mmol) and DMF (10 mL), and was added triethylamine (0.82 mL, 5.89 mmol) and NCS (0.79 g, 5.89 mmol) in an ice-water bath. The reaction mixture was stirred in an ice-water bath for 1 hour. The reaction mixture was added ice-water, extracted twice with ethyl acetate, washed with water, brine, dried over anhydrous sodium sulfate, filtered and the filtrate was evaporated to give 64-f (1.06 g crude, 100%). LC-MS (ESI): m/z 358.0 (M–H)−.

Synthesis of Compound 64-e

A reaction flask charged with 64-f (1.06 g, 2.94 mmol), DMF (4 mL) and ethanol (9 mL) was added Hydrazine hydrate (0.5 mL, 10.31 mmol) dropwise in a water bath. The reaction mixture was stirred at 52° C. for 10 hours. The solvent was concentrated, was added ice-water, extracted with ethyl acetate three times, washed with water, brine, dried over anhydrous sodium sulfate, filtered and the filtrate was evaporated, and the residue was purified by column chromatography (mobile phase: dichloromethane/methanol, 100/0 to 96/4) to give 64-e (230 mg, 22%). LC-MS (ESI): m/z 360.0 (M+H)+.

Synthesis of Compound 64-d

A reaction vial charged with 64-e (220 mg, 0.61 mmol), dichloromethane (5 mL) and triethylamine (0.13 mL, 0.92 mmol) was added difluoroacetic anhydride (0.080 mL, 0.73 mmol) dropwise in an ice-water bath. The reaction mixture was stirred in an ice-water bath for 1 hour, then was added difluoroacetic anhydride (10 mg, 0.057 mmol), stirred for 5 min in an ice-water bath and then added 3 drops of methanol. Removed the solvent at room temperature. The crude product was purified by column chromatography (mobile phase: dichloromethane/methanol, 100/0 to 96/4) to give 64-d (250 mg, 93%). LC-MS (ESI): m/z 437.9 (M+H)+.

Synthesis of Compound 64-c

A reaction flask charged with 64-d (250 mg, 0.57 mmol), Lawesson's reagent (462 mg, 1.14 mmol) and 1,4-dioxane (5 mL) was heated and stirred at 75° C. for 2 h under nitrogen atmosphere. Removed the solvent, the residue was purified by column purification (mobile phase: petroleum ether/ethyl acetate, 100/0 to 65/35) to obtain the crude product, which was diluted with ethyl acetate, petroleum ether, washed 4 times with 2% ammonia, washed with brine, dried over anhydrous sodium sulfate, filtered and the filtrate was evaporated to obtain 64-c (248 mg, 100%). LC-MS (ESI): m/z 435.9 (M+H)+.

Synthesis of Compound 64-b

A reaction vial charged with 64-c (248 mg, 0.57 mmol), DMF (2.5 mL) and tetrahydrofuran (2.5 mL) was added sodium hydrogen (68 mg, 1.70 mmol) in an ice-water bath, followed by SEMCl (0.20 mL, 1.13 mmol). The reaction mixture was stirred in an ice-water bath for 20 min. The reaction was quenched by dry ice, diluted with ethyl acetate and petroleum ether, washed carefully with water, brine, dried over anhydrous sodium sulfate, filtered and the filtrate was evaporated, and the residue was purified by column chromatography (mobile phase: petroleum ether/ethyl acetate, 100/0 to 80/20) to give compound 64-b (250 mg, 78%). LC-MS (ESI): m/z 583.0 (M+NH4)+.

Synthesis of Compound 64-a

A microwave tube charged with 64-b (70 mg, 0.12 mmol), RuPhos (10 mg, 0.021 mmol), RuPhos Pd G3 (9 mg, 0.011 mmol) and cesium carbonate (120 mg, 0.37 mmol) was added 1-(2-methanoneyl)-piperazine (40 mg, 0.26 mmol) dropwise. After capping, the above mixture was added anhydrous 1,4-dioxane (3 mL). After degassed and purged with nitrogen for 3 times, the reaction mixture was stirred at 70° C. for 6 hours. The reaction mixture was cooled to room temperature, diluted with ethyl acetate, washed with water, brine, dried over anhydrous sodium sulfate, filtered and the filtrate was evaporated. The residue was purified by column chromatography (mobile phase: (petroleum ether/dichloromethane 4:1)/ethyl acetate, 100/0 to 60/40) to give compound 64-a (75 mg, 88%). LC-MS (ESI): m/z 703.2 (M+NH4)+.

Synthesis of Compound 64

A reaction vial charged with 64-a (75 mg, 0.11 mmol), dichloromethane (2 mL) and water (0.040 mL, 2.22 mmol) was added trifluoroacetic acid (0.5 mL) dropwise in an ice-water bath. The reaction mixture was stirred at room temperature for 1 hour, diluted with ethyl acetate, washed with aqueous sodium bicarbonate solution and a small amount of sodium carbonate solid, brine, dried over anhydrous sodium sulfate, filtered and the filtrate was evaporated. The residue was dissolved in methanol (5 mL), added anhydrous potassium carbonate (80 mg), stirred at 50° C. for 20 minutes. The solvent was removed, diluted with dichloromethane and purified by column chromatography (mobile phase: dichloromethane/methanol, 100/0 to 96/4) to give compound 64 (45 mg, 74%). LC-MS(ESI): m/z 556.0 (M+H)+. 1H NMR (DMSO-d6, 400 MHz): δ 8.99 (1H, s), 8.93 (1H, d, J=1.2 Hz), 8.19 (1H, s), 7.70 (1H, t, J=53.2 Hz), 7.53 (1H, d, J=1.2 Hz), 3.82-3.70 (4H, m), 3.25-3.12 (4H, m), 2.96 (1H, p, J=6.8 Hz), 1.06 (6H, d, J=6.8 Hz), 1.04 (3H, s), 0.69-0.59 (2H, m), 0.43-0.35 (2H, m).

Example 65 Synthetic Route of Compound 65

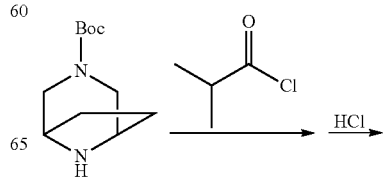

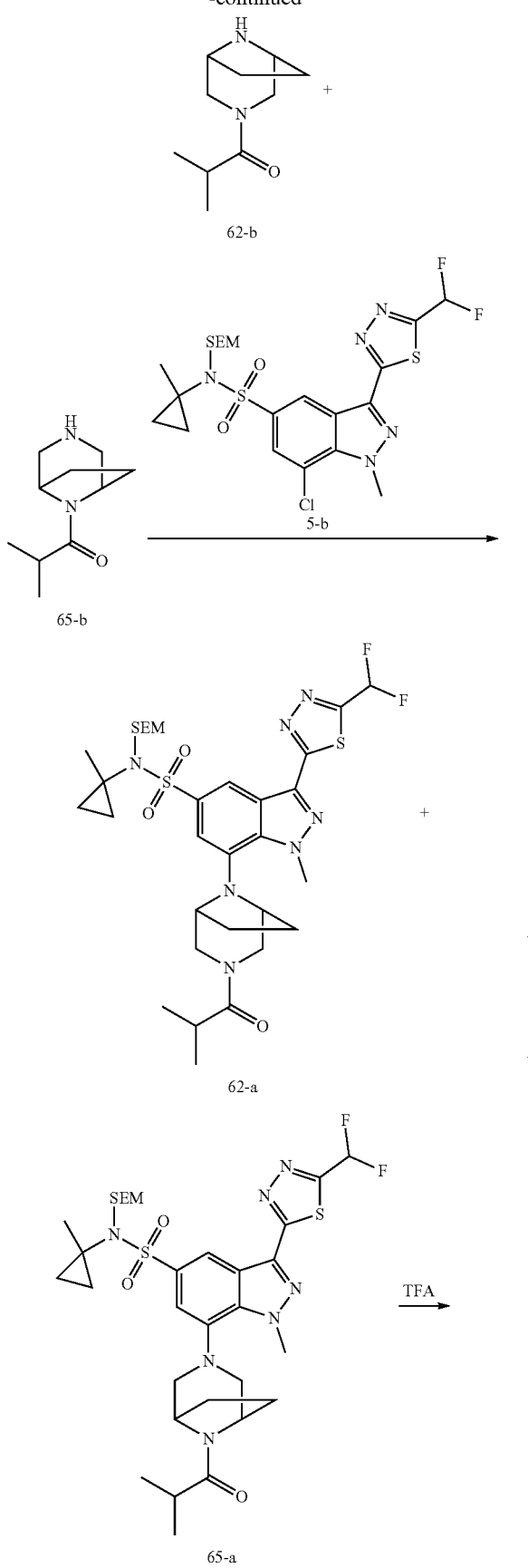

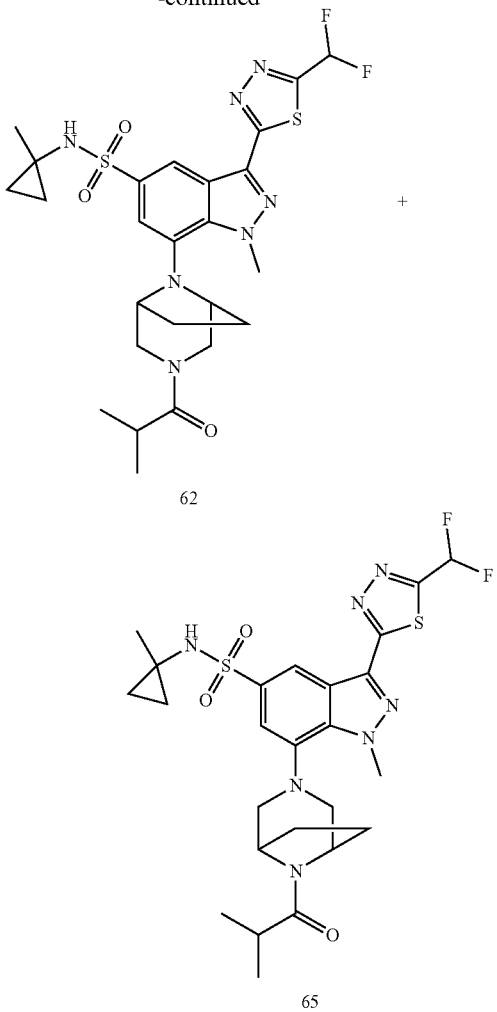

Synthesis of Mixture 65-b and 62-b

A mixture of compound 3,8-diazabicyclo[3.2.1]octane-3-carboxylic acid tert-butyl ester (300 mg, 1.41 mmol) in dichloromethane (20 mL) was added triethylamine (315 mg, 3.11 mmol), followed by dropwise addition of isobutyryl chloride (181 mg, 1.70 mmol) at 0° C. After stirring at room temperature for 2 h, the reaction mixture was concentrated at reduced pressure, added water (100 mL) and extracted with ethyl acetate (100 mL). The organic phase was washed with brine (100 mL), dried over sodium sulfate, filtered out desiccant and concentrated at reduced pressure to give the crude product, which was purified by column chromatography (mobile phase, PE/EA=1/1) to give 380 mg of compound, yield 95%. LC-MS (ESI): m/z 283.2 (M+H)+.

To the resulting compounds (380 mg, 1.35 mmol) was added HCl/1,4-dioxane (4 M, 10 mL) and the reaction was stirred at room temperature for 2 h. The reaction mixture was concentrated at reduced pressure, and the residue was added methanol (10 mL) and potassium carbonate (600 mg), and the reaction mixture was stirred for 20 min at room temperature. The reaction mixture was filtered through celite, and the filtrate was concentrated by rotary evaporation, the residue was dried in vacuum by an oil pump to obtain a mixture of 65-b and 62-b (150 mg, 61%). LC-MS (ESI): m/z 183.2 (M+H)+.

Synthesis of Mixtures 65-a and 62-a

A microwave tube charged with 1,4-dioxane (10 mL), compound 5-b (100 mg, 0.18 mmol), 2-dicyclohexylphosphino-2',6'-diisopropoxy-1,1'-biphenyl (33 mg, 0.07 mmol), methanesulfonic acid (2-dicyclohexylphosphino-2',6'-diisopropoxy-1,1'-biphenylyl) (2-amino-1,1'-biphenyl-2-yl)palladium(II) (30 mg, 0.04 mmol) and cesium carbonate (173 mg, 0.53 mmol) was stirred at room temperature for 5 min before adding a mixture of 65-b and 62-b (65 mg, 0.36 mmol). The mixture was purged with nitrogen for 3 min and then sealed and stirred at 70° C. for 15 h. The reaction mixture was cooled to room temperature, filtered through celite and the filtrate was concentrated at reduced pressure to give the crude product, which was purified by column chromatography (mobile phase, PE/EA=1/1) to give a mixture of 65-a and 62-a (60 mg, 48%). LC-MS (ESI): 710.3 m/z (M+H)⁺.

Synthesis of Compounds 62 and 65

A mixture of compound 5-a, mixture of 65-a and 62-a (60 mg, 0.09 mmol) was dissolved in dichloromethane (6 mL), to which trifluoroacetic acid (2 mL) was added at 0° C. The reaction mixture was stirred at room temperature for 2 h. The reaction mixture was removed from dichloromethane by rotary evaporation, and the pH was adjusted to 7-8 with saturated sodium bicarbonate solution and the aqueous phase was extracted with ethyl acetate (100 mL). The organic phase was washed with brine (100 mL), dried over sodium sulfate, filtered out desiccant, and concentrated at reduced pressure to obtain the crude product, which was purified by TLC (unfolding agent, PE/EA=1/2) to obtain two crude products, respectively, after the crude product was purified by preparative HPLC (basic conditions) to obtain compound 62 (4 mg, 8%). LC-MS (ESI): m/z 580.2 (M+H)⁺; compound 65 (11 mg, 22%), LC-MS (ESI): m/z 580.2 (M+H)⁺; $^1$H NMR (400 MHz, DMSO-$d_6$): δ 8.64 (s, 1H), 8.19 (s, 1H), 7.74 (1H, s), 7.69 (t, 1H, J=52.0 Hz), 4.70-4.67 (m, 1H), 4.58 (s, 3H), 4.57-4.53 (m, 1H), 3.29-3.23 (m, 1H), 3.18-3.13 (m, 1H), 3.04-2.99 (m, 1H), 2.97-2.92 (m, 1H), 2.91-2.82 (m, 1H), 2.21-2.14 (m, 1H), 2.12-2.01 (m, 2H), 1.92-1.81 (m, 1H), 1.12 (d, J=4.0 Hz, 3H), 1.05 (d, J=8.0 Hz, 3H), 1.00 (s, 3H), 0.63-0.58 (m, 2H), 0.39-0.34 (m, 2H).

Example 66 Synthetic Route of Compound 66

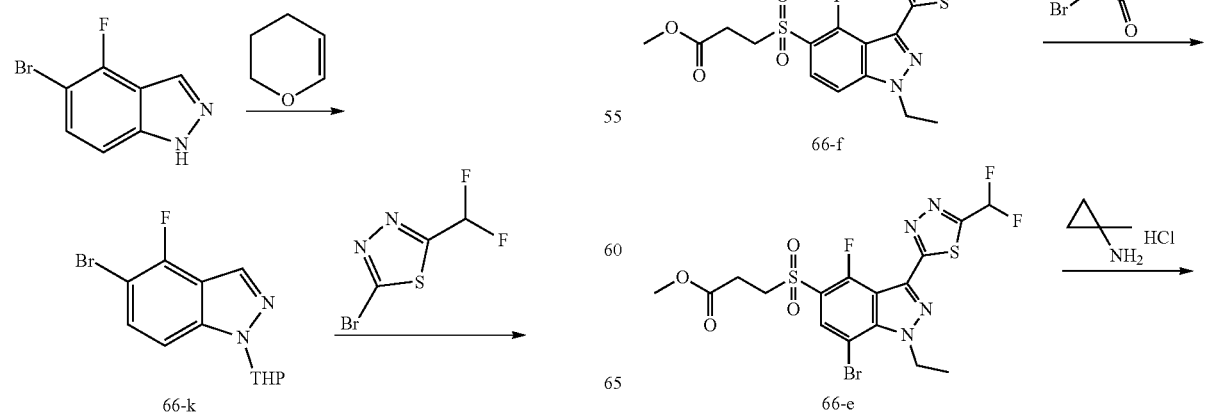

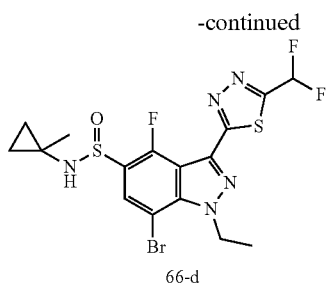

66-d m-CPBA

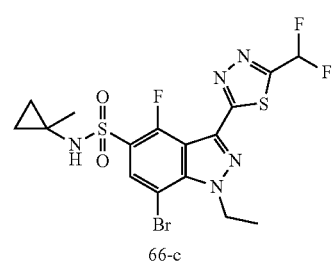

66-c

SEMCl

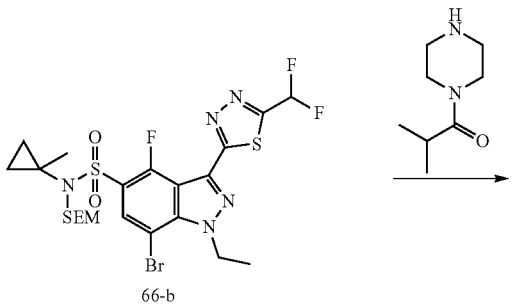
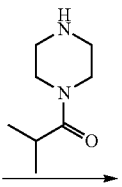

66-b

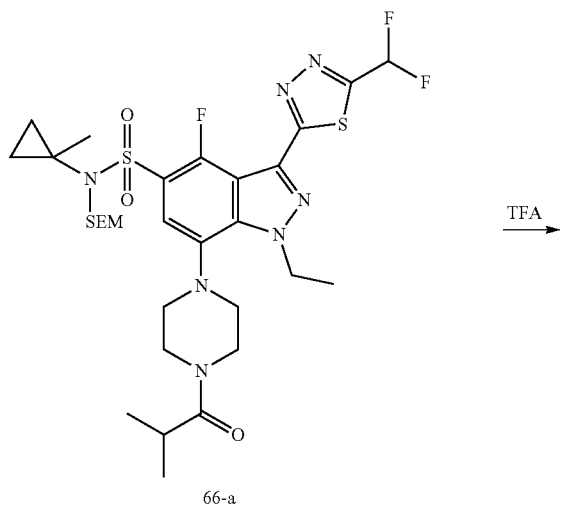

66-a

TFA

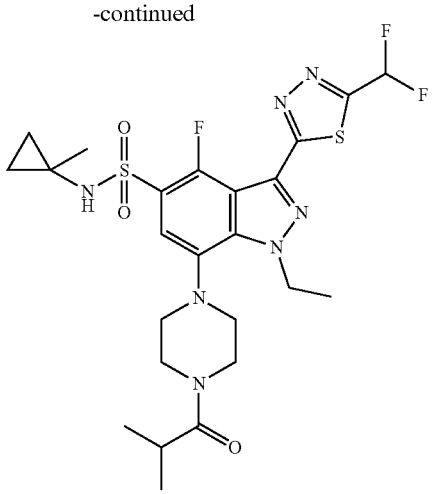

66

Synthesis of Compound 66-k p-toluenesulfonic acid monohydrate (20 mg, 0.11 mmol) and 3,4-dihydropyran (245 mg, 2.92 mmol) were added to a solution of compound 5-bromo-4-fluoroindazole (500 mg, 2.33 mmol) in dichloromethane (15 mL), and the reaction mixture was stirred at room temperature for 12 hours. The reaction mixture was concentrated at reduced pressure to give the crude product, which was purified by column chromatography (mobile phase, PE/EA 3/1) to give compound 66-k (637 mg, 92%). LC-MS (ESI): m/z 299.0 $(M+H)^+$.

Synthesis of Compound 66-j

The compounds bis(pinacol borate) (1058 mg, 4.12 mmol), 2,2'-bi(4-tert-butylpyridine) (168 mg, 0.63 mmol), methoxy(cyclooctadiene) chloroiridium dimer (207 mg, 0.31 mmol) were dissolved in methyl tert-butyl ether (40 mL) and stirred for 10 min at room temperature under nitrogen atmosphere before adding 66-k (623 mg, 2.08 mmol). After degassed and purged with nitrogen for 4 min, the reaction mixture was stirred in a sealed tube at 80° C. for 7 h. The reaction mixture was cooled, concentrated at reduced pressure at room temperature, and the residue was dissolved in toluene (20 mL), was added palladium acetate (47 mg, 0.21 mmol), 4,5-bis(diphenylphosphino)-9,9-dimethylxanthene (241 mg, 0.42 mmol), 2-bromo-5-difluoromethyl-1,3,4-thiadiazole (627 mg, 2.92 mmol), water (10 mL) and cesium carbonate (1357 mg, 4.16 mmol). Degassed and purged with nitrogen for 4 times, the reaction mixture was stirred at room temperature for 12 hours, then was added water (100 mL) and extracted with ethyl acetate (100 mL), the organic phases were washed with brine (100 mL), dried over sodium sulfate, filtered to remove the desiccant and concentrated at reduced pressure to obtain the crude product, which was purified by column chromatography (mobile phase, PE/EA 10/1) to give compound 66-j (547 mg, 61%). LC-MS (ESI): m/z 433.0 $(M+H)^+$.

Synthesis of Compound 66-i

A solution of compound 66-j (547 mg, 1.26 mmol), methyl 3-mercaptopropionate (455 mg, 3.79 mmol), tris (dibenzylideneacetone)dipalladium (116 mg, 0.13 mmol), 4,5-bis(diphenylphosphino)-9,9-dimethylxanthene (146 mg, 0.25 mmol) and diisopropylethylamine (653 mg. 5.05 mmol) in 1,4-dioxane (40 mL) was degassed and purged with nitrogen for three times, and stirred in an oil bath at 110° C. for 2.5 h. The reaction mixture was concentrated at reduced pressure to give the crude product, which was purified by column chromatography (mobile phase, PE/EA 3/1) to give compound 66-i (578 mg, 97%). LC-MS (ESI): m/z 473.6 (M+H)$^+$.

Synthesis of Compound 66-h

Compound 66-i (578 mg, 1.22 mmol) was dissolved in dichloromethane (12 mL), to which trifluoroacetic acid (4 mL) was added and the reaction mixture was stirred at room temperature for 12 h. The reaction mixture was adjusted to pH 7-8 with saturated sodium bicarbonate solution, then was added water (100 mL) and extracted with dichloromethane (100 mL), the organic phase was washed with brine (100 mL), dried over sodium sulfate, filtered to remove the desiccant, and the filtrate was concentrated at reduced pressure to obtain the crude product, which was purified by column chromatography (mobile phase, DCM/EA 10/1) to give compound 66-h (290 mg, 61%). LC-MS (ESI): m/z 389.5 (M+H)$^+$.

Synthesis of Compound 66-g

Potassium carbonate (206 mg, 1.49 mmol) and ethyl iodide (233 mg, 1.49 mmol) were added to a solution of compound 66-h (290 mg, 0.75 mmol) in N,N-dimethylformamide (10 mL), and the reaction mixture was stirred at room temperature for 2 h. The reaction mixture was added water (100 mL) and extracted with ethyl acetate (100 mL), the organic phases were washed with bine (100 mL), dried over sodium sulfate, filtered to remove the desiccant, and the filtrate was concentrated at reduced pressure to give the crude product, which was purified by column chromatography (mobile phase, PE/EA 3/1) to give compound 66-g (250 mg, 80%). LC-MS (ESI): m/z 417.6 (M+H)$^+$.

Synthesis of Compound 66-f m-chloroperoxybenzoic acid (266 mg, 1.80 mmol) was added to a solution of compound 66-g (250 mg, 0.60 mmol) in dichloromethane (15 mL) in an ice-water bath, and the reaction mixture was stirred for 2 h at room temperature. The reaction mixture was added saturated sodium bicarbonate solution (10 mL) and water (100 mL), extracted with dichloromethane (100 mL), the organic phase was washed with brine (50 mL), dried over sodium sulfate, filtered to remove the desiccant, and the filtrate was concentrated at reduced pressure to give the crude product, which was purified by column chromatography (mobile phase, PE/EA 1/1) to give compound 66-f (253 mg, 94%). LC-MS (ESI): m/z 449.3 (M+H)$^+$.

Synthesis of Compound 66-e

Dibromohydantoin (226 mg, 0.79 mmol) was added to a solution of compound 66-f (253 mg, 0.56 mmol) in dried dichloromethane (25 mL), followed by dropwise addition of trifluoromethanesulfonic acid (508 mg, 3.39 mmol) in an ice-water bath, and after the dropwise addition, the reaction mixture was stirred in an ice-water bath for 40 min. Ethyl acetate (25 mL) was added to the reaction mixture, and the dichloromethane was removed by concentration at reduced pressure at room temperature, and the residue was added water (100 mL) and extracted with ethyl acetate (100 mL), the organic phase was washed with brine (100 mL), dried over sodium sulfate, filtered to remove the desiccant, and concentrated at reduced pressure to obtain the crude product, which was purified by column chromatography (mobile phase, PE/EA 1/1) to give compound 66-e (270 mg, 91%). LC-MS (ESI): m/z 527.0 (M+H)$^+$.

Synthesis of Compound 66-d

Compound 66-e (240 mg, 0.46 mmol) was dissolved in dichloromethane (10 mL) and methanol (10 mL), to which sodium methanol (79 mg, 1.46 mmol) was added in an ice-water bath, and the reaction mixture was stirred for 1 h in an ice-water bath, then was added 1-methylcyclopropylamine hydrochloride (262 mg, 2.44 mmol) and stirred at room temperature for 10 min. Concentrate at reduced pressure and dried in vacuum with an oil pump for 3 hours. The residue was dissolved in N,N-dimethylformamide (10 mL), was added 1-methylcyclopropylamine hydrochloride (57 mg, 0.48 mmol), dimethylaminopyridine (59 mg, 0.48 mmol) and 1-(3-dimethylaminopropyl)-3-ethylcarbodiimide hydrochloride (187 mg, 0.98 mmol), and the reaction mixture was stirred at 30° C. for 36 hours. The reaction mixture was added water (100 mL), extracted with ethyl acetate (100 mL), and the organic phases were washed with water (50 mL) and brine (50 mL) in turn, dried over sodium sulfate, filtered to remove the desiccant, and concentrated at reduced pressure to obtain the crude product, which was purified by column chromatography (mobile phase, DCM/EA 10/1) to obtain 66-d (180 mg, 79%). LC-MS (ESI): m/z 494.0 (M+H)$^+$.

Synthesis of Compound 66-c

Compound 66-d (180 mg, 0.36 mmol) was dissolved in dichloromethane (10 mL), to which m-chloroperoxybenzoic acid (222 mg, 1.09 mmol) was added in an ice-water bath and the reaction mixture was stirred at room temperature for 3 h. The reaction mixture was stirred at room temperature for 1 hour after the addition of m-chloroperoxybenzoic acid (59 mg, 0.29 mmol). The reaction mixture was added saturated sodium bicarbonate solution (5 mL) and water (50 mL), extracted with dichloromethane (50 mL), the organic phase was washed with brine (50 mL), dried over sodium sulfate, filtered to remove the desiccant, and concentrated at reduced pressure to obtain the crude product, which was purified by column chromatography (mobile phase, PE/EA 3/1) to afford compound 66-c (184 mg, 100%). LC-MS (ESI): m/z 510.0 (M+H)$^+$.

Synthesis of Compound 66-b

A solution of compound 66-c (184 mg, 0.36 mmol) in tetrahydrofuran (5 mL) and N,N-dimethylformamide (5 mL) was added sodium hydrogen (43 mg, 1.08 mmol) in an ice-water bath, followed by the dropwise addition of 2-(trimethylsilyl)ethoxymethyl chloride (90 mg, 0.54 mmol). After the dropwise addition, the reaction mixture was stirred in an ice-water bath for 30 min. then was added dry ice (3 g) and stirred for 10 min, added water (100 mL), extracted with ethyl acetate (100 mL), the organic phases were washed with brine (50 mL), dried over sodium sulfate, filtered to remove the desiccant, the filtrate was concentrated at reduced pressure, and the crude product was purified by column chromatography (mobile phase, PE/EA 5/1) to give compound 66-b (194 mg, 84%). LC-MS (ESI): m/z 640.0 (M+H)⁺.

Synthesis of Compound 66-a

Compound 66-b (100 mg, 0.16 mmol), [1,3-bis[2,6-bis(1-ethylpropyl)phenyl]-4,5-dichloro-1,3-dihydro-2H-imidazol-2-ylidene]dichloro(2-methylpyridine)palladium (14 mg, 0.017 mmol), cesium carbonate (109 mg, 0.33 mmol) were added to 1,4-dioxane (10 mL) followed by addition of 2-methyl-1-(piperazin-1-yl)propan-1-one (53 mg, 0.34 mmol), and the mixture was purged with nitrogen for 3 min and then the mixture was stirred in a sealed tube at 90° C. for 15 h. The reaction mixture was cooled to room temperature, filtered through celite and the filtrate was concentrated at reduced pressure to give the crude product, which was purified by column chromatography (mobile phase, PE/EA 1/1) to give compound 66-a (70 mg, 61%). LC-MS (ESI): m/z 598.2 (M+H-118)⁺.

Synthesis of Compound 66

Compound 66-a (70 mg, 0.098 mmol) was dissolved in dichloromethane (4.5 mL) and trifluoroacetic acid (1.5 mL) was added to the above solution in an ice-water bath and the reaction mixture was stirred at room temperature for 2 h. The dichloromethane was removed by concentration at reduced pressure, and the residue was adjusted to pH 7-8 with saturated sodium bicarbonate solution, extracted with ethyl acetate (100 mL), the organic phase was washed with brine (100 mL), dried over sodium sulfate, filtered to remove the desiccant, and the filtrate was concentrated at reduced pressure to obtain the crude product, which was purified by preparative HPLC (basic conditions) to give compound 66 (12 mg, 21%). LC-MS (ESI): m/z 586.0 (M+H)⁺. ¹H NMR (400 MHz, DMSO-d₆): δ 8.47 (1H, s), 7.82-7.53 (2H, m), 4.93-4.85 (2H, m), 4.56-4.51 (1H, m), 4.14-4.08 (1H, m), 3.26-3.2 (2H, m), 3.01-2.84 (3H, m), 2.80-2.60 (2H, m), 1.55-1.50 (3H, m), 1.12-1.02 (9H, m), 0.67-0.62 (2H, m), 0.44-0.39 (2H, m).

Example 67 Synthetic Route of Compound 67

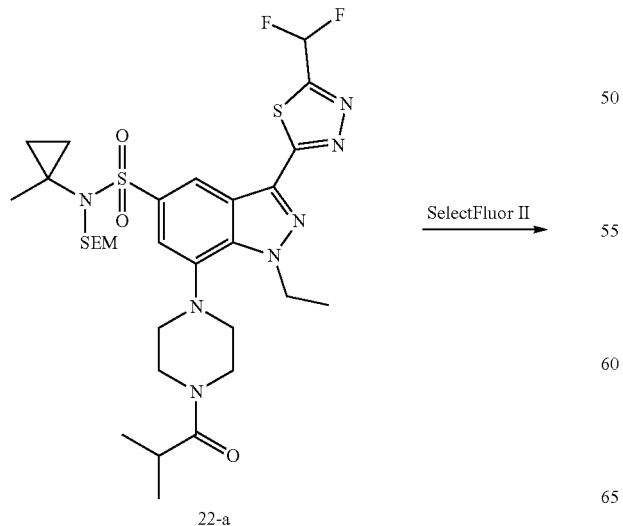

22-a

SelectFluor II →

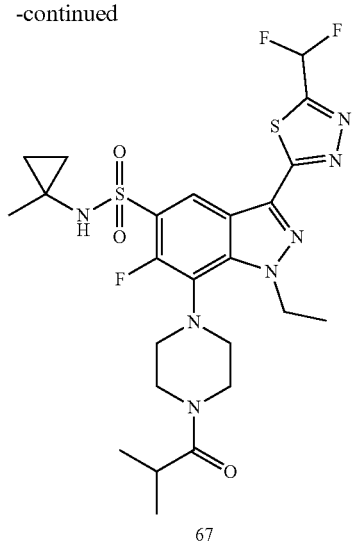

67

Synthesis of Compound 67

To a solution of 22-a (100 mg, 0.14 mmol) in acetonitrile (10 mL) at room temperature was added SelectFluor II (183 mg, 0.57 mmol) and AcOH (0.2 mL). The reaction mixture was heated at 50° C. for 2 h and then cooled to room temperature, was added methanol (10 mL) and potassium carbonate (200 mg) and continued stirring for 2 h at room temperature. Upon completion, the reaction was removed the organic solvent by concentration at reduced pressure at low temperature, then extracted with ethyl acetate, and the organic phase was washed with water, brine in turn, dried over anhydrous sodium sulfate, filtered and the filtrate was evaporated to obtain the crude product, which was purified by Prep-HPLC to give compound 67 (15 mg, 18%). LC-MS (ESI): m/z 586.0 [M+H]⁺; ¹H NMR (DMSO-d₆, 400 MHz): δ8.72 (1H, d, J=6.4 Hz), 8.45 (1H, s), 7.69 (1H, t, J=53.2 Hz), 4.89-4.95 (2H, m), 4.50-4.54 (1H, m), 4.07-4.11 (1H, m), 3.17-3.29 (4H, m), 3.05-3.18 (1H, m), 2.92-3.04 (1H, m), 2.81-2.92 (1H, m), 1.52 (3H, t, J=7.2 Hz), 1.11 (3H, s), 1.03-1.09 (6H, m), 0.65-0.71 (2H, m), 0.39-0.45 (2H, m).

Example 68 Synthetic Route of Compound 68

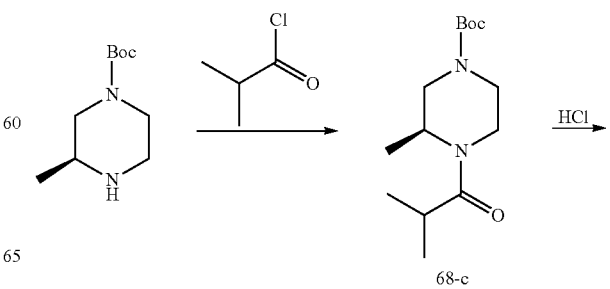

68-c

HCl →

-continued

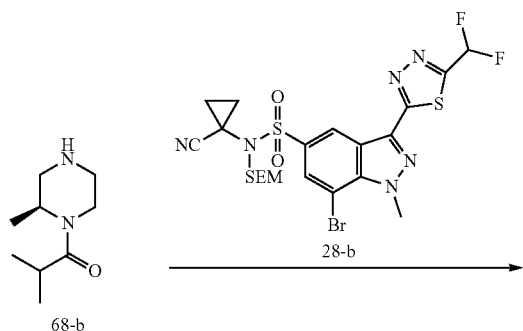

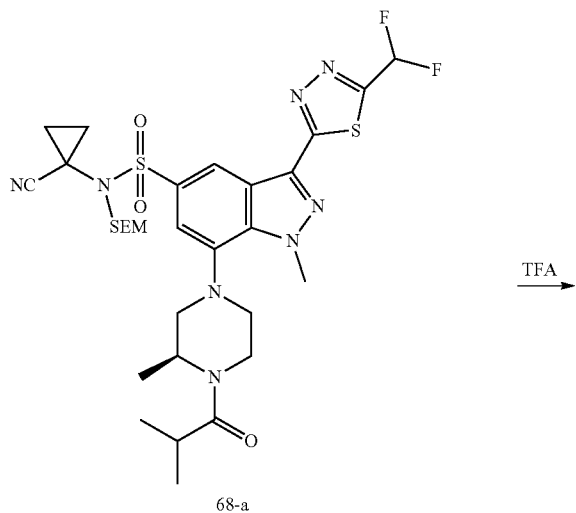

Synthesis of Compound 68-c

To a reaction vial charged with (S)-4-N-Boc-2-methylpiperazine (1 g, 4.99 mmol), dichloromethane (10 mL) and triethylamine (1.39 mL, 9.99 mmol) was added isobutyryl chloride (0.79 mL, 7.49 mmol) dropwise in an ice-water bath and the resulting mixture was stirred at room temperature overnight. The next day, the reaction was quenched with water, extracted with dichloromethane, washed with brine, dried over anhydrous sodium sulfate, concentrated to dryness and the residue was purified by column chromatography (mobile phase: methanol/dichloromethane: 0% to 10%) to give compound 68-c (1 g, 74%). LC-MS (ESI): m/z=271.3 $[M+H]^+$.

Synthesis of Compound 68-b

To a reaction flask charged with 68-c (1 g, 3.70 mmol) and acetonitrile (20 mL) with added HCl/1,4-dioxane (4 M, 4.62 mL, 18.49 mmol) dropwise in an ice-water bath and the reaction mixture was stirred at room temperature for 2 hours. After completion, the reaction was removed the solvent by concentration at reduced pressure, and the crude product was dissolved in methanol, neutralized by adding sodium bicarbonate powder and stirred for half an hour. Concentrated by filtration and dried in vacuum to give compound 68-b (500 mg, 79%). LC-MS (ESI): m/z 341.3 $[2M+H]^+$.

Synthesis of Compound 68-a

A microwave tube charged with 28-b (100 mg, 0.16 mmol), 68-b (55 mg, 0.32 mmol), RuPhos (30 mg, 0.065 mmol), methanesulfonic acid (2-dicyclohexylphosphino-2',6'-diisopropoxy-1,1'-biphenylyl)(2-amino-1,1'-biphenyl-2-yl)palladium(II) (RuPhos Pd G3) (27 mg, 0.032 mmol), cesium carbonate (158 mg, 0.48 mmol) and 1,4-dioxane (8 mL) with degassed and purged with nitrogen for 3 times, then was heated at 60° C. overnight. The reaction mixture was cooled to room temperature and removed 1,4-dioxane by concentration at reduced pressure. The residue was diluted with ethyl acetate, washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 68-a (38 mg, 33%). LC-MS (ESI): m/z 709.3 $[M+H]^+$.

Synthesis of Compound 68

Trifluoroacetic acid (1 mL) was added dropwise to a reaction vial charged with 68-a (38 mg, 0.054 mmol) and dichloromethane (5 mL) at room temperature. After the dropwise addition, the reaction mixture was stirred at room temperature for 4 h. The solvent was removed by concentration at room temperature. The residue was diluted with dichloromethane, washed with saturated sodium bicarbonate, brine, dried over anhydrous sodium sulfate, filtered, and the filtrate was evaporated to obtain the crude product, which was purified by Prep-HPLC to obtain compound 68 (15 mg, 48%). LC-MS (ESI): m/z 579.8 $[M+H]^+$.

269

Synthesis of Compound 69

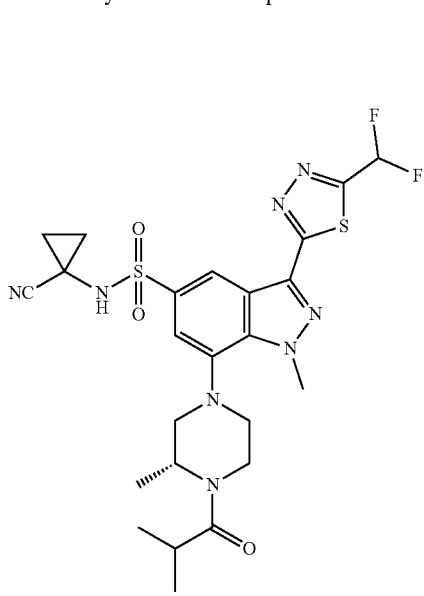

Referring to the synthesis of compound 68, compound 69 was obtained synthetically using (R)-2-methyl-1-(2-methylpiperazin-1-yl)prop-1-one instead of 68-b. LC-MS (ESI): m/z 579.4 [M+H]$^+$.

Example 70 Synthetic Route of Compound 70

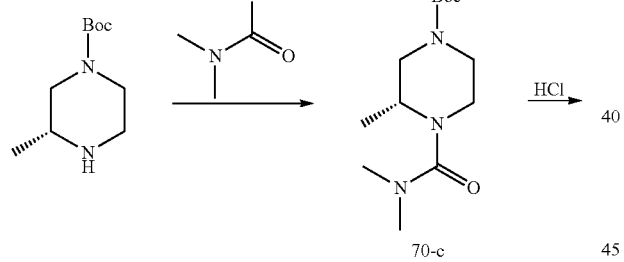

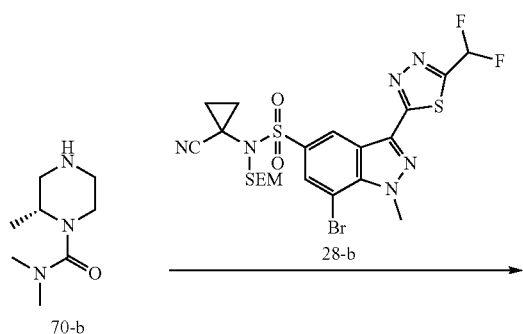

270

-continued

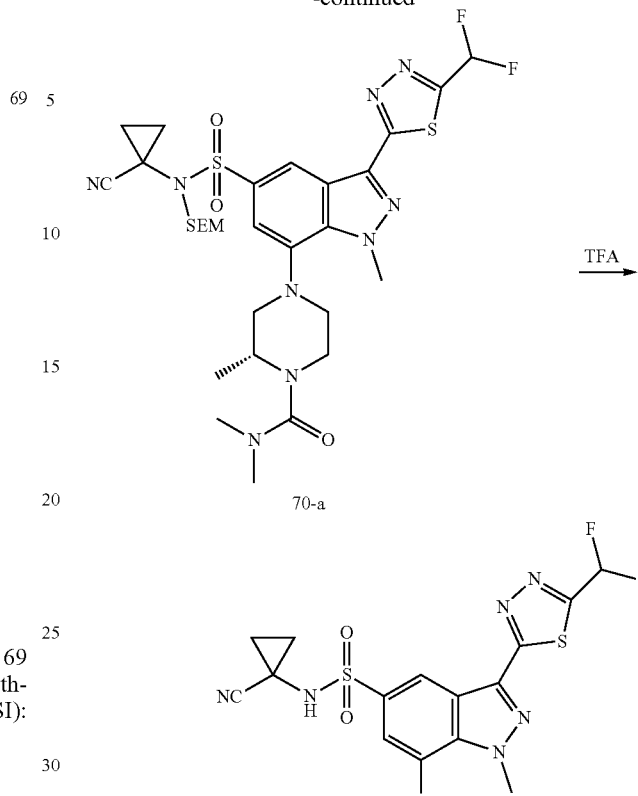

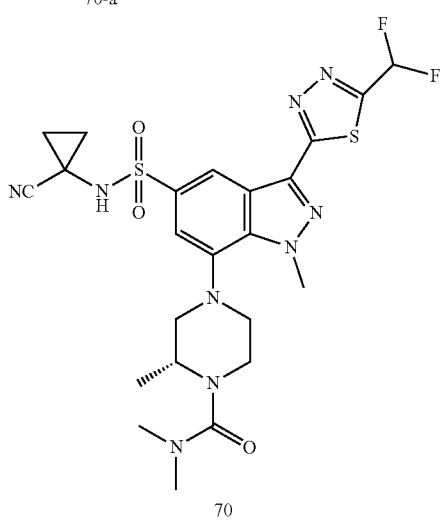

Synthesis of Compound 70-c

To a reaction vial charged with (R)-4-Boc-2-methylpiperazine (1 g, 4.99 mmol), dichloromethane (10 mL) and triethylamine (1.39 mL, 9.99 mmol) was added dimethylcarbamoyl chloride (0.69 mL, 7.49 mmol) dropwise in an ice-water bath, and after the dropwise addition, the reaction mixture was stirred at room temperature overnight. The next day, the reaction was quenched with water, extracted with dichloromethane, and the organic phase was washed with brine, dried over anhydrous sodium sulfate, evaporated, and the crude product was purified by column chromatography (mobile phase: methanol/dichloromethane: 0% to 10%) to give compound 70-c (1.2 g, 89%). LC-MS (ESI): m/z=272.3 [M+H]$^+$.

Synthesis of Compound 70-b

To a reaction flask charged with 70-c (1.2 g, 4.42 mmol) and acetonitrile (20 mL) was added HCl/1,4-dioxane solution (4 M, 5.53 mL, 22.11 mmol) dropwise in an ice-water bath. After the dropwise addition, the reaction mixture was stirred at room temperature for 2 hours. After completion, the reaction was removed the solvent by concentration at reduced pressure, and the residue was dissolved in methanol, neutralized by adding sodium bicarbonate powder and stirred for half an hour. Filtered, and the filtrate was concentrated at reduced pressure and dried in vacuum to give compound 70-b (500 mg, 66%). LC-MS (ESI): m/z 172.3 [M+H]$^+$.

Synthesis of Compound 70-a

A microwave tube charged with 28-b (100 mg, 0.16 mmol), 70-b (55 mg, 0.32 mmol), RuPhos (8 mg, 0.017 mmol), (SP-4-1)-[1,3-bis[2,6-bis(1-ethylpropyl)phenyl]-4,5-dichloro-1,3-dihydro-2H-imidazol-2-ylidene]dichloro(2-methylpyridine)palladium (CAS: 1612891-29-8) (14 mg, 0.017 mmol), cesium carbonate (158 mg, 0.48 mmol) and 1,4-dioxane (8 mL) was degassed and purged with nitrogen for 3 times, then was heated at 65° C. overnight. After the reaction was completed, the reaction mixture was cooled to room temperature and concentrated at reduced pressure to remove the 1,4-dioxane. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 70-a (50 mg, 44%). LC-MS (ESI): m/z 710.3 [M+H]$^+$.

Synthesis of Compound 70

To a reaction vial charged with 70-a (50 mg, 0.070 mmol), dichloromethane (5 mL) was added trifluoroacetic acid (1 mL) dropwise at room temperature. After the dropwise addition, the reaction mixture was stirred at room temperature for 4 h. The solvent was removed by concentration at room temperature at reduced pressure. The organic phase was washed with saturated sodium bicarbonate, brine, dried over anhydrous sodium sulfate, filtered and the filtrate was evaporated to obtain the crude product, which was purified by Prep-TLC (PE/EA=1/5) to afford the compound 70 (27 mg, 66%). LC-MS (ESI): m/z 580.0 [M+H]$^+$; $^1$H NMR (DMSO-d$_6$, 400 MHz): δ 9.20 (1H, s), 8.65 (1H, s), 7.71 (1H, t, J=53.2 Hz), 7.59 (1H, s), 4.53 (3H, s), 4.01-4.18 (1H, m), 3.01-3.60 (5H, m), 2.81 (6H, s), 2.61-2.73 (1H, m), 1.28-2.53 (7H, m).

Example 71 Synthesis of Compound 71

Example 72 Synthetic Route of Compound 72

Referring to the synthesis of compound 70, compound 71 was obtained by using tert-butyl (S)-3-methylpiperazine-1-carboxylate instead of tert-butyl (R)-3-methylpiperazine-1-carboxylate. LC-MS (ESI): m/z 580.1 [M+H]$^+$; $^1$H NMR (DMSO-d$_6$, 400 MHz): δ 9.20 (1H, s), 8.65 (1H, d, J=1.6 Hz), 7.71 (1H, t, J=53.2 Hz), 7.59 (1H, d, J=1.6 Hz), 4.53 (3H, s), 4.02-4.19 (1H, m), 3.01-3.61 (5H, m), 2.81 (6H, s), 2.61-2.74 (1H, m), 1.23-1.45 (7H, m).

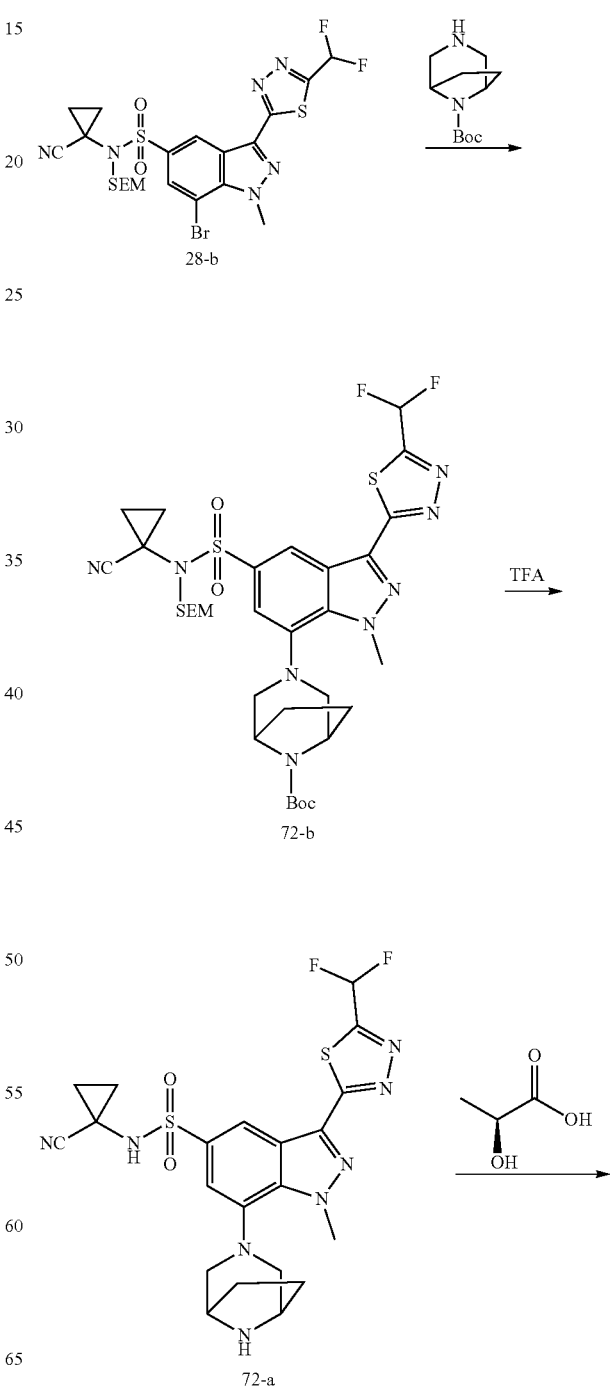

273
-continued

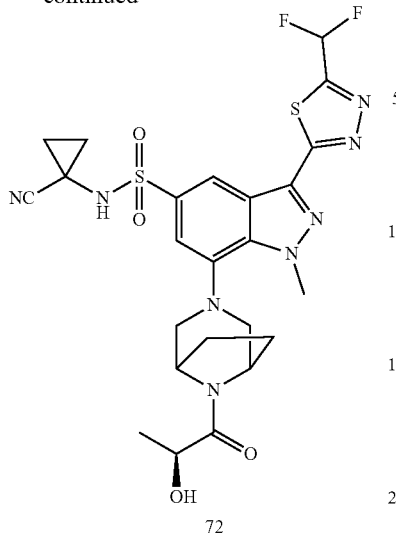

72

Synthesis of Compound 72-b

A microwave tube charged with 28-b (200 mg, 0.32 mmol), 8-BOC-3,8-diazabicyclo[3.2.1]octane (137 mg, 0.64 mmol), Ruphos (15 mg, 0.032 mmol), (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (CAS:1435347-24-2) (45 mg, 0.052 mmol), cesium carbonate (316 mg, 0.97 mmol) and 1,4-dioxane (8 mL) was degassed and purged with nitrogen for 3 times, then was heated at 70° C. overnight. After completion, the reaction mixture was cooled to room temperature and concentrated at reduced pressure to remove the 1,4-dioxane. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 72-b (150 mg, 62%). LC-MS (ESI): m/z 751.3 [M+H]$^+$.

Synthesis of Compound 72-a

To a reaction vial charged with 72-b (150 mg, 0.20 mmol) and dichloromethane (5 mL) with added trifluoroacetic acid (1 mL) dropwise at room temperature. After the dropwise addition, the reaction mixture was stirred at room temperature for 4 h. The solvent was removed by concentration at room temperature at reduced pressure. The organic phase was washed with saturated sodium bicarbonate, brine, dried over anhydrous sodium sulfate, filtered and the filtrate was evaporated to obtain the crude product, which was purified by a flash column chromatography (mobile phase: methanol/dichloromethane, 0% to 20%) to give compound 72-a (90 mg, 86%).

Synthesis of Compound 72

To a reaction vial charged with 72-a (20 mg, 0.038 mmol), L-lactic acid (7 mg, 0.078 mmol), dichloromethane (5 mL), DIPEA (0.033 mL, 0.19 mmol) and HOBT (10 mg, 0.074 mmol) was added EDCI (15 mg, 0.078 mmol) slowly in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate and concentrated. The crude product was purified by Prep-HPLC to give compound 72 (5 mg, 22%). LC-MS (ESI): m/z 593.2 [M+H]$^+$.

Example 73 Synthetic Route of Compound 73

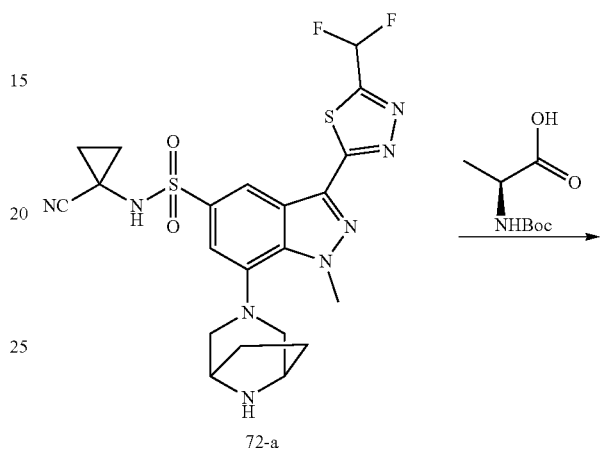

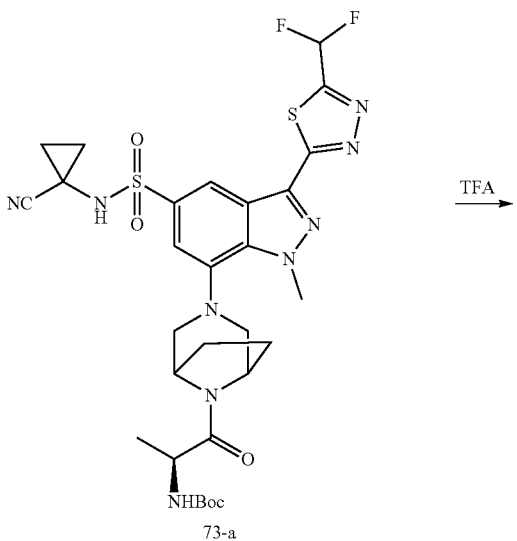

73-a

-continued

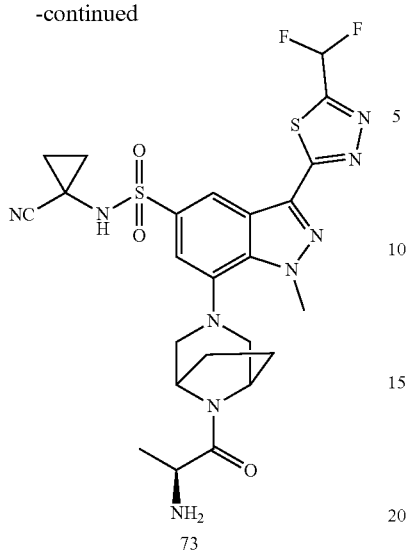

73

Synthesis of Compound 73-a

To a reaction flask charged with 72-a (50 mg, 0.096 mmol), N-Boc-L-alanine (36 mg, 0.19 mmol), dichloromethane (5 mL), DIPEA (0.084 mL, 0.48 mmol) and HOBT (26 mg, 0.19 mmol) was added EDCI (37 mg, 0.19 mmol) slowly in an ice-water bath. After addition, the reaction mixture was warmed to room temperature and stirred overnight. The next day, the reaction was quenched with water, extracted with dichloromethane, the organic phase was washed with brine, dried over anhydrous sodium sulfate and concentrated. The crude product was purified by a flash column chromatography (mobile phase: methanol/dichloromethane, 0% to 10%) to give compound 73-a (40 mg, 60%). LC-MS (ESI): m/z 692.2 [M+H]$^+$.

Synthesis of Compound 73

Trifluoroacetic acid (1 mL) was added dropwise to a reaction vial charged with 73-a (40 mg, 0.058 mmol) and dichloromethane (5 mL) at room temperature. After the dropwise addition, the reaction mixture was stirred at room temperature for 4 h. The solvent was removed by concentration at room temperature at reduced pressure and the residue was diluted with dichloromethane. The organic phase was washed with saturated sodium bicarbonate, brine, dried over anhydrous sodium sulfate, filtered and the filtrate was evaporated to obtain the crude product. The crude product was purified by Prep-HPLC to give compound 73 (22 mg, 64%). LC-MS (ESI): m/z 592.2 [M+H]$^+$.

Example 74 Synthetic Route of Compound 74

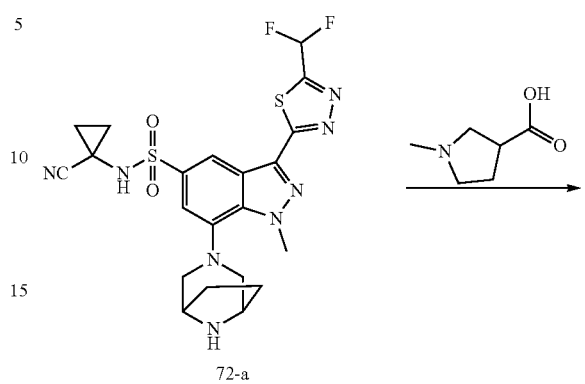

72-a

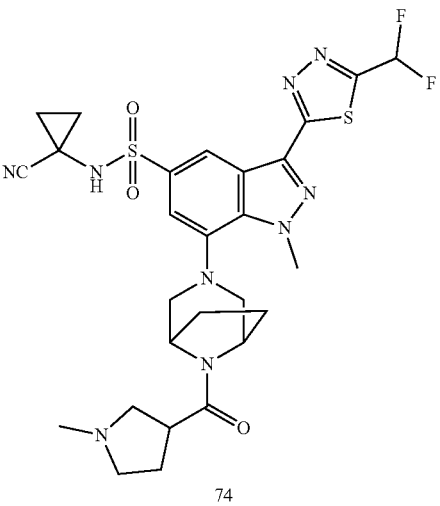

74

Synthesis of Compound 74

To a reaction flask charged with 72-a (40 mg, 0.077 mmol), 1-methylpyrrolidine-3-carboxylic acid (20 mg, 0.15 mmol), dichloromethane (5 mL), DIPEA (0.067 mL, 0.38 mmol) and HOBT (21 mg, 0.16 mmol) was added EDCI (30 mg, 0.16 mmol) slowly in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated. The crude product was purified by Prep-HPLC to give compound 74 (25 mg, 52%). LC-MS (ESI): m/z 632.3 [M+H]$^+$.

Example 75 Synthetic Route of Compound 75

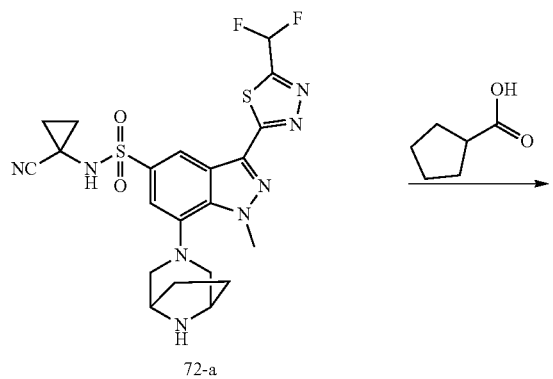

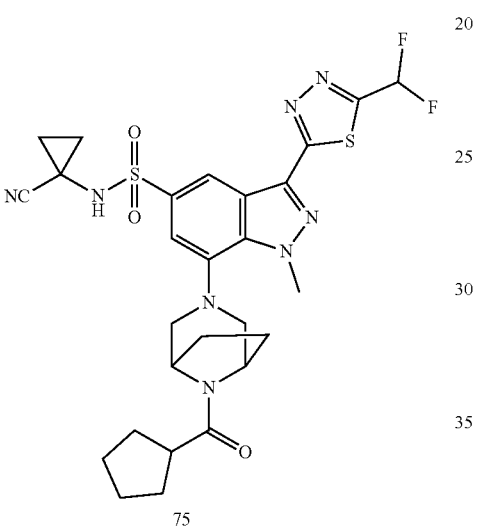

Synthesis of Compound 75

To a reaction flask charged with 72-a (40 mg, 0.077 mmol), cyclopentanecarboxylic acid (0.017 mL, 0.15 mmol), dichloromethane (5 mL), DIPEA (0.067 mL, 0.38 mmol) and HOBT (21 mg, 0.16 mmol) was added EDCI (30 mg, 0.16 mmol) slowly in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate and concentrated. The crude product was purified by Prep-HPLC to give compound 75 (20 mg, 42%). LC-MS (ESI): m/z 617.2 [M+H]$^+$; $^1$H NMR (DMSO-d$_6$, 400 MHz): δ 9.07 (1H, s), 8.70 (1H, s), 7.67 (1H, s), 7.71 (1H, t, J=53.2 Hz), 4.51-4.74 (2H, m), 4.60 (3H, s), 3.15-3.26 (2H, m), 3.00-3.07 (3H, m), 1.95-2.23 (3H, m), 1.77-1.94 (4H, m), 1.49-1.73 (5H, m), 1.26-1.46 (4H, m).

Example 76 Synthetic Route of Compound 76

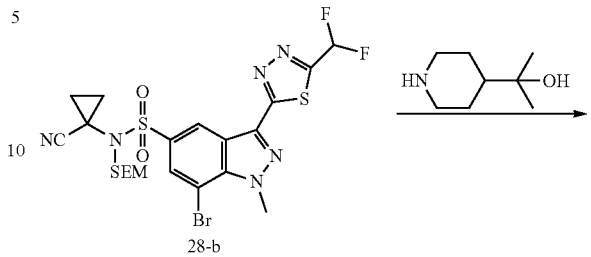

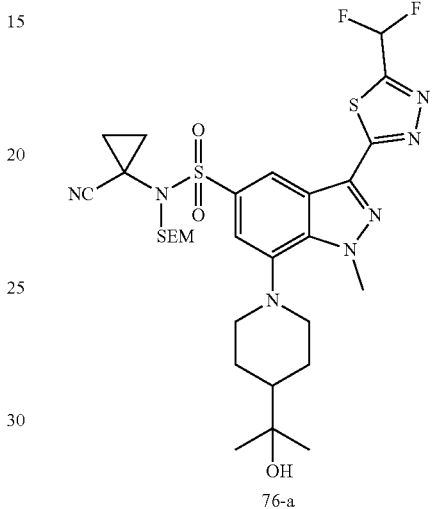

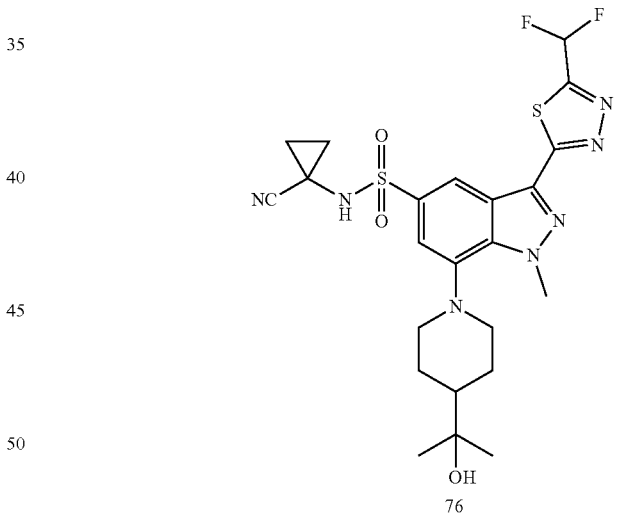

Synthesis of Compound 76-a

A microwave tube charged with 28-b (150 mg, 0.24 mmol), 2-(4-piperidinyl)-2-propanol (69 mg, 0.48 mmol), Ruphos (11 mg, 0.024 mmol), (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (CAS: 1435347-24-2) (33 mg, 0.038 mmol), cesium carbonate (237 mg, 0.73 mmol) and 1,4-dioxane (8 mL) was degassed and purged with nitrogen for 3 times, then was heated at 65° C. overnight. After completion, the reaction mixture was cooled to room temperature and concentrated at reduced pressure to remove the 1,4-dioxane. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 76-a (100 mg, 61%). LC-MS (ESI): m/z 682.5 [M+H]⁺.

Synthesis of Compound 76

Trifluoroacetic acid (1 mL) was added dropwise to a reaction vial charged with 76-a (100 mg, 0.15 mmol) and dichloromethane (5 mL) at room temperature. After the dropwise addition, the reaction mixture was stirred at room temperature for 4 h. The solvent was removed by concentration at room temperature at reduced pressure. The organic phase was washed with saturated sodium bicarbonate, brine, dried over anhydrous sodium sulfate, filtered and the filtrate was evaporated to obtain the crude product. The product was separated and purified by Prep-HPLC to give compound 76 (50 mg, 60%). LC-MS (ESI): m/z 552.2 [M+H]⁺; ¹H NMR (DMSO-d₆, 400 MHz): δ 9.21 (1H, br), 8.59 (1H, s), 7.69 (1H, t, J=53.2 Hz), 7.50 (1H, s), 4.47 (3H, s), 4.26 (1H, s), 3.30-3.70 (2H, m), 2.66-2.80 (2H, m), 1.81-1.98 (2H, m), 1.49-1.65 (2H, m), 1.35-1.47 (3H, m), 1.25-1.34 (2H, m), 1.13 (6H, s).

Example 77 Synthetic Route of Compound 77

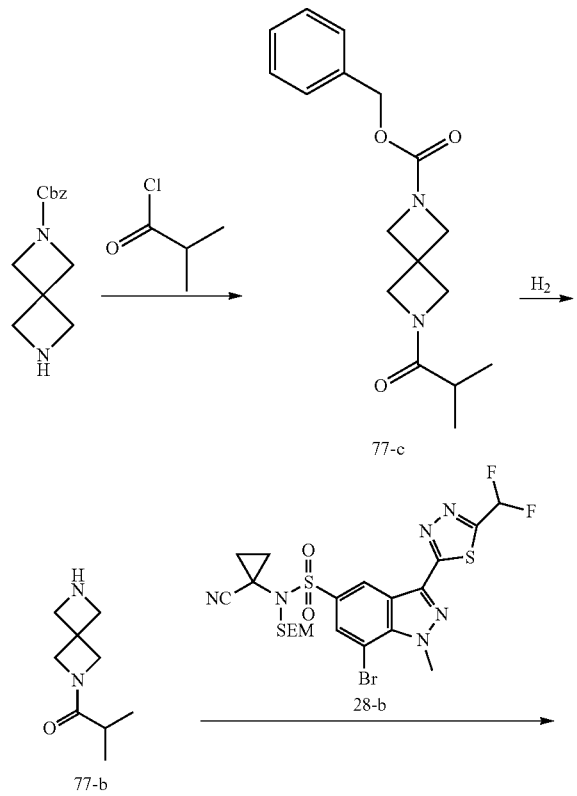

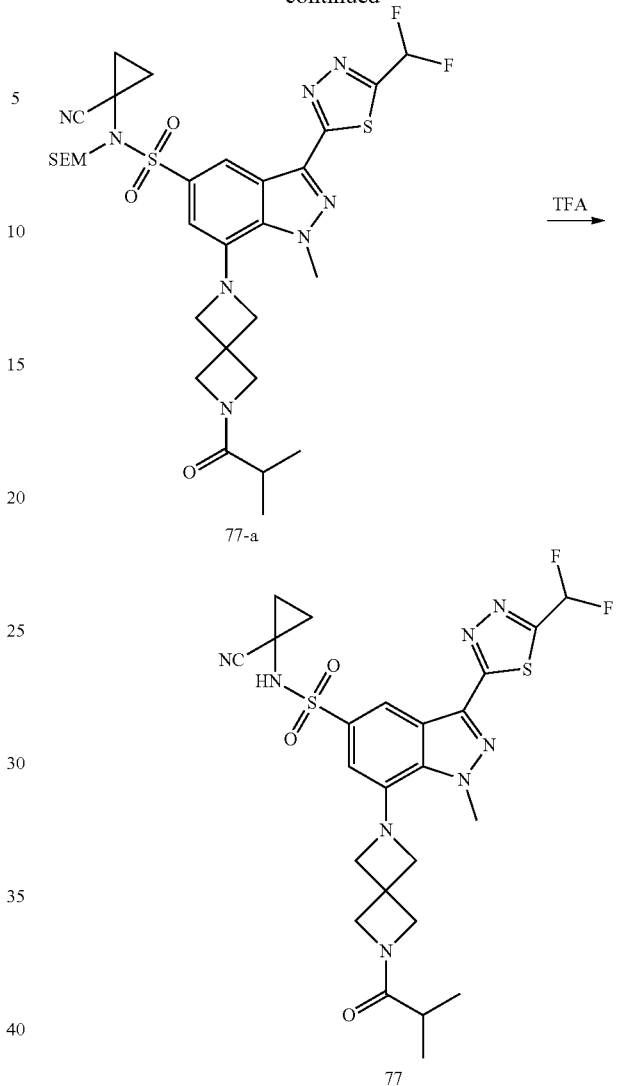

Synthesis of Compound 77-c

To a reaction vial charged with 2-CBZ-2,6-diazaspiro [3.3]heptane oxalate (500 mg, 1.55 mmol), dichloromethane (10 mL) and triethylamine (1.08 mL, 7.76 mmol) was added isobutyryl chloride (0.24 mL, 2.33 mmol) dropwise in an ice-water bath, and the reaction mixture was stirred at room temperature overnight. The next day, the reaction was quenched with water, extracted with dichloromethane, the organic phase was washed with brine, dried over anhydrous sodium sulfate, concentrated at reduced pressure, and the residue was purified by a flash column chromatography (mobile phase: methanol/dichloromethane: 0% to 10%) to give compound 77-c (300 mg, 64%). LC-MS (ESI): m/z=303.4 [M+H]⁺.

Synthesis of Compound 77-b

To a solution of compound 77-c (200 mg, 0.66 mmol) in ethyl acetate (10 mL) was slowly added Pd/C (10% mass fraction) (14 mg) and the reaction was stirred at room temperature for 2 h under hydrogen atmosphere. The reaction was filtered through celite and the filtrate was concentrated at reduced pressure to remove the solvent to give 77-b (90 mg, 81%). LC-MS (ESI): m/z 169.2 [M+H]+.

Synthesis of Compound 77-a

A microwave tube charged with 28-b (120 mg, 0.19 mmol), 77-b (65 mg, 0.39 mmol), Ruphos (9 mg, 0.019 mmol), (SP-4-1)-[1,3-bis[2,6-bis(1-ethylpropyl)phenyl]-4,5-dichloro-1,3-dihydro-2H-imidazol-2-ylidene]-dichloro(3-chloropyridine-KN)palladium (CAS:1435347-24-2) (27 mg, 0.031 mmol), cesium carbonate (189 mg, 0.58 mmol) and 1,4-dioxane (8 mL) was degassed and purged with nitrogen for 3 times, the reaction mixture was heated at 65° C. overnight. After completion, the reaction mixture was cooled to room temperature and the concentrated at reduced pressure to remove the 1,4-dioxane. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 77-a (100 mg, 75%). LC-MS (ESI): m/z 707.3 [M+H]+.

Synthesis of Compound 77

Trifluoroacetic acid (1 mL) was added dropwise a reaction vial charged with 77-a (100 mg, 0.14 mmol) and dichloromethane (5 mL) at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product, which was purified by Prep-HPLC to obtain compound 77 (30 mg, 37%). LC-MS (ESI): m/z 577.2 [M+H]+.

Example 78 Synthetic Route of Compound 78

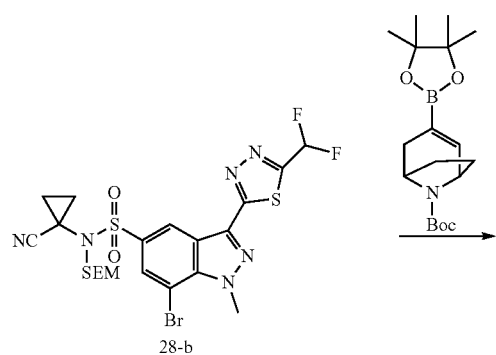

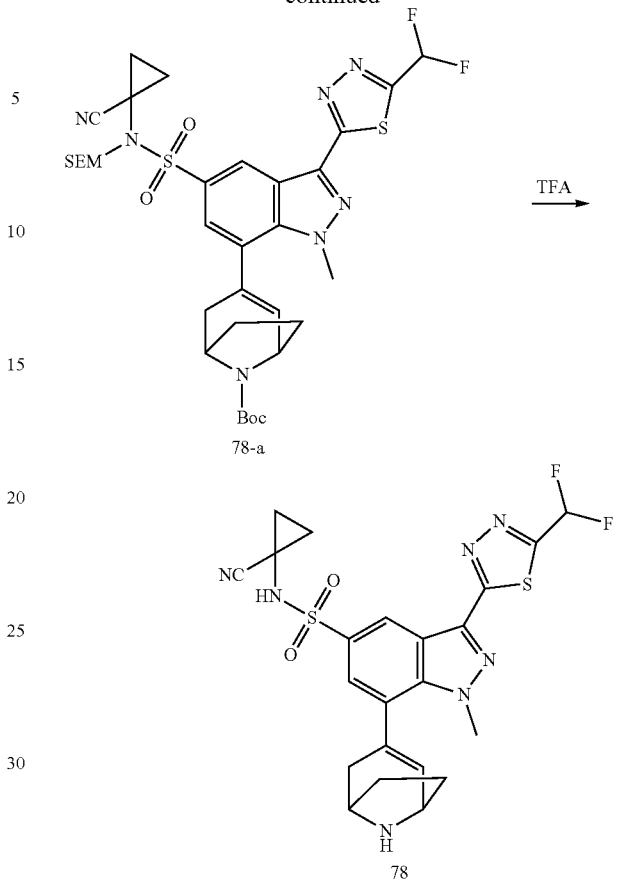

Synthesis of Compound 78-a

A reaction flask charged with 28-b (300 mg, 0.48 mmol), 8-tert-butoxycarbonyl-8-azabicyclo[3.2.1]oct-2-ene-3-boronic acid pinacol ester (195 mg, 0.58 mmol), [1,1'-bis(diphenylphosphino)ferrocene]dichloropalladium dichloride dichloromethane complex (35 mg, 0.048 mmol), potassium carbonate (201 mg, 1.45 mmol), 1,4-dioxane (20 mL) and H$_2$O (4 mL) was degassed and purged with nitrogen for 3 times, then was heated at 100° C. for 4 hours. After completion, the reaction mixture was cooled to room temperature and concentrated at reduced pressure to remove the organic solvent, and the residue was diluted with ethyl acetate, the organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 78-a (300 mg, 83%). LC-MS (ESI): m/z 748.4 [M+H]+.

Synthesis of Compound 78

Trifluoroacetic acid (3 mL) was added dropwise to a reaction vial charged with 78-a (300 mg, 0.40 mmol) and dichloromethane (10 mL) at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product. The product was purified by a flash column chromatography (mobile phase: methanol/dichloromethane, 0% to 25%) to give compound 78 (180 mg, 87%). LC-MS (ESI): m/z 518.6 $[M+H]^+$.

Example 79 Synthetic Route of Compound 79

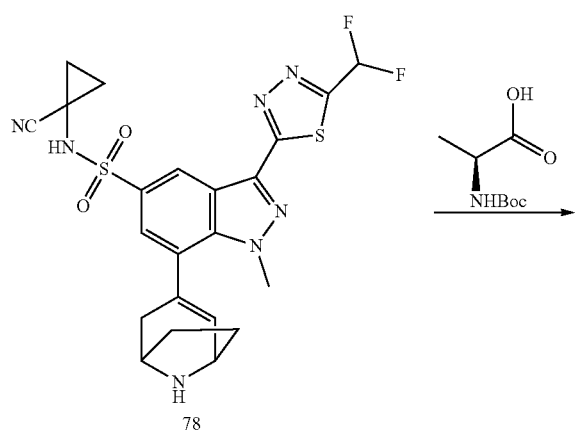

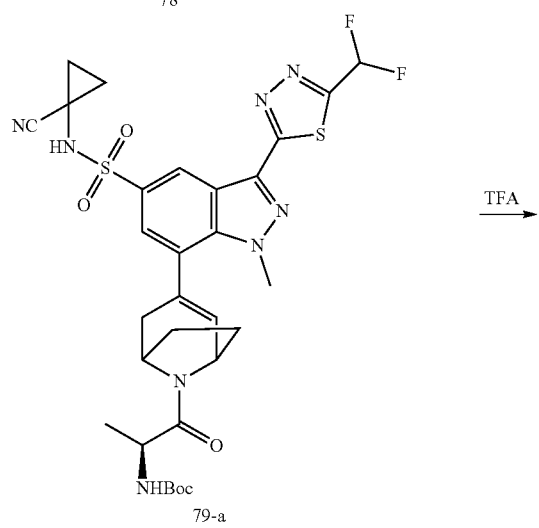

Synthesis of Compound 79-a

A reaction vial charged with 78 (50 mg, 0.097 mmol), N-Boc-L-alanine (37 mg, 0.19 mmol), dichloromethane (5 mL), DIPEA (0.084 mL, 0.48 mmol) and HOBT (26 mg, 0.19 mmol) was slowly added EDCI (37 mg, 0.19 mmol) in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by a flash column chromatography (mobile phase: methanol/dichloromethane, 0% to 10%) to give compound 79-a (50 mg, 75%). LC-MS (ESI): m/z=689.3 $[M+H]^+$.

Synthesis of Compound 79

To a reaction vial was added 79-a (50 mg, 0.073 mmol) and dichloromethane (5 mL). Trifluoroacetic acid (1 mL) was added dropwise to the above mixture at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product. The crude product was purified by Prep-HPLC to give compound 79 (30 mg, 70%). LC-MS (ESI): m/z 589.2 $[M+H]^+$.

Example 80 Synthetic Route of Compound 80

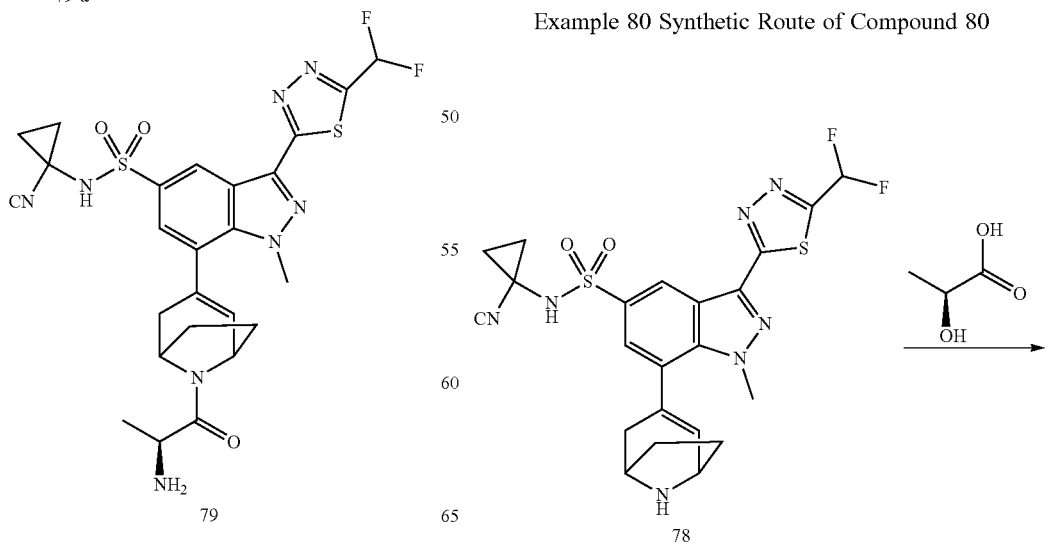

285

-continued

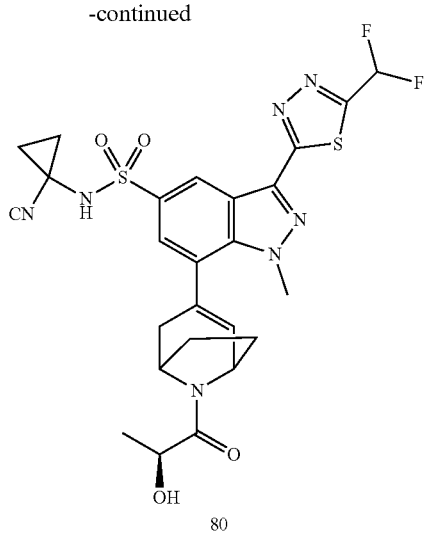

80

Synthesis of Compound 80

A reaction flask charged with 78 (40 mg, 0.077 mmol), L-lactic acid (14 mg, 0.16 mmol), dichloromethane (5 mL), DIPEA (0.067 mL, 0.39 mmol) and HOBT (21 mg, 0.16 mmol) was slowly added EDCI (30 mg, 0.16 mmol) in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by Prep-HPLC to give compound 80 (25 mg, 55%). LC-MS (ESI): m/z=590.3 [M+H]+.

Example 81 Synthesis of Compound 81

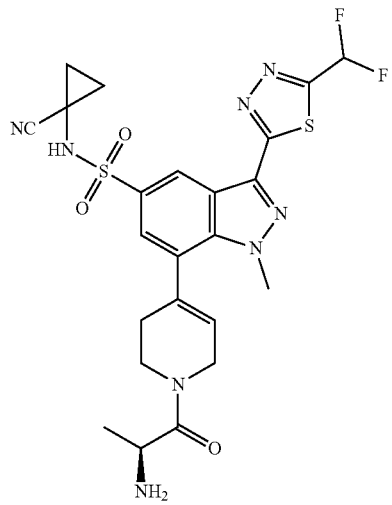

81

Referring to the synthesis of compounds 78 and 79, compound 81 was synthesized using N-Boc-1,2,5,6-tetrahydropyridine-4-boronic acid pinacol ester instead of 8-tert-butoxycarbonyl-8-azabicyclo[3.2.1]oct-2-ene-3-boronic acid pinacol ester with 28-b as the starting reactant. LC-MS (ESI): m/z 563.1 [M+H]+.

Example 82 Synthesis of Compound 82

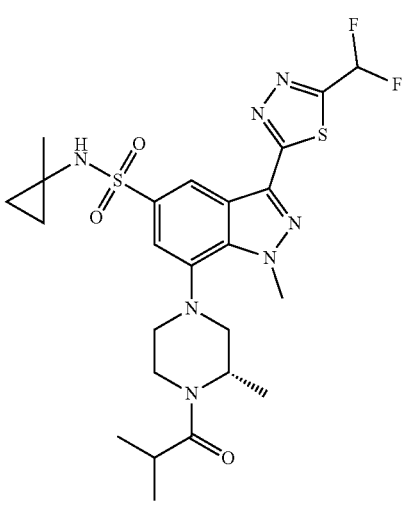

82

Referring to the synthesis of compound 5, compound 82 was synthesized using (S)-2-methyl-1-(2-methylpiperazin-1-yl)prop-1-one instead of 2-methyl-1-(piperazin-1-yl)prop-1-one, with using 5-b as the starting reactant. LC-MS (ESI): m/z 568.0 (M+H)+.

Example 83 Synthetic Route of Compound 83

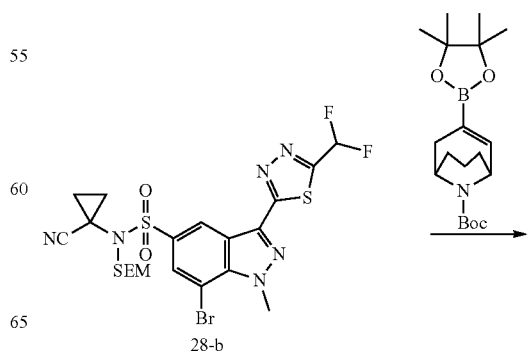

28-b

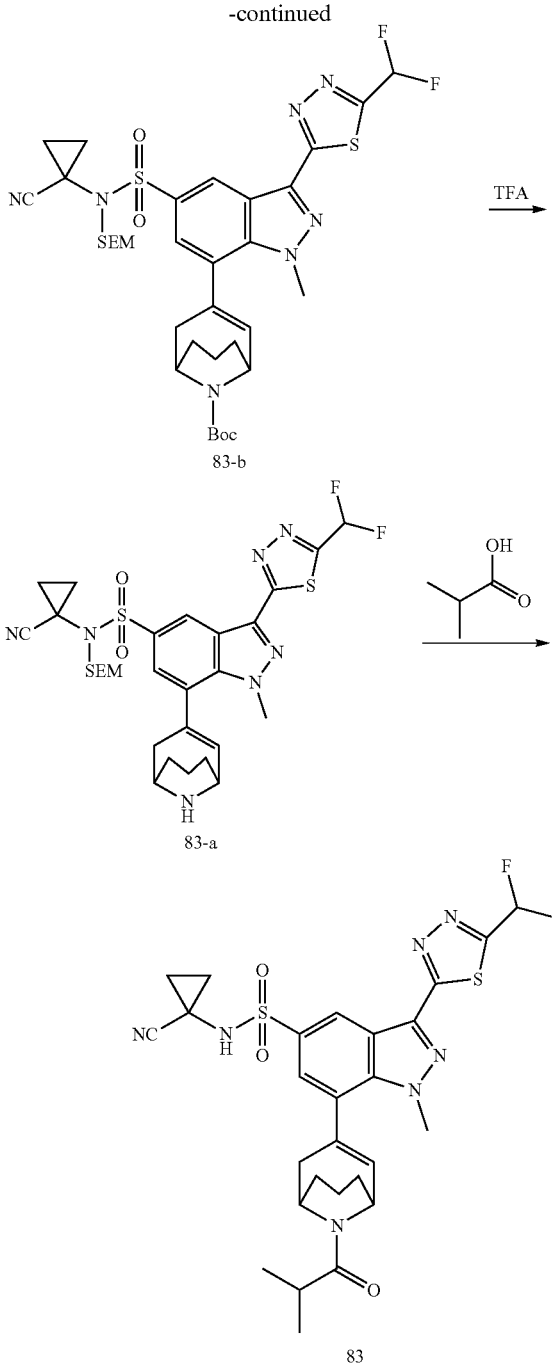

sulfate, filtered out the desiccant, and the filtrate was concentrated at reduced pressure to obtain the crude product, which was purified by column chromatography (mobile phase, PE/EA 3/1) to obtain compound 83-b (230 mg, 94%). LC-MS (ESI): m/z 762.6 (M+H)$^+$.

Synthesis of Compound 83-a

Compound 83-b (230 mg, 0.30 mmol) was dissolved in dichloromethane (6 mL), to which trifluoroacetic acid (2 mL) was added and the reaction was stirred for 2 h at room temperature. The reaction mixture was concentrated at reduced pressure to remove dichloromethane, and the residue was added ethyl acetate (50 mL), saturated sodium bicarbonate solution (10 mL), and potassium carbonate (200 mg), and continued stirring for 40 minutes. The mixture was extracted with ethyl acetate (100 mL), and the organic phase was washed with brine (50 mL), dried over sodium sulfate, filtered out the desiccant. The filtrate was concentrated at reduced pressure to give compound 83-a (150 mg, 94%). LC-MS (ESI): m/z 532.6 (M+H)$^+$.

Synthesis of Compound 83

Compound 83-a (150 mg, 0.28 mmol) was dissolved in N,N-dimethylformamide (6 mL), to which isobutyric acid (37 mg, 0.42 mmol), 1-hydroxybenzotriazole (76 mg, 0.56 mmol), N,N-diisopropylethylamine (73 mg, 0.56 mmol) were added in an ice-water bath, followed by addition of 1-(3-dimethylaminopropyl)-3-ethylcarbodiimide hydrochloride (108 mg, 0.56 mmol), and the reaction was stirred at room temperature for 3 h. The reaction mixture was added water (50 mL) and extracted with ethyl acetate (50 mL). The organic phases were washed with brine (50 mL), dried over sodium sulfate, filtered out the desiccant and the filtrate was concentrated at reduced pressure to give the crude product, which was purified by preparative HPLC (basic conditions) to give compound 83 (65 mg, 38%). LC-MS (ESI): 602.3 m/z (M+H)$^+$; $^1$H NMR (400 MHz, DMSO-d$_6$): δ 9.06 (1H, s), 8.87 (1H, s), 7.85-7.57 (2H, m), 6.06-6.00 (1H, m), 5.28-4.55 (2H, m), 4.15 (3H, d, J=4.0 Hz), 3.03-2.81 (2H, m), 2.47-2.31 (1H, m), 2.07-2.00 (1H, m), 1.91-1.80 (1H, m), 1.76-1.69 (2H, m), 1.67-1.56 (2H, m), 1.46-1.41 (2H, m), 1.34-1.30 (2H, m), 1.10-1.01 (6H, m).

Example 84 Synthetic Route of Compound 84

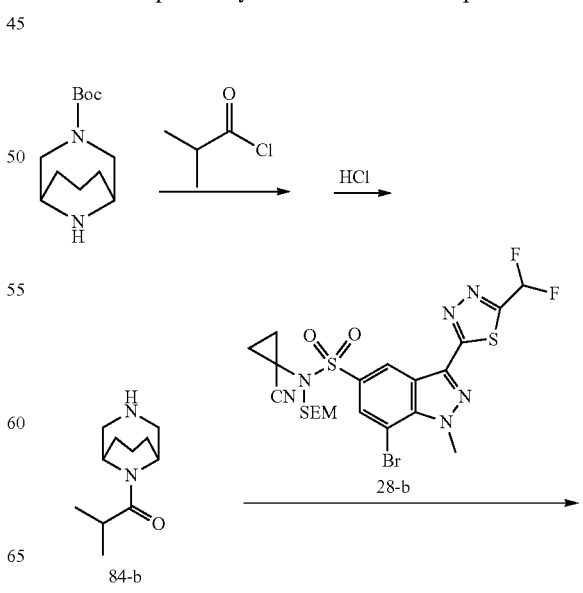

Synthesis of Compound 83-b

A solution of compound 28-b (200 mg, 0.32 mmol), tert-butyl 3-(4,4,5,5-tetramethyl-1,3,2-dioxaborolan-2-yl)-9-azabicyclo[3.3.1]non-2-ene-9-carboxylate (169 mg, 0.48 mmol), [1,1'-bis(diphenylphosphino)ferrocene]palladium dichloride (35 mg. 0.048 mmol), and potassium carbonate (134 mg, 0.97 mmol) in 1,4-dioxane (15 mL) and water (1.5 mL) was degassed and purged with nitrogen for three times, and then stirred at 100° C. for 4 h. The reaction mixture was filtered through celite. The filtrate was added water (100 mL), extracted with ethyl acetate (100 mL), and the organic phase was washed with brine (100 mL), dried over sodium

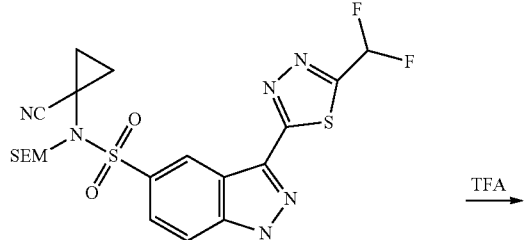

84-a

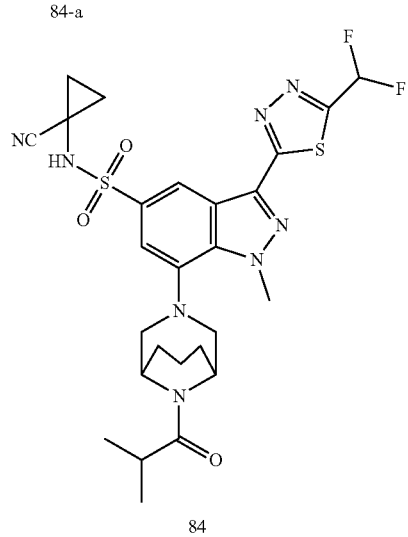

84

Synthesis of Compound 84-b

To a solution of compound 3,9-diazabicyclo[3.3.1]nonane-3-carboxylic acid tert-butyl ester (300 mg, 1.33 mmol) in dichloromethane (12 mL) was added triethylamine (295 mg, 2.92 mmol), followed by dropwise addition of isobutyryl chloride (169 mg, 1.59 mmol) in an ice-water bath. After the dropwise addition, the reaction mixture was stirred at room temperature for 2 hours. The reaction mixture was concentrated at reduced pressure and the residue was added water (100 mL), extracted with ethyl acetate (100 mL), and the organic phases were washed with brine (50 mL), dried over sodium sulfate, filtered off the desiccant. The filtrate was concentrated at reduced pressure to obtain the crude product, which was purified by column chromatography (mobile phase, PE/EA 1/1) to obtain a solid, which was added HCl/1,4-dioxane (4 M, 10 mL), and stirred at room temperature for 2 h. The reaction mixture was concentrated at reduced pressure to obtain the crude product, to which ethanol (1 mL), saturated sodium bicarbonate solution (2 mL) and sodium bicarbonate solid (300 mg) were added and stirred for 15 minutes. The mixture was concentrated at reduced pressure and the residue was added ethanol (10 mL) and continued concentration at reduced pressure, to the residue was added solution of 10% methanol in dichloromethane (10 mL) and stirred for 15 minutes. The mixture was filtered, and the filtrate was concentrated at reduced pressure, to which dichloromethane (20 mL) was added, dried over sodium sulfate, filtered off the desiccant, and the filtrate was concentrated at reduced pressure and dried in vacuum to give compound 84-b (200 mg, 77%). LC-MS (ESI): m/z 197.2 (M+H)⁺.

Synthesis of Compound 84-a

A solution of compounds 28-b (100 mg, 0.16 mmol), 84-b (48 mg, 0.24 mmol), [1,3-bis[2,6-bis(1-ethylpropyl)phenyl]-4,5-dichloro-1,3-dihydro-2H-imidazol-2-ylidene]dichloro(2-methylpyridine)palladium (14 mg, 0.017 mmol), 2-dicyclohexylphosphonium-2',6'-diisopropoxy-1,1'-biphenyl (8 mg, 0.017 mmol), and cesium carbonate (105 mg, 0.32 mmol) in 1,4-dioxane (3 mL) was degassed and purged with nitrogen for 3 min, and then stirred in a sealed tube at 80° C. for 12 h. The reaction mixture was cooled to room temperature, filtered through celite, and the filtrate was concentrated at reduced pressure to obtain the crude product, which was purified by column chromatography (mobile phase, PE/EA 1/1) to give compound 84-a (80 mg, 68%). LC-MS (ESI): 735.2 m/z (M+H)⁺.

Synthesis of Compound 84

Compound 84-a (80 mg, 0.11 mmol) was dissolved in dichloromethane (3 mL) and trifluoroacetic acid (1 mL) was added to the above mixture in an ice-water bath, and the reaction mixture was stirred at room temperature for 2 h. The dichloromethane was removed by concentration at reduced pressure, and the residue was adjusted to pH 7-8 with saturated sodium bicarbonate solution and extracted with ethyl acetate (50 mL). The organic phase was washed with brine (50 mL), dried over sodium sulfate, filtered off the desiccant and concentrated at reduced pressure to obtain the crude product, which was purified by preparative HPLC (basic conditions) to give compound 84 (30 mg, 46%). LC-MS (ESI): m/z 605.3 (M+H)⁺.

Example 85 Synthetic Route of Compound 85

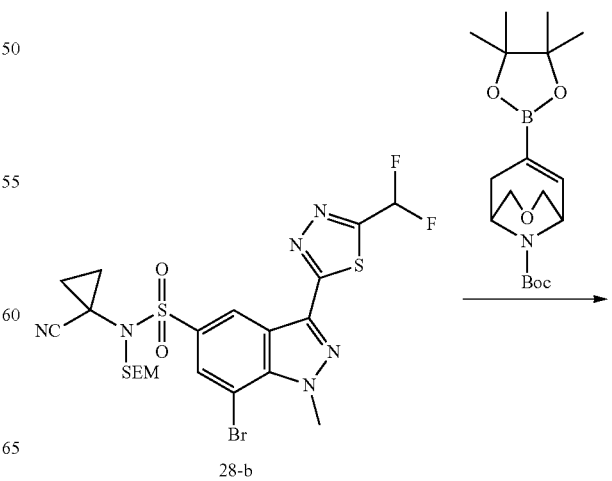

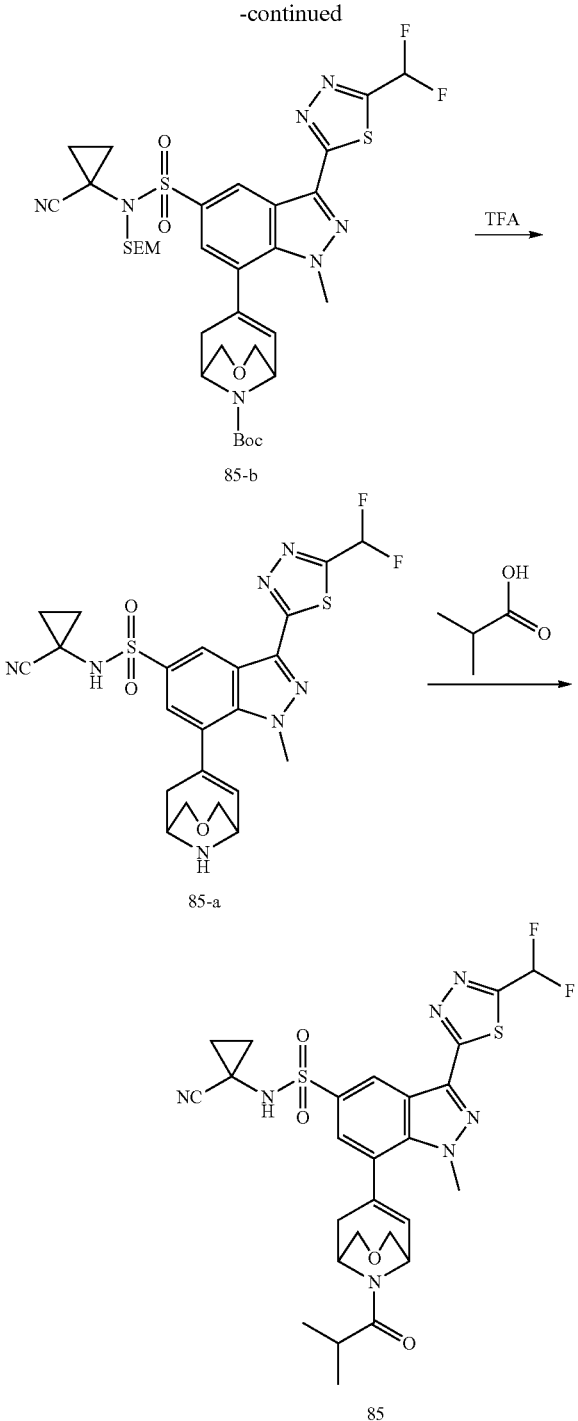

85-b 85-a

85 three times, and then stirred at 100° C. for 4 h. The reaction mixture was filtered through celite, and the filtrate was added water (100 mL), extracted with ethyl acetate (100 mL). The organic phases were washed with brine (100 mL), dried over sodium sulfate, filtered off the desiccant, and concentrated at reduced pressure to obtain the crude product, which was purified by column chromatography (mobile phase, PE/EA=3/1) to give compound 85-b (120 mg, 97%). LC-MS (ESI): m/z 764.4 (M+H)$^+$.

Synthesis of Compound 85-a

Compound 85-b (120 mg, 0.16 mmol) was dissolved in dichloromethane (3 mL), to which trifluoroacetic acid (1 mL) was added and the reaction was stirred at room temperature for 2 h. The reaction mixture was concentrated at reduced pressure to remove dichloromethane, and the residue was adjusted to pH 7-8 with saturated sodium bicarbonate solution, then extracted with ethyl acetate (50 mL). The organic phase was washed with brine (50 mL), dried over sodium sulfate, filtered off the desiccant, and the filtrate was concentrated at reduced pressure to give compound 85-a (83 mg, 99%). LC-MS (ESI): m/z 534.2 (M+H)$^+$.

Synthesis of Compound 85

To a solution of compound 85-a (83 mg, 0.16 mmol) in N,N-dimethylformamide (10 mL) was added isobutyric acid (21 mg, 0.24 mmol), 1-hydroxybenzotriazole (42 mg, 0.31 mmol) and N,N-diisopropylethylamine (40 mg, 0.31 mmol) followed by the addition of 1-(3-dimethylaminopropyl)-3-ethylcarbodiimide hydrochloride (60 mg, 0.31 mmol) in an ice-water bath and the reaction mixture was stirred for 12 h at room temperature. The reaction mixture was added water (100 mL), extracted with ethyl acetate (100 mL), and the organic phases were washed with brine (100 mL), dried over sodium sulfate, filtered off the desiccant. The filtrate was concentrated at reduced pressure to obtain the crude product, which was purified by preparative HPLC (basic conditions) to give compound 85 (38 mg, 40%). LC-MS (ESI): 604.2 m/z (M+H)$^+$; $^1$H NMR (400 MHz, DMSO-d$_6$): δ 9.18 (1H, s), 8.88 (1H, s), 7.86-7.57 (2H, m), 6.15-6.06 (1H, m), 5.08-4.75 (1H, m), 4.69-4.40 (1H, m), 4.32 (3H, s), 4.07-3.99 (1H, m), 3.81-3.76 (1H, m), 3.75-3.53 (2H, m), 3.01-2.94 (1H, m), 2.93-2.79 (1H, m), 2.78-2.56 (1H, m), 1.45-1.36 (2H, m), 1.35-1.26 (2H, m), 1.12-1.04 (6H, m).

Example 86 Synthetic Route of Compound 86

Synthesis of Compound 85-b

A solution of compound 28-b (100 mg, 0.16 mmol), 3-oxo-8-tert-butyryl-bicyclo-2-undecene-7-boronic acid ester (85 mg, 0.24 mmol), [1,1'-bis(diphenylphosphino) ferrocene]palladium dichloride (18 mg, 0.024 mmol), potassium carbonate (67 mg, 0.49 mmol) in 1,4-dioxane (10 mL) and water (1 mL) was degassed and purged with nitrogen for

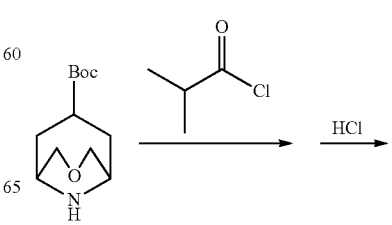

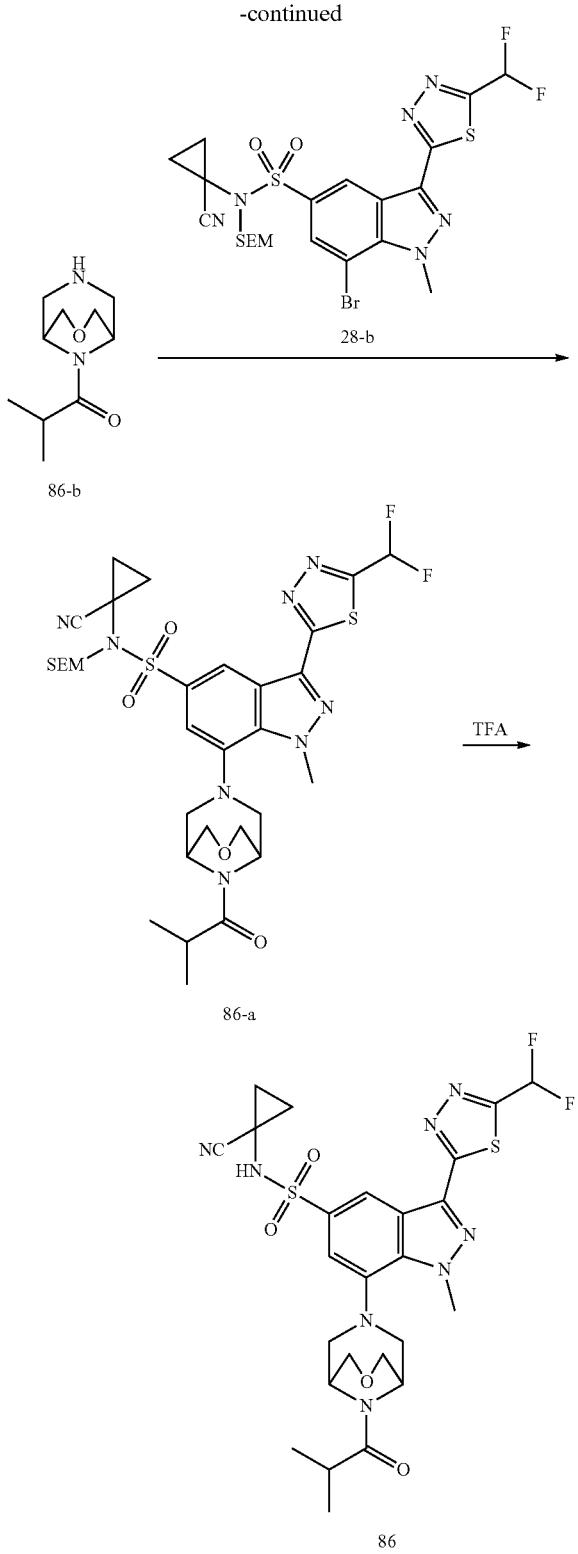

Synthesis of Compound 86-b

To a solution of compound 3-oxa-7,9-diazabicyclo[3.3.1]nonane-7-carboxylic acid tert-butyl ester (300 mg, 1.31 mmol) in dichloromethane (12 mL) was added triethylamine (293 mg, 2.89 mmol), followed by dropwise addition of isobutyryl chloride (168 mg, 1.58 mmol) in an ice-water bath. After the dropwise addition, the reaction mixture was stirred at room temperature for 2 hours. The reaction mixture was concentrated at reduced pressure and the residue was added water (100 mL), extracted with ethyl acetate (100 mL). The organic phases were washed with brine (50 mL), dried over sodium sulfate, filtered off the desiccant, and concentrated at reduced pressure to obtain the crude product, which was purified by column chromatography (mobile phase, PE/EA 1/1) to obtain a solid, which was added HCl/1,4-dioxane (4 M, 10 mL). The reaction mixture was stirred at room temperature for 2 h, then was concentrated at reduced pressure to obtain the crude product, which was added ethanol (1 mL), saturated sodium bicarbonate solution (2 mL) and sodium bicarbonate solid (300 mg) and stirred for 15 minutes. The mixture was concentrated at reduced pressure and ethanol (10 mL) was added to the residue and continued concentrating at reduced pressure, then was added a solution of methanol in dichloromethane (10% 1, 0 mL) to the residue and stirred for 5 min, dried over sodium sulfate, filtered off the desiccant, and the filtrate was concentrated at reduced pressure and dried in vacuum to obtain compound 86-b (150 mg, 58%). LC-MS (ESI): m/z 199.1 (M+H)$^+$.

Synthesis of Compound 86-a

A solution of compounds 28-b (100 mg, 0.16 mmol), 86-b (48 mg, 0.24 mmol), [1,3-bis[2,6-bis(1-ethylpropyl)phenyl]-4,5-dichloro-1,3-dihydro-2H-imidazol-2-ylidene]dichloro(2-methylpyridine)palladium (14 mg, 0.017 mmol), 2-dicyclohexylphosphoryl 2',6'-diisopropoxy-1,1'-biphenyl (8 mg, 0.017 mmol), and cesium carbonate (105 mg, 0.32 mmol) in 1,4-dioxane (4 mL) was purged with nitrogen for 3 min and then stirred in a sealed tube at 80° C. for 14 h. The reaction mixture was cooled to room temperature, filtered through celite, and the filtrate was concentrated at reduced pressure to obtain the crude product, which was purified by column chromatography (mobile phase, PE/EA 1/1) to give compound 86-a (60 mg, 51%). LC-MS (ESI): m/z 737.7 (M+H)$^+$.

Synthesis of Compound 86

Compound 86-a (60 mg, 0.081 mmol) was dissolved in dichloromethane (4.5 mL) and trifluoroacetic acid (1.5 mL) was added to the above solution in an ice-water bath and the reaction mixture was stirred at room temperature for 2 h. The reaction mixture was concentrated at reduced pressure to remove the dichloromethane, and the residue was adjusted to pH 7-8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to obtain the crude product, which was purified by preparative HPLC (basic conditions) to give compound 86 (26 mg, 53%). LC-MS (ESI): m/z 607.3 (M+H)$^+$.

Example 87 Synthetic Route of Compound 87

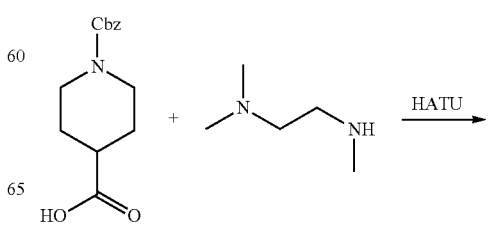

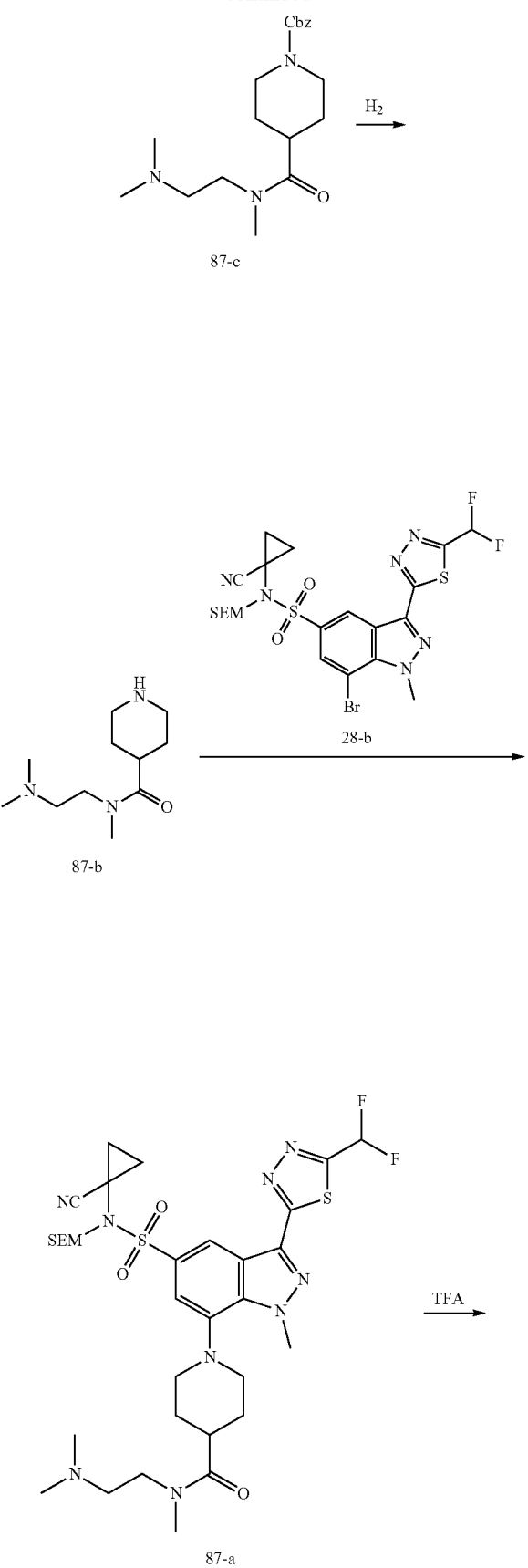

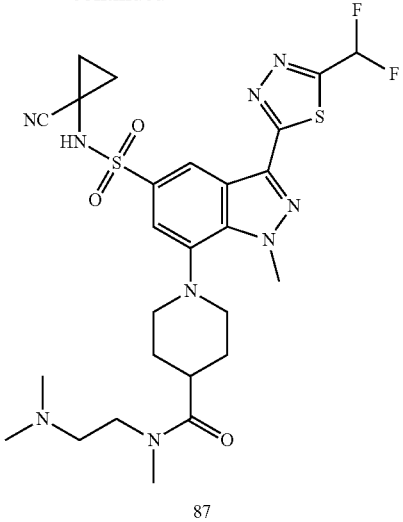 [SMILES: CN(C)CCN(C)C(=O)C1CCN(c2cc(S(=O)(=O)NC3(C#N)CC3)cc3c(-c4nnc(C(F)F)s4)nn(C)c23)CC1]

Synthesis of Compound 87-c

A reaction flask charged with N-Cbz-piperidine-4-carboxylic acid (789 mg, 3.00 mmol), N,N,N'-trimethylethylenediamine (400 mg, 3.92 mmol), DMF (10 mL), HATU (2568 mg, 6.75 mmol) and DIPEA (900 mg, 6.96 mmol) was stirred at room temperature under nitrogen atmosphere for 2 hours. The reaction was quenched by adding saturated aqueous sodium bicarbonate (100 mL), extracted with dichloromethane (50 mL*3), concentrated and purified by column chromatography (mobile phase: methanol/dichloromethane 0/100 to 1/10), and concentrated to give compound 87-c (790 mg, 76%). LC-MS (ESI): m/z 348.7 (M+H)$^+$.

Synthesis of Compound 87-b

A reaction vial charged with 87-c (350 mg, 1.01 mmol), 10% palladium carbon (107 mg), and ethanol (20 mL) was degassed and purged with hydrogen gas (500 mL) for 3 times and stirred for at room temperature 4 h. The reaction mixture was filtered and concentrated to give compound 87-b (179 mg, 83%). LC-MS (ESI): m/z 214.3 (M+H)$^+$.

Synthesis of Compound 87-a

A microwave tube was added 28-b (20 mg, 0.03 mmol), 87-b (18 mg, 0.08 mmol), 1,4-dioxane (1 mL), Ruphos (1 mg, 0.002 mmol), cesium carbonate (30 mg, 0.09 mmol), (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (5 mg, 0.006 mmol) was degassed and purged with nitrogen for three times, then stirred at 75° C. for 12 h, concentrated, washed with ethyl acetate (10 mL*3) and concentrated to give 87-a (26 mg), which was directly used in the next step.

Synthesis of Compound 87

A reaction flask charged with 87-a (20 mg, 0.027 mmol), dichloromethane (3 mL) and trifluoroacetic acid (1 mL) was stirred at room temperature under nitrogen atmosphere for 2 hours. The reaction mixture was concentrated, quenched by adding potassium carbonate (3 g) and water (20 mL), and combined with ethyl acetate (20 mL), then stirred at room temperature for 2 hours, extracted with ethyl acetate (20 mL*3), concentrated, and the residue was purified by Prep-HPLC to afford compound 87 (9.7 mg, 59%). $^1$H NMR (400 MHz, CDCl$_3$): δ8.89 (1H, s), 7.63 (1H, d, J=2.4 Hz), 7.10 (1H, t, J=54.0 Hz), 4.49 (3H, d, J=3.6 Hz), 3.58-3.69 (1H, m), 3.47-3.55 (1H, m), 3.42 (2H, d, J=12.4 Hz), 3.18 (2H, s), 3.00 (1H, s), 2.93 (2H, t, J=12.0 Hz), 2.63-2.80 (2H, m), 2.49-2.56 (1H, m), 2.45 (3H, s), 2.34 (2H, s), 2.05-2.23 (2H, m), 1.85-2.02 (3H, m), 1.60-1.67 (3H, m), 1.40-1.48 (2H, m).

Example 88 Synthetic Route of Compound 88

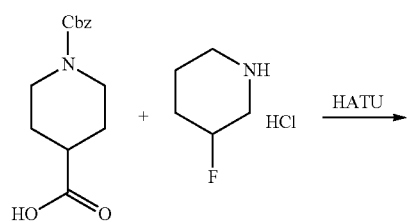

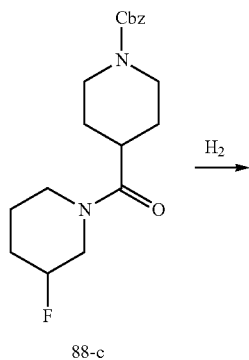

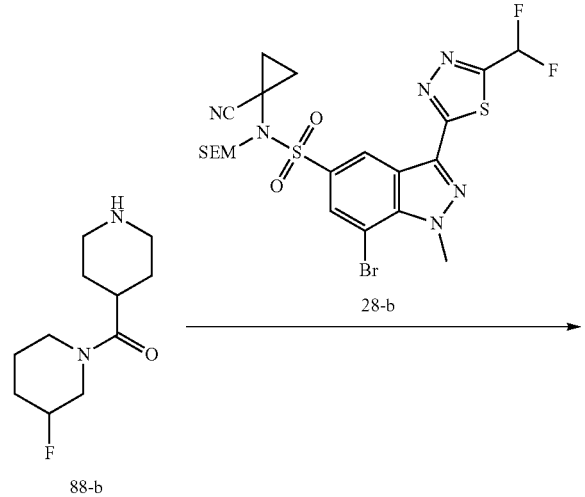

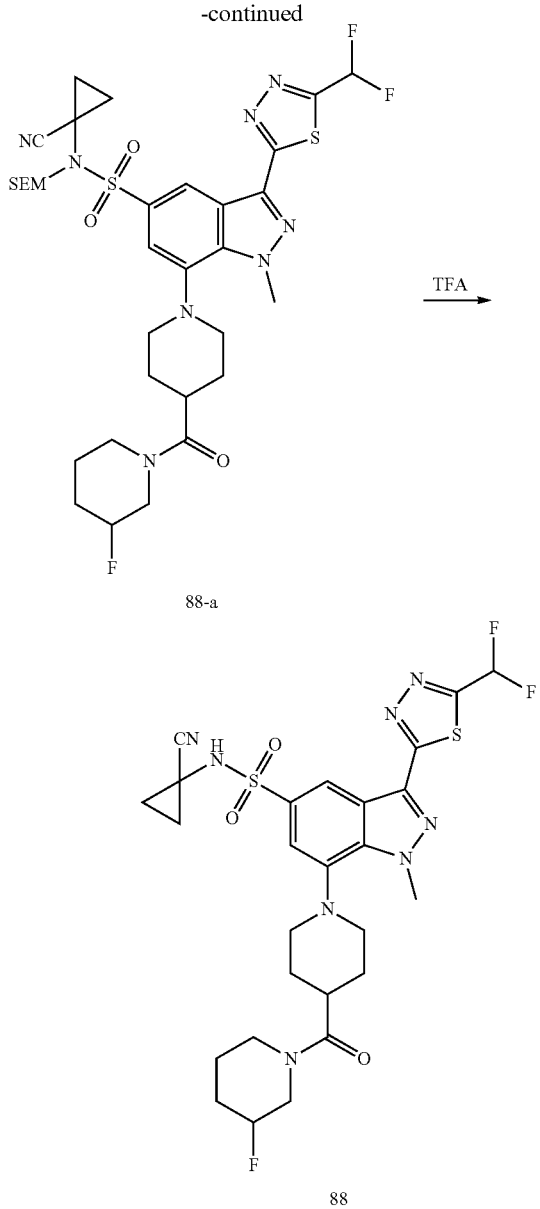

Synthesis of Compound 88-c

A solution of N-Cbz-piperidine-4-carboxylic acid (263 mg, 1.00 mmol), 3-fluoropyridine hydrochloride (100 mg, 0.72 mmol), HATU (500 mg, 1.32 mmol) and DIPEA (300 mg, 2.32 mmol) in DMF (3 mL) in a reaction vial was stirred at room temperature for 2 h under the protection of nitrogen. The reaction was quenched by adding saturated sodium bicarbonate solution (20 mL), extracted with dichloromethane (20 mL*3), and the organic phase was concentrated at reduced pressure. The residue was purified by column chromatography (mobile phase: methanol/dichloromethane 0/100 to 1/10) and concentrated at reduced pressure to give compound 88-c (263 mg, 76%). LC-MS (ESI): m/z 349.2 (M+H)$^+$.

Synthesis of Compound 88-b

A reaction vial charged with 88-c (263 mg, 0.75 mmol), 10% palladium carbon (80 mg), and ethanol (20 mL) was degassed and purged with hydrogen (1000 mL) three times and stirred at room temperature for 4 h. The reaction mixture was filtered and concentrated at reduced pressure to give compound 88-b (141 mg, 88%).

Synthesis of Compound 88-a

A microwave tube charged with 28-b (60 mg, 0.097 mmol), 88-b (21 mg, 0.098 mmol), Ruphos (4.5 mg, 0.0096 mmol), cesium carbonate (95 mg, 0.29 mmol), (SP-4-1)-[1, 3-bis[2,6-bis(1-ethylpropyl)phenyl]-4,5-dichloro-1,3-dihydro-2H-imidazol-2-ylidene]dichloro(3-chloropyridine-KN)palladium (17 mg, 0.020 mmol) was degassed and purged with nitrogen for three times, then was added 1,4-dioxane (3 mL) and degassed and purged with nitrogen for three times, then the reaction mixture was stirred at 88° C. for 12 h. The reaction mixture was concentrated at reduced pressure, washed with ethyl acetate (10 mL*3), concentrated at reduced pressure and purified by column chromatography (mobile phase: methanol/dichloromethane 0/100 to 1/10) to give compound 88-a (66 mg, 90%). LC-MS (ESI): m/z 753.8 (M+H)$^+$.

Synthesis of Compound 88

A reaction vial charged with 88-a (66 mg, 0.088 mmol), dichloromethane (3 mL) and trifluoroacetic acid (1 mL) was stirred at room temperature for 2 h under the protection of nitrogen. The reaction mixture was concentrated at reduced pressure and the residue was added potassium carbonate (3 g) and water (20 mL), and added ethyl acetate (20 mL), and the mixture was stirred at room temperature for 2 hours. The reaction mixture was extracted with ethyl acetate (20 mL*3), and the organic phase was concentrated at reduced pressure and purified by Prep-HPLC to give compound 88 (22 mg, 40%). LC-MS (ESI): m/z 623.7 (M+H)$^+$; $^1$H NMR (400 MHz, CDCl$_3$): δ8.87 (1H, d, J=1.2 Hz), 7.62 (1H, s), 7.10 (1H, t, J=53.6 Hz), 6.00 (1H, s), 4.59-4.86 (1H, m), 4.83 (3H, s), 3.83-4.16 (1H, m), 3.41-3.71 (2H, m), 3.42 (2H, d, J=11.6 Hz), 2.98-3.12 (1H, m), 2.91 (2H, t, J=11.6 Hz), 2.63-2.79 (1H, m), 2.09-2.26 (2H, m), 1.78-1.99 (4H, m), 1.55-1.67 (4H, m), 1.36-1.48 (2H, m).

Example 89 Synthesis of Compound 89

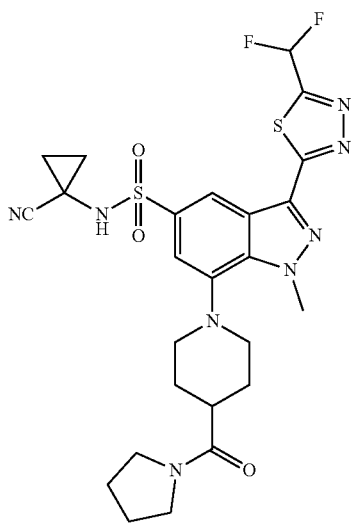

89

Referring to the synthesis of compound 88, compound 89 was synthesized using 4-piperidinyl(1-pyrrolidinyl)methanone instead of 88-b with 28-b as the starting reactant. LC-MS (ESI): m/z 591.7 (M+H)$^+$; $^1$H NMR (400 MHz, DMSO-d$_6$): δ9.02 (1H, brs), 8.61 (1H, d, J=1.2 Hz), 7.70 (1H, t, J=53.2 Hz), 7.54 (1H, d, J=1.6 Hz), 4.49 (3H, d, J=3.6 Hz), 3.55 (2H, t, J=6.8 Hz), 3.25-3.45 (4H, m), 2.78-2.96 (2H, m), 2.60-2.74 (1H, m), 1.84-1.98 (6H, m), 1.73-1.83 (2H, m), 1.39-1.46 (2H, m), 1.26-1.34 (2H, m).

Example 90 Synthetic Route of Compound 90

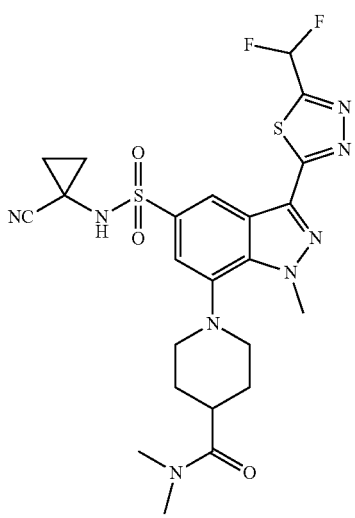

90

Referring to the synthesis of compound 88, compound 90 was synthesized by replacing 88-b with N,N-dimethylpiperidine-4-carboxamide using 28-b as the starting reactant. LC-MS (ESI): m/z 565.7 (M+H)$^+$. $^1$H NMR (400 MHz, CDCl$_3$): δ8.88 (1H, d, J=1.2 Hz), 7.62 (1H, d, J=0.8 Hz), 7.10 (1H, t, J=53.6 Hz), 5.90 (1H, s), 4.49 (3H, s), 3.42 (1H, d, J=11.6 Hz), 3.13 (3H, s), 3.00 (3H, s), 2.92 (2H, t, J=12.0 Hz), 2.63-2.80 (1H, m), 2.05-2.23 (2H, m), 1.92 (2H, d, J=12.4 Hz), 1.50-1.71 (2H, m), 1.40-1.48 (2H, m).

Example 91 Synthetic Route of Compound 91

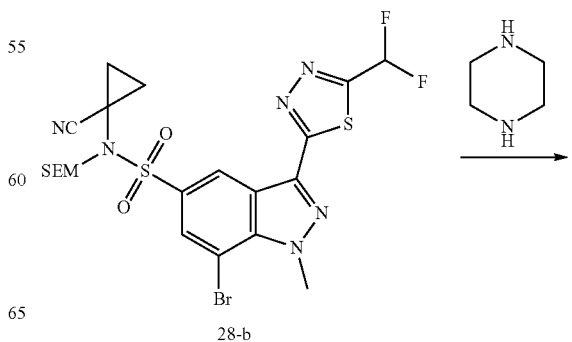

28-b

-continued

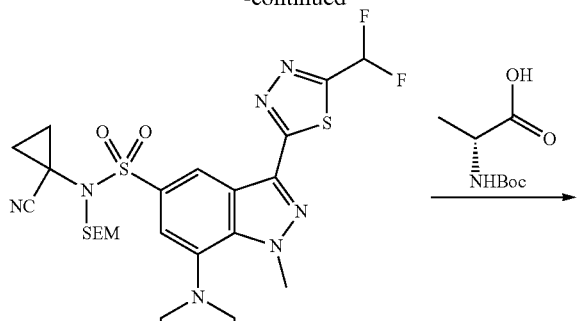

91-b

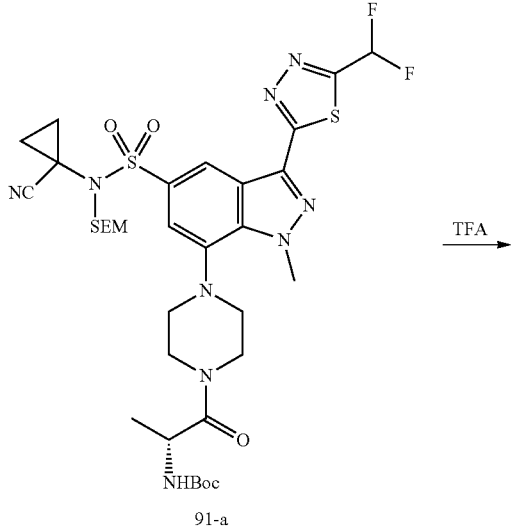

91-a

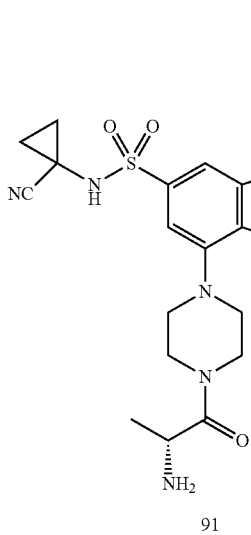

91

Synthesis of compound 91-b

A microwave tube charged with 28-b (150 mg, 0.24 mmol), piperazine (42 mg, 0.49 mmol), Ruphos (11.3 mg, 0.024 mmol), cesium carbonate (229 mg, 0.70 mmol) and Ruphos Pd G3 (40 mg, 0.048 mmol) was degassed and purged with nitrogen for three times, then was added 1,4-dioxane (5 mL) and degassed and purged with nitrogen for three times. The reaction mixture was stirred at 65° C. for 18 hours. The reaction mixture was concentrated at reduced pressure, and the residue was washed with ethyl acetate (10 mL*3), then the filtrate was concentrated at reduced pressure and purified by column chromatography (mobile phase: methanol/dichloromethane 1/20 to 1/10) to give compound 91-b (63 mg, 42%).

Synthesis of Compound 91-a

A reaction vial charged with 91-b (63 mg, 0.10 mmol), dichloromethane (6 mL), N-(tert-butoxycarbonyl)-D-alanine (38 mg, 0.20 mmol), EDCI (39 mg, 0.20 mmol), HOBt (27 mg, 0.20 mmol) and DIPEA (65 mg, 0.50 mmol) was stirred at room temperature for 2 h under the protection of nitrogen. The reaction mixture was concentrated at reduced pressure and purified by column chromatography (mobile phase: methanol/dichloromethane 0/100 to 1/10) to give compound 91-a (46 mg, 57%). LC-MS (ESI): m/z 796.6 $(M+H)^+$.

Synthesis of Compound 91

A reaction vial charged with 91-a (33 mg, 0.041 mmol), dichloromethane (3 mL) and trifluoroacetic acid (1 mL) was stirred at room temperature for 2 h under the protection of nitrogen. The reaction mixture was concentrated at reduced pressure and the residue was added potassium carbonate (3 g), water (20 mL) and ethyl acetate (20 mL), and the mixture was stirred at room temperature for 2 hours. The aqueous phase was extracted with ethyl acetate (20 mL*3), the organic phases were concentrated at reduced pressure and purified by Prep-HPLC to give compound 91 (3 mg, 13%). LC-MS (ESI): m/z 566.7 $(M+H)^+$.

Example 92 Synthetic Route of Compound 92

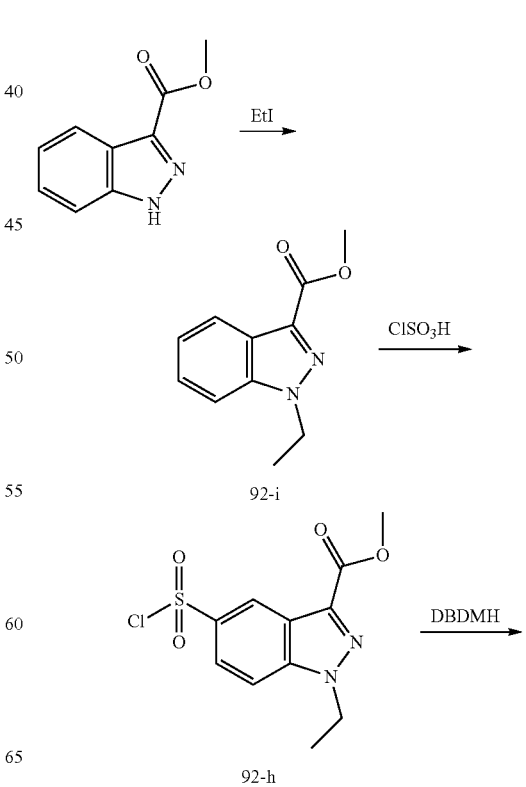

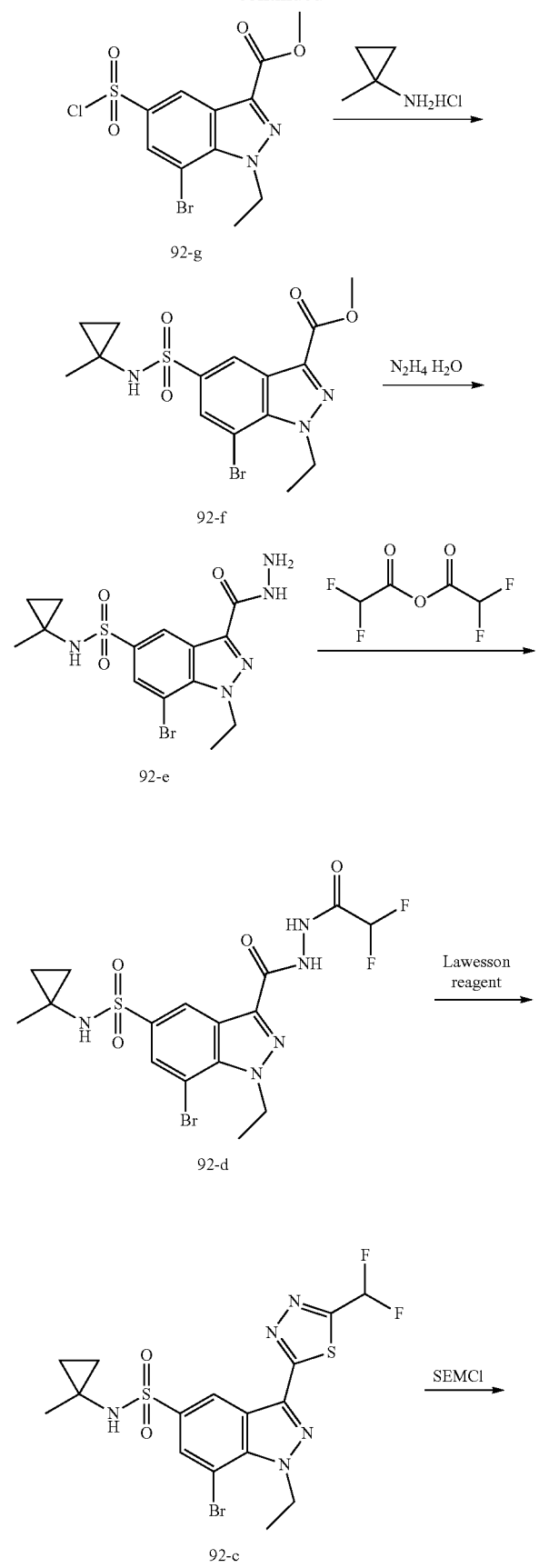
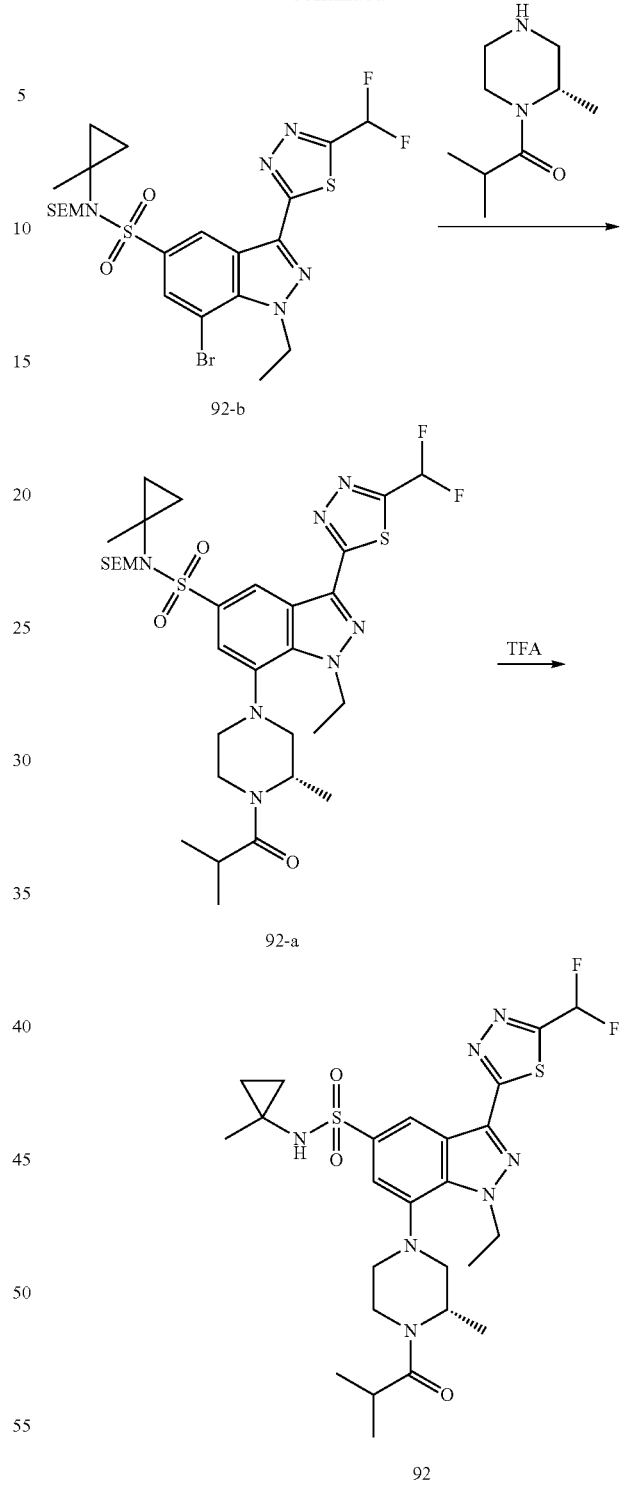
Synthesis of Compound 92-i
A reaction flask charged with methyl 1H-indazole-3-carboxylate (11.5 g, 65.27 mmol) and tetrahydrofuran (110 mL) was added potassium tert-butoxide (9.5 g, 84.66 mmol) in two batches over 5 min in an ice-water bath. After addition, the mixture was stirred in an ice-water bath for 1 hour. Then ethane iodide (6.7 mL, 82.91 mmol) was added dropwise in an ice-water bath. After the dropwise addition, the reaction mixture was stirred from the ice water bath to room temperature for 18 hours. The solvent was removed by concentration at reduced pressure, and the residue was diluted by adding ethyl acetate and then acetic acid (5 mL). The organic phase was washed sequentially with water, saturated sodium bicarbonate, brine, dried over anhydrous sodium sulfate, filtered, and the filtrate was evaporated to give 92-i (9.6 g, 72%). LC-MS (ESI): m/z 205.2 (M+H)$^+$.

Synthesis of Compound 92-h

A reaction flask charged with 92-i (9.6 g, 47.01 mmol) was added chlorosulfonic acid (25 mL) dropwise in an ice-water bath and stirred for 10 min. The reaction mixture was stirred at 68° C. for 18 hours (Attached tail gas drying and absorption device). The reaction mixture was cooled to room temperature, was added dropwise into ice (300 g), extracted with ethyl acetate. The organic phase was washed with water, brine, dried over anhydrous sodium sulfate, filtered. The filtrate was evaporated and the residue was dried by an oil pump to give 92-h (10.5 g, 74%).

Synthesis of Compound 92-g

A reaction flask charged with 92-h (10.5 g, 34.68 mmol), dibromohydantoin (13.88 g, 48.56 mmol) and dichloromethane (105 mL) was added TMSOTf (5.25 mL, 28.41 mmol) dropwise in an ice-water bath and stirred for 10 min, then was added trifluoromethanesulfonic acid (9 mL) dropwise to the suspension. After the dropwise addition, the reaction mixture was stirred at room temperature for 5 hours. Concentrated at reduced pressure to remove part of the solvent, the residue was diluted with ethyl acetate. The organic phase was washed with water, brine, dried over anhydrous sodium sulfate, filtered, and the filtrate was evaporated to give 92-g (13.23 g, 100%) as the crude product, which is a solid was directly used in the next step.

Synthesis of Compound 92-f

To a reaction flask charged with 1-methylcyclopropylamine hydrochloride (4.85 g, 45.07 mmol) and anhydrous dichloromethane (90 mL) was added DIPEA (22.40 g, 173.34 mmol) in an ice-water bath and the mixture was stirred for 10 min, then was added a solution of 92-g (13.23 g, 34.67 mmol) solution in anhydrous dichloromethane (90 mL) dropwise in an ice-water bath. After the dropwise addition, the reaction mixture was stirred in an ice-water bath for 1.5 hours. The organic phase was washed twice with 2% sodium bisulfate solution (600+400 mL), once with saturated sodium bicarbonate solution, once with brine, dried over anhydrous sodium sulfate, filtered, and the filtrate was evaporated to give 92-f (14.1 g, 98%). LC-MS (ESI): m/z 416.0 (M+H)$^+$.

Synthesis of Compound 92-e

Hydrazine hydrate (14 mL, 288.61 mmol) was added dropwise to a solution of 92-f (14.1 g, 33.87 mmol) in anhydrous ethanol (140 mL) in a reaction flask at room temperature. After the dropwise addition, the reaction mixture was heated at 58° C. for 4 hours. The reaction mixture was cooled to room temperature, concentrated at reduced pressure to remove the solvent, and the residue was added water and ethyl acetate, filtered, and the filter cake was washed with ethyl acetate and water. The ethyl acetate phase was separated, and the aqueous phase was extracted with ethyl acetate. The organic phases were combined, washed with water, brine, dried over anhydrous sodium sulfate, filtered. The filtrate was evaporated, and the residue was combined with the filter cake, dissolved with dichloromethane and methanol, evaporated, dried by an oil pump to give 92-e (14.1 g, 100%). LC-MS (ESI): m/z 415.9 (M+H)$^+$.

Synthesis of Compound 92-d 92-e (14.1 g, 33.87 mmol), dichloromethane (160 mL) and DMF (48 mL) were combined in a reaction flask. The solid was largely dissolved after ultrasonic treatment was performed for 2 min (note the exothermic phenomenon). The mixture was added triethylamine (9.9 mL, 71.22 mmol) and stirred for 5 min, followed by dropwise addition of difluoroacetic anhydride (6.9 g, 39.64 mmol) in an ice-water bath. After the dropwise addition, the reaction mixture was stirred in an ice-water bath for 30 min, then was added methanol (5 mL) and stirred in an ice-water bath for 5 min, and stirred at room temperature for 5 min. The dichloromethane was removed by concentration at reduced pressure. The residue was added ice water, ammonium chloride solid, and the resulting mixture was stirred for 1 min, then was added sodium bisulfate solid. The mixture was extracted twice with ethyl acetate, and the organic phase was washed with water, brine, dried over anhydrous sodium sulfate, filtered. The filtrate was evaporated to obtain the crude product, which was added ethyl acetate for slurrying, and then petroleum ether. The supernatant was discarded, and the solid was treated once with a solvent mixture of ethyl acetate and petroleum ether, concentrated at reduced pressure, dried by an oil pump to obtain 92-d (13.9 g, 83%). LC-MS(ESI): m/z 494.0 (M+H)$^+$.

Synthesis of Compound 92-c

A reaction flask charged with 92-d (13.9 g, 28.12 mmol), Lawesson's reagent (18.6 g, 45.99 mmol) and tetrahydrofuran (220 mL) was stirred at 70-75° C. for 12 hours. The reaction mixture was cooled to room temperature, and the solvent was removed by concentration at reduced pressure. The residue was diluted with ethyl acetate, and the organic phase was washed twice with 2% ammonia, brine, dried over anhydrous sodium sulfate, filtered. The filtrate was evaporated, and the residue was slurried with methanol, filtered to give 92-c (6.5 g, 47%). LC-MS (ESI): m/z 491.9 (M+H)$^+$.

Synthesis of Compound 92-b

A reaction flask charged with 92-c (6.5 g, 13.20 mmol), anhydrous THF (52 mL) and anhydrous DMF (52 mL) was added SEMCl (3.15 mL, 17.82 mmol) after stirring for 5 min in an ice-water bath. After addition, the mixture was stirred in an ice-water bath for 5 min, and then was added sodium hydrogen (1.06 g, 26.40 mol, 60%) in two batches with an interval of 2 min. The reaction mixture was stirred in an ice-water bath for 30 min and then quenched with dry ice. After concentrated at room temperature at reduced pressure for 30 min, the residue was added ice-water, extracted with ethyl acetate. The organic phase was washed with water, brine, dried over anhydrous sodium sulfate, filtered, and the filtrate was evaporated to give the crude product, which was purified by column chromatography (mobile phase: petroleum ether/ethyl acetate, 100/0 to 90/10) to give compound 92-b (6.7 g, 82%). LC-MS (ESI): m/z 639.1 (M+NH$_4$)$^+$.

Synthesis of Compound 92-a

A microwave tube charged with (S)-2-methyl-1-(2-methylpiperazin-1-yl)prop-1-one (65 mg, 0.38 mmol), Pd-PEPPSI-IHEPT (32 mg, 0.038 mmol) (cas: 1612891-29-8) and cesium carbonate (230 mg, 0.71 mmol) was sealed and was added a solution of 92-b (240 mg, 0.39 mmol) in anhydrous 1,4-dioxane (5 mL). After degassed and purged with nitrogen for 3 times, the reaction mixture was stirred at 90° C. for 6 h, then was added ethyl acetate and filtered. The filtrate was evaporated and the residue was purified by column chromatography (mobile phase: petroleum ether/ethyl acetate, 100/0 to 40/60) to give compound 92-a (140 mg, 52%). LC-MS (ESI): m/z 729.4 (M+NH$_4$)$^+$.

Synthesis of Compound 92

A reaction flask charged with 92-a (140 mg, 0.20 mmol) and dichloromethane (3.0 mL) was added trifluoroacetic acid (1.0 mL) while cooling in an ice-water bath. The reaction mixture was stirred in an ice-water bath for 5 min and then at room temperature for 2 h. The solvent was removed by concentration at reduced pressure at room temperature, and the residue was added ethyl acetate, saturated aqueous sodium bicarbonate and anhydrous potassium carbonate (300 mg), and the mixture was stirred at 50° C. for 1 hour. The reaction mixture was cooled to room temperature, partitioned, the organic phases were washed with brine, dried over anhydrous sodium sulfate, filtered and the filtrate was evaporated and the residue was purified by column chromatography (mobile phase: petroleum ether/ethyl acetate, 100/0 to 30/70) to give compound 92 (88 mg, 76%). LC-MS(ESI): m/z 582.1 (M+H)$^+$; $^1$H NMR (DMSO-d$_6$, 400 MHz): δ 8.64 (1H, d, J=1.2 Hz), 8.13 (1H, s), 7.70 (1H, t, J=53.2 Hz), 7.66 (1H, d, J=1.2 Hz), 5.03-4.79 (2.6H, m), 4.54-4.42 (0.4H, m), 4.40 (0.4H, d, J=13.6 Hz), 3.94 (0.6H, d, J=13.2 Hz), 3.65 (0.6H, t, J=12.5 Hz), 3.36-3.32 (0.8H, m), 3.26-3.04 (2.6H, m), 3.01-2.86 (1.2H, m), 2.70-2.58 (0.8H, m), 1.53 (3H, t, J=7.2 Hz), 1.46 (1.2H, d, J=6.8 Hz), 1.31 (1.8H, d, J=6.4 Hz), 1.13-0.98 (9H, m), 0.67-0.58 (2H, m), 0.43-0.34 (2H, m).

Example 93 Synthetic Route of Compound 93

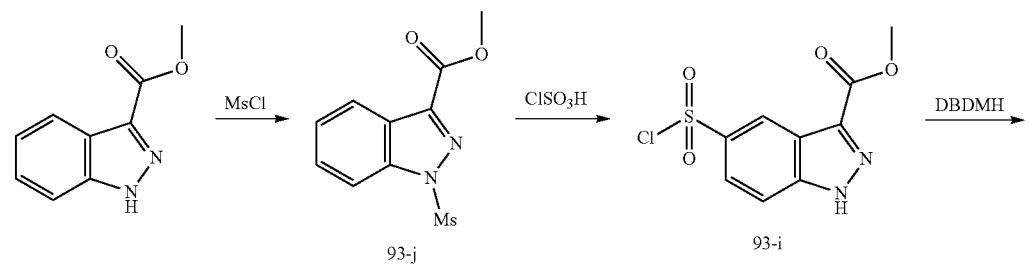

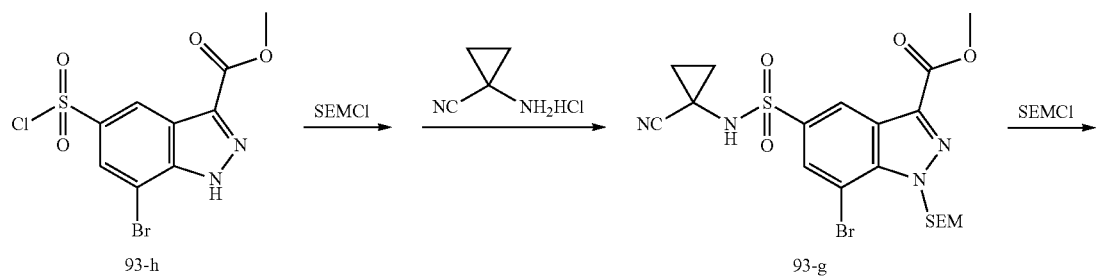

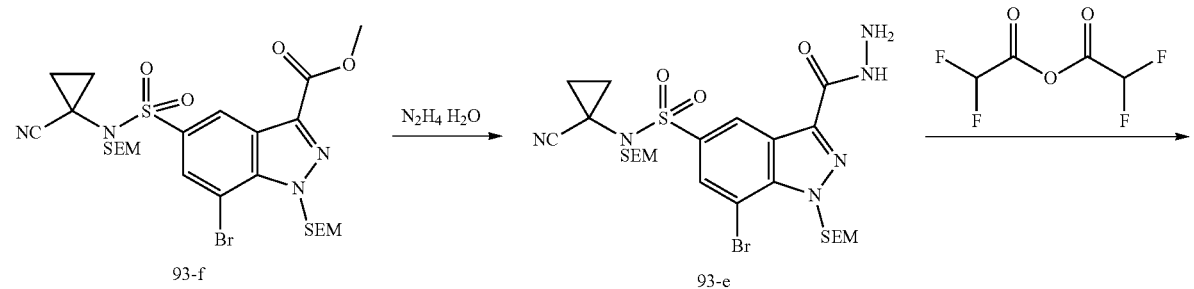

-continued
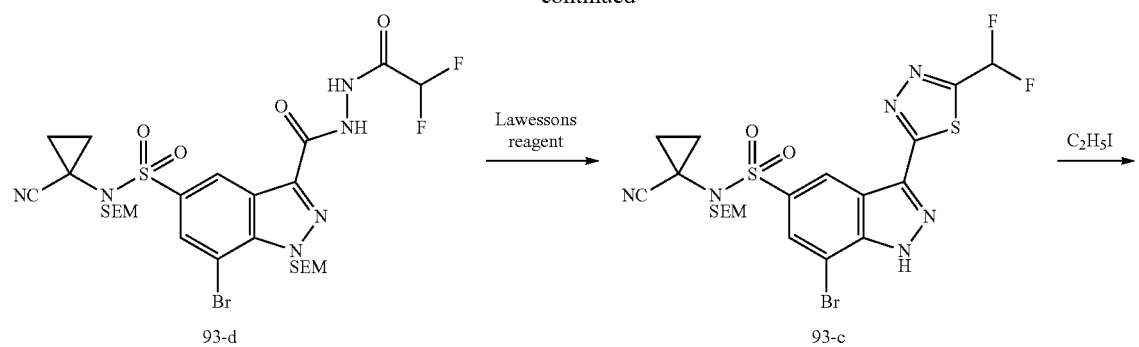
93-d → 93-c (Lawessons reagent) → (C₂H₅I)
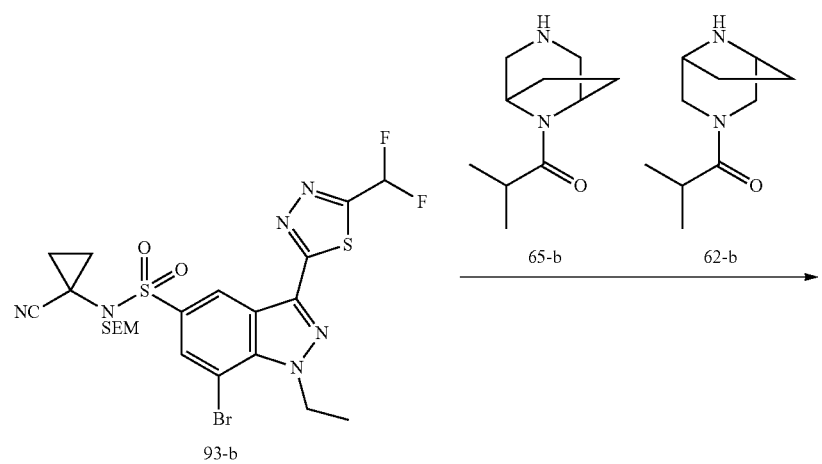
93-b
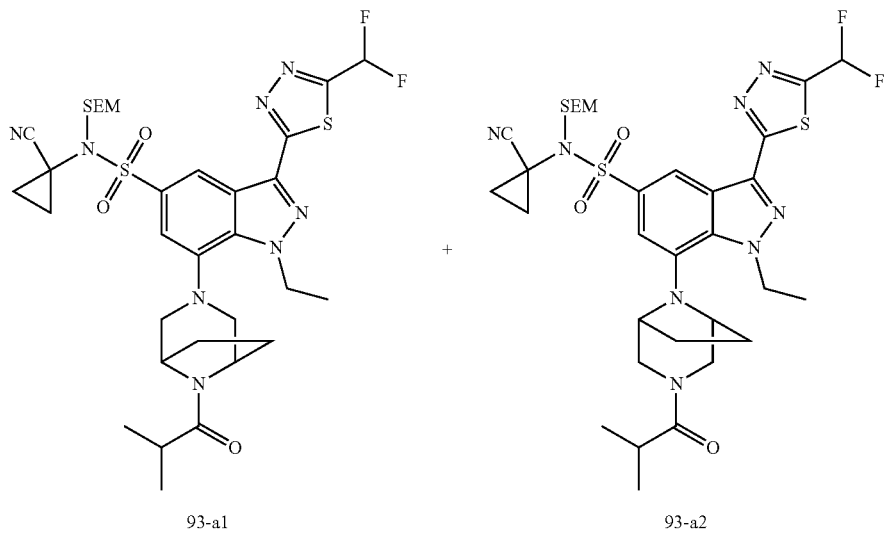
93-a1 + 93-a2

-continued

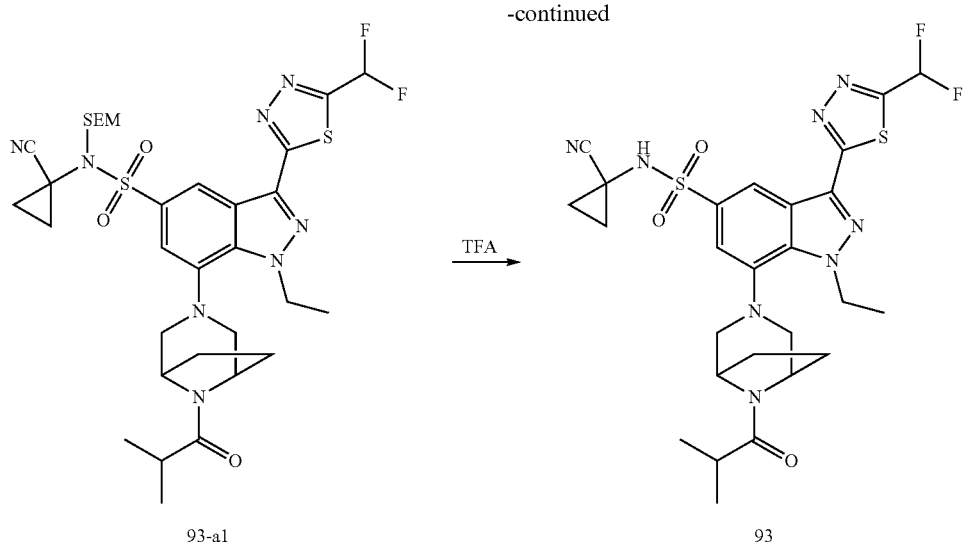

93-a1 → 93 (TFA)

Synthesis of Compound 93-j

A reaction flask charged with 3-methoxycarbonylindazole (12.4 g, 70.38 mmol) and dichloromethane (120 mL) was added triethylamine (14.67 mL, 105.57 mmol) dropwise in an ice-water bath and stirred for 5 min, then was added methanesulfonyl chloride (6.81 mL, 87.98 mmol) dropwise in an ice-water bath. After the dropwise addition, the reaction mixture was stirred in an ice-water bath for 1 hour. The organic phase was evaporated to dryness and the residue was added water and petroleum ether, filtered. The filter cake was washed with water, petroleum ether, dried by an oil pump and then lyophilized to give 93-j (16.4 g, 92%). LC-MS (ESI): m/z 254.9 (M+H)$^+$.

Synthesis of Compound 93-i

A reaction flask charged with chlorosulfonic acid (33 mL) was added 93-j (16.4 g, 64.50 mmol) in an ice-water bath. The reaction mixture was stirred in an ice-water bath for 5 min and then stirred at 65° C. for 5 h. The reaction mixture was cooled to room temperature and added dropwise to ice (400 g). The mixture was extracted with ethyl acetate, and the organic phase was washed with water, brine, dried over anhydrous sodium sulfate, filtered. The filtrate was evaporated to give 93-i (14.8 g, 84%).

Synthesis of Compound 93-h

A reaction flask charged with 93-i (14.8 g, 54.88 mmol) and dichloromethane (120 mL) was added TMSOTf (18 mL, 117.67 mmol) dropwise in an ice-water bath and stirred for 5 min. Then dibromohydantoin (15.41 g, 53.88 mmol) and trifluoromethanesulfonic acid (7.5 mL, 84.76 mmol) were added in an ice-water bath. The reaction mixture was stirred at room temperature for 2 hours. Dichloromethane (150 mL) and trifluoromethanesulfonic acid (7.5 mL, 84.76 mmol) were added dropwise to the suspension. The reaction mixture was stirred at room temperature for 5 hours. The reaction mixture was added to ice-water, extracted twice with ethyl acetate. The organic phase was washed twice with water, brine, dried over anhydrous sodium sulfate, filtered. The filtrate was evaporated and the residue was dried by an oil pump to give 93-h (19.05 g, 98%).

Synthesis of Compound 93-g

A reaction flask charged with 93-h (18.2 g, 51.47 mmol) and dichloromethane (200 mL) was stirred for 5 min in an ice-water bath, and was added SEMCl (9.11 mL, 51.48 mmol). After stirring for 5 min in an ice-water bath, the mixture was added triethylamine (7.16 mL, 51.48 mmol) dropwise over 15 min. The reaction mixture was stirred in an ice-water bath for 30 min to obtain reaction mixture A. To the second reaction flask, 1-amino-1-cyclopropyl cyanide hydrochloride (8.54 g, 72.07 mmol), pyridine (32 mL) and dichloromethane (60 mL) were added and the resulting mixture was stirred for 5 min in an ice-water bath, then was transferred into the reaction mixture A within 5 min in an ice-water bath by double needle. The reaction mixture was stirred for 1 hr in an ice-water bath, added aqueous sodium bisulfate (10%) in an ice-water bath, partition. The aqueous phase was extracted with dichloromethane once, and the organic phases were combined, washed with aqueous sodium bisulfate (5%), brine, dried over anhydrous sodium sulfate, filtered. The filtrate was evaporated to give 93-g (26 g, 95%). LC-MS (ESI): m/z 529.1 (M+H)$^+$.

Synthesis of Compound 93-f

A reaction flask charged with 93-g (24.8 g, 46.84 mmol) and dichloromethane (200 mL) was added triethylamine (13.0 mL, 93.53 mmol) in an ice-water bath and stirred for 5 min, then was added SEMCl (9.6 mL, 54.24 mmol) dropwise in an ice-water bath. The mixture was stirred for 2 h in an ice-water bath, then was added methanol (3 mL) and stirred for 5 min in an ice-water bath. The solvent was removed by concentration at room temperature at reduced pressure and the residue was diluted with ethyl acetate and petroleum ether. The organic phase was washed with 5% sodium bisulfate solution, washed with water, brine, dried over anhydrous sodium sulfate, filtered. The filtrate was evaporated and the residue was dried by an oil pump to give 93-f (30 g, 97%). LC-MS (ESI): m/z 659.1 (M+H)$^+$.

Synthesis of Compound 93-e

A reaction flask charged with 93-f (30 g, 45.47 mmol) and anhydrous ethanol (180 mL) was added hydrazine hydrate (13.5 mL, 278.31 mmol) at room temperature in a water bath and the reaction mixture was stirred at 55° C. for 2 hours, then was added hydrazine hydrate (5.0 mL, 103.08 mmol) and the reaction mixture was stirred at 55° C. for 2 hours. The reaction mixture was cooled to room temperature, concentrated at room temperature at reduced pressure to remove the solvent, the residue was added water, extracted twice with ethyl acetate. The organic phase was washed once with water, washed with brine, dried over anhydrous sodium sulfate, filtered, and the filtrate was evaporated to give 93-e (26 g, 87%). LC-MS (ESI): m/z 659.2 (M+H)$^+$.

Synthesis of Compound 93-d

A reaction flask charged with 93-e (26.0 g, 39.41 mmol) and dichloromethane (260 mL) was added triethylamine (8.0 mL, 57.56 mmol) in an ice-water bath. After stirred in an ice-water bath for 5 min, the reaction mixture was added difluoroacetic anhydride (6.7 g, 38.50 mmol) dropwise in 15 min, then stirred in an ice-water bath for 1 hour. The reaction mixture was added a small amount of methanol and stirred in an ice-water bath for 5 min, then was added aqueous sodium bisulfate solution (5%) and the aqueous phase was extracted 3 times with dichloromethane. The organic phase was combined, dried over anhydrous sodium sulfate, filtered. The filtrate was evaporated and the residue was purified by column chromatography (mobile phase: dichloromethane/methanol, 100/0 to 96.7/3.3) to give compound 93-d (19.0 g, 65%). LC-MS (ESI): m/z 754.2 (M+NH$_4$)$^+$.

Synthesis of Compound 93-c

A reaction flask charged with 93-d (19 g, 25.75 mmol), anhydrous THF (190 mL) and Lawesson's reagent (35 g, 86.54 mmol) was heated at 70° C. for 12 hours and 75° C. for 4 hours. The reaction mixture was cooled to room temperature, was added ammonia in a water bath and stirred for 5 min. The solvent was removed at reduced pressure, and the residue was diluted with ethyl acetate and petroleum ether. The organic phase was washed with water and ammonia (2%), and the aqueous phase was reverse extracted twice with ethyl acetate and petroleum ether (3:2). The combined organic phases were washed with brine, dried over anhydrous sodium sulfate, filtered. The filtrate was evaporated and the residue was purified by column purification (mobile phase: (petroleum ether/dichloromethane 5:1)/ethyl acetate, 100/0 to 75/25) to obtain 93-c (6.3 g, 40%). LC-MS (ESI): m/z 605.0 (M+H)$^+$.

Synthesis of Compound 93-b

A reaction flask charged with 93-c (1.2 g, 1.98 mmol), potassium carbonate (0.80 g, 5.79 mmol) and DMF (12 mL) was stirred at 75° C. for 5 h, then cooled to room temperature, was added iodoethane (0.62 g, 3.96 mmol) in a water bath at room temperature. The reaction mixture was stirred at room temperature for 2 hours, then was added ice-water, extracted twice with ethyl acetate. The organic phase was washed with water, brine, dried over anhydrous sodium sulfate, filtered, and the filtrate was evaporated and the residue was purified by column chromatography (mobile phase: petroleum ether/ethyl acetate, 100/0 to 75/25) to give compound 93-b (670 mg, 53%). LC-MS (ESI): m/z 633.1 (M+H)$^+$.

Synthesis of Compounds 93-a1 and 93-a2

A mixture of 65-b and 62-b (115 mg, 0.63 mmol) was added to a microwave tube and dried by an oil pump for 5 min, followed by addition of 93-b (200 mg, 0.32 mmol), RuPhos (8.0 mg, 0.017 mmol), Pd-PEPPSI-IHEPT (32 mg, 0.038 mmol) (cas. 1612891-29-8) and cesium carbonate (257 mg, 0.79 mmol). The mixture was sealed and was added anhydrous 1,4-dioxane (5 mL). After degassed and purged with nitrogen for 3 times, the reaction mixture was stirred at 85° C. for 18 hours. The reaction mixture was cooled to room temperature, diluted with ethyl acetate. The organic phase was washed with water, brine, dried over anhydrous sodium sulfate, filtered, and the filtrate was evaporated and the residue was purified twice by column chromatography (mobile phase: (petroleum ether/dichloromethane 5:1)/ethyl acetate, 100/0 to 60/40) to give compounds 93-a1 (66 mg, 28%) and 93-a2 (22 mg, 9.5%. LC-MS (ESI): m/z 735.3 (M+H)$^+$.

Synthesis of Compound 93

93-a1 (66 mg, 0.090 mmol) and dichloromethane (1.5 mL) were placed in a reaction flask were added trifluoroacetic acid (0.5 mL) while cooling in an ice-water bath. The reaction mixture was stirred in an ice-water bath for 10 minutes and then at room temperature for 2 hours. The solvent was removed by concentration at reduced pressure, and the residue was dried by an oil pump, diluted with ethyl acetate. The organic phase was washed once with water and once with brine, dried over anhydrous sodium sulfate, filtered. The filtrate was evaporated, and the crude product was purified by column chromatography (mobile phase: dichloromethane/methanol, 100/0 to 90/10) to give 93 (38.2 mg, 70%). LC-MS(ESI): m/z 605.2 (M+H)$^+$; $^1$H NMR (DMSO-d$_6$, 400 MHz): δ 9.27 (1H, s), 8.73 (1H, d, J=1.6 Hz), 7.82 (1H, d, J=1.6 Hz), 7.71 (1H, t, J=53.2 Hz), 5.01 (2H, q, J=7.2 Hz), 4.70 (1H, d, J=6.4 Hz), 4.57 (1H, d, J=4.8 Hz), 3.24-3.00 (4H, m), 2.87 (1H, p, J=6.8 Hz), 2.17-2.01 (3H, m), 1.96-1.84 (1H, m), 1.55 (3H, t, J=7.2 Hz), 1.46-1.39 (2H, m), 1.35-1.27 (2H, m), 1.12 (3H, d, J=6.8 Hz), 1.05 (3H, d, J=6.8 Hz).

Example 94 Synthetic Route of Compound 94

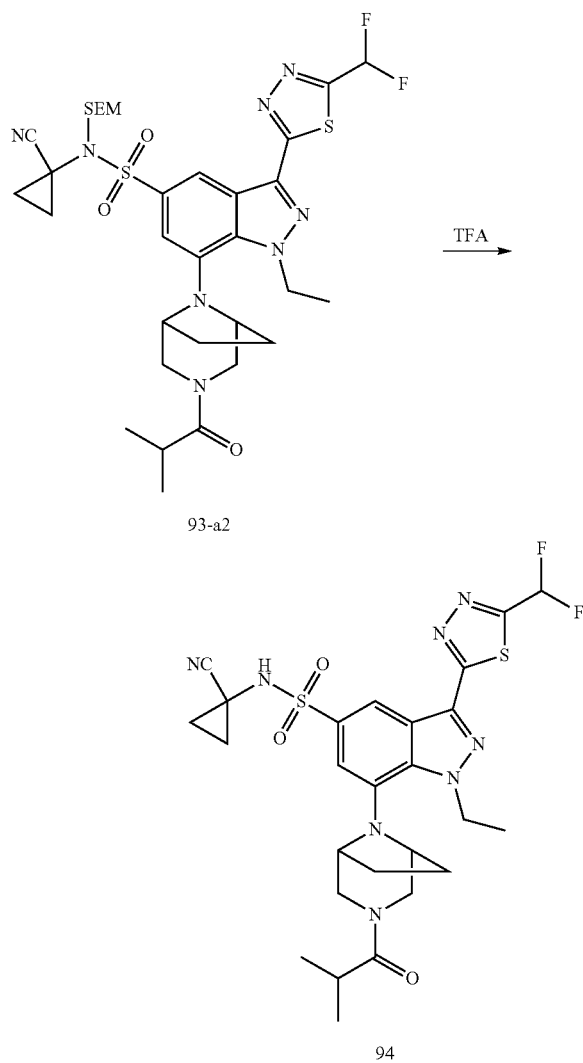

Synthesis of Compound 94

93-a2 (22 mg, 0.030 mmol) and dichloromethane (1.5 mL) were placed in a reaction flask, and trifluoroacetic acid (0.5 mL) was added while cooling in an ice-water bath. The reaction mixture was stirred in an ice-water bath for 10 minutes and then at room temperature for 2 hours. The solvent was removed by concentration at reduced pressure, and the residue was dried by an oil pump, diluted with ethyl acetate. The organic phase was washed once with water and once with brine, dried over anhydrous sodium sulfate, filtered. The filtrate was evaporated, and the residue was purified by column chromatography (mobile phase: dichloromethane/methanol, 100/0 to 90/10) to give 94 (12.3 mg, 68%). LC-MS(ESI): m/z 605.2 (M+H)$^+$; $^1$H NMR (DMSO-d$_6$, 400 MHz): δ 9.32 (1H, s), 8.60 (1H, d, J=1.6 Hz), 7.71 (1H, t, J=53.2 Hz), 7.35 (1H, d, J=1.6 Hz), 4.91 (2H, q, J=7.2 Hz), 4.29 (1H, d, J=12.8 Hz), 4.09-3.96 (2H, m), 3.93 (1H, d, J=12.8 Hz), 3.61 (1H, d, J=12.0 Hz), 3.08 (1H, d, J=12.8 Hz), 2.93 (1H, p, J=6.8 Hz), 2.07-1.99 (2H, m), 1.74 (1H, t, J=9.6 Hz), 1.60 (1H, t, J=8.0 Hz), 1.55 (3H, t, J=7.2 Hz), 1.46-1.40 (2H, m), 1.35-1.30 (2H, m), 1.09 (3H, d, J=6.8 Hz), 1.02 (3H, d, J=6.8 Hz).

Synthesis of Intermediate 65-b

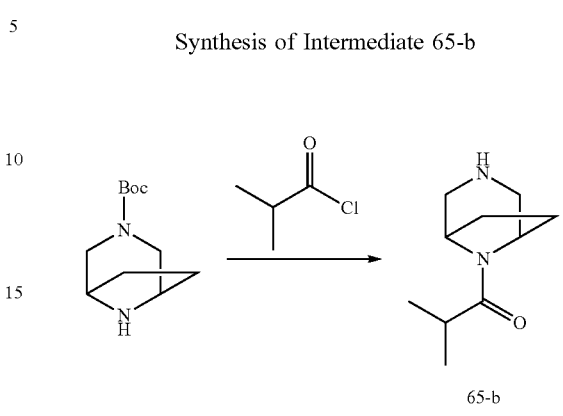

A solution of compound 3,8-diazabicyclo[3.2.1]octane-3-carboxylic acid tert-butyl ester (1 g, 4.71 mmol) in dichloromethane (25 mL) was added triethylamine (1.05 g, 10.36 mmol), and isobutyryl chloride (0.60 g, 5.65 mmol) was added dropwise at 0° C. The reaction mixture was stirred at room temperature for 2 h. The reaction mixture was concentrated at reduced pressure, added water (100 mL) and extracted with ethyl acetate (100 mL). The organic phase was washed with brine (100 mL), dried over sodium sulfate, filtered out desiccant, concentrated at reduced pressure, and the residue was purified by column chromatography (mobile phase, PE/EA 1/1) to obtain a colorless oily, which was added HCl/1,4-dioxane solution (4 M, 20 mL) and the mixture was stirred at room temperature for 2 h. The reaction mixture was concentrated at reduced pressure and the residue was added ethanol (15 mL), saturated sodium bicarbonate solution (2 mL) and sodium bicarbonate solid (1 g), then stirred at room temperature for 10 min. The mixture was concentrated, added dichloromethane/methanol=10/1 (20 mL) and stirred for 3 min, filtered, the filtrate was concentrated, and the residue was added dichloromethane (20 mL), dried over sodium sulfate, filtered out the desiccant, concentrated at reduced pressure, and dried in vacuum to obtain compound 65-b (650 mg, 76%). LC-MS (ESI): m/z 183.0 (M+H)$^+$.

Example 95 Synthetic Route of Compound 95

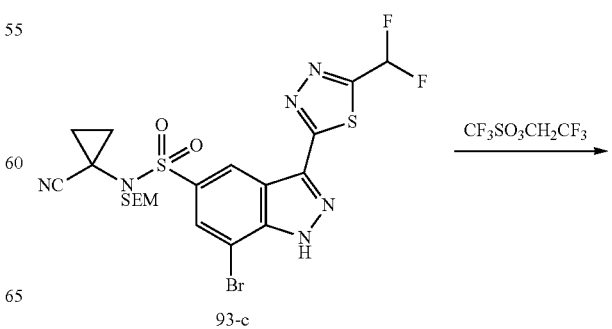

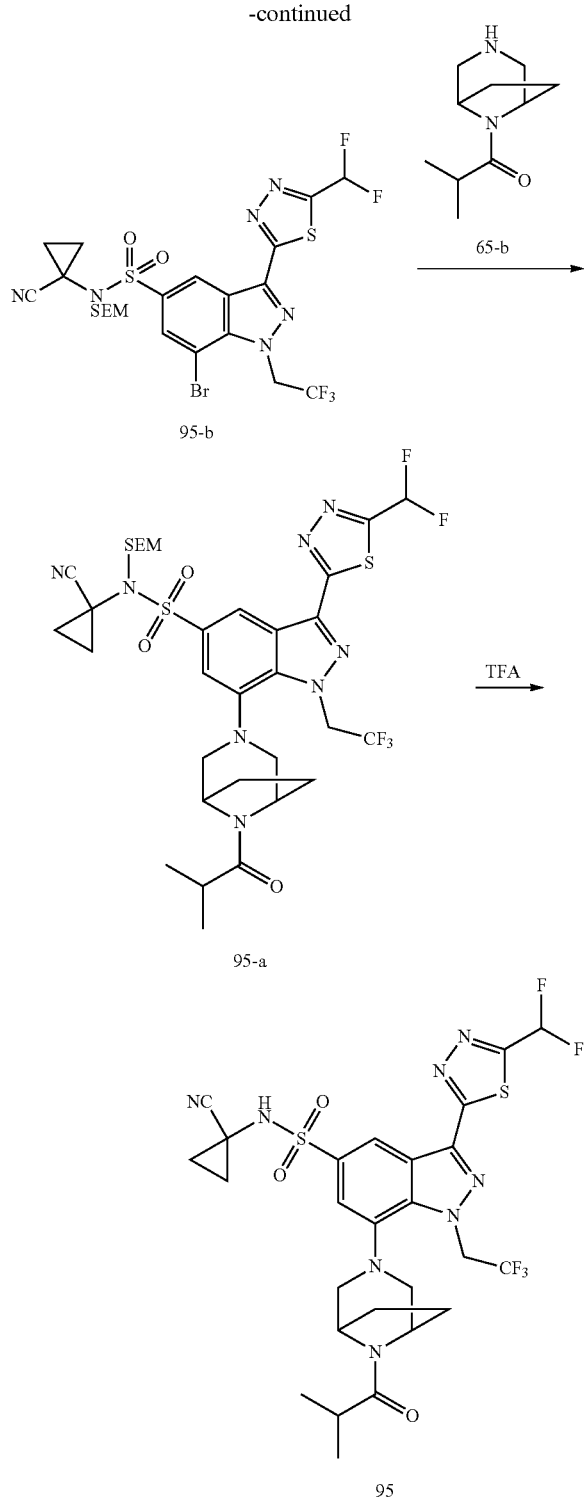

Synthesis of Compound 95-b

A reaction flask charged with 93-c (2.0 g, 3.30 mmol), potassium carbonate (1.37 g, 9.91 mmol), DMF (10 mL) and THF (5 mL) was added 2,2,2-Trifluoroethyl trifluoromethanesulfonate (1.15 g, 4.95 mmol) dropwise in a water bath at room temperature. After the dropwise addition, the reaction mixture was stirred at room temperature for 3 hours. THF was removed by concentration at reduced pressure, and the residue was added ice-water, extracted twice with ethyl acetate. The organic phase was washed with water, brine, dried over anhydrous sodium sulfate, filtered. The filtrate was evaporated and the residue was purified by column chromatography (mobile phase: petroleum ether/ethyl acetate, 100/0 to 75/25) to give the crude product as a colorless foamy solid. The crude solid (1.6 g) was combined with DMF (15 mL) and anhydrous potassium carbonate (450 mg) and stirred at 65° C. overnight. The reaction mixture was cooled to room temperature, added ice-water, extracted twice with ethyl acetate. The organic phase was washed with water, brine, dried over anhydrous sodium sulfate, filtered, and the filtrate was evaporated and the residue was purified by column chromatography (mobile phase: (petroleum ether/dichloromethane 5:1)/ethyl acetate, 100/0 to 60/40) to give compound 95-b (700 mg, 31%). LC-MS(ESI): m/z 687.0 (M+H)$^+$.

Synthesis of Compound 95-a

A microwave tube charged with 65-b (80 mg, 0.44 mmol) was dried by an oil pump for 5 min, then was added 95-b (160 mg, 0.23 mmol), RuPhos (8 mg, 0.017 mmol), Pd-PEPPSI-IHEPT-Cl (32 mg, 0.037 mmol) (cas: 1435347-24-2) and cesium carbonate (160 mg, 0.491 mmol), then was closed and added anhydrous 1,4-dioxane (5 mL). After degassed and purged with nitrogen for 3 times, the reaction mixture was stirred at 85° C. for 18 hours. The reaction mixture was cooled to room temperature, diluted with ethyl acetate, and the organic phase was washed with water, brine, dried over anhydrous sodium sulfate, filtered. The filtrate was evaporated and the residue was purified by column chromatography twice (mobile phase: (petroleum ether/dichloromethane 5:1)/ethyl acetate, 100/0 to 60/40) to give compound 95-a (75 mg, 41%). LC-MS (ESI): m/z 789.3 (M+H)$^+$.

Synthesis of Compound 95

A reaction flask charged with 95-a (75 mg, 0.095 mmol) and dichloromethane (1.5 mL) was added trifluoroacetic acid (0.5 mL) while cooling in an ice-water bath. The reaction mixture was stirred at room temperature for 1 hour. The solvent was removed by concentration at reduced pressure and ethyl acetate, saturated sodium bicarbonate solution and anhydrous potassium carbonate (150 mg) were added to the residue and the mixture was stirred at room temperature for 20 min. The ethyl acetate phase was washed with brine, dried over anhydrous sodium sulfate, filtered, the filtrate was evaporated, and purified by column chromatography (mobile phase: petroleum ether/(ethyl acetate/ethanol 94:6), 100/0 to 80/20) to obtain a solid. The solid was washed with methyl tert-butyl ether, petroleum ether and then lyophilized with acetonitrile and water to give compound 95 (32 mg, 51%). LC-MS(ESI): m/z 659.2 (M+H)$^+$; $^1$H NMR (DMSO-d$_6$, 400 MHz): δ 9.34 (1H, s), 8.82 (1H, s), 8.03 (1H, s), 7.72 (1H, t, J=53.2 Hz), 5.99 (2H, q, J=8.8 Hz), 4.76-4.54 (2H, m), 3.17-3.00 (4H, m), 2.88 (1H, p, J=6.7 Hz), 2.14-2.01 (2H, m), 1.99-1.86 (2H, m), 1.42 (2H, s), 1.38-1.31 (2H, m), 1.14 (3H, d, J=6.4 Hz), 1.05 (3H, d, J=6.8 Hz).

Example 96 Synthetic Route of Compound 96 and 97
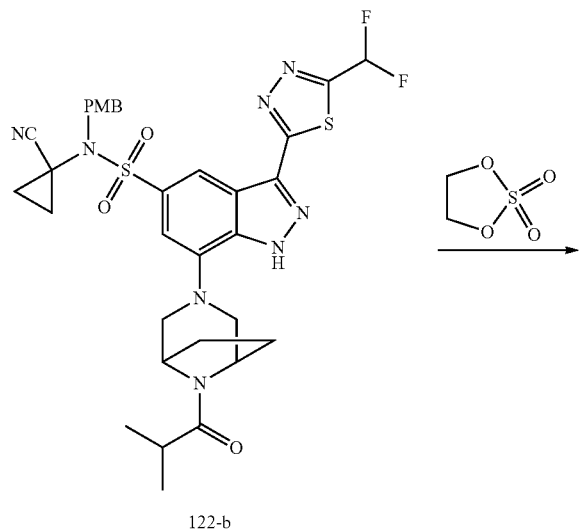
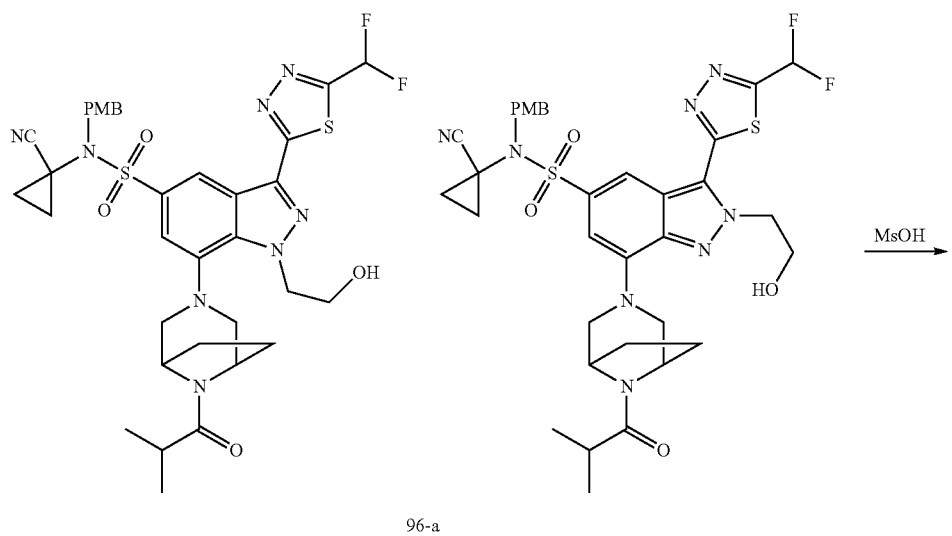
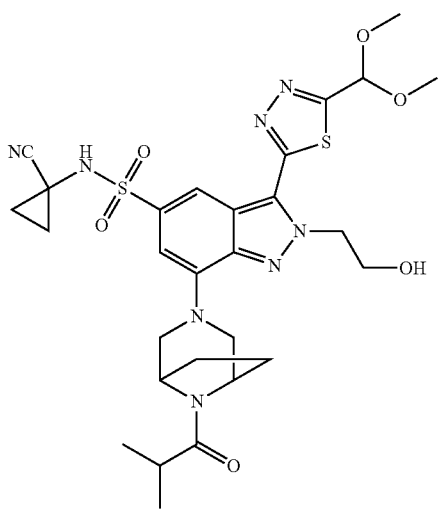

Synthesis of Compound 96-a 122-b (62 mg, 0.089 mmol) and DMF (3 mL) were placed in a reaction flask. Cesium carbonate (180 mg, 0.55 mmol) was added to the above mixture in a water bath and stirred for 5 min, then was added 1,3,2-Dioxazolylthiophene-2,2-dioxide (90 mg, 0.73 mmol) in a water bath and the reaction mixture was stirred at room temperature for 2 hours. The reaction mixture was diluted with ethyl acetate, added water and sodium bisulfate solid and the mixture was partitioned. The aqueous phase was extracted once with ethyl acetate, and the organic phases were combined, washed with brine, dried over anhydrous sodium sulfate, filtered. The filtrate was evaporated and the residue was dried by an oil pump. The residue was dissolved in 1,4-dioxane (3 mL), added water (0.5 mL), and a solution of water (6 drops) and concentrated sulfuric acid (2 drops). The reaction mixture was stirred at 60° C. for 2 hours. The reaction mixture was cooled to room temperature, added ethyl acetate and saturated aqueous sodium bicarbonate, partitioned. The aqueous phase was extracted with ethyl acetate once, and the organic phases were combined, washed with brine, dried over anhydrous sodium sulfate, filtered. The filtrate was evaporated, and the residue was purified by column chromatography (mobile phase: petroleum ether/(6% ethanol/ethyl acetate), 100/0 to 40/60) to give compound 96-a (50 mg, 76%). LC-MS (ESI): m/z 741.3 (M+H)$^+$.

Synthesis of Compound 96

A reaction flask charged with 96-a (50 mg, 0.067 mmol) and dichloromethane (2.0 mL) was added methanesulfonic acid (4 drops) in an ice-water bath. The reaction mixture was stirred at room temperature for 3 h. After diluted with dichloromethane and methanol, the residue was added anhydrous potassium carbonate and stirred at room temperature for 2 min. Filtered, the filtrate was evaporated and the residue was purified by Prep-HPLC (mobile phase: 10 mM aqueous ammonium bicarbonate and acetonitrile) to give compound 96 (2.2 mg, 5.1%). LC-MS(ESI): m/z 645.3 (M+H)$^+$; $^1$H NMR (DMSO-$d_6$, 400 MHz): δ 8.76 (1H, bs), 7.96 (1H, d, J=0.8 Hz), 6.80 (1H, d, J=0.8 Hz), 6.00 (1H, s), 5.10 (1H, t, J=5.6 Hz), 4.92 (2H, t, J=5.6 Hz), 4.72 (1H, d, J=5.6 Hz), 4.64-4.59 (1H, m), 4.31 (1H, d, J=11.2 Hz), 4.21 (1H, d, J=10.8 Hz), 3.96 (2H, q, J=5.2 Hz), 3.48 (6H, s), 3.05 (1H, d, J=11.2 Hz), 2.99 (1H, d, J=11.2 Hz), 2.87 (1H, p, J=6.8 Hz), 2.07-1.91 (3H, m), 1.85 (1H, s), 1.44-1.38 (2H, m), 1.32-1.23 (2H, m), 1.07 (3H, d, J=6.8 Hz), 1.04 (3H, d, J=6.8 Hz).

Synthesis of compound 97

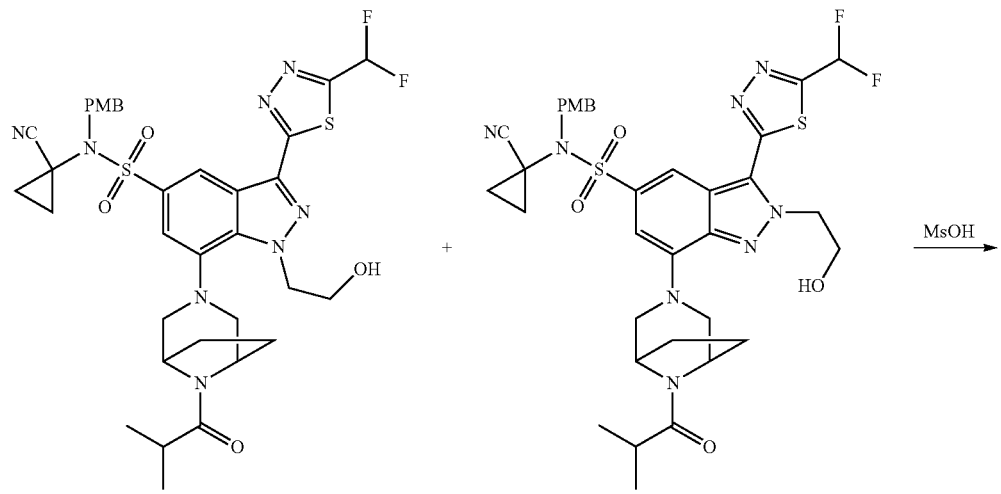

96-a

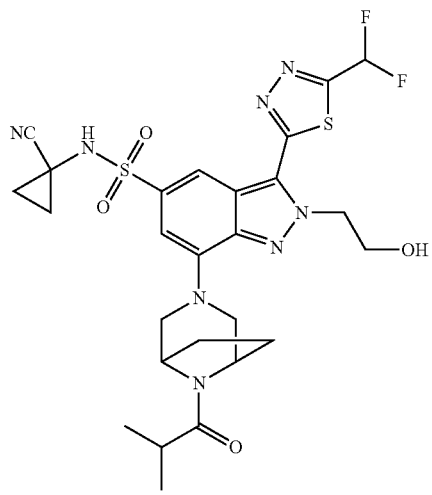

97

Another batch of 96-a was synthesized. 96-a (53 mg, 0.072 mmol) and dichloromethane (2.0 mL) were placed in a reaction flask, and the reaction mixture was added methanesulfonic acid (4 drops) in an ice-water bath. The reaction mixture was stirred for 1 h at room temperature, diluted with ethyl acetate, and added aqueous sodium bicarbonate and anhydrous sodium sulfate solid in an ice-water bath, partitioned. The aqueous phase was extracted twice with ethyl acetate, and the organic phases were combined, dried over anhydrous sodium sulfate, filtered. The filtrate was evaporated and the residue was purified by Prep-HPLC (mobile phase: 10 mM aqueous ammonium bicarbonate and acetonitrile) to give compound 97 (3.8 mg, 8.5%). LC-MS(ESI): m/z 621.2 (M+H)[+]; $^1$H NMR (DMSO-$d_6$, 400 MHz): δ 8.56 (1H, bs), 7.98 (1H, s), 7.76 (1H, t, J=52.8 Hz), 6.82 (1H, s), 5.14 (1H, t, J=5.2 Hz), 4.92 (2H, t, J=5.2 Hz), 4.74-4.70 (1H, m), 4.64-4.58 (1H, m), 4.31 (1H, d, J=11.2 Hz), 4.22 (1H, d, J=11.2 Hz), 4.01-3.92 (2H, q, J=5.2 Hz), 3.07 (1H, d, J=10.8 Hz), 3.01 (1H, d, J=11.2 Hz), 2.93-2.81 (1H, m), 2.07-1.79 (4H, m), 1.45-1.37 (2H, m), 1.33-1.24 (2H, m), 1.07 (3H, d, J=6.8 Hz), 1.04 (3H, d, J=6.8 Hz).

Example 97 Synthetic Route of Compound 98

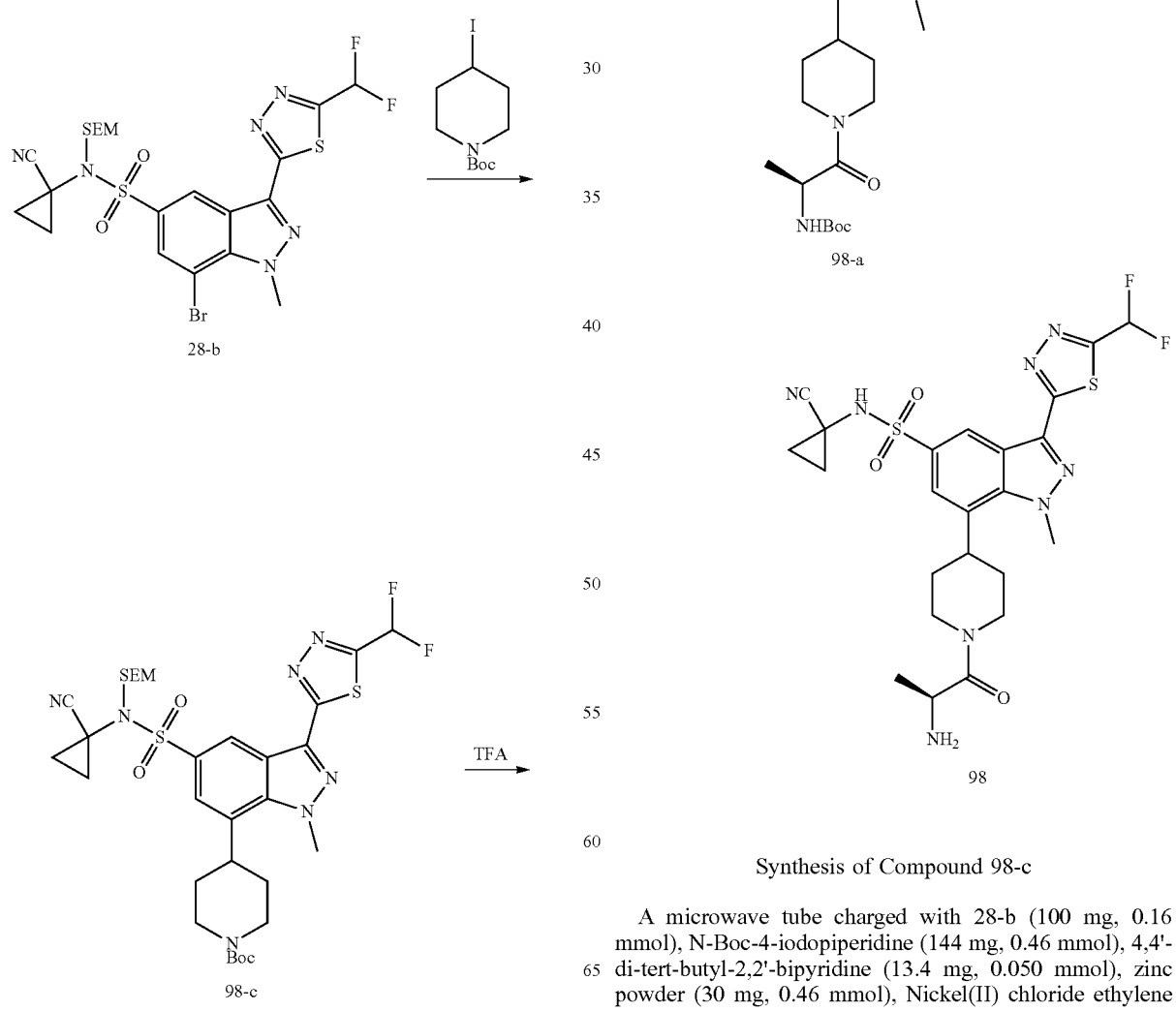

Synthesis of Compound 98-c

A microwave tube charged with 28-b (100 mg, 0.16 mmol), N-Boc-4-iodopiperidine (144 mg, 0.46 mmol), 4,4'-di-tert-butyl-2,2'-bipyridine (13.4 mg, 0.050 mmol), zinc powder (30 mg, 0.46 mmol), Nickel(II) chloride ethylene glycol dimethyl ether complex (12 mg. 0.055 mmol) and anhydrous magnesium chloride (8 mg, 0.084 mmol) was evacuated and added DMAc (5.0 mL) in an ice-water bath. After degassed and purged with nitrogen for 3 times, the reaction mixture was added triethylamine (0.012 mL, 0.089 mmol) and degassed and purged with nitrogen one more time, then the reaction mixture was stirred from ice water bath to room temperature for 18 hours. The reaction mixture was added ethyl acetate and petroleum ether, and the organic phase was washed with water, brine, dried over anhydrous sodium sulfate, filtered. The filtrate was evaporated and the residue was purified by column chromatography (mobile phase: petroleum ether/ethyl acetate, 100/0 to 60/40) to give compound 98-c (80 mg, 69%). LC-MS (ESI): m/z 724.3 (M+H)$^+$.

Synthesis of Compound 98-b

A reaction flask charged with 98-c (80 mg, 0.11 mmol) and dichloromethane (2.0 mL) was added trifluoroacetic acid (0.7 mL) while cooling in an ice-water bath. The reaction mixture was stirred in an ice-water bath for 10 min and then at room temperature for 3 hours. The solvent was removed by concentration at reduced pressure and the residue was dried by an oil pump, added ethyl acetate, saturated sodium bicarbonate solution and anhydrous potassium carbonate (300 mg) and stirred for 20 min at room temperature, then was added anhydrous sodium sulfate solid, partitioned. The aqueous phase was extracted once with ethyl acetate, and the organic phases were combined, dried over anhydrous sodium sulfate, filtered, and the filtrate was evaporated to give 98-b (54 mg, 99%). LC-MS (ESI): m/z 494.6 (M+H)$^+$.

Synthesis of Compound 98-a

A reaction flask charged with 98-b (36 mg, 0.073 mmol), N-tert-butoxycarbonyl-L-alanine (24 mg, 0.13 mmol), HOBt (17 mg, 0.13 mmol), dichloromethane (3 mL) and DIPEA (55 mg, 0.43 mmol) was added EDCI (24 mg, 0.13 mmol) in an ice-water bath. The reaction mixture was stirred at room temperature overnight. The reaction mixture was added ethyl acetate, brine and anhydrous sodium sulfate solid, partitioned. The aqueous phase was extracted once with ethyl acetate, and the organic phase was combined, dried over anhydrous sodium sulfate, filtered and the filtrate was evaporated to give 98-a (48 mg, 99%). LC-MS (ESI): m/z 665.3 (M+H)$^+$.

Synthesis of Compound 98

A reaction flask charged with 98-a (48 mg, 0.072 mmol) and dichloromethane (1.5 mL) was added trifluoroacetic acid (0.5 mL) while cooling in an ice-water bath. The reaction mixture was stirred at room temperature for 2 hours. The solvent was removed by concentration at reduced pressure and the residue was dried by an oil pump. The residue was added ethyl acetate, saturated aqueous sodium bicarbonate and anhydrous potassium carbonate (150 mg) and stirred for 5 min at room temperature, then added anhydrous sodium sulfate solid, partitioned. The aqueous phase was extracted with ethyl acetate once, and the organic phase was combined, dried over anhydrous sodium sulfate, filtered. The filtrate was evaporated to obtain the crude product, which was purified by column chromatography (mobile phase: dichloromethane/methanol, 100/0 to 80/20), concentrated at reduced pressure. The residue was dissolved in acetonitrile and water, filtered and lyophilized to give compound 98 (28.6 mg, 70%). LC-MS(ESI): m/z 563.2 (M−H)$^−$; $^1$H NMR (DMSO-d$_6$, 400 MHz): δ 8.73 (1H, d, J=1.6 Hz), 7.71 (1H, d, J=4.4 Hz), 7.63 (1H, t, J=53.2 Hz), 6.40 (3H, bs), 4.64-4.50 (1H, m), 4.43 (3H, s), 4.16-3.97 (2H, m), 3.78 (1H, t, J=11.2 Hz), 3.32-3.22 (1H, m), 2.81 (1H, t, J=12.4 Hz), 2.06-1.91 (2H, m), 1.77-1.50 (2H, m), 1.35-1.30 (2H, m), 1.25-1.11 (5H, m).

Example 98 Synthetic Route of Compound 99 and 100

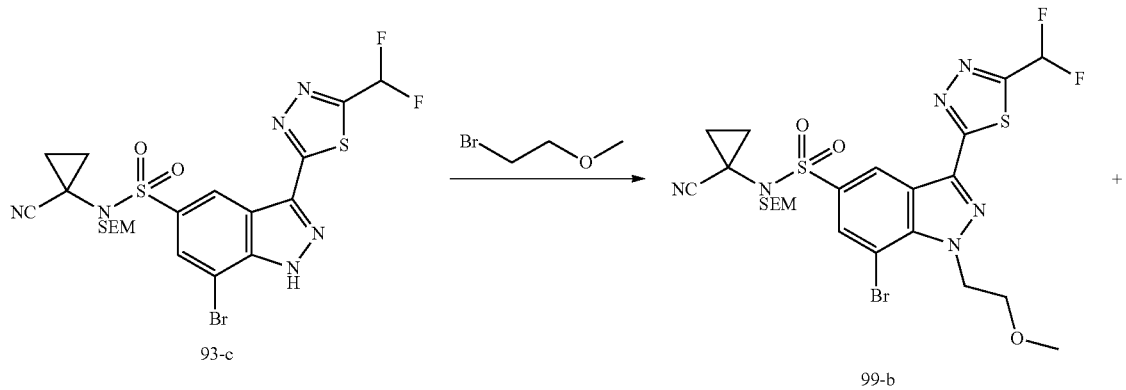

-continued

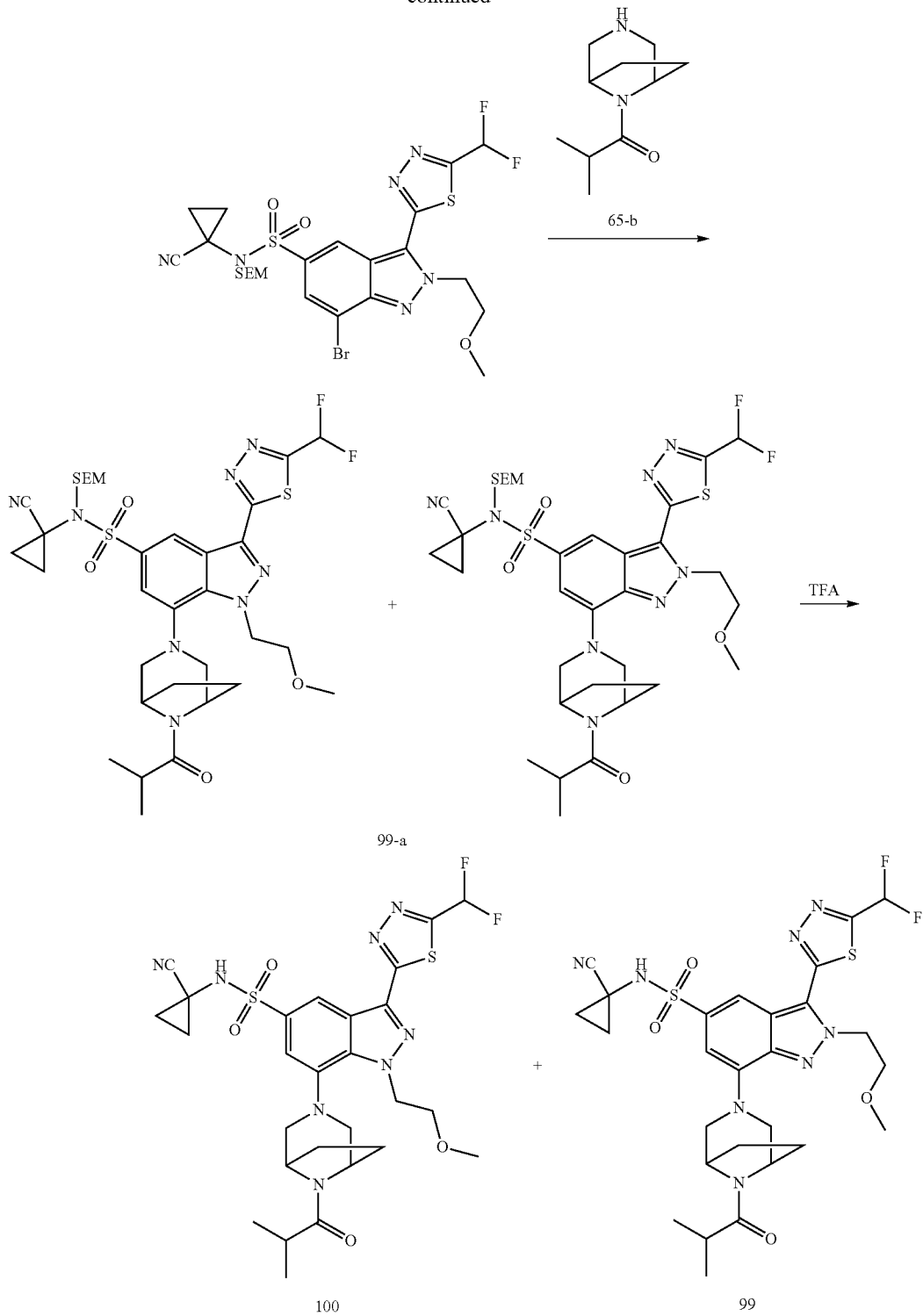

Synthesis of Compound 99-b 93-c (200 mg, 0.331 mmol), DMF (3 mL), potassium carbonate (46 mg, 0.33 mmol) and 2-bromoethyl methyl ether (92 mg, 0.66 mmol) were placed in a reaction flask and the reaction mixture was stirred at 60° C. for 20 hours. The reaction mixture was cooled to room temperature, added ice-water, extracted twice with ethyl acetate. The organic phase was washed with water, brine, dried over anhydrous sodium sulfate, filtered. The filtrate was evaporated, and the residue was purified by column chromatography (mobile phase: petroleum ether/ethyl acetate, 100/0 to 70/30) to give compound 99-b (190 mg, 87). LC-MS (ESI): m/z 663.1 (M+H)$^+$.

Synthesis of Compound 99-a 65-b (80 mg, 0.44 mmol) was added in a microwave tube and dried by an oil pump for 5 min, followed by the addition of 99-b (190 mg, 0.29 mmol), RuPhos (5.0 mg, 0.011 mmol), Pd-PEPPSI-IHEPT (27 mg, 0.031 mmol) (cas: 1435347-24-2) and cesium carbonate (190 mg, 0.58 mmol). The microwave tube was sealed and added anhydrous 1,4-dioxane (3.2 mL). After degassed and purged with nitrogen for 3 times, the reaction mixture was stirred at 75° C. for 18 hours. Supplemental Pd-PEPPSI-IHEPT (15 mg, 0.017 mmol) (cas: 1435347-24-2) and RuPhos (5 mg, 0.011 mmol) were added to the above mixture. The reaction mixture was stirred at 75° C. for 24 hours after purged with nitrogen once. The reaction mixture was cooled to room temperature, diluted with ethyl acetate, and the organic phases were washed with water, brine, dried over anhydrous sodium sulfate, filtered. The filtrate was evaporated and the residue was purified by column chromatography (mobile phase: (petroleum ether/dichloromethane 5:1)/ethyl acetate, 100/0 to 60/40) to give compound 99-a (80 mg, 36%). LC-MS (ESI): m/z 765.2 (M+H)$^+$.

Synthesis of Compounds 99 and 100

99-a (80 mg, 0.10 mmol) and dichloromethane (3 mL) were added to a reaction flask, and trifluoroacetic acid (1 mL) was added to the above while cooling in an ice-water bath. The reaction mixture was stirred in an ice-water bath for 10 minutes and then at room temperature for 4 hours. The solvent was removed by concentration at reduced pressure and the residue was dried by an oil pump. The residue was added ethyl acetate, saturated sodium bicarbonate solution and anhydrous potassium carbonate (150 mg) and stirred for 20 min at room temperature. The aqueous phase was extracted once with ethyl acetate, and the organic phases were combined and washed once with brine, dried over anhydrous sodium sulfate, filtered. The filtrate was evaporated, and the residue was purified by column chromatography (mobile phase: dichloromethane/methanol, 100/0 to 90/10), followed by prep-HPLC (mobile phase: 10 mM aqueous sodium bicarbonate and acetonitrile) to give compound 99 (1.7 mg, 2.6%) and compound 100 (30.4 mg, 48%).

Compound 99 LC-MS(ESI): m/z 635.3 (M+H)$^+$; $^1$H NMR (DMSO-d$_6$, 400 MHz): δ 8.76 (1H, bs), 7.95 (1H, d, J=0.4 Hz), 7.77 (1H, t, J=53.2 Hz), 6.83 (1H, s), 5.07 (2H, t, J=5.2 Hz), 4.75-4.70 (1H, m), 4.68-4.57 (1H, m), 4.31 (1H, d, J=10.8 Hz), 4.24 (1H, d, J=11.2 Hz), 3.95 (2H, t, J=4.8 Hz), 3.21 (3H, s), 3.14-2.98 (2H, m), 2.88 (1H, p, J=6.4 Hz), 2.09-1.79 (4H, m), 1.47-1.36 (2H, m), 1.34-1.27 (2H, m), 1.08 (3H, d, J=6.8 Hz), 1.05 (3H, d, J=6.4 Hz).

Compound 100 LC-MS(ESI): m/z 635.2 (M+H)$^+$; $^1$H NMR (DMSO-d$_6$, 400 MHz): δ 9.26 (1H, bs), 8.74 (1H, d, J=1.2 Hz), 7.89-7.54 (2H, m), 5.33-5.08 (2H, m), 4.69 (1H, d, J=6.8 Hz), 4.55 (1H, d, J=5.2 Hz), 3.91 (2H, t, J=5.2 Hz), 3.28-3.19 (1H, m), 3.19 (3H, s), 3.16-3.04 (2H, m), 3.03-2.95 (1H, m), 2.86 (1H, h, J=6.8 Hz), 2.20-1.96 (3H, m), 1.94-1.82 (1H, m), 1.46-1.37 (2H, m), 1.38-1.28 (2H, m), 1.12 (3H, d, J=6.4 Hz), 1.05 (3H, d, J=6.8 Hz).

Synthetic Route of Compound 101 and 102

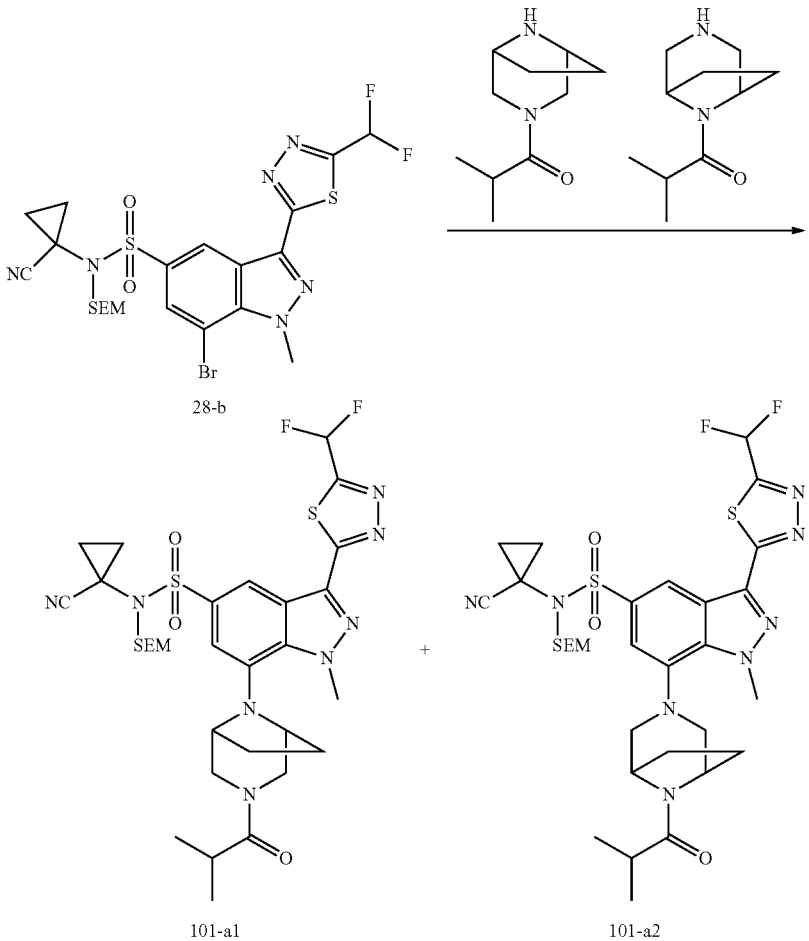

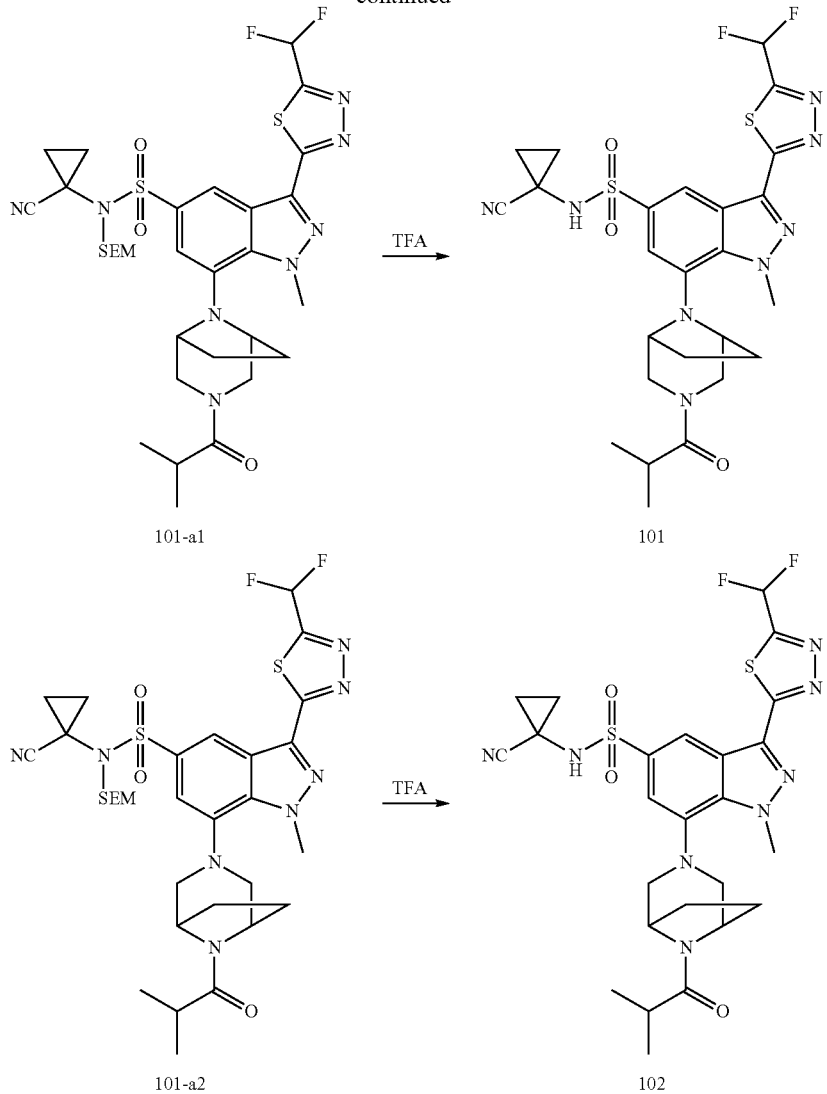

Synthesis of compound 101-a1 and 101-a2

A microwave tube charged with 28-b (300 mg, 0.48 mmol), a mixture of 65-b and 62b (177 mg, 0.97 mmol), RuPhos (23 mg, 0.048 mmol), (SP-4-1)-[1,3-bis[2,6-bis(1-ethylpropyl)phenyl]-4,5-dichloro-1,3-dihydro-2H-imidazol-2-ylidene]dichloro(2-methylpyridine)palladium (CAS: 1612891-29-8) (41 mg, 0.048 mmol), cesium carbonate (473 mg, 1.45 mmol) and 1,4-dioxane (8 mL) was degassed and purged with nitrogen for 3 times. The reaction mixture was heated to 70° C. and stirred overnight. After completion, the reaction mixture was cooled to room temperature and concentrated at reduced pressure to remove the 1,4-dioxane, and the residue was diluted with ethyl acetate. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compounds 101-a1 (50 mg, 14%) and 101-a2 (80 mg, 23%).

101-a1: LC-MS (ESI): m/z 721.3 [M+H]$^+$.
101-a2: LC-MS (ESI): m/z 721.3 [M+H]$^+$.

Synthesis of Compound 101

A reaction flask charged with 101-a1 (50 mg, 0.069 mmol) and dichloromethane (5 mL) was added trifluoroacetic acid (1 mL) dropwise at room temperature. After the dropwise addition, the reaction mixture was stirred at room temperature for 4 h. The solvent was removed by concentration at room temperature at reduced pressure. The organic phase was washed with saturated sodium bicarbonate, brine, dried over anhydrous sodium sulfate, filtered and the filtrate was evaporated. The residue was purified by Prep-TLC (PE/EA=1/2) to give compound 101 (10 mg, 24%). LC-MS (ESI): m/z 591.2 [M+H]$^+$; $^1$H NMR (DMSO-$d_6$, 400 MHz): δ 9.29 (1H, s), 8.57 (1H, s), 7.70 (1H, t, J=53.2 Hz), 7.31 (1H, s), 4.55 (3H, s), 4.22-4.31 (1H, m), 4.04-4.12 (2H, m), 3.85-3.94 (1H, m), 3.61-3.69 (1H, m), 3.07-3.15 (1H, m), 2.88-2.98 (1H, m), 1.98-2.06 (2H, m), 1.69-1.79 (1H, m), 1.53-1.64 (1H, m), 1.37-1.45 (2H, m), 1.27-1.35 (2H, m), 1.08 (3H, d, J=6.8 Hz), 1.01 (3H, d, J=6.8 Hz).

Synthesis of Compound 102

A reaction flask charged with 101-a2 (80 mg, 0.11 mmol) and dichloromethane (5 mL) was added trifluoroacetic acid (1 mL) dropwise at room temperature. After the dropwise addition, the reaction mixture was stirred at room temperature for 4 h. The solvent was removed by concentration at room temperature at reduced pressure. The organic phase was washed with saturated sodium bicarbonate, brine, dried over anhydrous sodium sulfate, filtered and the filtrate was evaporated to obtain the crude product, which was purified by Prep-TLC (PE/EA=1/2) to give compound 102 (35 mg, 53%). LC-MS (ESI): m/z 591.2 [M+H]$^+$; $^1$H NMR (DMSO-d$_6$, 400 MHz): δ 9.25 (1H, s), 8.70 (1H, d, J=1.2 Hz), 7.71 (1H, t, J=53.2 Hz), 7.75 (1H, d, J=1.2 Hz), 4.65-4.72 (1H, m), 4.59 (3H, s), 4.52-4.57 (1H, m), 3.13-3.30 (2H, m), 2.95-3.08 (2H, m), 2.81-2.92 (1H, m), 1.95-2.24 (3H, m), 1.79-1.94 (1H, m), 1.38-1.45 (2H, m), 1.26-1.35 (2H, m), 1.11 (3H, d, J=6.8 Hz), 1.04 (3H, d, J=7.2 Hz).

Synthesis of Compound 103

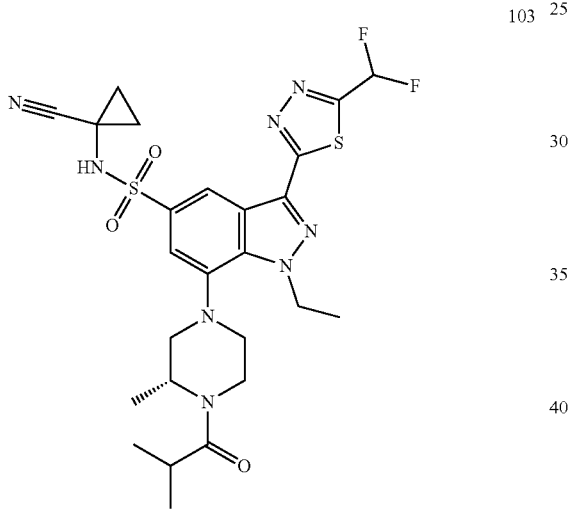

103

Referring to the synthesis of compound 68, compound 103 was synthesized using 93-b as the starting reactant, and replacing 68-b with (R)-2-methyl-1-(2-methylpiperazin-1-yl)propan-1-one. LC-MS (ESI): m/z 593.3 [M+H]$^+$; $^1$H NMR (DMSO-d$_6$, 400 MHz): δ 9.20 (1H, s), 8.70 (1H, s), 7.71 (1H, t, J=53.2 Hz), 7.66 (1H, s), 4.80-5.02 (2H, m), 4.36-4.56 (1H, m), 3.66-3.99 (1H, m), 3.07-3.35 (4H, m), 2.86-3.03 (1H, m), 2.50-2.72 (1H, m), 1.51 (3H, t, J=7.2 Hz), 1.26-1.48 (7H, m), 0.99-1.14 (6H, m).

Synthetic Route of Compound 104

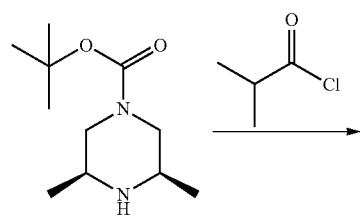

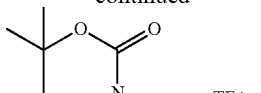

-continued

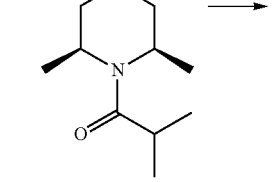

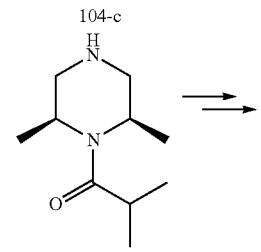

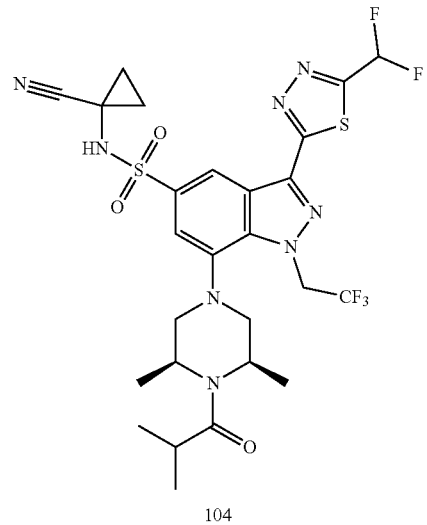

Synthesis of Compound 104-c

The compound cis-1-Boc-3,5-dimethylpiperazine (1.0 g, 4.67 mmoL), dichloromethane (20 mL), and diisopropylethylamine (2.31 mL, 14.00 mmoL) were placed in a reaction flask at room temperature. In an ice-water bath, isobutyryl chloride (587 uL, 5.50 mmoL) was added dropwise to the above mixture. After the dropwise addition, the reaction mixture was stirred at room temperature for 1 hour. The reaction mixture was concentrated at reduced pressure and the crude product was purified by a flash column chromatography (DCM/MeOH=10:1) to give compound 104-c (1.3 g, 98%). LC-MS (ESI): m/z=285.2 [M+H]$^+$.

Synthesis of Compound 104-b

Compound 104-c (1.3 g, 4.57 mmoL), dichloromethane (5 mL) and HCl/1,4-dioxane (20 mL, 4 M) were added to a reaction flask at room temperature. The reaction mixture was stirred at room temperature for 18 hours. The reaction mixture was concentrated at reduced pressure and the residue was suspended in saturated sodium bicarbonate solution (2 mL), then was added solid sodium bicarbonate (5 g) and the mixture was stirred at room temperature for 10 min. The mixture was added ethanol (10 mL), concentrated at reduced pressure. The residue was added ethanol (20 mL) again, concentrated at reduced pressure, and the residue was suspended in a mixture of dichloromethane and methanol (10:1, 50 mL), dried over anhydrous sodium sulfate, filtered, and the filtrate was concentrated at reduced pressure and the residue was dried in vacuum at room temperature to give compound 104-b (840 mg, 100%). LC-MS (ESI): m/z=185.3 [M+H]$^+$.

Synthesis of Compound 104

Referring to the synthesis of compound 95, compound 103 was synthesized by replacing 65-b with 104-b using 95-b as the starting reactant. LC-MS (ESI): m/z 661.2 [M+H]$^+$.

Synthesis of Compound 105

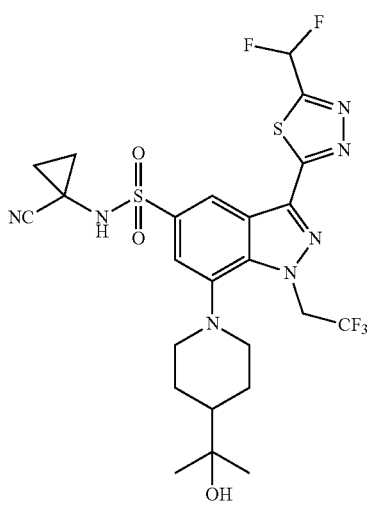

105

Referring to the synthesis of compound 95, compound 105 was synthesized by substituting 65-b with 2-(4-piperidinyl)-2-propanol using 95-b as the starting reactant. LC-MS (ESI): m/z 620.6 [M+H]$^+$.

Synthesis of Compound 106

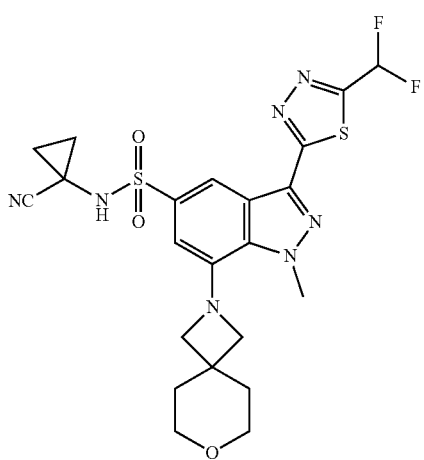

106

Referring to the synthesis of compound 29, compound 106 was synthesized using 7-oxa-2-azaspiro[3,5]nonane instead of morpholine, and using 28-b as the starting reactant. LC-MS (ESI): m/z 536.6 [M+H]$^+$.

Synthetic Route of Compound 107

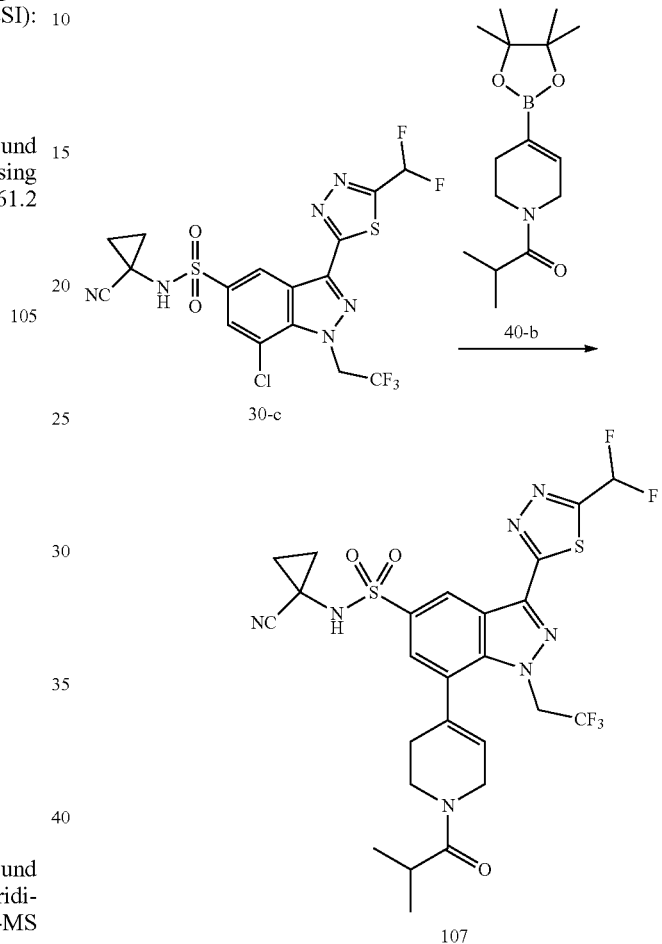

Synthesis of Compound 107

Compounds 30-c (1 g, 1.95 mmol), 40-b (0.82 g, 2.94 mmol), bis(di-tert-butyl-4-dimethylaminophenylphosphine) palladium chloride (140 mg, 0.19 mmol), and potassium phosphate (1.24 g, 5.84 mmol) were added to 1,4-dioxane (32 mL) and water (6.4 mL), and the reaction mixture was purged with nitrogen for 5 min and then stirred at 110° C. for 12 h in a sealed tube. The reaction mixture was cooled to room temperature, filtered through celite. The filtrate was added water (100 mL), and the aqueous phase was extracted with ethyl acetate (150 mL). The organic phase was washed with brine (100 mL), dried over sodium sulfate, filtered to remove the desiccant, and concentrated at reduced pressure to obtain the crude product, which was purified by column chromatography (mobile phase, PE/EA 3/1 to 1/2) to obtain the solid. The crude product was slurried with methyl tert-butyl ether (10 mL), filtered and the solid was washed with cold methyl tert-butyl ether (8 mL), collected and dried to give compound 107 (650 mg, 53%). LC-MS (ESI): m/z 630.2 (M+H)⁺; ¹H NMR ((400 MHz, DMSO-d₆): δ 9.29 (1H, s), 8.95 (1H, s), 7.88-7.59 (2H, m), 6.05 (1H, s), 5.61-5.46 (2H, m), 4.40-4.20 (2H, m), 3.89-3.75 (2H, m), 3.06-2.92 (1H, m), 2.74-2.54 (1H, m), 2.47-2.38 (1H, m), 1.49-1.43 (2H, m), 1.37-1.32 (2H, m), 1.07 (6H, d, J=8.0 Hz).

Synthesis of Compound 108

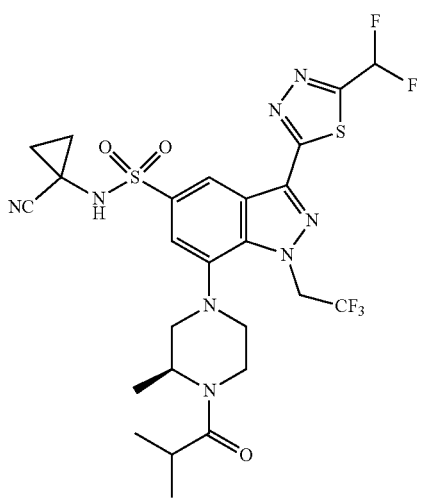

108

Referring to the synthesis of compound 95, compound 108 was synthesized using (S)-2-methyl-1-(2-methylpiperazin-1-yl)prop-1-one instead of 65-b, and using 95-b as the starting reactant. LC-MS (ESI): m/z 647.1 (M+H)⁺; ¹H NMR (400 MHz, DMSO-d₆): δ 8.10 (1H, s), 8.79 (1H, s), 7.92 (1H, s), 7.73 (1H, t, J=52.0 Hz), 5.95-5.82 (2H, m), 4.89-4.83 (1H, m), 4.52-4.38 (1H, m), 4.01-3.91 (1H, m), 3.65-3.54 (1H, m), 3.21-3.11 (2H, m), 3.00-2.87 (1H, m), 2.79-2.61 (1H, m), 1.45-1.40 (3H, m), 1.37-1.30 (2H, m), 1.31-1.24 (2H, m), 1.15-0.99 (6H, m).

Synthesis of Compound 109

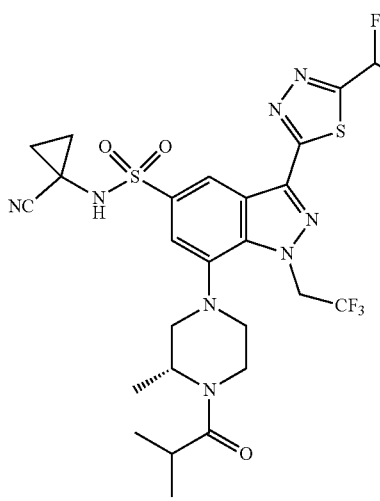

109

Referring to the synthesis of compound 95, compound 109 was synthesized using (R)-2-methyl-1-(2-methylpiperazin-1-yl)prop-1-one instead of 65-b, and using 95-b as the starting reactant. LC-MS (ESI): m/z 647.2 (M+H)⁺; ¹H NMR (400 MHz, DMSO-d₆): δ 9.02 (1H, s), 8.78 (1H, s), 7.92 (1H, s), 7.73 (1H, t, J=52.0 Hz), 5.96-5.83 (2H, m), 4.90-4.82 (1H, m), 4.54-4.38 (1H, m), 4.02-3.90 (1H, m), 3.67-3.52 (1H, m), 3.21-3.08 (2H, m), 3.00-2.90 (1H, m), 2.79-2.55 (1H, m), 1.45-1.40 (3H, m), 1.39-1.30 (2H, m), 1.28-1.22 (2H, m), 1.13-0.99 (6H, m).

Synthetic Route of Compound 110

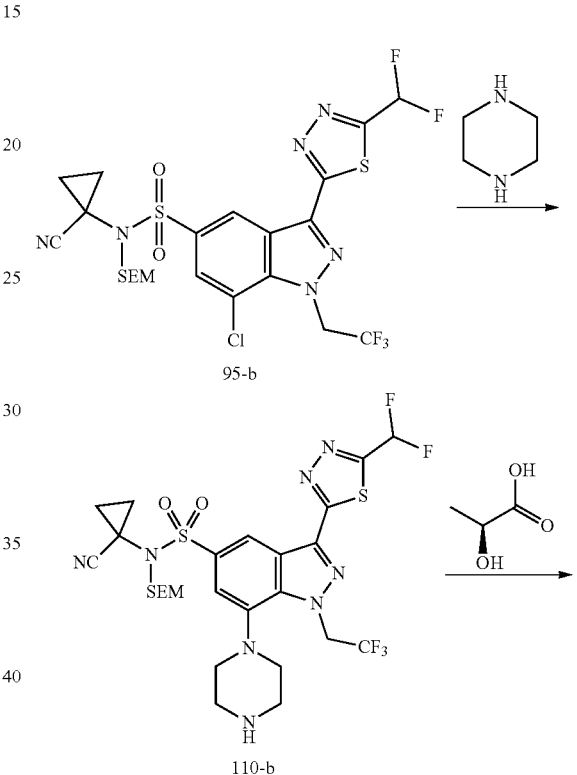

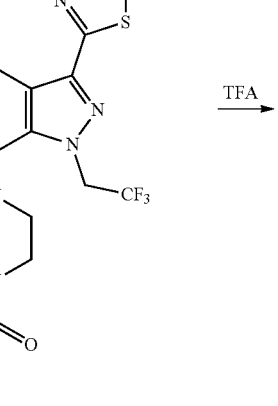

110-a

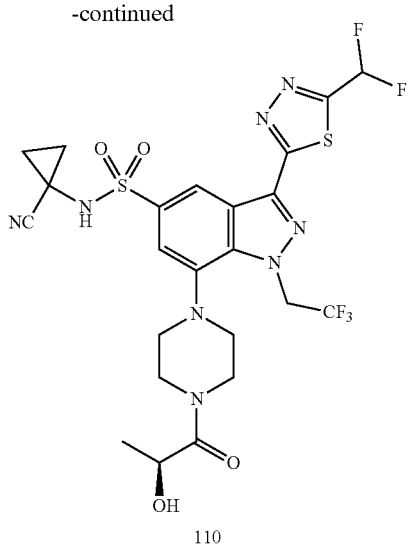

110

Synthesis of Compound 110-b

Compound 95-b (150 mg, 0.23 mmol), piperazine (40 mg, 0.46 mmol), [1,3-bis[2,6-bis(1-ethylpropyl)phenyl]-4,5-dichloro-1,3-dihydro-2H-imidazol-2-ylidene]dichloro(2-methylpyridine)palladium (20 mg, 0.024 mmol), 2-dicyclohexylphosphoryl-2',6'-diisopropoxy-1,1'-biphenyl (11 mg, 0.024 mmol), and cesium carbonate (152 mg, 0.47 mmol) were added to 1,4-dioxane (4.5 mL). The mixture was puffed with nitrogen for 3 min and then stirred at 80° C. for 15 h in a sealed tube. The reaction mixture was cooled to room temperature, filtered through celite, and the filtrate was concentrated at reduced pressure to obtain the crude product, which was purified by column chromatography (mobile phase, PE/EA 1/1) to give compound 110-b (72 mg, 45%). LC-MS (ESI): 693.3 m/z (M+H)$^+$.

Synthesis of Compound 110-a

Compound 110-b (72 mg, 0.10 mmol) and L-lactic acid (14 mg, 0.16 mmol) were dissolved in dried N,N-dimethylformamide (6 mL), to which 1-hydroxybenzotriazole (21 mg, 0.16 mmol) and N,N-diisopropylethylamine (20 mg, 0.16 mmol) were added in an ice-water bath. After the addition of 1-(3-dimethylaminopropyl)-3-ethylcarbodiimide hydrochloride (30 mg, 0.16 mmol), the reaction mixture was stirred at room temperature for 15 hours. Water (50 mL) was added to the reaction mixture and the aqueous phase was extracted with ethyl acetate (100 mL). The organic phase was washed with brine (50 mL), dried over sodium sulfate, filtered to remove the desiccant and concentrated at reduced pressure to obtain the crude product, which was purified by column chromatography (mobile phase, PE/EA 1/1) to give compound 110-a (35 mg, 46%). 1C-MS (ESI): 765.3 m/z (M+H)$^+$.

Synthesis of Compound 110

Compound 110-a (61 mg, 0.080 mmol) was dissolved in dichloromethane (3 mL), to which trifluoroacetic acid (1 mL) was added in an ice-water bath, and the reaction mixture was stirred at room temperature for 2 h. The dichloromethane was removed by concentration at reduced pressure, and the residue was adjusted to pH 7-8 with saturated sodium bicarbonate solution, the aqueous phase was extracted with ethyl acetate (50 mL), and the organic phase was washed with brine, dried over sodium sulfate, filtered off the desiccant, and concentrated at reduced pressure to obtain the crude product, which was purified by preparative HPLC (basic conditions) to obtain compound 110 (18 mg, 35%). LC-MS (ESI): m/z 635.1 (M+H)$^+$.

Synthetic Route of Compound 111

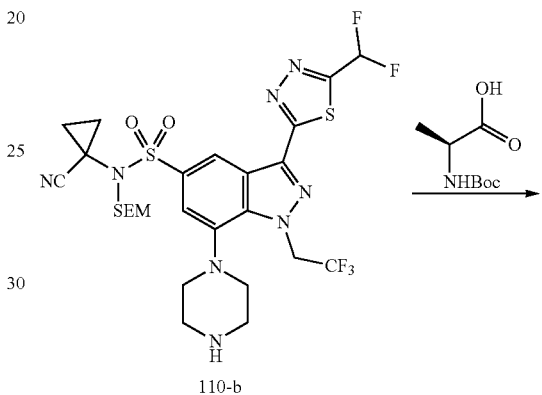

110-b

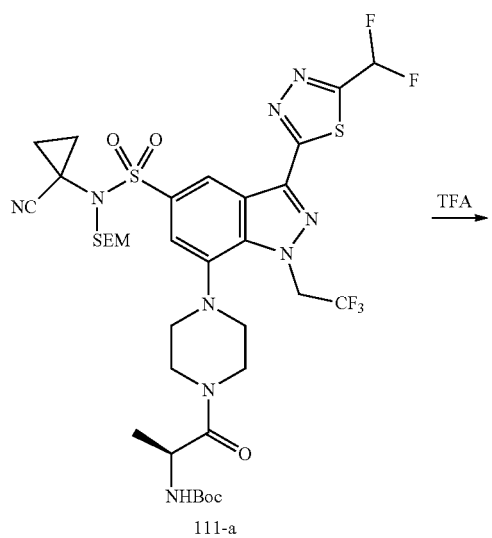

111-a

341

-continued

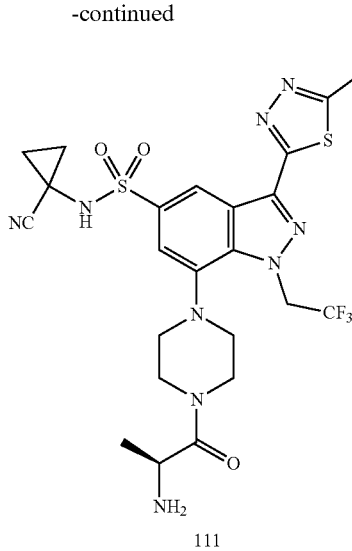

111

Synthesis of Compound 111-a 1-hydroxybenzotriazole (20 mg, 0.15 mmol) and N,N-diisopropylethylamine (19 mg, 0.15 mmol) were added to a solution of compound 110-b (52 mg, 0.075 mmol), N-tert-butoxycarbonyl-L-alanine (28 mg, 0.15 mmol) in dried N,N-dimethylformamide (6 mL), then 1-(3-dimethylaminopropyl)-3-ethylcarbodiimide hydrochloride (29 mg, 0.15 mmol) was added to the above mixture in an ice-water bath and the reaction was stirred at room temperature for 12 hours. The reaction mixture was added water (100 mL), extracted with ethyl acetate (100 mL). The organic phase was washed with brine (100 mL), dried over sodium sulfate, filtered off the desiccant and concentrated at reduced pressure to give the crude product, which was purified by column chromatography (mobile phase, PE/EA 1/1) to give compound 111-a (33 mg, 51%). LC-MS (ESI): 864.3 m/z (M+H)$^+$.

Synthesis of Compound 111

Compound 111-a (46 mg, 0.053 mmol) was dissolved in dichloromethane (4.5 mL) and was added trifluoroacetic acid (1.5 mL) in an ice-water bath, and the reaction mixture was stirred for 2 h at room temperature. The reaction mixture was concentrated at reduced pressure to remove the dichloromethane, and the residue was adjusted to pH 7-8 with saturated sodium bicarbonate solution and the aqueous phase was extracted with dichloromethane (50 mL). The organic phase was washed with brine (50 mL), dried over sodium sulfate, filtered off the desiccant and concentrated at reduced pressure to give the crude product, which was purified by preparative HPLC (basic conditions) to give compound 111 (10 mg, 30%). LC-MS (ESI): m/z 634.2 (M+H)$^+$.

342

Synthetic Routes of Compounds 112 and 113

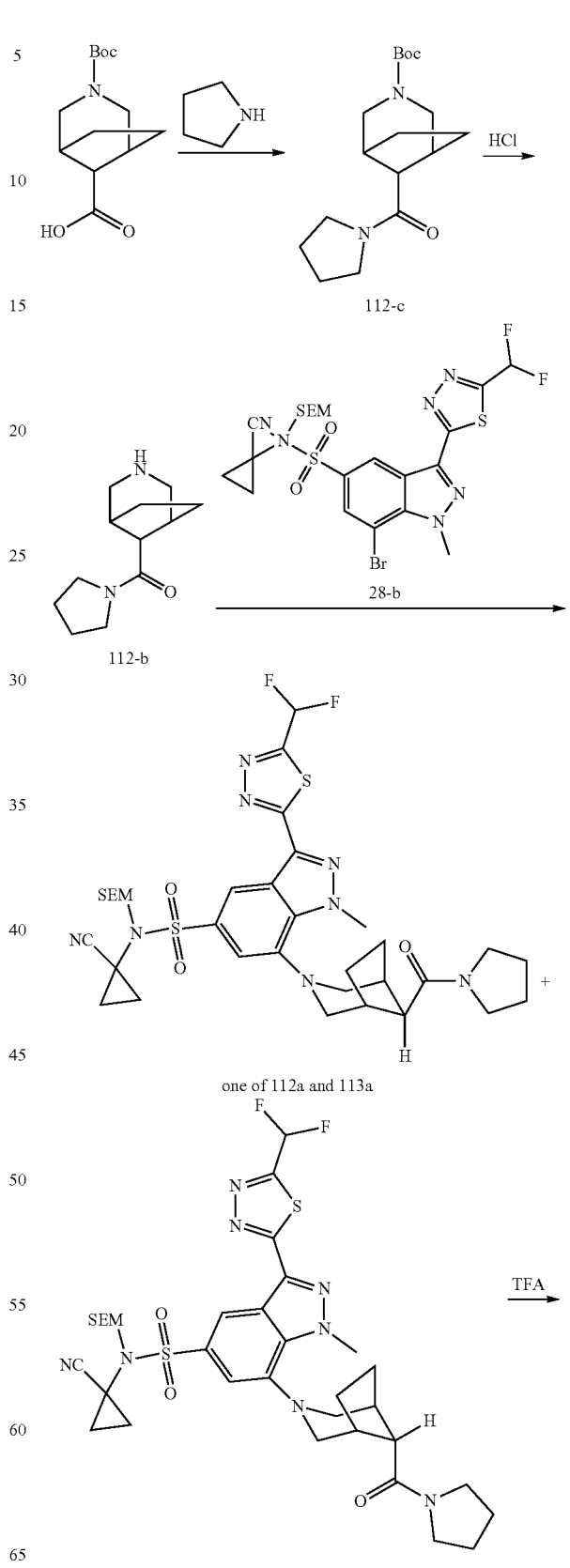

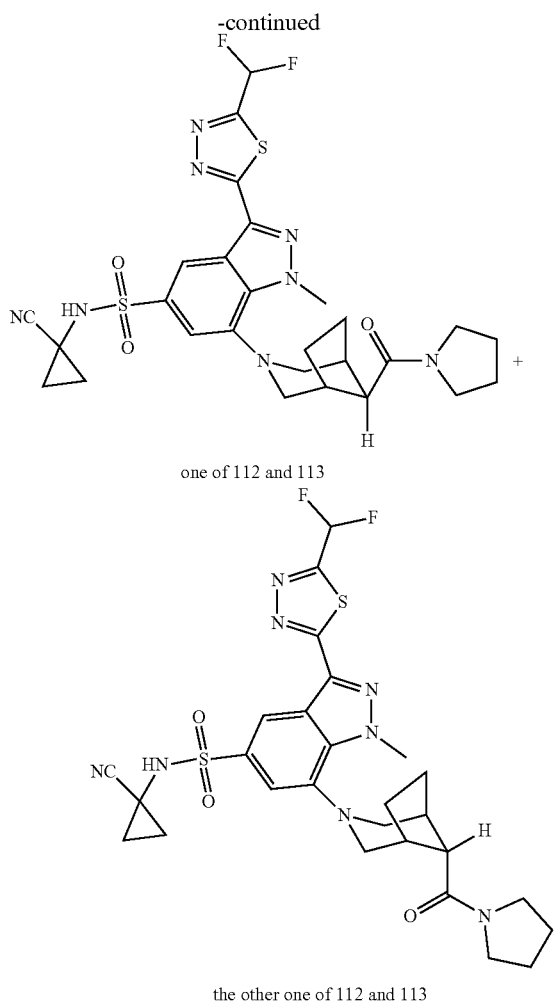

one of 112 and 113 the other one of 112 and 113

Synthesis of Compound 112-c

A reaction flask charged with 3-BOC-3-azabicyclo[3.2.1]octane-8-carboxylic acid (300 mg, 1.18 mmol), pyrrolidine (167 mg, 2.35 mmol), DMF (4 mL), HATU (893 mg, 2.35 mmol) and DIPEA (456 mg, 3.53 mmol) was stirred at room temperature for 2 hours under the protection of nitrogen. The reaction was quenched with saturated aqueous sodium bicarbonate (100 mL), extracted with dichloromethane (50 mL*3), the organic phase was concentrated at reduced pressure, and the residue was purified by column chromatography (mobile phase: methanol/dichloromethane 0/100 to 1/10) to give compound 112-c (249 mg, 69%). LC-MS (ESI): m/z 309.7 (M+H)+.

Synthesis of Compound 112-b

To a reaction vial was added 112-c (249 mg, 0.81 mmol), HCl/1,4-dioxane (4M, 1 mL, 4 mmol) and acetonitrile (3 mL) and the mixture was stirred at room temperature for 2 hours. The reaction mixture was concentrated at reduced pressure and the residue was added saturated sodium bicarbonate (2 mL), extracted with a mixture of dichloromethane/methanol=10/1 (10 mL*3) and the organic phase was concentrated at reduced pressure. The residue was dissolved into dichloromethane (20 mL), dried over sodium sulfate, filtered through a membrane and the filtrate was concentrated at reduced pressure to give compound 112-b (106 mg, 63%). LC-MS (ESI): m/z 209.2 (M+H)+.

Synthesis of Compounds 112-a and 113-a

A microwave tube charged with 28-b (100 mg, 0.16 mmol), 112-b (67 mg, 0.32 mmol), Ruphos (8 mg, 0.017 mmol), cesium carbonate (157 mg, 0.48 mmol), (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (28 mg, 0.032 mmol) was degassed and purged with nitrogen for three times, then was added 1,4-dioxane (2.5 mL) and degassed and purged with nitrogen for three times. The reaction mixture was stirred at 88° C. for 12 hours. The reaction mixture was concentrated at reduced pressure and the residue was washed with ethyl acetate (10 mL*3), concentrated at reduced pressure and purified by Prep-TLC (PE/EA=2/3) to give compounds 112-a (22 mg, 18%), 113-a (41 mg, 34%), LC-MS (ESI): m/z 747.8 (M+H)+.

Synthesis of Compounds 112 and 113

112-a (22 mg, 0.029 mmol) and 113-a (38 mg, 0.051 mmol) were added to two reaction vials respectively, and dichloromethane (3 mL) and trifluoroacetic acid (1 mL) were added to each vial respectively, and the two reaction vials were stirred at room temperature for 2 h under nitrogen atmosphere. The reaction mixtures were concentrated at reduced pressure and quenched with two parts of potassium carbonate (3 g) and water (20 mL), and ethyl acetate (20 mL) was added to each reaction vial and stirred for 2 h at room temperature. The different mixtures were extracted with ethyl acetate (20 mL*3), respectively, and the organic phase was concentrated at reduced pressure and purified by prep-HPLC to give compounds 112 (7 mg, 39%), 113 (10 mg, 32%). LC-MS (ESI): m/z 617.7 (M+H)+.

Synthetic Route of Compound 114

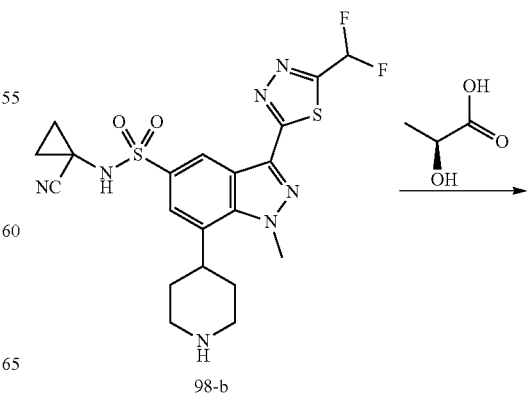

98-b

345

-continued

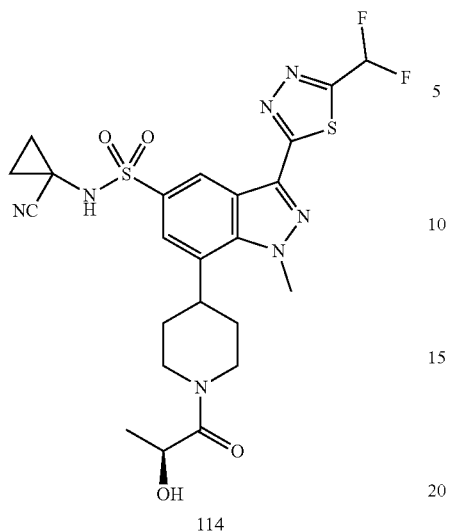

114

Synthesis of Compound 114

(S)-2-hydroxypropionic acid (19 mg, 0.21 mmoL), EDCI (27 mg, 0.14 mmoL), HOBt (19 mg, 0.14 mmoL) and DIPEA (59 uL 0.36 mmoL) were added to a solution of compound 98-b (35 mg, 0.071 mmoL) in dichloromethane (5 mL) under nitrogen atmosphere at room temperature. After addition, the reaction mixture was stirred at room temperature under nitrogen atmosphere overnight. The reaction mixture was concentrated at reduced pressure and the residue was dissolved in 2 mL of DMF then purified by Prep-HPLC (alkali method) to give compound 114 (10.5 mg, 26%). LC-MS (ESI): m/z=566.2[M+H]$^+$; $^1$H NMR (DMSO-d$_6$, 400 MHz): δ 9.25 (1H, brs), 8.81 (1H, d, J=1.6 Hz), 7.71 (1H, t, J=53.6 Hz), 7.78 (1H, s), 4.99-4.95 (1H, m), 4.67-4.56 (1H, m), 4.55-4.44 (1H, m), 4.51 (3H, s), 4.21 (1H, t, J=11.2 Hz), 3.84 (1H, t, J=10.8 Hz), 2.86 (1H, t, J=12 Hz), 2.11-1.96 (2H, m), 1.87-1.56 (3H, m), 1.46-1.37 (2H, m), 1.34-1.28 (2H, m), 1.27-1.16 (3H, m).

Synthetic Route of Compound 115

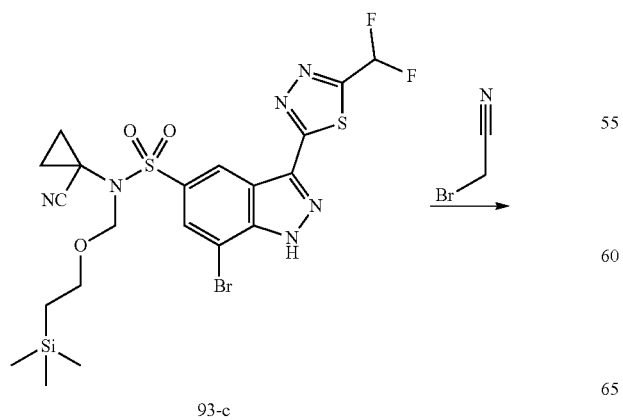

93-c

346

-continued

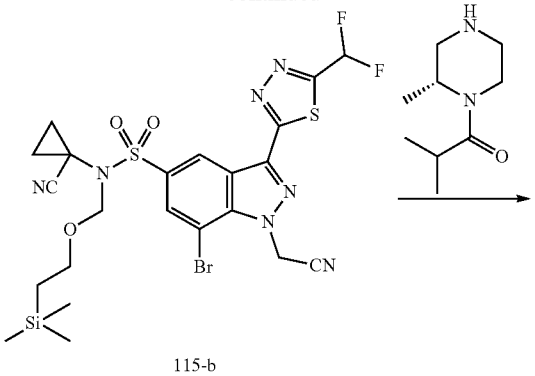

115-b

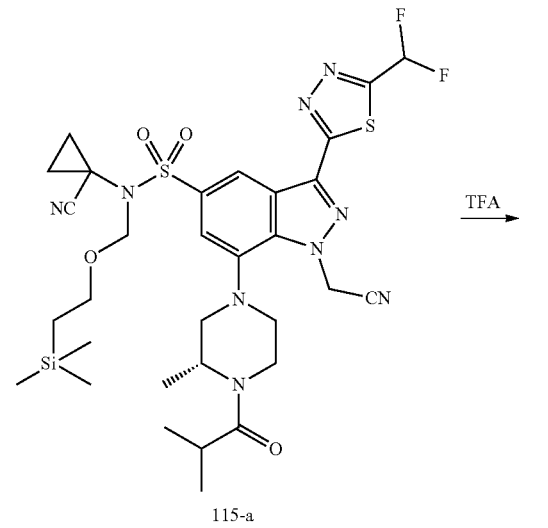

115-a

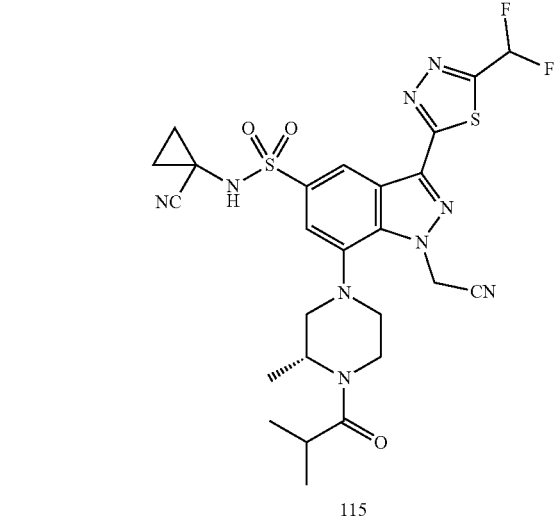

115

Synthesis of Compound 115-b

Potassium carbonate (76 mg, 0.55 mmoL) was added to a solution of compound 93-c (100 mg, 0.16 mmoL) in DMF (5 mL) at room temperature, then to the mixture was added bromoacetonitrile (23 uL, 0.33 mmoL) in an ice-water bath. After addition, the mixture was warmed to room temperature and stirred for 5 hours. 20 mL of water was added, and the aqueous phase was extracted with ethyl acetate (50 mL*2). The organic phase was washed with brine (100 mL*3), dried over anhydrous sodium sulfate, filtered. The filtrate was concentrated at reduced pressure, and the residue was purified by a flash column chromatography (PE/EA=1:1) to give compound 115-b (53 mg, 50%). LC-MS (ESI): m/z=643.9 [M+H]$^+$.

Synthesis of Compound 115-a

A sealed tube charged with compound 115-b (53 mg, 0.082 mmoL), (R)-2-methyl-1-(2-methylpiperazin-1-yl)propyl-1-one (28 mg, 0.16 mmoL), (SP-4-1)-[1,3-bis[2,6-bis(1-ethylpropyl)phenyl]-4,5-dichloro-1,3-dihydro-2H-imidazole (28 mg, 0.16 mmoL), (SP-4-1)-[1,3-bis[2,6-bis(1-ethylpropyl)phenyl]-4,5-dichloro-1,3-dihydro-2H-imidazole-2-ylidene]dichloro(2-methylpyridine)palladium (14 mg, 0.017 mmoL), RuPhos (8 mg, 0.017 mmoL), cesium carbonate (86 mg, 0.26 mmoL) and 1,4-dioxane (2 mL) was stirred at 90° C. for 18 h under nitrogen atmosphere. The reaction mixture was cooled to room temperature, filtered, and the filtrate was concentrated at reduced pressure, and the residue was purified by a flash column chromatography (PE/EA=1:1-EA) to give compound 115-a (20 mg, 33%). 1C-MS (ESI): m/z=734.2[M+H]$^+$.

Synthesis of Compound 115

Compound 115-a (20 mg, 0.027 mmoL) was dissolved in 3 mL of dichloromethane under nitrogen at room temperature, and trifluoroacetic acid (1 mL) and water (0.1 mL) were added to the above mixture in an ice-water bath. After addition, the reaction mixture was stirred at room temperature under nitrogen atmosphere for 2 hours. The reaction mixture was concentrate at reduced pressure at room temperature and the residue was suspended in 1 mL of saturated sodium bicarbonate solution, added about 200 mg of potassium carbonate, 50 mL of ethyl acetate and the mixture is stirred at room temperature for 1 hour. The mixture was extracted with ethyl acetate (50 mL*2) and the organic phase was dried over anhydrous sodium sulfate, filtered, concentrated at reduced pressure and the residue was purified by preparative HPLC (basic method) to give compound 115 (2.8 mg, 17%). LC-MS (ESI): m/z=604.3[M+H]$^+$.

Synthetic Route of Compound 116

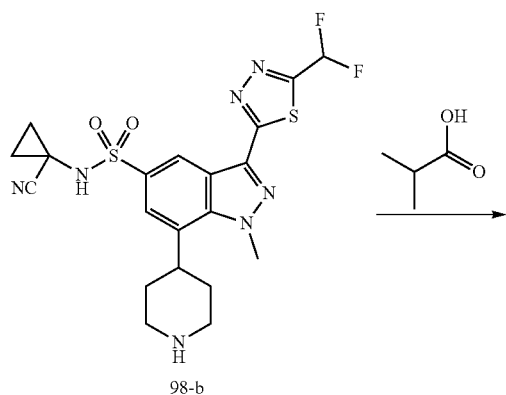

98-b

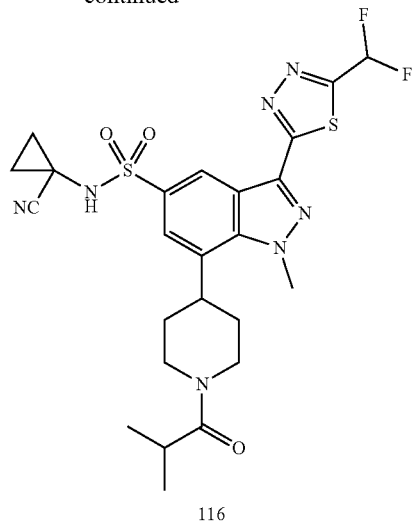

116

Synthesis of Compound 116

Isobutyric acid (14 mg, 0.16 mmoL), EDCI (36 mg, 0.19 mmoL), HOBt (26 mg, 0.19 mmoL) and DIPEA (79 uL, 0.48 mmoL) were added to a solution of compound 98-b (47 mg, 0.095 mmoL) in 8 mL of dichloromethane under nitrogen atmosphere in an ice-water bath. After addition, the reaction mixture was stirred at room temperature overnight under nitrogen atmosphere. The reaction mixture was concentrated at reduced pressure and the residue was dissolved in 2 mL of DMF and purified by Prep-HPLC (basic method) to give compound 116 (15.2 mg, 28%). LC-MS (ESI): m/z=564.2[M+H]$^+$.

Synthetic route of compound 117

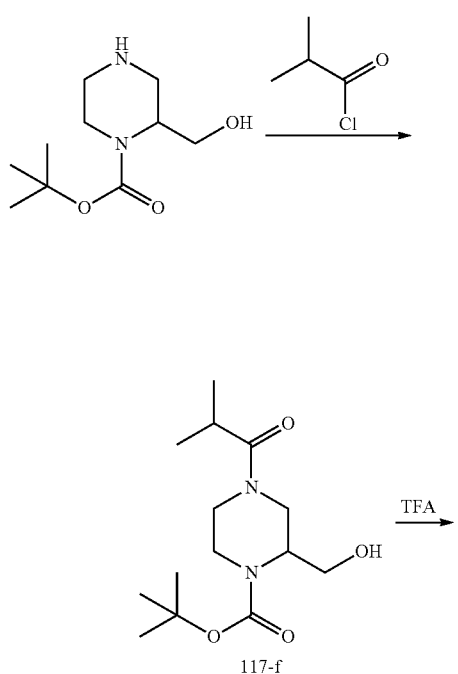

117-f

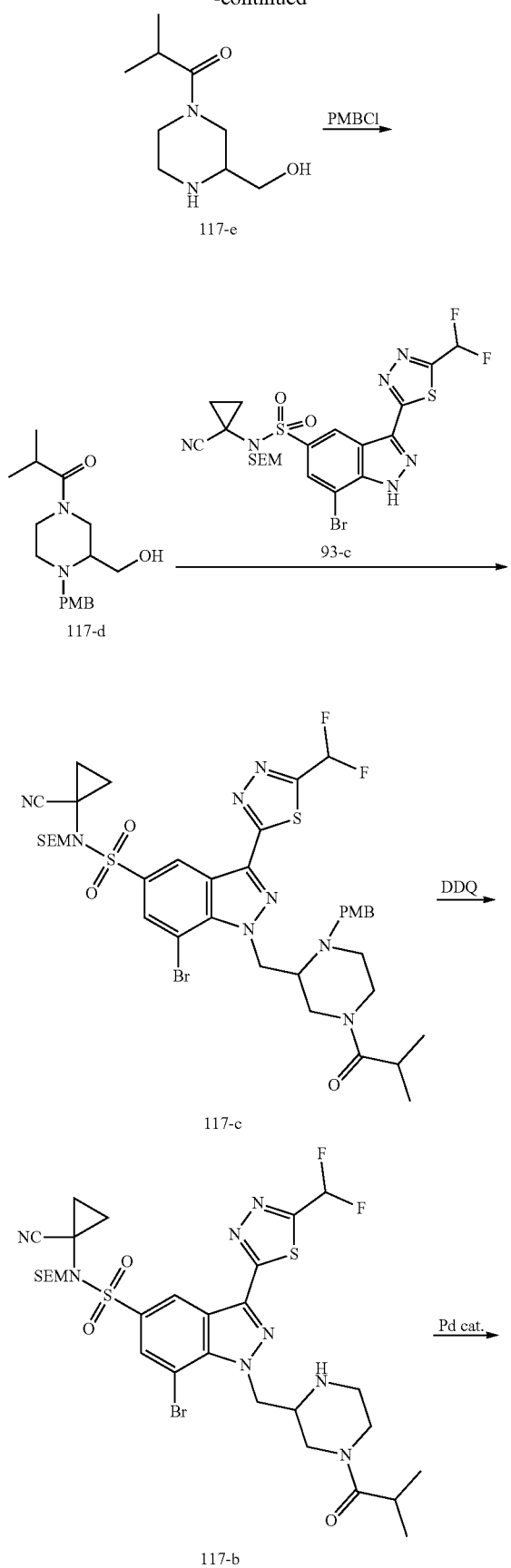
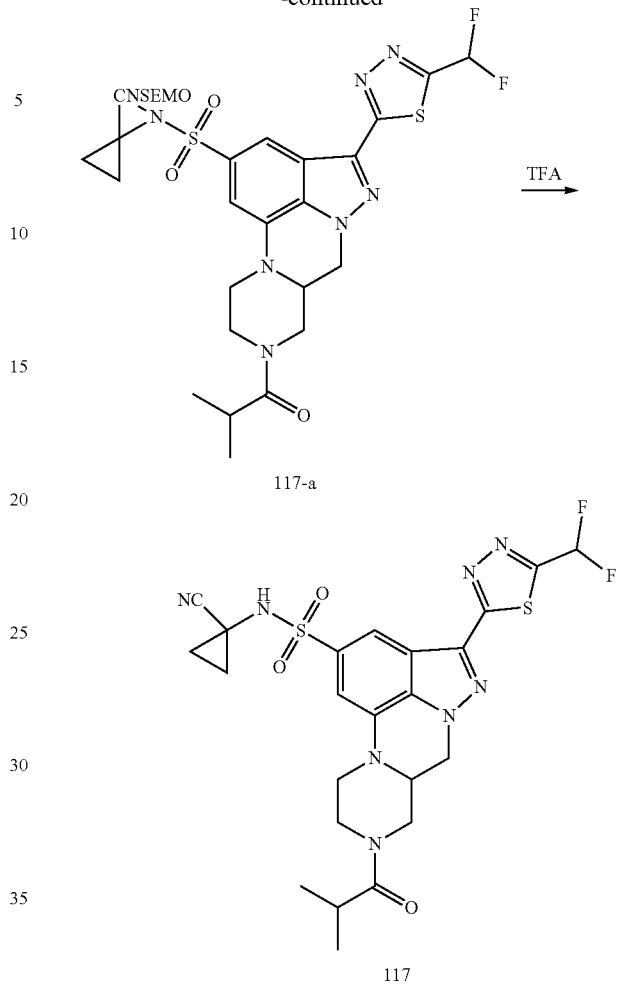

Synthesis of Compound 117-f

A reaction flask charged with 1-Boc-2-hydroxymethylpiperazine (1.08 g, 4.99 mmol) and dichloromethane (15 mL) was added triethylamine (1.39 mL, 9.99 mmol) in an ice-water bath followed by slow dropwise addition of isobutyryl chloride (0.59 g, 5.49 mmol) in an ice-water bath. After the dropwise addition, the reaction mixture was stirred in an ice-water bath for 3 hours. The solvent was removed by concentration at reduced pressure and the residue was diluted with ethyl acetate, the organic phase was washed with water, brine, dried over anhydrous sodium sulfate, filtered and the filtrate was evaporated to give 117-f (1.3 g, 91%). LC-MS (ESI): m/z 287.3 (M+H)$^+$.

Synthesis of Compound 117-e

Trifluoroacetic acid (3 mL) was added dropwise to a solution of 117-f (1.0 g, 3.49 mmol) in dichloromethane (12 mL) a reaction flask in an ice-water bath. After the dropwise addition, the reaction mixture was stirred from the ice water bath to room temperature for 3 hours. The solvent was removed by concentration at reduced pressure, and the residue was washed twice with methyl tert-butyl ether and dried by an oil pump to obtain a viscous liquid (1.04 g, 99%). The viscous liquid (500 mg) was added to anhydrous methanol (20 mL) and the solution was adjusted to pH>9 by adding a strong basic resin in an ice-water bath. Filtered, and the filtrate was evaporated to give 117-e (280 mg, 90%). LC-MS (ESI): m/z 187.2 (M+H)+.

Synthesis of Compound 117-d

A reaction flask charged with 117-e (280 mg, 1.50 mmol), THF (4 mL), DMF (1.3 mL) and potassium carbonate (465 mg, 3.37 mmol) was added paramethoxybenzyl chloride (281 mg, 1.79 mmol) at room temperature. The reaction mixture was stirred from room temperature to 40° C. for 72 hours. The reaction mixture was diluted with ethyl acetate, and the organic phase was washed with water. The aqueous phase was extracted once with ethyl acetate. The organic phases were combined, washed with brine, dried over anhydrous sodium sulfate, filtered. The filtrate was evaporated and the residue was purified by column chromatography (mobile phase: dichloromethane/methanol, 100/0 to 96/4) to give compound 117-d (340 mg, 74%). LC-MS (ESI): m/z 307.3 (M+H)+.

Synthesis of Compound 117-c

A reaction flask charged with 93-c (340 mg, 0.56 mmol), 117-d (180 mg, 0.59 mmol), THF (10 mL) and triphenylphosphine (368 mg, 1.40 mmol) was added diethyl azodicarboxylate (DEAD) (244 mg, 1.40 mmol) after stirred in an ice-water bath for 5 min. The reaction mixture was stirred at room temperature for 24 hours, then 30° C. for 6 hours. The solvent was removed by concentration at reduced pressure and the residue was purified by column chromatography (mobile phase: petroleum ether/ethyl acetate, 100/0 to 60/40) to give compound 117-c (160 mg, 32%). LC-MS (ESI): m/z 893.2 (M+H)+.

Synthesis of Compound 117-b

DDQ (2,3-dichloro-5,6-dicyano-1,4-benzoquinone) (57 mg, 0.25 mmol) was added to a mixture of 117-c (160 mg, 0.18 mmol) in dichloromethane (10 mL) in a reaction flask after stirred in an ice-water bath for 5 min. The reaction mixture was stirred in an ice-water bath for 1.5 h, then was added and extracted twice with ethyl acetate. The organic phase was washed with aqueous sodium bicarbonate (5%), brine, dried over anhydrous sodium sulfate, filtered and the filtrate was evaporated to give compound 117-b (130 mg, 93%). LC-MS (ESI): m/z 773.2 (M+H)+.

Synthesis of Compound 117-a

A microwave tube charged with 117-b (130 mg, 0.17 mmol), RuPhos (8 mg, 0.017 mmol), Pd-PEPPSI-IHEPT (32 mg, 0.037 mmol) (cas: 1435347-24-2) and cesium carbonate (110 mg, 0.34 mmol) was degassed and purged with nitrogen once, and was added anhydrous 1,4-dioxane (3.2 mL). Then degassed and purged with nitrogen twice, the reaction mixture was heated at 80° C. and stirred for 21 hours. The reaction mixture was diluted with ethyl acetate, and the organic phase was washed with water, brine, dried over anhydrous sodium sulfate, filtered. The filtrate was evaporated and the residue was purified by column chromatography (mobile phase: petroleum ether/(ethyl acetate: ethanol 94:6), 100/0 to 60/40) to give compound 117-a (70 mg, 59%). LC-MS (ESI): m/z 693.3 (M+H)+.

Synthesis of Compound 117

117-a (70 mg, 0.10 mmol) and dichloromethane (1.5 mL) were added to a reaction flask and trifluoroacetic acid (0.5 mL) was added to the above while cooling in an ice-water bath. The reaction mixture was stirred at room temperature for 2 hours, then solvent was removed by concentration at reduced pressure, and the residue was dried by an oil pump and was added ethyl acetate, saturated aqueous sodium bicarbonate and anhydrous potassium carbonate (150 mg), and stirred for 30 min at room temperature. The aqueous phase was extracted once with ethyl acetate, and the organic phases were combined, washed with brine, dried over anhydrous sodium sulfate, filtered. The filtrate was evaporated to obtain the crude product, purified by column chromatography (mobile phase: petroleum ether/(ethyl acetate: ethanol 94:6), 100/0 to 50/50), and the fractions were concentrated at reduced pressure. The residue was added acetonitrile and water and lyophilized to obtain compound 117 (43.2 mg. 77%). LC-MS(ESI): m/z 563.3 (M+H)+; 1HNMR (DMSO-$d_6$, 400 MHz): δ 9.11 (1H, s), 8.17 (1H, d, J=1.2 Hz), 7.70 (1H, t, J=53.2 Hz), 7.07 (1H, d, J=1.2 Hz), 5.01-4.91 (1H, m), 4.80-4.60 (1H, m), 4.45-4.19 (2H, m), 3.94 (1H, d, J=10.8 Hz), 3.67-3.42 (2H, m), 3.27-2.66 (3H, m), 1.45-1.20 (4H, m), 1.09-1.01 (6H, m).

Synthetic Route of Compound 118

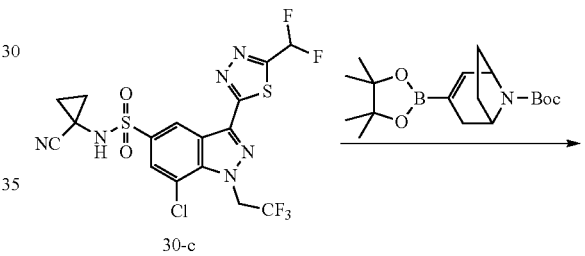

30-c

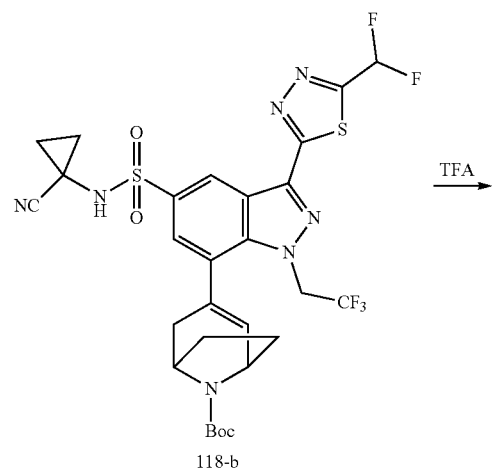

118-b

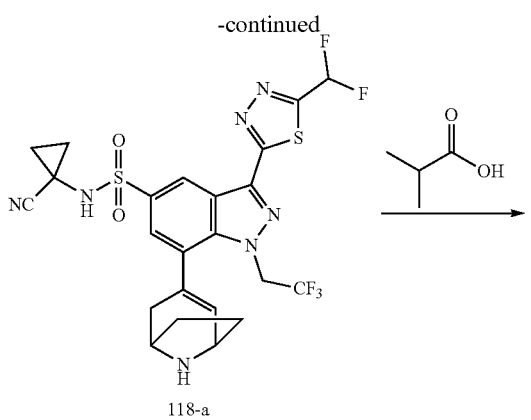

118-a

118

Synthesis of Compound 118-b

A microwave tube charged with 30-c (200 mg, 0.39 mmol), 8-tert-butoxycarbonyl-8-azabicyclo[3.2.1]oct-2-ene-3-boronic acid pinacol ester (206 mg, 0.61 mmol), dichlorodi-tert-butyl-(4-dimethylaminophenyl)phosphopalladium(II) (887919-35-9) (25 mg, 0.035 mmol), potassium phosphate (198 mg, 0.93 mmol), 1,4-dioxane (5 mL) and H$_2$O (1 mL) was degassed and purged with nitrogen for 3 times, then was heated to 110° C. and stirred overnight. After completion, the reaction mixture was cooled to room temperature, and the organic solvent was removed by concentration at reduced pressure. The residue was diluted by adding ethyl acetate, and the organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 118-b (150 mg, 56%). LC-MS (ESI): m/z 686.1 [M+H]$^+$.

Synthesis of Compound 118-a

Trifluoroacetic acid (3 mL) was added dropwise to a solution of 118-b (150 mg, 0.22 mmol) in dichloromethane (10 mL) in a reaction vial at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product. The compound 118-a (100 mg, 78%) was purified by a flash column chromatography (mobile phase: methanol/dichloromethane, 0% to 25%). LC-MS (ESI): m/z 586.5 [M+H]$^+$.

Synthesis of Compound 118

A reaction vial charged with 118-a (30 mg, 0.051 mmol), isobutyric acid (0.007 mL, 0.077 mmol), dichloromethane (5 mL), DIPEA (0.045 mL, 0.26 mmol) and HOBT (14 mg, 0.10 mmol) was added EDCI (20 mg, 0.10 mmol) slowly in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate and concentrated. The crude product was purified by Prep-HPLC to give compound 118 (18 mg, 54%). LC-MS (ESI): m/z=656.6 [M+H]$^+$.

Synthetic Route of Compound 119

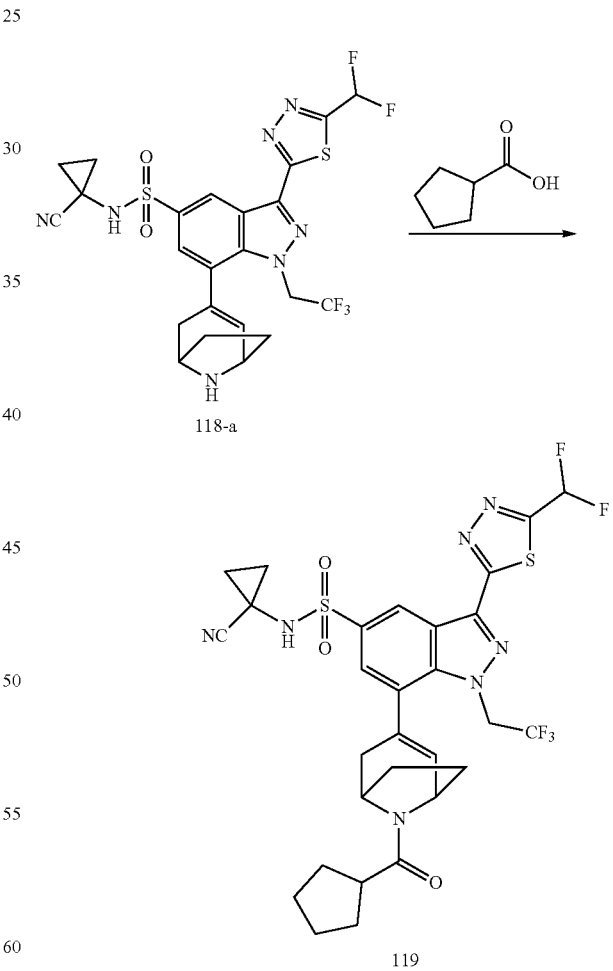

118-a

119

Synthesis of Compound 119

To a reaction flask, 118-a (30 mg, 0.051 mmol), cyclopentanecarboxylic acid (0.008 mL, 0.077 mmol), dichloromethane (5 mL), DIPEA (0.045 mL, 0.26 mmol) and HOBT (14 mg, 0.10 mmol) were added, and then EDCI (20 mg, 0.10 mmol) was slowly added in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by Prep-HPLC to give compound 119 (18 mg, 52%). LC-MS (ESI): m/z 682.5 [M+H]$^+$; $^1$H NMR (DMSO-$d_6$, 400 MHz): δ 9.34 (1H, s), 8.93 (1H, s), 7.73 (1H, t, J=53.2 Hz), 7.52-8.02 (1H, m), 6.28-6.41 (1H, m), 5.40-5.67 (2H, m), 4.66-4.98 (2H, m), 2.82-3.15 (2H, m), 1.50-2.40 (13H, m), 1.27-1.48 (4H, m).

Synthetic Route of Compound 120

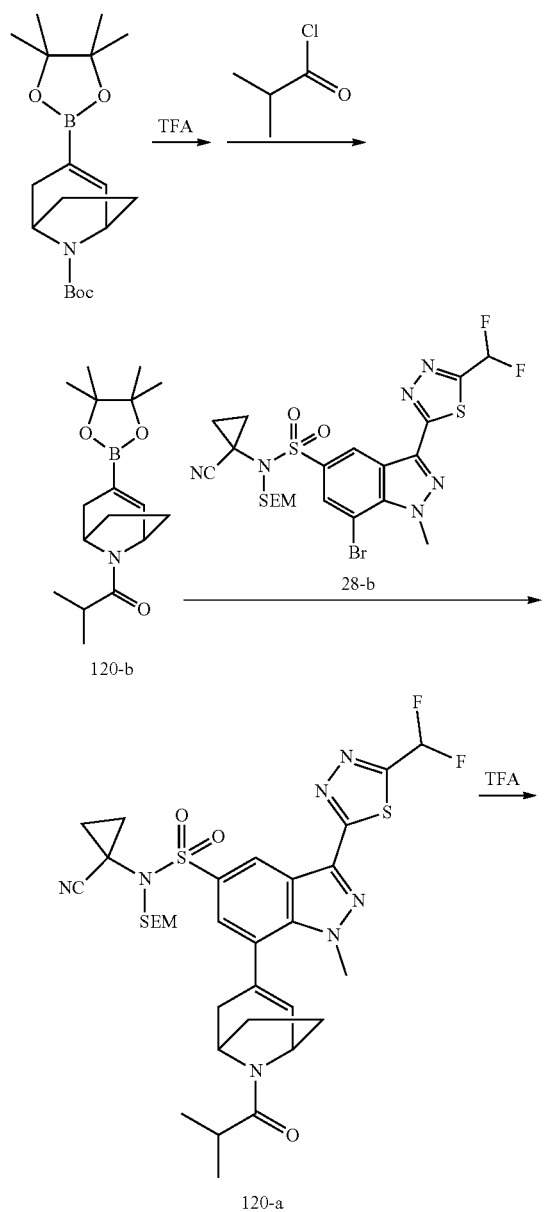

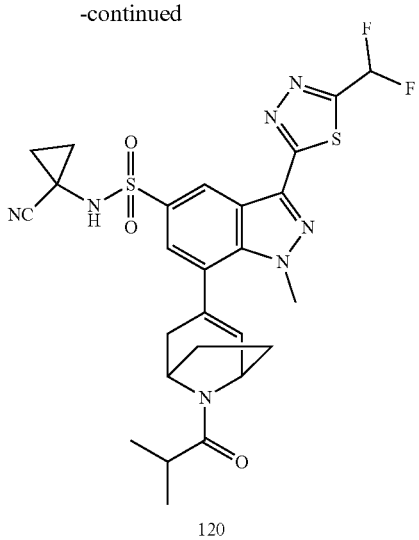

120

Synthesis of Compound 120-b

Compound 8-Boc-8-azabicyclo[3.2.1]oct-2-ene-3-boronic acid pinacol ester (2 g, 5.97 mmol) was dissolved in dichloromethane (8 mL), to which trifluoroacetic acid (2 mL) was added, and the reaction mixture was stirred at room temperature for 2 h. The reaction mixture was concentrated at reduced pressure, dried in vacuum, and the residue was added dichloromethane (30 mL), triethylamine (2 g, 19.76 mmol), followed by dropwise addition of isobutyryl chloride (670 mg, 6.29 mmol) in an ice-water bath. After the dropwise addition, the mixture was stirred at room temperature for 1 hour. The reaction mixture was concentrated at reduced pressure. To the residue was added water (100 mL), and the mixture was extracted with ethyl acetate (100 mL). The organic phase was washed with brine (100 mL), dried over sodium sulfate, filtered off the desiccant, and the filtrate was concentrated at reduced pressure, purified by column chromatography (mobile phase, PE/EA 1/1) to give compound 120-b (300 mg, 16%). LC-MS (ESI): m/z 306.3 (M+H)$^+$.

Synthesis of Compound 120-a

A reaction flask charged with 28-b (100 mg, 0.16 mmol), 120-b (74 mg, 0.24 mmol), [1,1'-bis(diphenylphosphino)ferrocene]dichloropalladium dichloride dichloromethane complex (12 mg, 0.016 mmol), potassium carbonate (67 mg, 0.48 mmol), 1,4-dioxane (10 mL) and H$_2$O (2 mL) was degassed and purged with nitrogen for 3 times, then was heated to 100° C. and stirred for 4 hours. After completion, the reaction mixture was cooled to room temperature, concentrated at reduced pressure to remove the organic solvent, and the residue was diluted with ethyl acetate. The organic phase was washed with water, brine, dried over anhydrous sodium sulfate, filtered and the filtrate was evaporated to obtain the crude product, which was purified by a flash column chromatography (mobile phase: ethyl acetate/petroleum ether, 0% to 100%) to give compound 120-a (70 mg, 61%). LC-MS (ESI): m/z 718.3 [M+H]$^+$.

Synthesis of Compound 120

Trifluoroacetic acid (1 mL) was added dropwise to a solution of 120-a (70 mg, 0.098 mmol) in dichloromethane (5 mL) in a reaction vial at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product, which was purified by Prep-HPLC to give compound 120 (30 mg, 52%). LC-MS (ESI): m/z 588.3 [M+H]$^+$.

Synthetic Route of Compound 121

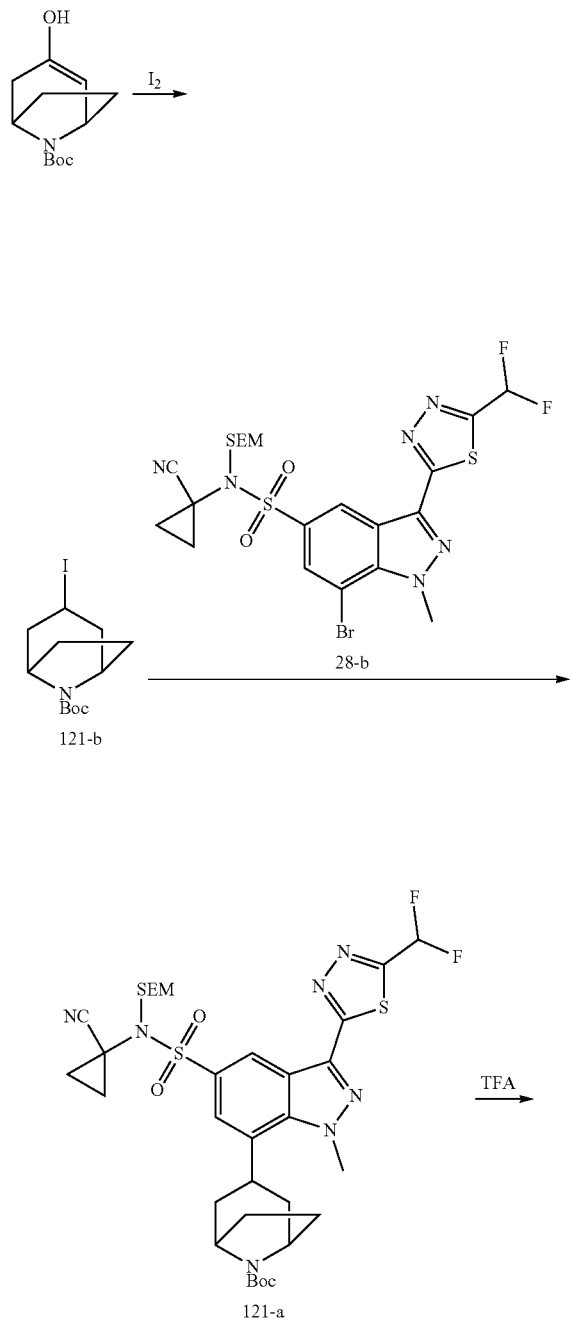

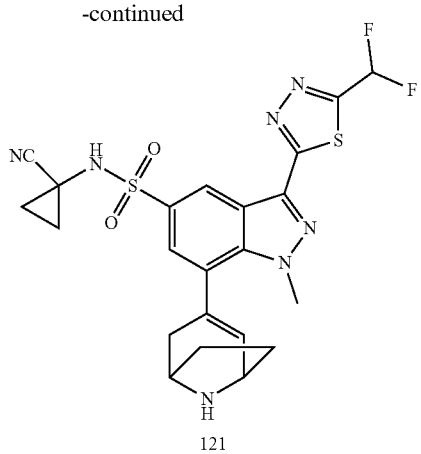

Synthesis of Compound 121-b

The compound 3-hydroxy-8-azabicyclo[3.2.1]octane-8-carboxylic acid tert-butyl ester (2000 mg, 8.80 mmol), imidazole (720 mg, 10.56 mmol), triphenylphosphine (2770 mg, 10.56 mmol) were dissolved in dichloromethane (100 mL) in an ice-water bath, to which iodine (4680 mg, 10.56 mmol) was added, and then the reaction mixture was stirred at room temperature overnight. To the reaction mixture was added water (100 mL), saturated sodium sulfite solution (100 mL), and the aqueous phase was extracted with dichloromethane (100 mL). The organic phase was washed with brine (200 mL), dried over sodium sulfate, filtered off the desiccant, and the filtrate was concentrated at reduced pressure to obtain the crude product, which was purified by column chromatography (mobile phase: petroleum ether/ethyl acetate, 10/1) to give 121-b (1.3 g, 44%). 44%). $^1$H NMR (400 MHz, CDCl$_3$): δ 4.58-4.47 (1H, m), 4.15-3.95 (2H, m), 2.50-2.25 (2H, m), 2.22-2.15 (2H, m), 1.95-1.88 (2H, m), 1.68-1.60 (2H, m), 1.48 (9H, s).

Synthesis of Compound 121-a

A microwave tube charged with 28-b (90 mg, 0.15 mmol), 121-b (144 mg, 0.43 mmol), 4,4'-di-tert-butyl-2,2'-bipyridine (10 mg, 0.037 mmol), zinc powder (30 mg, 0.46 mmol), ethylene glycol dimethyl ether nickel chloride (10 mg, 0.046 mmol) and anhydrous magnesium sulfate (18 mg, 0.15 mmol) was degassed and purged with nitrogen, and was added DMAc (3.0 mL) in an ice-water bath. The mixture was degassed and purged with nitrogen for 3 times, was added triethylamine (0.012 mL, 0.089 mmol), degassed and purged with nitrogen once, and the reaction mixture was stirred in an ice-water bath for 10 minutes, then warmed to room temperature and stirred for 16 hours. The reaction mixture was added ethyl acetate and petroleum ether, the organic phase was washed with water, brine, dried over anhydrous sodium sulfate, filtered. The filtrate was evaporated and the residue was purified by column chromatography (mobile phase: petroleum ether/ethyl acetate, 100/0 to 70/30) to give compound 121-a (100 mg, 92%). LC-MS (ESI): m/z 750.3 (M+H)$^+$.

Synthesis of Compound 121

Trifluoroacetic acid (1.0 mL) was added to a solution of 121-a (100 mg, 0.13 mmol) in dichloromethane (3.0 mL) in a reaction vial while cooling in an ice-water bath. The reaction mixture was stirred in an ice-water bath for 10 minutes and then at room temperature for 2 hours. The solvent was removed by concentration at reduced pressure and dried by an oil pump. The residue was added ethyl acetate, saturated aqueous sodium bicarbonate and anhydrous potassium carbonate (300 mg) and stirred for 20 min at room temperature. The aqueous phase was extracted once with ethyl acetate, and the organic phase was combined, dried over anhydrous sodium sulfate, filtered. The filtrate was evaporated, and the crude product was purified on silica gel plate (mobile phase: dichloromethane/methanol, 5/1) to give 121 (50 mg, 72%). LC-MS (ESI): m/z 520.4 (M+H)$^+$.

Synthetic Route of Compound 122

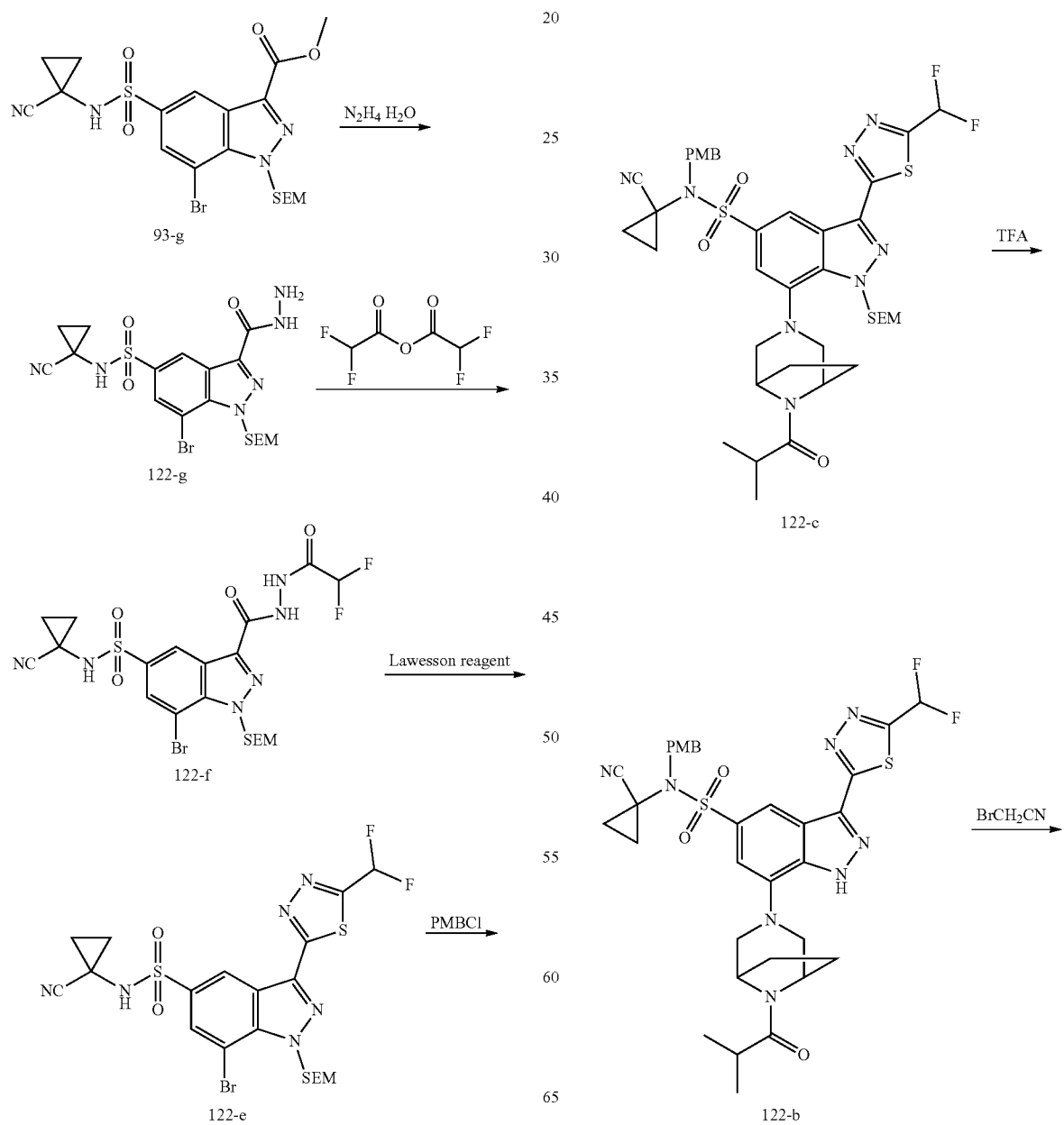

-continued

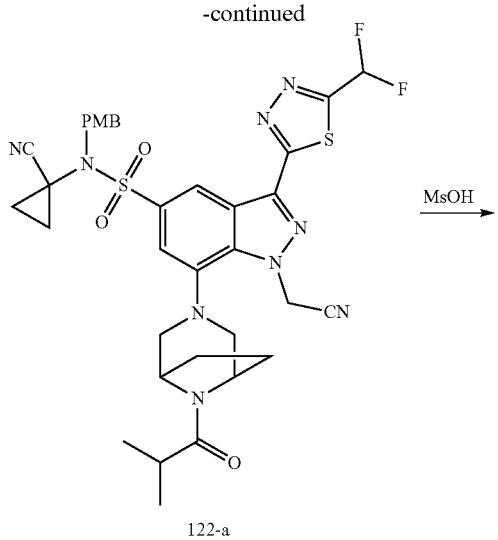

122-a

122

Synthesis of Compound 122-g

A reaction flask charged with 93-g (1.20 g, 2.27 mmol), anhydrous ethanol (12 mL) and hydrazine hydrate (1.0 mL, 20.62 mmol) was stirred at 55° C. for 2 hours. The reaction mixture was cooled to room temperature and the solvent was removed by concentration at reduced pressure. The residue was added water, extracted twice with dichloromethane. The organic phase was dried over anhydrous sodium sulfate, filtered, and the filtrate was evaporated to give 122-g (1.2 g, 100%). LC-MS (ESI): m/z 529.1 (M+H)$^+$.

Synthesis of Compound 122-f

A solution of 122-g (1.2 g, 2.27 mmol), dichloromethane (12.5 mL) and triethylamine (0.63 mL, 4.53 mmol) in a reaction flask was stirred in an ice-water bath for 5 min, then was added difluoroacetic anhydride (0.43 g, 2.49 mmol) dropwise in 10 min. After the dropwise addition, the reaction mixture was stirred in an ice-water bath for 1 h, then was added concentrated ammonia (0.4 mL) and stirred in an ice-water bath for 5 min. The mixture was dried over anhydrous sodium sulfate, filtered, and the filtrate was evaporated to dryness after adding a small amount of dry ice, and the residue was diluted with ethyl acetate, and the organic phase was washed with sodium bisulfate and sodium sulfate saturated solution, dried over anhydrous sodium sulfate, filtered, and the filtrate was evaporated and the residue was purified by column chromatography (mobile phase: dichloromethane/MeOH 100/0 to 96/4) to give compound 122-f (770 mg, 56%). LC-MS (ESI): m/z 624.1 (M+NH$_4$)$^+$.

Synthesis of Compound 122-e

A mixture of 122-f (770 mg, 1.27 mmol), Lawesson's reagent (635 mg, 1.57 mmol) and anhydrous tetrahydrofuran (9 mL) in a reaction flask was stirred at 70° C. for 2 hours. The reaction mixture was added supplemental Lawesson's reagent (635 mg, 1.57 mmol) and stirred at 65° C. for 6 hours. Another supplemental Lawesson's reagent (635 mg, 1.57 mmol) was added, and the reaction mixture was stirred at 75° C. for 4 hours. The solvent was removed by concentration at reduced pressure, and the residue was added a small amount of methanol and concentrated ammonia, and the solvent was removed by concentration at reduced pressure. The residue was purified by column chromatography (mobile phase: petroleum ether/ethyl acetate, 100/0 to 50/50) to give compound 122-e (220 mg, 29%). LC-MS (ESI): m/z 605.0 (M+H)$^+$.

Synthesis of Compound 122-d

Compound 122-e (195 mg, 0.32 mmoL), potassium carbonate (111 mg, 0.80 mmoL), DMF (8 mL) were added to a reaction vial at room temperature, followed by the dropwise addition of 4-methoxybenzyl chloride (66 uL, 0.48 mmoL). After the dropwise addition, the reaction mixture was stirred at room temperature overnight, was added water (10 mL), extracted with ethyl acetate (50 mL). The organic phase was washed with brine (50 mL*3), dried over anhydrous sodium sulfate, filtered, and the filtrate was concentrated at reduced pressure, and the crude product was purified by a flash column chromatography (PE/EA=1:1) to give compound 122-d (180 mg, 77%). LC-MS (ESI): m/z 725.0 (M+H)$^+$.

Synthesis of Compound 122-c 65-b (70 mg, 0.38 mmol) was added to a microwave tube and dried by an oil pump for 5 min, then was added 122-d (170 mg, 0.23 mmol), RuPhos (8 mg, 0.017 mmol), Pd-PEPPSI-IHEPT-Cl (32 mg, 0.037 mmol) (cas: 1435347-24-2) and cesium carbonate (150 mg, 0.46 mmol). The microwave tube was sealed and was added anhydrous 1,4-dioxane (3.2 mL). After degassed and purged with nitrogen for 3 times, the reaction mixture was stirred at 90° C. for 3 hours. The reaction mixture was cooled to room temperature, diluted with ethyl acetate. The organic phase was washed with water, brine, dried over anhydrous sodium sulfate, filtered. The filtrate was evaporated and the residue was purified by column chromatography (mobile phase: (petroleum ether/dichloromethane 5:1)/ethyl acetate, 100/0 to 60/40) to give compound 122-c (190 mg, 100%). LC-MS (ESI): m/z 827.3 (M+H)$^+$.

Synthesis of Compound 122-b

TFA (2.5 mL) was added dropwise to a solution of 122-c (190 mg, 0.23 mmol) in dichloromethane (5 mL) in a reaction flask in an ice-water bath. The reaction mixture was stirred at room temperature for 3 hours. The solvent was removed by concentration at reduced pressure at room temperature, and the residue was added ethyl acetate, saturated aqueous sodium bicarbonate and anhydrous potassium carbonate (200 mg) and stirred at room temperature for 30 min. The aqueous phase was extracted once with ethyl acetate. The organic phases were combined, washed with brine, dried over anhydrous sodium sulfate, filtered and the filtrate was evaporated to give 122-b (160 mg, 100%). LC-MS (ESI): m/z 697.2 (M+H)$^+$.

Synthesis of Compound 122-a

A reaction flask charged with 122-b (50 mg, 0.072 mmol), potassium carbonate (80 mg, 0.58 mmol) and DMF (2.5 mL) was added bromacetonitrile (40 mg, 0.33 mmol) dropwise at room temperature and stirred for 5 hours. The reaction mixture was added ice water, extracted twice with ethyl acetate. The organic phase was washed with water, brine, dried over anhydrous sodium sulfate, filtered. The filtrate was evaporated and the residue was purified by column chromatography (mobile phase: petroleum ether/(6% ethanol/ethyl acetate), 100/0 to 50/50) to give compound 122-a (23 mg, 44%). LC-MS (ESI): m/z 736.7 (M+H)$^+$.

Synthesis of Compound 122

122-a (23 mg, 0.031 mmol) and dichloromethane (2.0 mL) were added to a reaction flask, and the reaction mixture was added methanesulfonic acid (4 drops) in an ice-water bath. The reaction mixture was stirred at room temperature for 2 h, then diluted with ethyl acetate. The organic phase was washed with saturated aqueous sodium bicarbonate, dried over anhydrous sodium sulfate, filtered. The filtrate was evaporated and the residue was purified by column chromatography (mobile phase: petroleum ether/(6% ethanol/ethyl acetate), 100/0 to 20/80) to give compound 122 (10.4 mg, 54%). LC-MS(ESI): m/z 616.4 (M+H)$^+$; $^1$H NMR (DMSO-d$_6$, 400 MHz): δ 9.33 (1H, s), 8.79 (1H, d, J=1.2 Hz), 7.97 (1H, d, J=1.2 Hz), 7.73 (1H, t, J=53.2 Hz), 6.25 (2H, d, J=4.8 Hz), 4.70 (1H, d, J=6.8 Hz), 4.59 (1H, d, J=4.8 Hz), 3.24-2.98 (4H, m), 2.96-2.83 (1H, m), 2.26-1.86 (4H, m), 1.48-1.41 (2H, m), 1.37-1.30 (2H, m), 1.13 (3H, d, J=6.8 Hz), 1.05 (3H, d, J=6.8 Hz).

Synthetic Route of Compound 123

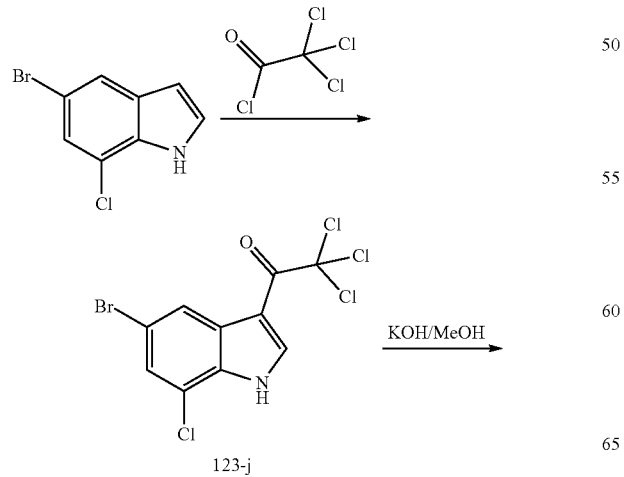

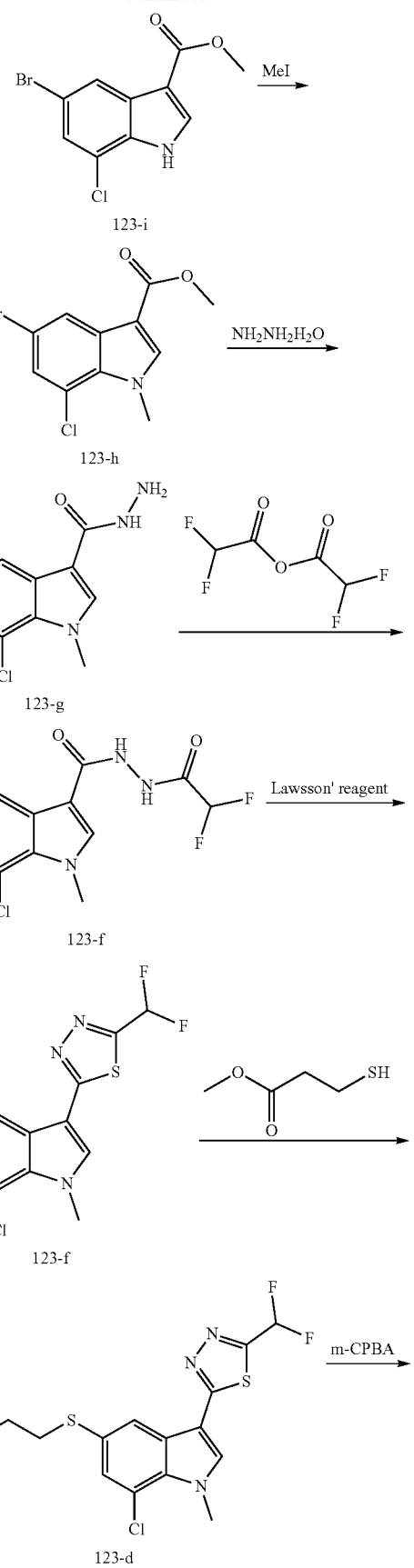

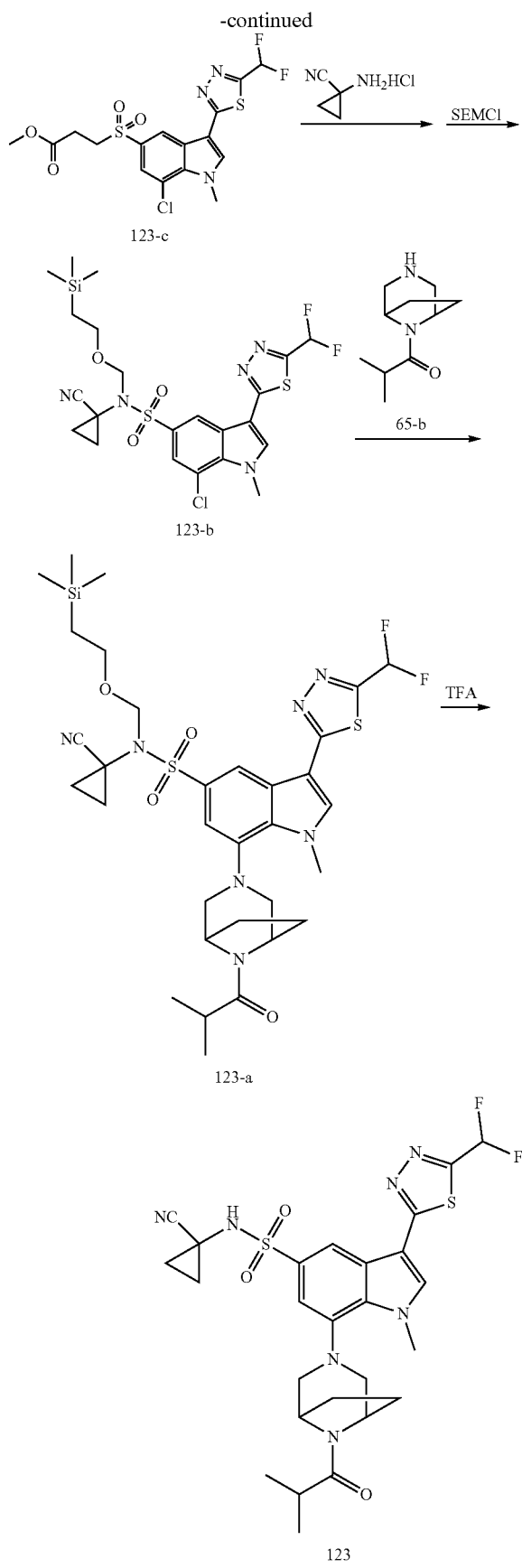

Synthesis of Compound 123-j

5-Bromo-7-chloro-1H-indole (3.0 g, 13.02 mmoL) in dichloromethane (20 mL) at room temperature was added trichloroacetyl chloride (5.84 mL, 52.06 mmoL) and pyridine (4.21 mL, 52.06 mmoL) dropwise at room temperature under nitrogen atmosphere sequentially, and the mixture was stirred at 48° C. for 18 h under nitrogen atmosphere. The reaction mixture was cooled to room temperature, then poured into a mixture of ice-water (50 mL) and extracted with dichloromethane (50 mL*2). The organic phase was dried over anhydrous sodium sulfate, filtered, and the filtrate was concentrated at reduced pressure, and the residue was dried in vacuum for 2 h to give about 10 g (theoretically 4.89 g) of crude product (123-j, 100%), which was used directly in the next step.

Synthesis of Compound 123-i 123-j (4.89 g, 13.01 mmoL) was suspended in methanol (50 mL) at room temperature, then was added KOH (1.88 g, 33.50 mmoL) in batches, and the reaction mixture was stirred at room temperature overnight under nitrogen atmosphere. After concentrated to about 20 mL at reduced pressure, the reaction mixture was added water (50 mL) and the pH was adjusted to 6 with 1 M hydrochloric acid, extracted with ethyl acetate (50 mL*2), the organic phase was washed with brine (100 mL), dried over anhydrous sodium sulfate, filtered. The filtrate was concentrated at reduced pressure, and the residue was slurried with 20 mL of DCM, filtered. The filter cake was washed with DCM (5 mL), and the solid was collected, dried in vacuum for 2 h to give 2.8 g. The filtrate was concentrated at reduced pressure and the residue was purified by a flash column chromatography (PE/EA=1:1) to give 380 mg of product. The two products were combined to give a total of compound 123-i (3.18 g, 85%). LC-MS (ESI): m/z=286.1 [M–H]$^-$.

Synthesis of Compound 123-h

NaH (655 mg, 16.38 mmoL, 60%) was added in batches to a solution of 123-i (3.15 g, 10.92 mmoL) in DMF (20 mL) in an ice-water bath under nitrogen. The mixture was stirred for 30 min at room temperature under nitrogen and was added iodomethane (1.02 mL, 16.38 mmoL) dropwise. After the dropwise addition, the reaction mixture was stirred at room temperature for 2 hours under nitrogen atmosphere. The reaction was quenched with saturated ammonium chloride solution (100 mL) in an ice-water bath, extracted with ethyl acetate (100 mL*2), and the organic phase was washed with brine (100 mL*5), dried over anhydrous sodium sulfate, filtered, concentrated at reduced pressure, and the residue was suspended in methanol (10 mL) and stirred for 30 min. The mixture was filtered and the filter cake was washed with methanol (10 mL), the solid was collected and dried in vacuum for 2 h to give compound 123-h (2.8 g, 85%). $^1$H NMR (DMSO-$d_6$, 400 MHz): δ 3.81 (3H, s), 4.11 (3H, s), 7.45 (1H, d, J=1.2 Hz), 8.07 (1H, d, J=1.2 Hz), 8.20 (1H, s).

Synthesis of Compound 123-g 123-h (700 mg, 2.31 mmoL) was suspended in 20 mL of ethanol at room temperature, then was added hydrazine hydrate (4 mL, 67.92 mmoL, 85%) and the reaction mixture was stirred at 85° C. under nitrogen atmosphere for 72 hours. The reaction mixture was cooled in an ice-water bath, filtered and the filter cake was washed with ethanol (10 mL) and the solid was collected and dried in vacuum for 2 h to give compound 123-g (305 mg, 44%). LC-MS (ESI): m/z=302.0[MS+H]$^+$.

Synthesis of Compound 123-f 123-g (290 mg, 0.96 mmoL) was dissolved in 20 mL of DCM at room temperature, and was added TEA (400 uL, 2.88 mmoL), followed by the dropwise addition of difluoroacetic anhydride (131 uL, 1.05 mmoL) in an ice-water bath, and the reaction mixture was stirred for 6 h in an ice-water bath. The reaction mixture was filtered and the filter cake was washed with DCM (5 mL), the solid was collected and dried in vacuum for 2 h to give compound 123-f (238 mg, 65%). LC-MS (ESI): m/z=379.9 [MS+H]$^+$.

Synthesis of Compound 123-e 123-f (238 mg, 0.62 mmoL) was dissolved in 10 mL of 1,4-dioxane at room temperature, then was added Lawesson's reagent (379 mg, 0.94 mmoL) and the reaction mixture was stirred at 80° C. for 3 h under nitrogen. The reaction mixture was concentrated at reduced pressure and the residue was dissolved in 100 mL of dichloromethane, washed sequentially with saturated sodium bicarbonate (100 mL), water (100 mL), and the organic phase was dried over anhydrous sodium sulfate, filtered. The filtrate was concentrated at reduced pressure, and the residue was purified by a flash column chromatography (PE/EA=1:1) to give compound 123-e (172 mg, 73%). LC-MS (ESI): m/z=378.0 [MS+H]$^+$.

Synthesis of Compound 123-d 123-e (172 mg, 0.45 mmoL) was dissolved in 10 mL of 1,4-dioxane at room temperature, and the mixture was added tris(dibenzylideneacetone)dipalladium (42 mg, 0.045 mmoL), 4,5-bis(diphenylphosphino)-9,9-dimethyloxanthene (52 mg, 0.091 mmoL), DIPEA (225 uL, 1.36 mmoL) and methyl 3-mercaptopropionate (56 uL, 0.50 mmoL), and the resulting mixture was stirred at 80° C. for 3 h under nitrogen atmosphere. The reaction mixture was cooled to room temperature, concentrated at reduced pressure and the residue was purified by a flash column chromatography (PE/EA=1:1) to give compound 123-d (170 mg, 90%). LC-MS (ESI): m/z=418.5[MS+H]$^+$.

Synthesis of Compound 123-c

A solution of 123-d (170 mg, 0.41 mmoL) in 10 mL of DCM was added m-CPBA (248 mg, 1.22 mmoL) under nitrogen atmosphere in an ice-water bath. After addition, the mixture was stirred under nitrogen atmosphere in an ice-water bath for 2 h. The reaction mixture was added saturated sodium bicarbonate (50 mL), extracted with DCM (100 mL). The organic phase was washed with saturated sodium bicarbonate (100 mL), dried over anhydrous sodium sulfate, filtered. The filtrate was concentrated at reduced pressure and the residue was purified by a flash column chromatography (DCM/MeOH=20:1) to give compound 123-c (205 mg, crude). LC-MS (ESI): m/z=450.1 [MS+H]$^+$.

Synthesis of Compound 123-b

Sodium methoxide (72 mg, 1.34 mmoL) was added to a solution of 123-c (200 mg, 0.44 mmoL) in a mixture of 5 mL of methanol and 10 mL of DCM in an ice-water bath, and the reaction mixture was stirred under nitrogen atmosphere at room temperature for 60 min, then was added 1-aminocyclopropyl cyanide hydrochloride (211 mg, 1.78 mmoL) in an ice-water bath, and the resulting mixture was stirred in an ice-water bath for 15 min. The mixture was concentrated at reduced pressure and dried in vacuum for 2 h. The residue was dissolved in dried DMF (8 mL) and then was added 1-aminocyclopropyl cyanide hydrochloride (53 mg, 0.44 mmoL), triethylamine (124 uL, 0.89 mmoL), and NCS (178 mg, 1.34 mmoL) sequentially in an ice-water bath, and the reaction mixture was stirred at room temperature for 1 h. The reaction was quenched by adding water (50 mL), extracted with ethyl acetate (50 mL*2). The organic phase was washed with water (100 mL) and brine (100 mL) in turn, dried over anhydrous sodium sulfate, filtered, and the filtrate was concentrated at reduced pressure, and the residue was dissolved in DCM (10 mL), was added triethylamine (247 uL, 1.78 mmoL), and 2-(trimethylsilyl)ethoxymethyl chloride (237 uL, 1.34 mmoL) in an ice-water bath, and the resulting mixture was stirred at room temperature for 2 hours. The reaction mixture was added saturated aqueous NaHCO$_3$, and the aqueous phase was extracted with DCM (50 mL*2). The organic phase was dried over anhydrous sodium sulfate, filtered and the filtrate was concentrated at reduced pressure, and the residue was purified by a flash column chromatography (PE/EA=1:1) to give compound 123-b (110 mg, 43%). LC-MS (ESI): m/z=574.1[MS+H]$^+$.

Synthesis of Compound 123-a

A sealed tube charged with 123-b (100 mg, 0.17 mmoL) and 2 mL of 1,4-dioxane was added 65-b (79 mg, 0.43 mmoL), (SP-4-1)-[1,3-bis[2,6-bis(1-ethylpropyl)phenyl]-4,5-dichloro-1,3-dihydro-2H-imidazol-2-ylidene]dichloro(2-methylpyridine) palladium (29 mg, 0.035 mmoL), RuPhos (16 mg, 0.035 mmoL) and cesium carbonate (182 mg, 0.56 mmoL) and the reaction mixture was stirred at 80° C. under nitrogen overnight. The reaction mixture was cooled to room temperature, was added 20 mL of water, extracted with DCM (50 mL*2). The organic phase was dried over anhydrous sodium sulfate, filtered, and the filtrate was concentrated at reduced pressure, and the residue was purified by a flash column chromatography (PE/EA=1:1-1:3) to give compound 123-a (65 mg, 52%). LC-MS (ESI): m/z=720.7 [MS+H]$^+$.

Synthesis of Compound 123

Trifluoroacetic acid (2 mL) and water (0.1 mL) were added to a solution of compound 123-a (65 mg, 0.090 mmoL) in 6 mL of dichloromethane in an ice-water bath under nitrogen atmosphere, then the reaction mixture was stirred at room temperature under nitrogen atmosphere for 2 h. The reaction mixture was concentrated at reduced pressure at room temperature, and the residue was suspended in 1 mL of saturated sodium bicarbonate, was added about 500 mg of potassium carbonate and 50 mL of ethyl acetate. The mixture was stirred at room temperature for 1 h. The mixture was extracted with ethyl acetate (50 mL*2), and the organic phase was dried over anhydrous sodium sulfate, filtered. The filtrate was concentrated at reduced pressure, and the residue was purified by prep-HPLC (basic method) to give compound 123 (24.1 mg, 45%). LC-MS (ESI): m/z=590.3[M+H]$^+$; $^1$H NMR (400 MHz, DMSO-d$_6$): δ 8.82 (1H, brs), 8.68 (1H, s), 8.55 (1H, s), 7.63 (1H, t, J=53.6 Hz), 7.66 (1H, s), 4.65 (1H, d, J=6.4 Hz), 4.51 (1H, d, J=4.8 Hz), 3.13 (1H, d, J=10.0 Hz), 3.04 (2H, s), 2.99 (1H, d, J=10.8 Hz), 2.89-2.82 (1H, m), 2.22-1.92 (3H, m), 1.89-1.73 (1H, m), 1.40-1.32 (2H, m), 1.28-1.20 (2H, m), 1.12 (3H, d, J=6.4 Hz), 1.03 (3H, d, J=6.8 Hz).

Example 118 Synthetic Route of Compound 124

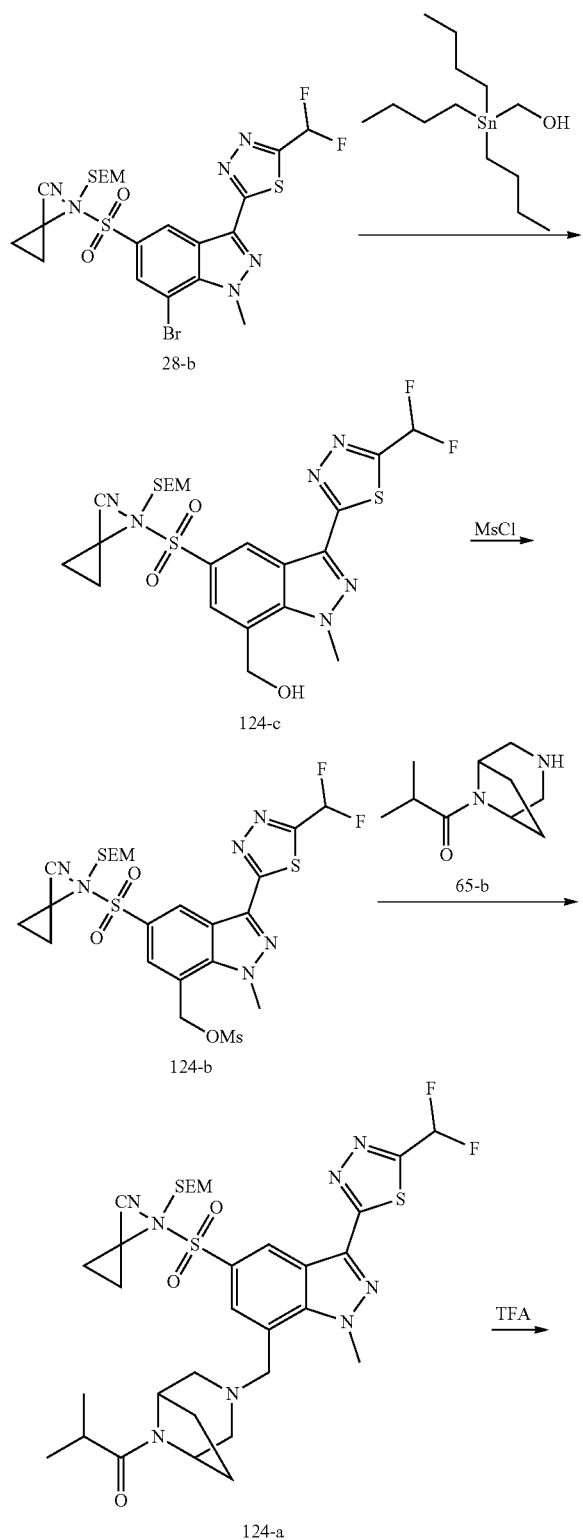

-continued

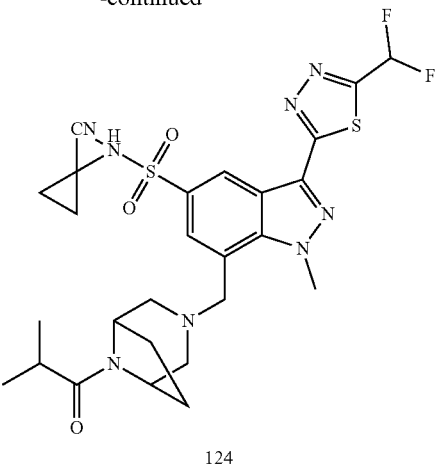

Synthesis of Compound 124-c

A reaction vial charged with tributyltin methanol (249 mg, 0.78 mmol), 28-b (160 mg, 0.26 mmol), 1,4-dioxane (5 mL) and tetrakis(triphenylphosphine)palladium (90 mg, 0.08 mmol) was stirred at 110° C. under nitrogen for 18 h. The reaction mixture was concentrated and purified by column chromatography (mobile phase: ethyl acetate/petroleum ether 1/3 to 1/1) and concentrated to give compound 124-c (53 mg, 36%). LC-MS (ESI): m/z 571.5 (M+H)$^+$.

Synthesis of Compound 124-b

A reaction vial charged with 124-c (50 mg, 0.09 mmol), dichloromethane (5 mL) and triethylamine (300 mg, 2.97 mmol) was stirred in an ice-water bath for 10 min, then was added methanesulfonyl chloride (30 mg, 0.26 mmol), and the mixture was stirred in an ice-water bath for 2 hours. Water (10 mL) was added to quench the reaction, and the aqueous phase was extracted with dichloromethane (10 mL*3). The organic phase was dried over sodium sulfate and concentrated to give compound 124-b (63 mg), which was used directly in the next step. LC-MS (ESI): m/z 649.1 (M+H)$^+$.

Synthesis of Compound 124-a

A reaction vial charged with 65-b (48 mg, 0.26 mmol), 124-b (56 mg, 0.09 mmol), DMF (3 mL), potassium iodide (2 mg, 0.014 mmol) and triethylamine (9 mg, 0.09 mmol) was stirred at room temperature for 3 h under nitrogen atmosphere. The reaction was quenched by adding saturated sodium bicarbonate (10 mL), extracted with ethyl acetate (20 mL*2) and concentrated to give 124-a (53 mg, 84%), which was used directly into the next reaction. LC-MS (ESI): m/z 736.2 (M+H)$^+$.

Synthesis of Compound 124

A reaction vial charged with 124-a (53 mg, 0.07 mmol), dichloromethane (3 mL) and trifluoroacetic acid (1 mL) was stirred at room temperature for 2 h under nitrogen atmosphere. The reaction mixture was concentrated, added solid potassium carbonate (3 g), water (10 mL) to quench the reaction, and ethyl acetate (10 mL), and the mixture was stirred at room temperature for 2 hours. Extracted with Ethyl acetate (20 mL*3), concentrated and purified by prep-HPLC to give compound 124 (14.3 mg, 33%). LC-MS (ESI): m/z 605.7 (M+H)+.

Example 119 Synthetic Route of Compound 125

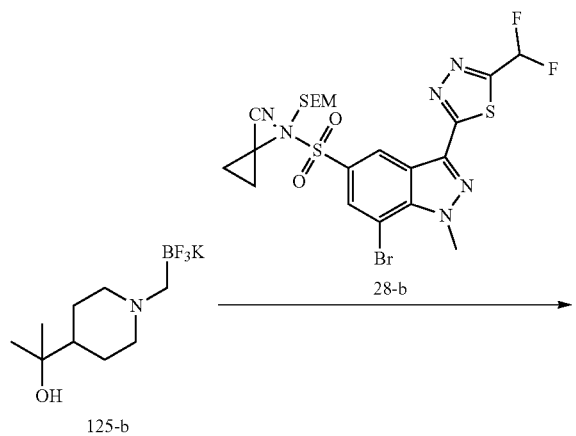

28-b 125-b

TFA →

125-a

125

Synthesis of Compound 125-b

Compound 125-b was prepared according to methods in CN104557872A.

Synthesis of Compound 125-a

A microwave tube charged with 28-b (30 mg, 0.05 mmol), 125-b (101 mg, 0.38 mmol), tetrahydrofuran (3 mL), water (0.3 mL), Xphos (23 mg, 0.05 mmol), palladium acetate (11 mg, 0.05 mmol) and cesium carbonate (200 mg, 0.61 mmol) was degassed and purged with nitrogen three times, added 1,4-dioxane (3 mL) and the reaction mixture was stirred at 79° C. for 12 hours under nitrogen atmosphere. The reaction mixture was concentrated at reduced pressure, washed with ethyl acetate (10 mL*3), concentrated at reduced pressure and was used directly in the next step 125-a (20 mg, 59%). LC-MS (ESI): m/z 697.2 (M+H)+.

Synthesis of Compound 125

A reaction vial charged with 125-a (20 mg, 0.03 mmol), dichloromethane (3 mL), H$_2$O (1 mL) and trifluoroacetic acid (1 mL) was stirred at room temperature for 2 h under nitrogen atmosphere. The reaction mixture was concentrated at reduced pressure and quenched with saturated sodium bicarbonate (10 mL), and the aqueous phase was extracted with dichloromethane (10 mL*3). The organic phase was concentrated at reduced pressure and the residue was purified by prep-HPLC to give compound 125 (6 mg, 37%). LC-MS (ESI): m/z 566.7 (M+H)+.

Synthetic Route of Compound 126

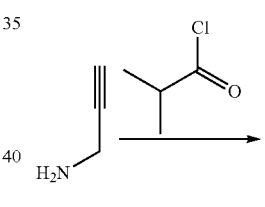

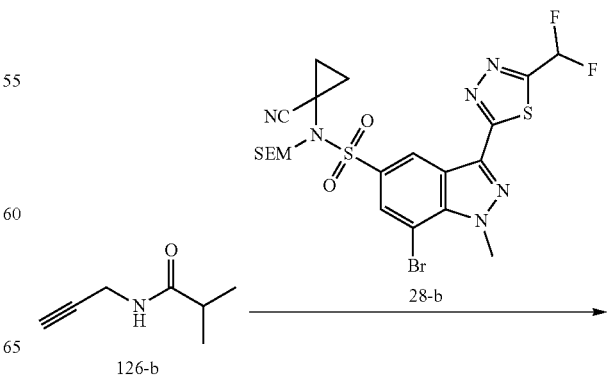

126-b

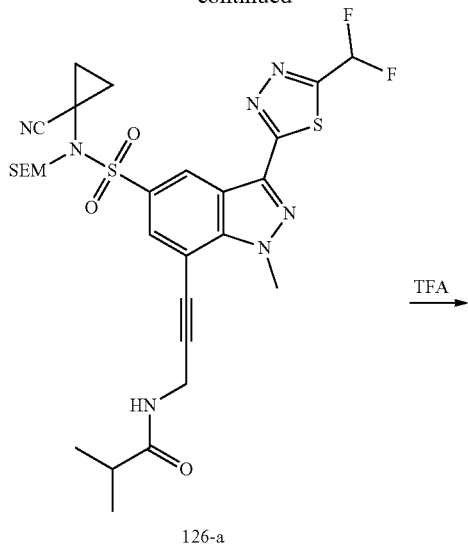

126-a

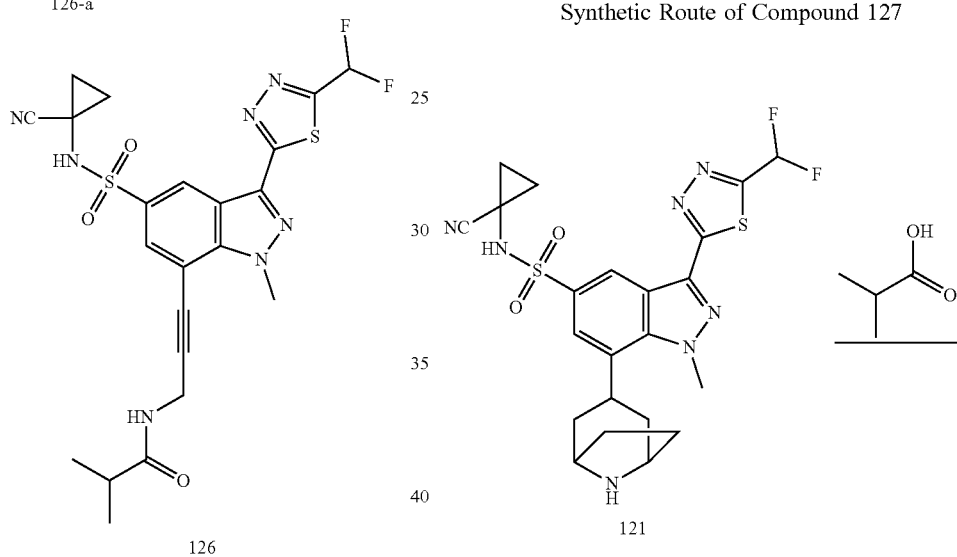

cuprous iodide (30 mg, 0.10 mmol) was stirred at 90° C. for 4 h under nitrogen atmosphere. The reaction mixture was concentrated at reduced pressure and purified by column chromatography (mobile phase: petroleum ether/ethyl acetate 1/3 to 2/3) and concentrated at reduced pressure to give compound 126-a (49 mg, 74%). LC-MS (ESI): m/z 664.5 (M+H)+.

Synthesis of Compound 126

A reaction vial charged with 126-a (49 mg, 0.074 mmol), dichloromethane (3 mL) and trifluoroacetic acid (1 mL) was stirred at room temperature for 2 h under nitrogen atmosphere. The reaction mixture was concentrated at reduced pressure and the residue was quenched by adding potassium carbonate (3 g) and water (10 mL), then was added ethyl acetate (10 mL) and the mixture was stirred at room temperature for 2 hours. The mixture was extracted with ethyl acetate (20 mL*2) and the organic phase was concentrated at reduced pressure to give compound 126 (23 mg, 58%). LC-MS (ESI): m/z 534.6 (M+H)+.

Synthetic Route of Compound 127

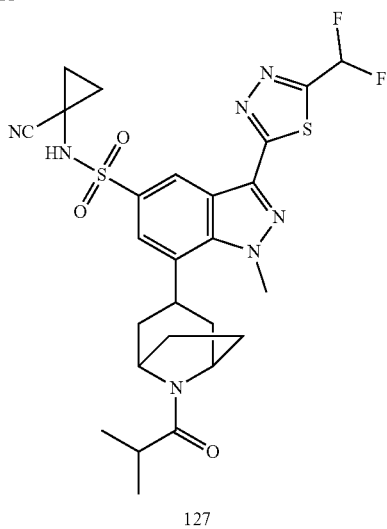

Synthesis of Compound 126-b

Isobutyryl chloride (0.98 mL, 9.37 mmol) was added dropwise to a mixture of propargylamine (0.5 mL, 7.81 mmol), dichloromethane (10 mL) and triethylamine (3.26 mL, 23.42 mmol) in a reaction flask in an ice-water bath. After addition, the resulting mixture was stirred at room temperature overnight. The next day, the reaction was quenched with water, extracted with dichloromethane, washed with brine, dried over anhydrous sodium sulfate, concentrated to dryness and purified by column chromatography (mobile phase: methanol/dichloromethane: 0% to 10%) to give compound 126-b (0.6 g, 61%). 1H NMR (DMSO-d6, 400 MHz): δ 8.18 (1H, s), 3.81-3.84 (2H, m), 3.07 (1H, t, J=2.4 Hz), 2.36 (1H, hept, J=6.8 Hz), 0.99 (6H, d, J=6.8 Hz).

Synthesis of Compound 126-a

A reaction vial charged with 28-b (62 mg, 0.10 mmol), triethylamine (10 mL), 126-b (35 mg, 0.28 mmol), tetrakis (triphenylphosphine)palladium (30 mg, 0.026 mmol) and Synthesis of Compound 127

A reaction flask charged with 121 (25 mg, 0.048 mmol), isobutyric acid (0.009 mL, 0.096 mmol), dichloromethane (5 mL), DIPEA (0.042 mL, 0.24 mmol) and HOBT (13 mg, 0.096 mmol) was added EDCI (19 mg, 0.099 mmol) slowly in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by Prep-HPLC to give compound 127 (15 mg, 53%). LC-MS (ESI): m/z=590.3 [M+H]$^+$.

Synthetic Route of Compound 128

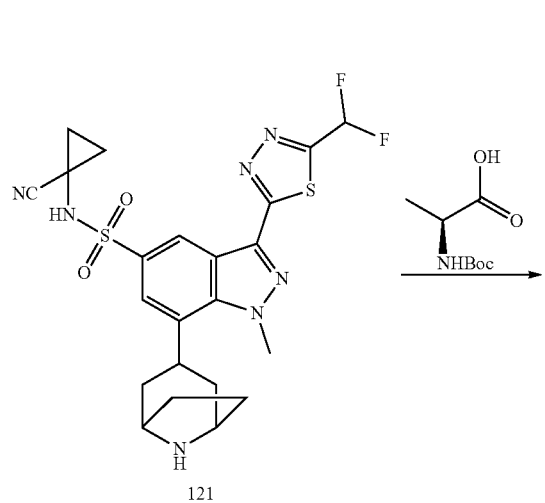

121

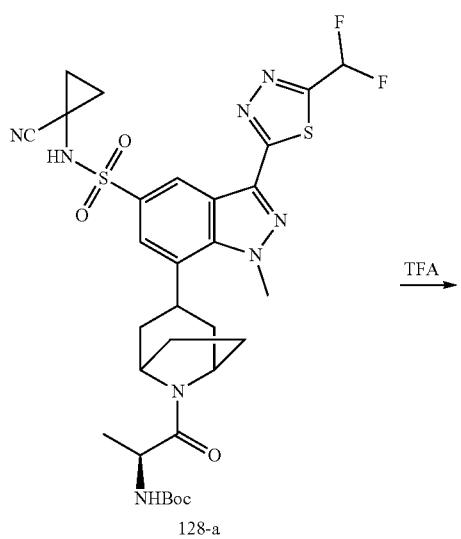

128-a

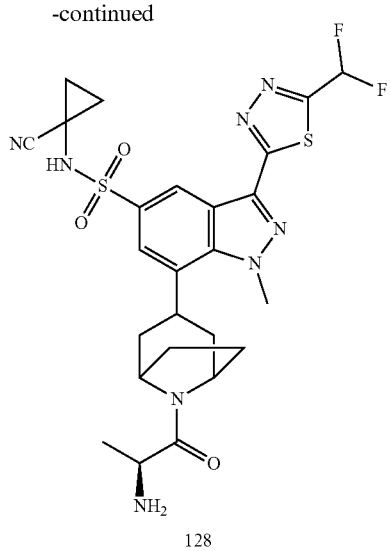

128

Synthesis of Compound 128-a

A reaction flask charged with 121 (40 mg, 0.077 mmol), N-Boc-L-alanine (29 mg, 0.15 mmol), dichloromethane (5 mL), DIPEA (0.067 mL, 0.39 mmol) and HOBT (21 mg, 0.16 mmol) was added EDCI (30 mg, 0.16 mmol) slowly in an ice-water bath. After addition, the reaction mixture was warmed to room temperature and stirred overnight. The next day, the reaction was quenched with water, extracted with dichloromethane. The organic phase was washed with brine, dried over anhydrous sodium sulfate, and concentrated at reduced pressure. The residue was purified by a flash column chromatography (mobile phase: methanol/dichloromethane, 0% to 10%) to give compound 128-a (35 mg, 66%). LC-MS (ESI): m/z=691.2 [M+H]$^+$.

Synthesis of Compound 128

Trifluoroacetic acid (1 mL) was added dropwise to a solution of 128-a (35 mg, 0.051 mmol) in dichloromethane (5 mL) in a reaction vial at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and the filtrate was evaporated to obtain the crude product. The crude product was purified by Prep-HPLC to give compound 128 (20 mg, 67%). LC-MS (ESI): m/z 591.2 [M+H]$^+$.

Synthetic Route of Compound 129

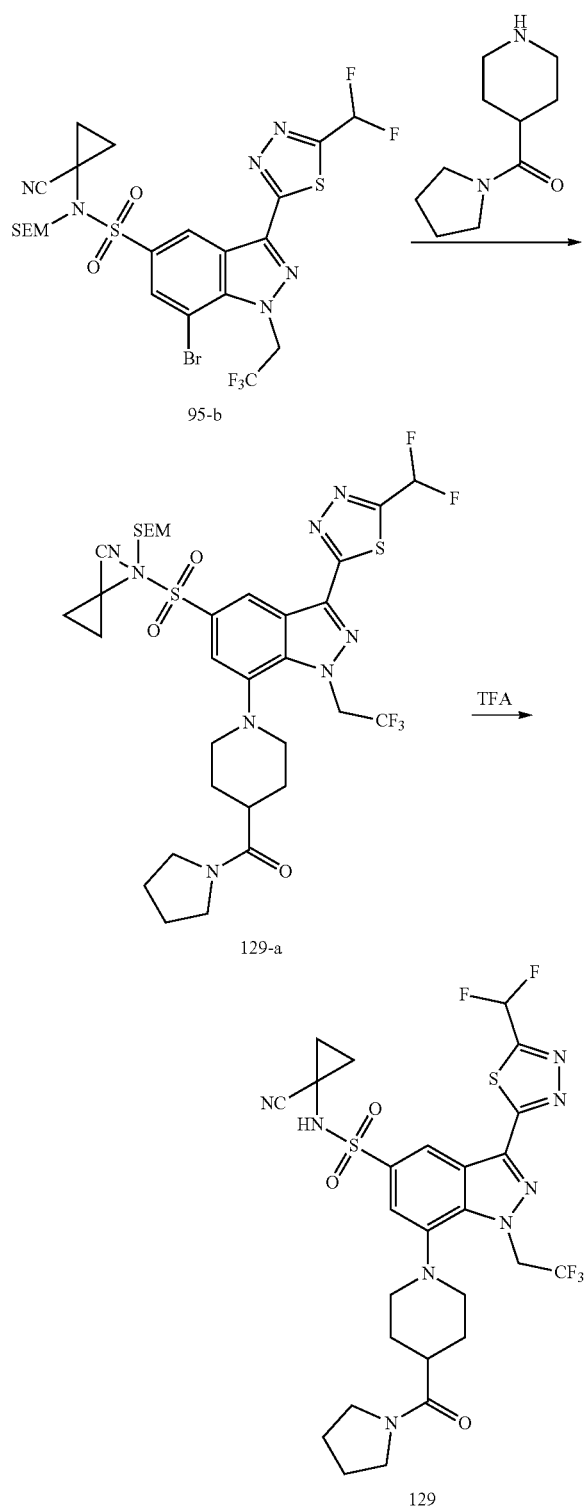

Synthesis of Compound 129-a

A microwave tube charged with 95-b (20 mg, 0.03 mmol), 4-piperidinyl (1-pyrrolidinyl) methanone (10.6 mg, 0.06 mmol), Ruphos (2 mg, 0.004 mmol), cesium carbonate (28 mg, 0.09 mmol) and (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (8 mg, 0.01 mmol) was degassed and purged with nitrogen for three times, then was added 1,4-dioxane (1 mL) and degassed and purged with nitrogen for three more times. The reaction mixture was stirred at 75° C. for 18 hours. The reaction mixture was concentrated at reduced pressure and the residue was washed with ethyl acetate (5 mL*3) and concentrated at reduced pressure to give compound 129-a (22 mg, 96%). LC-MS (ESI): m/z 789.7 (M+H)$^+$.

Synthesis of Compound 129

A reaction vial charged with 129-a (22 mg, 0.03 mmol), dichloromethane (3 mL) and trifluoroacetic acid (1 mL) was stirred at room temperature for 2 h under the protection of nitrogen. The reaction mixture was concentrated at reduced pressure, and the residue was added potassium carbonate (3 g), water (20 mL) and ethyl acetate (20 mL), and the mixture was stirred at room temperature for 2 hours. The mixture was extracted with ethyl acetate (20 mL*2), and the organic phase was concentrated at reduced pressure and purified by prep-HPLC to give compound 129 (6.1 mg, 33%). LC-MS (ESI): m/z 659.6 (M+H)$^+$.

Synthetic Route of Compound 130

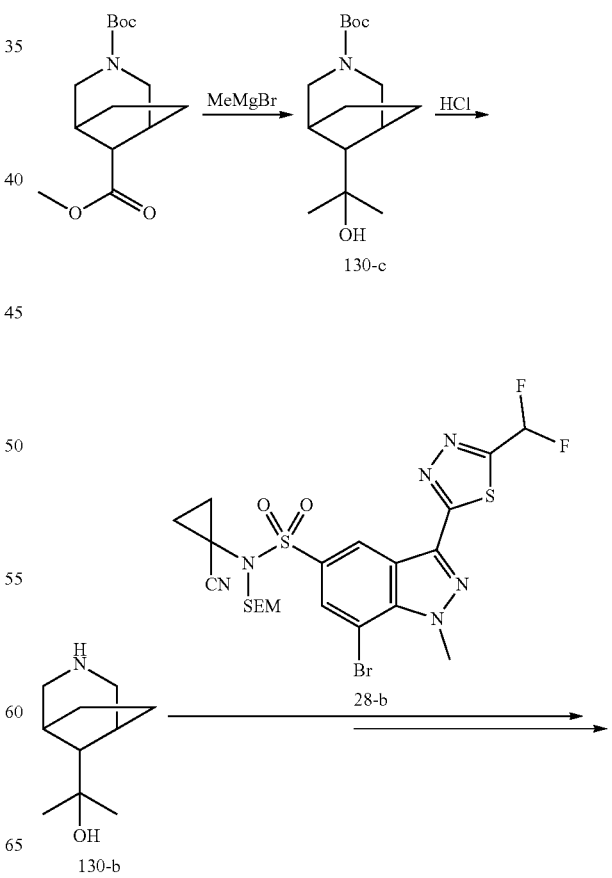

379
-continued

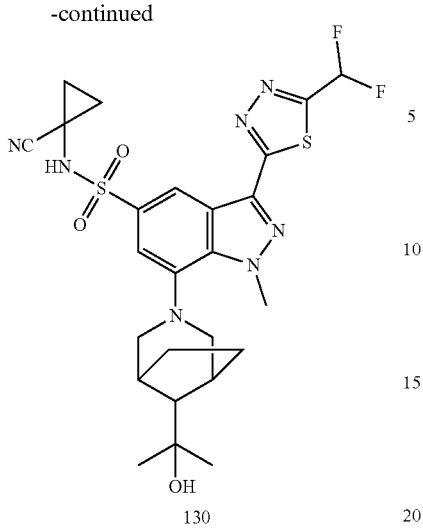

130

Synthesis of Compound 130-c

A solution of compound 3-Boc-3-azabicyclo[3.2.1]octane-8-carboxylic acid methyl ester (500 mg, 1.86 mmol) in dried tetrahydrofuran (10 mL) was degassed and purged with nitrogen for three times, then was added methylmagnesium bromide (708 mg, 5.94 mmol) dropwise in an ice-water bath. After addition, the reaction mixture was stirred in an ice-water bath for 1.5 hours, then was added saturated ammonium chloride solution (10 mL) and water (50 mL) dropwise, the aqueous phase was extracted with ethyl acetate (50 mL), the organic phase was washed with brine (50 mL), dried over sodium sulfate, filtered to remove the desiccant, concentrated at reduced pressure and purified by column chromatography (mobile phase, PE/EA 3/1) to give compound 130-c (100 mg, 20%). LC-MS (ESI): m/z 270.2 (M+H)$^+$.

Synthesis of Compound 130-b

Compound 130-c (200 mg, 0.74 mmol) was dissolved in 1,4-dioxane (2 mL), to which was added HCl/1,4-dioxane (4 M, 10 mL) and the mixture was stirred at room temperature for 2 h. The reaction mixture was concentrated at reduced pressure and the residue was added ethanol (2 mL), saturated sodium bicarbonate solution (1 mL) and sodium bicarbonate solid (200 mg) and the mixture was stirred for 15 min, then concentrated at reduced pressure. The residue was added ethanol (10 mL), concentrated at reduced pressure, added a solution of dichloromethane (20 mL) containing 10% methanol, stirred for 10 min, dried over sodium sulfate, filtered off the desiccant. The filtrate was concentrated at reduced pressure and dried in vacuum to afford compound 130-b (114 mg, 90%). LC-MS (ESI): m/z 170.2 (M+H)$^+$.

Synthesis of Compound 130

Referring to the synthesis of compound 68, compound 130 was synthesized by using 130-b instead of 68-b. LC-MS (ESI): m/z 578.3 (M+H)$^+$.

380
Synthetic Route of Compound 131

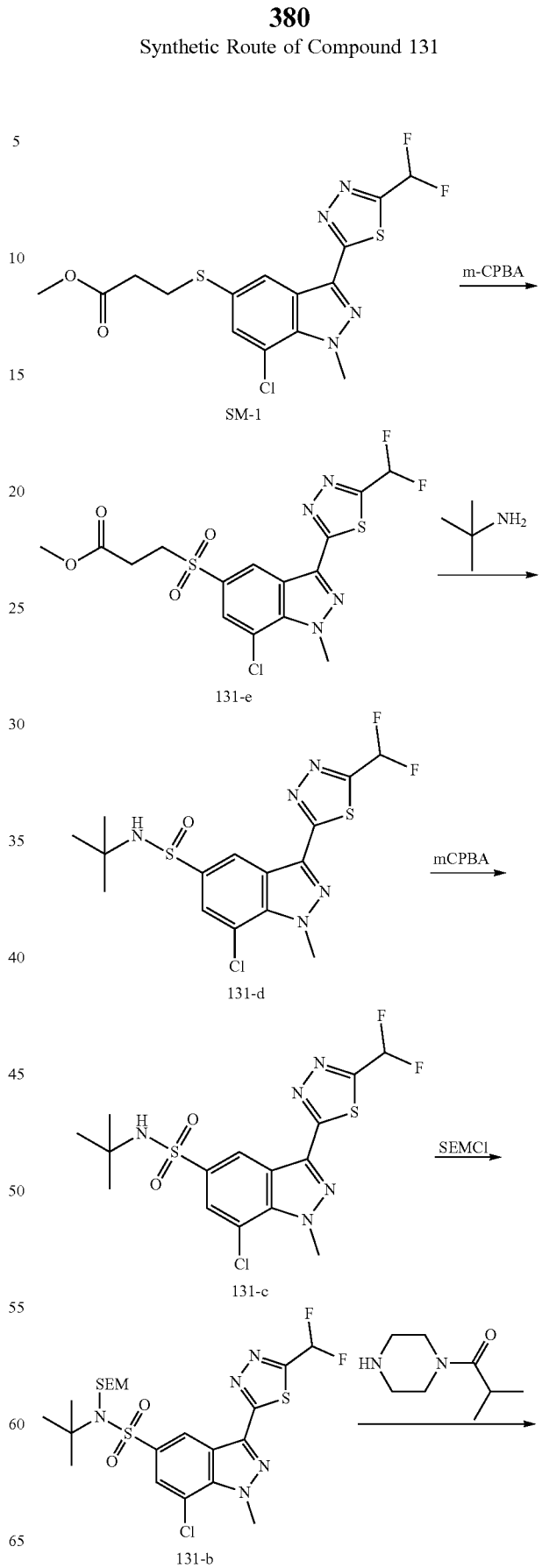

-continued

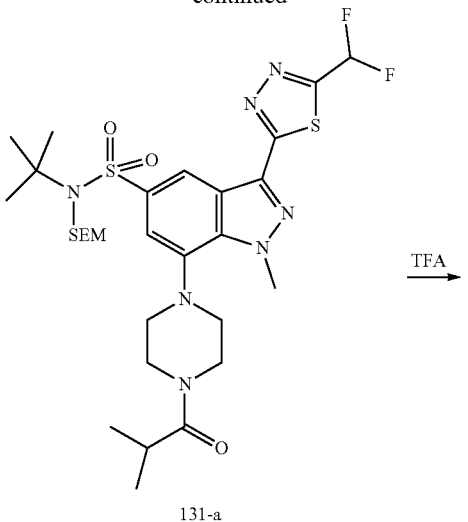

131-a

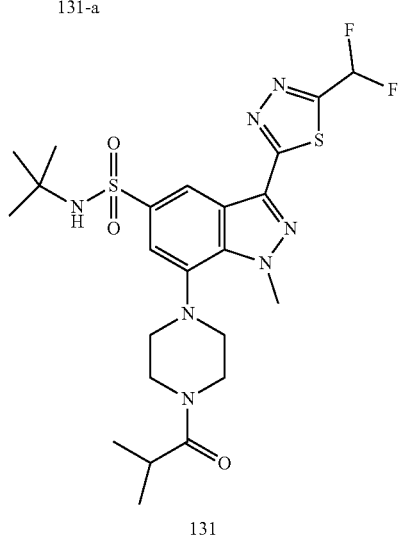

131

Synthesis of Compound 131-e

To a solution of 17-e (460 mg, 1.10 mmol) in dichloromethane (20 mL) was added m-CPBA (569 mg, 3.30 mmol) in an ice-water bath. After addition, the reaction was stirred in an ice-water bath for 1 h. After completion, the solvent was removed by concentration at reduced pressure at room temperature, and the residue was diluted with ethyl acetate. The organic phase was washed sequentially with saturated sodium bicarbonate, water, brine, dried over anhydrous sodium sulfate, filtered and concentrated at reduced pressure to obtain the crude product, which was purified by a flash column chromatography (mobile phase: ethyl acetate/ petroleum ether, 0% to 100%) to give compound 131-e (400 mg, 81%). LC-MS (ESI): m/z=451.4 [M+H]$^+$.

Synthesis of Compound 131-d

To a reaction vial was added 131-e (300 mg, 0.67 mmol), methanol (10 mL) and dichloromethane (10 mL). The reaction mixture was cooled in an ice-water bath and was added sodium methanol (108 mg, 2.00 mmol). After addition, the reaction mixture was kept in an ice-water bath for 1 hour. After stirring, the reaction mixture was concentrated at room temperature at reduced pressure to remove the solvent, and then dried under vacuum for 20 minutes. The residue was added DMF (5 mL) and a small amount of 3 A molecular sieve and cooled in an ice-water bath for 3 min, then was added DIPEA (0.70 mL, 3.99 mmol), HOBT (270 mg, 2.00 mmol) and tert-butylamine (0.21 mL, 2.00 mmol), and was slowly added EDCI (383 mg, 2.00 mmol) under an ice-water bath. The ice water bath was withdrawn and the reaction mixture was warmed to 90° C. and stirred for 3 hours. After completion, the reaction mixture was cooled to room temperature, diluted with ethyl acetate, the organic phase was washed with water, brine, dried over anhydrous sodium sulfate, filtered and concentrated at reduced pressure to obtain the crude product, which was purified by a flash column chromatography (mobile phase: ethyl acetate/petroleum ether, 0% to 100%) to give 131-d (200 mg, 72%). LC-MS (ESI): m/z=420.0 [M+H]$^+$.

Synthesis of Compound 131-c

To a solution of 131-d (200 mg, 0.48 mmol) in dichloromethane (10 mL) was added m-CPBA (123 mg, 0.71 mmol) in an ice-water bath. After addition, the reaction was warmed to room temperature and stirred for 1 hour. After completion, the solvent was removed by concentration at reduced pressure at room temperature, and the residue was diluted by adding ethyl acetate. The organic phase was washed sequentially with saturated sodium bicarbonate, water, brine, dried over anhydrous sodium sulfate, filtered and concentrated at reduced pressure to obtain the crude product, which was purified by a flash column chromatography (mobile phase: ethyl acetate/petroleum ether, 0% to 100%) to give compound 131-c (160 mg, 77%). LC-MS (ESI): m/z=436.1 [M+H]$^+$.

Synthesis of Compound 131-b

Sodium hydrogen (60% in oil, 29 mg, 0.73 mmol) was added to a solution of 131-c (160 mg, 0.37 mmol) in THF (10 mL) in a reaction vial in an ice-water bath. The reaction mixture was stirred under ice water bath for 10 min and was added SEMCl (0.13 mL, 0.73 mmol). After addition, continued stirring for 1 hour. After completion, the reaction was carefully quenched with dry ice powder, continued stirring for 30 min, diluted by adding ethyl acetate. The organic phase was washed sequentially with water, brine, dried over anhydrous sodium sulfate, filtered and concentrated at reduced pressure to obtain the crude product, which was purified by a flash column chromatography (mobile phase: ethyl acetate/petroleum ether 0% to 50%) to give compound 131-b (60 mg, 29%). LC-MS (ESI): m/z=392.0 [M+H-118-tBu]$^+$; $^1$H NMR (DMSO-d$_6$, 400 MHz): δ 8.87 (1H, s), 8.08 (1H, s), 7.71 (1H, t, J=53.2 Hz), 5.00 (2H, s), 4.50 (3H, s), 3.58 (2H, t, J=8.0 Hz), 1.33 (9H, s), 0.97 (2H, t, J=8.0 Hz), 0.01 (9H, s).

Synthesis of Compound 131-a

A microwave tube charged with 131-b (60 mg, 0.11 mmol), 2-methyl-1-(piperazin-1-yl)propan-1-one (33 mg, 0.21 mmol), Ruphos (5 mg, 0.011 mmol), (SP-4-1)-[1,3-bis [2,6-bis(1-ethylpropyl)phenyl]-4,5-dichloro-1,3-dihydro-2H-imidazol-2-ylidene]dichloro(3-chloropyridine-KN)palladium (CAS:1435347-24-2) (15 mg, 0.017 mmol), cesium carbonate (104 mg, 0.32 mmol) and 1,4-dioxane (8 mL) was degassed and purged with nitrogen for 3 times and the reaction mixture was heated at 80° C. overnight. After completion, the reaction mixture was cooled to room temperature and concentrated at reduced pressure to remove the 1,4-dioxane, and the residue was diluted with ethyl acetate. The organic phase was washed with water, brine, dried over anhydrous Na2SO4, filtered, and the filtrate was concentrated at reduced pressure to obtain the crude product, which was purified by column chromatography (mobile phase: EA/PE, 0% to 100%) to give 131-a (40 mg, 55%). LC-MS (ESI): m/z 703.3 [M+NH$_4$]$^+$.

Synthesis of Compound 131

A reaction vial charged with 131-a (40 mg, 0.058 mmol), dichloromethane (5 mL). was added trifluoroacetic acid (1 mL) dropwise at room temperature. After the dropwise addition, the reaction mixture was stirred at room temperature for 4 hours. The solvent was removed by concentration at reduced pressure at room temperature, and the residue was diluted by adding dichloromethane. The organic phase was washed with saturated sodium bicarbonate, brine, dried over anhydrous sodium sulfate, filtered and concentrated at reduced pressure to obtain the crude product. The compound 131 (18 mg, 56%) was obtained after purification by Prep-HPLC separation. LC-MS (ESI): m/z 556.2 [M+H]$^+$; $^1$H NMR (DMSO-d$_6$, 400 MHz): δ 8.57 (1H, s), 7.70 (1H, t, J=53.2 Hz), 7.63 (1H, s), 7.61 (1H, s), 4.50 (3H, s), 4.40-4.65 (1H, m), 3.97-4.25 (1H, m), 3.21-3.61 (3H, m), 2.57-3.12 (4H, m), 1.09 (9H, s), 1.06 (6H, d, J=6.8 Hz).

Synthesis Route of Compound 132

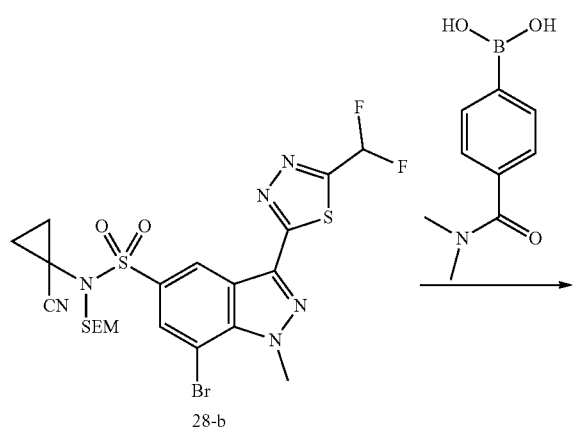

28-b

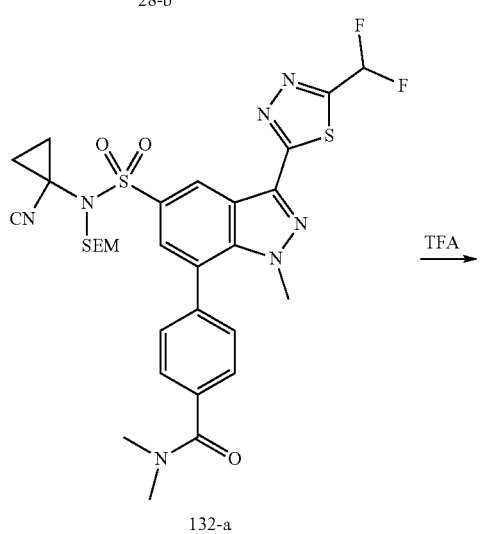

132-a

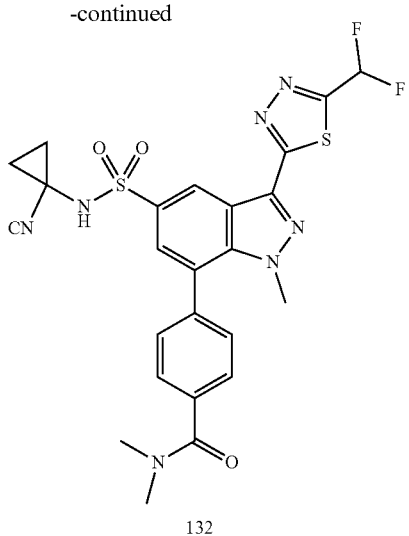

132

Synthesis of Compound 132-a

Compound 28-b (100 mg, 0.16 mmol), 4-(N,N-dimethylaminocarbonyl)phenylboronic acid (47 mg, 0.24 mmol), [1,1'-bis(diphenylphosphino)ferrocene]palladium dichloride (12 mg, 0.016 mmol) and potassium carbonate (45 mg, 0.33 mmol) were added to 1,4-dioxane (10 mL) and water (1 mL), degassed and purged with nitrogen for 3 times and then the mixture was heated and stirred at 100° C. for 6 h. The reaction mixture was filtered through celite, and the filtrate was added water (100 mL), extracted with ethyl acetate (100 mL), and the organic phase was washed with brine (50 mL), dried over sodium sulfate, filtered off the desiccant. The filtrate was concentrated under reduced pressure to obtain the crude product, which was purified by column chromatography (mobile phase, PE/EA 1/1) to give compound 132-a (60 mg, 54%). LC-MS (ESI): m/z 688.2 (M+H)$^+$.

Synthesis of Compound 132

A solution of compound 132-a (60 mg, 0.28 mmol) in dichloromethane (3 mL) was added trifluoroacetic acid (1 mL) under an ice-water bath, and the reaction mixture was stirred at room temperature for 2 h. The dichloromethane was removed by concentration at reduced pressure, and the residue was adjusted to pH 7-8 with saturated sodium bicarbonate solution and extracted with ethyl acetate (50 mL). The organic phase was washed with brine (50 mL), dried over sodium sulfate, filtered off the desiccant, and the filtrate was concentrated under reduced pressure to obtain the crude product, which was purified by preparative HPLC (basic conditions) to give compound 132 (35 mg, 72%). LC-MS (ESI): m/z 558.2 (M+H)$^+$; $^1$H NMR (400 MHz, DMSO-d$_6$): δ 9.09 (1H, s), 8.98 (1H, s), 7.90-7.55 (6H, m), 3.77 (3H, s), 3.02 (6H, d, J=16.0 Hz), 1.48-1.42 (2H, m), 1.36-1.30 (2H, m).

Synthesis of Compound 133

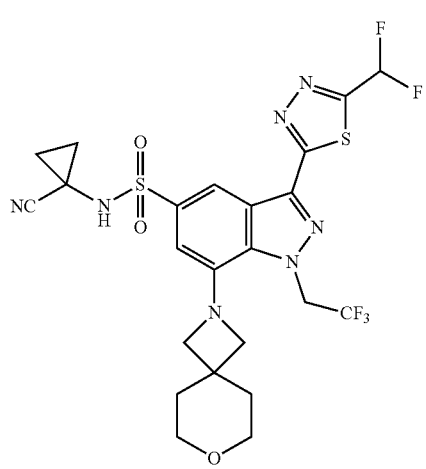

133

Referring to the synthesis of compound 95, compound 133 was synthesized by replacing 65-b with 7-oxa-2-azaspiro[3,5]nonane, and using 95-b as the starting reactant. LC-MS (ESI): m/z 604.2 [M+H]$^+$.

Synthesis of Compound 134

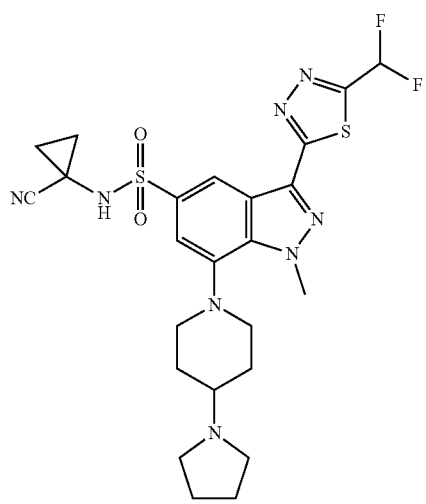

134

Referring to the synthesis of compound 68, compound 134 was synthesized using 4-pyrrolidin-1-yl-piperidine instead of 68-b. LC-MS (ESI): m/z 563.2 [M+H]$^+$.

Example 131 Synthesis of Compound 135

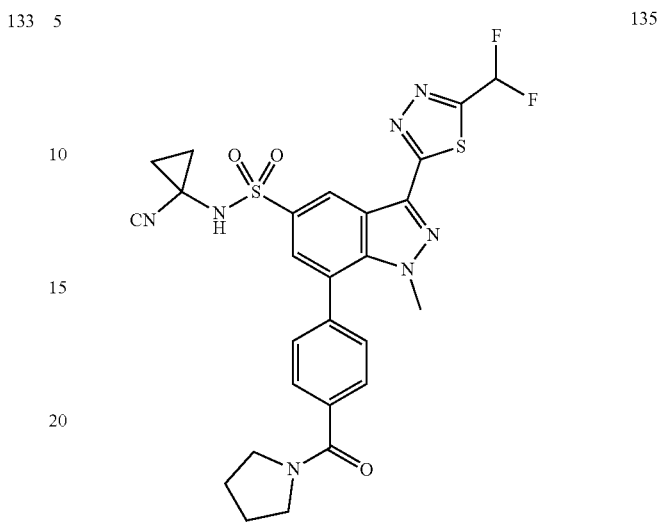

135

Referring to the synthesis of compound 132, compound 135 was synthesized using (4-(pyrrolidine-1-carbonyl)-phenyl)boronic acid instead of 4-(N,N-dimethylaminocarbonyl) phenylboronic acid with 28-b as starting material. LC-MS (ESI): m/z 584.3 (M+H)$^+$; $^1$H NMR (400 MHz, DMSO-d$_6$): δ 8.98 (1H, s), 8.88 (1H, s), 7.90-7.55 (6H, m), 3.76 (3H, s), 3.55-3.45 (4H, m), 2.00-1.80 (4H, m), 1.48-1.40 (2H, m), 1.36-1.30 (2H, m).

Example 132 Synthesis Route of Compound 136

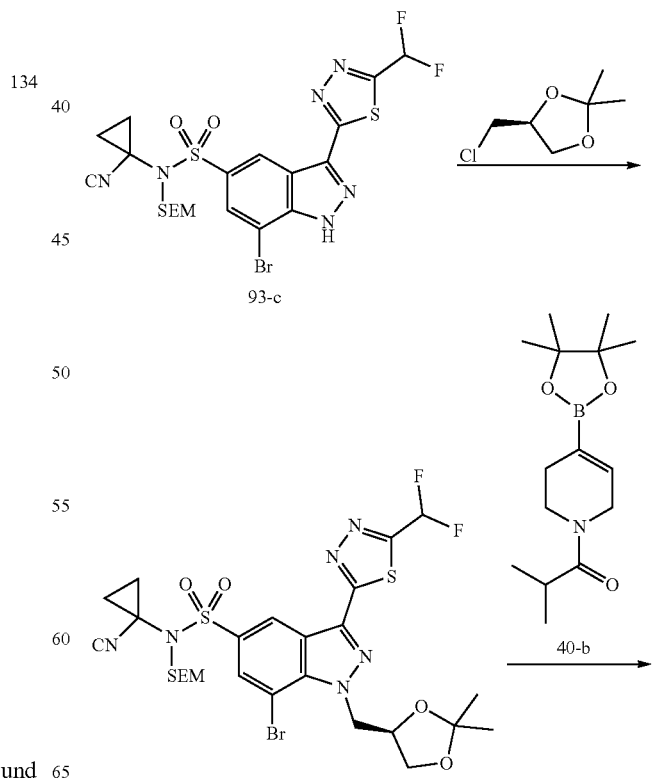

-continued

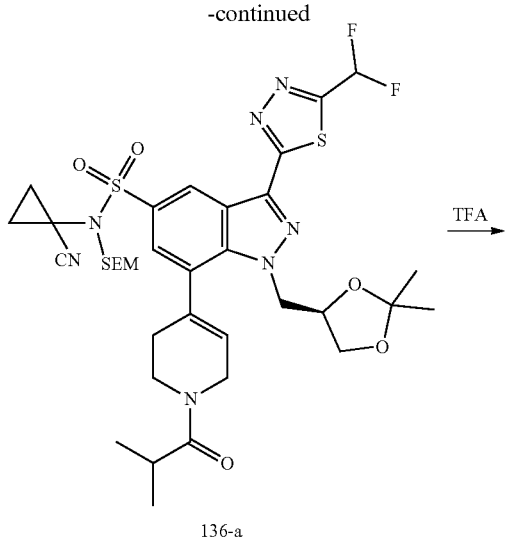

136-a

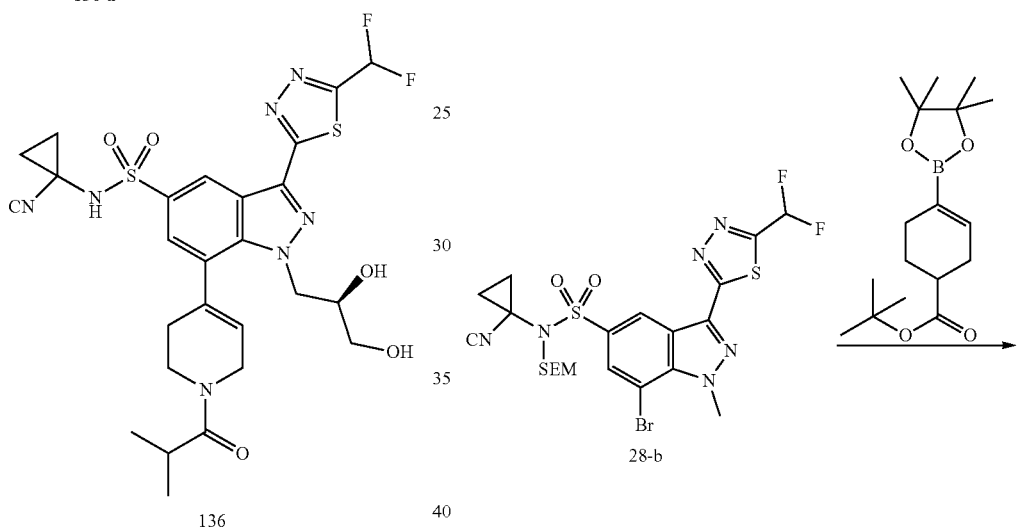

136

Synthesis of Compound 136-b

A microwave tube charged with 93-c (80 mg, 0.13 mmol), (S)-(−)-4-chloromethyl-2,2-dimethyl-1,3-dioxolane (180 mg, 1.20 mmol), potassium iodide solid (20 mg, 0.033 mmol), cesium carbonate (129 mg, 0.40 mmol) and DMF (2 mL) was stirred at 95° C. for 4 hours under nitrogen atmosphere. The reaction was quenched by adding water (10 mL), extracted with ethyl acetate (10 mL*3), the organic phases were concentrated and purified by column chromatography (mobile phase: petroleum ether/ethyl acetate 10/1 to 3/1) to give compound 136-b (40 mg, 42%). LC-MS (ESI): m/z 719.1 (M+H)$^+$.

Synthesis of Compound 136-a

A vial charged with 136-b (40 mg, 0.056 mmol), 40-b (155 mg, 0.56 mmol), PdCl$_2$(dppf)·CH$_2$Cl$_2$ (30 mg, 0.04 mmol), 1,4-dioxane (4 mL), water (1 mL) and potassium carbonate (38 mg, 0.28 mmol) was stirred at 100° C. for 3 hours under nitrogen atmosphere. The reaction mixture was concentrated at reduced pressure and purified by column chromatography (mobile phase: petroleum ether/ethyl acetate 3/1 to 1/1) to give compound 136-a (42 mg, 95%). LC-MS (ESI): m/z 792.1 (M+H)$^+$.

Synthesis of Compound 136

A reaction flask charged with 136-a (41 mg, 0.05 mmol), dichloromethane (3 mL) and trifluoroacetic acid (1 mL) was stirred for 2 h at room temperature under the protection of nitrogen. The reaction mixture was concentrated at reduced pressure and the residue was added potassium carbonate (3 g), water (10 mL) and ethyl acetate (10 mL), and the mixture was stirred at room temperature for 2 hours. The mixture was extracted with ethyl acetate (10 mL*3) and the organic phase was concentrated at reduced pressure and the residue was purified by prep-HPLC to give compound 136 (10.8 mg, 34%). LC-MS (ESI): m/z 622.2 (M+H)$^+$.

Example 133 Synthesis Route of Compound 137

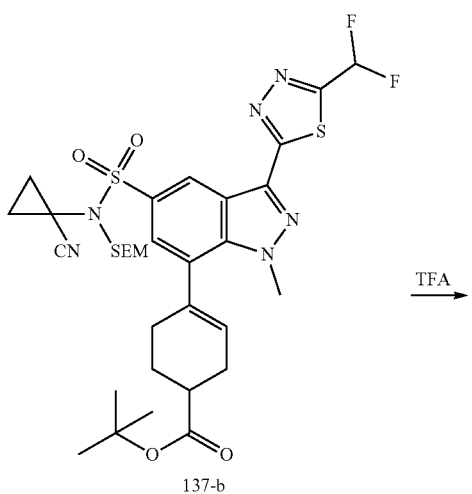

137-b

-continued

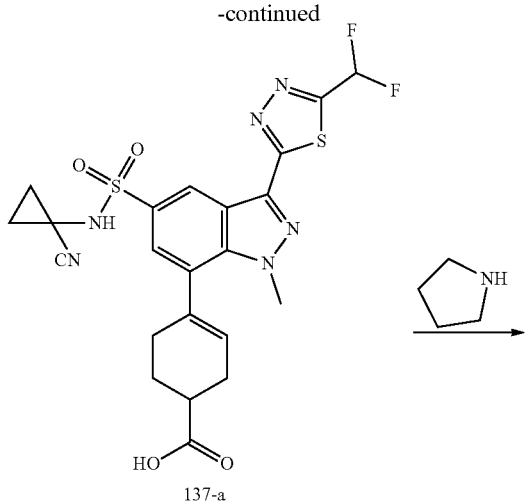

137-a

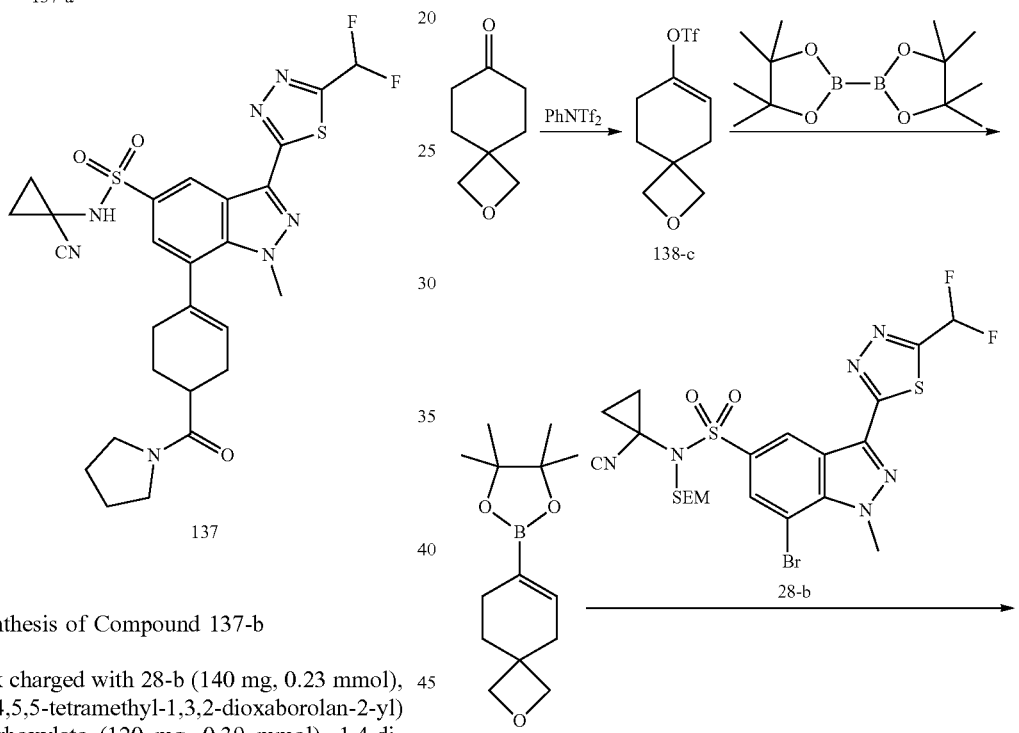

Synthesis of Compound 137-b

A reaction flask charged with 28-b (140 mg, 0.23 mmol), tert-butyl 4-(4,4,5,5-tetramethyl-1,3,2-dioxaborolan-2-yl)cyclohex-3-enecarboxylate (120 mg, 0.39 mmol), 1,4-dioxane (12 mL), PdCl$_2$(dppf)·CH$_2$Cl$_2$ (36 mg, 0.04 mmol), water (3 mL) and potassium carbonate (180 mg, 1.30 mmol) was stirred at 90° C. for 3 h under nitrogen atmosphere. The reaction mixture was concentrated at reduced pressure and purified by column chromatography (mobile phase: petroleum ether/ethyl acetate 3/1 to 1/1) to give compound 137-b (121 mg, 74%). LC-MS (ESI): m/z 721.6 (M+H)$^+$.

Synthesis of Compound 137-a

A reaction flask charged with 137-b (121 mg, 0.17 mmol), dichloromethane (3 mL) and trifluoroacetic acid (1 mL) was stirred at room temperature for 2 h under the protection of nitrogen. The reaction mixture was concentrated at reduced pressure and the residue was added potassium carbonate (3 g), water (10 mL) and ethyl acetate (10 mL), and the mixture was stirred at room temperature for 2 h. The reaction was quenched and pH was adjusted to 5 with diluted hydrochloric acid. The reaction was extracted with ethyl acetate (10 mL*3), dried over anhydrous sodium sulfate, and the organic phase was concentrated at reduced pressure to give compound 137-a (90 mg, 100%). LC-MS (ESI): m/z 535.6 (M+H)$^+$.

Synthesis of Compound 137

A reaction flask charged with 137-a (54 mg, 0.10 mmol), DMF (4 mL), HATU (190 mg, 0.50 mmol), DIPEA (130 mg, 1.00 mmol) and pyrrolidine (60 mg, 0.84 mmol) was stirred at room temperature for 2 h under the protection of nitrogen. The reaction was quenched with saturated sodium bicarbonate (10 mL), extracted with ethyl acetate (10 mL*3), and the organic phase was concentrated at reduced pressure and the residue was purified by pre-HPLC to give compound 137 (14.9 mg, 25%). LC-MS (ESI): m/z 588.3 (M+H)$^+$.

Synthesis Route of Compound 138

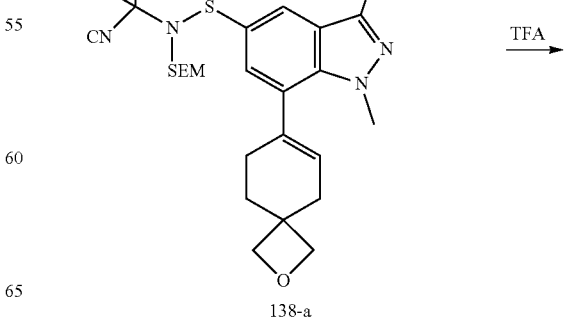

391
-continued

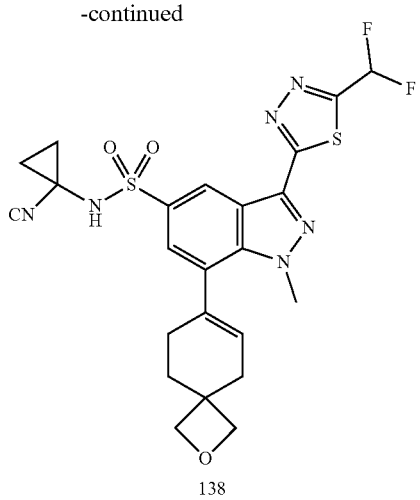

138

Synthesis of Compound 138-c

A solution of 2-oxaspiro[3.5]nonan-7-one (560 mg, 4.00 mmol) in tetrahydrofuran (20 mL) was stirred at −78° C. for 10 min, then was added LiHMDS (4.80 mL, 4.80 mmol) dropwise slowly and stirred at −78° C. for 2 h under nitrogen atmosphere. A solution of N-phenyl bis(trifluoromethanesulfonyl)imide (1784 mg, 5.00 mmol) in tetrahydrofuran (20 mL) was added slowly dropwise to the above mixture and warmed slowly from −78° C. to room temperature and stirred at for 11 hr. The reaction was quenched with saturated ammonium chloride (60 mL), extracted with ethyl acetate (20 mL*3). The organic phase was concentrated at reduced pressure and and the residue was purified by column chromatography (mobile phase: petroleum ether/ethyl acetate 10/0 to 10/1), and the eluent was concentrated to give compound 138-c (460 mg, 42%).

Synthesis of Compound 138-b

A reaction vial charged with 138-c (460 mg, 1.69 mmol), biboronic acid pinacol ester (858 mg, 3.38 mmol), 1,4-dioxane (20 mL), PdCl$_2$(dppf)·CH$_2$Cl$_2$ (276 mg, 0.34 mmol) and potassium acetate (498 mg, 5.07 mmol) was stirred at 80° C. for 12 hours under nitrogen atmosphere. The reaction mixture was used directly in the next step.

Synthesis of Compound 138-a

A microwave tube charged with 28-b (78 mg, 0.13 mmol), reaction mixture of 138-b, PdCl$_2$(dppf)·CH$_2$Cl$_2$ (60 mg, 0.07 mmol), water (5 mL) and potassium carbonate (73 mg, 0.53 mmol) was stirred at 90° C. for 3 hours under nitrogen atmosphere. The reaction mixture was concentrated at reduced pressure, quenched with water (10 mL), extracted with ethyl acetate (10 mL*3) and purified by thin layer silica gel plate (mobile phase: petroleum ether/ethyl acetate=2/3) to give compound 138-a (110 mg). LC-MS (ESI): m/z 663.1 (M+H)$^+$.

Synthesis of Compound 138

138-a (110 mg, 0.17 mmol) was added to a reaction vial, followed by dichloromethane (3 mL) and trifluoroacetic acid (1 mL), and the mixture was stirred at room temperature for 2 hours under nitrogen atmosphere. The reaction mixture was concentrated at reduced pressure and quenched by solid potassium carbonate (3 g) and water (10 mL), then was added ethyl acetate (10 mL) to the reaction mixture and stirred for 2 h at room temperature. Extracted with ethyl acetate (10 mL*3) and purified by thin layer silica gel plate (mobile phase: petroleum ether/ethyl acetate 1/1) to give compound 138 (16 mg, 18%). LC-MS (ESI): m/z 533.6 (M+H)$^+$.

Example 135 Synthetic Route of Compound 139

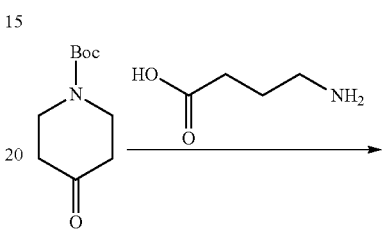

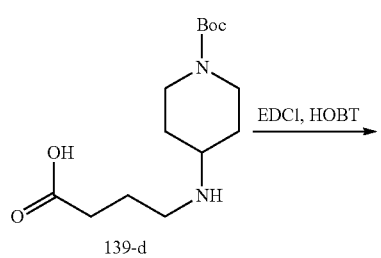

139-d

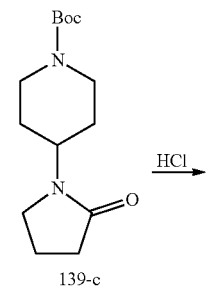

139-c

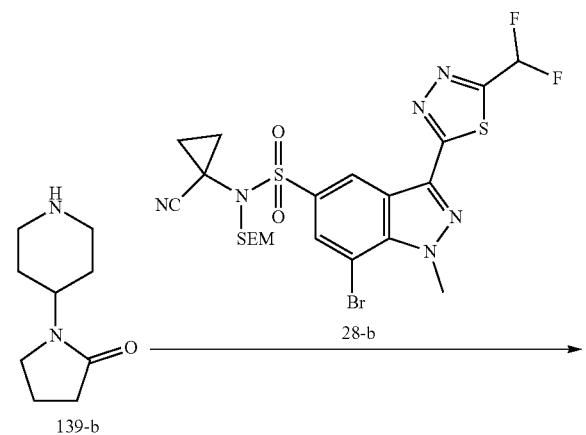

139-b

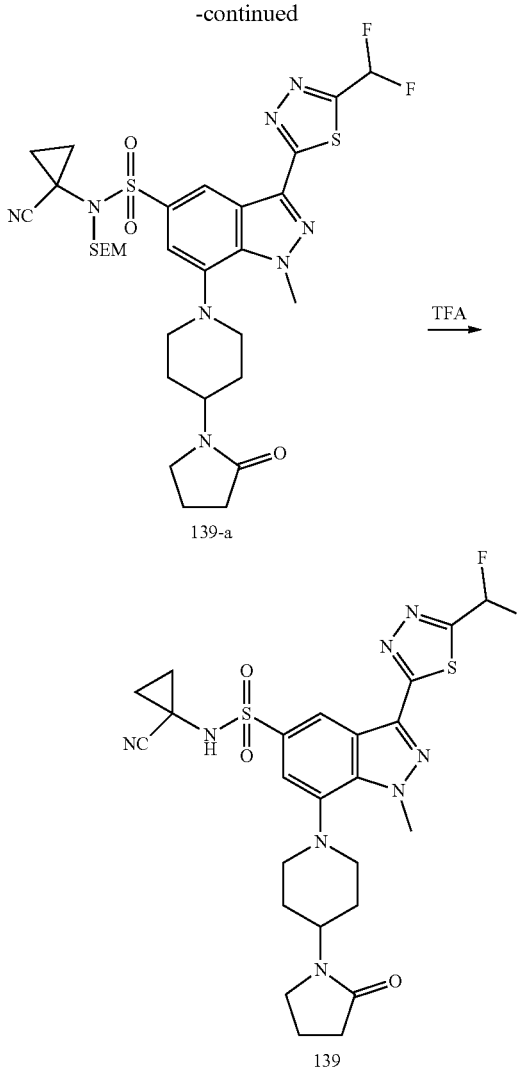

139-a

139

Synthesis of Compound 139-d

Compound N-Boc-4-piperidone (1.0 g, 5.02 mmol) and 4-aminobutyric acid (559 mg, 5.42 mmol) were dissolved in methanol (10 mL) and was slowly added Pd/C (10% weight percentage) (200 mg) and the reaction mixture was stirred at room temperature under hydrogen atmosphere for 4 h. After completion, the reaction mixture was filtered through celite and the filtrate was concentrated at reduced pressure to remove the solvent to give 139-d (900 mg, 63%). LC-MS (ESI): m/z 287.2 [M+H]$^+$.

Synthesis of Compound 139-c

To a reaction flask charged with 139-d (900 mg, 3.14 mmol), DMF (15 mL), triethylamine (1.31 mL, 9.43 mmol) and HOBT (637 mg, 4.71 mmol) was added EDCI (904 mg, 4.71 mmol) slowly. After addition, the reaction mixture was stirred at 35° C. and overnight. The next day, the reaction mixture was cooled to room temperature, diluted with ethyl acetate, and the organic phase was washed with water, brine, dried over anhydrous sodium sulfate, filtered and evaporated to obtain the crude product, which was purified by a flash column chromatography (mobile phase: methanol/dichloromethane, 0% to 10%) to give compound 139-c (130 mg, 15%). LC-MS (ESI): m/z=269.1 [M+H]$^+$.

Synthesis of Compound 139-b

To a reaction vial charged with 139-c (130 mg, 0.48 mmol) and acetonitrile (10 mL) was added HCl/1,4-dioxane (4 M, 0.61 mL, 2.42 mmol) dropwise in an ice-water bath and the reaction mixture was stirred at room temperature for 2 hours. After completion, the solvent was removed by concentration at reduced pressure, and the crude product was dissolved in methanol, neutralized by adding sodium bicarbonate powder and stirred for half an hour. Filtered, and the filtrate was concentrated and dried in vacuum to give compound 139-b (60 mg, 74%). LC-MS (ESI): m/z 169.2 [M+H]$^+$.

Synthesis of Compound 139-a

A microwave tube charged with 28-b (50 mg, 0.081 mmol), 139-b (27 mg, 0.16 mmol), Ruphos (4 mg, 0.008 mmol), (SP-4-1)-[1,3-bis[2,6-bis(1-ethylpropyl)phenyl]-4,5-dichloro-1,3-dihydro-2H-imidazol-2-ylidene]-dichloro(3-chloropyridine-KN)palladium (CAS:1435347-24-2) (11 mg, 0.013 mmol), cesium carbonate (79 mg, 0.24 mmol) and 1,4-dioxane (8 mL) was degassed and purged with nitrogen for 3 times, then was heated to 80° C. and stirred overnight. Upon completion, the reaction mixture was cooled to room temperature and concentrated at reduced pressure to remove the 1,4-dioxane. The residue was added EA, and the organic phase was washed with water, brine, dried over anhydrous sodium sulfate, filtered and evaporated to obtain the crude product, which was purified on a flash column chromatography (mobile phase: methanol/dichloromethane, 0% to 10%) to give compound 139-a (20 mg, 35%). LC-MS (ESI): m/z 707.2 [M+H]$^+$.

Synthesis of Compound 139

Trifluoroacetic acid (1 mL) was added dropwise to a solution of 139-a (20 mg, 0.028 mmol) in dichloromethane (5 mL) in a reaction flask at room temperature. After the dropwise addition, the reaction mixture was stirred at room temperature for 4 h. The solvent was removed by concentration at room temperature at reduced pressure. The residue was diluted with dichloromethane, and the organic phase was washed with saturated sodium bicarbonate, brine, dried over anhydrous sodium sulfate, filtered and evaporated to obtain the crude product, which was purified by pre-HPLC to give compound 139 (8 mg, 49%). LC-MS (ESI): m/z 577.2 [M+H]$^+$.

Example 136 Synthetic Route of Compound 140

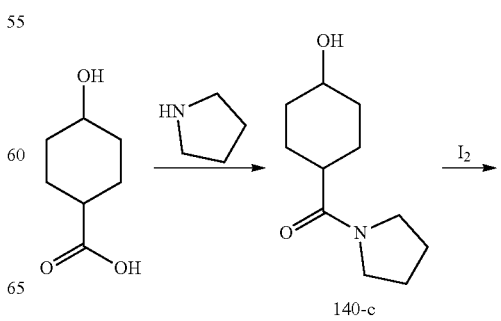

140-c

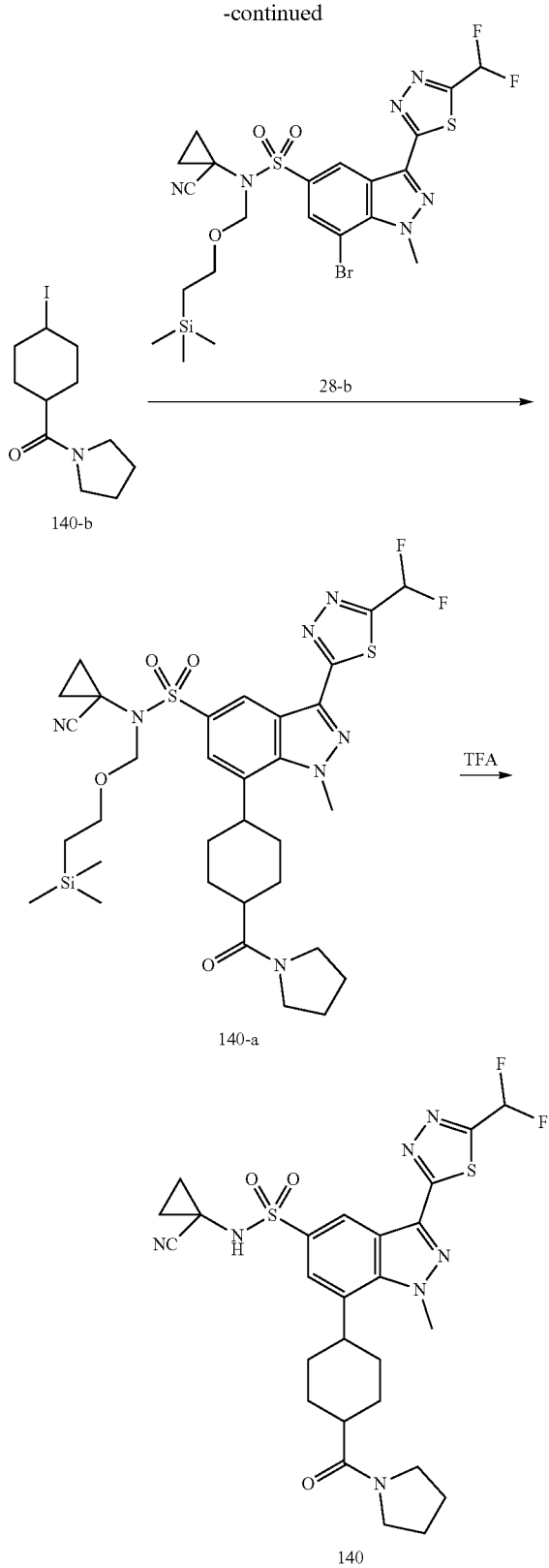

Synthesis of Compound 140-c

EDCI (2.66 g, 13.87 mmoL), HOBt (1.87 g, 13.87 mmoL), DIPEA (3.44 mL, 20.81 mmoL) and tetrahydropyrrole (0.60 mL, 7.28 mmoL) were added to a solution of compound 4-hydroxycyclohexanecarboxylic acid (1.0 g, 6.94 mmoL) in DCM (20 mL) in an ice-water bath. The reaction mixture was warmed to room temperature and stirred overnight. The reaction mixture was concentrated at reduced pressure and the residue was purified by a flash column chromatography (DCM:MeOH=10:1) to give compound 140-c (1.3 g, crude). LC-MS (ESI): m/z=198.2[M+H]$^+$.

Synthesis of Compound 140-b

A solution of compound 140-c (1.25 g, 6.34 mmoL) in DCM (40 mL) was added imidazole (518 mg, 7.60 mmoL), triphenylphosphine (1.99 g, 7.60 mmoL). The reaction mixture was cooled in an ice-water bath, degassed and purged with nitrogen for three times, and then was added iodine (3.37 g, 7.60 mmoL) in two batches. After addition, the reaction mixture was stirred at room temperature for 12 hours. At room temperature, the reaction mixture was added saturated sodium thiosulfate solution (100 mL) and water (100 mL), and the mixture was extracted with DCM (100 mL), the organic phase was washed with brine, dried over anhydrous sodium sulfate, filtered, and the filtrate was concentrated at reduced pressure, and the crude product was purified by a flash column chromatography (DCM:EA=10:1) to give compound 140-b (200 mg, 10%). LC-MS (ESI): m/z=308.0[M+H]$^+$.

Synthesis of Compound 140-a

A microwave tube charged with 28-b (50 mg, 0.081 mmoL), 140-b (75 mg, 0.24 mmoL), 4,4'-di-tert-butyl-2,2'-dipyridine (6.5 mg, 0.024 mmoL), zinc powder (15.8 mg, 0.24 mmoL), nickel(II) chloride ethylene glycol dimethyl ether complex (5.3 mg, 0.024 mmoL), anhydrous magnesium chloride (8.5 mg, 0.089 mmoL) and potassium iodide (14.7 mg, 0.089 mmoL) was added N'N-dimethylacetamide (3 mL) and triethylamine (11 uL, 0.081 mmoL) in an ice-water bath after degassed and purged with nitrogen for 3 times. The reaction mixture was warmed to room temperature and stirred overnight, then was added water (30 mL), the aqueous phase was extracted with ethyl acetate (50 mL*2), the organic phase was washed with brine (100 mL*3), dried over anhydrous sodium sulfate, filtered, and the filtrate was concentrated at reduced pressure. The residue was purified by a flash column chromatography (DCM:MeOH=10:1) to give compound 140-a (44 mg, 76%). LC-MS (ESI): m/z=720.1 [M+H]$^+$.

Synthesis of Compound 140

A solution of compound 140-a (44 mg, 0.061 mmoL) in 6 mL of dichloromethane was added trifluoroacetic acid (2 mL) and water (0.1 mL) in an ice-water bath. The reaction mixture was stirred at room temperature under nitrogen atmosphere for 2 hours. The reaction mixture was concentrated at reduced pressure at room temperature, and the residue was suspended in 1 mL of saturated sodium bicarbonate, added about 200 mg of potassium carbonate, 20 mL of ethyl acetate, and the mixture was stirred at room temperature for 1 h. The reaction mixture was added with 20 mL of water and extracted with ethyl acetate (50 mL). The organic phase was dried over anhydrous sodium sulfate, filtered, and the filtrate was concentrated at reduced pressure, and the residue was purified by Prep-HPLC (alkali method, NH₄HCO₃) to give compound 140 (13.2 mg, 37%). LC-MS (ESI): m/z=590.3[M+H]⁺.

Example 137 Synthetic Route of Compound 141

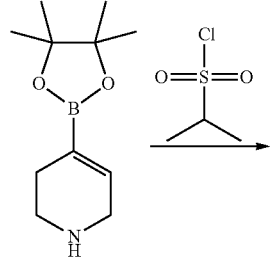

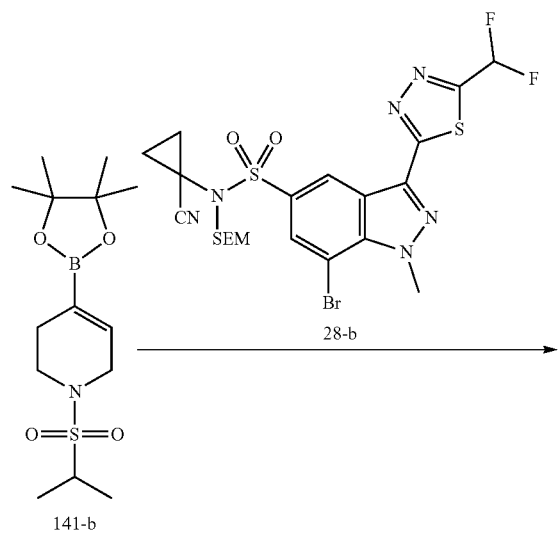

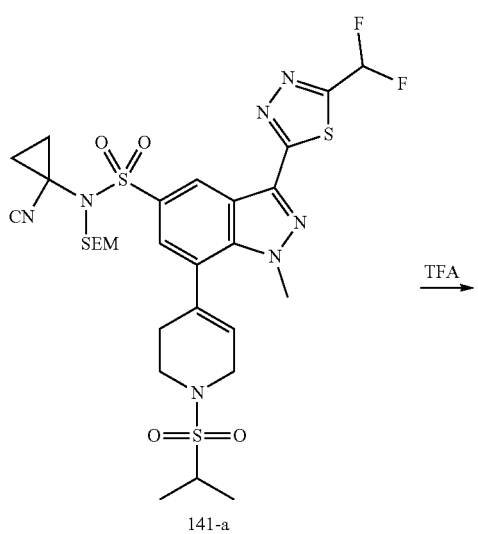

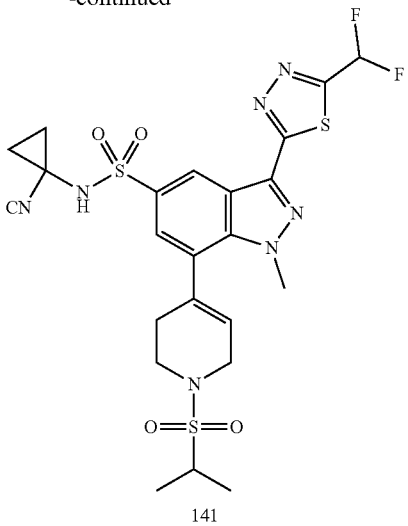

Synthesis of Compound 141-b

A solution of compound 1,2,3,6-tetrahydropyridine-4-boronic acid pinacol ester (200 mg, 0.96 mmol) in dichloromethane (20 mL) was added triethylamine (194 mg, 1.92 mmol). Isopropylsulfonyl chloride (164 mg, 1.15 mmol) was added dropwise to the above mixture in an ice-water bath, and the reaction mixture was stirred at room temperature for 2 h. The reaction mixture was added water (100 mL), extracted with dichloromethane (100 mL), and the organic phase was washed with brine (100 mL), dried over sodium sulfate, filtered off the desiccant, and the filtrate was concentrated at reduced pressure to obtain the crude product, which was purified by column chromatography (mobile phase, PE/EA 1/1) to give compound 141-b (120 mg, 40%). LC-MS (ESI): m/z 316.2 (M+H)⁺.

Synthesis of Compound 141-a

Compound 28-b (50 mg, 0.081 mmol), 141-b (51 mg, 0.16 mmol), [1,1'-bis(diphenylphosphino)ferrocene]palladium dichloride (12 mg, 0.016 mmol) and potassium carbonate (33 mg, 0.24 mmol) were added to 1,4-dioxane (10 mL) and water (1 mL). After degassed and purged with nitrogen for three times, the reaction mixture was stirred at 100° C. for 6 hours. The reaction mixture was filtered through celite, and the filtrate was added water (100 mL), extracted with ethyl acetate (100 mL), and the organic phase was washed with brine (100 mL), dried over sodium sulfate, filtered off the desiccant, and the filtrate was concentrated at reduced pressure to obtain the crude product, which was purified by column chromatography (mobile phase, PE/EA 1/1) to obtain compound 141-a (50 mg, 85%). LC-MS (ESI): m/z 728.2 (M+H)⁺.

Synthesis of Compound 141

Compound 141-a (50 mg, 0.069 mmol) was dissolved in dichloromethane (4.5 mL) to which trifluoroacetic acid (1.5 mL) was added in an ice-water bath and the reaction mixture was stirred at room temperature for 2 h. The reaction mixture was concentrated at reduced pressure to remove the dichloromethane, and the residue was adjusted to pH 7-8 with saturated sodium bicarbonate solution and extracted with ethyl acetate (50 mL). The organic phase was washed with brine (50 mL), dried over sodium sulfate, filtered off the desiccant, and the filtrate was concentrated at reduced pressure to give the crude product, which was purified by preparative HPLC (basic conditions) to give compound 141 (33 mg, 80%). LC-MS (ESI): m/z 598.4 (M+H)+.

Example 138 Synthetic Route of Compound 142

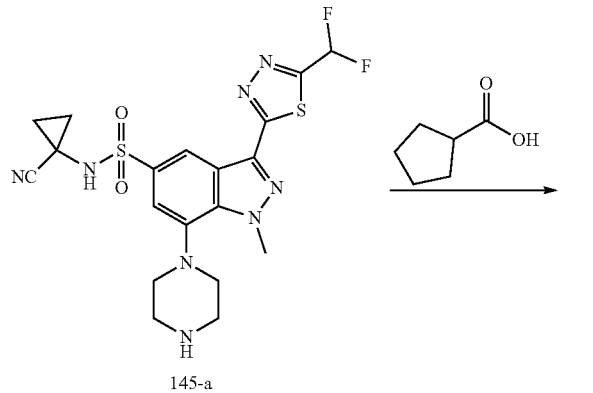

145-a

142

Synthesis of Compound 142

EDCI (8 mg, 0.040) was slowly added to a mixture of 145-a (10 mg, 0.020 mmol), cyclopentanecarboxylic acid (4 mg, 0.030 mmol), dichloromethane (5 mL), DIPEA (0.018 mL, 0.10 mmol) and HOBT (6 mg, 0.040 mmol) in a reaction flask in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by Prep-TLC (ethyl acetate/petroleum ether: 4/1) to give compound 142 (4 mg, 34%). LC-MS (ESI): m/z 591.2 [M+H]+.

Example 139 Synthetic Route of Compound 143

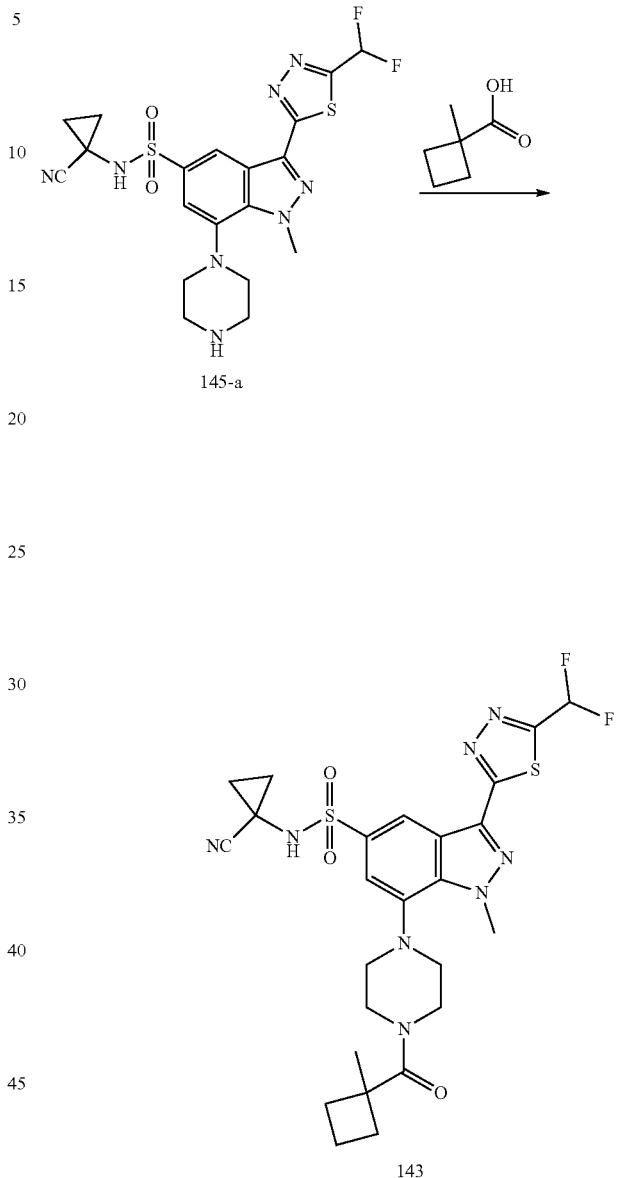

145-a

143

Synthesis of Compound 143

EDCI (8 mg, 0.040 mmol) was added slowly to a reaction flask charged with 145-a (10 mg, 0.020 mmol), 1-methyl-cyclobutanecarboxylic acid (4 mg, 0.030 mmol), dichloromethane (5 mL), DIPEA (0.018 mL, 0.10 mmol) and HOBT (6 mg, 0.040 mmol) in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The crude product was purified by Prep-TLC (ethyl acetate/petroleum ether: 4/1) to give compound 143 (2 mg, 17%). LC-MS (ESI): m/z 591.2 [M+H]+.

401
Example 140 Synthetic Route of Compound 144

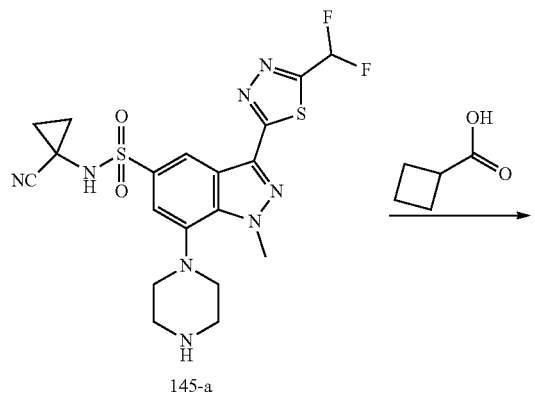

145-a

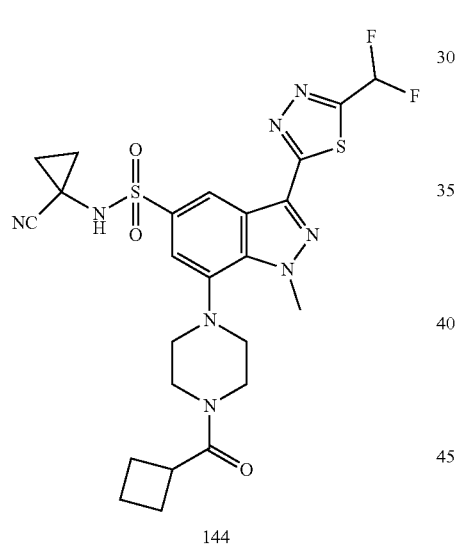

144

Synthesis of Compound 144

EDCI (8 mg, 0.040) was slowly added to a mixture of 145-a (10 mg, 0.020 mmol), cyclobutanecarboxylic acid (3 mg, 0.030 mmol), dichloromethane (5 mL), DIPEA (0.018 mL, 0.10 mmol) and HOBT (6 mg, 0.040 mmol) in a reaction flask in an ice-water bath. After addition, the reaction mixture was warmed to room temperature and stirred overnight. The next day, the reaction was quenched with water, extracted with dichloromethane, and the organic phase was washed with brine, dried over anhydrous sodium sulfate, and concentrated at reduced pressure. The residue was purified by Prep-TLC (ethyl acetate/petroleum ether: 4/1) to give compound 144 (5 mg, 43%). LC-MS (ESI): m/z 577.2 [M+H]$^+$.

402
Example 141 Synthetic Route of Compound 145

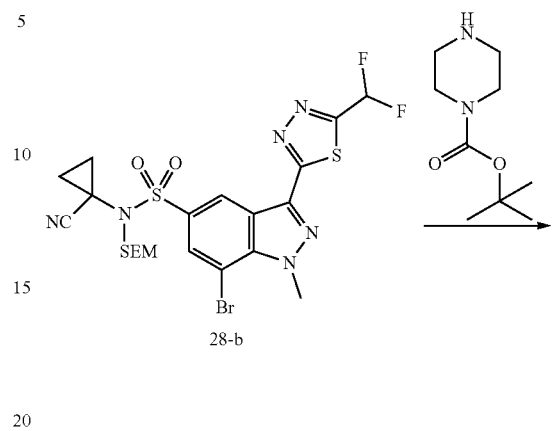

28-b

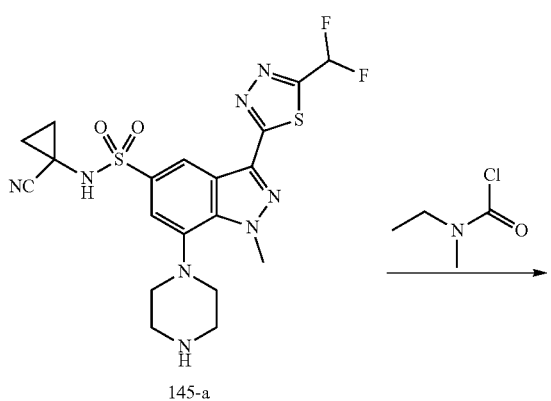

145-a

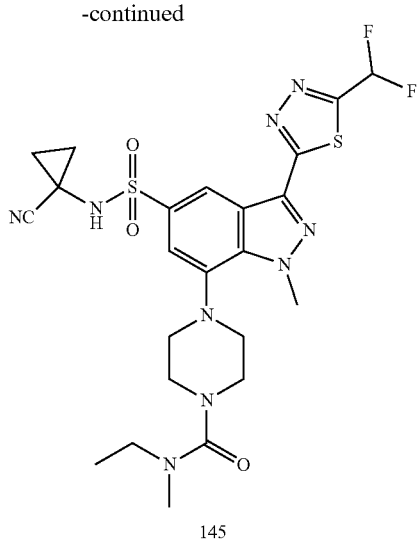

145

Synthesis of Compound 145-b

A microwave tube charged with 28-b (250 mg, 0.40 mmol), 1-tert-butoxycarbonyl piperazine (150 mg, 0.81 mmol), Ruphos (19 mg, 0.04 mmol), cesium carbonate (394 mg, 1.21 mmol) and (SP-4-1)-[1,3-bis[2,6-bis(1-ethylpropyl)phenyl]-4,5-dichloro-1,3-dihydro-2H-imidazol-2-ylidene]dichloro(3-chloropyridine-KN)palladium (69 mg, 0.08 mmol) was degassed and purged with nitrogen for three times, then was added 1,4-dioxane (4 mL) and degassed and purged with nitrogen for three more times, and the reaction mixture was heated and stirred at 88° C. for 12 h. The reaction mixture was concentrated at reduced pressure and purified by column chromatography (mobile phase: dichloromethane/methanol=100/0 to 10/1) to give compound 145-b (126 mg, 43%/). LC-MS (ESI): m/z 725.2 (M+H)$^+$.

Synthesis of Compound 145-a

A reaction vial charged with 145-b (126 mg, 0.17 mmol), dichloromethane (3 mL) and trifluoroacetic acid (1 mL) was stirred at room temperature for 2 h under the protection of nitrogen. The reaction mixture was concentrated at reduced pressure and the residue was added potassium carbonate (3 g), water (10 mL) and ethyl acetate (10 mL), and the mixture was stirred at room temperature for 2 hours. The mixture was extracted with ethyl acetate (10 mL*3), dried over sodium sulfate and the organic phase was concentrated at reduced pressure to give compound 145-a (72 mg, 84%). LC-MS (ESI): m/z 495.6 (M+H)$^+$.

Synthesis of Compound 145

A vial charged with 145-a (10 mg, 0.02 mmol), triethylamine (60 mg, 0.59 mmol), tetrahydrofuran (4 mL) and N-ethyl-N-methylcarbamoyl chloride (30 mg, 0.25 mmol) was stirred at 40° C. for 18 h under nitrogen atmosphere. The reaction mixture was concentrated at reduced pressure and the residue was purified by thin layer silica gel plate (mobile phase: petroleum ether/ethyl acetate=1/3) to give compound 145 (3.7 mg, 32%). LC-MS (ESI): m/z 580.3 (M+H)$^+$.

Example 142 Synthetic Route of Compound 146

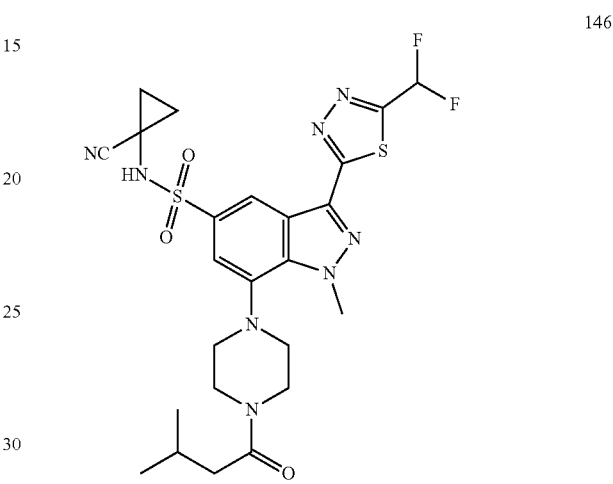

146

Referring to the synthesis of compound 68, compound 146 was synthesized using 3-methyl-1-(piperazin-1-yl)butan-1-one instead of 68-b. LC-MS (ESI): m/z 579.4 [M+H]$^+$.

Example 143 Synthesis of Compound 147

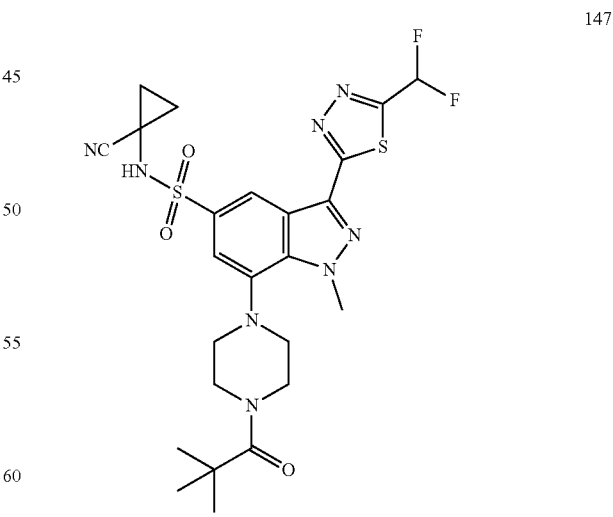

147

Referring to the synthesis of compound 68, compound 147 was obtained synthetically using 2,2-dimethyl-1-(piperazin-1-yl)propan-1-one instead of 68-b. LC-MS (ESI): m/z 579.3 (M+H)$^+$.

Example 144 Synthetic Route of Compound 148

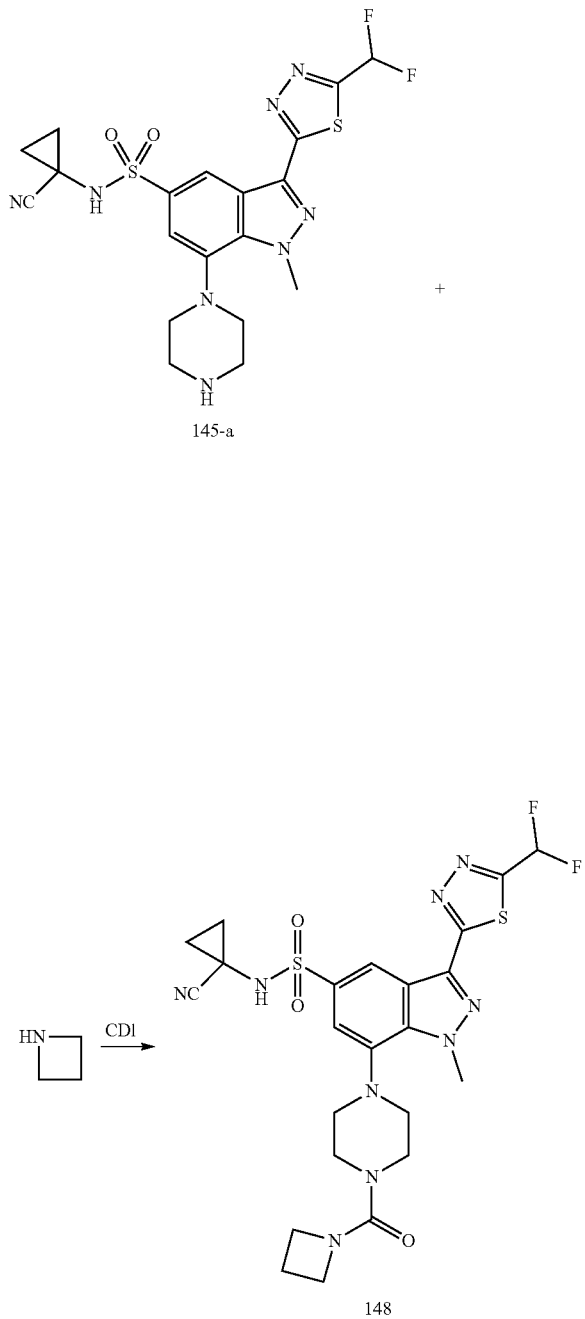

Synthesis of Compound 148

To a reaction vial was added 145-a (10 mg, 0.02 mmol), DIPEA (80 mg, 0.62 mmol), CDI (60 mg, 0.37 mmol) and dichloromethane (6 mL). The mixture was stirred at 30° C. for 12 hours under nitrogen atmosphere, then was added azetidine (10 mg, 0.18 mmol) and the mixture was stirred for 2 hours. The reaction mixture was concentrated at reduced pressure and purified by preparative HPLC to give compound 148 (5 mg, 43%). LC-MS (ESI): m/z 578.2 (M+H)$^+$.

Synthesis of contrast compound 1' and contrast compound 2'

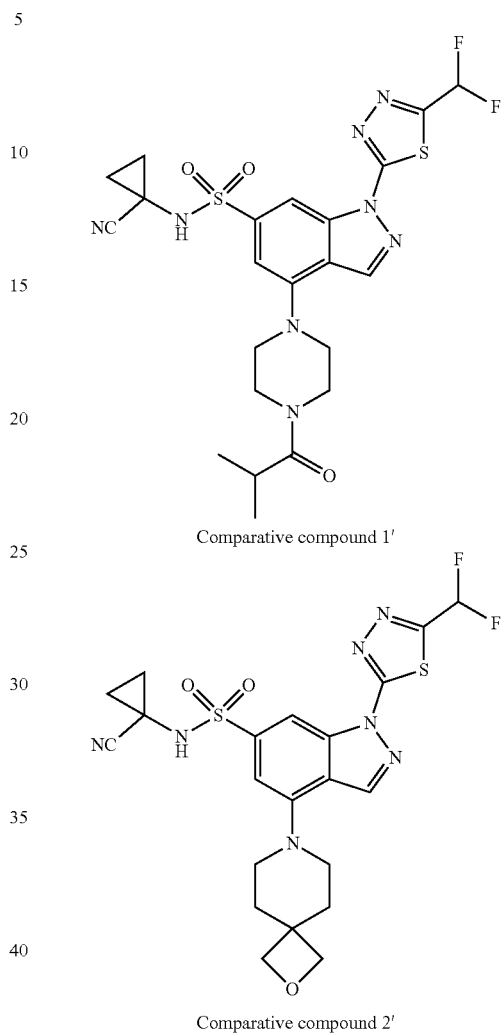

The title compounds were prepared according to WO2021055744A1.

Bioactivity Test

PARG Enzyme Inhibition Assay

Experimental Procedure

PARG in vitro assays were conducted in standard 384-well plates in a total volume of 15 μL. 5 μL of PARG (389-976) (manufactured by Chempartner Chemical Co., Ltd.) in buffer (50 mM Tris-HCL 7.5, 30 mM KCl, 1 mM EDTA, 3 mM DTT, tween-20 0.01%, BSA 0.025%) was added at a final concentration of 1.5 pM to the 384-well plates containing the compounds to be tested, which was incubated for 30 min at room temperature. To the above mixture was added 5 μL Bio PARylated His-TEV-PARP1 (2-1014) substrate (manufactured by Chempartner Chemical Co., Ltd.) at a final concentration of 12 nM, after addition, the resulting mixture was incubated for 30 minutes at room temperature. Then to the mixture was added detection reagent (5 μL) which was buffered with 50 mM Tris-HCL 7.5, 30 mM KCl, 1 mM EDTA, 3 mM DTT, tween-20 0.01%, BSA 0.025%, and consisted of 3 pM of compound PDD00017273 and 9 nM Mab anti-6HIS XL665 (Cisbio: 61HISXLA) and 0.9 nM streptavidin affinity terbium cryptate (Cisbio: 610SATLA), all at 3× working concentrations (final concentrations of 1 pM, 3 nM and 0.3 nM, respectively). After 120 min incubation in the dark at room temperature, TR-FRET signals were measured at Ex 340 and Em 665 and Em 615. The ratio for each well was calculated as Em 665/Em 615 and the compound inhibition rate was calculated based on the obtained data.

Results of PARG bioactivity (enzyme inhibition assay) assay.

TABLE 1

PARG biochemical activity of representative compounds of the present invention

| Compound No. | $IC_{50}$ (PARG enzyme) |
|---|---|
| 1 | *** |
| 2 | *** |
| 3 | *** |
| 4 | (1.0 nM) *** |
| 5 | *** |
| 6 | (0.5 nM) |
| 7 | *** |
| 8 | *** |
| 9 | *** |
| 10 | ** |
| 11 | ** |
| 12 | *** |
| Comparative compound 1' | *** (1.9 nM) |

***represents $IC_{50}$ < 100 nM;
** represents 100 nM ≤ $IC_{50}$ < 1 μM;
* represents $IC_{50}$ ≥ 1 μM

TABLE 2

PARG biochemical activity of representative compounds of the present invention

| Compound No. | $IC_{50}$ (PARG enzyme) |
|---|---|
| 13 | *** |
| 14 | *** |
| 15 | *** |
| 16 | *** |
| 17 | *** |
| 18 | (0.6 nM) *** |
| 19 | (0.9 nM) *** |
| 20 | *** |
| 21 | *** |
| 22 | *** |
| 23 | *** |
| 24 | *** |
| 25 | *** |
| 26 | *** |
| 27 | *** |
| 28 | *** |
| 29 | *** |
| 30 | *** |
| 31 | *** |
| 32 | *** |
| 33 | *** |
| 34 | *** |
| 35 | *** |
| 36 | *** |

TABLE 2-continued

PARG biochemical activity of representative compounds of the present invention

| Compound No. | $IC_{50}$ (PARG enzyme) |
|---|---|
| 37 | *** |
| 38 | *** |
| 40 | *** |
| 41 | *** |
| 42 | *** |
| 43 | *** |
| 44 | *** |
| 45 | *** |
| 46 | *** (0.9 nM) |
| 47 | *** |
| 48 | *** |
| 49 | *** |
| 50 | *** |
| 51 | *** |
| 52 | *** |
| 53 | *** |
| 54 | *** |
| 55 | *** |
| 56 | *** |
| 57 | *** |
| 58 | *** |
| 59 | *** |
| 60 | *** |
| 61 | *** |
| 62 | *** |
| 63 | *** |
| 64 | *** |
| 65 | *** |
| Comparative compound 2' | *** (2.3 nM) |

***represents $IC_{50}$ < 100 nM;
** represents 100 nM ≤ $IC_{50}$ < 1 μM;
* represents $IC_{50}$ ≥ 1 μM

TABLE 3

PARG biochemical activity of representative compounds of the present invention

| Compound No. | $IC_{50}$ (PARG enzyme) |
|---|---|
| 66 | *** |
| 67 | *** |
| 68 | *** |
| 69 | *** |
| 70 | *** |
| 71 | *** |
| 72 | *** |
| 73 | *** |
| 74 | *** |
| 75 | *** |
| 76 | *** |
| 77 | *** |
| 78 | *** |
| 79 | *** |
| 80 | *** |
| 81 | *** |
| 82 | *** |
| 83 | *** |
| 84 | *** |
| 85 | *** |
| 86 | *** |
| 87 | *** |
| 88 | *** |
| 89 | *** |
| 90 | *** |
| 91 | *** |
| 92 | *** |
| 93 | *** |

TABLE 3-continued

PARG biochemical activity of representative compounds of the present invention

| Compound No. | IC$_{50}$ (PARG enzyme) |
|---|---|
| 94 | *** |
| 95 | *** |
| 96 | ** |
| 97 | *** |
| 98 | *** |
| 99 | *** |
| 100 | *** |
| 101 | *** |
| 102 | *** |
| 103 | *** |
| 104 | *** |
| 105 | *** |
| 106 | *** |
| 107 | *** |
| 108 | *** |
| 109 | *** |
| 110 | *** |
| 111 | *** |
| 112 | *** |
| 113 | *** |
| 114 | *** |
| 115 | *** |
| 116 | *** |
| 117 | *** |
| 118 | *** |
| 119 | *** |
| 120 | *** |
| 121 | *** |
| 122 | *** |
| 123 | *** |
| 124 | *** |
| 125 | *** |
| 126 | *** |
| 127 | *** |
| 128 | *** |
| 129 | *** |
| 130 | ** |
| 131 | *** |
| 132 | *** |
| 133 | *** |
| 134 | *** |
| 135 | *** |
| 136 | *** |
| 137 | *** |
| 138 | *** |
| 139 | *** |
| 140 | *** |
| 141 | *** |
| 142 | *** |
| 143 | *** |
| 144 | *** |
| 145 | *** |
| 146 | *** |
| PDD00017273# | *** |

***represents IC$_{50}$ < 100 nM;
** represents 100 nM ≤ IC$_{50}$ < 1 μM;
* represents IC$_{50}$ ≥ 1 μM
PDD 00017273: a PARG inhibitor reported by the literature.

PARG Cell Inhibition Assay

Experimental Procedure

UWB1.289 cells were used and the medium was 50% MEBM+50% 1640+3% FBS+1×PS. The cells were cultured according to ATCC standard operation and the cells were assayed in exponential growth phase for the experiment. Re-suspend cell in medium to a proper concentration, only cells with viability greater than 90% are used for assays.

Seed cells UWB1.289 in each culture medium, incubate overnight at 37° C., 5% $CO_2$.

Test compounds was diluted with DMSO in gradient. Add test compound in cell plate, incubate at 37° C.

Add compounds and $H_2O_2$ mixture into cell plate, incubate at 37° C. Use 100 nM PDD00017273 as positive control.

Remove solution and recovery cell, incubate at 37° C.

Remove solution in the plate and add Cold-MeOH, incubate at −20° C.

Wash 4 times with PBS.

Add blocking buffer into cell plate, incubate at RT.

Add PAR mAb, incubate at 4° C. overnight.

Wash 4 times with PBST.

Add secondary antibody and DNA stain DRAQ5, incubate at RT.

Wash 3 times with PBST and 2 times with PBS. Turn plate upside down and centrifuge 1000 rpm 1 min.

Scan plate using LI-COR for best result.

Calculate the % inhibition according to the following formula: % inhibition=(compound signal value−negative control signal average)/(positive control signal average−negative control signal average)×100. Use the formula Y=Bottom+(Top−Bottom)/(1+10^((Log IC$_{50}$−X)*Hill-Slope)) to fit the curve to obtain the IC$_{50}$ values.

TABLE 4

Cellular activity of PARG, a representative compound of the present invention

| Compound No. | IC$_{50}$ (PARG cell) |
|---|---|
| 3 | **** (9.6 nM) |
| 5 | **** (3.1 nM) |
| 17 | **** (3.6 nM) |
| 19 | **** |
| 21 | **** |
| 22 | **** |
| 23 | **** |
| 26 | **** |
| 30 | **** |
| 33 | **** |
| 40 | **** |
| 48 | **** |
| 51 | **** |
| Comparative compound 1' | *** (14.7 nM) |
| PDD00017273 | *** (13.4 nM) |

The invention claimed is:
1. A compound containing structure of a five-membered heteroaromatic ring represented by formula II, a pharmaceutically acceptable salt thereof, or a stereoisomer thereof,

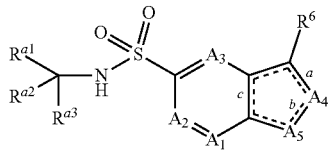

II wherein, $=\!=$ represents a single bond or a double bond;

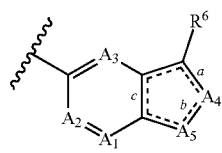

both rings of are aromatic;

$R^{a1}$, $R^{a2}$ and $R^{a3}$ are independently hydrogen, halogen, cyano, $C_{1-6}$ alkyl, $C_{2-6}$ alkenyl, $C_{2-6}$ alkynyl, —$OR^{a-1}$, $C(=O)$ $R^{a-2}$, —$NR^{a-31}R^{a-32}$, —$C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

or, $R^{a2}$ and $R^{a3}$, together with the carbon atom to which they are attached form $C_{3-7}$ cycloalkane, $C_{3-7}$ cycloalkane substituted with one or more $R^{a2-1}$, "3- to 8-membered heterocycloalkyl containing 1 to 3 hetroatoms independently selected from O, S and N", "3- to 8-membered heterocycloalkyl containing 1 to 3 heteroatoms independently selected from O, S and N" substituted with one or more $R^{a2-2}$; provided that when multiple substituents are present, the substituents are the same or different;

$R^{a2-1}$ and $R^{a2-2}$ are independently halogen, oxo, hydroxyl, $C_{1-6}$ alkyl, or $C_{1-6}$ alkyl substituted with one or more halogen, —$OC_{1-6}$ alkyl, and —$OC_{1-6}$ alkyl substituted with one or more halogen;

$R^{a-1}$, $R^{a-2}$, $R^{a-31}$, $R^{a-32}$, $R^{a-4}$, $R^{a-51}$ and $R^{a-52}$ are independently hydrogen, $C_{1-6}$ alkyl, or, $C_{1-6}$ alkyl substituted with one or more halogens;

$A_1$ is $CR^1$;

$R^1$ is hydrogen, cyano, $C_{2-6}$ alkenyl, $C_{2-6}$ alkynyl, $C_{1-6}$ alkyl, $C_{1-6}$ alkyl substituted with one or more $R^{1-1}$, halogen, hydroxyl, —$OC_{1-6}$ alkyl, —$OC_{1-6}$ alkyl substituted with one or more $R^{1-2}$, —$C(=O)$ $R^{1a}$, —$NR^{1b1}R^{1b2}$, —$C(=O)OR^{1c}$, —$C(=O)NR^{1d1}R^{1d2}$, $C_{3-10}$ cycloalkyl, $C_{3-10}$ cycloalkyl substituted with one or more $R^{1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-2}$, $R^{1-3}$, $R^{1-4}$, $R^{1-5}$, $R^{1-6}$, $R^{1-7}$, $R^{1-8}$ and $R^{1-9}$ are independently azide, halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, —$C(=O)$ $R^{11a}$, —$NR^{11b1}R^{11b2}$, —$C(=O)OR^{11c}$, —$C(=O)NR^{11d1}R^{11d2}$, —$S(O)_2NR^{11e1}$, $R^{11e2}$, —$S(O)_2$ $R^{11f}$, $C_{3-10}$ cycloalkyl, $C_{3-10}$ cycloalkyl substituted with one or more $R^{1-1-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-1-8}$, provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, —$C(=O)$ $R^{11g}$, hydroxyl, oxo, $C_{1-6}$ alkyl, or, $C_{1-6}$ alkyl substituted with one or more $R^{1-1-1-1}$; provided that when multiple substituents are present, the substituents are the same or different;

$R^{1-1-1-1}$ is halogen, hydroxyl, —$OC_{1-6}$ alky or —$NR^aR^b$, $R^a$ and $R^b$ are independently hydrogen or $C_{1-6}$ alkyl;

$R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d1}$, $R^{11d2}$, $R^{11e1}$, $R^{11e2}$, $R^{11f}$ and $R^{11g}$ are independently hydrogen, $C_{1-6}$ alkyl, $C_{1-6}$ alkyl substituted with one or more $R^{1-2-1}$, —$OC_{1-6}$ alkyl, —$OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$ or, —$C(=O)$ $R^{11h}$;

$R^{11h}$ is $C_{1-6}$ alky; provided that when multiple substituents are present, the substituents are the same or different; $R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, hydroxyl, —$NR^{12c}R^{12d}$, oxo, $C_{1-6}$ alkyl, $C_{1-6}$ alkyl substituted with one or more $R^{1-2-1-1}$, $R^{12c}$ and $R^{12d}$ are independently hydrogen or $C_{1-6}$ alkyl; provided that when multiple substituents are present, the substituents are the same or different;

$R^{1-2-1-1}$ is independently halogen, hydroxyl, —$OC_{1-6}$ alkyl or —$NR^cR^d$, $R^c$ and $R^d$ are independently hydrogen or $C_{1-6}$ alkyl;

or, when the number of $R^{1-3}$, $R^{1-4}$, $R^{1-5}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-5}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$ two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form "3- to 8-membered carbon ring", "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aromatic ring, $C_{6-20}$ aromatic ring substituted with one or more $R^{1-3-3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1-3-4}$, $C_{5-7}$ cyclic olefin, $C_{5-7}$ cyclic olefin substituted with one or more $R^{1-3-5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1-3-6}$, provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen; provided that when multiple substituents are present, the substituents are the same or different;

or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$, $R^{12c}$ and $R^{12d}$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-4-1}$;

$R^{1-4-1}$ is independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen; provided that when multiple substituents are present, the substituents are the same or different;

$A_2$ and $A_3$ are independently $CR^2$, $R^2$ is hydrogen or halogen;

b is a single bond, both a and c are a double bond, $A_4$ is N, $A_4$ is $NR^{5d}$, $R^6$ is independently "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$;

$R^{6-1}$ is halogen, hydroxyl, —CN, $C_{1-6}$ alkyl, $C_{1-6}$ alkyl substituted with one or more halogen, $C_{1-6}$ alkyl substituted with one or more —$OC_{1-6}$ alkyl, —$OC_{1-6}$ alkyl, or, $C_{1-6}$ alkyl —O— substituted with one or more halogen; provided that when multiple substituents are present, the substituents are the same or different;

$R^{5d}$ is

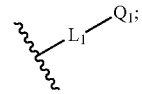

$L_1$ is a bond, $C_{1-6}$ alkylene or —C(=O)—;

$Q_1$ is hydrogen, halogen, cyano, $C_{2-6}$ alkenyl, $C_{2-6}$ alkynyl, hydroxyl, —C(=O) $R^{52a}$, —$NR^{52b1}R^{52b1}$, —C(=O)$OR^{52c}$, —C(=O)$NR^{52d1}R^{52d2}$, $C_{1-6}$ alkyl substituted with one or more halogen, $C_{1-6}$ alkyl substituted with one or more hydroxyl, —$OC_{1-6}$ alkyl, —$OC_{1-6}$ alkyl substituted with one or more $R^{5-1-1}$, $C_{6-20}$ aryl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, $C_{3-12}$ cycloalkyl, $C_{3-12}$ cycloalkyl substituted with one or more $R^{5-1-4}$, "4-to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{5-1-5}$, $C_{5-7}$ cycloalkenyl, $C_{5-7}$ cycloalkenyl substituted with one or more $R^{5-1-6}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{5-1-7}$; provided that when multiple substituents are present, the substituents are the same or different;

or, $R^1$ and $R^{5d}$, together with the atoms to which they are attached independently form "5- to 12-membered heterocyclic olefin containing 1 to 3 heteroatoms independently selected from O, S and N";

$R^{5-1-1}$, $R^{5-1-2}$, $R^{5-1-3}$, $R^{5-1-4}$, $R^{5-1-5}$, $R^{5-1-6}$ and $R^{5-1-7}$ are independently halogen, hydroxyl, oxo, cyano, $C_{1-6}$ alkyl, $C_{1-6}$ alkyl substituted with one or more halogen, $C_{2-6}$ alkenyl, $C_{2-6}$ alkynyl, —$OC_{1-6}$ alkyl, —$OC_{1-6}$ alkyl substituted with one or more halogen, —C(=O) $R^{51a}$, —$NR^{51b1}R^{51b2}$, —C(=O)$OR^{51c}$, or, —C(=O)$NR^{51d1}R^{51d2}$; provided that when multiple substituents are present, the substituents are the same or different;

$R^{52a}$, $R^{52b1}$, $R^{52b}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$;

$R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different.

2. A compound containing structure of a five-membered heteroaromatic ring represented by formula II, a pharmaceutically acceptable salt thereof, or a stereoisomer thereof,

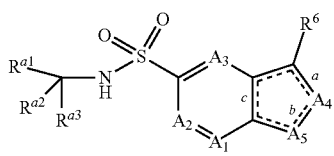

II wherein, === represents a single bond or a double bond;

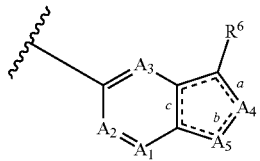

both rings of are aromatic;

$R^{a1}$ is cyano, $C_{1-6}$ alkyl, or, $C_{1-6}$ alkyl substituted with one or more $R^{a1-1}$, $R^{a1-1}$ is halogen;

$R^{a2}$ and $R^{a3}$ are independently $C_{1-6}$ alkyl, or, $R^{a2}$ and $R^{a3}$, together with the carbon atom to which they are attached form $C_{3-7}$ cycloalkane;

$A_1$ is $CR^1$;

$R^1$ is hydrogen, $C_{1-6}$ alkyl substituted with one or more $R^{1-1}$, halogen, $C_{3-10}$ cycloalkyl substituted with one or more $R^{1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

$R^{1-1}$, $R^{1-3}$, $R^{1-4}$, $R^{1-5}$, $R^{1-7}$, $R^{1-8}$ and $R^{1-9}$ are independently azide, halogen, hydroxyl, $C_{1-6}$ alkyl, $C_{1-6}$ alkyl substituted with one or more $R^{1-1-1}$, —$C(=O)$ $R^{11a}$, —$NR^{11b1}R^{11b2}$, —$C(=O)NR^{11d1}R^{11d2}$, —$S(O)_2R^{11f}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N", substituted with one or more $R^{1-1-4}$, or, "5- to 12-membered heteroaryl containing 1 to 4 heteroatoms independently selected from O, S and N"; provided that when multiple substituents are present, the substituents are the same or different;

$R^{1-1-1}$ and $R^{1-1-4}$ are independently -$C(=O)$ $R^{11g}$, oxo, hydroxyl, or, $C_{1-6}$ alkyl substituted with one or more $R^{1-1-1-1}$; provided that when multiple substituents are present, the substituents are the same or different;

$R^{1-1-1-1}$ is independently hydroxyl;

$R^{11a}$, $R^{11b1}$, $R^{11b2}$, $R^{11d1}$, $R^{11d2}$, $R^{11f}$ and $R^{11g}$ are independently hydrogen, $C_{1-6}$ alkyl, $C_{1-6}$ alkyl substituted with one or more $R^{1-2-1}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N" substituted with one or more $R^{1-2-4}$, $C_{6-20}$ aryl, "5- to 12-membered heteroaryl containing 1 to 4 heteroatoms independently selected from O, S and N", or —$C(=O)$ $R^{11h}$; $R^{11h}$ is $C_{1-6}$ alky; provided that when multiple substituents are present, the substituents are the same or different;

$R^{1-2-1}$, $R^{1-2-3}$ and $R^{1-2-4}$ are independently halogen, hydroxyl, —$NR^{12c}R^{12d}$, or $C_{1-6}$ alkyl; $R^{12c}$ and $R^{12d}$ are independently hydrogen or $C_{1-6}$ alkyl; provided that when multiple substituents are present, the substituents are the same or different;

or, when the number of $R^{1-4}$ and $R^{1-8}$ is more than one, two optional $R^{1-4}$, two optional $R^{1-8}$, together with the atoms to which they are attached, independently form "3- to 8-membered heterocycle containing 1 to 3 heteroatoms independently selected from O, S and N", or "5- to 12-membered heteroaromatic ring containing 1 to 4 heteroatoms independently selected from O, S and N";

or, $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with one or more $R^{1-4-1}$;

$R^{1-4-1}$ is independently oxo, or halogen;

$A_2$ and $A_3$ are independently $CR^2$, $R^2$ is hydrogen or halogen;

b is a single bond, both a and c are a double bond, $A_4$ is N, $A_4$ is $NR^{5d}$, $R^{5d}$ is

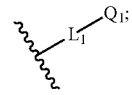

$L_1$ is a bond or $C_{1-6}$ alkylene;

$Q_1$ is hydrogen, cyano, hydroxyl, $C_{1-6}$ alkyl substituted with one or more halogen, $C_{1-6}$ alkyl substituted with one or more hydroxyl, —$OC_{1-6}$ alkyl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl; provided that when multiple substituents are present, the substituents are the same or different;

or, $R^1$ and $R^{5d}$, together with the atoms to which they are attached form "5- to 12-membered heterocyclic olefin containing 1 to 3 heteroatoms independently selected from O, S and N";

$R^{5-1-2}$ and $R^{5-1-3}$ are independently halogen or $C_{1-6}$ alkyl;

$R^6$ is "5-membered heteroaryl containing 1 to 4 heteroatoms independently selected from O, S and N" substituted with one or more $R^{6-1}$;

$R^{6-1}$ is $C_{1-6}$ alkyl, $C_{1-6}$ alkyl substituted with one or more halogen or $C_{1-6}$ alkyl substituted with one or more $OC_{1-6}$ alkyl.

3. The compound containing structure of a five-membered heteroaromatic ring represented by formula II, a pharmaceutically acceptable salt thereof, or a stereoisomer thereof according to claim 1, wherein, $R^{a1}$ is cyano, $C_{1-6}$ alkyl, or, $C_{1-6}$ alkyl substituted with one or more $R^{a1-1}$, $R^{a1-1}$ is halogen;

and/or, $R^{a2}$ and $R^{a3}$, together with the carbon atom to which they are attached form $C_{3-7}$ cycloalkane;

and/or, $A_1$ is $CR^1$;

and/or, $R^1$ is hydrogen, $C_{1-6}$ alkyl substituted with one or more $R^{1-1}$, halogen, $C_{3-10}$ cycloalkyl substituted with one or more $R^{1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$; provided that when multiple substituents are present, the substituents are the same or different;

and/or, $R^{1-1}$ is independently halogen, or, "4- to 10-membered heterocycloalkyl containing 1 to 3 heteroatoms independently selected from O, S and N" substituted with one or more $R^{1-1-4}$; and/or, in $R^{1-1}$, $R^{1-1-4}$ is independently —C(=O) $R^{11g}$ or $C_{1-6}$ alkyl substituted with one or more $R^{1-1-1-1}$; $R^{11g}$ is $C_{1-6}$ alkyl; $R^{1-1-1-1}$ is independently hydroxyl;

and/or, $R^{1-3}$ is independently —C(=O)$NR^{11d1}R^{11d2}$, $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N";

and/or, $R^{1-4}$ is independently azide, hydroxyl, $C_{1-6}$ alkyl, $C_{1-6}$ alkyl substituted with one or more $R^{1-1-1}$, $C_{6-20}$ aryl, —C(=O) $R^{11a}$, —C(=O)$NR^{11d1}R^{11d2}$, —$S(O)_2R^{11f}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-1-4}$, or, "5- to 12-membered heteroaryl containing 1 to 4 heteroatoms independently selected from O, S and N"; provided that when multiple substituents are present, the substituents are the same or different; when the number of $R^{1-4}$ is more than one, two optional $R^{1-4}$, together with the atoms to which they are attached, independently form "3- to 8-membered heterocycle containing 1 to 3 heteroatoms independently selected from O, S and N"; when the number of $R^{1-4}$ is more than one, two optional $R^{1-4}$, together with the atoms to which they are attached, independently form "5- to 12-membered heteroaromatic ring containing 1 to 4 heteroatoms independently selected from O, S and N";

and/or, in $R^{1-4}$, $R^{1-1-1}$ is hydroxyl;

and/or, in $R^{1-4}$, $R^{11a}$ is $C_{1-6}$ alkyl, $C_{3-10}$ cycloalkyl, $C_{1-6}$ alkyl substituted with one or more $R^{1-2-1}$, $C_{3-10}$ cycloalkyl substituted with one or more $R^{1-2-3}$, $C_{6-20}$ aryl, or "5- to 12-membered heteroaryl containing 1 to 4 heteroatoms independently selected from O, S and N"; $R^{1-2-1}$ is independently halogen, hydroxyl or —$NR^{12c}R^{12d}$, $R^{12e}$ and $R^{12d}$ are independently hydrogen; $R^{1-2-3}$ is independently $C_{1-6}$ alkyl;

and/or, in $R^{1-4}$, $R^{11d1}$ and $R^{11d2}$ are independently $C_{1-6}$ alkyl, $C_{1-6}$ alkyl substituted with one or more $R^{1-2-1}$, $R^{1-2-1}$ is independently —$NR^{12c}R^{12d}$, $R^{12c}$ and $R^{12d}$ are independently $C_{1-6}$ alkyl; or, $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with one or more $R^{1-4-1}$, $R^{1-4-1}$ is independently halogen;

and/or, in $R^{1-4}$, $R^{11f}$ is $C_{1-6}$ alkyl;

and/or, in $R^{1-4}$, $R^{1-1-4}$ is oxo;

and/or, $R^{1-5}$ is independently —C(=O)$NR^{11d1}R^{11d2}$, $R^{11d1}$ and $R^{11d2}$ are independently $C_{1-6}$ alkyl, or $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N";

and/or, $R^{1-7}$ is independently —C(=O)$NR^{11d1}R^{11d2}$, or, when the number of $R^{1-7}$ is more than one, two optional $R^{1-7}$, together with the atoms to which they are attached, independently form "3- to 8-membered heterocyclic containing 1 to 3 heteroatoms independently selected from O, S and N";

and/or, in $R^{1-7}$, $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N";

and/or, $R^{1-8}$ and is independently —C(=O) $R^{11a}$, —$S(O)_2R^{11f}$, —C(=O)$NR^{11d1}R^{11d2}$, or, when the number of $R^{1-8}$ is more than one, two optional $R^{1-8}$, together with the atoms to which they are attached, independently form "3- to 8-membered heterocyclic alkene containing 1 to 3 heteroatoms independently selected from O, S and N";

and/or, in $R^{1-8}$, $R^{11a}$ is $C_{1-6}$ alkyl, $C_{3-10}$ cycloalkyl, $C_{1-6}$ alkyl substituted with one or more $R^{1-2-1}$; $R^{1-2-1}$ is independently hydroxyl or $—NR^{12c}R^{12d}$, $R^{12c}$ and $R^{12d}$ are independently hydrogen;

and/or, in $R^{1-8}$, $R^{11f}$ is $C_{1-6}$ alkyl;

and/or, in $R^{1-8}$, $R^{11d2}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N";

and/or, $R^{1-9}$ is $—NR^{11b1}R^{11b2}$, $R^{11b1}$ and $R^{11b2}$ are independently hydrogen or $—C(=O)$ $R^{11h}$, $R^{11h}$ is $C_{1-6}$ alkyl;

and/or, $L_1$ is a bond or $C_{1-6}$ alkylene; $Q_1$ is hydrogen, cyano, hydroxyl, $C_{1-6}$ alkyl substituted with one or more halogen, $C_{1-6}$ alkyl substituted with one or more hydroxyl, $—OC_{1-6}$ alkyl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl;

and/or, $R^{5-1-2}$ is independently halogen;

and/or, $R^{5-1-3}$ is independently $C_{1-6}$ alkyl.

4. The compound containing structure of a five-membered heteroaromatic ring represented by formula II, a pharmaceutically acceptable salt thereof, or a stereoisomer thereof according to claim 1, wherein, $R^{a1}$, $R^{a2}$ and $R^{a3}$ are independently $C_{1-6}$ alkyl;

and/or, $L_1$ is a bond or $C_{1-6}$ alkylene; $Q_1$ is hydrogen, $C_{3-12}$ cycloalkyl, or $C_{1-6}$ alkyl substituted with one or more halogen; or, $L_1$ is $C_{1-6}$ alkylene, $Q_1$ is hydrogen, cyano, hydroxyl, $C_{1-6}$ alkyl substituted with one or more hydroxyl, $—OC_{1-6}$ alkyl, $C_{6-20}$ aryl substituted with one or more $R^{5-1-2}$ "5- to 12-membered heteroaryl containing 1 to 4 heteroatoms independently selected from O, S and N", or "5- to 12-membered heteroaryl containing 1 to 4 heteroatoms independently selected from O, S and N" substituted with one or more $R^{5-1-3}$.

5. The compound containing structure of a five-membered heteroaromatic ring represented by formula II, a pharmaceutically acceptable salt thereof, or a stereoisomer thereof according to claim 1, wherein, $A_1$ is $CR^1$, $R^1$ is hydrogen, halogen, or $C_{1-6}$ alkyl substituted with one or more $R^{1-1}$; provided that when multiple substituents are present, the substituents are the same or different; $R^{1-1}$ is halogen;

$A_5$ is $NR^{5d}$, $R^{5d}$ is

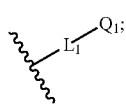

$L_1$ is a bond or $C_{1-6}$ alkylene;

$Q_1$ is $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, or $C_{3-12}$ cycloalkyl;

or, $A_1$ is $CR^1$, $A_5$ is $NR^{5d}$; $R^1$ is $C_{1-6}$ alkyl substituted with one or more $R^{1-1}$, $C_{3-10}$ cycloalkyl substituted with one or more $R^{1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, or, $C_{2-6}$ alkynyl substituted with one or more $R^{1-9}$;

$R^{5d}$ is

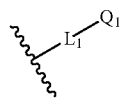

$L_1$ is a bond or $C_{1-6}$ alkylene;

$Q_1$ is hydrogen, cyano, hydroxyl, $C_{1-6}$ alkyl substituted with one or more halogen, $C_{1-6}$ alkyl substituted with one or more hydroxyl, $—OC_{1-6}$ alkyl, "5- to 12-membered heteroaryl containing 1 to 4 heteroatoms independently selected from O, S and N" substituted with one or more $R^{5-1-3}$, or $C_{3-12}$ cycloalkyl.

6. The compound containing structure of a five-membered heteroaromatic ring represented by formula II, a pharmaceutically acceptable salt thereof, or a stereoisomer thereof according to claim 1, wherein, when the definition of $R^{a1}$, $R^{a2}$, $R^{a3}$, $R^{a1-1}$, $R^{a2-1}$, $R^{a2-2}$, $R^{a-1}$, $R^{a-2}$, $R^{a-31}$, $R^{a-32}$, $R^{a-4}$, $R^{a-51}$, $R^{a-52}$, $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{1-1-1-1}$, $R^{1-2-1}$, $R^{1-2-2}$, $R^{1-2-3}$, $R^{1-2-4}$, $R^{1-2-5}$, $R^{1-2-6}$, $R^{1-2-7}$, $R^{1-2-8}$, $R^{1-2-1-1}$, $R^{1-3-1}$, $R^{1-3-2}$, $R^{1-3-3}$, $R^{1-3-4}$, $R^{1-3-5}$, $R^{1-3-6}$, $R^{1-4-1}$, $A_2$, $A_3$, $R^{6-1}$, $Q_1$, $R^{5-1-1}$, $R^{3-1-2}$, $R^{5-1-3}$, $R^{5-1-4}$, $R^{5-1-5}$, $R^{5-1-6}$, $R^{5-1-7}$, $R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$, $R^{51d2}$ and $R^{1-5-1}$ refers to halogen, the halogen is fluorine, chlorine, bromine or iodine;

and/or, when the definition of $R^{a1}$, $R^{a2}$, $R^{a3}$, $R^{a1-1}$, $R^{a2-1}$, $R^{a2-2}$, $R^{a-1}$, $R^{a-2}$, $R^{a-31}$, $R^{a-32}$, $R^{a-4}$, $R^{a-51}$, $R^{a-52}$, $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-1-1}$, $R^{1-1-2}$, $R^{1-1-3}$, $R^{1-1-4}$, $R^{1-1-5}$, $R^{1-1-6}$, $R^{1-1-7}$, $R^{1-1-8}$, $R^{1-1-1-1}$, $R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11e1}$, $R^{11d1}$, $R^{11d2}$, $R^{11e1}$, $R^{11e2}$, $R^{11f}$ and $R^{11g}$, $R^{1-2-1}$, $R^{1-2-2}$, $R^{1-2-3}$, $R^{1-2-4}$, $R^{1-2-5}$, $R^{1-2-6}$, $R^{1-2-7}$, $R^{1-2-8}$, $R^{1-2-1-1}$, $R^{1-3-1}$, $R^{1-3-2}$, $R^{1-3-3}$, $R^{1-3-4}$, $R^{1-3-5}$, $R^{1-3-6}$, $R^{1-4-1}$, $R^{6-1}$, $Q_1$, $R^{5-1-1}$, $R^{5-1-2}$, $R^{5-1-3}$, $R^{5-1-4}$, $R^{5-1-5}$, $R^{5-1-6}$, $R^{5-1-7}$, $R^{52a}$, $R^{52b1}$, $R^{52b2}$, $R^{52c}$, $R^{52d1}$, $R^{52d2}$, $R^{51a}$, $R^{51b1}$, $R^{51b2}$, $R^{51c}$, $R^{51d1}$, $R^{51d2}$ and $R^{1-5-1}$ refers to $C_{1-6}$ alkyl, the $C_{1-6}$ alkyl is $C_{1-4}$ alkyl;

and/or, when the definition of $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d2}$, $R^{11d2}$, $R^{11e1}$, $R^{11e2}$, $R^{11f}$ and $R^{11g}$ refers to $C_{3-10}$ cycloalkyl, the $C_{3-10}$ cycloalkyl is cyclohexyl, cyclopentyl, cyclobutyl or cyclopropyl;

and/or, when the definition of $R^1$, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1a}$, $R^{1b1}$, $R^{1b2}$, $R^{1c}$, $R^{1d1}$, $R^{1d2}$, $R^{11a}$, $R^{11b1}$, $R^{11b2}$, $R^{11c}$, $R^{11d2}$, $R^{11d2}$, $R^{11e1}$, $R^{11e2}$, $R^1$If, $R^{11g}$ and $Q_1$ refers to $C_{6-20}$ aryl, the $C_{6-20}$ aryl is $C_{6-10}$ aryl;

and/or, when $R^{a1}$ is $C_{1-6}$ alkyl substituted with one or more halogen, the $C_{1-6}$ alkyl substituted with one or more halogen is $C_{1-2}$ alkyl substituted with one halogen;

and/or, when $R^{a2}$ and $R^{a3}$, together with the carbon atom to which they are attached form $C_{3-7}$ cycloalkane, the $C_{3-7}$ cycloalkane is $C_{3-6}$ cycloalkane;

and/or, when $R^1$ is $C_{1-6}$ alkyl substituted with one or more $R^{1-1}$ and $R^{1-1}$ is halogen, the $R^1$ is $C_{1-2}$ alkyl substituted with two or three halogen;

and/or, when $R^{1-1}$ is independently "4- to 10-membered heterocycloalkyl containing 1 to 3 heteroatoms independently selected from O, S and N" substituted with one or more $R^{1-1-4}$, the "4-to 10-membered heterocycloalkyl containing 1 to 3 heteroatoms independently selected from O, S and N" substituted with one or more $R^{1-1-4}$ is monocyclic or bridged cycloalkyl;

and/or, when $R^1$ is "4- to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{1-4}$, the "4- to 12-membered heterocycloalkyl containing 1 to 3 heteroatoms independently selected from O, S and N" and the "4- to 12-membered heterocycloalkyl containing 1 to 3 heteroatoms independently selected from O, S and N" in the "4- to 12-membered heterocycloalkyl containing 1 to 3 heteroatoms independently selected from O, S and N" substituted with one or more $R^{1-4}$ is monocyclic heteroalkyl, spirocyclic heteroalkyl, fused hetero alkyl or bridged cycloalkyl;

and/or, when $R^1$ is "4- to 12-membered heterocycloalkyl containing 1 to 3 heteroatoms independently selected from O, S and N" substituted with one or more $R^{1-4}$, the "4- to 12-membered heterocycloalkyl containing 1 to 3 heteroatoms independently selected from O, S and N" substituted with one or more $R^{1-4}$ is "6-membered heterocycloalkyl containing 1 to 3 heteroatoms independently selected from O, S and N" substituted with one or more $R^{1-4}$; and/or, in $R^{1-3}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "3- to 6-membered heterocyclic alkane containing 1 heteroatom being N, or, 3- to 6-membered heterocyclic alkane containing 2 heteroatoms being N and O";

and/or, when $R^{1-4}$ is "4- to 10-membered heterocycloalkyl containing 1 to 3 heteroatoms independently selected from O, S and N" substituted with one or more $R^{1-1-4}$, the "4- to 10-membered heterocycloalkyl containing 1 to 3 heteroatoms independently selected from O, S and N" substituted with one or more $R^{1-1-4}$ is "4- to 6-membered heterocycloalkyl containing 1 heteroatom being N";

and/or, in $R^{1-5}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "3- to 6-membered heterocyclic alkane containing 1 heteroatom being N, or, 3- to 6-membered heterocyclic alkane containing 2 heteroatoms being N and O";

and/or, when $R^1$ is "5- to 12-membered heteroaryl containing 1 to 4 heteroatoms independently selected from O, S and N", or "5- to 12-membered heteroaryl containing 1 to 4 heteroatoms independently selected from O, S and N" substituted with $R^{1-6}$, the "5- to 12-membered heteroaryl containing 1 to 4 heteroatoms independently selected from O, S and N" and "5- to 12-membered heteroaryl containing 1 to 4 heteroatoms independently selected from O, S and N" in the "5- to 12-membered heteroaryl containing 1 to 4 heteroatoms independently selected from O, S and N" substituted with $R^{1-6}$ are "5- to 9-membered heteroaryl containing 1 to 3 heteroatoms independently selected from O, S and N";

and/or, when two optional $R^{1-4}$, together with the atoms to which they are attached, independently form "5- to 12-membered heteroaromatic ring containing 1 to 4 heteroatoms independently selected from O, S and N", the "5- to 12-membered heteroaromatic ring containing 1 to 4 heteroatoms independently selected from O, S and N" is "5- to 6-membered heteroaromatic ring containing 1 to 2 heteroatoms independently selected from O, S and N";

and/or, in $R^{1-4}$, when $R^{11a}$ is $C_{1-6}$ alkyl substituted with one or more $R^{1-2-1}$, $R^{1-2-1}$ is halogen, the $R^{11a}$ is $C_{1-2}$ alkyl substituted with one or more halogen;

and/or, in $R^{1-4}$, when $R^{11a}$ is "5- to 12-membered heteroaryl containing 1 to 4 heteroatoms independently selected from O, S and N", the "5- to 12-membered heteroaryl containing 1 to 4 heteroatoms independently selected from O, S and N" is "5- to 6-membered heteroaryl containing 1 to 2 heteroatoms independently selected from O, S and N";

and/or, in $R^{1-4}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", or "3- to 8-membered heterocyclic alkane containing 1 to 3 heteroatoms, wherein, one heteroatom is N, the other one or two heteroatoms independently selected from O, S and N" substituted with $R^{1-1-4}$, the "3- to 8-membered heterocyclic alkane containing 1 to 3 heteroatoms, wherein, one heteroatom is N, the other one or two heteroatoms independently selected from O, S and N" is "4- to 6-membered heterocyclic alkane containing 1 heteroatom being N";

and/or, in $R^{1-7}$, when $R^{11d1}$ and $R^{11d2}$ together with the nitrogen atom to which they are attached independently form "3- to 8-membered heterocyclic alkane containing 1 to 3 heteroatoms, wherein, one heteroatom is N, the other one or two heteroatoms independently selected from O, S and N", the "3- to 8-membered heterocyclic alkane containing 1 to 3 heteroatoms, wherein, one heteroatom is N, the other one or two heteroatoms independently selected from O, S and N" is "4- to 6-membered heterocyclic alkane containing 1 heteroatom being N";

and/or, when $R^1$ is "5- to 7-membered heterocycloalkenyl containing 1 to 3 heteroatoms independently selected from O, S and N" substituted with one or more $R^{1-8}$, or "5- to 7-membered heterocycloalkenyl containing 1 to 3 heteroatoms independently selected from O, S and N" substituted with one or more $R^{1-8}$, the "5- to 7-membered heterocycloalkenyl containing 1 to 3 heteroatoms independently selected from O, S and N" is monocyclic or bridged heterocycloalkenyl;

and/or, when $R^1$ is $C_{2-6}$ alkynyl substituted with one or more $R^{1-9}$, the $C_{2-6}$ alkynyl is $C_{2-3}$ alkynyl;

and/or, when $Q_1$ is $C_{1-6}$ alkyl substituted with one or more halogen, the $Q_1$ is $C_{1-2}$ alkyl substituted with 2 to 3 halogen;

and/or, when $Q_1$ is $C_{1-6}$ alkyl substituted with one or more hydroxyl, the $Q_1$ is $C_{1-2}$ alkyl substituted with 1 to 3 hydroxyl;

and/or, when $Q_1$ is "5- to 12-membered heteroaryl containing 1 to 4 heteroatoms independently selected from O, S and N", or "5- to 12-membered heteroaryl containing 1 to 4 heteroatoms independently selected from O, S and N" substituted with one or more $R^{5-1-3}$, the "5- to 12-membered heteroaryl containing 1 to 4 heteroatoms independently selected from O, S and N" is "5- to 9-membered heteroaryl containing 1 to 2 heteroatoms independently selected from S and N";

and/or, when $Q_1$ is $C_{3-12}$ cycloalkyl, the $C_{3-12}$ cycloalkyl is $C_{3-6}$ cycloalkyl;

and/or, when $R^1$ and $R^{5d}$, together with the atoms to which they are attached form "5- to 12-membered heterocyclic olefin containing 1 to 3 heteroatoms independently selected from O, S and N"; the "5- to 12-membered heterocyclic olefin containing 1 to 3 heteroatoms independently selected from O, S and N" is "5- to 7-membered heterocyclic olefin containing 1 to 2 heteroatoms independently selected from O and N";

and/or, when $L_1$ is $C_{1-6}$ alkylene, the $C_{1-6}$ alkylene is —$CH_2$—, —$CH_2CH_2$—, —$CH_2CH_2CH_2$—, —$CH(CH_3)CH_2$—, —$CH_2CH_2CH_2CH_2$—, —$CH(CH_3)CH_2CH_2$—, —$CH_2CH(CH_3)CH_2$— or —$C(CH_3)_2CH_2$—.

7. The compound containing structure of a five-membered heteroaromatic ring represented by formula II, a pharmaceutically acceptable salt thereof, or a stereoisomer thereof according to claim 1, wherein,

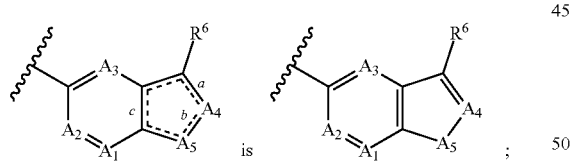

and/or, $A_2$ is CH or CF;
and/or, $A_3$ is CH or CF; and/or, $A_1$ is $CR^1$; $R^1$ is hydrogen, —F, —$CF_3$,

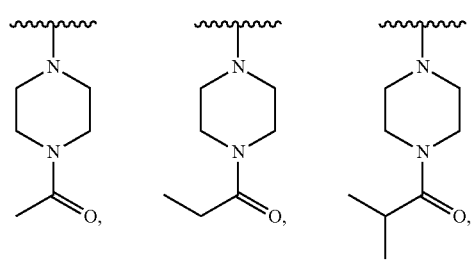

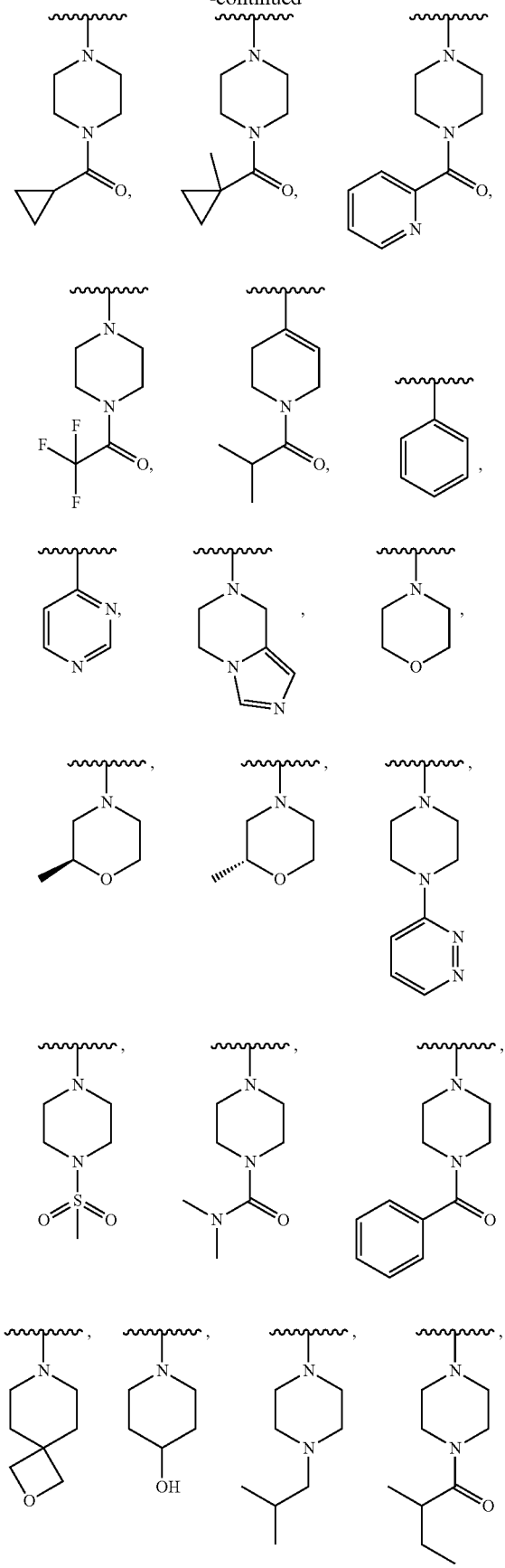

425
-continued
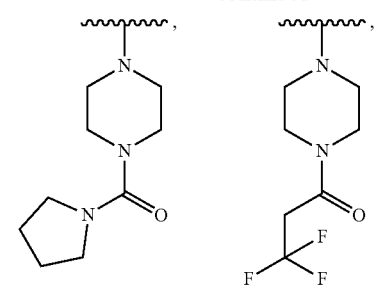 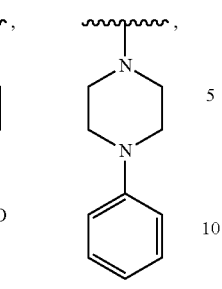
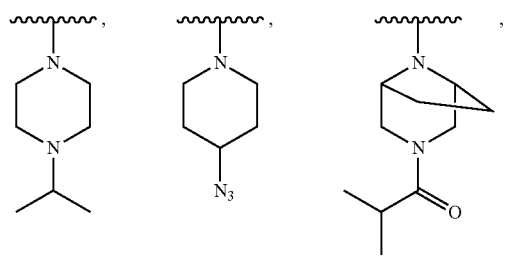
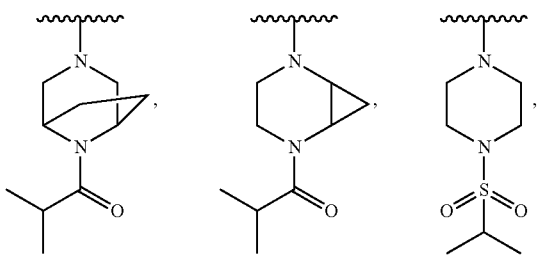
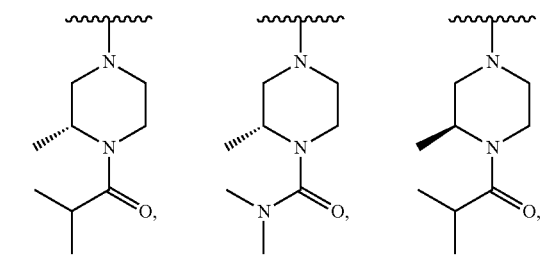
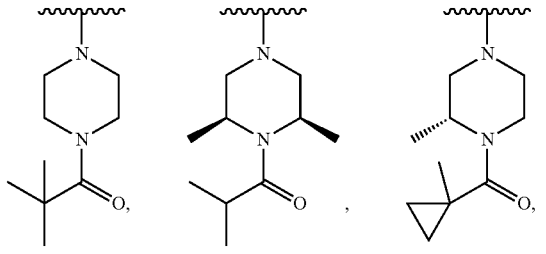
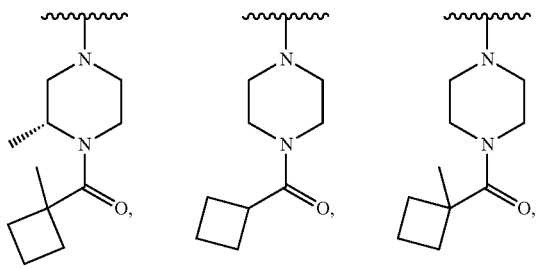
426
-continued
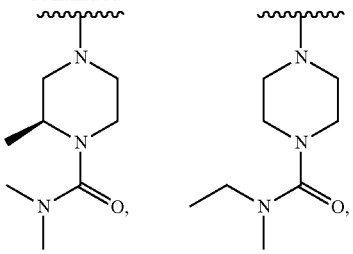
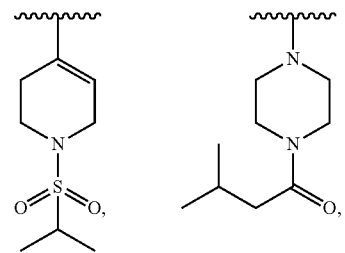
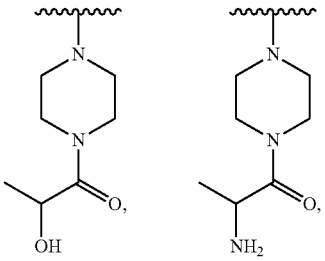
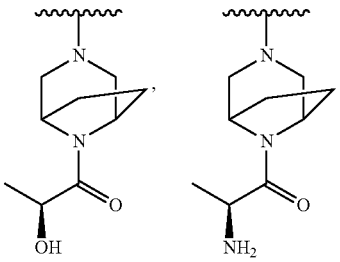
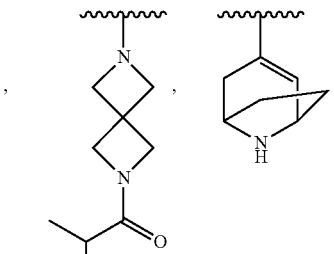
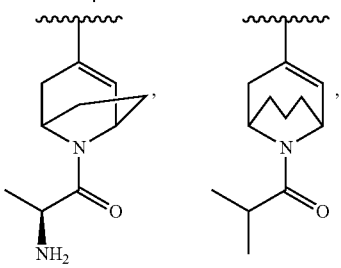

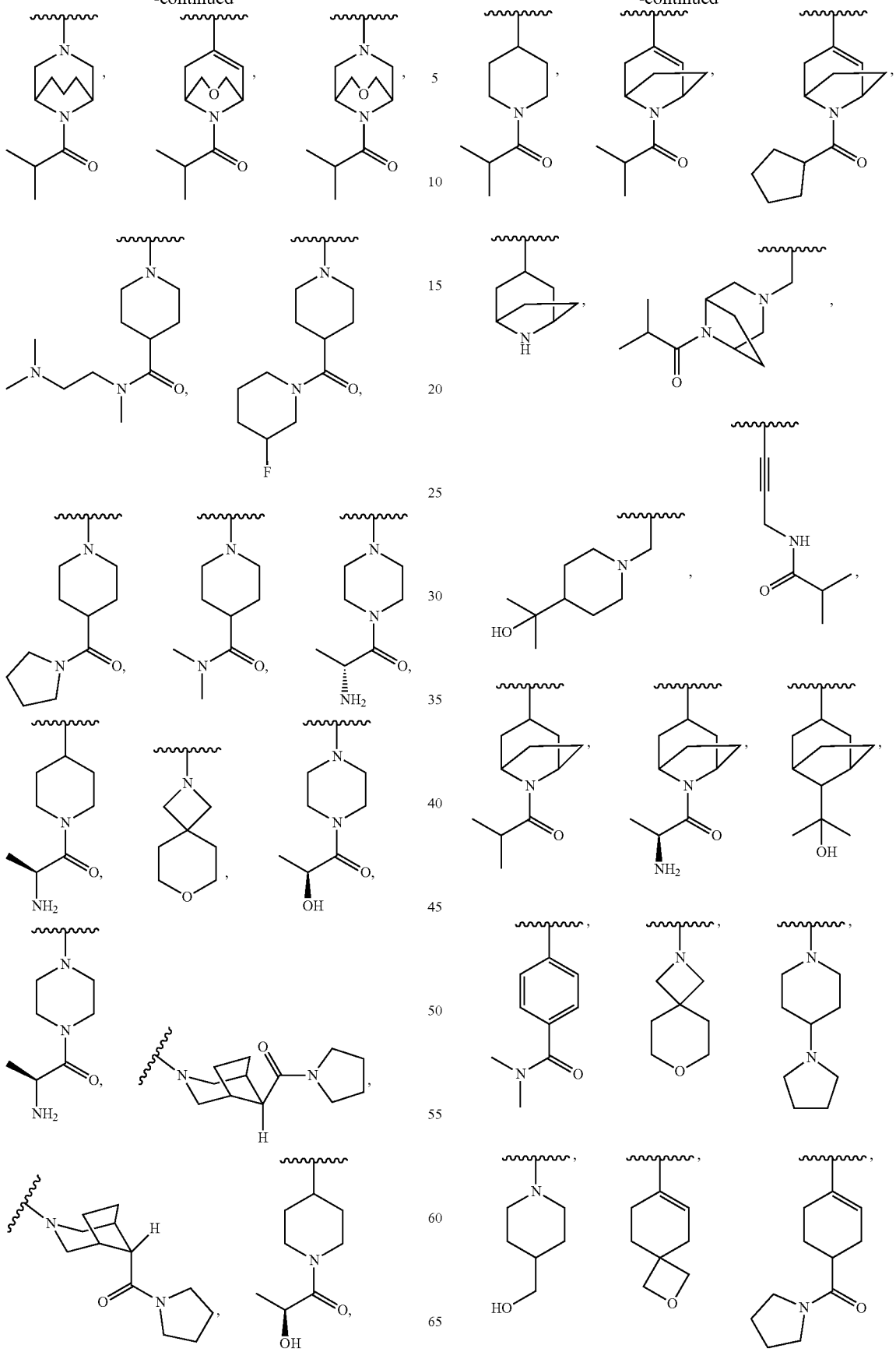

-continued

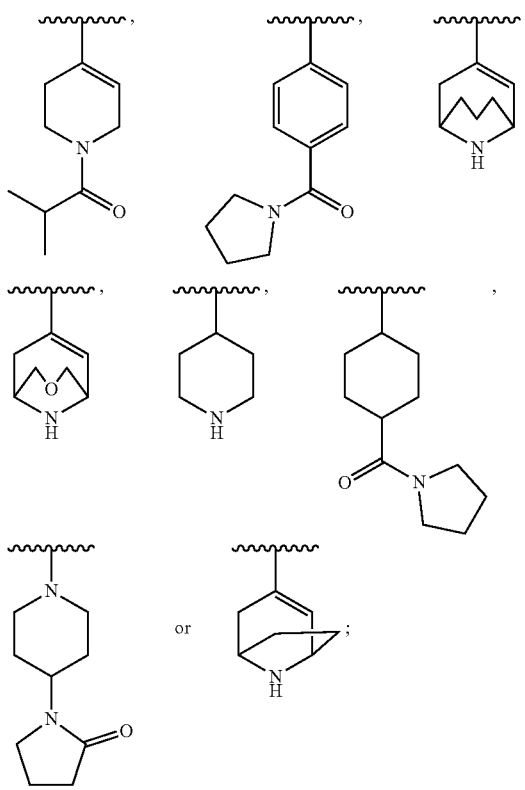

and/or, $A_4$ is N;
and/or, $A_5$ is $NR^{5d}$, $R^{5d}$ is H, —$CH_3$,

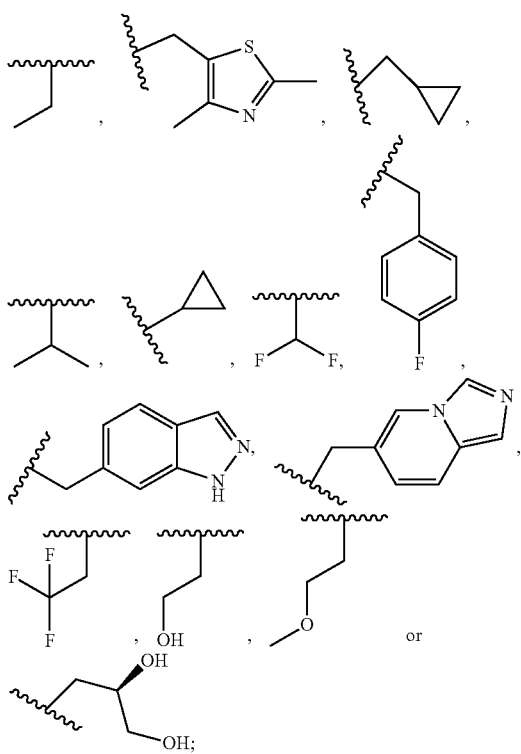

and/or, $R^6$ is

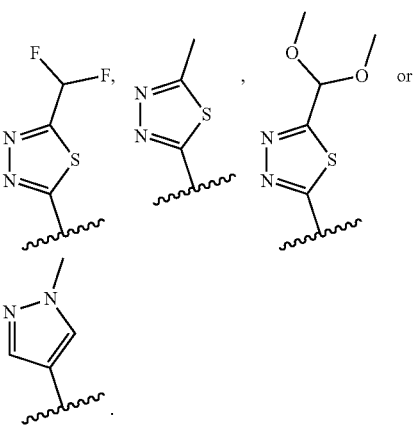

8. The compound containing structure of a five-membered heteroaromatic ring represented by formula II, a pharmaceutically acceptable salt thereof, or a stereoisomer thereof according to claim 1, wherein, compound containing structure of a five-membered heteroaromatic ring represented by Formula II is defined as solution 1, solution 2 or solution 3;
solution 1: A compound containing structure of a five-membered heteroaromatic ring represented by formula IV, a pharmaceutically acceptable salt thereof, a stereoisomer thereof,

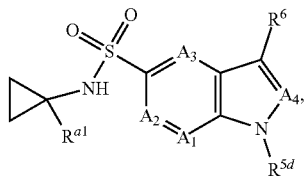

IV wherein, $R^{a1}$ is hydrogen, halogen, cyano, $C_{1-6}$ alkyl, $C_{2-6}$ alkenyl, $C_{2-6}$ alkynyl, —$OR^{a-1}$, $C(=O)R^{a-2}$, —$NR^{a-31}R^{a-32}$, —$C(=O)OR^{a-4}$, —$C(=O)NR^{a-51}R^{a-52}$, or, $C_{1-6}$ alkyl substituted with one or more $R^{a1-1}$, $R^{a1-1}$ is halogen, hydroxyl or —$OC_{1-6}$ alkyl;

$A_1$ is $CR^1$;
$R^1$ is hydrogen, $C_{1-6}$ alkyl substituted with one or more $R^{1-1}$, halogen, $C_{3-10}$ cycloalkyl, $C_{3-10}$ cycloalkyl substituted with one or more $R^{1-3}$, "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N" or "5- to 7-membered heterocycloalkenyl containing 1 to 3 heteroatoms independently selected from O, S and N" substituted with one or more $R^{1-8}$, provided that when multiple substituents are present, the substituents are the same or different;
$R^{1-1}$, $R^{1-3}$, $R^{1-4}$, $R^{1-5}$, $R^{1-6}$, $R^{1-7}$ and $R^{1-8}$ are independently halogen, hydroxyl, cyano, oxo, $C_{1-6}$ alkyl, $C_{1-6}$ alkyl substituted with one or more $R^{1\text{-}1\text{-}1}$, $C_{2\text{-}6}$ alkenyl, $C_{2\text{-}6}$ alkynyl, —$OC_{1\text{-}6}$ alkyl, —$OC_{1\text{-}6}$ alkyl substituted with one or more $R^{1\text{-}1\text{-}2}$, —C(=O) $R^{11a}$, —$NR^{11b1}R^{11b2}$, —C(=O)$OR^{11c}$, —C(=O)$NR^{11d1}R^{11d2}$, —S(O)$_2NR^{11e1}R^{11e2}$, —S(O)$_2R^{11f}$, $C_{3\text{-}10}$ cycloalkyl, $C_{3\text{-}10}$ cycloalkyl substituted with one or more $R^{1\text{-}1\text{-}3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1\text{-}1\text{-}4}$, $C_{6\text{-}20}$ aryl, $C_{6\text{-}20}$ aryl substituted with one or more $R^{1\text{-}1\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1\text{-}1\text{-}6}$, $C_{5\text{-}7}$ cycloalkenyl, $C_{5\text{-}7}$ cycloalkenyl substituted with one or more $R^{1\text{-}1\text{-}7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1\text{-}1\text{-}8}$; provided that when multiple substituents are present, the substituents are the same or different;

$R^{1\text{-}1\text{-}1}$, $R^{1\text{-}1\text{-}2}$, $R^{1\text{-}1\text{-}3}$, $R^{1\text{-}1\text{-}4}$, $R^{1\text{-}1\text{-}5}$, $R^{1\text{-}1\text{-}6}$, $R^{1\text{-}1\text{-}7}$ and $R^{1\text{-}1\text{-}8}$ are independently halogen, hydroxyl, oxo, $C_{1\text{-}6}$ alkyl, or, $C_{1\text{-}6}$ alkyl substituted with one or more $R^{1\text{-}1\text{-}1\text{-}1}$; provided that when multiple substituents are present, the substituents are the same or different;

$R^{1\text{-}1\text{-}1\text{-}1}$ is halogen, hydroxyl, —$OC_{1\text{-}6}$ alky or —$NR^aR^b$, $R^a$ and $R^b$ are independently hydrogen or $C_{1\text{-}6}$ alkyl;

$R^{11a}$, $R^{11b1}$, $R^{11b2}$, $R^{11c}$, $R^{11d1}$, $R^{11d2}$, $R^{11e1}$, $R^{11e2}$ and $R^{11f}$ are independently hydrogen, $C_{1\text{-}6}$ alkyl, $C_{1\text{-}6}$ alkyl substituted with one or more $R^{1\text{-}2\text{-}1}$, —$OC_{1\text{-}6}$ alkyl, —$OC_{1\text{-}6}$ alkyl substituted with one or more $R^{1\text{-}2\text{-}2}$, $C_{3\text{-}10}$ cycloalkyl, $C_{3\text{-}10}$ cycloalkyl substituted with one or more $R^{1\text{-}2\text{-}3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1\text{-}2\text{-}4}$, $C_{6\text{-}20}$ aryl, $C_{6\text{-}20}$ aryl substituted with one or more $R^{1\text{-}2\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1\text{-}2\text{-}6}$, $C_{5\text{-}7}$ cycloalkenyl, $C_{5\text{-}7}$ cycloalkenyl substituted with one or more $R^{1\text{-}2\text{-}7}$, "5- to 7-membered heterocycloalkenyl containing 1 to 3 heteroatoms independently selected from O, S and N", or "5- to 7-membered heterocycloalkenyl containing 1 to 3 heteroatoms independently selected from O, S and N" substituted with one or more $R^{1\text{-}2\text{-}8}$, provided that when multiple substituents are present, the substituents are the same or different;

$R^{1\text{-}2\text{-}1}$, $R^{1\text{-}2\text{-}2}$, $R^{1\text{-}2\text{-}3}$, $R^{1\text{-}2\text{-}4}$, $R^{1\text{-}2\text{-}5}$, $R^{1\text{-}2\text{-}6}$, $R^{1\text{-}2\text{-}7}$ and $R^{1\text{-}2\text{-}8}$ are independently halogen, oxo, $C_{1\text{-}6}$ alkyl, $C_{1\text{-}6}$ alkyl substituted with one or more $R^{1\text{-}2\text{-}1\text{-}1}$; provided that when multiple substituents are present, the substituents are the same or different;

$R^{1\text{-}2\text{-}1\text{-}1}$ is independently halogen, hydroxyl, —$OC_{1\text{-}6}$ alkyl or —$NR^cR^d$, $R^c$ and $R^d$ are independently hydrogen or $C_{1\text{-}6}$ alkyl;

or, when the number of $R^{1\text{-}3}$, $R^{1\text{-}4}$, $R^{1\text{-}5}$, $R^{1\text{-}6}$, $R^{1\text{-}7}$, $R^{1\text{-}8}$, $R^{1\text{-}1\text{-}3}$, $R^{1\text{-}1\text{-}4}$, $R^{1\text{-}1\text{-}5}$, $R^{1\text{-}1\text{-}6}$, $R^{1\text{-}1\text{-}7}$, $R^{1\text{-}1\text{-}8}$, $R^{1\text{-}2\text{-}3}$, $R^{1\text{-}2\text{-}4}$, $R^{1\text{-}2\text{-}5}$, $R^{1\text{-}2\text{-}6}$, $R^{1\text{-}2\text{-}7}$ or $R^{1\text{-}2\text{-}8}$ is more than one, two optional $R^{1\text{-}3}$, two optional $R^{1\text{-}4}$, two optional $R^{1\text{-}5}$, two optional $R^{1\text{-}6}$, two optional $R^{1\text{-}7}$, two optional $R^{1\text{-}8}$, two optional $R^{1\text{-}1\text{-}3}$, two optional $R^{1\text{-}1\text{-}4}$, two optional $R^{1\text{-}1\text{-}5}$, two optional $R^{1\text{-}1\text{-}6}$, two optional $R^{1\text{-}1\text{-}7}$, two optional $R^{1\text{-}1\text{-}8}$, two optional $R^{1\text{-}2\text{-}3}$, two optional $R^{1\text{-}2\text{-}4}$, two optional $R^{1\text{-}2\text{-}5}$, two optional $R^{1\text{-}2\text{-}6}$, two optional $R^{1\text{-}2\text{-}7}$ or two optional $R^{1\text{-}2\text{-}8}$, together with the atoms to which they are attached, independently form 3- to 8-membered carbon ring, "3- to 8-membered carbon ring" substituted with one or more $R^{1\text{-}3\text{-}1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1\text{-}3\text{-}2}$, $C_{6\text{-}20}$ aromatic ring, $C_{6\text{-}20}$ aromatic ring substituted with one or more $R^{1\text{-}3\text{-}3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1\text{-}3\text{-}4}$, $C_{5\text{-}7}$ cyclic olefin, $C_{5\text{-}7}$ cyclic olefin substituted with one or more $R^{1\text{-}3\text{-}5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1\text{-}3\text{-}6}$, provided that when multiple substituents are present, the substituents are the same or different;

$R^{1\text{-}3\text{-}1}$, $R^{1\text{-}3\text{-}2}$, $R^{1\text{-}3\text{-}3}$, $R^{1\text{-}3\text{-}4}$, $R^{1\text{-}3\text{-}5}$ and $R^{1\text{-}3\text{-}6}$ are independently oxo, hydroxyl, halogen, $C_{1\text{-}6}$ alkyl, $C_{1\text{-}6}$ alkyl substituted with one or more halogen, —$OC_{1\text{-}6}$ alkyl, or, —$OC_{1\text{-}6}$ alkyl substituted with one or more halogen;

or, $R^{a\text{-}31}$ and $R^{a\text{-}32}$, $R^{a\text{-}51}$ and $R^{a\text{-}52}$, $R^{1b1}$ and $R^{1b2}$, $R^{1d1}$ and $R^{1d2}$, $R^{11b1}$ and $R^{11b2}$, $R^{11d2}$ and $R^{11d2}$, $R^{11e1}$ and $R^{11e2}$, $R^a$ and $R^b$, Re and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1\text{-}4\text{-}1}$; $R^{1\text{-}4\text{-}1}$ is independently oxo, hydroxyl, halogen, $C_{1\text{-}6}$ alkyl, $C_{1\text{-}6}$ alkyl substituted with one or more halogen, —$OC_{1\text{-}6}$ alkyl, or, —$OC_{1\text{-}6}$ alkyl substituted with one or more halogen;

$A_2$ and $A_3$ are independently $CR^2$, $R^2$ is hydrogen or halogen;

$A_4$ is N;

$R^{5d}$ is

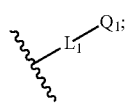

$L_1$ is a bond or $C_{1\text{-}6}$ alkylene;

$Q_1$ is hydrogen, halogen, cyano, $C_{2\text{-}6}$ alkenyl, $C_{2\text{-}6}$ alkynyl, hydroxyl, —C(=O) $R^{52a}$, —$NR^{52b1}R^{52b2}$, —C(=O)$OR^{52c}$, —C(=O)$NR^{52d1}R^{52d2}$, $C_{1\text{-}6}$ alkyl substituted with one or more halogen, —$OC_{1\text{-}6}$ alkyl, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5\text{-}1\text{-}3}$, $C_{3\text{-}12}$ cycloalkyl, $C_{3\text{-}12}$ cycloalkyl substituted with one or more $R^{5\text{-}1\text{-}4}$, "4- to 12-membered heterocycloalkyl containing 1 to 3 heteroatoms independently selected from O, S and N" or "4- to 12-membered heterocycloalkyl containing 1 to 3 heteroatoms independently selected from O, S and N" substituted with one or more $R^{5\text{-}1\text{-}5}$; provided that when multiple substituents are present, the substituents are the same or different;

$R^{5\text{-}1\text{-}3}$, $R^{5\text{-}1\text{-}4}$ and $R^{5\text{-}1\text{-}5}$ are independently halogen, hydroxyl, oxo, cyano, $C_{1\text{-}6}$ alkyl, $C_{1\text{-}6}$ alkyl substituted with one or more halogen, $-OC_{1\text{-}6}$ alkyl, $-OC_{1\text{-}6}$ alkyl substituted with one or more halogen, $-C(=O)R^{51a}$, $-NR^{51b1}R^{51b2}$, $-C(=O)OR^{51c}$, or $-C(=O)NR^{51d1}R^{51d2}$; provided that when multiple substituents are present, the substituents are the same or different;

$R^{52a}$, $R^{52b1}$, $R^{52b}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1\text{-}6}$ alkyl, or, $C_{1\text{-}6}$ alkyl substituted with one or more halogen;

or, $R^{52b1}$ and $R^{52b}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1\text{-}5\text{-}1}$, $R^{1\text{-}5\text{-}1}$ is oxo, hydroxyl, halogen, $C_{1\text{-}6}$ alkyl, $C_{1\text{-}6}$ alkyl substituted with one or more halogen, $-OC_{1\text{-}6}$ alkyl, $-OC_{1\text{-}6}$ alkyl substituted with one or more halogen; provided that when multiple substituents are present, the substituents are the same or different;

$R^6$ is independently "5-membered heteroaryl containing 1 to 4 heteroatoms independently selected from O, S and N", or "5-membered heteroaryl containing 1 to 4 heteroatoms independently selected from O, S and N" substituted with one or more $R^{6\text{-}1}$;

$R^{6\text{-}1}$ is $C_{1\text{-}6}$ alkyl, or $C_{1\text{-}6}$ alkyl substituted with one or more halogen;

solution 2: A compound containing structure of a five-membered heteroaromatic ring represented by Formula IV', a pharmaceutically acceptable salt thereof, a stereoisomer thereof,

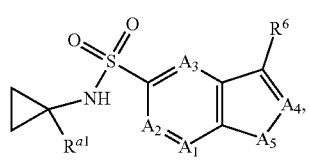

IV'

$R^{a1}$ is hydrogen, halogen, cyano, $C_{1\text{-}6}$ alkyl, $C_{2\text{-}6}$ alkenyl, $C_{2\text{-}6}$ alkynyl, $-OR^{a\text{-}1}$, $-C(=O)R^{a\text{-}2}$, $-NR^{a\text{-}31}R^{a\text{-}32}$, $-C(=O)OR^{a\text{-}4}$, $-C(=O)NR^{a\text{-}51}R^{a\text{-}52}$, or, $C_{1\text{-}6}$ alkyl substituted with one or more $R^{a1\text{-}1}$, $R^{a1\text{-}1}$ is halogen, hydroxy or $-OC_{1\text{-}6}$ alkyl;

$A_1$ is $CR^1$;

$R^1$ is hydrogen, $C_{1\text{-}6}$ alkyl, $C_{1\text{-}6}$ alkyl substituted with one or more $R^{1\text{-}1}$, halogen, $C_{3\text{-}10}$ cycloalkyl, $C_{3\text{-}10}$ cycloalkyl substituted with one or more $R^{1\text{-}3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1\text{-}4}$, $C_{6\text{-}20}$ aryl, $C_{6\text{-}20}$ aryl substituted with one or more $R^{1\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1\text{-}6}$, $C_{5\text{-}7}$ cycloalkenyl, $C_{5\text{-}7}$ cycloalkenyl substituted with one or more $R^{1\text{-}7}$, "5- to 7-membered heterocycloalkenyl containing 1 to 3 heteroatoms independently selected from O, S and N", or "5- to 7-membered heterocycloalkenyl containing 1 to 3 heteroatoms independently selected from O, S and N" substituted with one or more $R^{1\text{-}8}$; provided that when multiple substituents are present, the substituents are the same or different;

$R^{1\text{-}1}$, $R^{1\text{-}3}$, $R^{1\text{-}4}$, $R^{1\text{-}5}$, $R^{1\text{-}6}$, $R^{1\text{-}7}$ and $R^{1\text{-}8}$ are independently azide, halogen, hydroxyl, cyano, oxo, $C_{1\text{-}6}$ alkyl, $C_{1\text{-}6}$ alkyl substituted with one or more $R^{1\text{-}1\text{-}1}$, $C_{2\text{-}6}$ alkenyl, $C_{2\text{-}6}$ alkynyl, $-OC_{1\text{-}6}$ alkyl, $-OC_{1\text{-}6}$ alkyl substituted with one or more $R^{1\text{-}1\text{-}2}$, $-C(=O)R^{11a}$, $-NR^{11b1}R^{11b2}R^{11b2}$, $-C(=O)OR^{11c}$, $-C(=O)NR^{11d1}R^{11d2}$, $-S(O)_2NR^{11e1}R^{11e2}$, $-S(O)_2R^{11f}$, $C_{3\text{-}10}$ cycloalkyl, $C_{3\text{-}10}$ cycloalkyl substituted with one or more $R^{1\text{-}1\text{-}3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1\text{-}1\text{-}4}$, $C_{6\text{-}20}$ aryl, $C_{6\text{-}20}$ aryl substituted with one or more $R^{1\text{-}1\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1\text{-}1\text{-}6}$, $C_{5\text{-}7}$ cycloalkenyl, $C_{5\text{-}7}$ cycloalkenyl substituted with one or more $R^{1\text{-}1\text{-}7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1\text{-}1\text{-}8}$, provided that when multiple substituents are present, the substituents are the same or different;

$R^{1\text{-}1\text{-}1}$, $R^{1\text{-}1\text{-}2}$, $R^{1\text{-}1\text{-}3}$, $R^{1\text{-}1\text{-}4}$, $R^{1\text{-}1\text{-}5}$, $R^{1\text{-}1\text{-}6}$, $R^{1\text{-}1\text{-}7}$ and $R^{1\text{-}1\text{-}8}$ are independently halogen, hydroxyl, oxo, $C_{1\text{-}6}$ alkyl, or, $C_{1\text{-}6}$ alkyl substituted with one or more $R^{1\text{-}1\text{-}1\text{-}1}$, provided that when multiple substituents are present, the substituents are the same or different;

$R^{1\text{-}1\text{-}1\text{-}1}$ is halogen, hydroxyl, $-OC_{1\text{-}6}$ alkyl or $-NR^aR^b$, $R^a$ and $R^b$ are independently hydrogen or $C_{1\text{-}6}$ alkyl;

$R^{11a}$, $R^{11b1}$, $R^{11b2}$, $R^{11c}$, $R^{11d2}$, $R^{11d2}$, $R^{11e1}$, $R^{11e2}$, and $R^{11f}$ are independently hydrogen, $C_{1\text{-}6}$ alkyl, $C_{1\text{-}6}$ alkyl substituted with one or more $R^{1\text{-}2\text{-}1}$, $-OC_{1\text{-}6}$ alkyl, $-OC_{1\text{-}6}$ alkyl substituted with one or more $R^{1\text{-}2\text{-}2}$, $C_{3\text{-}10}$ cycloalkyl, $C_{3\text{-}10}$ cycloalkyl substituted with one or more $R^{1\text{-}2\text{-}3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1\text{-}2\text{-}4}$, $C_{6\text{-}20}$ aryl, $C_{6\text{-}20}$ aryl substituted with one or more $R^{1\text{-}2\text{-}5}$, "5- to 12-membered heteroaryl containing 1 to 4 heteroatoms independently selected from O, S and N", "5- to 12-membered heteroaryl containing 1 to 4 heteroatoms independently selected from O, S and N"

substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$ or, —C(=O) $R^{11h}$; $R^{11h}$ is $C_{1-6}$ alky; provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, hydroxyl, —$NR^{12c}R^{12d}$, oxo, $C_{1-6}$ alkyl, $C_{1-6}$ alkyl substituted with one or more $R^{1-2-1-1}$, $R^{12e}$ and $R^{12d}$ are independently hydrogen or $C_{1-6}$ alkyl; provided that when multiple substituents are present, the substituents are the same or different;

$R^{1-2-1-1}$ is independently halogen, hydroxyl, —$OC_{1-6}$ alkyl or —$NR^aR^d$, Re and $R^d$ are independently hydrogen or $C_{1-6}$ alkyl;

or, when the number of $R^{1-3}$, $R^{1-4}$, $R^{1-5}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1}$-2-3, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-5}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3-to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aromatic ring, $C_{6-20}$ aromatic ring substituted with one or more $R^{1-3-3}$, "5- to 12-membered heteroaromatic ring containing 1 to 4 heteroatoms independently selected from O, S and N", "5- to 12-membered heteroaromatic containing 1 to 4 heteroatoms independently selected from O, S and N" substituted with one or more $R^{1-3-4}$, $C_{5-7}$ cyclic olefin, $C_{5-7}$ cyclic olefin substituted with one or more $R^{1-3-5}$, "5- to 7-membered hetero cyclic olefin containing 1 to 3 heteroatoms independently selected from O, S and N", "5- to 7-membered hetero cyclic olefin containing 1 to 3 heteroatoms independently selected from O, S and N" substituted with one or more $R^{1-3-6}$; provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen;

or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-4-1}$; $R^{1-4-1}$ is independently oxo, hydroxyl, halogen, $C_{1-6}$ alkyl, $C_{1-6}$ alkyl substituted with one or more halogen, —$OC_{1-6}$ alkyl, or, —$OC_{1-6}$ alkyl substituted with one or more halogen;

$A_2$ and $A_3$ are independently $CR^2$, $R^2$ is hydrogen or halogen;
$A_4$ is N;
$A_5$ is $NR^{5d}$;
$R^{5d}$ is

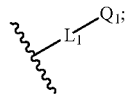

$L_1$ is a bond or $C_{1-6}$ alkylene;
$Q_1$ is hydrogen, halogen, cyano, $C_{2-6}$ alkenyl, $C_{2-6}$ alkynyl, hydroxyl, —C(=O) $R^{52a}$, —$NR^{52b1}R^{52b2}$, —C(=O)$OR^{52c}$, —C(=O)$NR^{52d1}R^{52d2}$, $C_{1-6}$ alkyl substituted with one or more halogen, —$OC_{1-6}$ alkyl, $C_{6-20}$ aryl, $C_{6-20}$ aryl substituted with one or more $R^{5-1-2}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{5-1-3}$, $C_{3-12}$ cycloalkyl, $C_{3-12}$ cycloalkyl substituted with one or more $R^{5-1-4}$, "4-to 12-membered heterocycloalkyl containing 1 to 3 heteroatoms independently selected from O, S and N", or "4- to 12-membered heterocycloalkyl containing 1 to 3 heteroatoms independently selected from O, S and N" substituted with one or more $R^{5-1-5}$; provided that when multiple substituents are present, the substituents are the same or different;

$R^{5-1-2}$, $R^{5-1-3}$, $R^{5-1-4}$ and $R^{5-1-5}$ are independently halogen, hydroxyl, oxo, cyano, $C_{1-6}$ alkyl, $C_{1-6}$ alkyl substituted with one or more halogen, —$OC_{1-6}$ alkyl, —$OC_{1-6}$ alkyl substituted with one or more halogen, —C(=O) $R^{51a}$, —$NR^{51b1}R^{51b2}$, —C(=O)$OR^{51c}$, or, —C(=O)$NR^{51d1}R^{51d2}$; provided that when multiple substituents are present, the substituents are the same or different;

$R^{52a}$, $R^{52b1}$, $R^{52b}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$; $R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different;

$R^6$ is independently "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$; $R^{6-1}$ is $C_{1-6}$ alkyl, or, $C_{1-6}$ alkyl substituted with one or more halogen;

solution 3: A compound containing structure of a five-membered heteroaromatic ring represented by Formula IV'", a pharmaceutically acceptable salt thereof, or a stereoisomer thereof,

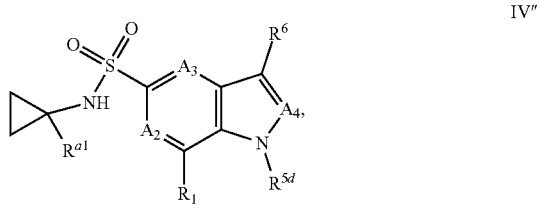

$R^{a1}$ is hydrogen, halogen, cyano, $C_{1-6}$ alkyl, $C_{2-6}$ alkenyl, $C_{2-6}$ alkynyl, $—OR^{a-1}$, $—C(=O) R^{a-2}$, $—NR^{a-31}R^{a-32}$, $—C(=O)OR^{a-4}$, $—C(=O)NR^{a-51}R^{a-52}$, or, $C_{1-6}$ alkyl substituted with one or more $R^{a1-1}$, $R^{a1-1}$ is halogen, hydroxy or —$OC_{1-6}$ alkyl;

$R^1$ is $C_{3-10}$ cycloalkyl, $C_{3-10}$ cycloalkyl substituted with one or more $R^{1-3}$, "4- to 12-membered heterocycloalkyl containing 1 to 3 heteroatoms independently selected from O, S and N", "4- to 12-membered heterocycloalkyl containing 1 to 3 heteroatoms independently selected from O, S and N" substituted with one or more $R^{1-4}$, $C_{6-20}$ aryl, $C_{6-20}$ aryl substituted with one or more $R^{1-5}$ "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-6}$, $C_{5-7}$ cycloalkenyl, $C_{5-7}$ cycloalkenyl substituted with one or more $R^{1-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-8}$, provided that when multiple substituents are present, the substituents are the same or different;

$R^{1-3}$, $R^{1-4}$, $R^{1-5}$, $R^{1-6}$, $R^{1-7}$ and $R^{1-8}$ are independently halogen, hydroxyl, cyano, oxo, $C_{1-6}$ alkyl, $C_{1-6}$ alkyl substituted with one or more $R^{1-1-1}$, $C_{2-6}$ alkenyl, $C_{2-6}$ alkynyl, —$OC_{1-6}$ alkyl, —$OC_{1-6}$ alkyl substituted with one or more $R^{1-1-2}$, $—C(=O) R^{11a}$, $—NR^{11b1}R^{11b2}$, $—C(=O)OR^{11c}$, $—C(=O)NR^{11d1}$, $R^{11d2}$, $—S(O)_2NR^{11e1}R^{11e2}$, $C_{3-10}$ cycloalkyl, $C_{3-10}$ cycloalkyl substituted with one or more $R^{1-1-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-1-4}$, $C_{6-20}$ aryl, $C_{6-20}$ aryl substituted with one or more $R^{1-1-5}$, "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-1-6}$, $C_{5-7}$ cycloalkenyl, $C_{5-7}$ cycloalkenyl substituted with one or more $R^{1-1-7}$, "5- to 7-membered heterocycloalkenyl containing 1 to 3 heteroatoms independently selected from O, S and N", "5-to 7-membered heterocycloalkenyl containing 1 to 3 heteroatoms independently selected from O, S and N" substituted with one or more $R^{1-1-8}$, provided that when multiple substituents are present, the substituents are the same or different;

$R^{1-1-1}$, $R^{1-1-2}$, $R^{1-1-3}$, $R^{1-1-4}$, $R^{1-1-5}$, $R^{1-1-6}$, $R^{1-1-7}$ and $R^{1-1-8}$ are independently halogen, oxo, $C_{1-6}$ alkyl, or, $C_{1-6}$ alkyl substituted with one or more $R^{1-1-1-1}$; Provided that when multiple substituents are present, the substituents are the same or different;

$R^{1-1-1-1}$ is independently halogen, hydroxyl, $C_{1-6}$ alkyO— or —$NR^aR^b$, $R^a$ and $R^b$ are independently hydrogen or $C_{1-6}$ alkyl;

$R^{11a}, R^{11b1}, R^{11b2}, R^{11c}, R^{11d2}, R^{11d2}, R^{11e1}$ and $R^{11e2}$ are independently hydrogen, $C_{1-6}$ alkyl, $C_{1-6}$ alkyl substituted with one or more $R^{1-2-1}$, —$OC_{1-6}$ alkyl, —$OC_{1-6}$ alkyl substituted with one or more $R^{1-2-2}$, $C_{3-10}$ cycloalkyl, $C_{3-10}$ cycloalkyl substituted with one or more $R^{1-2-3}$, "4- to 10-membered heterocycloalkyl containing 1 to 3 heteroatoms independently selected from O, S and N", "4- to 10-membered heterocycloalkyl containing 1 to 3 heteroatoms independently selected from O, S and N" substituted with one or more $R^{1-2-4}$, $C_{6-20}$ aryl, $C_{6-20}$ aryl substituted with one or more $R^{1-2-5}$, "5- to 12-membered heteroaryl containing 1 to 3 heteroatoms independently selected from O, S and N", "5- to 12-membered heteroaryl containing 1 to 3 heteroatoms independently selected from O, S and N" substituted with one or more $R^{1-2-6}$, $C_{5-7}$ cycloalkenyl, $C_{5-7}$ cycloalkenyl substituted with one or more $R^{1-2-7}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-2-8}$, provided that when multiple substituents are present, the substituents are the same or different;

$R^{1-2-1}$, $R^{1-2-2}$, $R^{1-2-3}$, $R^{1-2-4}$, $R^{1-2-5}$, $R^{1-2-6}$, $R^{1-2-7}$ and $R^{1-2-8}$ are independently halogen, oxo, $C_{1-6}$ alkyl, $C_{1-6}$ alkyl substituted with one or more $R^{1-2-1-1}$; provided that when multiple substituents are present, the substituents are the same or different;

$R^{1-2-1-1}$ is halogen, hydroxyl, —$OC_{1-6}$ alkyl or —$NR^aR^d$, Re and $R^d$ are independently hydrogen or $C_{1-6}$ alkyl;

or, when the number of $R^{1-3}$, $R^{1-4}$, $R^{1-6}$, $R^{1-7}$, $R^{1-8}$, $R^{1-1-3}$, $R^{1-1-4}$, $R^{1-1-5}$, $R^{1-1-6}$, $R^{1-1-7}$, $R^{1-1-8}$, $R^{1-2-3}$, $R^{1-2-4}$, $R^{1-2-5}$, $R^{1-2-6}$, $R^{1-2-7}$ or $R^{1-2-8}$ is more than one, two optional $R^{1-3}$, two optional $R^{1-4}$, two optional $R^{1-6}$, two optional $R^{1-7}$, two optional $R^{1-8}$, two optional $R^{1-1-3}$, two optional $R^{1-1-4}$, two optional $R^{1-1-5}$, two optional $R^{1-1-6}$, two optional $R^{1-1-7}$, two optional $R^{1-1-8}$, two optional $R^{1-2-3}$, two optional $R^{1-2-4}$, two optional $R^{1-2-5}$, two optional $R^{1-2-6}$, two optional $R^{1-2-7}$ or two optional $R^{1-2-8}$, together with the atoms to which they are attached, independently form 3- to 8-membered carbon ring, "3- to 8-membered carbon ring" substituted with one or more $R^{1-3-1}$, "3- to 8-membered heterocycle containing 1 to 3 heteroatoms independently selected from O, S and N", "3- to 8-membered heterocycle containing 1 to 3 heteroatoms independently selected from O, S and N" substituted with one or more $R^{1-3-2}$, $C_{6-20}$ aryl, $C_{6-20}$ aryl substituted with one or more $R^{1-3-3}$, "5- to 12-membered heteroaryl containing 1 to 4 heteroatoms independently selected from O, S and N", "5- to 12-membered heteroaryl containing 1 to 4 heteroatoms independently selected from O, S and N" substituted with one or more $R^{1-3-4}$, $C_{5-7}$ cycloalkenyl, $C_{5-7}$ cycloalkenyl substituted with one or more $R^{1-3-5}$, "5- to 7-membered heterocycloalkenyl containing 1 to 3 heteroatoms independently selected from O, S and N", "5- to 7-membered heterocycloalkenyl containing 1 to 3 heteroatoms independently selected from O, S and N" substituted with one or more $R^{1-3-6}$, provided that when multiple substituents are present, the substituents are the same or different;

$R^{1-3-1}$, $R^{1-3-2}$, $R^{1-3-3}$, $R^{1-3-4}$, $R^{1-3-5}$ and $R^{1-3-6}$ are independently oxo, hydroxyl, halogen, $C_{1-6}$ alkyl, $C_{1-6}$ alkyl substituted with one or more halogen, $-OC_{1-6}$ alkyl, or, $-OC_{1-6}$ alkyl substituted with one or more halogen; or, $R^{a-31}$ and $R^{a-32}$, $R^{a-51}$ and $R^{a-52}$, $R^{1b1}$ and $R^{1b2}$, $R^{1d1}$ and $R^{1d2}$, $R^{11b1}$ and $R^{11b2}$, $R^{11d1}$ and $R^{11d2}$, $R^{11e1}$ and $R^{11e2}$, $R^a$ and $R^b$, $R^c$ and $R^d$ together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-4-1}$, $R^{1-4-1}$ is oxo, hydroxyl, halogen, $C_{1-6}$ alkyl, $C_{1-6}$ alkyl substituted with one or more halogen, $C_{1-6}$ alkyl-O—, or, $C_{1-6}$ alkyl-O— substituted with one or more halogen;

$A_2$ and $A_3$ are independently $CR^2$, $R^2$ is hydrogen or halogen;

$A_4$ is N;

$R^{5d}$ is

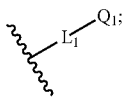

$L_1$ is a bond or $C_{1-6}$ alkylene;

$Q_1$ is hydrogen, halogen, cyano, $C_{2-6}$ alkenyl, $C_{2-6}$ alkynyl, hydroxyl, —C(=O) $R^{52a}$, —$NR^{52b1}R^{52b2}$, —C(=O)$O^{R52c}$, —C(=O)$NR^{52d1}R^{52d2}$, $C_{1-6}$ alkyl substituted with one or more halogen, $C_{1-6}$ alkyl-O—, $C_{3-12}$ cycloalkyl, $C_{3-12}$ cycloalkyl substituted with one or more $R^{5-1-4}$, "4- to 12-membered heterocycloalkyl containing 1 to 3 heteroatoms independently selected from O, S and N", or, "4-to 12-membered heterocycloalkyl containing 1 to 3 heteroatoms independently selected from O, S and N" substituted with one or more $R^{5-1-5}$; provided that when multiple substituents are present, the substituents are the same or different;

$R^{5-1-4}$ and $R^{5-1-5}$ are independently halogen, hydroxyl, oxo, cyano, $C_{1-6}$ alkyl, $C_{1-6}$ alkyl substituted with one or more halogen, —$OC_{1-6}$ alkyl, —$OC_{1-6}$ alkyl substituted with one or more halogen, —C(=O) $R^{51a}$, —$NR^{51b1}R^{51b2}$, —C(=O)$OR^{51c}$, or, —C(=O)$NR^{51d1}R^{51d2}$; Provided that when multiple substituents are present, the substituents are the same or different;

$R^{52a}$, $R^{52b1}$, $R^{52b}$, $R^{52c}$, $R^{52d1}$, $R^{52d2}$, $R^{51a}$, $R^{51b1}$, $R^{51b2}$, $R^{51c}$, $R^{51d1}$ and $R^{51d2}$ are independently hydrogen, $C_{1-6}$ alkyl, or, $C_{1-6}$ alkyl substituted with one or more halogen;

or, $R^{52b1}$ and $R^{52b2}$, $R^{52d1}$ and $R^{52d2}$, $R^{51b1}$ and $R^{51b2}$, $R^{51d1}$ and $R^{51d2}$, together with the nitrogen atom to which they are attached independently form "3- to 8-membered heterocycle containing 1 to 3 heteroatoms, wherein, one heteroatom is N, the other one or two heteroatoms independently selected from O, S and N", or "3- to 8-membered heterocycle containing 1 to 3 heteroatoms, wherein, one heteroatom is N, the other one or two heteroatoms independently selected from O, S and N" substituted with one or more $R^{1-5-1}$, $R^{1-5-1}$ is oxo, hydroxyl, halogen, $C_{1-6}$ alkyl, $C_{1-6}$ alkyl substituted with one or more halogen, —$OC_{1-6}$ alkyl, —$OC_{1-6}$ alkyl substituted with one or more halogen; provided that when multiple substituents are present, the substituents are the same or different;

$R^6$ is "5-membered heteroaryl containing 1 to 4 heteroatoms independently selected from O, S and N", or, "5-membered heteroaryl containing 1 to 4 heteroatoms independently selected from O, S and N" substituted with one or more $R^{6-1}$;

$R^{6-1}$ is $C_{1-6}$ alkyl, or $C_{1-6}$ alkyl substituted with one or more halogen.

9. The compound containing structure of a five-membered heteroaromatic ring represented by formula II, a pharmaceutically acceptable salt thereof, or a stereoisomer thereof according to claim 1, wherein, the compound containing structure of a five-membered heteroaromatic ring represented by formula II is any one of the following structures:

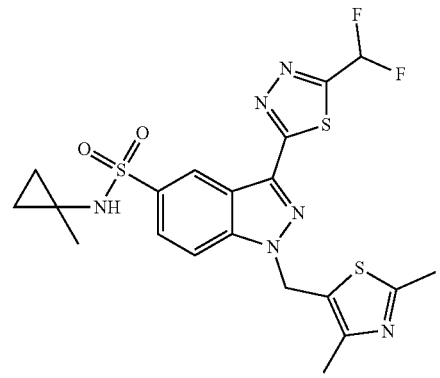

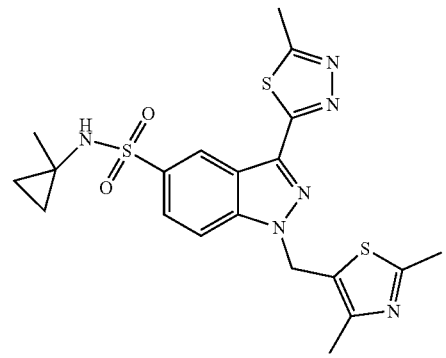

441
-continued
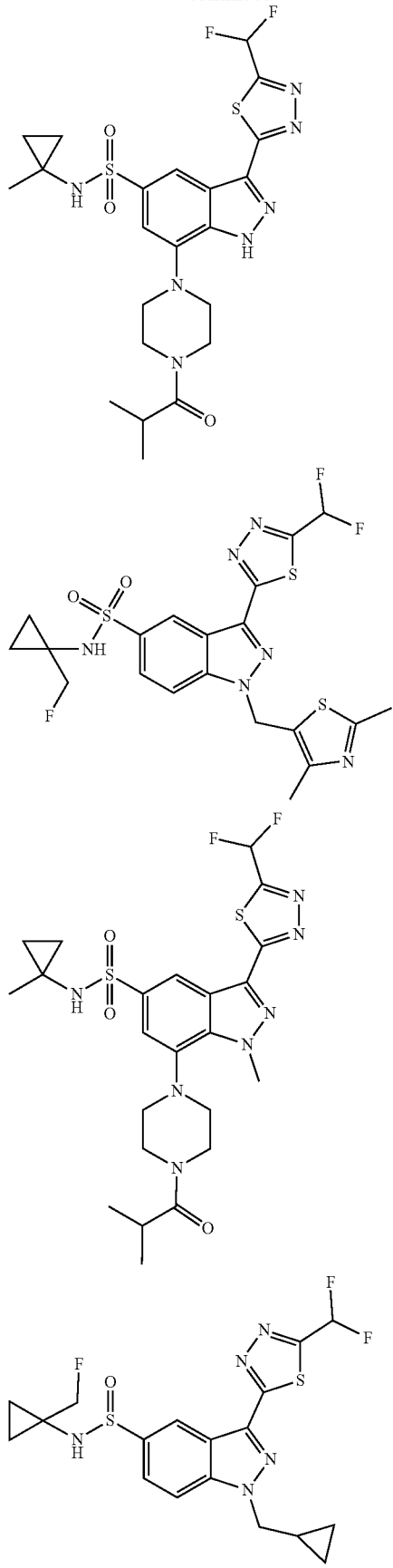
442
-continued
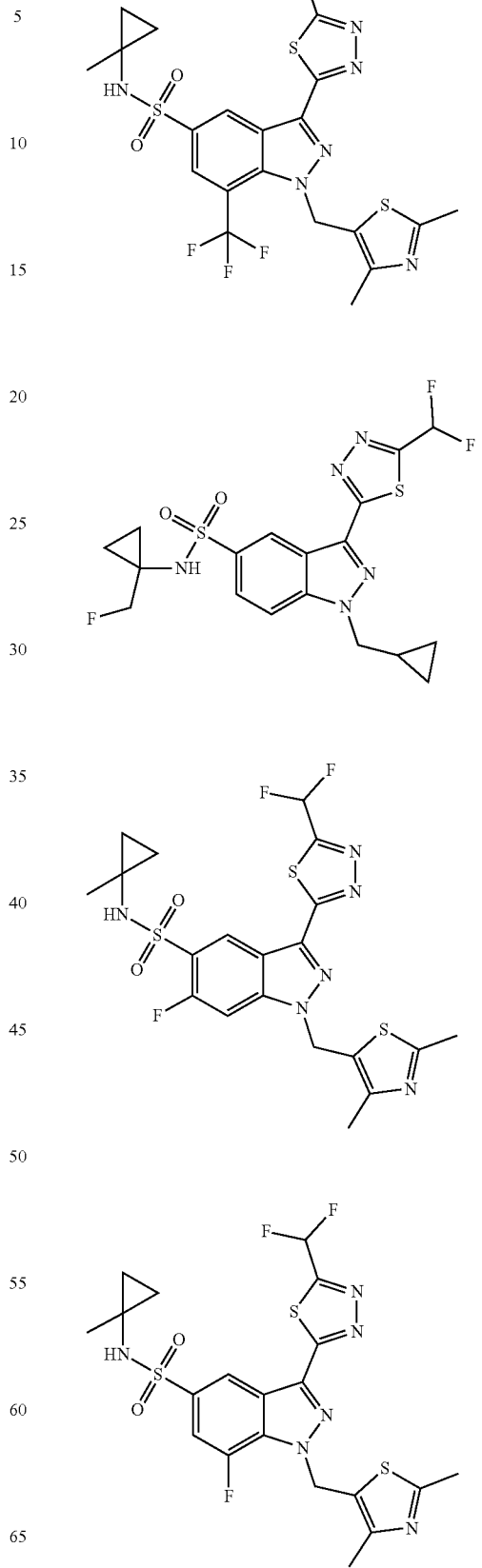

443
-continued
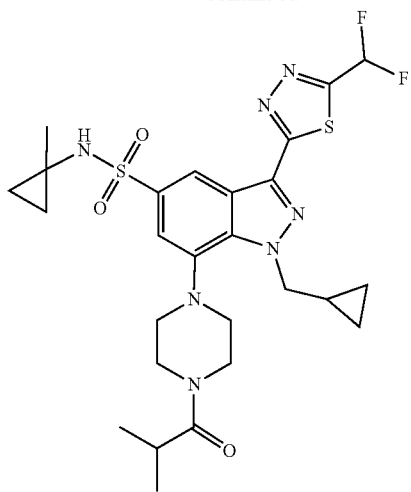
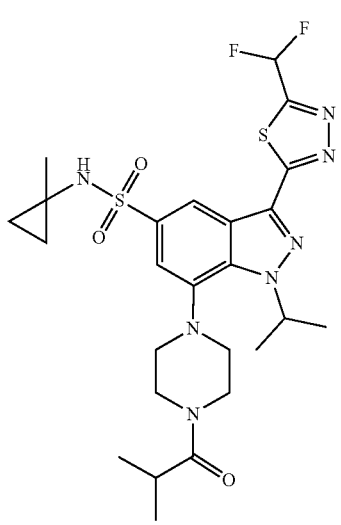
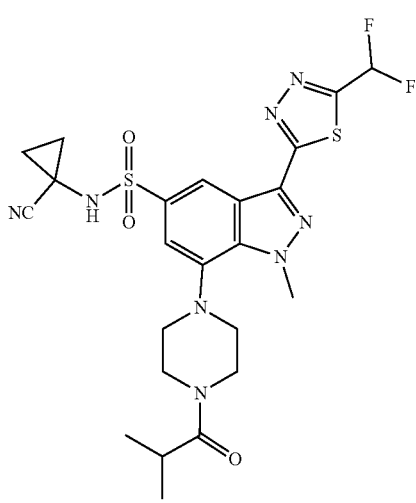
444
-continued
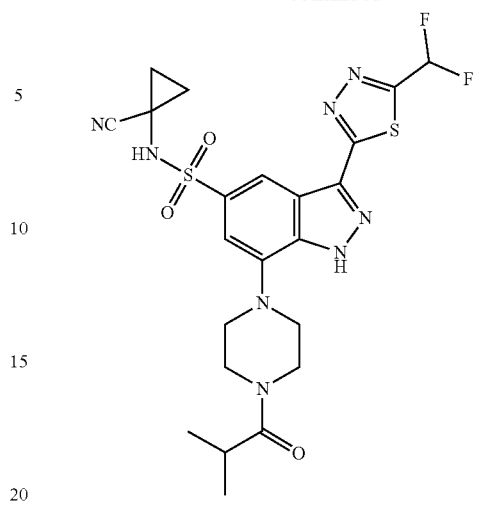
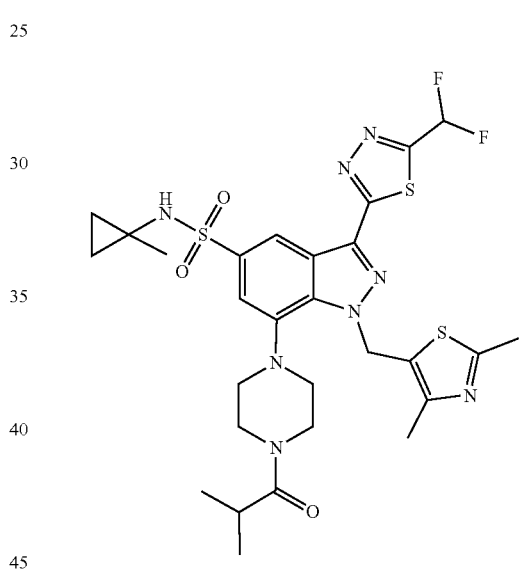
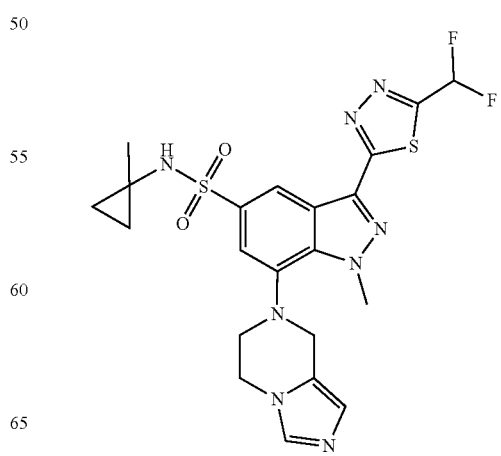

445
-continued
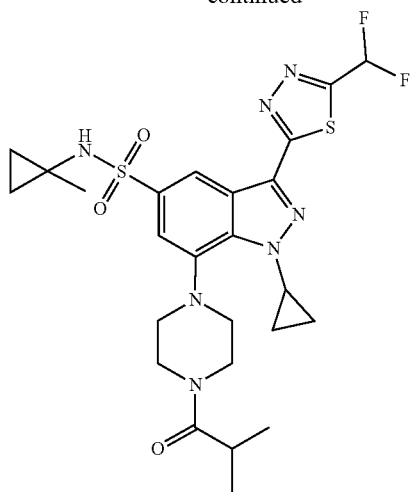
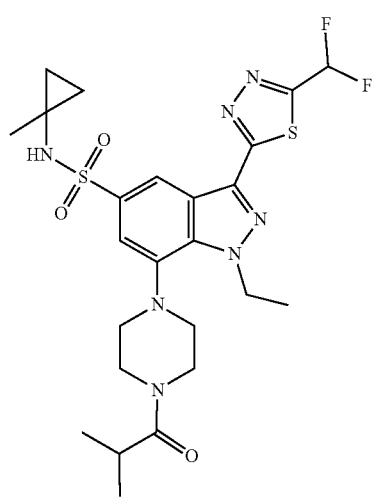
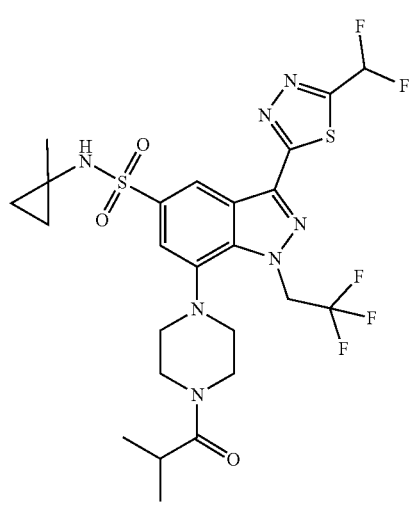
446
-continued
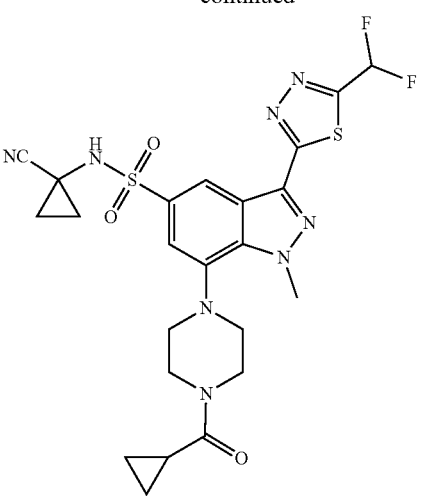
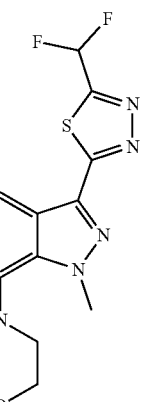
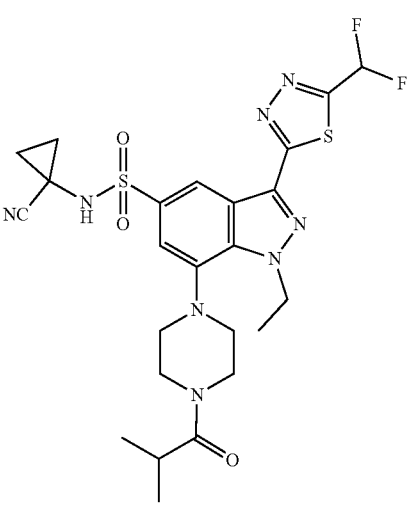

447
-continued
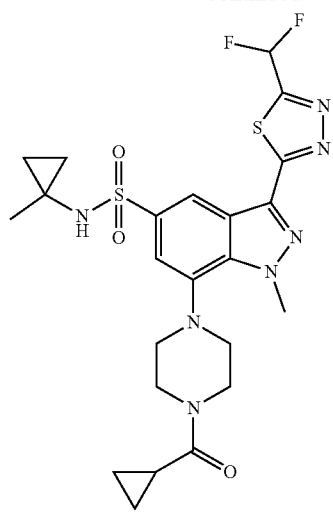
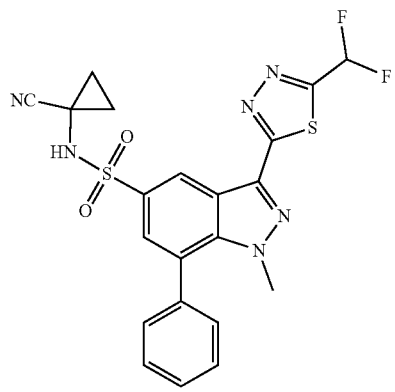
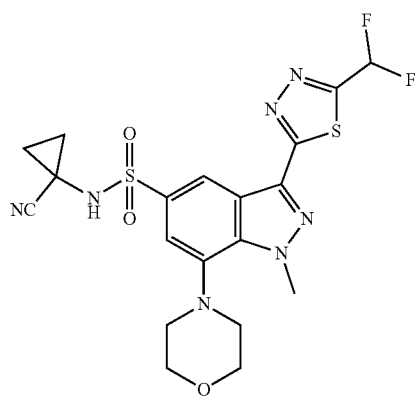
448
-continued
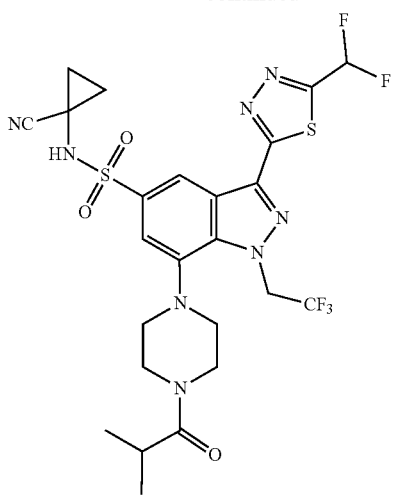
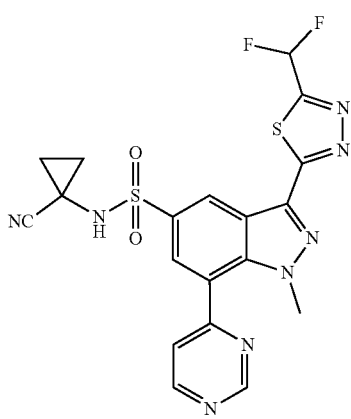
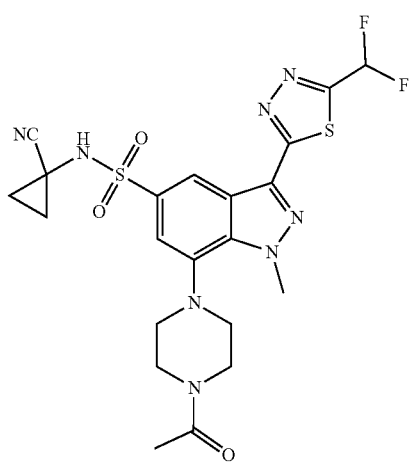

449
-continued
450
-continued
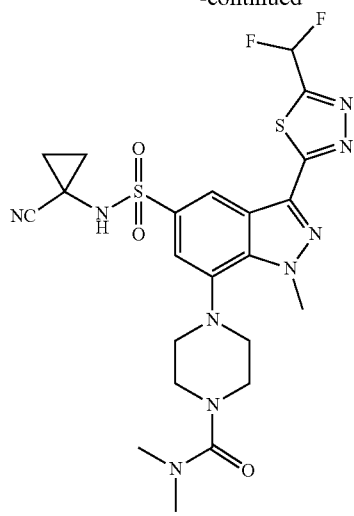
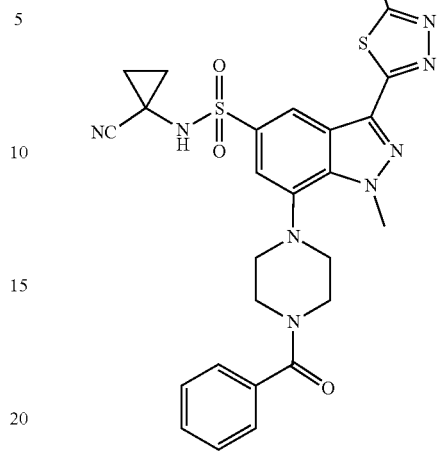
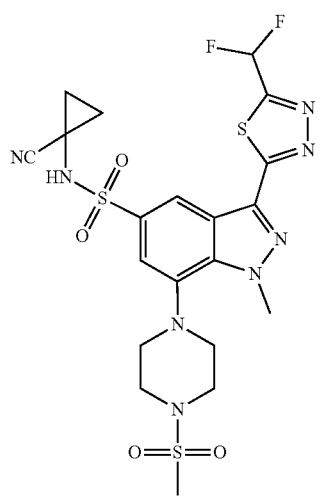
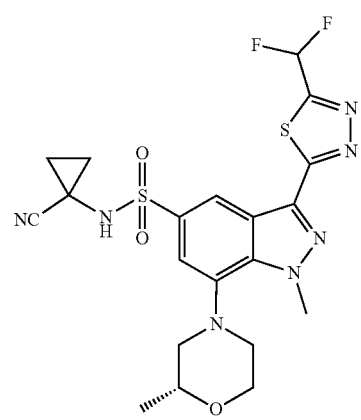
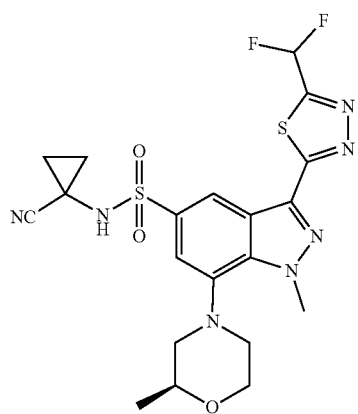
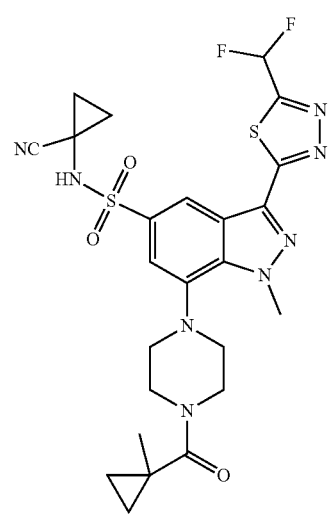

451
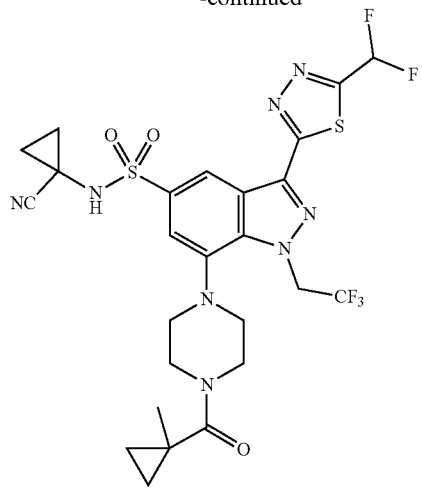
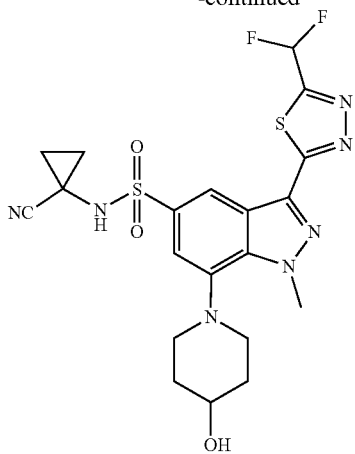
452
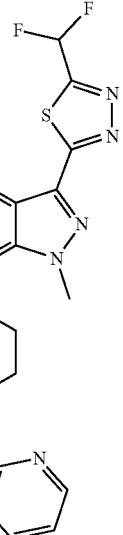
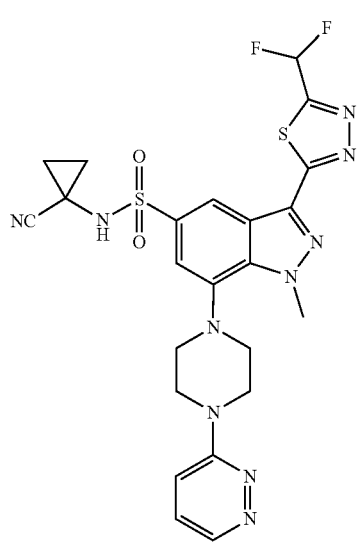
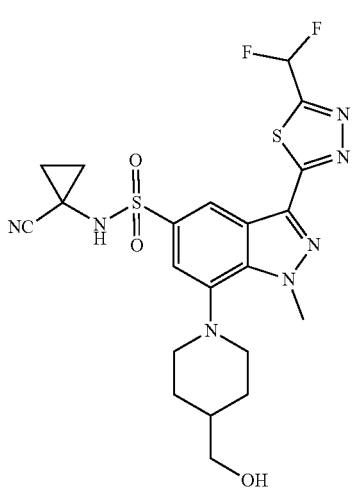

453
-continued
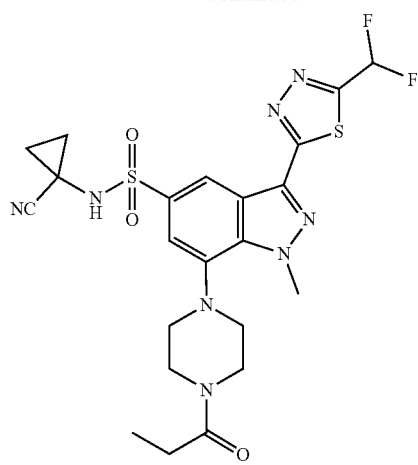
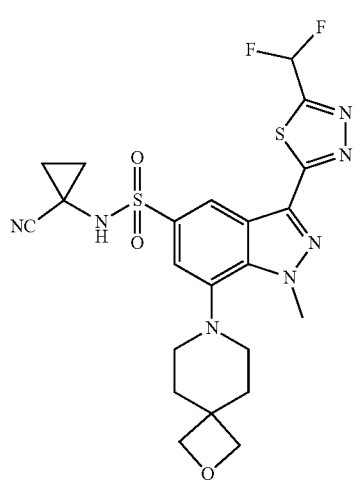
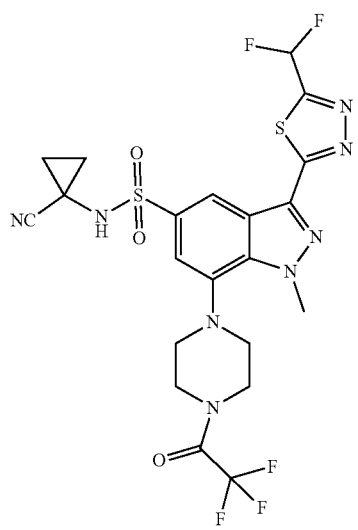
454
-continued
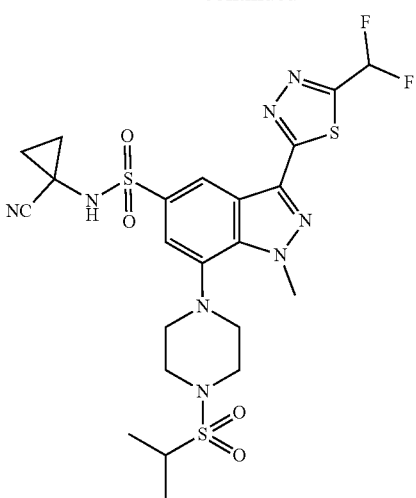
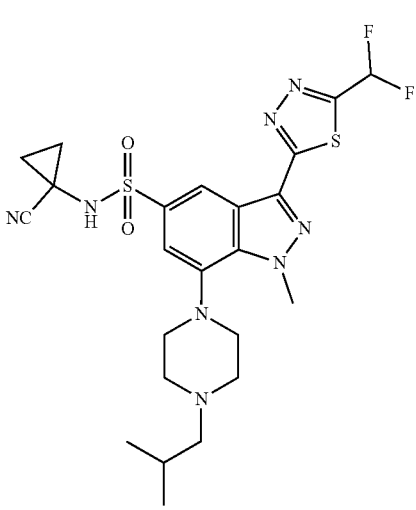
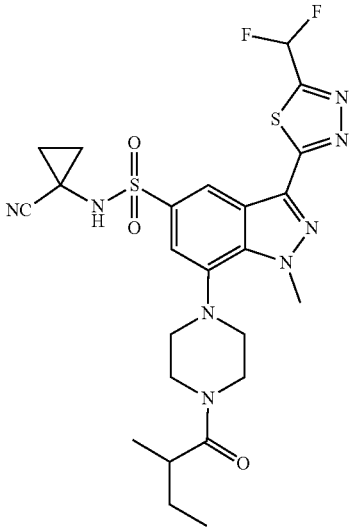

455
-continued
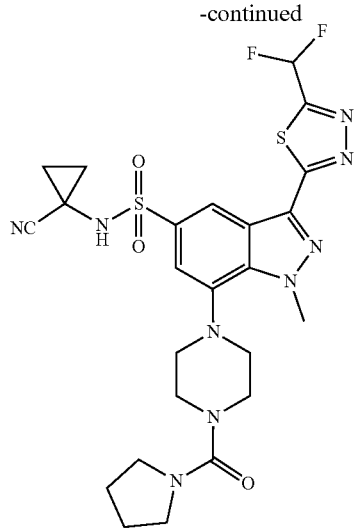
456
-continued
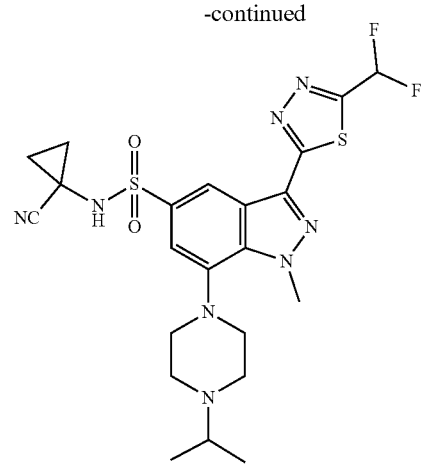
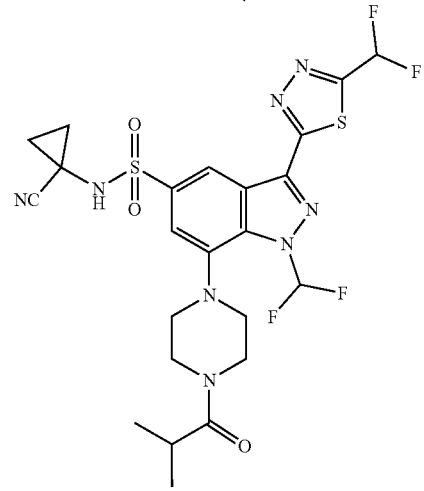
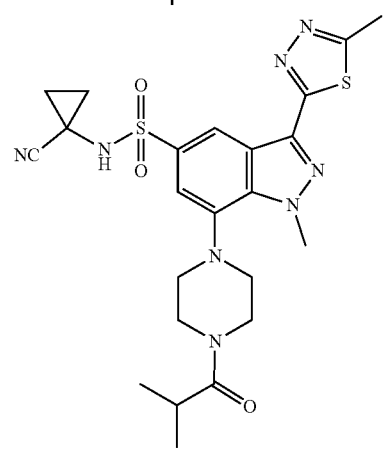
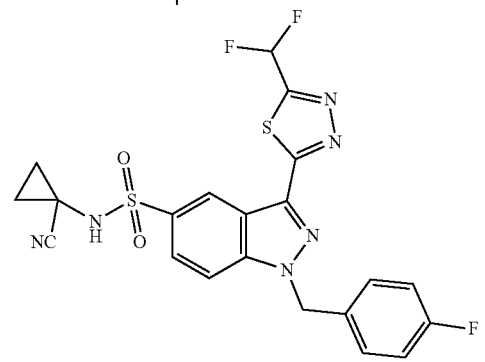

457
-continued
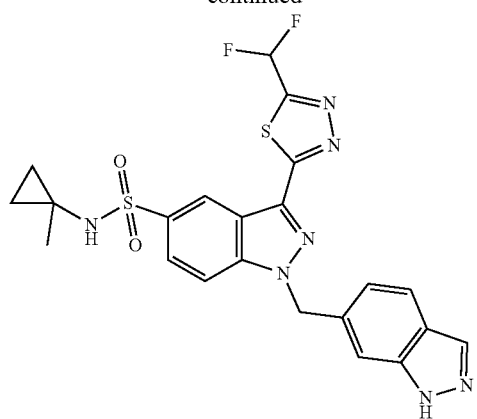
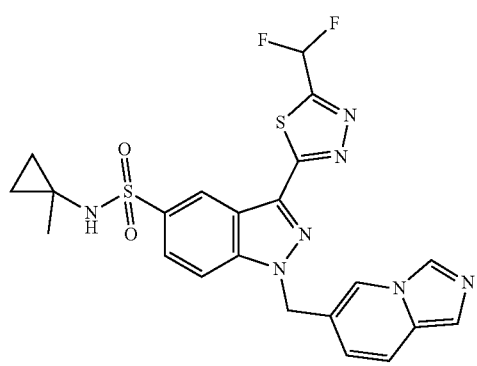
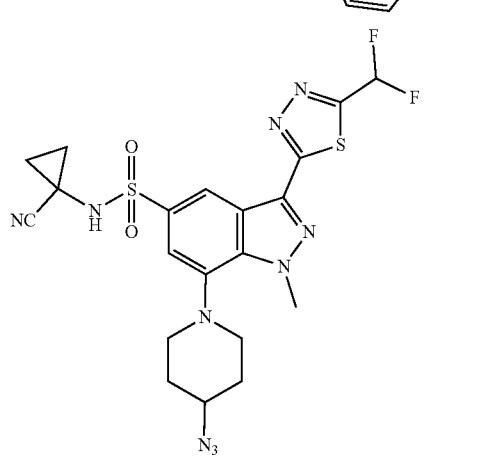
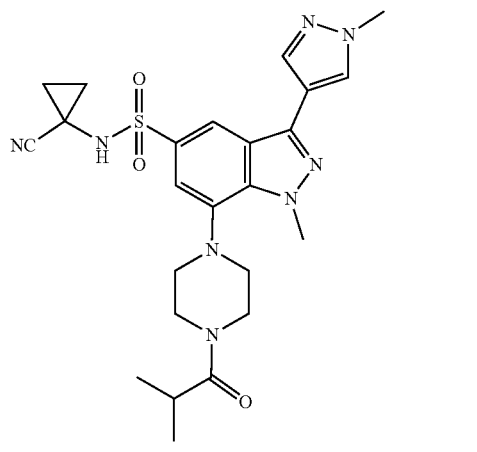
458
-continued
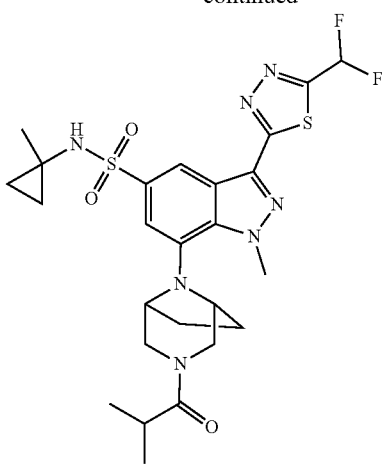
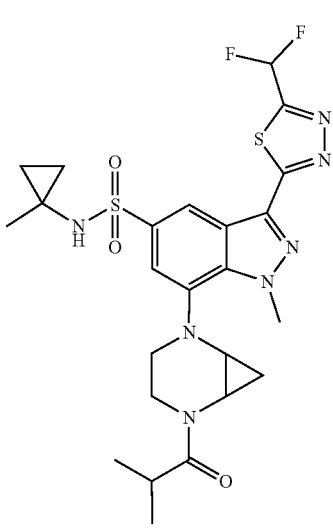
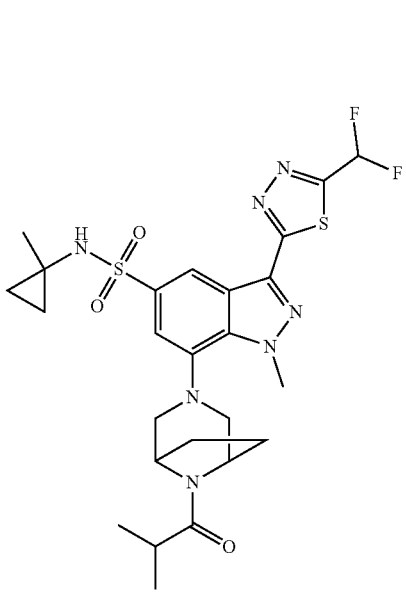

459
-continued
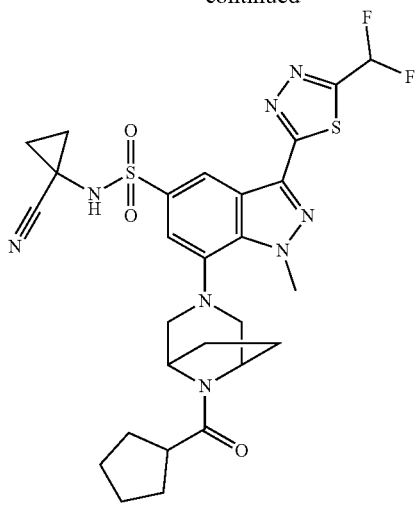
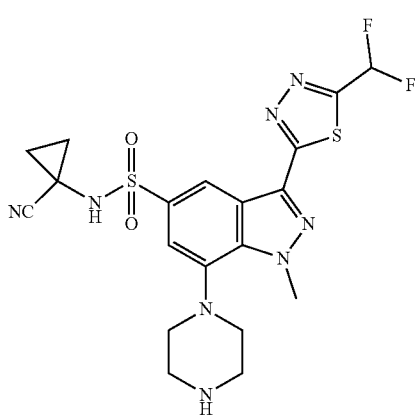
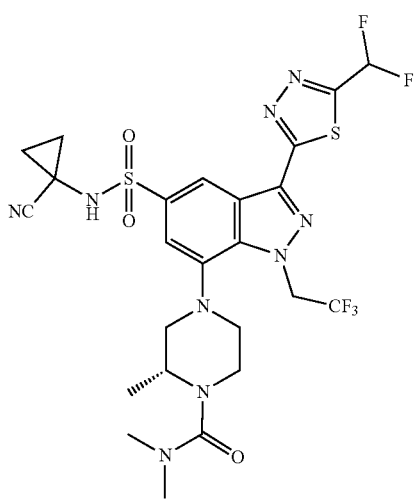
460
-continued
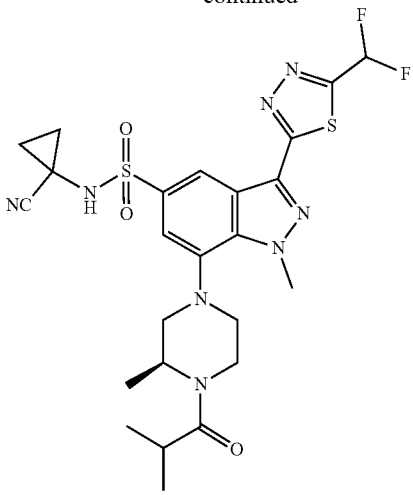
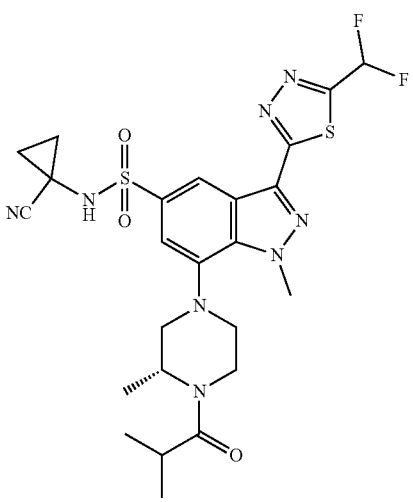
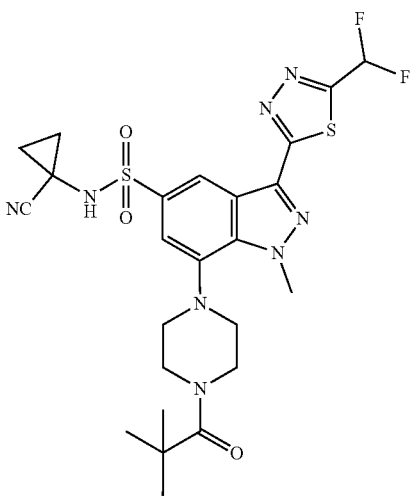

461
-continued
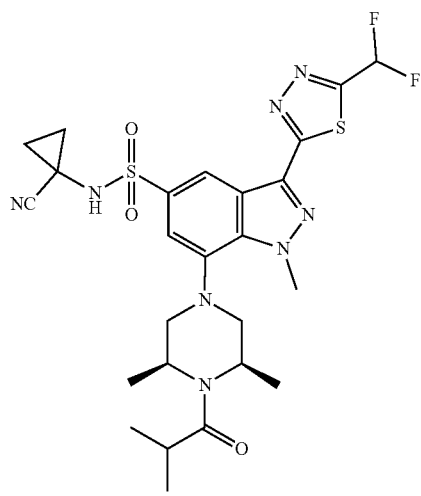
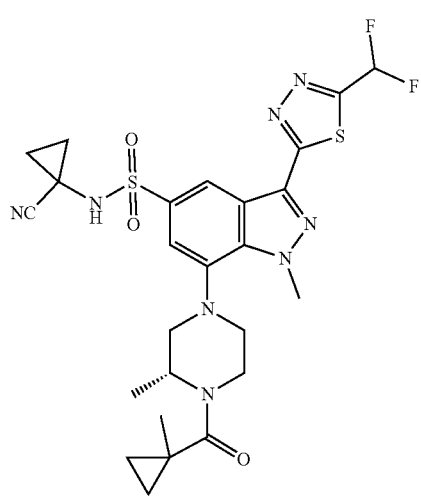
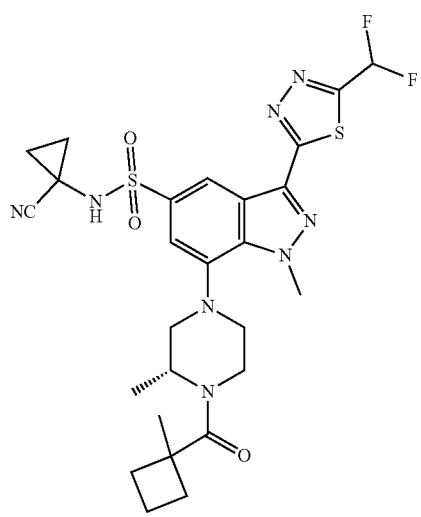
462
-continued
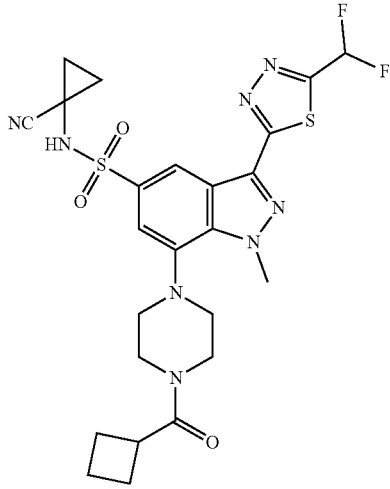
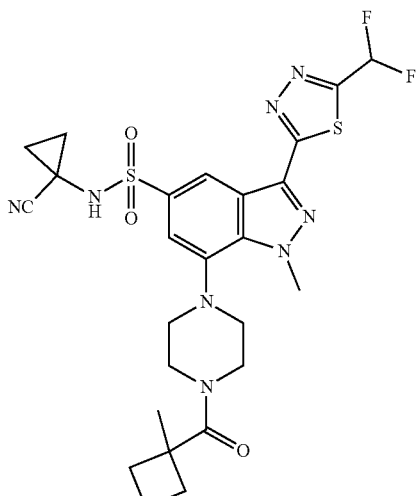
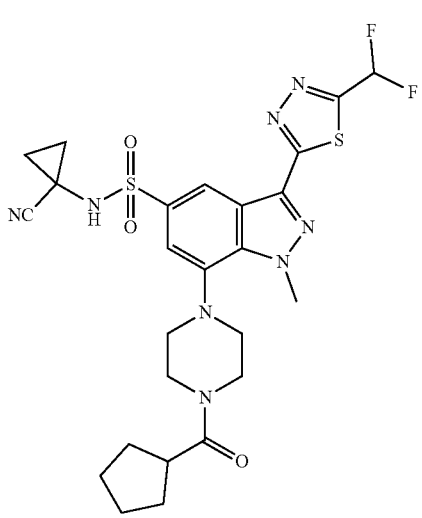

463
-continued
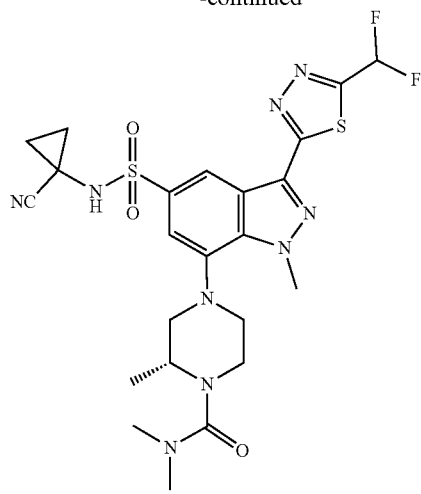
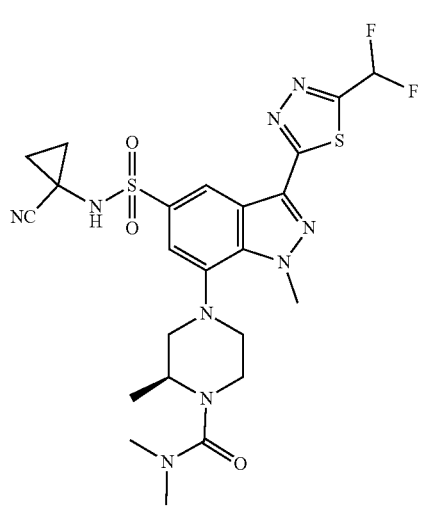
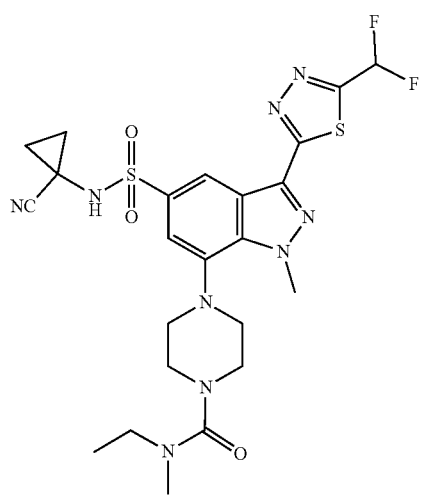
464
-continued
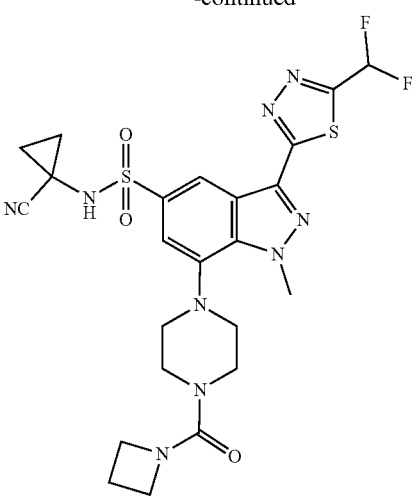
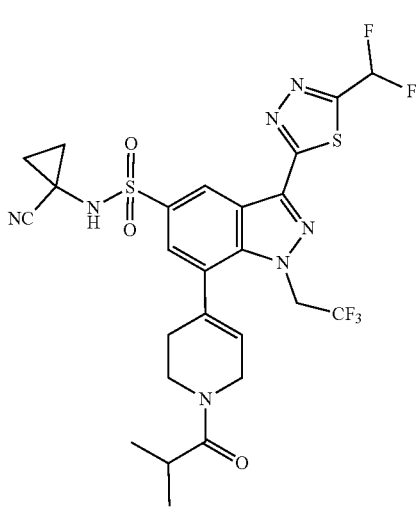
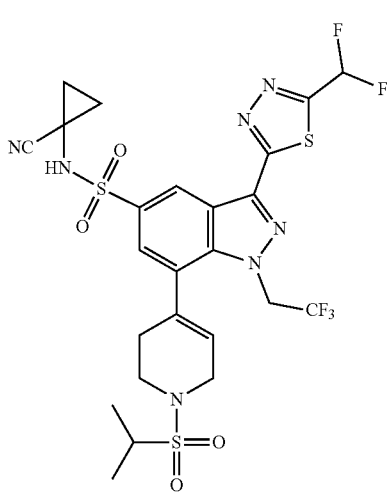

465
-continued
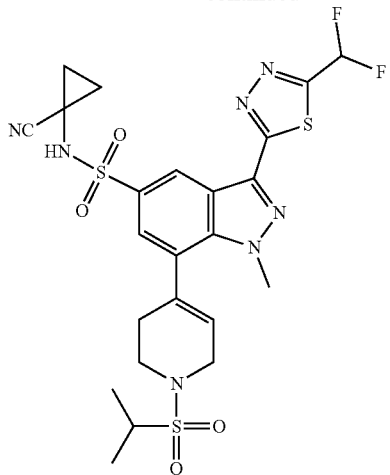
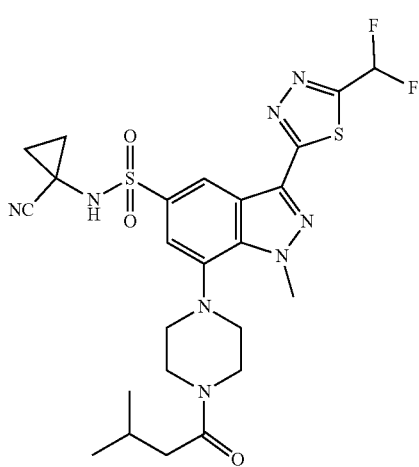
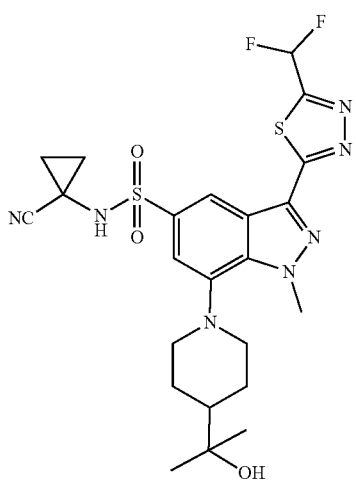
466
-continued
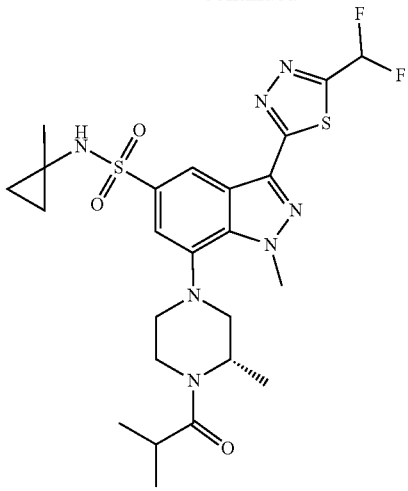
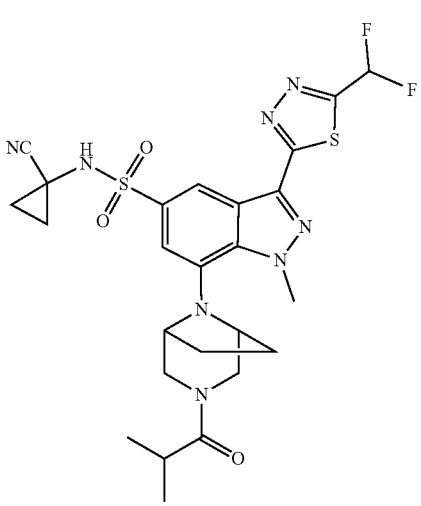
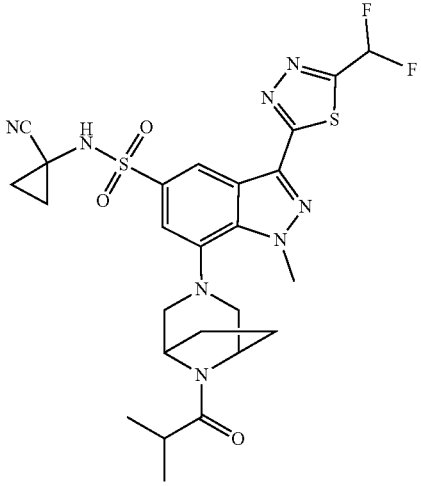

467
-continued
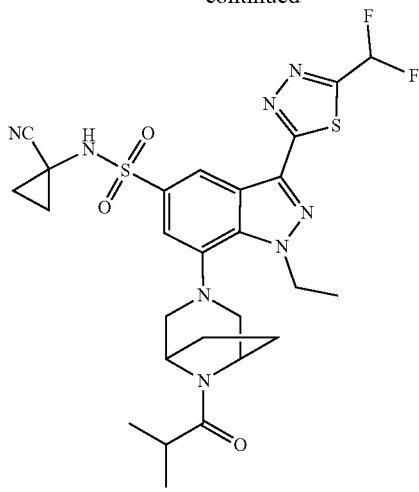
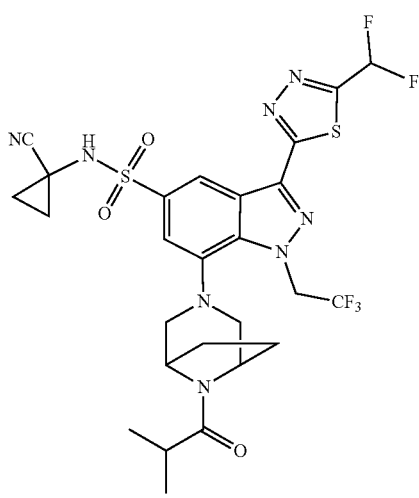
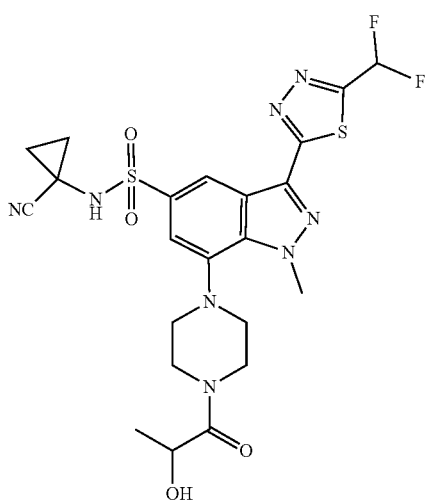
468
-continued
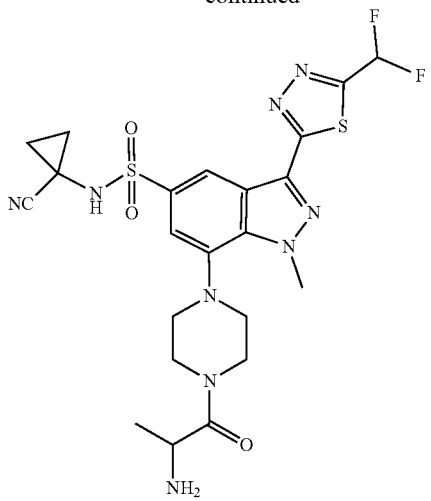
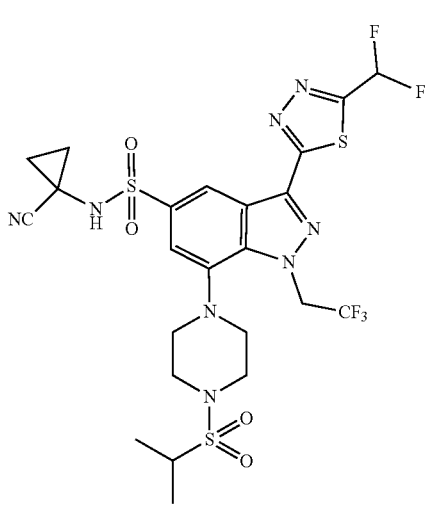
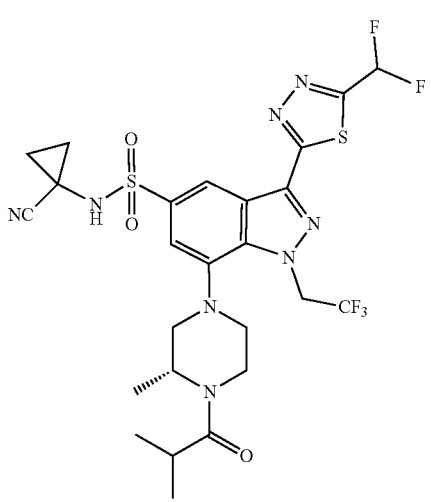

469
-continued
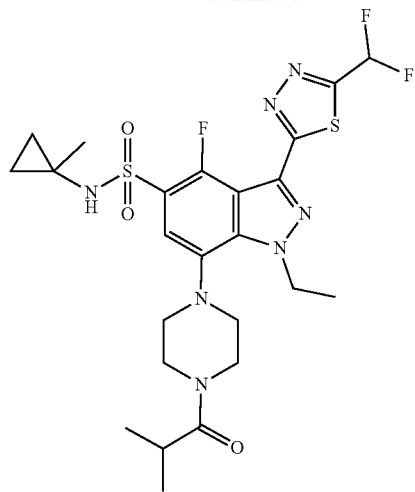
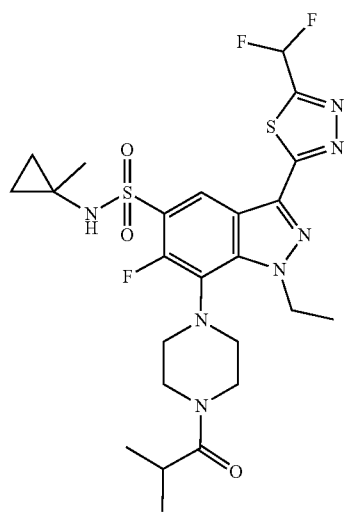
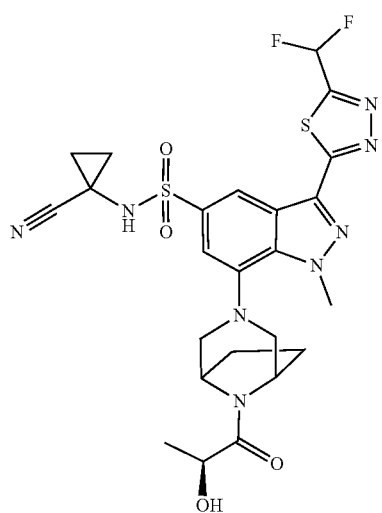
470
-continued
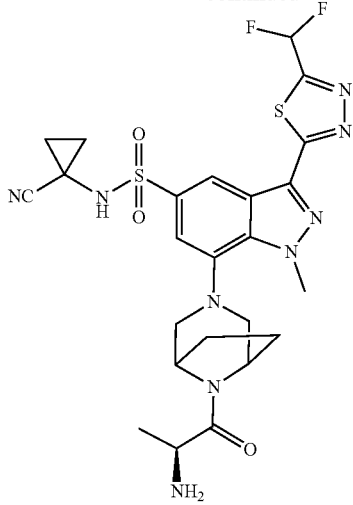
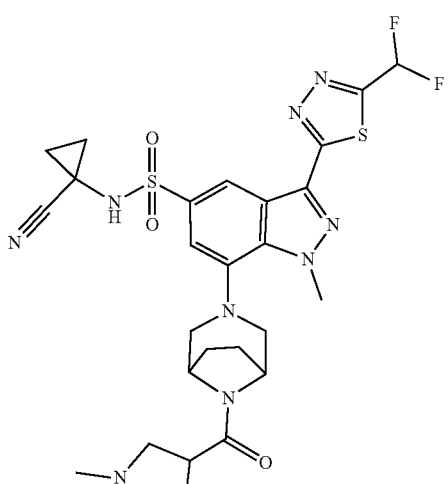
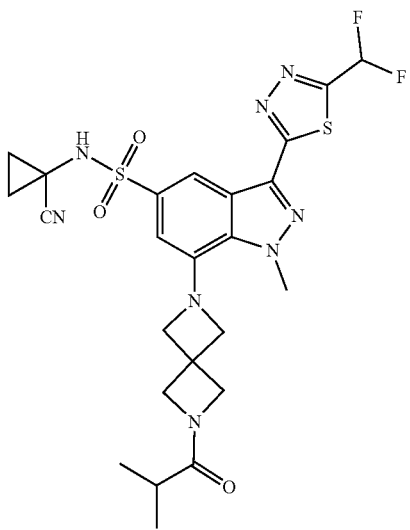

-continued
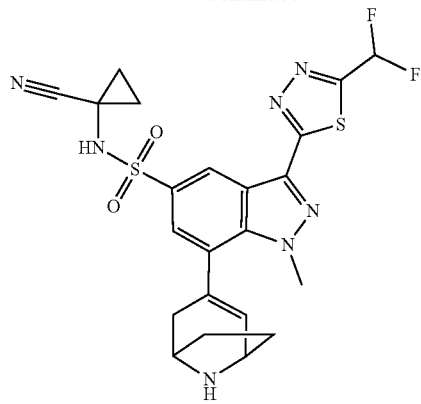
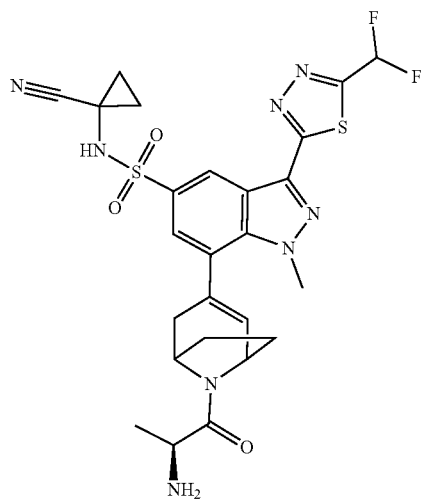
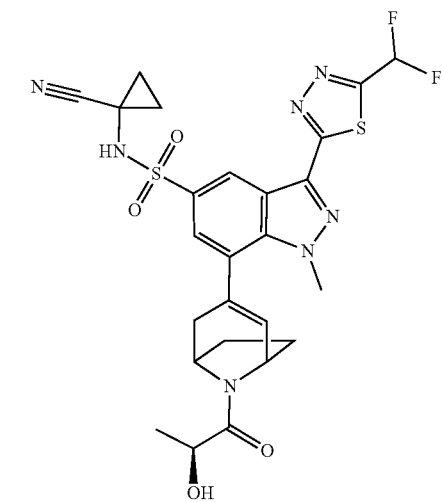
-continued
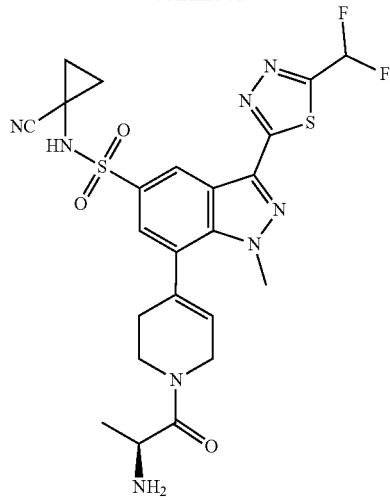
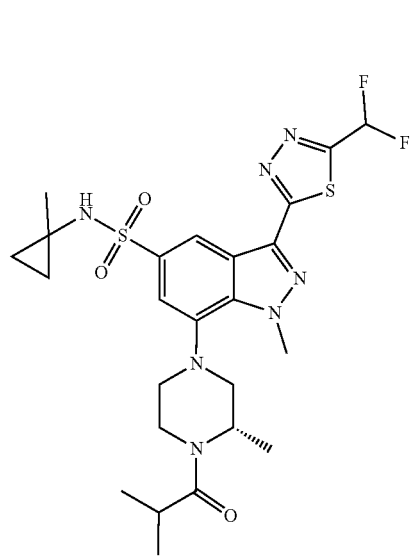
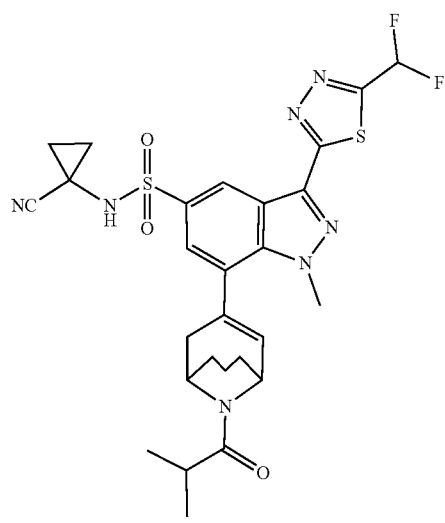

473
-continued
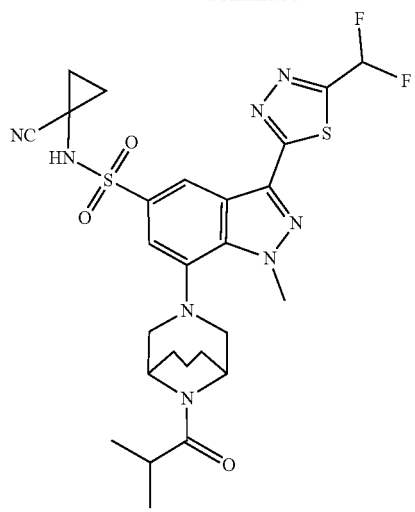
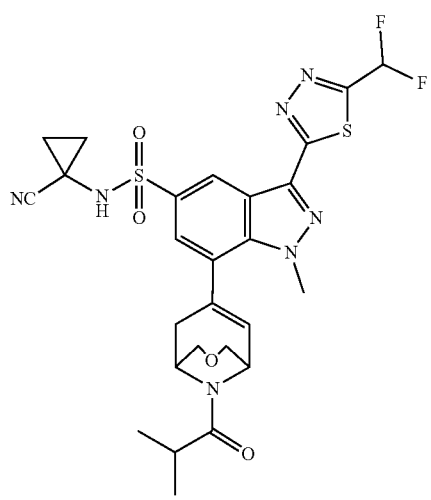
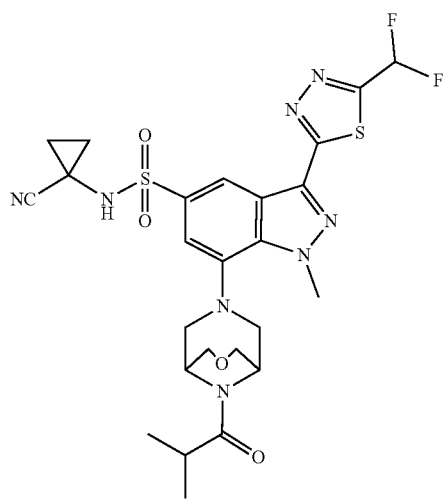
474
-continued
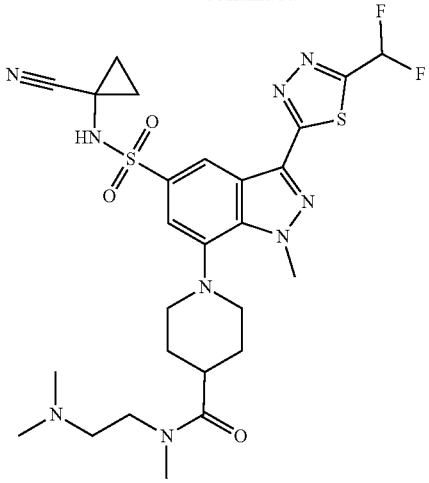
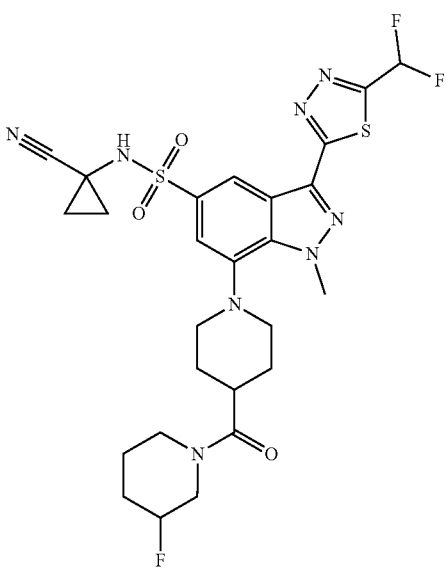
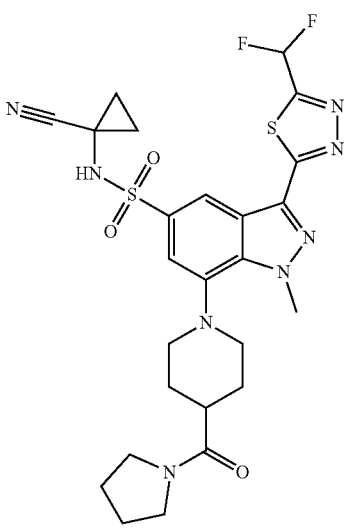

475
-continued
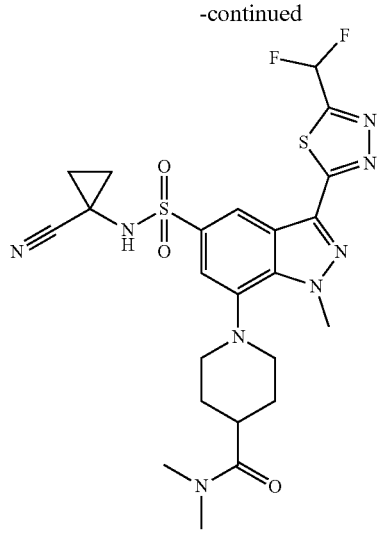
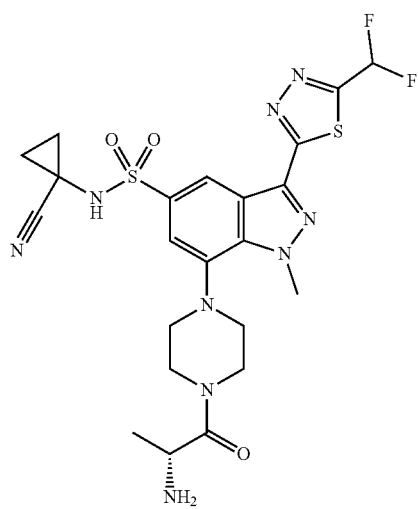
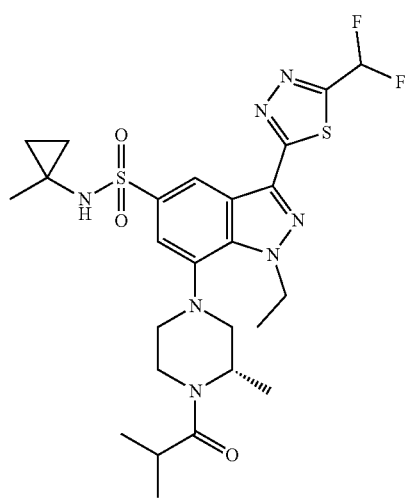
476
-continued
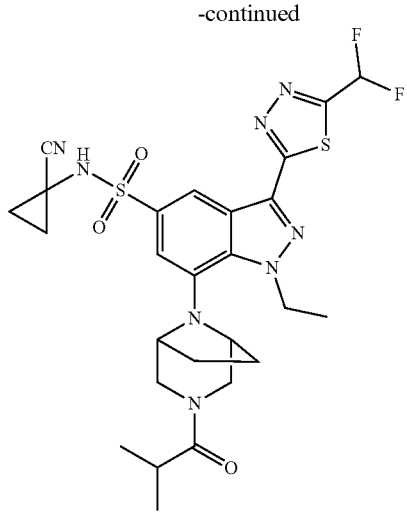
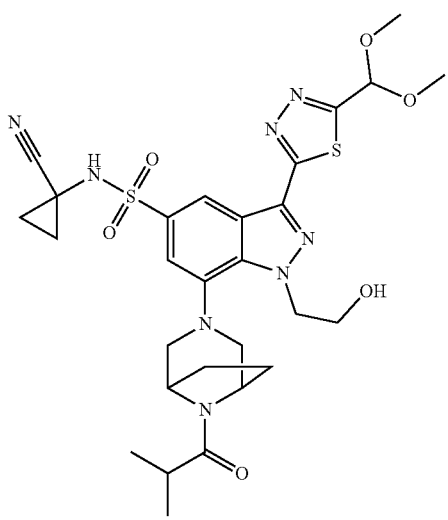
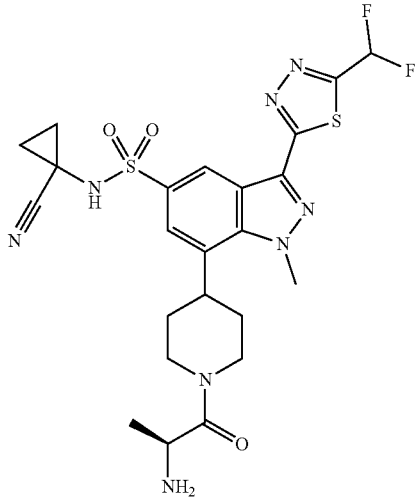

477
-continued
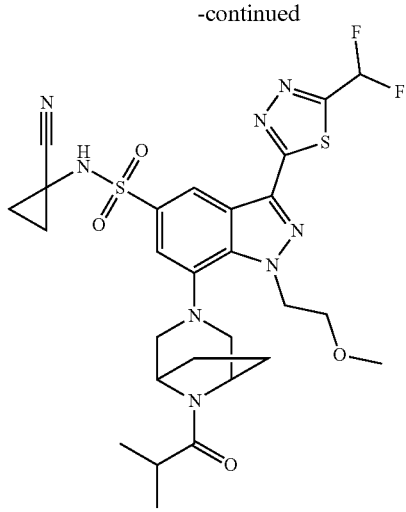
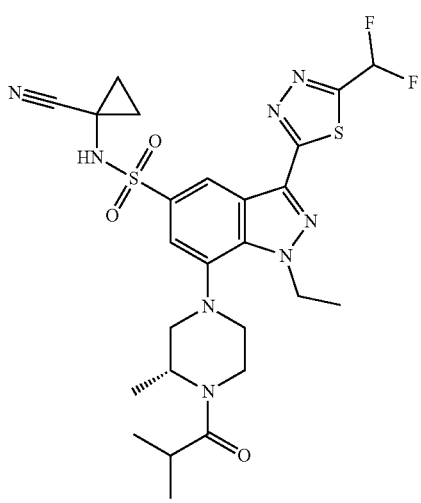
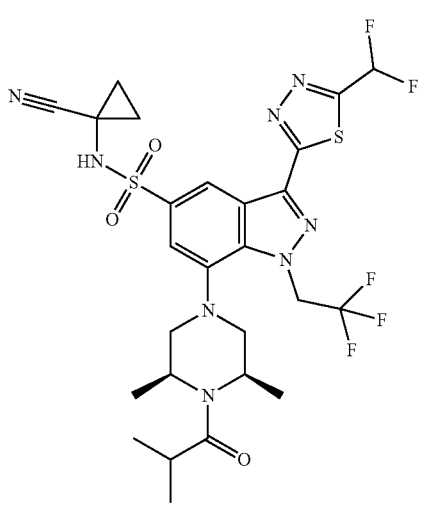
478
-continued
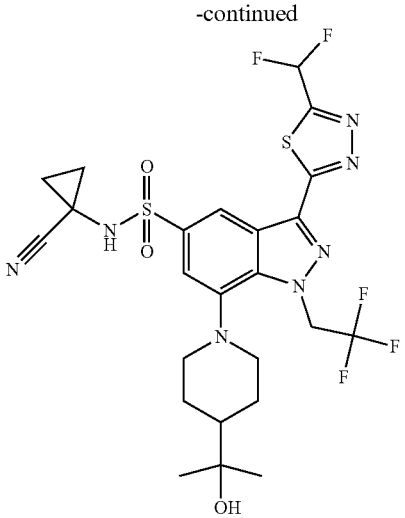
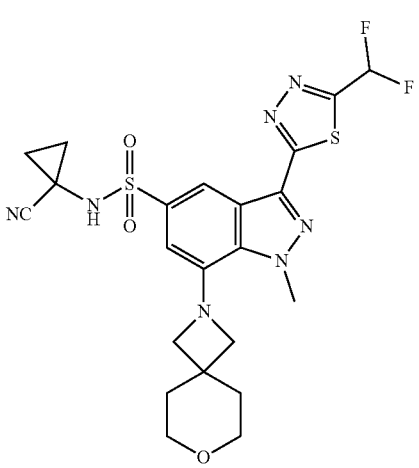
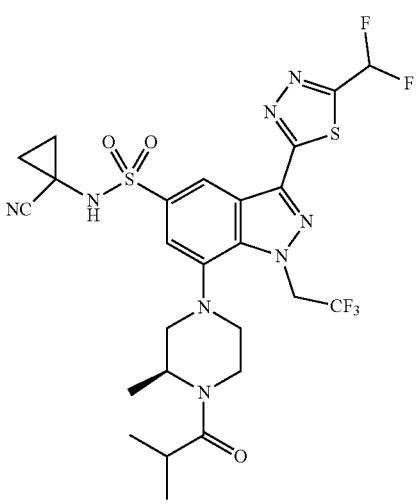

479
-continued
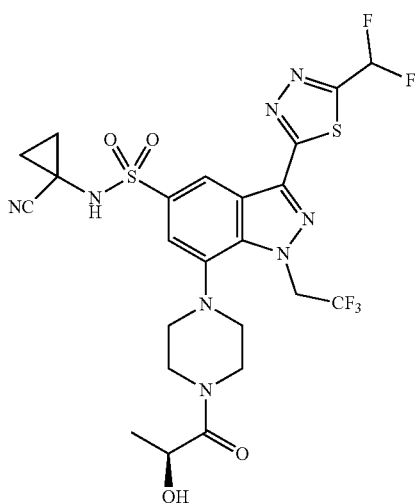
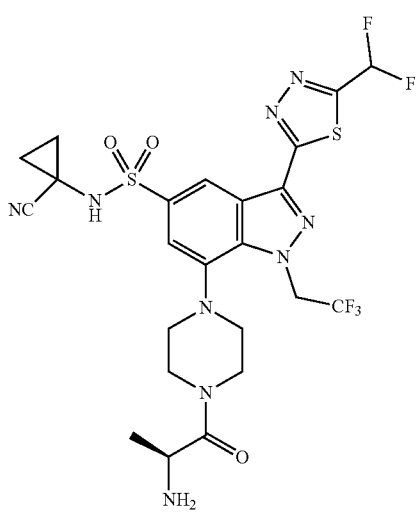
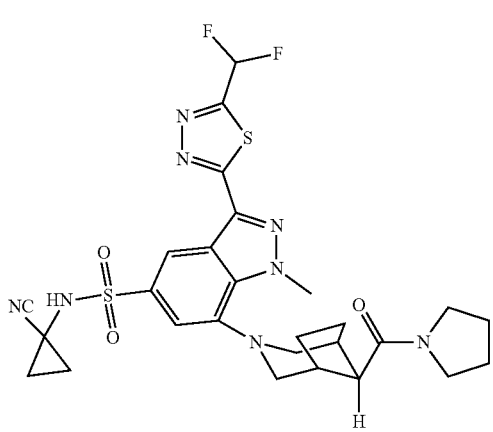
480
-continued
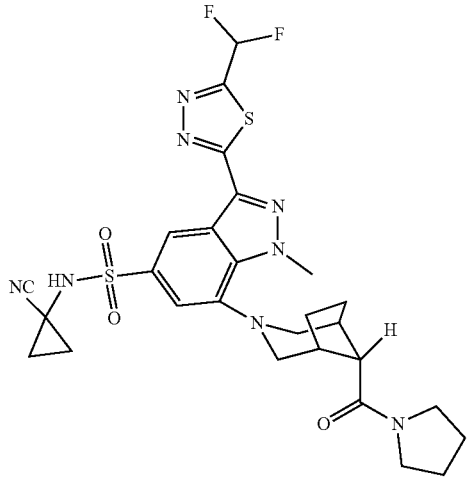
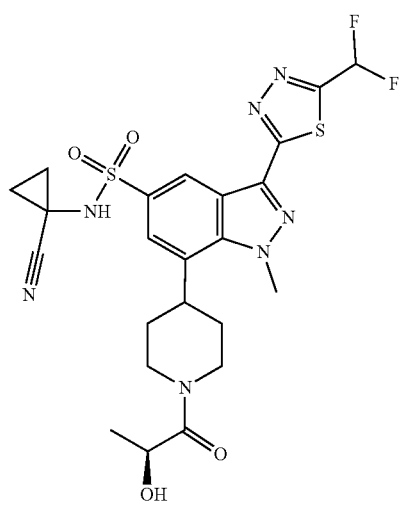
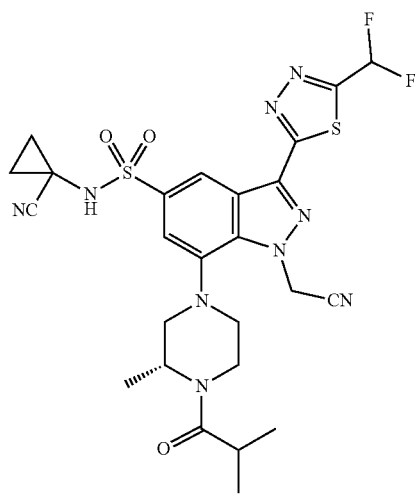

481
-continued
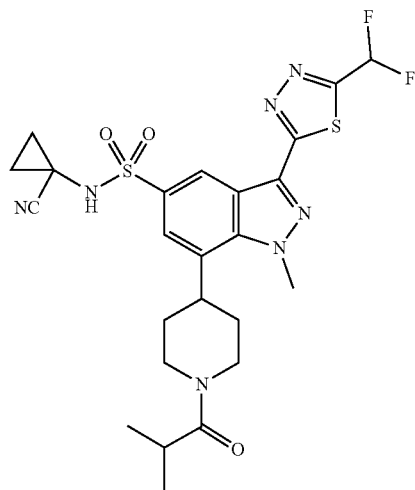
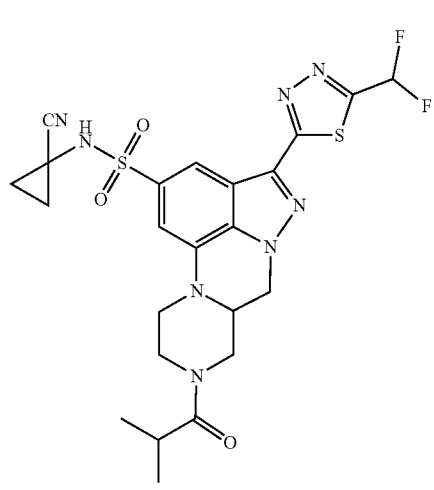
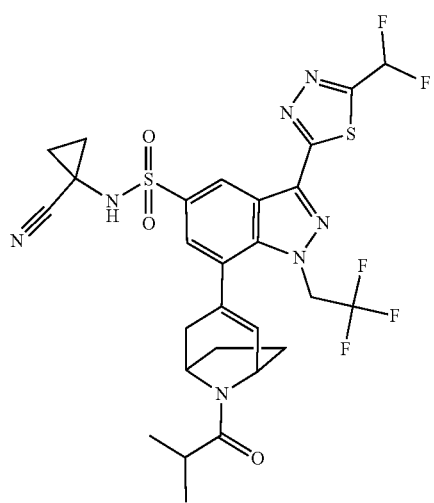
482
-continued
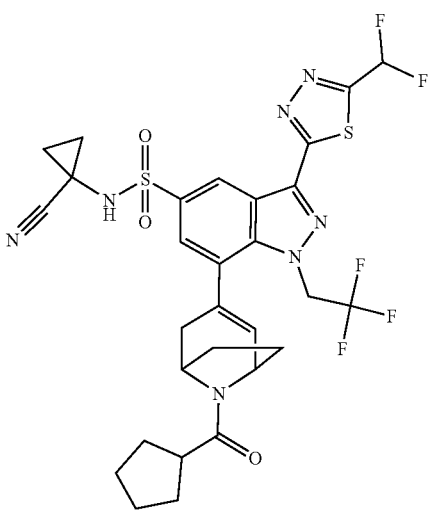
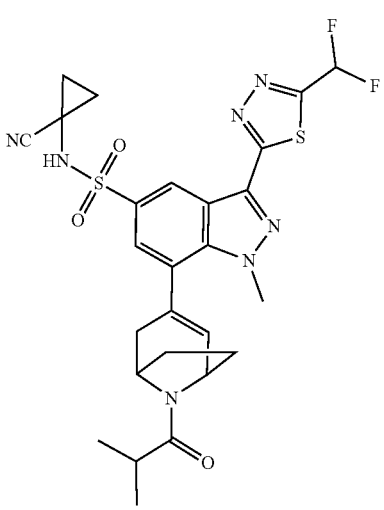
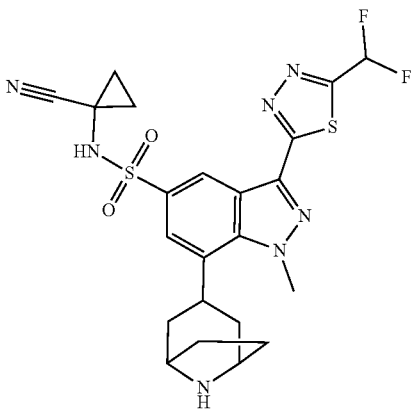

483
-continued
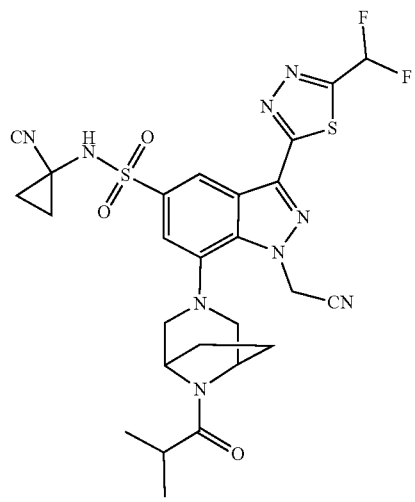
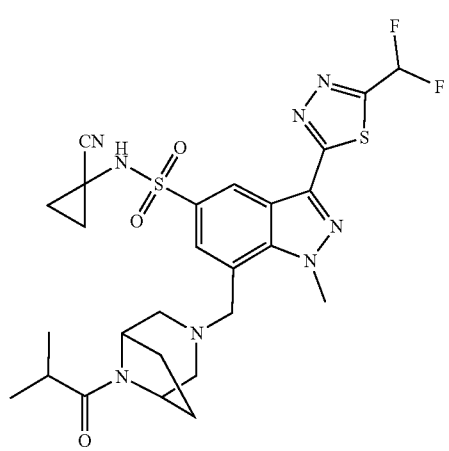
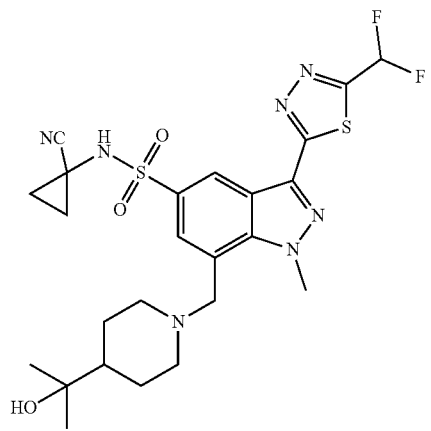
484
-continued
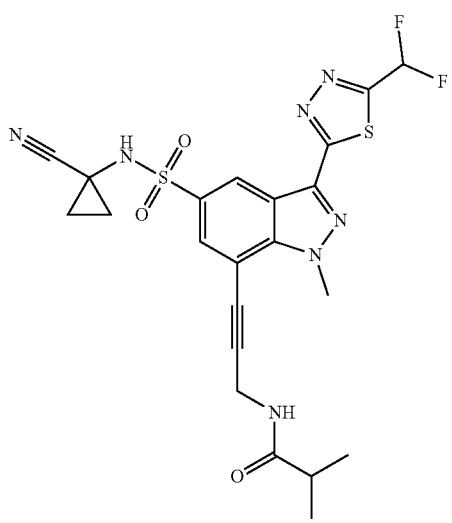
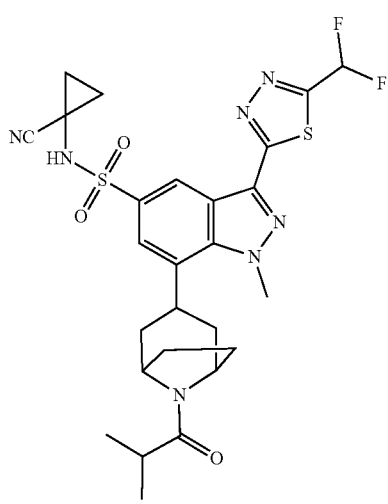
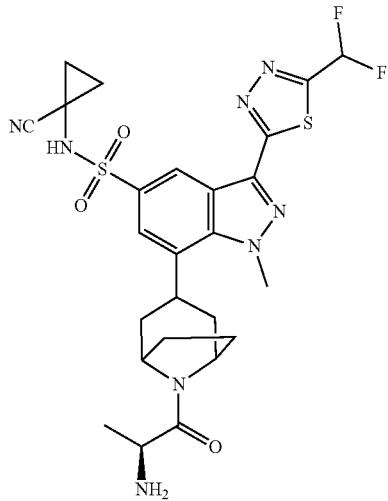

485
-continued
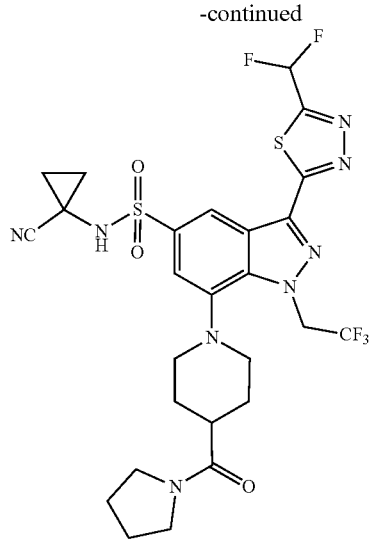
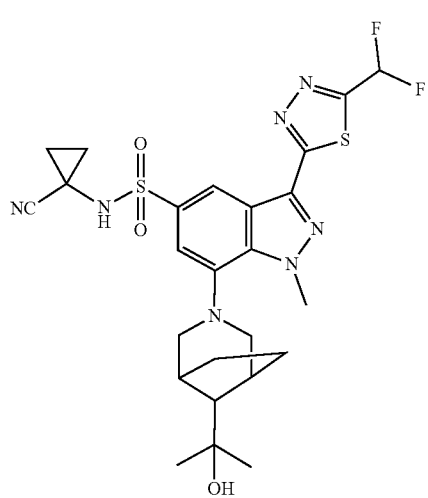
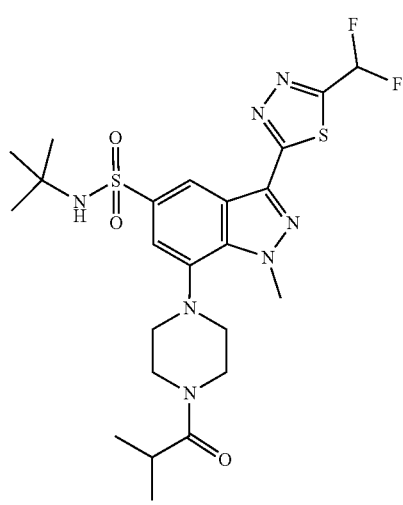
486
-continued
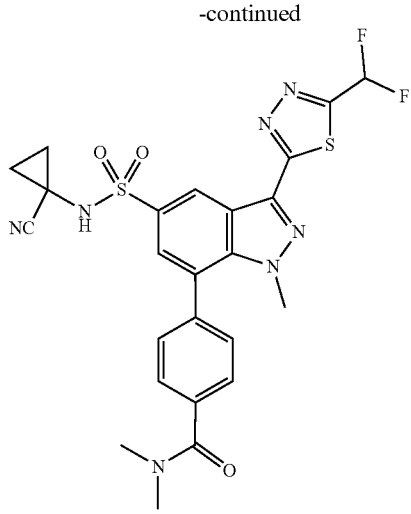
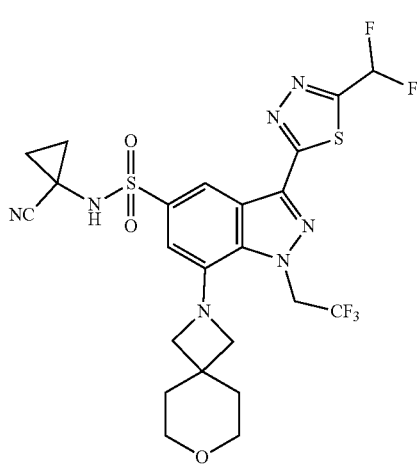
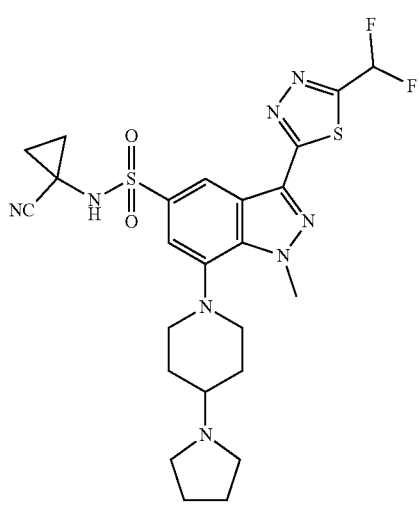

487
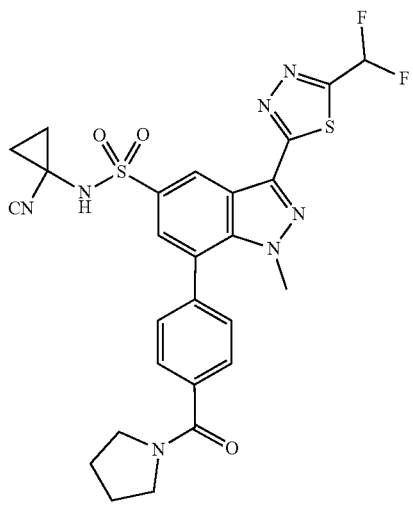
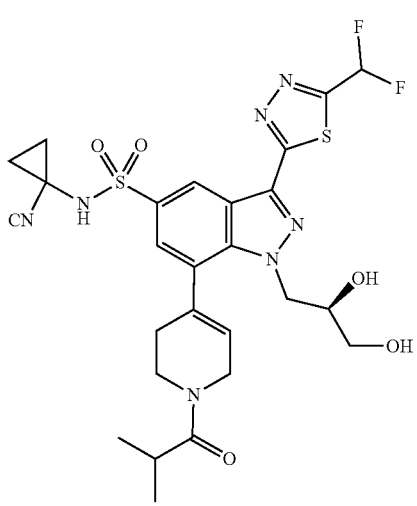
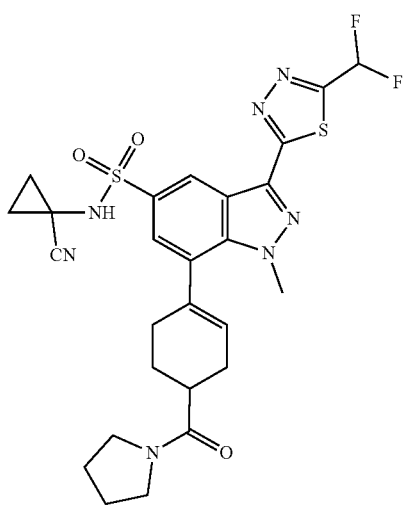
488
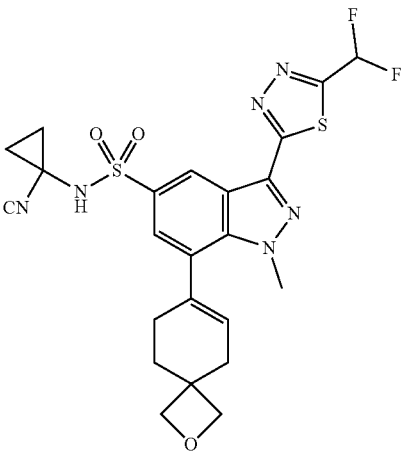
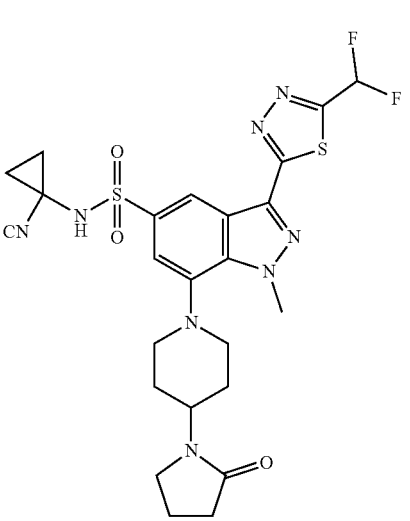
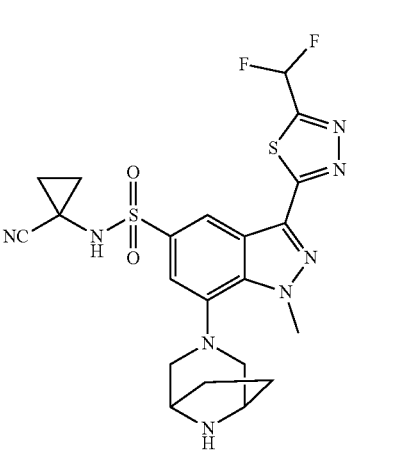

489
-continued
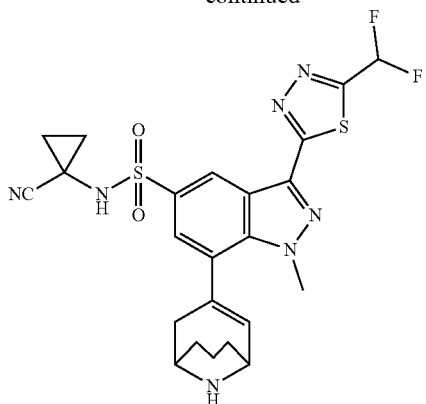
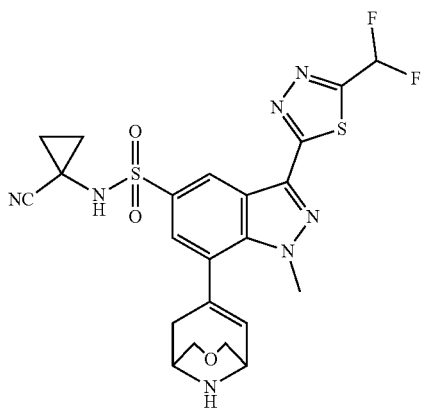
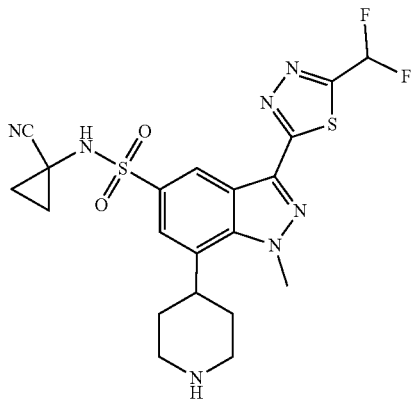
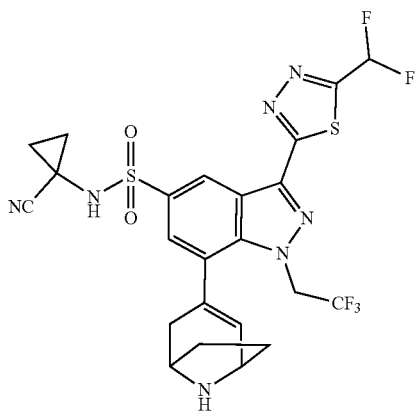
490
-continued
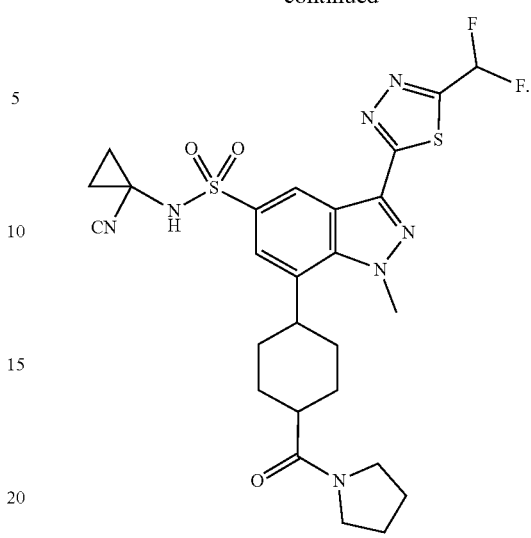
10. A method for preparing the compound containing structure of a five-membered heteroaromatic ring represented by formula II according to claim 2, wherein the method comprises conducting reaction steps according to any one of the following routes:
route I,
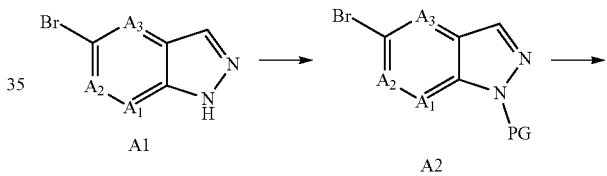
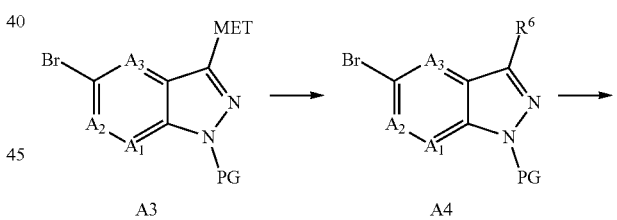
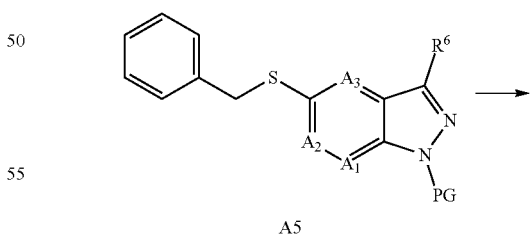
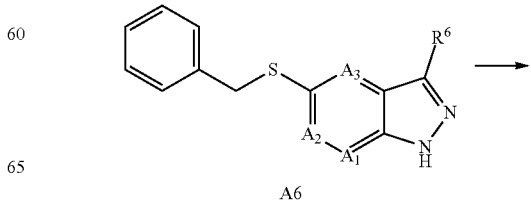

-continued

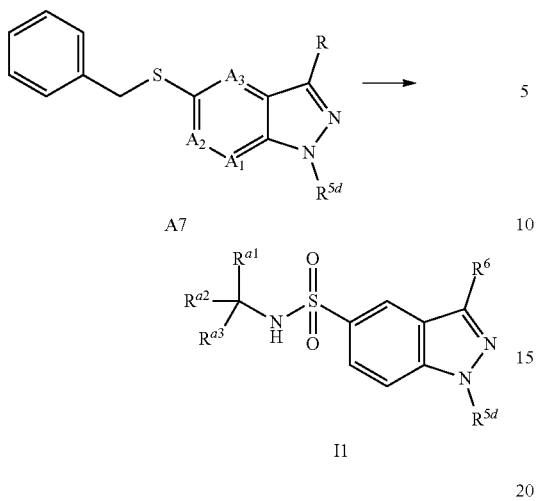

wherein, $R^{a1}$, $R^{a2}$, $R^{a3}$, $R^{5d}$, $R^6$, $A_1$, $A_2$, $A_3$ are as defined in claim 1; MET is a metallic group; PG is a protecting group; the route I comprises the following steps: compound $A_1$ was introduced protecting group to obtain compound A2, A2 was converted to A3 containing MET, then was converted to A4 by coupling reaction, A4 was converted to benzylthio compound A5, A5 is deprotected to give compound A6, which is converted to compound A7 by nucleophilic substitution and other reactions, and A7 is further converted to obtain compound I1;

route III,

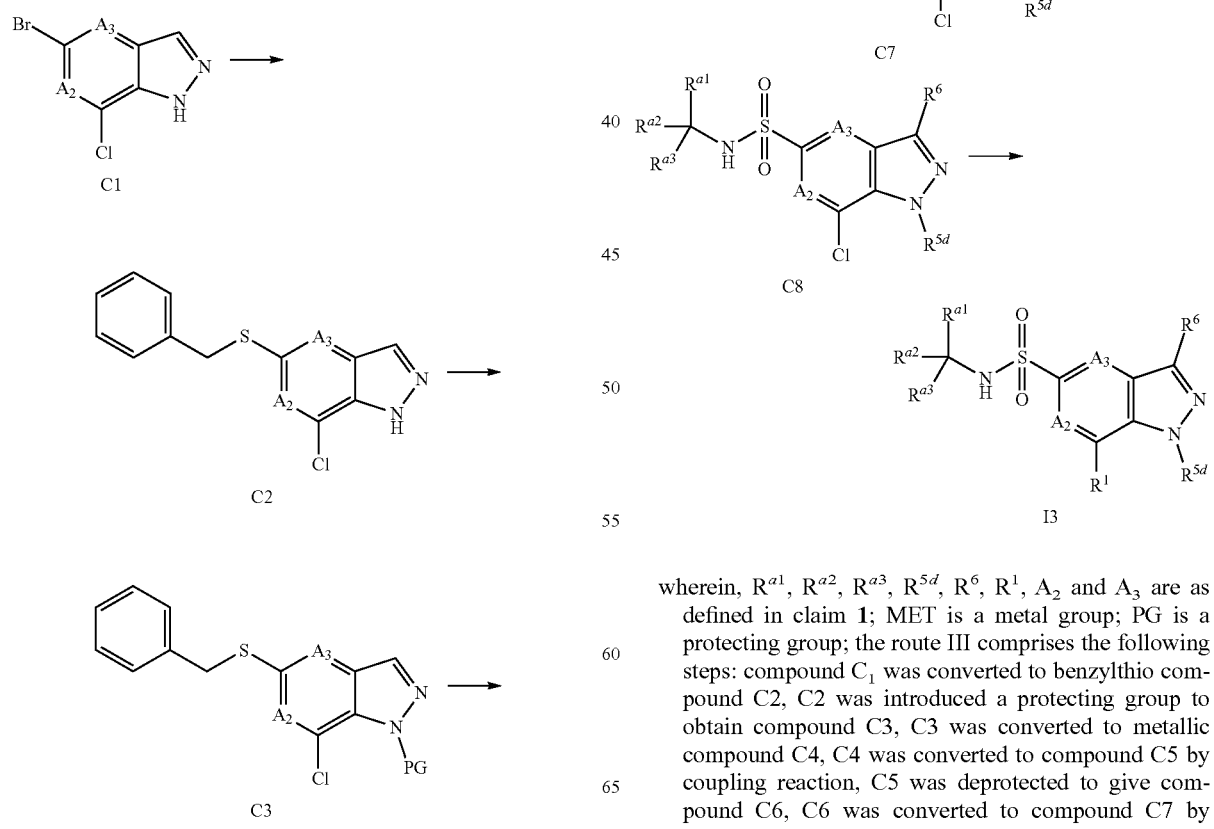

wherein, $R^{a1}$, $R^{a2}$, $R^{a3}$, $R^{5d}$, $R^6$, $R^1$, $A_2$ and $A_3$ are as defined in claim 1; MET is a metal group; PG is a protecting group; the route III comprises the following steps: compound $C_1$ was converted to benzylthio compound C2, C2 was introduced a protecting group to obtain compound C3, C3 was converted to metallic compound C4, C4 was converted to compound C5 by coupling reaction, C5 was deprotected to give compound C6, C6 was converted to compound C7 by nucleophilic substitution or other reactions, C7 is further transformed to compound C8, and C8 transformed to compound I3 by nucleophilic substitution, coupling or other reactions;

route IV

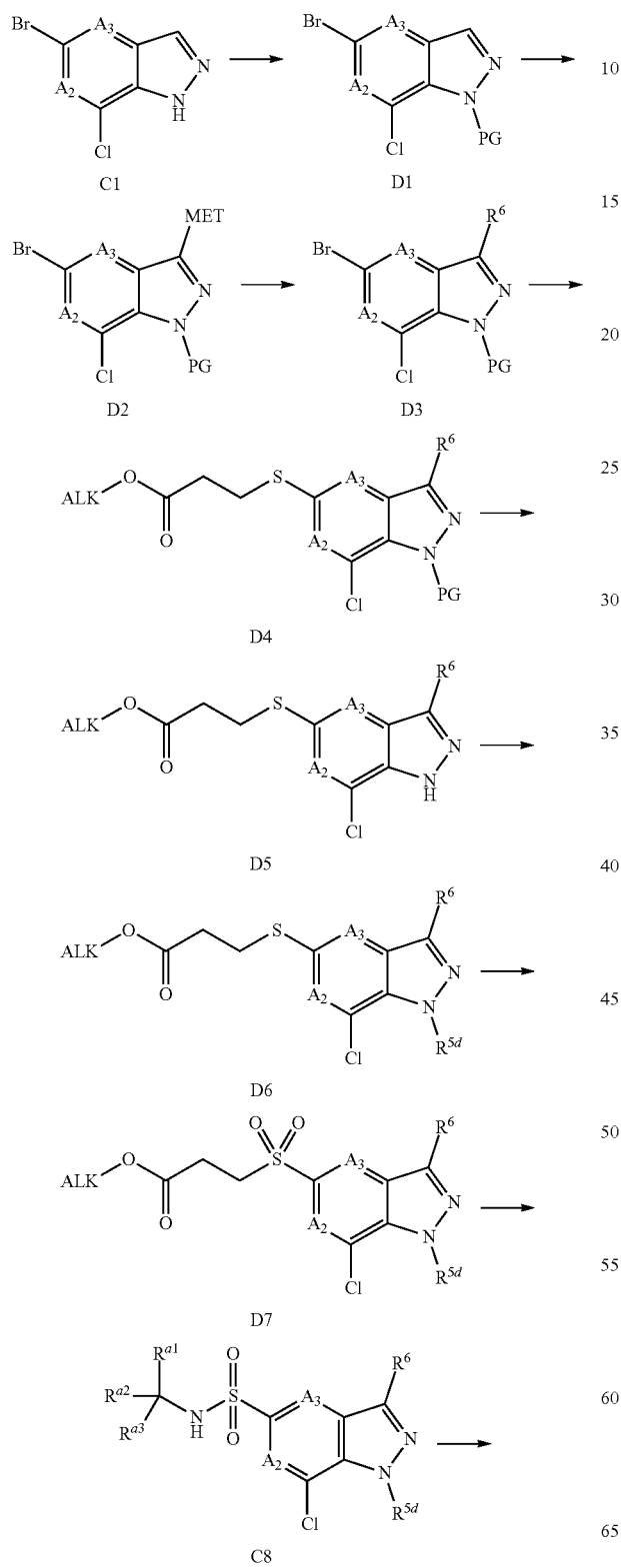

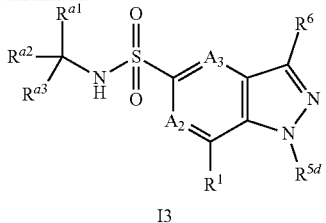

wherein, $R^{a1}$, $R^{a2}$, $R^{a3}$, $R^{5d}$, $R^6$, $R^1$, $A_2$ and $A_3$ are as defined in claim 1; MET is a metal group; PG is a protecting group; ALK is $C_{1-6}$ alkyl; the route IV comprises the following steps:

compound $C_1$ was introduced a protecting group to obtain compound D1, D1 was converted to metallic compound D2, D2 was converted to compound D3 by coupling reaction, D3 was converted to compound D4, D4 was deprotected to afford compound D5, D5 was converted to compound D6 by nucleophilic substitution and (or) other reactions, D6 is oxidized to obtain compound D7, D7 is further converted to obtain compound C8, C8 is converted by nucleophilic substitution, coupling or other reactions to obtain compound I3;

route V

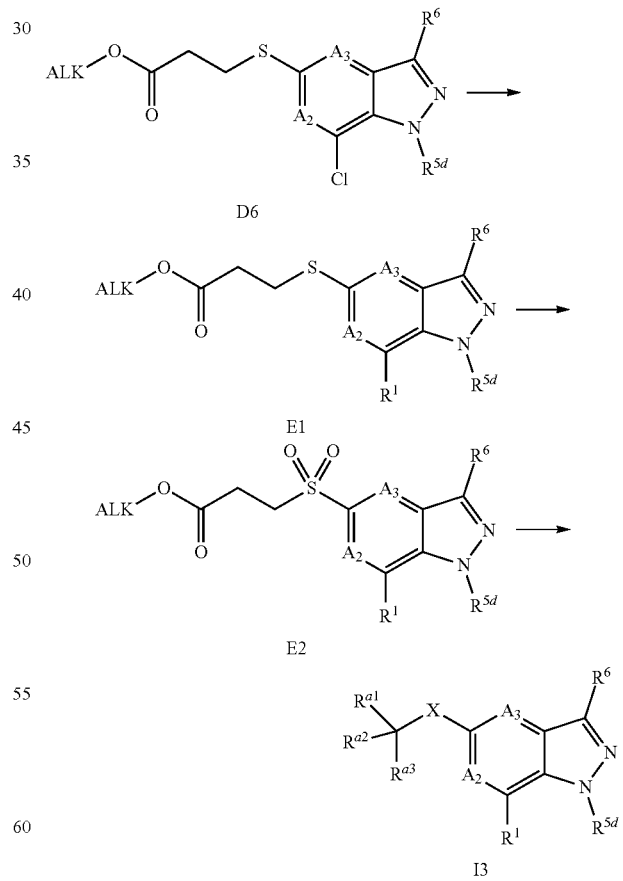

wherein, $R^{a1}$, $R^{a2}$, $R^{a3}$, X, $R^{5d}$, $R^6$, $R^1$, $A_2$ and $A_3$ are as defined in claim 1; ALK is $C_{1-6}$ alkyl; the route V is described as follows: compound D6 was converted to compound E1 by nucleophilic substitution, coupling or other reactions, E1 was oxidized to give compound E2, which was further converted to give compound I3.

11. A pharmaceutical composition comprising a substance A and a pharmaceutically acceptable excipient, wherein the substance A is a therapeutically effective amount of the compound containing structure of a five-membered heteroaromatic ring of formula II, the pharmaceutically acceptable salt thereof, or the stereoisomer thereof according to claim 1.

12. A method for inhibiting polyadenosine diphosphate ribose hydrolase (PARG) in a subject in need thereof, comprising: administering a therapeutically effective amount of a substance A to the subject, wherein the substance A is the compound containing structure of a five-membered heteroaromatic ring of formula II, the pharmaceutically acceptable salt thereof, or the stereoisomer thereof according to claim 1.

13. A method for treating a polyadenosine diphosphate ribose hydrolase (PARG) related disease in a subject in need thereof, comprising: administering an effective amount of a substance A, wherein the substance A is the compound containing structure of a five-membered heteroaromatic ring of formula II, the pharmaceutically acceptable salt thereof, or the stereoisomer thereof according to claim 1, wherein the PARG related disease is ovarian cancer.

\* \* \* \* \*